(12) United States Patent
Babu et al.

(10) Patent No.: US 10,954,252 B1
(45) Date of Patent: Mar. 23, 2021

(54) INHIBITORS OF HUMAN IMMUNODEFICIENCY VIRUS REPLICATION

(71) Applicant: ViiV HEALTHCARE UK (NO.5) LIMITED, Middlesex (GB)

(72) Inventors: Suresh Babu, Bangalore (IN); Makonen Belema, Wallingford, CT (US); John A. Bender, Wallingford, CT (US); Christiana Iwuagwu, Wallingford, CT (US); John F. Kadow, Branford, CT (US); Selvakumar Kumaravel, Bangalore (IN); Pulicharla Nagalakshmi, Bangalore (IN); B. Narasimhulu Naidu, Branford, CT (US); Manoj Patel, Wallingford, CT (US); Kevin M. Peese, Branford, CT (US); Ramkumar Rajamani, Wallingford, CT (US); Mark Saulnier, Wallingford, CT (US); Alan Xiangdong Wang, Wallingford, CT (US)

(73) Assignee: ViiV HEALTHCARE UK (NO.5) LIMITED, Middlesex (GB)

( * ) Notice: Subject to any disclaimer, the term of this patent is extended or adjusted under 35 U.S.C. 154(b) by 0 days.

(21) Appl. No.: 16/606,345

(22) PCT Filed: May 1, 2018

(86) PCT No.: PCT/IB2018/053014
§ 371 (c)(1),
(2) Date: Oct. 18, 2019

(87) PCT Pub. No.: WO2018/203235
PCT Pub. Date: Nov. 8, 2018

Related U.S. Application Data

(60) Provisional application No. 62/651,345, filed on Apr. 2, 2018, provisional application No. 62/594,624, filed on Dec. 5, 2017, provisional application No. 62/500,005, filed on May 2, 2017.

(51) Int. Cl.
*C07D 401/14* (2006.01)
*C07D 403/14* (2006.01)
*C07D 471/04* (2006.01)
*C07D 487/04* (2006.01)
*C07D 513/04* (2006.01)
*A61P 31/18* (2006.01)
*A61K 45/06* (2006.01)

(52) U.S. Cl.
CPC ............ *C07D 513/04* (2013.01); *A61P 31/18* (2018.01); *C07D 401/14* (2013.01); *C07D 403/14* (2013.01); *C07D 471/04* (2013.01); *C07D 487/04* (2013.01); *A61K 45/06* (2013.01)

(58) Field of Classification Search
CPC .. C07D 401/14; C07D 403/14; C07D 471/04; C07D 487/04; C07D 513/04
See application file for complete search history.

(56) References Cited

FOREIGN PATENT DOCUMENTS

| WO | WO 2013/006738 A1 | 1/2013 |
|---|---|---|
| WO | WO 2014/110297 A1 | 7/2014 |
| WO | WO 2014/134566 A2 | 9/2014 |
| WO | WO 2016/033243 A1 | 3/2016 |

*Primary Examiner* — Emily A Bernhardt
(74) *Attorney, Agent, or Firm* — Robert H. Brink; Duke M. Fitch; Edward R. Gimmi

(57) ABSTRACT

Compounds of Formula I, including pharmaceutically acceptable salts thereof, and compositions and methods for treating human immunodeficiency virus (HIV) infection are set forth.

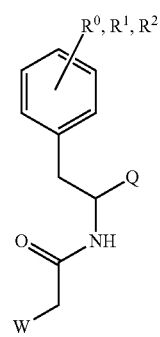

11 Claims, No Drawings

INHIBITORS OF HUMAN IMMUNODEFICIENCY VIRUS REPLICATION

This application is a § 371 of International Application No. PCT/IB2018/053014, filed 1 May 2018, which claims the benefit of U.S. Provisional Application Nos. 62/651,345, filed 2 Apr. 2018, 62/594,624, filed 5 Dec. 2017, and 62/500,005, filed 2 May 2017.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. HIV continues to be a major global public health issue. In 2015, an estimated 36.7 million people were living with HIV (including 1.8 million children)—a global HIV prevalence of 0.8%. The vast majority of this number live in low- and middle-income countries. In the same year, 1.1 million people died of AIDS-related illnesses.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase strand transfer inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity (cobicistat) has recently been approved for use in combinations with antiretroviral agents (ARVs) that require boosting.

Despite the armamentarium of agents and drug combinations, there remains a medical need for new anti-retroviral agents, due in part to the need for chronic dosing to combat infection. Significant problems related to long-term toxicities are documented, creating a need to address and prevent these co-morbidities (e.g. CNS, CV/metabolic, renal disease). Also, increasing failure rates on current therapies continue to be a problem, due either to the presence or emergence of resistant strains or to non-compliance attributed to drug holidays or adverse side effects. For example, despite therapy, it has been estimated that 63% of subjects receiving combination therapy remained viremic, as they had viral loads >500 copies/mL (Oette, M, Kaiser, R, Daumer, M, et al. Primary HIV Drug Resistance and Efficacy of First-Line Antiretroviral Therapy Guided by Resistance Testing. J Acq Imm Def Synd 2006; 41(5): 573-581). Among these patients, 76% had viruses that were resistant to one or more classes of antiretroviral agents. As a result, new drugs are needed that are easier to take, have high genetic barriers to the development of resistance and have improved safety over current agents. In this panoply of choices, novel MOAs that can be used as part of the preferred HAART regimen can still have a major role to play since they should be effective against viruses resistant to current agents.

Certain potentially therapeutic compounds have now been described in the art and set forth in Blair, Wade S. et. al. Antimicrobial Agents and Chemotherapy (2009), 53(12), 5080-5087, Blair, Wade S. et al. PLoS Pathogens (2010), 6(12), e1001220, Thenin-Houssier, Suzie; Valente, Susana T. Current HIV Research, 2016, 14, 270-282, and PCT Patent applications with the following numbers: WO 2012065062, WO 2013006738, WO 2013006792, WO 2014110296, WO 2014110297, WO 2014110298, WO 2014134566, WO 2015130964, and WO 2016033243.

What is now needed in the art are additional compounds which are novel and useful in the treatment of HIV. Additionally, these compounds should provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

Briefly, in one aspect, the present invention discloses a compound of Formula I, or a pharmaceutically acceptable salt thereof:

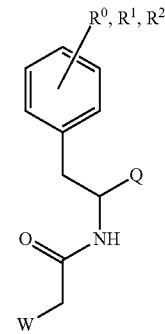

Formula I wherein: $R^0$, $R^1$, and $R^2$ are each independently hydrogen, Cl, F, -OMe, —CN, —$C_1$-$C_3$alkyl, or —$C_3$-$C_5$cycloalkyl, wherein —$C_1$-$C_3$alkyl may be optionally substituted with from 1-3 fluorines;

Q is selected from:

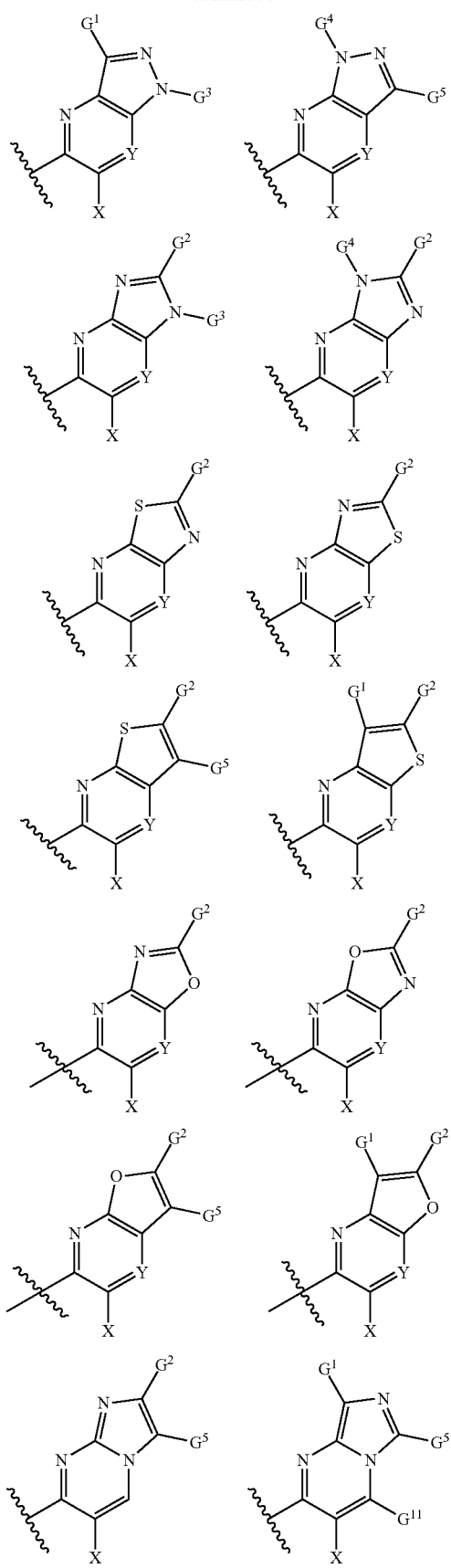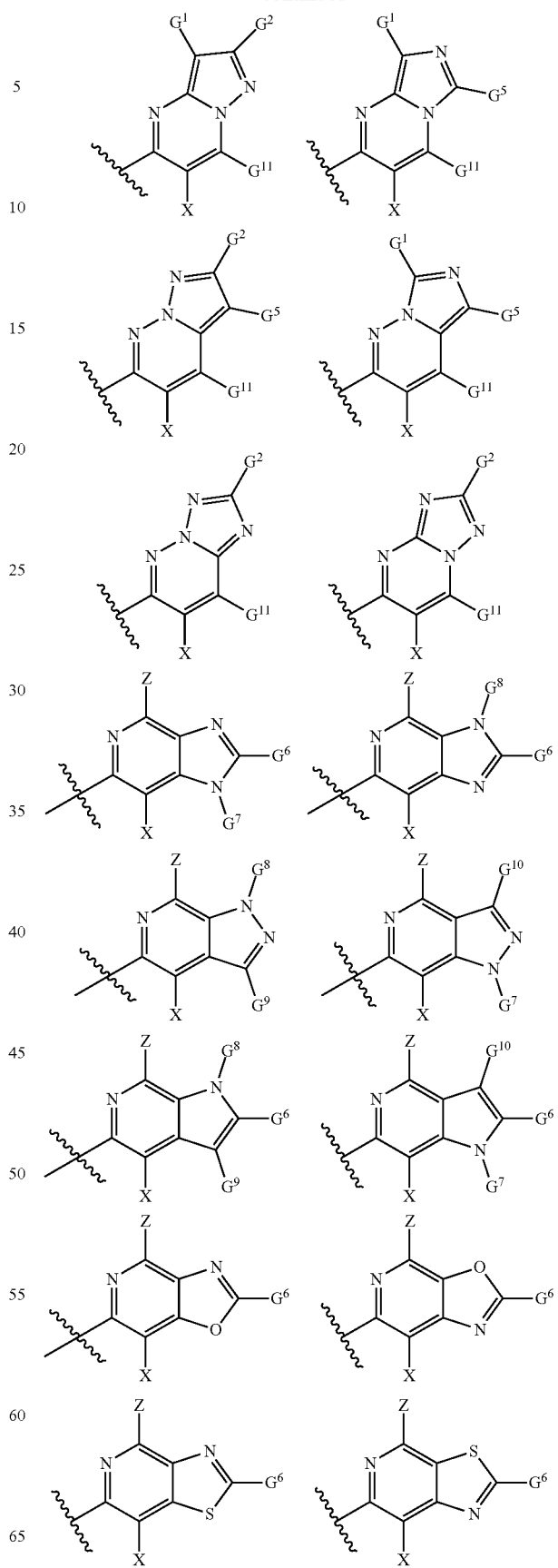

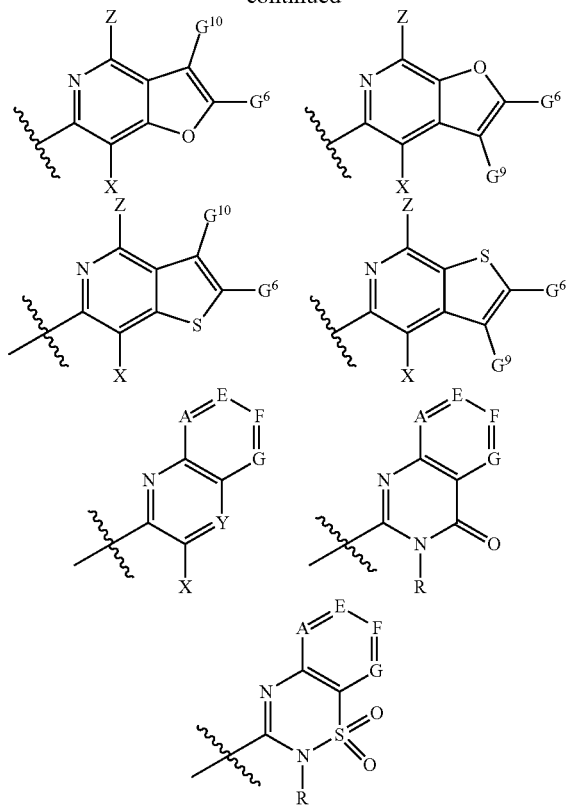

$G^1$ is hydrogen, $C_1$-$C_5$alkyl, —$SO_2CH_3$, —$CO_2H$, —$C(O)$ $NG^{12}G^{13}$-($C_1$-$C_3$alkyl)$SO_2CH_3$, —($C_1$-$C_3$ alkyl)$C(O)$ $NG^{12}G^{13}$, —($C_1$-$C_3$alkyl)$NG^{12}G^{13}$, —($C_1$-$C_3$alkyl)$CO_2H$, —$CCC(CH_3)_2SO_2CH_3$, —($C_1$-$C_3$alkyl)$CO_2H$, Cl, or F wherein $C_1$-$C_3$alkyl or $C_1$-$C_5$alkyl is optionally substituted with 1-3 fluorines;

$G^2$ is hydrogen, $C_1$-$C_5$alkyl, —$SO_2CH_3$, —$CO_2H$, —$C(O)$ $NG^{12}G^{13}$, —$NG^{12}G^{13}$, —($C_1$-$C_3$ alkyl)$SO_2CH_3$, —($C_1$-$C_3$alkyl)$C(O)NG^{12}G^{13}$, —($C_1$-$C_3$alkyl)$NG^{12}G^{13}$, —($C_1$-$C_3$alkyl)$CO_2H$, —$CCC(CH_3)_2SO_2CH_3$, —($C_1$-$C_3$alkyl) $CO_2H$, Cl, or F, wherein $C_1$-$C_3$alkyl or $C_1$-$C_5$alkyl is optionally substituted with 1-3 fluorines or 1-2 $CH_3$ groups;

$G^3$ is hydrogen, —$SO_2CH_3$, benzyl, or $C_1$-$C_3$alkyl, wherein $C_1$-$C_3$alkyl is optionally substituted with 1-3 fluorines;

$G^4$ is hydrogen, $C_1$-$C_3$alkyl, -benzyl, —$SO_2(C_1$-$C_3$alkyl), —($C_2$-$C_3$alkyl)$SO_2CH_3$, —$C(O)NG^{12}G^{13}$, —($C_1$-$C_3$alkyl) $C(O)NG^{12}G^{13}$, —($C_2$-$C_3$alkyl)$C(O)NG^{12}G^{13}$, —($C_1$-$C_3$alkyl)$CO_2H$, —($C_1$-$C_3$alkyl)$CO_2H$, wherein $C_1$-$C_3$alkyl is optionally substituted with 1-3 fluorines;

$G^5$ is hydrogen, $C_1$-$C_3$alkyl, —$SO_2(C_1$-$C_3$alkyl), —$C(O)$ $NG^{12}G^{13}$, $CO_2H$, —$N^{12}G^{13}$, or CN wherein $C_1$-$C_3$alkyl is optionally substituted with 1-3 fluorines or chorines;

$G^6$ is hydrogen or methyl wherein methyl is optionally substituted with 1-3 fluorines;

$G^7$ is hydrogen, or $C_1$-$C_3$alkyl wherein $C_1$-$C_3$alkyl is optionally substituted with 1-3 fluorines;

$G^8$ is hydrogen, $C_1$-$C_3$alkyl, -benzyl, —$SO_2(C_1$-$C_3$alkyl), —($C_2$-$C_3$alkyl)$SO_2CH_3$, —$C(O)NG^{12}G^{13}$-($C_1$-$C_3$alkyl)$C$ $(O)NG^{12}G^{13}$, —($C_2$-$C_3$alkyl)$C(O)NG^{12}G^{13}$, —($C_1$-$C_3$alkyl)$CO_2H$, —($C_1$-$C_3$alkyl)$CO_2H$, wherein $C_1$-$C_3$alkyl is optionally substituted with 1-3 fluorines;

$G^9$ is hydrogen or methyl wherein methyl is optionally substituted with 1-3 fluorines;

$G^{10}$ is hydrogen or methyl wherein methyl is optionally substituted with 1-3 fluorines;

Y is N or C-$G^{11}$;

$G^{11}$ is hydrogen, $C_1$-$C_3$alkyl, —$O(C_1$-$C_3$alkyl), —$SO_2CH_3$, —$CO_2H$, —$NG^{12}G^{13}$, CN, or —$C(O)NG^{12}G^{13}$ wherein $C_1$-$C_3$alkyl is optionally substituted with 1-3 fluorines;

Z is hydrogen, —$C_1$-$C_3$alkyl, —$NH_2$, —$SO_2(C_1$-$C_3$alkyl), —$O(C_1$-$C_3$alkyl), —($C_1$-$C_3$alkyl)$SO_2CH_3$, —$C(O)$ $NG^{12}G^{13}$, —($C_1$-$C_3$alkyl)$C(O)NG^{12}G^{13}$, —($C_1$-$C_3$alkyl) $NG^{12}G^{13}$, —$CCC(CH_3)_2SO_2CH_3$, —$CCC(CH_3)_2OH$, —($C_1$-$C_3$alkyl)$COOH$, —$CCC(CH_3)_2C(O)N^{12}G^{13}$, —$CCC$ $(CH_3)_2COOH$, —$CCC(CH_3)_3$, —$CCC(CH_3)_2OC_1$-$C_3$alkyl, wherein —$C_1$-$C_3$alkyl is optionally substituted with 1-3 fluorines;

$G^{12}$ and $G^{13}$ are each independently hydrogen, or $C_1$-$C_3$alkyl;

A is N or C-$G^{14}$;

E is N or C-$G^{14}$;

F is N or C-$G^{15}$;

G is N, C-$G^{16}$;

with the proviso that no more than two of A, E, F, or G may be N;

$G^{14}$ is hydrogen, —$C_1$-$C_5$alkyl, —$C_3$-$C_6$cycloalkyl, —$SO_2CH_3$, —$CO_2H$, —$C(O)NG^{12}G^{13}$, —$NG^{12}G^{13}$, —($C_1$-$C_3$alkyl)$SO_2CH_3$, —($C_1$-$C_3$alkyl)$C(O)NG^{12}G^{13}$, —($C_1$-$C_3$alkyl)$NG^{12}G$, —($C_1$-$C_3$ alkyl)$CO_2H$, —$CCC(CH_3)_2$ $SO_2CH_3$, —($C_1$-$C_3$alkyl)$CO_2H$, Cl, F, Br, —CN, or —O—$C_1$-$C_5$alkyl, wherein $C_1$-$C_5$alkyl, —O—$C_1$-$C_5$alkyl, or —$C_3$-$C_6$cycloalkyl is optionally substituted with 1-3 fluorines;

$G^{15}$ is hydrogen, $C_1$-$C_5$alkyl, —$C_3$-$C_5$cycloalkyl, —$SO_2CH_3$, —$CO_2H$, —$C(O)N^{12}G^{13}$, —$NG^{12}G^{13}$, CN, Cl, F, Br, or —O—$C_1$-$C_5$alkyl, wherein $C_1$-$C_5$alkyl, $C_1$-$C_5$cycloalkyl or —O—$C_1$-$C_5$alkyl or —O—$C_1$-$C_5$alkyl, is optionally substituted with 1-3 fluorines;

$G^{16}$ is hydrogen, —$C_1$-$C_5$alkyl, —$NH_2$, Cl, F, Br, —CN, or —O—$C_1$-$C_5$alkyl, wherein $C_1$-$C_5$alkyl or —O—$C_1$-$C_5$alkyl is optionally substituted with 1-3 fluorines;

X is

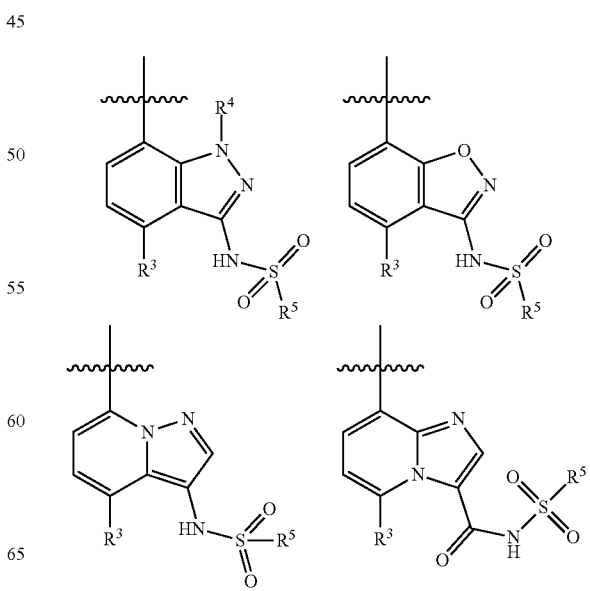

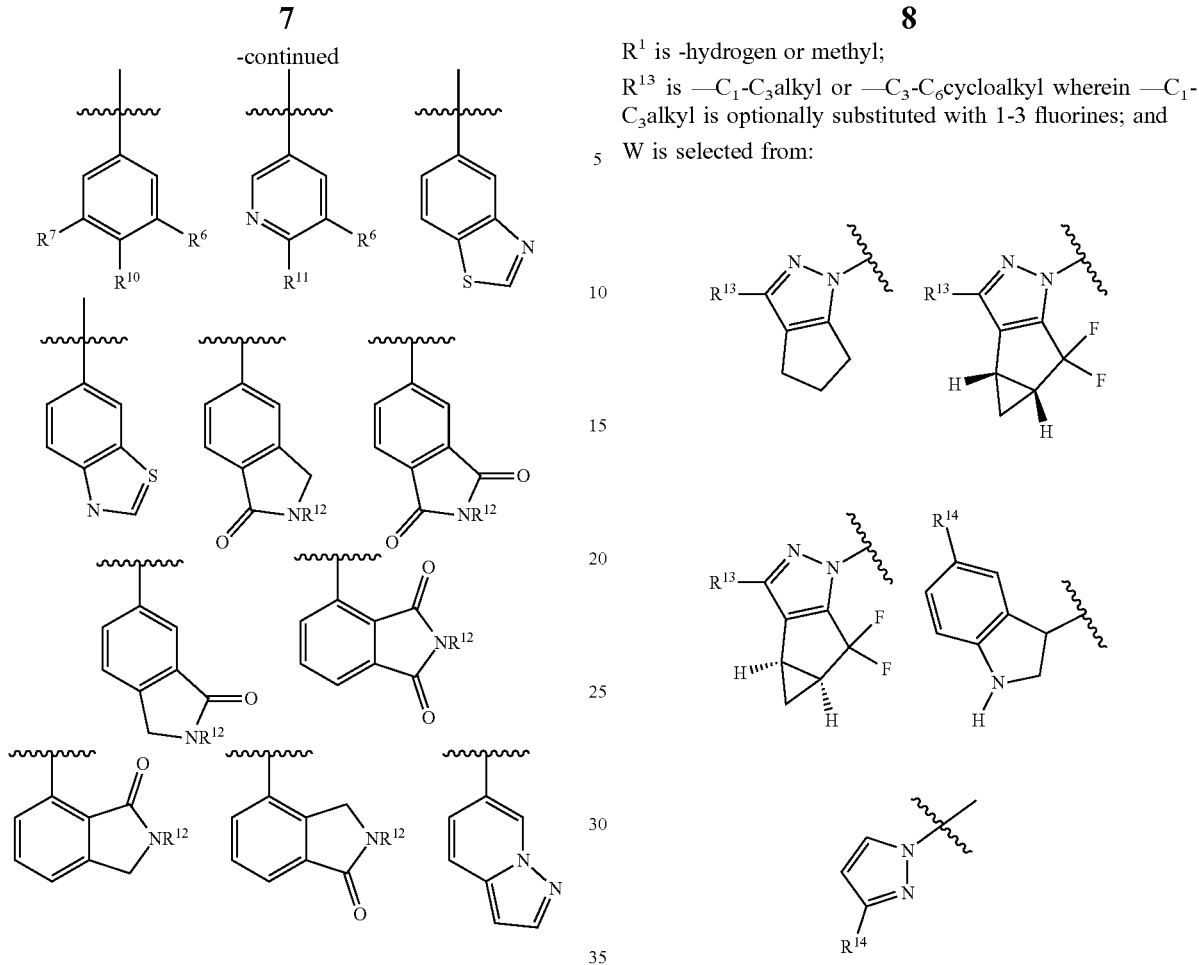

R=X;
$R^3$ is hydrogen, Cl, F, -OMe, —CN, —$C_1$-$C_3$alkyl, or —$C_3$-$C_5$cycloalkyl, wherein —$C_1$-$C_3$alkyl may be optionally substituted with from 1-3 fluorines;
$R^4$ is hydrogen, $C_1$-$C_3$alkyl, or —$SO_2CH_3$ wherein $C_1$-$C_3$alkyl is optionally substituted with 1-3 fluorines;
$R^5$ is $C_1$-$C_6$alkyl, $C_3$-$C_6$cycloalkyl, or $NG^{12}$, $G^{13}$;
$R^6$ and $R^7$ are each independently hydrogen, chlorine, fluorine, —$OC_1$-$C_3$alkyl, —CN, —$CO_2H$, —$CONG^{12}G^{13}$, —$NG^{12}G^{13}$, —$NHCOR^8$, or —$CONHSO_2R^9$ or —$NHSO_2R^9$ wherein —$C_1$-$C_3$alkyl, —$OC_1$-$C_3$alkyl, or —$C_3$-$C_5$cycloalkyl is optionally substituted with 1-3 fluorines;
$R^8$ is —$C_1$-$C_3$alkyl;
$R^9$ is —$C_1$-$C_6$alkyl, —$C_3$-$C_5$cycloalkyl or $NG^{12}$, $G^{13}$ wherein —$C_3$-$C_5$cycloalkyl is optionally substituted with a methyl group;
$R^{10}$ is hydrogen, chlorine, fluorine, —$C_1$-$C_3$alkyl, —$OC_1$-$C_3$alkyl, —$C_3$-$C_5$cycloalkyl, —CN, —$CO_2H$, —$SO_2C_1$-$C_3$alkyl, —$SO_2NR^aR^b$, —$CONG^{12}G^{13}$, —$NG^{12}G^{13}$, —NHCOR$^8$, or —$CONHSO_2R^9$ or —$NHSO_2R^9$ wherein —$C_1$-$C_3$alkyl, —$OC_1$-$C_3$alkyl, or —$C_3$-$C_5$cycloalkyl is optionally substituted with 1-3 fluorines;
$R^a$ and $R^b$ are independently H, —$C_1$-$C_3$alkyl, or together with the N to which they are attached form a morpholine, azetidine, pyrrolidine, piperidine, piperazine, or N-Me piperazine;
$R^{11}$ is hydrogen, —$C_1$-$C_3$alkyl, $C_3$-$C_5$cycloalkyl —$OC_1$-$C_3$alkyl, —$CONG^{12}G^{13}$, —$NG^{12}G^{13}$, —$NHCOR^8$, —$CONHSO_2R^9$ or —$NHSO_2R^9$ wherein —$C_1$-$C_3$alkyl, —$OC_1$-$C_3$alkyl, or —$C_3$-$C_5$ cycloalkyl is optionally substituted with 1-3 Fluorines;
$R^1$ is -hydrogen or methyl;
$R^{13}$ is —$C_1$-$C_3$alkyl or —$C_3$-$C_6$cycloalkyl wherein —$C_1$-$C_3$alkyl is optionally substituted with 1-3 fluorines; and
W is selected from:

wherein $R^1$ is —$NHSO_2CH_3$, —$C_1$-$C_3$alkyl, —$C_3$-$C_6$cycloalkyl, —OH, —F, Cl, Br, or methyl, wherein methyl is optionally substituted with 1-3 fluorines.

In another aspect, the present invention discloses a composition comprising a compound of Formula I or a pharmaceutically acceptable salt thereof.

In another aspect, the present invention discloses a method of treating HIV infection comprising administering a composition comprising a compound of Formula I or a pharmaceutically acceptable salt thereof to a patient.

In another aspect, the present invention discloses a compound of Formula (I) or pharmaceutically acceptable salt thereof for use in therapy.

In another aspect, the present invention discloses a compound of Formula (I) or pharmaceutically acceptable salt thereof for use in treating HIV infection.

In another aspect, the present invention discloses the use of a compound of Formula (I) or pharmaceutically acceptable salt thereof in the manufacture of a medicament for the treatment of HIV infection.

DETAILED DESCRIPTION OF THE EMBODIMENTS

A preferred subset of the compounds of Formula 1 are compounds of Formula II, or pharmaceutically acceptable salts thereof:

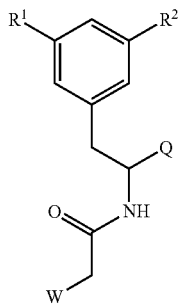

II wherein Q and W are as defined above for Formula I. Particularly preferred compounds of Formula II are those where $R^1$ and $R^2$ are each independently hydrogen or F. Most preferably, $R^1$ and $R^2$ are each F.

Preferably, the compounds and salts of this invention are those in which the stereochemistry of the carbon to which Q is bonded is as depicted below in Formula III:

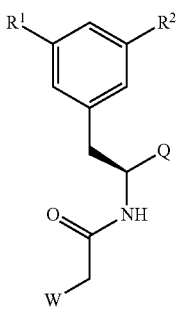

III

The salts of compounds of formula (I) are pharmaceutically acceptable. Such salts may be acid addition salts or base addition salts For a review of suitable pharmaceutically acceptable salts see Berge et al, J. Pharm, Sci., 66, 1-19, 1977. In an embodiment, acid addition salts are selected from the hydrochloride, hydrobromide, hydroiodide, sulphate, bisulfate, nitrate, phosphate, hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate. In an embodiment, base addition salts include metal salts (such as sodium, potassium, aluminium, calcium, magnesium and zinc) and ammonium salts (such as isopropylamine, diethylamine, diethanolamine salts). Other salts (such as trifluoroacetates and oxalates) may be used in the manufacture of compounds of formula (I) and their pharmaceutically acceptable salts, and are included within the scope of the invention. All possible stoichiometric and non-stoichiometric forms of the salts of compounds of formula (I) are included within the scope of the invention. Acid and base addition salts may be prepared by the skilled chemist, by treating a compound of formula (I) with the appropriate acid or base in a suitable solvent, followed by crystallisation and filtration.

Some of the compounds of the invention exist in stereoisomeric forms. The invention includes all stereoisomeric forms of the compounds including enantiomers and diastereromers including atropisomers. The term homochiral is used as a descriptor, per accepted convention, to describe a structure which is a single stereoisomer. Absolute stereochemistry was not assigned in all cases. Thus the compound is drawn at the chiral center as unspecified but labelled as homochiral and in the procedures it is identified by its properties such as for example first eluting off a normal or chiral column per the conventions of chemists. It should be noted that the provided experimental procedures teach how to make the exact compound even if not drawn with absolute configuration. Methods of making and separating stereoisomers are known in the art. The invention includes all tautomeric forms of the compounds. The invention includes atropisomers and rotational isomers.

For the compounds of Formula I, the scope of any instance of a variable substituent can be used independently with the scope of any other instance of a variable substituent. As such, the invention includes combinations of the different aspects. In some examples, the stereochemistry of all the centers were not unambiguously assigned so they can be referred to as diastereomer 1 and diastereomer 2 or enantiomer 1 or enantiomer 2 etc. and these are understood by chemists skilled in the art. In other cases, atropisomers can be observed and these are understood to convert at slow or fast rates or even not at all depending on the conditions for handling the compound. These are referred to as mixtures of atropisomers where they interconvert at ambient temperatures or as atropisomer 1 and atropisomer 2 where they were isolated. Since the compounds are identified by their properties rather than exact structural assignment from a crystal structure, it is understood in the art that where not specified, atropisomers are covered and inferred to be covered by the chemical structure.

In the method of this invention, preferred routes of administration are oral and by injection to deliver subcutaneously.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including multiple compounds; or (2) separate pharmaceutical compositions each including one of the compounds. Alternatively, the combination may be administered separately in a sequential manner wherein one treatment agent is administered first and the other second or vice versa, and the different agents could be administered on different schedules if appropriate. Such sequential administration may be close in time or remote in time. The amounts of the compound(s) of Formulas I, II, or III or salts thereof and the other pharmaceutically active agent(s) and the relative timings of administration will be selected in order to achieve the desired combined therapeutic effect.

As such, the compounds of the present invention may be used in combination with one or more agents useful in the prevention or treatment of HIV.

Examples of such agents include

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents; Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Integrase inhibitors such as raltegravir, elvitegravir, GSK1349572 (dolutegravir), GSK1265744A (cabotegravir), and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

The scope of combinations of compounds of this invention with HIV agents is not limited to those mentioned above, but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmacokinetic boosters) include, but are not limited to, ritonavir, GS-9350, and SPI-452.

Ritonavir is 10-hydroxy-2-methyl-5-(1-methyethyl)-1-1 [2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-glycoprotein (Pgp) cell transport system, thereby resulting in increased concentrations of active compound within the organism.

GS-9350 (cobicistat) is a compound for use as a pharmacological enhancer.

In one embodiment of the present invention, a compound of Formula I is used in combination with ritonavir. In one embodiment, the combination is an oral fixed dose combination. In another embodiment, the compound of Formula I is formulated as a long acting parenteral injection and ritonavir is formulated as an oral composition. In one embodiment, is a kit containing the compound of Formula I formulated as a long acting parenteral injection and ritonavir formulated as an oral composition. In another embodiment, the compound of Formula I is formulated as a long acting parenteral injection and ritonavir is formulated as an injectable composition. In one embodiment, is a kit containing the compound of Formula I formulated as a long acting parenteral injection and ritonavir formulated as an injectable composition.

In another embodiment of the present invention, a compound of Formula I is used in combination with GS-9350. In one embodiment, the combination is an oral fixed dose combination. In another embodiment, the compound of Formula I is formulated as a long acting parenteral injection and GS-9350 is formulated as an oral composition. In one embodiment, is a kit containing the compound of Formula I formulated as a long acting parenteral injection and GS-9350 formulated as an oral composition. In another embodiment, the compound of Formula I is formulated as a long acting parenteral injection and GS-9350 is formulated as an injectable composition. In one embodiment, is a kit containing the compound of Formula I formulated as a long acting parenteral injection and GS-9350 formulated as an injectable composition.

EXAMPLES

The compounds of the invention according to the various embodiments can be made by various methods available in the art, including those of the following schemes in the specific examples which follow. The structure numbering and variable numbering shown in the synthetic schemes may be distinct from, and should not be confused with, the structure or variable numbering in the claims or the rest of the specification. The variables in the schemes are meant only to illustrate how to make some of the compounds of the invention.

Abbreviations used in the schemes generally follow conventions used in the art. Some specific chemical abbreviations used in the examples are defined as follows: "DMF" for N,N-dimethylformamide; "MeOH" for methanol; "Ar" for aryl; "TFA" for trifluoroacetic acid; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HATU" for (1-[Bis(dimethylamino)methylene]-1H-1,2,3-triazolo[4,5-b]pyridinium 3-oxid hexafluorophosphate) "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t"

for triplet, "q" for quartet, "m" for multiplet, "br" for broad, "Hz" for hertz, and "α", "β", "R", "S", "E", and "Z" are stereochemical designations familiar to one skilled in the art.

The following examples are provided by way of illustration only, and should not be construed as limiting the scope of the invention. Table 1 presents additional compounds of the invention prepared using similar methods. Absolute stereochemistry was not determined in all instances. In the examples where absolute stereochemistry has not been assigned, isomers or slowly interconverting atropisomers that were separated by chiral or other chromatography are labelled as "First", "Second", etc. as per their order of elution from the column.

Methyl 6-amino-3-bromo-5-mercaptopicolinate (Int 1a)

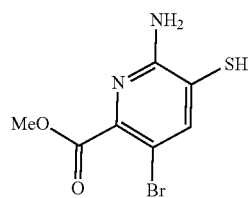

To a solution of ethyl 3-mercaptopropanoate (3.27 mL, 25.8 mmol) in DMF (100 mL) at 0° C. was added 60% NaH (1.10 g, 27.4 mmol) and the resulting mixture was stirred for 1 h. Methyl 6-amino-3,5-dibromopicolinate (5.00 g, 16.1 mmol) was then added and the mixture was stirred at room temperature for 16 h. Water was then added and the mixture was extracted with ethyl acetate (200 mL×2). The aqueous layer was then acidified with conc. HCl (pH=2) and precipitate formed was filtered, washed with water and dried under high vac to afford HCl salt of title compound (2.4 g) as yellow solid. $^1$H NMR (400 MHz, DMSO-$d_6$) δ 12.54 (br.s, 1H), 7.65 (s, 3H), 3.87 (s, 3H). LC/MS (M+H)$^+$=262.65.

Methyl 6-bromothiazolo[4,5-b]pyridine-5-carboxylate (Int 1b)

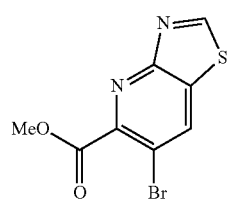 [SMILES: COC(=O)c1nc2ncsc2cc1Br]

A mixture of methyl 6-amino-3-bromo-5-mercaptopicolinate (3.00 g, 11.4 mmol) in formic acid (15 mL) was heated at 100° C. for 2 h. The mixture was then concentrated, diluted with DCM and washed with sat. NaHCO$_3$ solution, dried (Na$_2$SO$_4$), filtered and concentrated. The residue was then purified by Biotage (5-70% EtOAc/hexanes) to afford title compound (2.2 g) as an off-white solid. $^1$H NMR (400 MHz, CDCl$_3$) δ 9.38 (s, 1H), 8.65 (s, 1H), 4.06 (s, 3H). LC/MS (M+H)$^+$=274.60.

6-bromothiazolo[4,5-b]pyridine-5-carbaldehyde (Int 1c)

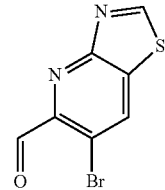 [SMILES: O=Cc1nc2ncsc2cc1Br]

To a solution of methyl 6-bromothiazolo[4,5-b]pyridine-5-carboxylate (2.10 g, 7.69 mmol) in THF (100 mL) at −78° C. was added 1M DIBAL-H (19.2 mL, 19.2 mmol) over 20 min and stirred for an additional 2.5 h at −78° C. Mixture was then quenched with methanol, diluted with ethyl acetate and washed with Sat. NH$_4$Cl solution. The organic layer was then dried (Na$_2$SO$_4$), filtered and concentrated. The residue was then purified by Biotage (5-100% EtOAc/hexanes) to afford title compound (510 mg) as an off-white solid. $^1$H NMR (400 MHz, CDCl$_3$) δ 10.30 (s, 1H), 9.45 (s, 1H), 8.71 (s, 1H). LC/MS (M+H)$^+$=242.65.

N-((6-bromothiazolo[4,5-b]pyridin-5-yl)methylene)-2-methylpropane-2-sulfinamide (Int 1d)

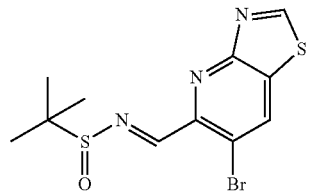 [SMILES: CC(C)(C)S(=O)/N=C/c1nc2ncsc2cc1Br]

To a solution of 6-bromothiazolo[4,5-b]pyridine-5-carbaldehyde (0.500 g, 2.057 mmol) in CH$_2$Cl$_2$ (20 mL) was added 2-methylpropane-2-sulfinamide (274 mg, 2.26 mmol) followed by cupric sulfate (657 mg, 4.11 mmol) and the resulting mixture was stirred at room temp for 16 h. Mixture was then filtered through a pad of Celite and the pad was washed with dichloromethane. The filtrate was then concentrated and purified by Biotage (5-100% EtOAc/hexanes) to afford title compound (480 mg). $^1$H NMR (400 MHz, CDCl$_3$) δ 9.39 (s, 1H), 9.15 (s, 1H), 8.67 (s, 1H), 1.36 (s, 9H). LC/MS (M+H)$^+$=345.55. (Note: the E/Z makeup was not determined).

N-(1-(6-bromothiazolo[4,5-b]pyridin-5-yl)-2-(3,5-difluorophenyl)ethyl)-2-methylpropane-2-sulfinamide (Int 1e)

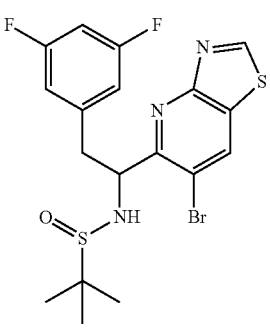 [SMILES: CC(C)(C)S(=O)NC(Cc1cc(F)cc(F)c1)c1nc2ncsc2cc1Br]

To a stirred suspension of magnesium turnings (126 mg, 5.20 mmol) in ethyl ether (7 mL) was added dropwise 1-(bromomethyl)-3,5-difluorobenzene (0.67 mL, 5.20 mmol) over 10 min and the mixture was stirred at room temp for 1 h. This Grignard reagent was then added slowly to a previously stirred solution of (E)-N-((6-bromothiazolo[4,5-b]pyridin-5-yl)methylene)-2-methylpropane-2-sulfinamide (900 mg, 2.60 mmol) in THF (20 mL) at −78° C. and the mixture was allowed to warm to room temp and stirred for an additional 1 h. Mixture was then quenched with saturated ammonium chloride solution and extracted with ethyl acetate (50 mL). Organic layer was then washed with water (25 mL) and brine (25 mL), dried (Na$_2$SO$_4$), filtered and concentrated. The residue was then purified by Biotage (5-100% EtOAc/hexanes) to afford two diastereomers, each as a racemate. [Note: Although inconsequential for the current process, the stereoseparation was done in order to get a read on the diastereoselectivity of this procedure.]

First-eluting diastereomer (660 mg, light yellow solid): $^1$H NMR (400 MHz, CDCl$_3$) δ 9.31 (s, 1H), 8.52 (s, 1H), 6.78 (dd, J=8.3, 2.0 Hz, 2H), 6.73-6.56 (m, 1H), 5.27 (td, J=9.4, 5.0 Hz, 1H), 5.10 (d, J=9.5 Hz, 1H), 3.20 (dd, J=13.8, 4.8 Hz, 1H), 2.99 (dd, J=13.8, 9.3 Hz, 1H), 1.15 (s, 9H). LC/MS (M+H)$^+$=475.70.

Second-eluting diastereomer (140 mg): $^1$H NMR (400 MHz, CDCl$_3$) δ 9.32 (s, 1H), 8.47 (s, 1H), 6.67-6.57 (m, 3H), 5.42-5.33 (m, 1H), 4.61 (d, J=10.0 Hz, 1H), 3.48-3.35 (m, 2H), 1.14 (s, 9H). LC/MS (M+H)$^+$=475.70.

1-(6-bromothiazolo[4,5-b]pyridin-5-yl)-2-(3,5-difluorophenyl)ethanamine, HCl (Int 1f)

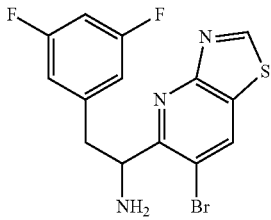 [SMILES: NC(Cc1cc(F)cc(F)c1)c1nc2ncsc2cc1Br]

To a solution of N-(1-(6-bromothiazolo[4,5-b]pyridin-5-yl)-2-(3,5-difluorophenyl)ethyl)-2-methylpropane-2-sulfinamide (770 mg, 1.623 mmol) in 1,4-Dioxane (5 mL) was added 4M HCl (4.06 mL, 16.2 mmol) in dioxane and the resulting mixture was stirred at room temp for 2 h. Mixture was then concentrated and dried under high vac to afford the HCl salt of title compound (640 mg) as an off-white solid. $^1$H NMR (400 MHz, DMSO-d$_6$) δ 9.84 (s, 1H), 9.11 (s, 1H), 8.75 (br.s, 3H), 7.15 (tt, J=9.4, 2.4 Hz, 1H), 6.94-6.75 (m, 2H), 5.08 (q, J=5.6 Hz, 1H), 3.27 (d, J=7.0 Hz, 2H). LC/MS (M+H)$^+$=369.55.

tert-butyl (1-(6-bromothiazolo[4,5-b]pyridin-5-yl)-2-(3,5-difluorophenyl)ethyl)carbamate (Int 1g)

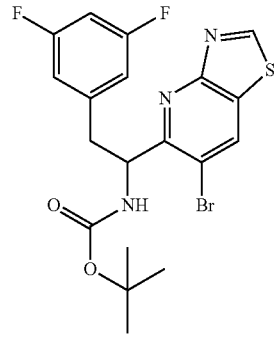 [SMILES: CC(C)(C)OC(=O)NC(Cc1cc(F)cc(F)c1)c1nc2ncsc2cc1Br]

To a stirred solution of compound 1-(6-bromothiazolo[4,5-b]pyridin-5-yl)-2-(3,5-difluorophenyl)ethanamine, HCl (90.0 mg) in DCM (3 mL) at 0° C. was added TEA (0.062 mL, 0.443 mmol) followed by Boc$_2$O (0.062 mL, 0.266 mmol) and the mixture was warmed to room temp and stirred for an additional 2 h. The mixture was then diluted with DCM (25 mL) and washed with water (10 mL) followed by brine (10 mL). The organic layer was then dried (Na$_2$SO$_4$), filtered and concentrated. The residue was then purified by biotage (5-50% EtOAc/hexanes) to afford the title product (80 mg) as off-white solid. $^1$H NMR (400 MHz, DMSO-d$_6$) δ 9.73 (s, 1H), 9.01 (s, 1H), 7.60 (d, J=8.8 Hz, 1H), 7.16-6.97 (m, 3H), 5.36-5.13 (m, 1H), 3.10-2.85 (m, 2H), 1.27 (s, 9H). LC/MS (M+H)$^+$=471.50 tert-butyl (1-(6-(benzo[d]thiazol-5-yl)thiazolo[4,5-b]pyridin-5-yl)-2-(3,5-difluorophenyl)ethyl)carbamate (Int 1h)

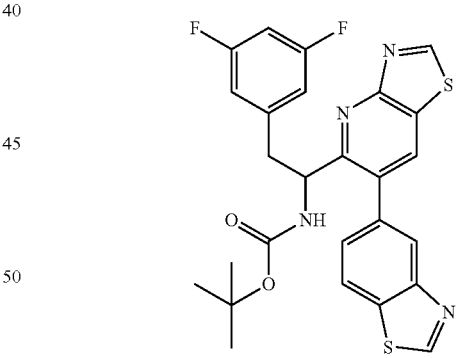

To a microwave vial was added tert-butyl (1-(6-bromothiazolo[4,5-b]pyridin-5-yl)-2-(3,5-difluorophenyl)ethyl)carbamate (50 mg, 0.106 mmol), 5-(4,4,5,5-tetramethyl-1,3,2-dioxaborolan-2-yl)benzo[d]thiazole (33.3 mg, 0.128 mmol) followed by 1,4-Dioxane (3 mL) and 1N sodium bicarbonate (0.638 mL, 0.638 mmol) and the mixture was degassed for 10 min. PdCl$_2$(dppf)-CH$_2$Cl$_2$ adduct (8.7 mg, 10.6 μmol) was then added and the mixture was heated in microwave at 140° C. for 1 h. Mixture was then diluted with ethyl acetate (25 mL) and washed with water (10 mL) and brine (10 mL), dried (Na$_2$SO$_4$), filtered and concentrated. The residue was then purified by Biotage (5-80% EtOAc/hexanes) to afford the title product (27 mg) as off-white solid.

¹H NMR (400 MHz, CDCl₃) 9.45-9.37 (m, 1H), 9.11 (s, 1H), 8.20 (s, 1H), 8.06 (d, J=8.3 Hz, 1H), 7.84-7.75 (m, 1H), 7.32 (br d, J=4.5 Hz, 1H), 6.63-6.49 (m, 1H), 6.17 (br d, J=6.3 Hz, 2H), 6.09-5.97 (m, 1H), 5.50-5.32 (m, 1H), 3.01 (br d, J=7.0 Hz, 2H), 1.41 (s, 9H). LC/MS (M+H)⁺=525.60.

1-(6-(benzo[d]thiazol-5-yl)thiazolo[4,5-b]pyridin-5-yl)-2-(3,5-difluorophenyl)ethanamine, HCl (Int 1i)

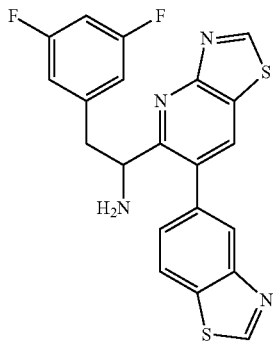 [SMILES: NC(Cc1cc(F)cc(F)c1)c1nc2ncsc2cc1-c1ccc2scnc2c1]

To a solution of tert-butyl (1-(6-(benzo[d]thiazol-5-yl)thiazolo[4,5-b]pyridin-5-yl)-2-(3,5-difluorophenyl)ethyl)carbamate (25 mg, 0.048 mmol) in MeOH (1 mL) and 1,4-Dioxane (1 mL) was added 4M HCl (0.238 mL, 0.953 mmol) in dioxane and the mixture was stirred at room temp for 1 h. Reaction mixture was then concentrated and dried under high vacuum to afford title product (22 mg) as off-white solid, which was used as is in the next step. ¹H NMR (400 MHz, DMSO-d₆) δ 9.90 (s, 1H), 9.52 (s, 1H), 8.73 (br d, J=4.0 Hz, 3H), 8.28 (d, J=8.3 Hz, 1H), 7.87 (br s, 1H), 7.27 (br d, J=7.8 Hz, 1H), 6.99 (tt, J=9.4, 2.3 Hz, 1H), 6.30 (dd, J=8.0, 2.0 Hz, 2H), 4.85-4.72 (m, 1H), 3.52-3.42 (m, 1H), 3.23-3.05 (m, 1H). LC/MS (M+H)⁺=424.65.

N-(1-(6-(benzo[d]thiazol-5-yl)thiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Separated Enantiomers are Examples 1.1 & 1.2)

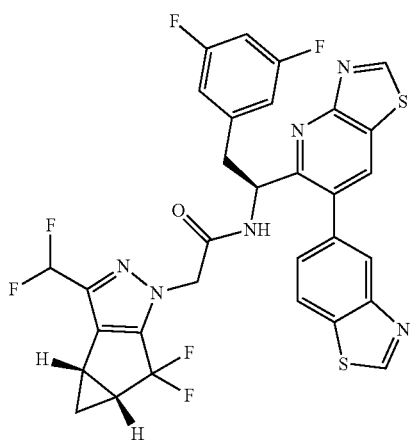 [SMILES: O=C(Cn1nc(C(F)F)c2c1C(F)(F)[C@@H]1C[C@H]21)N[C@@H](Cc1cc(F)cc(F)c1)c1nc2ncsc2cc1-c1ccc2scnc2c1]

To a mixture of 1-(6-(benzo[d]thiazol-5-yl)thiazolo[4,5-b]pyridin-5-yl)-2-(3,5-difluorophenyl)ethanamine, HCl (22 mg) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (16.4 mg, 0.062 mmol) in DMF (1 mL) was added DIEA (0.033 mL, 0.191 mmol) followed by HATU (23.6 mg, 0.062 mmol) and the resulting mixture was stirred at room temp for 16 h. Reaction mixture was then purified by prep HPLC to afford title product (22 mg), which was subjected to chiral separation (chiralcel OD 21×250 mm 10 μm, 25-100% heptane/ethanol) to afford two diastereomers as Example 1.1 and 1.2

Example 1.1 (First Eluting Diastereomer, 6.3 mg)

¹H NMR (500 MHz, Methanol-d₄) δ 10.60 (d, J=0.9 Hz, 1H), 10.26 (s, 1H), 9.81 (br d, J=7.9 Hz, 1H), 9.40 (s, 1H), 9.04 (d, J=7.9 Hz, 1H), 8.78 (s, 1H), 8.23 (br d, J=7.9 Hz, 1H), 7.74-7.65 (m, 1H), 7.83-7.54 (m, 1H), 7.23 (br d, J=7.3 Hz, 2H), 6.27-6.11 (m, 1H), 5.64-5.48 (m, 2H), 4.02-3.94 (m, 1H), 3.91-3.84 (m, 1H), 3.74 (q, J=7.3 Hz, 2H), 2.18-2.17 (m, 1H), 2.00 (t, J=7.2 Hz, 2H), 1.78-1.62 (m, 1H). LC/MS (M+H)⁺=671.1.

Example 1.2 (Second Eluting Diastereomer, 7.1 mg)

¹H NMR (500 MHz, Methanol-d₄) δ 10.60 (d, J=0.9 Hz, 1H), 10.26 (s, 1H), 9.81 (br d, J=7.9 Hz, 1H), 9.40 (s, 1H), 9.04 (d, J=7.9 Hz, 1H), 8.78 (s, 1H), 8.23 (br d, J=7.9 Hz, 1H), 7.74-7.65 (m, 1H), 7.83-7.54 (m, 1H), 7.23 (br d, J=7.3 Hz, 2H), 6.27-6.11 (m, 1H), 5.64-5.48 (m, 2H), 4.02-3.94 (m, 1H), 3.91-3.84 (m, 1H), 3.74 (q, J=7.3 Hz, 2H), 2.18-2.17 (m, 1H), 2.00 (t, J=7.2 Hz, 2H), 1.78-1.62 (m, 1H). LC/MS (M+H)⁺=671.1.

tert-butyl (1-(6-bromothiazolo[4,5-b]pyridin-5-yl)-2-(3,5-difluorophenyl)ethyl)carbamate (Int 1g-E1 & Int 1g-E2)

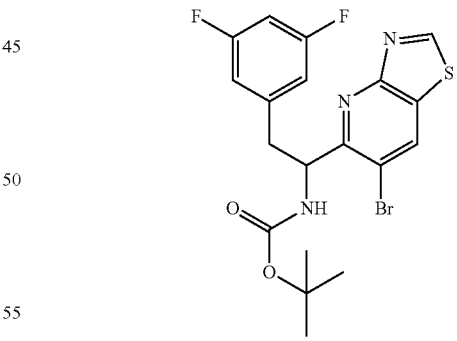

The racemic mixture (Int 1g) was submitted to chiral SFC separation (Chiralpak AD-H preparative column, 30×250 mm, 5 μm, Mobile Phase: 30% MeOH in CO₂, 150 bar) to afford the individual enantiomers.

Int 1g-E1 (first eluting enantiomer, 54 mg): ¹H NMR (400 MHz, Methanol-d₄) δ 9.61 (s, 1H), 8.83 (s, 1H), 6.87 (br d, J=6.8 Hz, 2H), 6.81-6.73 (m, 1H), 6.80-6.71 (m, 1H), 5.59 (br dd, J=9.0, 5.3 Hz, 1H), 3.34-3.29 (m, 12H), 3.29-3.18 (m, 1H), 3.08-2.90 (m, 1H), 1.37 (s, 7.8H), 1.26 (s, 1.2H). LC/MS (M+H)⁺=471.55.

Int 1g-E2 (second eluting enantiomer, afforded the relatively more active final product, 60 mg).

tert-butyl (1-(6-(4-chloro-1-methyl-3-(methylsulfonamido)-1H-indazol-7-yl)thiazolo[4,5-b]pyridin-5-yl)-2-(3,5-difluorophenyl)ethyl)carbamate (Int 2a, (Single Enantiomer))

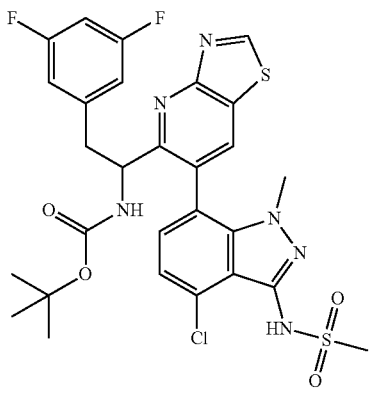 [SMILES: Cn1nc(NS(C)(=O)=O)c2c(Cl)ccc(-c3cc4scnc4nc3C(Cc3cc(F)cc(F)c3)NC(=O)OC(C)(C)C)c21]

To a microwave vial was added tert-butyl (1-(6-bromothiazolo[4,5-b]pyridin-5-yl)-2-(3,5-difluorophenyl)ethyl)carbamate (Int 1g-E2, 45 mg, 0.096 mmol), N-(4-chloro-1-methyl-7-(4,4,5,5-tetramethyl-1,3,2-dioxaborolan-2-yl)-1H-indazol-3-yl)methanesulfonamide (44.3 mg, 0.115 mmol) followed by 1,4-dioxane (4 mL) and IN sodium bicarbonate (0.574 mL, 0.574 mmol) and the mixture was degassed for 10 min. $PdCl_2(dppf)\text{-}CH_2Cl_2$ adduct (7.8 mg, 9.6 µmol) was then added and the mixture was heated in microwave at 140° C. for 1 h. The reaction mixture was then filtered through a plug of ceilite, and the pad was washed with ethyl acetate. Water was then added to the mixture and extracted with ethyl acetate (2×25 mL). The combined organic layer was dried ($Na_2SO_4$), filtered and concentrated to the title compound (30 mg) as a mixture of atropisomers (in a ~1:3 ratio by LC/MS). Crude was used as is in the next step without further purification. LC/MS $(M+H)^+=649.12$, (M-tBu)=592.50.

N-(7-(5-(1-amino-2-(3,5-difluorophenyl)ethyl)thiazolo[4,5-b]pyridin-6-yl)-4-chloro-1-methyl-1H-indazol-3-yl)methanesulfonamide, HCl (Int 2b, (Single Enantiomer))

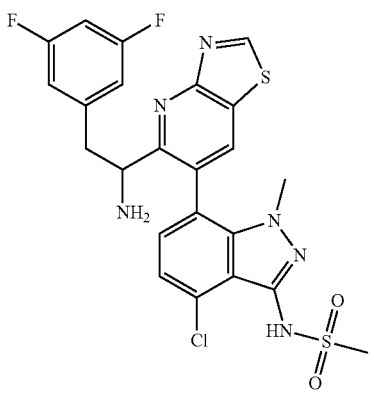 [SMILES: Cn1nc(NS(C)(=O)=O)c2c(Cl)ccc(-c3cc4scnc4nc3C(N)Cc3cc(F)cc(F)c3)c21]

To a solution of tert-butyl (1-(6-(4-chloro-1-methyl-3-(methylsufonamido)-1H-indazol-7-yl)thiazolo[4,5-b]pyridin-5-yl)-2-(3,5-difluorophenyl)ethyl)carbamate (Int 2a, 30.0 mg, 0.046 mmol) in methanol (1 mL) and 1,4-Dioxane (1 mL) was added 4M HCl (0.231 mL, 0.924 mmol) in dioxane and the resulting mixture was stirred at room temp for 3 h. The reaction mixture was then concentrated and dried under high vac to afford the title product (27 mg) as brown solid, which was used in the next step without further purification. LC/MS $(M+H)^+=549.10$.

N-(1-(6-(4-chloro-1-methyl-3-(methylsulfonamido)-1H-indazol-7-yl)thiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 1.3, 1.4, 1.5, & 1.6)

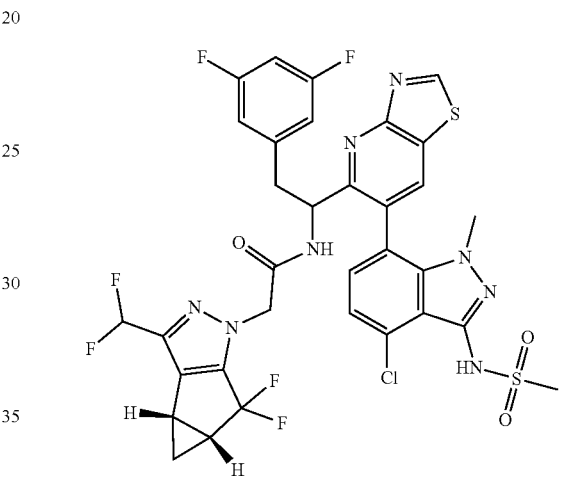

To a mixture of N-(7-(5-(1-amino-2-(3,5-difluorophenyl)ethyl)thiazolo[4,5-b]pyridin-6-yl)-4-chloro-1-methyl-1H-indazol-3-yl)methanesulfonamide, HCl (Int 2b, 45 mg) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (26.4 mg, 0.100 mmol) in DMF (2 mL) was added DIEA (0.054 mL, 0.307 mmol) followed by HATU (38.0 mg, 0.100 mmol) and the resulting mixture was stirred at room temp for 16 h. The reaction mixture was then purified by prep HPLC to afford a mixture of atropisomers (26 mg, approx 25:75). $^1$H NMR (400 MHz, DMSO-$d_6$) δ 9.86-9.84 (m, 1H), 9.22 (d, J=8.5 Hz, 0.7H), 9.06 (d, J=8.0 Hz, 0.3H), 8.72 (s, 0.3H), 8.69 (s, 0.7H), 7.16-6.90 (m, 4H), 6.55 (dd, J=8.3, 2.3 Hz, 1.4H), 6.47-6.40 (m, 0.6H), 5.18-5.05 (m, 0.3H), 4.97-4.86 (m, 0.7H), 4.80-4.58 (m, 2H), 3.19-3.12 (m, 4.5H), 3.06-2.96 (m, 4.5H), 2.90 (s, 1H), 2.46-2.41 (m, 1H), 1.44-1.29 (m, 1H), 0.96-0.90 (m, 0.3H), 0.83 (br d, J=2.8 Hz, 0.7H). LC/MS $(M+H)^+=795.0$.

Atropisomers were separated (Column: Xbridge prep C18, 30×50 mm, 5 µm; Flow rate: 40 mL/min; Mobile Phase A: 10 mM $NH_4OAc$ in 95% Water/5% ACN; Mobile Phase B: 10 mM $NH_4OAc$ in 5% Water/95% ACN; 20% B to 90% B over 20 min, then hold for 5 min at 100% B) but slowly interconverts when left in methanol at ambient temperature according to an LC/MS analysis done under the following conditions: Column: Xbridge C18 3.5 µm, 3.0×150 mm, Flow rate: 1 mL/min; Mobile Phase A: 10 mmol ($NH_4$) $HCO_3$ in $H_2O$ (pH=9.5): MeOH (95:5); Mobile Phase B: 10 mmol (NH₄)HCO₃ in H₂O (pH=9.5): MeOH (5:95); 10% B to 100% B over 15 min, then hold for 3 min at 100% B.

Example 1.3 (First Eluting Isomer (Diastereomer 2, Atropisomer 1)

(92:8 after 2 h, 63:37 after 24 h and 42:58 after 2 days)

Example 1.4 (Second Eluting Isomer (Diastereomer 2, Atropisomer 1))

(6:94 after 2 h, 23:77 after 24 h and 30:70 after 2 days)
Example 1.5 and 1.6 were prepared from Int 1g-E1 according to procedure described for Example 1.3 and 1.4.

Example 1.5 (First Eluting Isomer (Diastereomer 1, Atropisomer 1))

LC/MS (M+H)⁺=795.0.

Example 1.6 (Second Eluting Isomer (Diastereomer 1, Atropisomer 2))

LC/MS (M+H)⁺=795.0.

N-(1-(6-(4-chloro-1-methyl-3-(methylsulfonamido)-1H-indazol-7-yl)thiazolo[4,5-b]pyridin-5-yl)-2-(3,5-difluorophenyl)ethyl)-2-(5-hydroxy-1H-indol-3-yl)acetamide (Example 1.7)

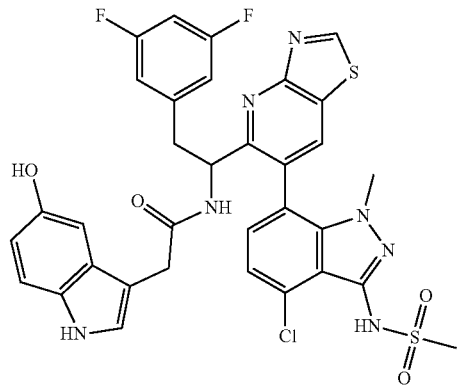 [SMILES: Cn1nc(NS(C)(=O)=O)c2c(Cl)ccc(-c3cc4scnc4nc3C(Cc3cc(F)cc(F)c3)NC(=O)Cc3c[nH]c4ccc(O)cc34)c21]

To a mixture of N-(7-(5-(1-amino-2-(3,5-difluorophenyl)ethyl)thiazolo[4,5-b]pyridin-6-yl)-4-chloro-1-methyl-1H-indazol-3-yl)methanesulfonamide HCl (Int 2b, 22 mg) and 2-(5-hydroxy-1H-indol-3-yl)acetic acid (9.96 mg, 0.052 mmol) in DMF (1 mL) was added DIEA (0.028 mL, 0.160 mmol) followed by HATU (19.81 mg, 0.052 mmol) and the resulting mixture was stirred at room temp for 16 h. The reaction mixture was then purified by prep HPLC to afford the title product (8 mg) as a mixture of atropisomers (approx 25:75). ¹H NMR (500 MHz, DMSO-d₆) δ 10.42-10.37 (m, 0.4H), 10.34-10.27 (m, 0.6H), 9.84-9.81 (m, 1H), 8.69 (s, 0.6H), 8.67-8.66 (s, 0.4H), 8.66 (s, 1H), 8.50 (d, J=8.4 Hz, 0.6H), 8.34 (d, J=8.1 Hz, 0.4H), 7.41-7.29 (m, 0.4H), 7.25 (d, J=7.3 Hz, 0.6H), 7.14-6.86 (m, 4H), 6.85-6.83 (m, 1H), 6.68 (d, J=2.2 Hz, 0.6H), 6.62-6.59 (m, 0.4H), 6.57-6.53 (m, 2H), 6.52-6.45 (m, 1H), 5.16-5.08 (m, 0.4H), 4.97 (td, J=8.7, 5.3 Hz, 0.6H), 3.45-3.26 (m, 2H), 3.12-3.01 (m, 1H), 2.94 (s, 1H), 2.51-2.50 (m, 6H). LC/MS (M+H)⁺=722.1.

Methyl 6-bromo-2-methylthiazolo[4,5-b]pyridine-5-carboxylate (Int 3a)

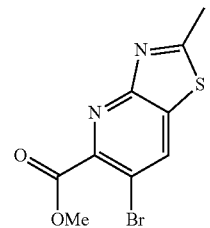

To a suspension of methyl 6-amino-3-bromo-5-mercaptopicolinate (500.0 mg, 1.900 mmol) in DCE (25 mL) was added acetyl chloride (0.136 mL, 1.900 mmol) and the mixture was stirred for 30 min at room temp and then heated at 80° C. for 3 h. The reaction mixture was then cooled to room temperature, diluted with dichloromethane and washed with water, dried (Na₂SO₄), filtered and concentrated to afford the title compound (480 mg) as off-white solid. ¹H NMR (400 MHz, CDCl₃) δ 8.47 (s, 1H), 4.04 (s, 3H), 2.92 (s, 3H). LC/MS (M+H)⁺=286.6.

6-Bromo-2-methylthiazolo[4,5-b]pyridine-5-carbaldehyde (Int 3b)

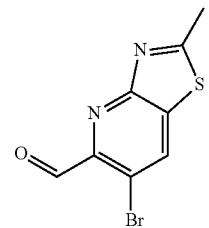

To a solution of methyl 6-bromo-2-methylthiazolo[4,5-b]pyridine-5-carboxylate (515 mg, 1.79 mmol) in THF (25 mL) at −78° C. was added 1M DIBAL-H (3.59 mL, 3.59 mmol) over 20 min and stirred for an additional 2.5 h at −78° C. Mixture was then quenched with methanol, diluted with ethyl acetate and washed with sat. NH₄Cl solution. The organic layer was then dried (Na₂SO₄), filtered and concentrated. The residue was then purified by Biotage (5-100% EtOAc/hexanes) to afford the title compound (280 mg) as off-white solid. ¹H NMR (400 MHz, CDCl₃) δ 10.24 (s, 1H), 8.53 (s, 1H), 2.97 (s, 3H). LC/MS (M+H)⁺=256.6.

N-((6-bromo-2-methylthiazolo[4,5-b]pyridin-5-yl)methylene)-2-methylpropane-2-sulfinamide (Int 3c)

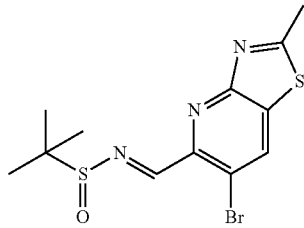 [SMILES: Cc1nc2nc(/C=N/S(=O)C(C)(C)C)c(Br)cc2s1]

To a solution of 6-bromo-2-methylthiazolo[4,5-b]pyridine-5-carbaldehyde (280 mg, 1.089 mmol) in CH$_2$Cl$_2$ (15 mL) was added 2-methylpropane-2-sulfinamide (145 mg, 1.20 mmol) followed by cupric sulfate (348 mg, 2.178 mmol) and the resulting mixture was stirred at room temp for 16 h. Mixture was then filtered through a pad of Celite and the pad was washed with dichloromethane. The filtrate was then concentrated and purified by Biotage (5-100% EtOAc/hexanes) to afford the title compound (350 mg) as white solid. $^1$H NMR (400 MHz, CDCl$_3$) δ 9.10 (s, 1H), 8.49 (s, 1H), 2.94 (s, 3H), 1.34 (s, 9H). LC/MS (M+H)$^+$=359.65.

N-(1-(6-bromo-2-methylthiazolo[4,5-b]pyridin-5-yl)-2-(3,5-difluorophenyl)ethyl)-2-methylpropane-2-sulfinamide (Int 3d)

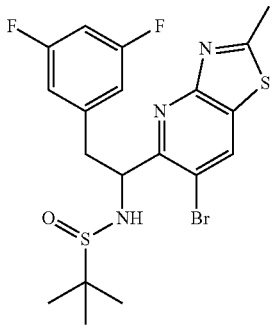 [SMILES: Cc1nc2nc(C(Cc3cc(F)cc(F)c3)NS(=O)C(C)(C)C)c(Br)cc2s1]

To a stirred solution of magnesium turning (47.2 mg, 1.943 mmol) in ethyl ether (3 mL) was added drop wise 1-(bromomethyl)-3,5-difluorobenzene (0.251 mL, 1.943 mmol) and the mixture was stirred at rt for 1 hr. This Grignard reagent was then added slowly to a previously stirred solution of N-((6-bromo-2-methylthiazolo[4,5-b]pyridin-5-yl)methylene)-2-methylpropane-2-sulfinamide (350 mg, 0.971 mmol) in THF (10 mL) at −78° C. and the mixture was allowed to warm to room temp and stirred for an additional 1 h. The reaction mixture was then quenched with saturated ammonium chloride solution and extracted with ethyl acetate. Organic layer was then washed with water and brine, dried (Na$_2$SO$_4$), filtered and concentrated. The residue was then purified by Biotage (5-100% EtOAc/hexanes) and although the two diastereomers were separable and they were mixed (290 mg) and processed as such.

1-(6-bromo-2-methylthiazolo[4,5-b]pyridin-5-yl)-2-(3,5-difluorophenyl)ethan-1-amine (Int 3e)

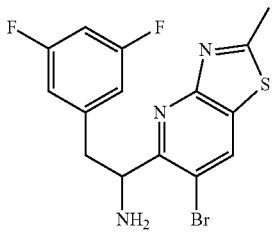

To a solution of N-(1-(6-bromo-2-methylthiazolo[4,5-b]pyridin-5-yl)-2-(3,5-difluorophenyl)ethyl)-2-methylpropane-2-sulfinamide (290 mg, 0.594 mmol) in 1,4-Dioxane (5 mL) was added 4M HCl (1.48 mL, 5.94 mmol) in dioxane and the resulting mixture was stirred at room temp for 2 h. The reaction mixture was then concentrated and dried under high vacuum to afford the title compound (230 mg) as off-white solid. $^1$H NMR (400 MHz, DMSO-d$_6$) δ 8.93 (s, 1H), 8.79 (br d, J=3.5 Hz, 3H), 7.13 (tt, J=9.5, 2.1 Hz, 1H), 6.83 (br d, J=6.3 Hz, 2H), 5.08-4.97 (m, 1H), 3.36-3.20 (m, 2H), 2.90 (s, 3H). LC/MS (M+H)$^+$=383.60.

tert-butyl (1-(6-bromo-2-methylthiazolo[4,5-b]pyridin-5-yl)-2-(3,5-difluorophenyl)ethyl)carbamate (Int 3f-E1 and Int 3f-E2)

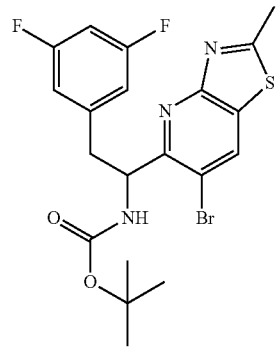 [SMILES: Cc1nc2nc(C(Cc3cc(F)cc(F)c3)NC(=O)OC(C)(C)C)c(Br)cc2s1]

To a stirred solution of compound 1-(6-bromo-2-methylthiazolo[4,5-b]pyridin-5-yl)-2-(3,5-difluorophenyl)ethan-1-amine (230 mg, 0.599 mmol) in DCM (5 mL) at 0° C. was added TEA (0.167 mL, 1.197 mmol) followed by Boc$_2$O (0.169 mL, 0.718 mmol) and the resulting mixture was allowed to warm to room temperature and stirred for an additional 2 h. The mixture was then diluted with DCM (25 mL) and washed with water (10 mL), brine (10 mL), dried (Na$_2$SO$_4$), filtered and concentrated. The residue was then purified by Biotage (5-40% EtOAc/hexanes) to afford 250 mg of racemic mixture which was submitted for chiral SFC separation (Chiralpak AD-H preparative column, 30×250 mm, 5 μm, Mobile Phase: 30% MeOH in CO$_2$, 150 bar) to afford two enantiomers.

Int 3f-E1 (first eluting enantiomer, 85 mg): $^1$H NMR (400 MHz, CDCl$_3$) δ 8.34 (s, 1H), 6.74-6.56 (m, 3H), 6.01 (br d, J=9.0 Hz, 1H), 5.70-5.52 (m, 1H), 3.20 (dd, J=13.3, 6.0 Hz, 1H), 3.03-2.97 (m, 1H), 2.92 (s, 3H), 1.39 (s, 9H). LC/MS (M+H)$^+$=483.60. Int 3f-E2 (second eluting enantiomer, 90 mg): affords the relatively more active final product.

tert-butyl (1-(6-(4-chloro-1-methyl-3-(methylsulfonamido)-1H-indazol-7-yl)-2-methylthiazolo[4,5-b]pyridin-5-yl)-2-(3,5-difluorophenyl)ethyl)carbamate (Int 3g (Single Enantiomer as Mix of Atropisomers))

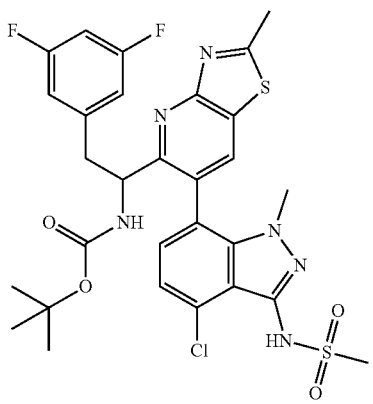 [SMILES: Cc1nc2nc(C(Cc3cc(F)cc(F)c3)NC(=O)OC(C)(C)C)c(-c3ccc(Cl)c4c(NS(C)(=O)=O)nn(C)c34)cc2s1]

To a microwave vial was added tert-butyl (1-(6-bromo-2-methylthiazolo[4,5-b]pyridin-5-yl)-2-(3,5-difluorophenyl)ethyl)carbamate (Int 3f-E2, 90.0 mg, 0.186 mmol), N-(4-chloro-1-methyl-7-(4,4,5,5-tetramethyl-1,3,2-dioxaborolan-2-yl)-1H-indazol-3-yl)methanesulfonamide (86 mg, 0.223 mmol) followed by 1,4-dioxane (3 mL) and 1N sodium bicarbonate (1.12 mL, 1.12 mmol) and the mixture was degassed for 10 min. $PdCl_2(dppf)\text{-}CH_2Cl_2$ adduct (15.17 mg, 0.019 mmol) was then added and the mixture was heated in microwave at 140° C. for 1 h. The reaction mixture was then filtered through a plug of Ceilite and washed with ethyl acetate. Water was then added to the mixture and extracted with ethyl acetate (2×25 mL). The organic layer was dried ($Na_2SO_4$), filtered and concentrated. The residue was then purified by biotage (5-100% EtOAc/hexanes) to afford the title compound (75 mg) as a mixture of atropisomers (~1:3 by LC/MS). $^1$H NMR (400 MHz, $CDCl_3$) δ 8.09 (br s, 0.2H), 8.03 (s, 0.8H), 7.40-7.28 (m, 1H), 7.26-7.16 (m, 0.4H), 6.96 (d, J=7.8 Hz, 0.6H), 6.68-6.45 (m, 1.2H), 6.34-6.23 (m, 1.8H), 6.19 (d, J=7.5 Hz, 1H), 5.82 (d, J=9.5 Hz, 0.6H), 5.60 (br d, J=9.8 Hz, 0.4H), 5.24 (br d, J=6.0 Hz, 0.3H), 4.79 (td, J=8.9, 6.3 Hz, 0.7H), 3.42 (s, 1H), 3.38 (s, 2H), 3.31 (s, 2H), 3.25-3.09 (m, 1H), 3.06-2.91 (m, 5H), 1.39 (s, 3H), 1.34 (s, 6H). LC/MS $(M+H)^+=662.45$, $(M\text{-}tBu)=606.50$.

N-(7-(5-(1-amino-2-(3,5-difluorophenyl)ethyl)-2-methylthiazolo[4,5-b]pyridin-6-yl)-4-chloro-1-methyl-1H-indazol-3-yl)methanesulfonamide, HCl (Int 3h)

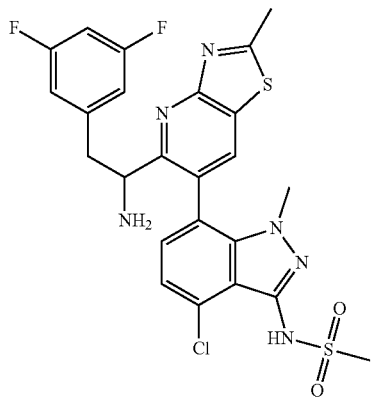 [SMILES: Cc1nc2nc(C(N)Cc3cc(F)cc(F)c3)c(-c3ccc(Cl)c4c(NS(C)(=O)=O)nn(C)c34)cc2s1]

To a solution of tert-butyl (1-(6-(4-chloro-1-methyl-3-(methylsulfonamido)-1H-indazol-7-yl)-2-methylthiazolo[4,5-b]pyridin-5-yl)-2-(3,5-difluorophenyl)ethyl)carbamate (Int 3g) (70 mg, 0.106 mmol) in methanol (1 mL) and 1,4-dioxane (1 mL) was added 4M HCl (0.528 mL, 2.111 mmol) in dioxane and the resulting mixture was stirred at room temp for 3 h. The reaction mixture was then concentrated and dried under high vacuum to afford the title compound (59 mg) as brown solid, which was used in the next step without further purification. LC/MS $(M+H)^+=563.55$

N-(1-(6-(4-chloro-1-methyl-3-(methylsulfonamido)-1H-indazol-7-yl)-2-methylthiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 2.1 & 2.2 (Each Compound is a Homochiral Diastereomer as a Mix of Atropisomers)

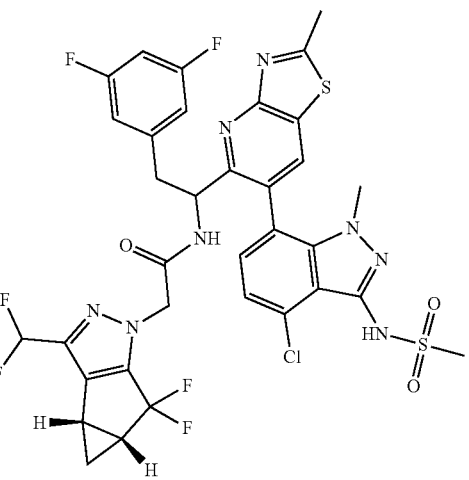

To a mixture of N-(7-(5-(1-amino-2-(3,5-difluorophenyl)ethyl)-2-methylthiazolo[4,5-b]pyridin-6-yl)-4-chloro-1-methyl-1H-indazol-3-yl)methanesulfonamide, HCl (Int 3h) (30.0 mg) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (15.5 mg, 0.059 mmol) in DMF (1.5 mL) was added DIEA (0.037 mL, 0.213 mmol) followed by HATU (22.3 mg, 0.059 mmol) and the resulting mixture was stirred at room temp for 16 h. Mixture was then purified by prep HPLC and although the atropisomers were separable they were recombined to afford Example 2.1 (31 mg; atropisomers ratio, ~25:75): $^1$H NMR (500 MHz, Methanol-$d_4$) δ 8.39 (s, 0.3H), 8.36 (s, 0.7H), 7.26-7.19 (m, 0.3H), 7.13 (d, J=7.7 Hz, 0.7H), 6.76-6.69 (m, 1H), 6.65-6.57 (m, 1H), 6.46 (br d, J=6.2 Hz, 0.6H), 6.40-6.34 (m, 1.4H), 5.35 (dd, J=8.8, 5.9 Hz, 0.3H), 5.14 (t, J=7.2 Hz, 0.7H), 4.77-4.68 (m, 1H), 3.42-3.37 (m, 1H), 3.32 (s, 3H), 3.28 (s, 1H), 3.26 (s, 2H), 3.22 (dd, J=13.6, 7.0 Hz, 1H), 3.08-3.04 (m, 1H), 3.01-2.99 (m, 3H), 2.96 (s, 1H), 2.54-2.40 (m, 2H), 1.40-1.33 (m, 1H), 1.10-0.91 (m, 1H). LC/MS $(M+H)^+=809.0$.

Example 2.2 was prepared from Int 3f-E1 according to the procedure described for Example 2.1

N-(1-(6-(4-chloro-1-methyl-3-(methylsulfonamido)-1H-indazol-7-yl)-2-methylthiazolo[4,5-b]pyridin-5-yl)-2-(3,5-difluorophenyl)ethyl)-2-(3-(difluoromethyl)-5,6-dihydrocyclopenta[c]pyrazol-1(4H)-yl)acetamide (Example 2.3 & 2.4) (Each of the Examples is a Single Enantiomer which is a Mix of Atropisomers)

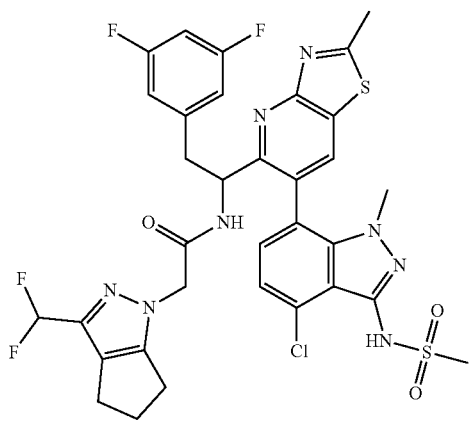 [SMILES: Cc1nc2nc(C(Cc3cc(F)cc(F)c3)NC(=O)Cn3nc(C(F)F)c4c3CCC4)c(-c3ccc(Cl)c4c(NS(C)(=O)=O)nn(C)c34)cc2s1]

To a mixture of N-(7-(5-(1-amino-2-(3,5-difluorophenyl)ethyl)-2-methylthiazolo[4,5-b]pyridin-6-yl)-4-chloro-1-methyl-1H-indazol-3-yl)methanesulfonamide, HCl (Int 3h, 30 mg) and 2-(3-(difluoromethyl)-5,6-dihydrocyclopenta[c]pyrazol-1(4H)-yl)acetic acid (12.7 mg, 0.059 mmol) in DMF (1.5 mL) was added DIEA (0.037 mL, 0.213 mmol) followed by HATU (22.3 mg, 0.059 mmol) and the resulting mixture was stirred at room temp for 16 h. The reaction mixture was then purified by prep HPLC and although the atropisomers (~25:75 ratio) were separable they were recombined to afford Example 2.3 (29 mg): $^1$H NMR (500 MHz, Methanol-$d_4$) δ 8.39 (s, 0.3H), 8.32 (s, 0.7H), 7.25 (d, J=7.7 Hz, 0.3H), 7.15 (d, J=7.3 Hz, 0.7H), 6.76-6.68 (m, 1H), 6.66-6.62 (m, 1.6H), 6.51-6.45 (m, 1H), 6.41-6.36 (m, 1.4H), 5.37-5.30 (m, 0.3H), 5.13 (t, J=7.2 Hz, 0.7H), 3.41-3.36 (m, =2H), 3.29 (s, 2H), 3.28 (s, 1H), 3.26 (s, 2H), 3.25-3.21 (m, 1H), 3.09-3.02 (m, 1H), 3.01-2.98 (m, 4H), 2.74-2.62 (m, 3H), 2.61-2.51 (m, 3H). LC/MS (M+H)$^+$=761.1.

Example 2.4, a mixture of atropisomers, was prepared from Int 3f-E1 according to the procedure described for the preparation of Example 2.3

5,6-dibromo-2-methylpyridin-3-amine (Int 4a)

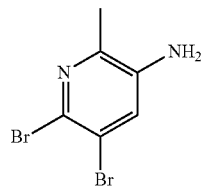

To a stirred solution of 5-bromo-2-methylpyridin-3-amine (10.0 g, 53.5 mmol) in acetonitrile (100 mL) was added NBS (9.99 g, 56.0 mmol) and the resulting reaction mixture was stirred at RT for 2 h. The reaction mixture was diluted with ethyl acetate (200 mL), washed with water (2×50 mL) and brine (2×50 mL), dried (Na$_2$SO$_4$), filtered and concentrated to a brown solid. The crude product was then purified by Combiflash chromatography (120 g Redisep® SiO$_2$ column, eluting with 5%-20% EtOAc in hexanes) to afford the title compound (12 g). $^1$H NMR (300 MHz, DMSO-$d_6$) δ ppm 7.24 (s, 1H), 5.52 (br. s., 2H), 2.20 (s, 3H).

N-(5,6-dibromo-2-methylpyridin-3-yl)acetamide (Int 4b)

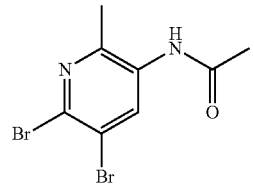

To a stirred solution of 5,6-dibromo-2-methylpyridin-3-amine (6.00 g, 22.6 mmol) in CHCl$_3$ (60 mL) was added acetic anhydride (8.5 mL, 90 mmol) and potassium acetate (2.66 g, 27.1 mmol), and the resulting reaction mixture was stirred at RT for 2 h and then refluxed for 2 h. The reaction mixture was cooled to RT, diluted with DCM (200 mL), washed with water (2×50 mL), brine (2×50 mL), dried (Na$_2$SO$_4$), filtered and concentrated. The resultant crude material was then triturated with hexanes, filtered and dried to afford the title compound (6.5 g), which was taken to the next step without any purification. LC/MS: m/z=306.9 [M+H]$^+$. $^1$H NMR (400 MHz, DMSO-$d_6$) δ ppm 9.60 (s, 1H), 8.32 (s, 1H), 2.38 (s, 3H), 2.08-2.14 (m, 3H).

5,6-dibromo-1H-pyrazolo[4,3-b]pyridine (Int 4c)

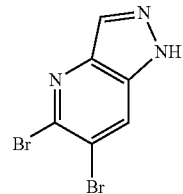 [SMILES: Brc1cc2[nH]ncc2nc1Br]

To a stirred solution of N-(5,6-dibromo-2-methylpyridin-3-yl)acetamide (6.5 g, 21.1 mmol) in toluene (70 mL) was added acetic anhydride (5.97 mL, 63.3 mmol), potassium acetate (2.49 g, 25.3 mmol), tert-butyl nitrite (4.05 mL, 33.8 mmol) and the reaction mixture was refluxed for 12 h. The reaction mixture was cooled to RT, diluted with ethyl acetate (2×100 mL), washed with water (2×50 mL), brine (2×50 mL) dried (Na$_2$SO$_4$), filtered and concentrated to crude brown solid. The crude product was dissolved in 1:1 mixture of THF and MeOH (60 mL), NaOH (10 mL, 2 M solution, 20 mmol) was added, stirred at RT for 2 h and concentrated under reduced pressure. The crude product was dissolved in ethyl acetate (2×100 mL), washed with water (2×50 mL), brine (100 mL), dried (Na$_2$SO$_4$), filtered, and concentrated to afford the title compound (4.9 g) which was taken to the next step without any purification. LC/MS: m/z=275.9 [M+H]$^+$. $^1$H NMR (300 MHz, DMSO-$d_6$) δ ppm 13.70 (br. s., 1H), 8.55 (s, 1H), 8.34 (s, 1H).

5,6-dibromo-1-((2-(trimethylsilyl)ethoxy)methyl)-1H-pyrazolo[4,3-b]pyridine (Int 4d)

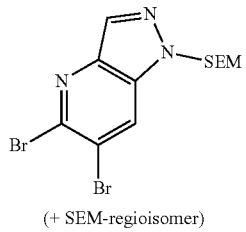 [SMILES: C[Si](C)(C)CCOCn1ncc2nc(Br)c(Br)cc21]

(+ SEM-regioisomer)

To a stirred solution of 5,6-dibromo-1H-pyrazolo[4,3-b]pyridine (500 mg, 1.81 mmol) in DMF (5 mL) was added sodium hydride (79.0 mg, 1.99 mmol) at 0° C. and stirred for 30 min. SEM-Cl (0.480 mL, 2.71 mmol) was added slowly and the solution was allowed to warm to RT and stirred for 1 h. The reaction mixture was cooled to 0° C., quenched with ice cold water and extracted with ethyl acetate (100 mL). The organic layer was washed with water (50 mL), brine (50 mL), dried ($Na_2SO_4$), filtered, and concentrated to afford the title compound (650 mg) as mixture (26:60) of regioisomers which was directly processed to next step without any purification. LC/MS: m/z=406.0 [M+H]+.

6-bromo-1-((2-(trimethylsilyl)ethoxy)methyl)-5-vinyl-1H-pyrazolo[4,3-b]pyridine (Int 4e)

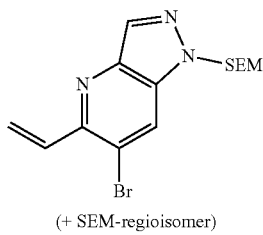 [SMILES: C=Cc1nc2cnn(COCC[Si](C)(C)C)c2cc1Br]

(+ SEM-regioisomer)

To a stirred solution of 5,6-dibromo-1-((2-(trimethylsilyl)ethoxy)methyl)-1H-pyrazolo[4,3-b]pyridine and its SEM-regioisomer (10.00 g, 24.56 mmol) in DMF (120 mL) was added tributyl(vinyl)tin (6.23 g, 19.65 mmol), $Pd(PPh_3)_4$ (1.703 g, 1.47 mmol) under nitrogen atmosphere and the reaction mixture was heated 100° C. for overnight. The reaction mixture was cooled to RT, diluted with water (100 mL) and extracted with ethyl acetate (2×250 mL). The organic layer was washed with ice-cold water (2×100 mL), brine (2×50 mL), dried ($Na_2SO_4$), filtered, and concentrated to brown colored gummy compound. The crude was suspended in pet-ether (100 mL), stirred for 10 minutes and collected the organic layer. Extraction was repeated once again with pet-ether (100 mL) and the combined pet-ether solution was washed with 10% aqueous KF solution (2×50 mL), water (50 mL), brine (50 mL), dried ($Na_2SO_4$), filtered and concentrated to afford the tittle compound as a mixture of regioisomers (22:50). The crude product was directly submitted to next step without any purification. LC/MS: m/z=355.2 [M+H]+.

6-bromo-1-((2-(trimethylsilyl)ethoxy)methyl)-1H-pyrazolo[4,3-b]pyridine-5-carbaldehyde (Int 4f)

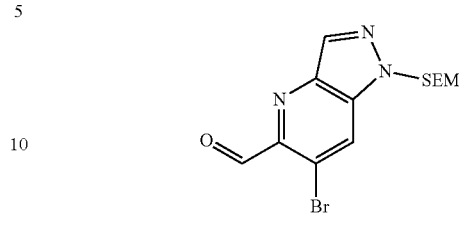

A stirred solution of 6-bromo-1-((2-(trimethylsilyl)ethoxy)methyl)-5-vinyl-1H-pyrazolo[4,3-b]pyridine and its SEM-regioisomer (3.00 g, 8.47 mmol) in mixture of MeOH (10 mL) and DCM (10 mL) was purged with ozone at −70° C. until the solution become blue. The reaction mixture was then purged with nitrogen gas to remove the excess of ozone. To the reaction mixture was added dimethyl sulfide (1.25 mL, 16.9 mmol) and allowed to warm to RT and stirred for 12 h. The reaction mixture was diluted with ethyl acetate (50 mL), washed with water (20 mL) and brine (20 mL), dried ($Na_2SO_4$), filtered and concentrated to afford the product as brown color liquid, which was directly submitted to next step without any purification. LC/MS: m/z=356.2 [M+H]+. [Note: It was not apparent at this stage if there was a mixture of regioisomers or not.]

N-((6-bromo-1-((2-(trimethylsilyl)ethoxy)methyl)-1H-pyrazolo[4,3-b]pyridin-5-yl)methylene)-2-methylpropane-2-sulfinamide (Int 4g)

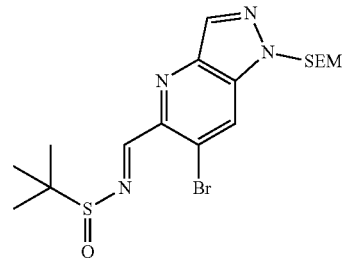 [SMILES: CC(C)(C)S(=O)/N=C/c1nc2cnn(COCC[Si](C)(C)C)c2cc1Br]

To a stirred solution of crude 6-bromo-1-((2-(trimethylsilyl)ethoxy)methyl)-1H-pyrazolo[4,3-b]pyridine-5-carbaldehyde prepared above (3.00 g, 8.42 mmol) in DCM (30 mL) was added 2-methylpropane-2-sulfinamide (1.123 g, 9.26 mmol) and $CuSO_4$ (2.69 g, 16.84 mmol) and stirred at RT for 16 h. The reaction mixture was diluted with ethyl acetate (2×100 mL), washed with water (2×50 mL) and brine (2×50 mL), dried ($Na_2SO_4$), filtered and concentrated under reduced pressure. The resultant crude brown oil was purified by Combiflash chromatography (40 g Redisep® $SiO_2$ column, eluting with 5%-30% EtOAc in hexanes) to afford title compound (1.6 g). [Note: the sample processed from hereon is believed to be a single SEM-regioisomer as indicated above. The E/Z ratio for current case was not determined]. LC/MS: m/z=460.2 [M+H]+. $^1$H NMR (300 MHz, DMSO-$d_6$) δ ppm 8.91 (s, 1H), 8.87 (s, 1H), 8.63 (s, 1H), 5.82 (s, 2H), 3.54 (t, J=7.93 Hz, 2H), 1.23 (s, 9H), 0.81 (t, J=8.12 Hz, 2H), −0.12 (s, 9H).

N-(1-(6-bromo-1-((2-(trimethylsilyl)ethoxy)methyl)-1H-pyrazolo[4,3-b]pyridin-5-yl)-2-(3,5-difluorophenyl)ethyl)-2-methylpropane-2-sulfinamide (Int 4h (Mix of Diasteromers))

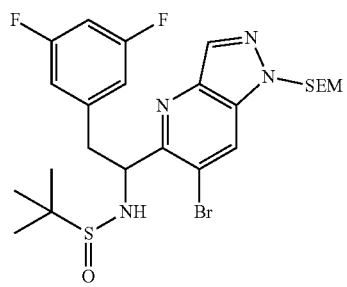

To magnesium turning (0.180 g, 7.40 mmol) in diethyl ether (5 mL) at RT was added drop wise 1-(bromomethyl)-3,5-difluorobenzene (0.957 mL, 7.40 mmol) over 15 min, and the mixture was stirred for 1 h. To a stirred solution of N-((6-bromo-1-((2-(trimethylsilyl)ethoxy)methyl)-1H-pyrazolo[4,3-b]pyridin-5-yl)methylene)-2-methylpropane-2-sulfinamide (1.70 g, 3.70 mmol) in diethyl ether (5 mL) at −20° C. was added drop wise the above Grignard reagent, and the mixture was stirred at the same temperature for 10 min. The reaction mixture was then allowed to warm to RT and stirred for 2 h. It was then cooled to 0° C., quenched with saturated NH4Cl solution and extracted with ethyl acetate (2×100 mL). The combined organic layer was washed with water (2×50 mL) and brine, dried (Na$_2$SO$_4$), filtered and concentrated under reduced pressure to afford the crude compound as brown liquid. The crude product was purified by Combiflash chromatography (40 g Redisep® SiO$_2$ column, eluting with 5%-30% EtOAc in hexanes) to afford the title compound (1.3 g) as a mixture of diastereomers in a ratio of ~56:28. LC/MS: m/z=587.3 [M+H]$^+$.

1-(6-bromo-1-((2-(trimethylsilyl)ethoxy)methyl)-1H-pyrazolo[4,3-b]pyridin-5-yl)-2-(3,5-difluorophenyl)ethan-1-amine (Int 4i, (Racemic))

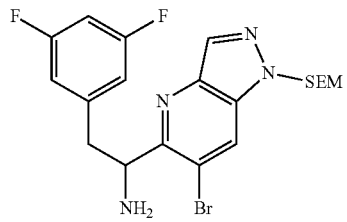

To a stirred solution of N-(1-(6-bromo-1-((2-(trimethylsilyl)ethoxy)methyl)-1H-pyrazolo[4,3-b]pyridin-5-yl)-2-(3,5-difluorophenyl)ethyl)-2-methylpropane-2-sulfinamide (Int 4h, 750 mg, 1.28 mmol) in 1,4-dioxane (2 mL) was added 4M HCl in 1,4-dioxane (2.5 mL, 10 mmol) and stirred at RT for 2 h. Volatiles were removed under reduced pressure and the residue was dissolved in ether and concentrated on a rotary evaporator twice to afford the title compound as HCl salt (600 mg) which was directly submitted to next step without any purification. LC/MS: m/z=483.9 [M+H]$^+$. $^1$H NMR (400 MHz, DMSO-d$_6$) δ ppm 8.79 (s, 1H), 8.65 (br. s., 3H), 8.52 (s, 1H), 7.09-7.16 (m, 1H), 6.81 (d, J=6.53 Hz, 2H), 5.82 (dd, J=15.6, 11.6 Hz, 2H), 5.09-5.18 (m, 1H), 3.50-3.59 (m, 2H), 3.26 (d, J=7.03 Hz, 2H), 0.78 (dd, J=16.0, 8.4 Hz, 2H), −0.12 (m, 9H).

tert-butyl (1-(6-bromo-1-((2-(trimethylsilyl)ethoxy)methyl)-1H-pyrazolo[4,3-b]pyridin-5-yl)-2-(3,5-difluorophenyl)ethyl)carbamate (Int 4j)

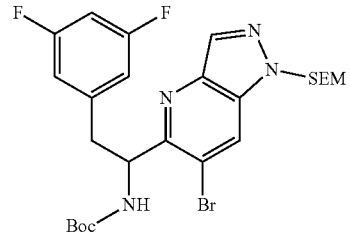 [SMILES: CC(C)(C)OC(=O)NC(Cc1cc(F)cc(F)c1)c1nc2cnn(COCC[Si](C)(C)C)c2cc1Br]

To a stirred solution of 1-(6-bromo-1-((2-(trimethylsilyl)ethoxy)methyl)-1H-pyrazolo[4,3-b]pyridin-5-yl)-2-(3,5-difluorophenyl)ethanamine hydrochloride salt (Int 4i, 600.0 mg, 1.15 mmol) in DCM (10 mL) was added TEA (0.32 mL, 2.31 mmol) and Boc$_2$O (0.32 mL, 1.40 mmol) at 0° C. and the reaction mixture was allowed to warm to RT and stirred for 2 h. The reaction mixture was diluted with DCM (2×20 mL), washed with water (2×10 mL) and brine (20 mL), dried (Na$_2$SO$_4$), filtered, and concentrated. The crude product was then purified by Combiflash chromatography (120 g Redisep® SiO$_2$ column, eluting with 5%-10% EtOAc in hexanes) to afford the title compound (160 mg), the SEM-regiochemistry of which was confirmed by long range NMR correlation studies. LC/MS: m/z=584.9 [M+H]$^+$. $^1$H NMR (300 MHz, DMSO-d$_6$) δ ppm 8.68 (s, 1H), 8.42 (s, 1H), 7.41 (d, J=8.69 Hz, 1H), 6.89-7.21 (m, 3H), 5.78 (s, 2H), 5.22-5.39 (m, 1H), 3.51 (t, J=7.74 Hz, 2H), 3.00-3.25 (m, 2H), 1.27 (s, 9H), 0.79 (t, J=7.93 Hz, 2H), −0.12 (s, 9H).

tert-butyl (1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethyl)carbamate (Int 4k)

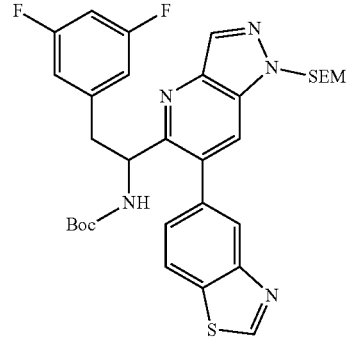 [SMILES: CC(C)(C)OC(=O)NC(Cc1cc(F)cc(F)c1)c1nc2cnn(COCC[Si](C)(C)C)c2cc1-c1ccc2scnc2c1]

To a stirred solution of compound tert-butyl (1-(6-bromo-1-((2-(trimethylsilyl)ethoxy)methyl)-1H-pyrazolo[4,3-b]pyridin-5-yl)-2-(3,5-difluorophenyl)ethyl)carbamate (Int 4j, 150 mg, 0.257 mmol) in DMF (1 mL) was degassed with nitrogen for 10 min and then added 5-(4,4,5,5-tetramethyl-1,3,2-dioxaborolan-2-yl)benzo[d]thiazole (81 mg, 0.308 mmol), K$_2$CO$_3$ (107 mg, 0.77 mmol) followed by Pd(Ph$_3$P)$_4$ (17.8 mg, 0.015 mmol) and the reaction mixture was heated to 100° C. and stirred for 2 h. The reaction mixture was cooled to RT, diluted with ethyl acetate (50 mL), washed with water (20 mL) and brine (20 mL), dried (Na$_2$SO$_4$), filtered, and concentrated. The crude product was purified by Combiflash chromatography (12 g Redisep SiO$_2$ column, eluting with 5-20% EtOAc in hexanes) to afford the title product (120 mg). LC/MS: m/z=638.2 [M+H]$^+$. $^1$H NMR (300 MHz, DMSO-d$_6$) δ ppm 9.51 (s, 1H), 8.46 (s, 1H), 8.32 (d, J=7.93 Hz, 1H), 8.12 (s, 1H), 8.07 (s, 1H), 7.53 (d, J=9.07 Hz, 1H), 7.32 (d, J=9.07 Hz, 1H), 6.85-6.97 (m, 1H), 6.37 (d, J=6.80 Hz, 2H), 5.81 (s, 2H), 4.99-5.10 (m, 1H), 3.55 (t, J=8.12 Hz, 2H), 2.94 (d, J=7.18 Hz, 2H), 1.23 (s, 9H), 0.77-0.86 (m, 2H), −0.12 (s, 9H).

1-(6-(benzo[d]thiazol-5-yl)-1-((2-(trimethylsilyl) ethoxy) methyl)-1H-pyrazolo [4, 3-b]pyridin-5-yl)-2-(3, 5-difluorophenyl) ethan-1-amine (Int 41)

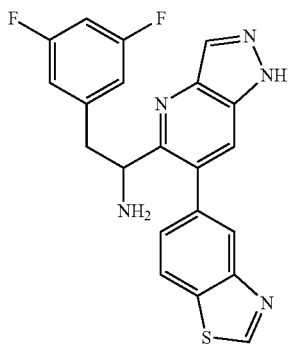 [SMILES: NC(Cc1cc(F)cc(F)c1)c1nc2cn[nH]c2cc1-c1ccc2scnc2c1]

To a stirred solution of tert-butyl (1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethyl) carbamate (Int 4j, 240 mg, 0.37 mmol) in DCM (5 mL) was added TFA (1.00 mL, 13.0 mmol) drop wise at 0° C. and the resulting solution was slowly warmed to RT and stirred for 3 h. The reaction mixture was concentrated under reduced pressure and the crude product was purified by reverse phase preparative HPLC to afford the title compound (110 mg). LC/MS: m/z=408.1 [M+H]$^+$. $^1$H NMR (400 MHz, DMSO-d$_6$) δ ppm 13.32-13.44 (br. s., 1H), 9.49 (s, 1H), 8.38 (s, 1H), 8.26 (d, J=8.53 Hz, 1H), 7.94 (s, 1H), 7.83 (s, 1H), 7.41 (d, J=8.53 Hz, 1H), 6.84-6.96 (m, 1H), 6.37 (d, J=6.53 Hz, 2H), 4.13-4.26 (m, 1H), 3.05 (dd, J=13.2, 6.6 Hz, 1H), 2.80 (dd, J=13.2, 6.6 Hz, 2H).

N-(1-(6-(benzo[d]thiazol-5-yl)-1H-pyrazolo[4,3-b] pyridin-5-yl)-2-(3,5-difluorophenyl)ethyl)-2-((3bS, 4aR)-3-(difluoromethyl)-5,5-difluoro-3b,4,4a,5-tetrahydro-1H-cyclopropa[3,4]cyclopenta[1,2-c] pyrazol-1-yl)acetamide (Example 3.1 & 3.2, (Each is a Homochiral Diastereomer))

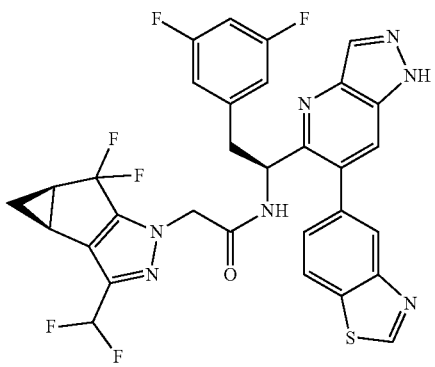 [SMILES: O=C(Cn1nc(C(F)F)c2c1C(F)(F)[C@@H]1C[C@H]21)N[C@@H](Cc1cc(F)cc(F)c1)c1nc2cn[nH]c2cc1-c1ccc2scnc2c1]

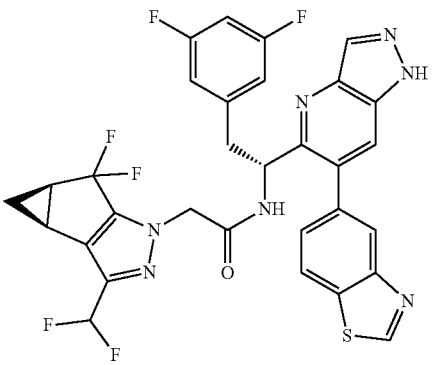 [SMILES: O=C(Cn1nc(C(F)F)c2c1C(F)(F)[C@@H]1C[C@H]21)N[C@H](Cc1cc(F)cc(F)c1)c1nc2cn[nH]c2cc1-c1ccc2scnc2c1]

To a stirred solution of 1-(6-(benzo[d]thiazol-5-yl)-1H-pyrazolo [4, 3-b] pyridin-5-yl)-2-(3,5-difluorophenyl) ethanamine (Int 41, 25 mg, 0.061 mmol) in DMF (2 mL) was added 2-((3bS,4aR)-3-(Difluoromethyl)-5,5-difluoro-3b,4,4a,5-tetrahydro-1H-cyclopropa[3,4]cyclopenta[1,2-c]pyrazol-1-yl)acetic acid (16.2 mg, 0.061 mmol), HATU (24.5 mg, 0.064 mmol) and DIPEA (5.4 μL, 0.031 mmol) and the resulting solution was stirred at RT for 2 h. The reaction mixture was diluted with ethyl acetate (20 mL), washed with water (10 mL) and brine (10 mL), dried (Na$_2$SO$_4$), filtered and concentrated. The residual material was purified by reverse phase HPLC followed by chiral separation using SFC (Chiralcel OD-H (250×21) mm, 5 μm; co-solvent, 30% of (methanol and acetonitrile) 1:1; column temperature, 25° C.; Loadability/Injection, 2 mg/mL; total flow, 80 g/min; back pressure, 100 bar; UV detection, 221 nM) to afford two diastereomers.

Example 3.1 (First Eluting Diastereomer; Retention Time=4.20 Min)

LC/MS retention time=2.58 min; m/z=634.0 [M+H]$^+$. Ascentis Express C18 (2.1×50) mm, 2.7 m column; Flow rate: 1.1 mL/min; Mobile Phase A: 0.1% TFA in 95% Water/5% ACN; Mobile Phase B: 0.1% TFA in 5% Water/95% ACN; 0% B to 100% B over 4 min; Detection: UV at 220 nm. $^1$H NMR (300 MHz, Methanol-d$_4$) δ ppm 9.34 (s, 1H), 8.35 (s, 1H), 8.14 (d, J=8.4 Hz, 1H), 7.84 (s, 1H), 7.78 (s, 1H), 7.38 (d, J=6.3 Hz, 1H), 6.72 (t, J=54 Hz, 1H), 6.70-6.60 (m, 1H), 6.23 (d, J=6.6 Hz, 2H), 5.56 (t, J=7.1 Hz, 1H), 4.90 (s, 2H), 3.20-2.94 (m, 2H), 2.48 (m, 2H), 1.44-1.28 (m, 1H), 1.16-1.03 (m, 1H).

Example 3.2: (Second Eluting Diastereomer; Retention Time=5.3 Min)

LC/MS retention time=2.58 min; m/z=634.0 [M+H]$^+$. Ascentis Express C18 (2.1×50) mm, 2.7 micron column; Flow rate: 1.1 mL/min; Mobile Phase A: 0.1% TFA in 95% Water/5% ACN; Mobile Phase B: 0.1% TFA in 5% Water/95% ACN; 0% B to 100% B over 4 min, Detection: UV at 220 nm. $^1$H NMR (300 MHz, Methanol-d$_4$) δ ppm 9.35 (s, 1H), 8.34 (s, 1H), 8.15 (d, J=8.3 Hz, 1H), 7.90 (s, 1H), 7.78 (s, 1H), 7.39 (d, J=7.0 Hz, 1H), 6.72 (t, J=54 Hz, 1H), 6.70-6.60 (m, 1H), 6.23 (d, J=6.6 Hz, 2H), 5.57 (t, J=7.0 Hz, 1H), 3.17-2.93 (m, 2H), 2.48 (m, 2H), 1.44-1.28 (m, 1H), 1.16-1.03 (m, 1H).

N-(1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethyl)-2-methylpropane-2-sulfinamide (Int 5a)

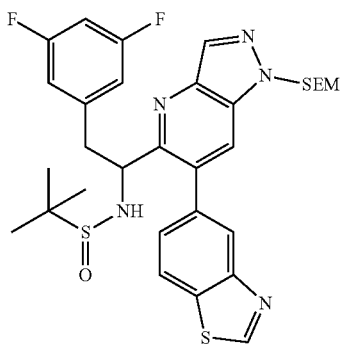 [SMILES: CC(C)(C)S(=O)NC(Cc1cc(F)cc(F)c1)c1nc2cnn(COCC[Si](C)(C)C)c2cc1-c1ccc2scnc2c1]

A stirred solution of N-(1-(6-bromo-1-((2-(trimethylsilyl)ethoxy)methyl)-1H-pyrazolo[4,3-b]pyridin-5-yl)-2-(3,5-difluorophenyl)ethyl)-2-methylpropane-2-sulfinamide (mixture of diastereomers; 250 mg, 0.425 mmol) in DMF (5 mL) was degassed with nitrogen for 10 min. 5-(4,4,5,5-tetramethyl-1,3,2-dioxaborolan-2-yl)benzo[d]thiazole (133 mg, 0.511 mmol), $K_2CO_3$ (176 mg, 1.276 mmol) were added followed by $Pd(Ph_3P)_4$ (29.5 mg, 0.026 mmol) and the resulting solution was heated to 100° C. and stirred for 2 h. The reaction mixture was cooled to RT, diluted with ethyl acetate (50 mL), washed with water (20 mL) and brine (20 mL), dried ($Na_2SO_4$), filtered, and concentrated. The crude product was purified by Combiflash chromatography (12 g Redisep® $SiO_2$ column, eluting with 5%-20% EtOAc in hexanes) to afford title compound (150 mg). LC/MS: m/z=642.4 [M+H]$^+$. $^1$H NMR (400 MHz, DMSO-d$_6$) δ ppm 9.64 (s, 1H), 8.63 (d, J=1.00 Hz, 1H), 8.43 (d, J=8.53 Hz, 1H), 8.27 (d, J=1.00 Hz, 1H), 8.0 (m, 1H), 7.42 (m, 1H), 7.08 (m, 1H), 6.50 (d, J=6.0 Hz, 2H), 5.80 (s, 2H), 5.74 (d, J=8.53 Hz, 1H), 4.92 (m, 1H), 3.54 (t, J=8.03 Hz, 2H), 3.08-3.27 (m, 2H), 0.90-0.98 (m, 9H), 0.72-0.82 (m, 2H), −0.12 (m, 9H).

1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethan-1-amine (Int 5b)

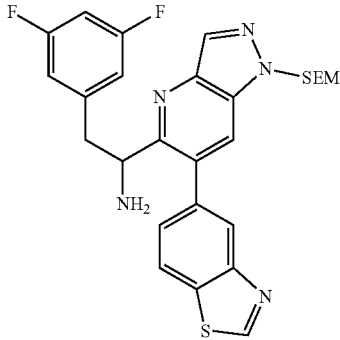 [SMILES: C[Si](C)(C)CCOCn1ncc2nc(C(N)Cc3cc(F)cc(F)c3)c(-c3ccc4scnc4c3)cc21]

To a stirred solution of N-(1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethyl)-2-methylpropane-2-sulfinamide (400.0 mg, 0.623 mmol) in 1,4-dioxane (10 mL) was added 4M HCl in 1,4-dioxane (4 mL, 16 mmol) dropwise at 0° C. and resulting mixture was warmed to RT and stirred for 1 h. Volatiles were removed under reduced pressure and the residue was treated with ether and concentrated on a rotary evaporator (2×) to afford the title compound as HCl salt (320 mg) which was directly processed to the next step. LC/MS: m/z=538.3 [M+H]$^+$. $^1$H NMR (400 MHz, DMSO-d$_6$) δ ppm 9.51 (s, 1H), 8.74 (br. s., 3H), 8.57 (d, J=1.00 Hz, 1H), 8.21-8.30 (m, 2H), 7.76-7.84 (m, 1H), 7.21-7.29 (m, 1H), 6.93-7.03 (m, 1H), 6.22 (d, J=6.53 Hz, 2H), 5.84 (dd, J=20.0, 11.6 Hz, 2H), 4.73-4.81 (m, 1H), 3.62 (t, J=8.03 Hz, 2H), 3.22 (dd, J=17.6, 5.6 Hz, 2H), 0.80 (m, 2H), −0.09 (m, 9H).

N-(1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethyl)-2-(5-hydroxy-1H-indol-3-yl)acetamide (Int 5c)

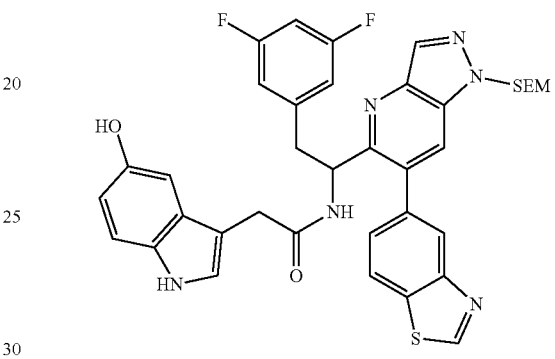

To the stirred solution of 1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethanamine/hydrochloride (100 mg, 0.174 mmol) in DMF (1.0 mL) were added 5-hydroxyindole-3-acetic acid (36.6 mg, 0.192 mmol), HATU (72.8 mg, 0.192 mmol), DIPEA (0.046 mL, 0.261 mmol) and the mixture was stirred at RT for 2 h. The reaction mixture was diluted with ethyl acetate (50 mL), washed with water (20 mL) and brine (20 mL), dried ($Na_2SO_4$), filtered and concentrated to a brown colored gummy crude compound, which was directly processed to the next step without any purification.
LC/MS: m/z=711.4 [M+H]$^+$.

N-(1-(6-(benzo[d]thiazol-5-yl)-1H-pyrazolo[4,3-b]pyridin-5-yl)-2-(3,5-difluorophenyl)ethyl)-2-(5-hydroxy-1H-indol-3-yl)acetamide (Example 3.3 & 3.4, (Each a Single Enantiomer))

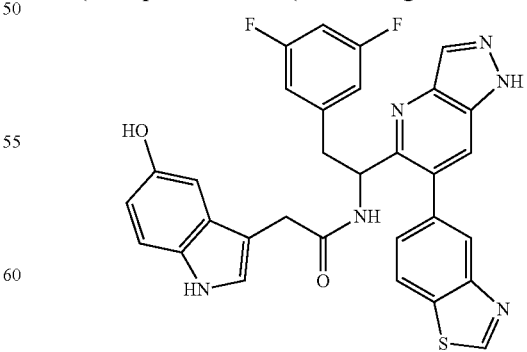

To a stirred solution of N-(1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethyl)-2-(5-hydroxy-1H-indol-3-yl)acetamide (90.0 mg, 0.127 mmol) in THF (2 mL) was added Bu$_4$NF in THF (1.50 mL, 1M in THF, 11.5 mmol) drop wise followed by ethylene diamine (0.051 mL, 0.76 mmol) and stirred at 65° C. for 2 h. The reaction mixture was diluted with ethyl acetate (20 mL), washed with water (10 mL) and brine (10 mL), dried (Na$_2$SO$_4$), filtered and concentrated. The crude product was purified by reverse phase HPLC followed by chiral separation using SFC (Lux Cellulose-2 (250×21.5) mm, 5 µm; co-solvent, 40% methanol; column temperature, 30° C.; total flow, 70 g/min; back pressure, 100 bar; Loadability/Injection, 5 mg/mL; detection, 220 nM) to afford two enantiomers, with retention times of 8 min and 11 min.

Example 3.3 (First Eluting)

LC/MS retention time=1.70 min; m/z=581.1 [M+H]$^+$. X-Bridge BEH C18 (2.1×50) mm, 2.5 µm; flow rate 0.5 mL/min; Mobile Phase A: 5 mmol NH$_4$OAc in 95% Water/5% ACN; Mobile Phase B: 5 mmol NH$_4$OAc in 5% Water/95% ACN; 20% B to 90% B over 2 min; Detection: UV at 220 nm. $^1$H NMR (400 MHz, DMSO-d$_6$) δ ppm 13.5 (br. s, 1H), 10.47 (s, 1H), 9.47 (s, 1H), 8.54 (d, J=8.07 Hz, 1H), 8.50 (s, 1H), 8.38 (s, 1H), 8.19 (d, J=8.40 Hz, 1H), 7.99 (s, 1H), 7.83 (s, 1H), 7.45 (d, J=9.05 Hz, 1H), 7.07 (d, J=8.56 Hz, 1H), 6.95 (s, 1H), 6.88 (t, J=9.2 Hz, 1H), 6.80 (s, 1H), 6.57 (dd, J=8.56, 2.20 Hz, 1H), 6.57 (d, J=8.31 Hz, 1H), 6.32 (d, J=6.60 Hz, 2H), 5.19-5.34 (t, J=7.6 Hz, 1H), 3.41 (s, 2H), 2.88-3.06 (m, 2H).

Example 3.4 (Second Eluting)

LC/MS retention time (under same condition)=1.71 min; m/z=581.2 [M+H]$^+$.

N-(1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethyl)-2-(5-fluoro-1H-indol-3-yl)acetamide (Int 6a)

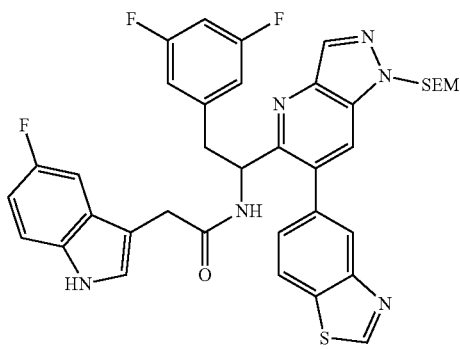 [SMILES: C[Si](C)(C)CCOCn1ncc2nc(C(Cc3cc(F)cc(F)c3)NC(=O)Cc3c[nH]c4ccc(F)cc34)c(-c3ccc4scnc4c3)cc21]

To the stirred solution of 1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethanamine/hydrochloride salt (80.0 mg, 0.139 mmol) in DMF (1.0 mL) was added 2-(5-fluoro-1H-indol-3-yl)acetic acid (29.6 mg, 0.153 mmol), HATU (58.3 mg, 0.153 mmol) and DIPEA (0.037 mL, 0.21 mmol) and the resulting solution was stirred at RT for 2 h. The reaction mixture was diluted with ethyl acetate (50 mL), washed with water (20 mL) and brine (20 mL), dried (Na$_2$SO$_4$), filtered and concentrated to a brown colored gummy crude compound, which was directly processed to next step without any purification. LC/MS: m/z=713.5 [M+H]$^+$. $^1$H NMR (400 MHz, Methanol-d$_4$) δ ppm 9.43 (s, 1H), 8.32 (s, 1H), 8.18 (d, J=8.53 Hz, 1H), 8.09 (s, 1H), 7.98 (s, 1H), 7.81-7.85 (m, 1H), 7.64-7.70 (m, 1H), 7.57-7.61 (m, 1H), 7.40 (d, J=13.2 Hz, 4.4 Hz, 1H), 7.31 (s, 1H), 7.22 (dd, J=12.0 Hz, 2.4 Hz, 1H), 6.88 (m, 1H), 6.6 (m, 1H), 6.19 (d, J=6.02 Hz, 2H), 5.80 (s, 2H), 5.57-5.61 (m, 1H), 3.74 (d, J=5.6 Hz, 2H), 3.50 (t, J=8.0 Hz, 2H), 2.92-3.03 (m, 2H), 0.94 (t, J=8.0 Hz, 2H), −0.10 (s, 9H).

N-(1-(6-(benzo[d]thiazol-5-yl)-1H-pyrazolo[4,3-b]pyridin-5-yl)-2-(3,5-difluorophenyl)ethyl)-2-(5-fluoro-1H-indol-3-yl)acetamide (Example 3.5 & 3.6)

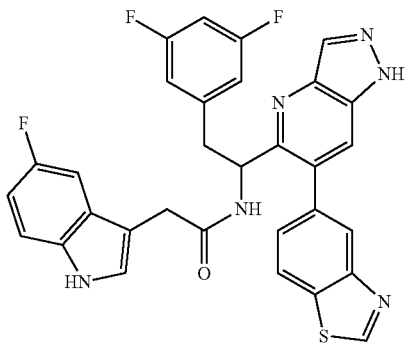 [SMILES: O=C(Cc1c[nH]c2ccc(F)cc12)NC(Cc1cc(F)cc(F)c1)c1nc2cn[nH]c2cc1-c1ccc2scnc2c1]

To a stirred solution of compound N-(1-(6-(benzo[d]thiazol-5-yl)-1-((2-(trimethylsilyl)ethoxy)methyl)-1H-pyrazolo[4,3-b]pyridin-5-yl)-2-(3,5-difluorophenyl)ethyl)-2-(5-fluoro-1H-indol-3-yl)acetamide (60.0 mg, 0.084 mmol) in THF (2 mL) was added Bu$_4$NF in THF (0.40 mL of 1M in THF, 0.40 mmol), ethylene diamine (33.4 mg, 0.556 mmol) at RT and the resulting solution was heated to 60° C. and stirred for 3 h. The reaction mixture was cooled to RT, diluted with ethyl acetate (50 mL), washed with water (20 mL) and brine (20 mL), dried (Na$_2$SO$_4$), filtered and concentrated. The crude product was purified by reverse phase HPLC followed by chiral separation using SFC (Chiralpak IA (250×21) mm 5 µm; co-solvent, 40% methanol; column temperature, 30° C.; total flow, 70 g/min; back pressure, 100 bar; Injection, 5 mg/mL; detection, 290 nM) to afford two enantiomers, with retention times of 6 min and 8 min.

Example 3.5 (First Eluting Enantiomer)

LC/MS retention time=2.47 min; m/z=583.1 [M+H]$^+$. KINETIX XB-C18, (3×75) mm, 2.6 µm; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4 min, then hold 0.5 min at 100% B with flow rate 1.5 mL/min; Detection: UV at 220 nm. $^1$H NMR (400 MHz, Methanol-d$_4$) δ ppm 9.32 (s, 1H), 8.22 (s, 1H), 8.10 (d, J=8.4 Hz, 1H), 7.75 (s, 1H), 7.68 (s, 1H), 7.30 (d, J=8.0 Hz, 1H), 7.18 (dd, J=13.2 Hz, 4.4 Hz, 1H), 7.09 (s, 1H), 6.98 (dd, J=12.0 Hz, 2.4 Hz, 1H), 6.83 (t, J=9.29 Hz, 1H), 6.59 (tt, J=9.16, 2.38 Hz, 1H), 6.18 (d, J=6.02 Hz, 2H), 5.50-5.66 (m, 1H), 3.50 (s, 2H), 3.03-3.14 (m, 1H), 2.84-2.98 (m, 1H).

Example 3.6 (Second Eluting Enantiomer)

LC/MS retention time=2.47 min; m/z=581.1. [M−H]$^−$ under same analytical condition as above.

Separate Enantiomers of Either (R) or (S) tert-butyl (1-(6-bromo-1-((2-(trimethylsilyl)ethoxy)methyl)-1H-pyrazolo[4,3-b]pyridin-5-yl)-2-(3,5-difluorophenyl)ethyl)carbamate (Int 4j-E1 & Int 4j-E2)

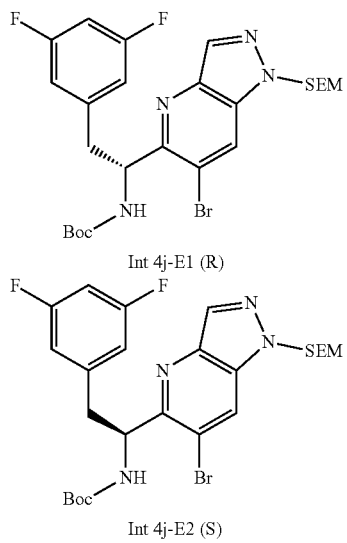

Int 4j-E1 (R)

Int 4j-E2 (S)

Enantiomers of Int 4j were separated by chiral SFC [Whelk-01 (R,R) (250×30) mm, 5 µm; co-solvent, 20% (0.2% DEA in IPA); column temperature, 25° C.; total flow, 70 g/min; back pressure, 100 bar; Injection, 20 mg/mL; detection, 290 nM]. The second eluting isomer (Int 4j-E2) affords the relatively more active final analog.

tert-butyl (S)-(1-(6-(4-chloro-1-methyl-3-(methylsulfonamido)-1H-indazol-7-yl)-1-((2-(trimethylsilyl)ethoxy)methyl)-1H-pyrazolo[4,3-b]pyridin-5-yl)-2-(3,5-difluorophenyl)ethyl)carbamate (Int 7a)

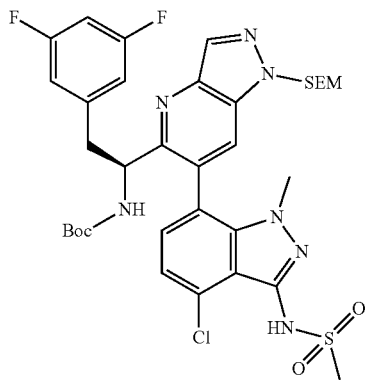 [SMILES: Cn1nc(NS(C)(=O)=O)c2c(Cl)ccc(-c3cc4c(cnn4COCC[Si](C)(C)C)nc3[C@H](Cc3cc(F)cc(F)c3)NC(=O)OC(C)(C)C)c21]

To a solution of tert-butyl (S)-(1-(6-bromo-1-((2-(trimethylsilyl)ethoxy)methyl)-1H-pyrazolo[4,3-b]pyridin-5-yl)-2-(3,5-difluorophenyl)ethyl)carbamate (Int 4j-E2, 220 mg, 0.377 mmol) in 1,4-dioxane (2 mL) in a microwave vial was added N-(4-chloro-1-methyl-7-(4,4,5,5-tetramethyl-1,3,2-dioxaborolan-2-yl)-1H-indazol-3-yl)methanesulfonamide (364 mg, 0.943 mmol), NaHCO₃ (190 mg, 2.26 mmol) and the mixture was degassed with nitrogen gas for 2 min. PdCl₂(dppf)-CH₂Cl₂ adduct (18.5 mg, 0.023 mmol) was added and the resulting reaction mixture was heated and stirred at 135° C. in a microwave synthesizer. The reaction mixture was cooled to RT, extracted with ethyl acetate (100 mL), washed with water (50 mL) and brine (2×50 mL), dried (Na₂SO₄), filtered, and concentrated to a red colored liquid. The crude compound was purified by reverse phase HPLC to afford the title compound (160 mg) as mixture of atropisomers, in a 21:71 LC ratio. LC/MS retention time: m/z=762.4 [M+H]⁺.

(S)—N-(7-(5-(1-amino-2-(3,5-difluorophenyl)ethyl)-1-((2-(trimethylsilyl)ethoxy)methyl)-1H-pyrazolo[4,3-b]pyridin-6-yl)-4-chloro-1-methyl-1H-indazol-3-yl)methanesulfonamide (Int 7b)

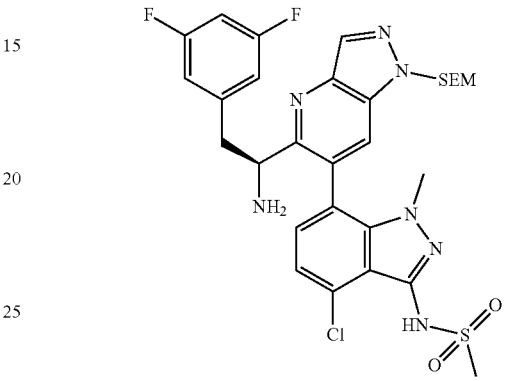

To a stirred solution of tert-butyl (1-(6-(4-chloro-1-methyl-3-(methylsulfonamido)-1H-indazol-7-yl)-1-((2-(trimethylsilyl)ethoxy)methyl)-1H-pyrazolo[4,3-b]pyridin-5-yl)-2-(3,5-difluorophenyl)ethyl)carbamate (90 mg, 0.118 mmol) in 1,4-dioxane (2 mL) was added 4M HCl in 1,4-dioxane (1 mL, 4 mmol) drop wise at 0° C. The solution was allowed to warm to RT and stirred for 6 h. The reaction mixture was concentrated under reduced pressure, diluted with water (20 mL), basified with saturated NaHCO₃ solution and extracted with ethyl acetate (2×25 mL). The organic layer was washed with water (20 mL) and brine (10 mL), dried (Na₂SO₄), filtered and concentrated to afford the title compound (70 mg) as a mixture of atropisomers which was directly processed to next step without any purification. LC/MS: m/z=662.5 [M+H]⁺.

N—((S)-1-(6-(4-chloro-1-methyl-3-(methylsulfonamido)-1H-indazol-7-yl)-1-((2-(trimethylsilyl)ethoxy)methyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 7c)

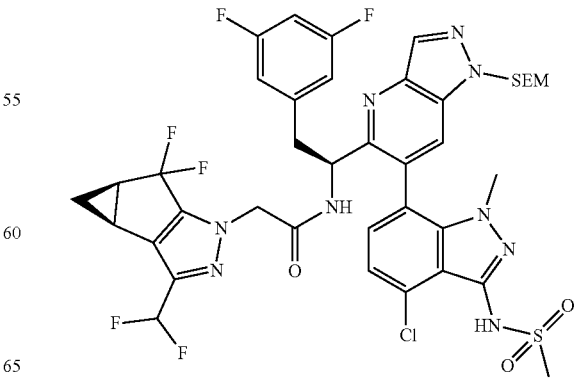

To a stirred solution of N-(7-(5-(1-amino-2-(3,5-difluorophenyl)ethyl)-1-((2-(trimethylsilyl)ethoxy)methyl)-1H-pyrazolo[4,3-b]pyridin-6-yl)-4-chloro-1-methyl-1H-indazol-3-yl)methanesulfonamide (50 mg, 0.072 mmol) in DMF (0.5 mL) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (18.91 mg, 0.072 mmol), HATU (28.6 mg, 0.075 mmol) and the resulting reaction mixture was stirred at RT for 2 h. The reaction mixture was diluted with ethyl acetate (20 mL), washed with water (10 mL) and brine (10 mL), dried (Na₂SO₄), filtered, and concentrated to a crude pale yellow colored gummy solid as a mixture of atropisomers, which was processed directly to next step without any purification. LC/MS: m/z=908.9 [M+H]⁺.

N—((S)-1-(6-(4-chloro-1-methyl-3-(methylsulfonamido)-1H-indazol-7-yl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 3.7)

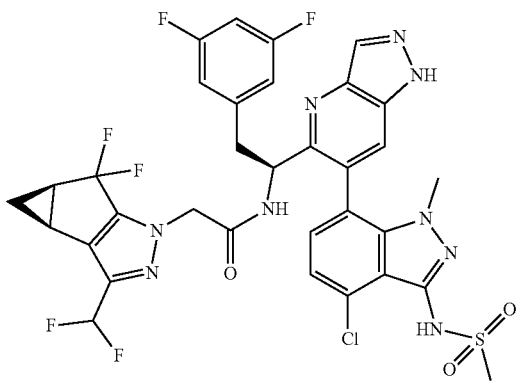 [SMILES: Cn1nc(NS(C)(=O)=O)c2c(Cl)ccc(-c3cc4[nH]ncc4nc3[C@H](Cc3cc(F)cc(F)c3)NC(=O)Cn3nc(C(F)F)c4c3C(F)(F)[C@@H]3C[C@H]43)c21]

To a stirred solution of N—((S)-1-(6-(4-chloro-1-methyl-3-(methylsulfonamido)-1H-indazol-7-yl)-1-((2-(trimethylsilyl)ethoxy)methyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (50 mg, 0.055 mmol) in THF (2 mL) was added Bu₄NF in THF (0.4 mL of 1 M solution, 0.4 mmol), ethylene diamine (21.8 mg, 0.36 mmol) at RT and the reaction mixture was slowly warmed to 60° C. and stirred for 2 h. The reaction mixture was diluted with ethyl acetate (10 mL), washed with water (10 mL) and brine (10 mL), dried (Na₂SO₄), filtered and the filtrate concentrated under reduced pressure to a brown colored gummy solid. The crude compound was then purified by reverse phase-HPLC purification to afford the title compound (11 mg). Exact atropisomer make up was not determined.

Prep-HPLC fractions were concentrated immediately after the purification and observed one set of peaks in its ¹H NMR. The compound become ~30:70 ratio after 3 days in solution as identified by HPLC (SUNFIRE C18 (4.6×150) mm, 3.5 µm; Flow rate 1 mL/min; Mobile Phase A: 0.05% TFA in 95% Water/5% ACN; Mobile Phase B: 0.05% TFA in 5% Water/95% ACN; 10% B to 100% B over 25 min, then hold for 5 min at 100% B; Detection: UV at 254 and 220 nm).

The following data was acquired right after separation LC/MS retention time=2.87 min; m/z=778.1 [M+H]⁺. KINETIX XB-C18, (3×75) mm, 2.6 µm; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 20% B to 100% B over 4 min, then hold 0.5 min at 100% B with flow rate 1.5 mL/min; Detection: UV at 220 nm.

¹H NMR (400 MHz, Methanol-d₄) δ ppm 8.39 (d, J=1.00 Hz, 1H), 7.95 (d, J=1.00 Hz, 1H), 7.14 (d, J=7.53 Hz, 1H), 6.75 (m, 1H), 6.71 (t, J=39.6 Hz, 1H), 6.62 (d, J=7.6 Hz, 1H), 6.31 (dd, J=8.53, 2.01 Hz, 2H), 5.09 (t, J=7.03 Hz, 1H), 3.27 (s, 3H), 3.26 (s, 3H), 3.18 (dd, J=13.20, 6.80 Hz, 1H), 2.95 (dd, J=13.05, 7.03 Hz, 1H), 2.43-2.52 (m, 2H), 1.33-1.45 (m, 1H), 1.03-1.09 (m, 1H).

N—((R)-1-(6-(4-chloro-1-methyl-3-(methylsulfonamido)-1H-indazol-7-yl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 3.8)

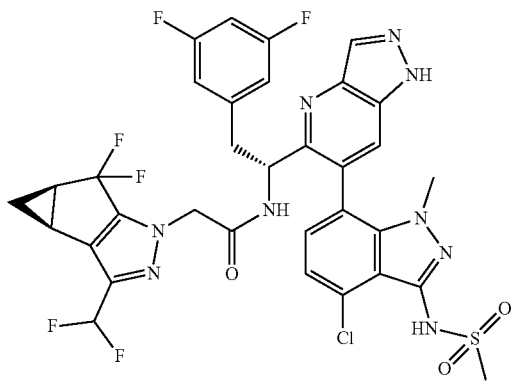 [SMILES: Cn1nc(NS(C)(=O)=O)c2c(Cl)ccc(-c3cc4[nH]ncc4nc3[C@@H](Cc3cc(F)cc(F)c3)NC(=O)Cn3nc(C(F)F)c4c3C(F)(F)[C@@H]3C[C@H]43)c21]

(R)-(1-(6-bromo-1-((2-(trimethylsilyl)ethoxy)methyl)-1H-pyrazolo[4,3-b]pyridin-5-yl)-2-(3,5-difluorophenyl)ethyl)carbamate was elaborated using the procedure described above to afford the title compound as a mixture of atropisomers. LC/MS retention time=2.63 min, 2.79 min; m/z=778.2 [M+H]⁺. KINETIX XB-C18, (3×75) mm, 2.6 µm; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 20% B to 100% B over 4 min, then hold 0.5 min at 100% B with flow rate 1.5 mL/min; Detection: UV at 220 nm.

Tert-butyl (2-(3, 5-difluorophenyl)-1-(6-(6-isopropylpyridin-3-yl)-1-((2-(trimethylsilyl) ethoxy) methyl)-1H-pyrazolo [4, 3-b] pyridin-5-yl) ethyl) carbamate (Int 8a which is a Single Enatiomer)

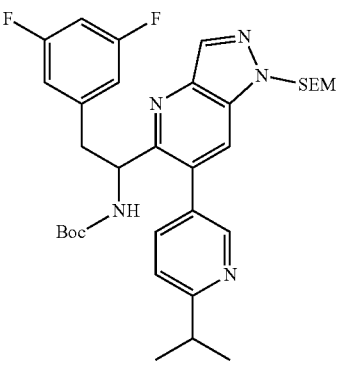 [SMILES: CC(C)c1ccc(-c2cc3c(cnn3COCC[Si](C)(C)C)nc2C(Cc2cc(F)cc(F)c2)NC(=O)OC(C)(C)C)cn1]

To a solution of tert-butyl (1-(6-bromo-1-((2-(trimethylsilyl)ethoxy)methyl)-1H-pyrazolo[4,3-b]pyridin-5-yl)-2-(3,5-difluorophenyl)ethyl)carbamate (Int 4j-E2, 100 mg, 0.171 mmol) in DMF (2 mL) was added 2-isopropyl-5-(4,4,5,5-tetramethyl-1,3,2-dioxaborolan-2-yl)pyridine (50.8 mg, 0.206 mmol), K$_2$CO$_3$ (71.1 mg, 0.514 mmol) and the solution was degassed with nitrogen gas for 2 min. Pd(Ph$_3$P)$_4$ (11.9 mg, 10.3 µmol) was added and the resulting reaction mixture was heated to 100° C. and stirred for 2 h. The reaction mixture was cooled to RT, extracted with ethyl acetate (100 mL), washed with water (50 mL), brine (2×50 mL), dried (Na$_2$SO$_4$), filtered, and concentrated to a red colored liquid. The crude product was purified with a silica gel column (eluting with 10% ethyl acetate in hexanes) to afford the title compound (80 mg). LC/MS retention time=2.18 min; m/z=624.5 [M+H] ACQUITY BEH C18 (3×50) mm, 1.7 µm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm.

2-(3,5-difluorophenyl)-1-(6-(6-isopropylpyridin-3-yl)-1-((2-(trimethylsilyl)ethoxy)methyl)-1H-pyrazolo[4,3-b]pyridin-5-yl)ethan-1-amine (Int 8b)

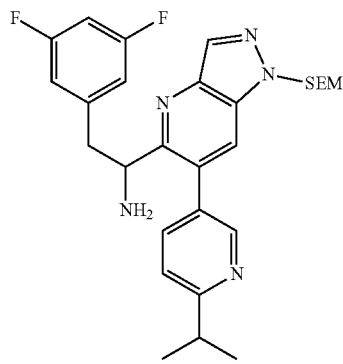 [SMILES: CC(C)c1ccc(-c2cc3c(cnn3COCC[Si](C)(C)C)nc2C(N)Cc2cc(F)cc(F)c2)cn1]

To a stirred solution of tert-butyl (2-(3,5-difluorophenyl)-1-(6-(6-isopropylpyridin-3-yl)-1-((2-(trimethylsilyl)ethoxy)methyl)-1H-pyrazolo[4,3-b]pyridin-5-yl)ethyl)carbamate (Int 8a, 80.0 mg, 0.128 mmol) in 1,4-dioxane (4 mL) was added 4M HCl in 1,4-dioxane (0.5 mL, 2 mmol) drop wise at 0° C. The solution was allowed to warm to RT and stirred for 2 h. The reaction mixture was concentrated under reduced pressure to afford the title compound (65 mg) which was directly processed to next step without further purification. LC/MS retention time=1.71 min; m/z=524.5 [M+H] ACQUITY BEH C18 (3×50) mm, 1.7 µm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm. 2-((3 bS,4aR)-3-(difluoromethyl)-5,5-difluoro-3 b,4,4a,5-tetrahydro-1H-cyclopropa[3,4]cyclopenta[1,2-c]pyrazol-1-yl)-N-(2-(3,5-difluorophenyl)-1-(6-(6-isopropylpyridin-3-yl)-1-((2-(trimethylsilyl)ethoxy)methyl)-1H-pyrazolo[4,3-b]pyridin-5-yl)ethyl)acetamide (Int 8c, (single homochiral diastereomer))

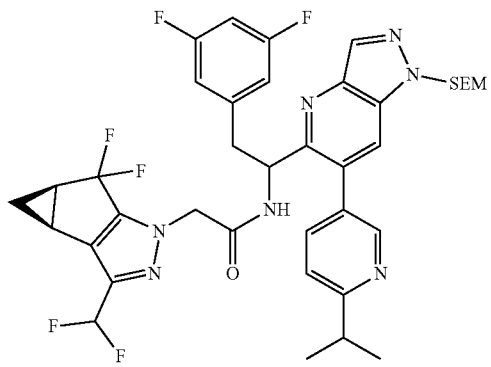 [SMILES: CC(C)c1ccc(-c2cc3c(cnn3COCC[Si](C)(C)C)nc2C(Cc2cc(F)cc(F)c2)NC(=O)Cn2nc(C(F)F)c3c2C(F)(F)[C@@H]2C[C@H]32)cn1]

To a stirred solution of 2-(3,5-difluorophenyl)-1-(6-(6-isopropylpyridin-3-yl)-1-((2-(trimethylsilyl)ethoxy)methyl)-1H-pyrazolo[4,3-b]pyridin-5-yl)ethan-1-amine (Int. 8b, 65 mg, 0.124 mmol) in DMF (2 mL) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetic acid (32.8 mg, 0.124 mmol) and HATU (49.6 mg, 0.130 mmol) and DIPEA (0.022 mL, 0.124 mmol) stirred at RT for 2 h. The reaction mixture was diluted with ethyl acetate (20 mL), washed with water (10 mL) and brine (10 mL), dried (Na$_2$SO$_4$), filtered, and concentrated to a crude pale yellow colored gummy solid (85 mg), which was directly processed to next step. LC/MS retention time=1.88 min; m/z=770.6 [M+H] ACQUITY BEH C18 (3×50) mm, 1.7 µm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-(2-(3,5-difluorophenyl)-1-(6-(6-isopropylpyridin-3-yl)-1H-pyrazolo[4,3-b]pyridin-5-yl)ethyl)acetamide (Example 3.9 (as a Single Homochiral Diastereomer)

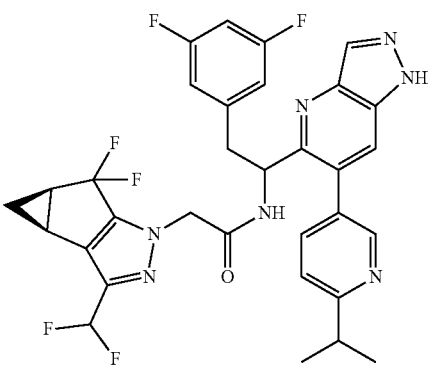 [SMILES: CC(C)c1ccc(-c2cc3[nH]ncc3nc2C(Cc2cc(F)cc(F)c2)NC(=O)Cn2nc(C(F)F)c3c2C(F)(F)[C@@H]2C[C@H]32)cn1]

To a stirred solution of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-(2-(3,5-difluorophenyl)-1-(6-(6-isopropylpyridin-3-yl)-1-((2-(trimethylsilyl)ethoxy)methyl)-1H-pyrazolo[4,3-b]pyridin-5-yl)ethyl)acetamide (Int. 8c, 80.0 mg, 0.104 mmol) in THF (2 mL) was added Bu₄NF in THF (0.40 mL, 0.40 mmol), ethylene diamine (41.2 mg, 0.686 mmol) at RT and the reaction mixture was slowly warmed to 60° C. and stirred for 2 h. The reaction mixture was diluted with ethyl acetate (10 mL), washed with water (10 mL) and brine (10 mL), dried (Na₂SO₄), filtered and the filtrate concentrated under reduced pressure to a brown color gummy solid. The crude compound was then purified by reverse phase-HPLC purification to afford the title compound (35 mg). LC/MS retention time=2.84 min; m/z=640.1 [M+H]⁺. KINETIX XB-C18, (3×75) mm, 2.6 μm; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 20% B to 100% B over 4 min, then hold 0.5 min at 100% B with flow rate 1.5 mL/min; Detection: UV at 220 nm. ¹H NMR (400 MHz, DMSO-d₆) δ ppm 13.42 (br.s, 1H), 9.12 (d, J=8.4 Hz, 1H), 8.34 (s, 2H), 7.85 (s, 1H), 7.67 (dd, J=8.0. 2.0 Hz, 1H), 7.36 (d, J=8.0 Hz, 1H), 6.92 (m, 1H), 6.90 (t, J-54.0 Hz, 1H), 6.33 (d, J=7.2 Hz, 2H), 5.22 (m, 1H), 4.75 (dd, J=19.2, 16.4 Hz, 2H), 3.05-3.20 (m, 1H), 2.80-2.97 (m, 2H), 2.38-2.44 (m, 2H), 1.33 (m, 1H), 1.30 (d, J=6.85 Hz, 6H), 0.86 (m, 1H).

N-(1-(6-(4-(difluoromethoxy)phenyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 3.10, (a Single Homochiral Diastereomer))

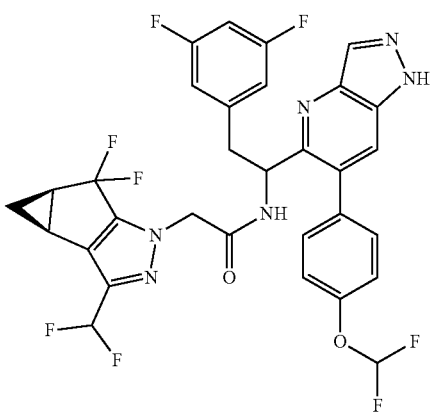 [SMILES: O=C(Cn1nc(C(F)F)c2c1C(F)(F)[C@@H]1C[C@H]21)NC(Cc1cc(F)cc(F)c1)c1nc2cn[nH]c2cc1-c1ccc(OC(F)F)cc1]

Example 3.10 was prepared from Int 4j-E2 and 2-(4-(difluoromethoxy) phenyl)-4, 4, 5, 5-tetramethyl-1, 3, 2-dioxaborolane using the procedure described for the preparation of Example 3.9. LC/MS retention time=2.97 min, m/z=663.2 [M+H]⁺. KINETIX XB-C18, (3×75) mm, 2.6 μm; Flow rate: 1 mL/min; Mobile Phase A: 10 mM HCO₂NH₄ in 98% Water/2% ACN; Mobile Phase B: 10 mM HCO₂NH₄ in 2% Water/98% ACN; 20% B to 100% B over 4 min, then hold 0.5 min at 100% B with flow rate 1.5 mL/min; Detection: UV at 220 nm. ¹H NMR (400 MHz, Methanol-d₄) δ ppm 8.20 (s, 1H), 7.63 (s, 1H), 7.09 (s, 4H), 6.78 (t, J=74 Hz, 1H), 6.60 (t, J=54 Hz, 1H), 6.57 (t, J=7.2 Hz, 1H), 6.20 (m, 2H), 5.41 (t, J=7.2 Hz, 1H), 4.81 (s, 2H), 3.02 (dd, J=12.0, 8.0 Hz, 1H), 2.88 (dd, J=12.0, 7.2 Hz, 1H), 2.36 (m, 2H), 1.22-1.38 (m, 1H), 0.94-1.11 (m, 1H).

1-(6-bromo-1-((2-(trimethylsilyl)ethoxy)methyl)-1H-pyrazolo[4,3-b]pyridin-5-yl)-2-(3,5-difluorophenyl)ethan-1-amine (Int 4i-E2, Single Enatiomer))

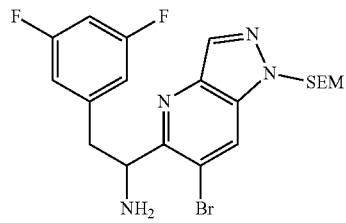

To a stirred solution of tert-butyl (1-(6-bromo-1-((2-(trimethylsilyl)ethoxy)methyl)-1H-pyrazolo[4,3-b]pyridin-5-yl)-2-(3,5-difluorophenyl)ethyl)carbamate (Int 4j-E2, 200.0 mg, 0.343 mmol) in 1,4-dioxane (4 mL) was added 4M HCl in 1,4-dioxane (2.50 mL, 10.0 mmol) drop wise at 0° C. The solution was allowed to warm to RT and stirred for 2 h. The reaction mixture was concentrated under reduced pressure to afford the title compound (140 mg) as HCl salt which was directly processed into next step without any purification. LC/MS retention time=1.24 min; m/z=483.2 [M+H]⁺. ACQUITY BEH C18 (2.1×50) mm, 1.7 μm; Flow rate: 1.1 mL/min; Mobile Phase A: 0.1% TFA in 95% Water/5% ACN; Mobile Phase B: 0.1% TFA in 5% Water/95% ACN; 0% B to 98% B over 1.6 min, then hold for 0.6 min at 90% B; Detection: UV at 220 nm.

N-(1-(6-bromo-1-((2-(trimethylsilyl)ethoxy)methyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 9a (Homochiral Diastereomer))

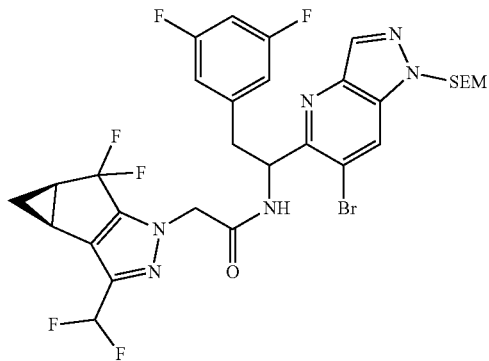 [SMILES: C[Si](C)(C)CCOCn1ncc2nc(C(Cc3cc(F)cc(F)c3)NC(=O)Cn3nc(C(F)F)c4c3C(F)(F)[C@@H]3C[C@H]43)c(Br)cc21]

To a stirred solution of 1-(6-bromo-1-((2-(trimethylsilyl)ethoxy)methyl)-1H-pyrazolo[4,3-b]pyridin-5-yl)-2-(3,5-difluorophenyl)ethanamine/HCl (Int 4i-E2, 120 mg) in DMF (2 mL) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (61.0 mg, 0.231 mmol), HATU (92 mg, 0.242 mmol) and DIPEA (0.081 mL, 0.462 mmol) and the mixture was stirred at RT for 2 h. The reaction mixture was diluted with ethyl acetate (20 mL), washed with water (10 mL) and brine (10 mL), dried (Na$_2$SO$_4$), filtered, and concentrated to afford title compound (140 mg) which was directly processed into next step without any purification. LC/MS retention time=1.63 min, m/z=729.3 [M+H]$^+$. ACQUITY BEH C18 (2.1×50) mm, 1.7 μm; Flow rate: 1.1 mL/min; Mobile Phase A: 0.1% TFA in 95% Water/5% ACN; Mobile Phase B: 0.1% TFA in 5% Water/95% ACN; 0% B to 98% B over 1.6 min, then hold for 0.6 min at 90% B; Detection: UV at 220 nm.

N-(1-(6-(4-cyclopropylphenyl)-1-((2-(trimethylsilyl) ethoxy)methyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide (Int 9b (Homochiral Diastereomer)

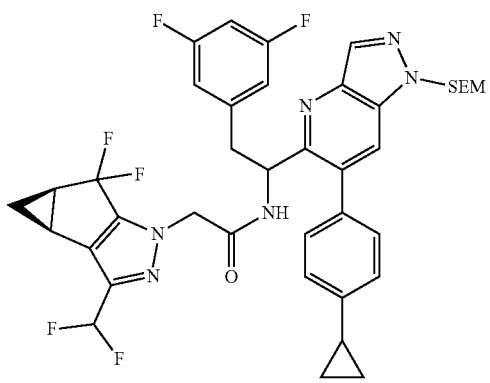 [SMILES: C[Si](C)(C)CCOCn1ncc2nc(C(Cc3cc(F)cc(F)c3)NC(=O)Cn3nc(C(F)F)c4c3C(F)(F)[C@@H]3C[C@H]43)c(-c3ccc(C4CC4)cc3)cc21]

To a solution of N-(1-(6-bromo-1-((2-(trimethylsilyl) ethoxy)methyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int. 9a, 75 mg, 0.103 mmol) in 1,4-dioxane (4 mL) was added (4-cyclopropylphenyl) boronic acid (41.6 mg, 0.257 mmol) and sodium carbonate (32.7 mg, 0.308 mmol) and the solution was degassed with nitrogen gas for 2 min. PdCl$_2$(dppf)-CH$_2$Cl$_2$ adduct (5.0 mg, 6.2 μmol) was added and the resulting reaction mixture was heated to 135° C. and stirred for 1 h in a microwave synthesizer. The reaction mixture was cooled to RT, extracted with ethyl acetate (100 mL), washed with water (50 mL), brine (2×50 mL), dried (Na$_2$SO$_4$), filtered, and concentrated to a red colored liquid. The crude product was added to a silica gel column and was eluted with 20% ethyl acetate in hexanes to afford the title product (65 mg). LC/MS retention time=1.76 min, m/z=776.5 [M+H]$^+$. ACQUITY BEH C18 (2.1×50) mm, 1.7 μm; Flow rate: 1.1 mL/min; Mobile Phase A: 0.1% TFA in 95% Water/5% ACN; Mobile Phase B: 0.1% TFA in 5% Water/95% ACN; 0% B to 98% B over 1.6 min, then hold for 0.6 min at 90% B; Detection: UV at 220 nm.

N-(1-(6-(4-cyclopropylphenyl)-1H-pyrazolo[4,3-b] pyridin-5-yl)-2-(3,5-difluorophenyl)ethyl)-2-((3bS, 4aR)-3-(difluoromethyl)-5,5-difluoro-3b,4,4a,5-tetrahydro-1H-cyclopropa[3,4]cyclopenta[1,2-c] pyrazol-1-yl)acetamide (Example 3.11 (Homochiral))

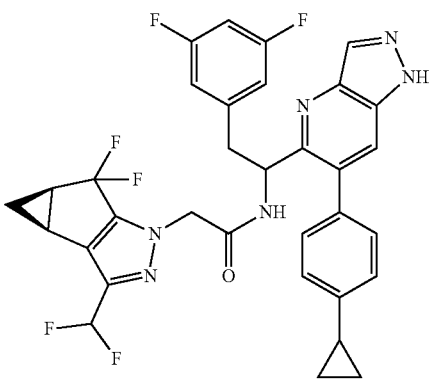 [SMILES: O=C(Cn1nc(C(F)F)c2c1C(F)(F)[C@@H]1C[C@H]21)NC(Cc1cc(F)cc(F)c1)c1nc2cn[nH]c2cc1-c1ccc(C2CC2)cc1]

To a stirred solution of N-(1-(6-(4-cyclopropylphenyl)-1-((2-(trimethylsilyl)ethoxy)methyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int. 9b, 80.0 mg, 0.104 mmol) in THF (2 mL) was added Bu$_4$NF in THF (0.4 mL, 1 M solution, 0.4 mmol), ethylene diamine (41.4 mg, 0.689 mmol) at RT and the reaction mixture was slowly warmed to 60° C. and stirred for 2 h. The reaction mixture was diluted with ethyl acetate (10 mL), washed with water (10 mL), brine (10 mL), dried (Na$_2$SO$_4$), filtered and the filtrate concentrated under reduced pressure to a brown colored gummy solid. The crude compound was then purified by reverse phase-HPLC purification to afford the title compound (25 mg). LC/MS retention time=3.20 min; m/z=367.2 [M+H]$^+$. KINETIX XB-C18, (3×75) mm, 2.6 m; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4 min, then hold 0.5 min at 100% B with flow rate 1.5 mL/min; Detection: UV at 220 nm. $^1$H NMR (400 MHz, Methanol-d$_4$) δ ppm 8.20 (s, 1H), 7.70 (s, 1H), 7.15 (d, J=8.4 Hz, 2H), 7.07 (d, J=8.4 Hz, 2H), 6.71 (t, J=54 Hz, 1H), 6.65 (t, J=8.0 Hz, 1H), 6.23 (dd, J=8.4, 1.6 Hz, 2H). 5.58 (t, J=7.2 Hz, 1H), 4.84 (s, 2H), 3.03 (dd, J=12.0, 8.0 Hz, 1H), 2.90 (dd, J=12.0, 7.2 Hz, 1H), 2.54 (m, 2H), 1.97 (m, 1H), 1.41 (m, 1H), 1.10 (m, 1H), 1.05 (dd, J=8.31, 2.20 Hz, 2H), 0.74 (m, 2H).

Methyl 6-bromo-1H-imidazo[4,5-b]pyridine-5-carboxylate (Int 10a)

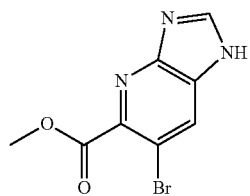

To a stirred solution of 6-bromo-3H-imidazo[4,5-b]pyridine-5-carboxylic acid (1.60 g, 6.61 mmol) in methanol (16 mL) was added conc. sulphuric acid (0.324 mL, 6.08 mmol) and the resulting solution was refluxed for 16 h. The reaction mixture was evaporated under reduced pressure and to the residue was added 10% MeOH in DCM (50 mL) and stirred for 20 min. Solid sodium bicarbonate was added and stirred the solution to become basic. The organic layer was decanted and this process was repeated twice. The combined organic layer was concentrated to dryness to afford the title compound (1 g) as a pale yellow oil. LC/MS: m/z=256.3 [M+H]$^+$. Column: Acquity BEH C8 (2.1×50 mm), 1.7 µm, Flow: 0.7 mL/min; Mobile Phase A: 5 mmol ammonium acetate: ACN (95:5); Mobile Phase B: 5 mmol ammonium acetate: ACN (5:95); Gradient time 2.4 min; 20% B to 100% B over 1.6 min, then hold for 0.2 min at 100% B of flow rate 0.7 ml/min; Detection: UV at 220 nm. $^1$H NMR (400 MHz, DMSO-d$_6$) δ ppm 13.32 (br. s., 1H), 8.65 (s, 1H), 8.46 (s, 1H), 3.91 (s, 3H).

methyl 6-bromo-1-((2-(trimethylsilyl)ethoxy)methyl)-1H-imidazo[4,5-b]pyridine-5-carboxylate (Int 10b)

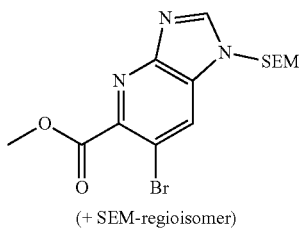 [SMILES: COC(=O)c1nc2ncn(COCC[Si](C)(C)C)c2cc1Br]

(+ SEM-regioisomer)

To a solution of methyl 6-bromo-3H-imidazo[4,5-b]pyridine-5-carboxylate (1.10 g, 4.30 mmol) in DMF (10 mL) was added NaH (0.189 g, 4.73 mmol) and stirred for 10 min. SEM-Cl (1.143 mL, 6.44 mmol) was added and stirred further at RT for 1 h. The reaction mixture was cooled to 0° C., quenched with ice cold water and extracted with ethyl acetate (2×50 mL). The combined organic layer was washed with water (50 mL) and brine (50 mL), dried (Na$_2$SO$_4$), filtered and concentrated to afford the title compound (650 mg) as mixture (26:60) of regioisomers. Sample was directly processed to next step without further purification. LC/MS retention time=1.32 and 1.39 min; m/z=386.5 [M+H]$^+$, Column: Acquity BEH C8 (2.1×50 mm, 1.7µ: Flow: 0.7 mL/min; Mobile Phase A: 5 mmol ammonium acetate: ACN (95:5) Mobile Phase B: 5 mmol ammonium acetate: ACN (5:95) Gradient time 2.4 min 20% B to 100% B over 1.6 minutes, then hold for 0.2 min at 100% B of flow rate 0.7 mL/min; Detection: UV at 220 nm). $^1$H NMR (400 MHz, DMSO-d$_6$, major regioisomer) δ ppm 8.82 (s, 1H), 8.62 (d, J=8.53 Hz, 1H), 5.64 (s, 2H) 3.92 (s, 3H), 3.45-3.65 (m, 2H), 0.74-0.92 (m, 2H), −0.01 (s, 9H).

(6-bromo-1-((2-(trimethylsilyl)ethoxy)methyl)-1H-imidazo[4,5-b]pyridin-5-yl)methanol (Int 10c)

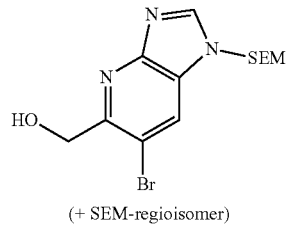 [SMILES: C[Si](C)(C)CCOCn1cnc2nc(CO)c(Br)cc21]

(+ SEM-regioisomer)

To a stirred solution of methyl 6-bromo-3-((2-(trimethylsilyl)ethoxy)methyl)-3H-imidazo[4,5-b]pyridine-5-carboxylate (1.60 g, 4.14 mmol) in THF (70 mL) was added LiAlH$_4$ (0.52 mL of 2.4 M in THF, 1.24 mmol) drop wise at −78° C. The reaction mixture was allowed to warm to RT and stirred for 1 h. The reaction mixture cooled to −50° C., slowly quenched with saturated sodium sulphate and extracted with ethyl acetate (2×100 mL). The combined organic layer was washed with brine (100 mL), dried over anhydrous sodium sulphate, filtered, concentrated under reduced pressure. The crude product was purified by Combiflash chromatography (40 g Redisep® SiO$_2$ column, eluting with 5-10% MeOH in CHCl$_3$) to afford the title compound (1.32 g) as a yellow oil. LC/MS retention time=1.29 min and 1.39 min; m/z=358.4 [M+1]$^+$. ACQUITY BEH C18 (3×50) mm, 1.7 µm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 90% B over 1 min, then hold for 0.6 min at 90% B; Detection: UV at 220 nm. $^1$H NMR (400 MHz, DMSO-d$_6$, mixture of regioisomer, integrated together) δ ppm 8.65 (1H), 8.36 (1H), 5.66 (2H), 5.20 (1H), 4.72 (2H), 3.59 (1H), 3.43-3.52 (1H), 0.77-0.89 (2H), −0.05 (m, 9H).

6-Bromo-1-((2-(trimethylsilyl)ethoxy)methyl)-1H-imidazo[4,5-b]pyridine-5-carbaldehyde (Int 10d)

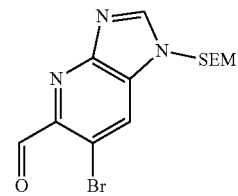 [SMILES: C[Si](C)(C)CCOCn1cnc2nc(C=O)c(Br)cc21]

To a solution of (5-bromo-1-((2-(trimethylsilyl)ethoxy)methyl)-1H-pyrazolo[3,4-b]pyridin-6-yl)methanol (1.20 g, 3.35 mmol) in DCM (30 mL) was added Dess-Martin periodinane (2.84 g, 6.70 mmol) at 0-5° C. and the resulting suspension was stirred at the same temperature for 1 h and at RT for 2 h. The reaction mixture was filtered through Celite pad, washed with DCM (3×50 mL) and the combined filtrate solution was washed with 10% aqueous NaHCO$_3$ solution (3×50 mL), water (2×50 mL), brine (50 mL), dried over anhydrous sodium sulphate, filtered and concentrated to afford the title compound (1.0 g, pale yellow liquid) as mixture of regioisomers. LC/MS retention time=2.56 and 2.79 min; m/z=356 [M+H]$^+$. Column: KINETIX C18, 75×3 mm 2.6 µm; Flow: 1 mL/min; Mobile Phase A: 98%

Water/2% Acetonitrile/10 mM HCOONH₄; Mobile Phase B: 2% Water/98% Acetonitrile/10 mM HCOONH₄; Gradient time 4.6 min; 20% B to 100% B over 4 minutes, then hold for 0.6 min. at 100% B of flow rate 1.5 mL/min; Detection: UV at 254 nm. The crude product was taken to the next step without further purification.

N-((6-bromo-1-((2-(trimethylsilyl)ethoxy)methyl)-1H-imidazo[4,5-b]pyridin-5-yl)methylene)-2-methylpropane-2-sulfinamide (Int 10e)

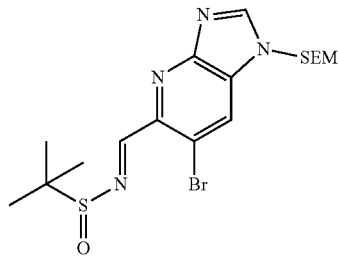 [SMILES: CC(C)(C)S(=O)/N=C/c1nc2ncn(COCC[Si](C)(C)C)c2cc1Br]

To a stirred solution of 6-bromo-3-((2-(trimethylsilyl)ethoxy)methyl)-3H-imidazo[4,5-b]pyridine-5-carbaldehyde (1.10 g, 3.09 mmol) in DCM (10 mL), 2-methylpropane-2-sulfinamide (0.449 g, 3.70 mmol) and CuSO₄.5H₂O (1.542 g, 6.17 mmol) was added and the reaction mass was stirred at RT for 16 h. The reaction mixture was diluted with DCM (2×100 mL), washed with water (2×50 mL) and brine (2×50 mL), dried (Na₂SO₄), filtered and concentrated under reduced pressure. The resultant crude brown liquid was purified by Combiflash chromatography (40 g Redisep® SiO₂ column, eluting with 5-10% MeOH in CHCl₃) to afford title compound (0.70 g) as mixture of regioisomers. LC/MS retention time=2.84 and 3.09 min; m/z=460.2 [M+H]⁺. Column: KINETIX C18, 75×3 mm 2.6 μm; Flow: 1 mL/min; Mobile Phase A: 98% Water/2% Acetonitrile/10 mM HCOONH₄; Mobile Phase B: 2% Water/98% Acetonitrile/10 mM HCOONH₄; Gradient time 4.6 min 20% B to 100% B over 4 minutes, then hold for 0.6 min at 100% B of flow rate 1.5 mL/min; Detection: UV at 220 nm).

N-(1-(6-bromo-1-((2-(trimethylsilyl)ethoxy)methyl)-1H-imidazo[4,5-b]pyridin-5-yl)-2-(3,5-difluorophenyl)ethyl)-2-methylpropane-2-sulfinamide (Int 10f)

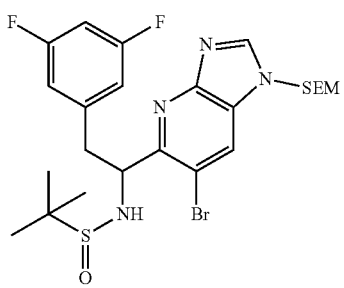 [SMILES: CC(C)(C)S(=O)NC(Cc1cc(F)cc(F)c1)c1nc2ncn(COCC[Si](C)(C)C)c2cc1Br]

To magnesium turning (0.063 g, 2.61 mmol) in diethyl ether (5 mL) was added 1-(bromomethyl)-3,5-difluorobenzene (0.338 mL, 2.61 mmol) drop wise for 15 min at RT and stirred for 1 h to afford Grignard reagent. To a stirred solution of N-((6-bromo-3-((2-(trimethylsilyl)ethoxy)methyl)-3H-imidazo[4,5-b]pyridin-5-yl)methylene)-2-methylpropane-2-sulfinamide (0.6 g, 1.306 mmol) in diethyl ether (5 mL) at 0° C. was added drop wise the Grignard reagent prepared above and the mixture was stirred at the same temperature for 30 min. The reaction mixture was cooled to 0° C., quenched with saturated NH4Cl solution and extracted with ethyl acetate (2×30 mL). The combined organic layer was washed with water (2×50 mL) and brine, dried (Na₂SO₄), filtered and concentrated under reduced pressure to afford the crude compound as brown liquid. The crude product was purified by Combiflash chromatography (24 g Redisep® SiO₂ column, eluting with 5-10% MeOH in CHCl₃) to afford the title compound (0.20 g) as mixture of regio- and diasteromers, although only two peaks were observed in LC/MS analysis. LC/MS retention time=3.38 and 3.78 min; m/z=587 [M+H]⁺. Column: KINETIX C18, 75×3 mm 2.6 μm; Flow: 1 mL/min; Mobile Phase A: 98% Water/2% Acetonitrile/10 mM HCOONH₄; Mobile Phase B: 2% Water/98% Acetonitrile/10 mM HCOONH₄; Gradient time 4.6 min 20% B to 100% B over 4 min, then hold for 0.6 min at 100% B of flow rate 1.5 mL/min; detection: UV at 220 nm.

1-(6-bromo-1-((2-(trimethylsilyl)ethoxy)methyl)-1H-imidazo[4,5-b]pyridin-5-yl)-2-(3,5-difluorophenyl)ethan-1-amine (Int 10g)

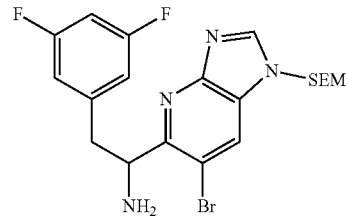 [SMILES: C[Si](C)(C)CCOCn1cnc2nc(C(N)Cc3cc(F)cc(F)c3)c(Br)cc21]

To a stirred solution of N-(1-(6-bromo-3-((2-(trimethylsilyl)ethoxy)methyl)-3H-imidazo[4,5-b]pyridin-5-yl)-2-(3,5-difluorophenyl)ethyl)-2-methylpropane-2-sulfinamide from above (0.20 g, 0.34 mmol) in dioxane (2 mL) was added 4M HCl in dioxane (0.10 mL, 0.34 mmol) drop wise and the reaction mass was stirred at RT for 1 h. Volatiles were removed under reduced pressure and the residue was co-distilled with ether two times to afford the title compound as HCl salt (150 mg), of unknown SEM-regiochemical composition, which was directly processed to next step without any purification. LC/MS: m/z=483.9 [M+H]⁺.

tert-butyl (1-(6-bromo-1-((2-(trimethylsilyl)ethoxy)methyl)-1H-imidazo[4,5-b]pyridin-5-yl)-2-(3,5-difluorophenyl)ethyl)carbamate (Int 10h)

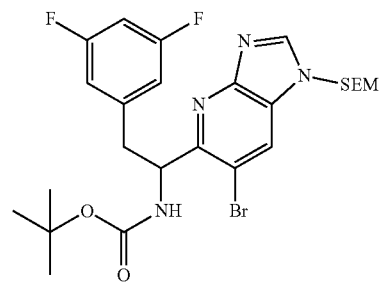 [SMILES: CC(C)(C)OC(=O)NC(Cc1cc(F)cc(F)c1)c1nc2ncn(COCC[Si](C)(C)C)c2cc1Br]

To a stirred solution of 1-(6-bromo-3-((2-(trimethylsilyl)ethoxy)methyl)-3H-imidazo[4,5-b]pyridin-5-yl)-2-(3,5-difluorophenyl)ethan-1-amine (300 mg, 0.621 mmol) in DCM (2 mL) was added TEA (0.432 mL, 3.10 mmol) and (Boc)₂O (0.173 mL, 0.745 mmol) at 0° C. and the reaction mixture was allowed to warm to RT and stirred for 2 h. The reaction mixture diluted with DCM (2×20 mL), washed with water (2×10 mL) and brine (20 mL), dried (Na₂SO₄), filtered, and concentrated. The crude product was then purified by Combiflash chromatography (120 g Redisep® SiO₂ column, eluting with 5%-10% EtOAc in hexanes) to afford the title compound (0.20 g) as mixture of regioisomers. LC/MS retention time=1.86 and 1.94 min; m/z=583.0 [M+H]⁺. Column: Acquity BEH C₈ (2.1×50 mm), 1.7 µm: Flow: 0.7 mL/min; Mobile Phase A: 5 mmol ammonium acetate: ACN (95:5); Mobile Phase B: 5 mmol ammonium acetate: ACN (5:95); Gradient time 2.4 min, 20% B to 100% B over 1.6 min, then hold for 0.2 min at 100% B of flow rate 0.7 mL/min; Detection: UV at 220 nm.

tert-butyl (1-(6-bromo-1H-imidazo[4,5-b]pyridin-5-yl)-2-(3,5-difluorophenyl)ethyl)carbamate (Int 10i-E1 & Int 10i-E2 (Each a Single Enatiomer))

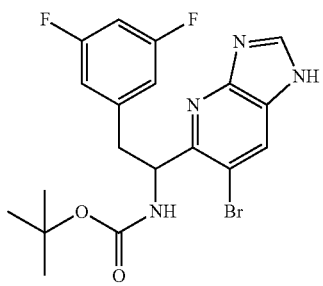 [SMILES: CC(C)(C)OC(=O)NC(Cc1cc(F)cc(F)c1)c1nc2nc[nH]c2cc1Br]

To a stirred solution of tert-butyl (1-(6-bromo-3-((2-(trimethylsilyl)ethoxy)methyl)-3H-imidazo[4,5-b]pyridin-5-yl)-2-(3,5-difluorophenyl)ethyl)carbamate (164 mg, 0.281 mmol) in THF (1.0 mL) was added TBAF (1.85 mL, 0.281 mmol) and ethylenediamine (0.019 mL, 0.28 mmol) and the reaction mass was stirred at 70° C. for 1 h. The reaction mixture was cooled to RT, diluted with ethyl acetate (50 mL), washed with water (20 mL) and brine (20 mL), dried (Na₂SO₄), filtered, and concentrated. The crude was then purified by prep-HPLC followed by the separation of enantiomers by chiral SFC (Chiralpak AD-H (250×21) mm, 5 µm; Injection volume: 10 mg/1 mL; co-solvent: 0.2% DEA in MeOH; column temp. 30° C.; CO₂%: 80, Co-solvent %: 20; flow rate: 70 g/min, UV: 295 nm).

Int 10i-E1 (First-eluting enantiomer; retention time: 3.1 min): LC/MS: m/z=453.0 [M+H]⁺. ¹H NMR (400 MHz, Methanol-d₄) δ ppm 8.43 (s, 1H), 8.24 (s, 1H), 6.69-6.90 (m, 3H), 5.56 (dd, J=8.28, 5.27 Hz, 1H), 3.13-3.27 (dd, J=13.55, 9.04 Hz, 1H), 3.00 (dd, J=13.55, 9.04 Hz, 1H), 1.39 (s, 9H).

Int 10i-E2: (Second-eluting enantiomer; retention time: 3.6 min). LC/MS: m/z=453.0 [M+H]⁺.

tert-butyl (1-(6-(4-chloro-1-methyl-3-(methylsulfonamido)-1H-indazol-7-yl)-1H-imidazo[4,5-b]pyridin-5-yl)-2-(3,5-difluorophenyl)ethyl)carbamate (Int 10j (Single Enatiomer as Mix of Atropisomers)

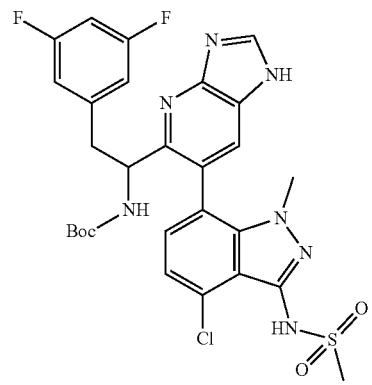 [SMILES: Cn1nc(NS(C)(=O)=O)c2c(Cl)ccc(-c3cc4[nH]cnc4nc3C(Cc3cc(F)cc(F)c3)NC(=O)OC(C)(C)C)c21]

To a solution of tert-butyl (1-(6-bromo-3H-imidazo[4,5-b]pyridin-5-yl)-2-(3,5-difluorophenyl)ethyl)carbamate (40.0 mg, 0.088 mmol) and N-(4-chloro-1-methyl-7-(4,4,5,5-tetramethyl-1,3,2-dioxaborolan-2-yl)-1H-indazol-3-yl)methanesulfonamide (Int 10i-E1, 85.0 mg, 0.221 mmol) in dioxane (2 mL) was added a solution of NaHCO₃ (44.5 mg, 0.529 mmol) in water (0.5 mL) and the reaction mixture was degassed with nitrogen for 10 min. PdCl₂(dppf)-CH₂Cl₂ adduct (4.3 mg, 5.29 µmol) was added and the reaction mixture was heated to 130° C. and stirred under microwave radiation for 1 h. The reaction mixture was cooled to RT, diluted with ethyl acetate (5 mL), washed with water (5 mL) and brine (5 mL), dried (Na₂SO₄), filtered, concentrated and the crude product was purified by prep-HPLC to afford the title compound (40 mg) as mixture of atropisomers. LC/MS retention time=2.29 and 2.33 min; m/z=632.0 [M+H]⁺. Column: KINETIX C18, 75×3 mm 2.6 µm; Flow: 1 mL/min; Mobile Phase A: 98% Water/2% Acetonitrile/10 mM HCOONH₄; Mobile Phase B: 2% Water/98% Acetonitrile/10 mM HCOONH₄; Gradient time 4.6 min; 20% B to 100% B over 4 minutes, then hold for 0.6 min at 100% B of flow rate 1.5 mL/min; Detection: UV at 220 nm.

N-(7-(5-(1-amino-2-(3,5-difluorophenyl)ethyl)-1H-imidazo[4,5-b]pyridin-6-yl)-4-chloro-1-methyl-1H-indazol-3-yl)methanesulfonamide (Int 10k (Single Enatiomer as Mix of Atropisomers))

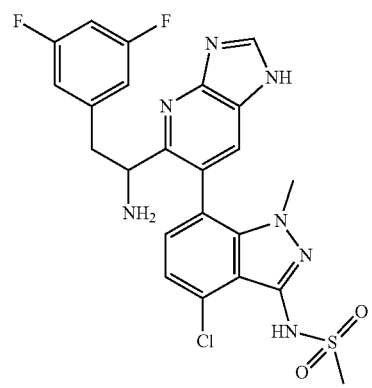 [SMILES: Cn1nc(NS(C)(=O)=O)c2c(Cl)ccc(-c3cc4[nH]cnc4nc3C(N)Cc3cc(F)cc(F)c3)c21]

To a stirred solution of tert-butyl (1-(6-(4-chloro-1-methyl-3-(methylsulfonamido)-1H-indazol-7-yl)-3H-imidazo[4,5-b]pyridin-5-yl)-2-(3,5-difluorophenyl)ethyl)carbamate (Int. 10j, 40 mg, 0.063 mmol) in dioxane (1 mL) was added 4M HCl dioxane (0.50 mL, 0.063 mmol) drop wise at 0° C. and the resulting solution was slowly warmed to RT and stirred for 1 h. The reaction mixture was concentrated under reduced pressure and the residue was co-distilled with ether two times to afford the title compound (40 mg) as mixture of atropisomers. LC/MS retention time=1.23 and 1.75 min; m/z=532.1 [M+H]$^+$. Column: KINETIX C18, 75×3 mm 2.6 µm; Flow: 1 mL/min; Mobile Phase A: 98% Water/2% Acetonitrile/10 mM HCOONH$_4$; Mobile Phase B: 2% Water/98% Acetonitrile/10 mM HCOONH$_4$; Gradient time 4.6 min; 20% B to 100% B over 4 minutes, then hold for 0.6 min at 100% B of flow rate 1.5 mL/min; Detection: UV at 220 nm.

N-(1-(6-(4-chloro-1-methyl-3-(methylsulfonamido)-1H-indazol-7-yl)-1H-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 4.1 (Homochiral Diastereomer as a Mix of Atropisomers))

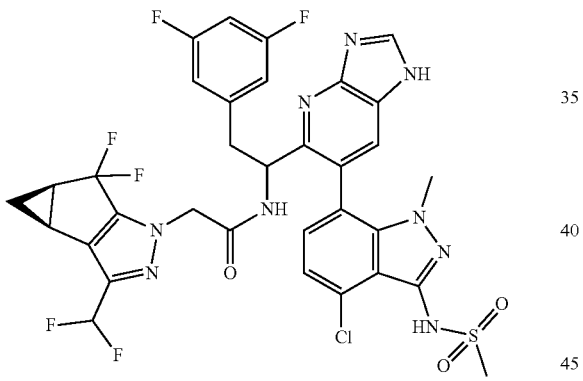

To a stirred solution of N-(7-(5-(1-amino-2-(3,5-difluorophenyl)ethyl)-1H-imidazo[4,5-b]pyridin-6-yl)-4-chloro-1-methyl-1H-indazol-3-yl)methanesulfonamide (Int. 10k, 40.0 mg, 0.075 mmol) in DCM (1 mL) was added ((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (23.8 mg, 0.090 mmol), DIPEA (0.013 mL, 0.075 mmol) and HATU (28.6 mg, 0.075 mmol) and the resulting solution was stirred at RT for 1 h. The reaction mixture was diluted with DCM (5 mL), washed with water (5 mL), brine (5 mL), dried (Na$_2$SO$_4$), filtered and concentrated. The crude was purified by reverse phase HPLC to afford the title compound (10.9 mg) as mixture of atropisomers. LC/MS retention time=2.50 and 2.64 min; m/z=778.1 [M+H]$^+$. Column: KINETIX C18, 75×3 mm 2.6 µm; Flow: 1 mL/min; Mobile Phase A: 98% Water/2% Acetonitrile/10 mM HCOONH$_4$; Mobile Phase B: 2% Water/98% Acetonitrile/10 mM HCOONH$_4$; Gradient time 4.6 min 20% B to 100% B over 4 minutes, then hold for 0.6 min at 100% B of flow rate 1.5 ml/min; Detection: UV at 254 nm.

Example 4.2

Example 4.2 is prepared as a homochiral compound which is a mixture of atropisomers in a similar fashion like Example 4.1 from Int 10i-E2. LC/MS retention time=2.51 and 2.64 min; m/z=778.1 [M+H]$^+$. Column: KINETIX C18, 75×3 mm 2.6 µm; Flow: 1 mL/min; Mobile Phase A: 98% Water/2% Acetonitrile/10 mM HCOONH$_4$; Mobile Phase B: 2% Water/98% Acetonitrile/10 mM HCOONH$_4$; Gradient time 4.6 min 20% B to 100% B over 4 min, then hold for 0.6 min at 100% B of flow rate 1.5 mL/min; Detection: UV at 254 nm.

6-bromo-1-tosyl-1H-pyrrolo[3,2-b]pyridine (Int 11a)

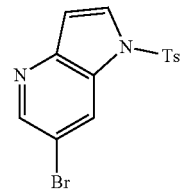

To a stirred solution of 6-bromo-1H-pyrrolo[3,2-b]pyridine (3.00 g, 15.2 mmol) in DMF (50 mL) was added NaH (1.218 g, 30.5 mmol) at 0° C. and stirred at RT for 5 min. Tosylchloride (5.81 g, 30.5 mmol) was added and the resulting mixture was stirred at RT for 1 h. The reaction mixture was quenched with water and the product was filtered and dried to afford the title compound as brown solid. LC/MS: m/z=351.3 [M+H]$^+$. $^1$H NMR (400 MHz, DMSO-d$_6$) δ ppm 8.63 (d, J=2.0 Hz, 1H), 8.47 (s, 1H), 8.20 (d, J=3.9 Hz, 1H), 7.99 (d, J=8.6 Hz, 2H), 7.44 (d, J=7.8 Hz, 2H), 6.99 (dd, J=3.7, 0.7 Hz, 1H), 2.35 (s, 3H).

6-bromo-1-tosyl-1H-pyrrolo[3,2-b]pyridine 4-oxide (Int 11b)

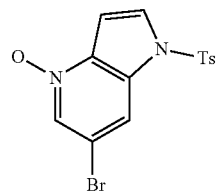

To a stirred solution of 6-bromo-1-tosyl-1H-pyrrolo[3,2-b]pyridine (0.16 g, 0.456 mmol) in DCM (3 mL) at 0° C. was added m-CPBA (0.157 g, 0.911 mmol) and the resulting reaction mixture was stirred at RT overnight. The reaction mixture was cooled, the solid precipitated out was filtered and to the filtrate was added 10% aqueous sodium bicarbonate solution and extracted with DCM (2×20 mL). The combined organic layer was washed with water (20 mL) and brine (20 mL), dried over anhydrous sodium sulphate, filtered and the filtrate concentrated under reduced pressure to afford the pure title compound (0.16 g). LC/MS: m/z=369.2 [M+H]$^+$.

6-bromo-1-tosyl-1H-pyrrolo[3,2-b]pyridine-5-carbonitrile (Int 11c)

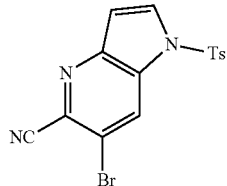 [SMILES: Cc1ccc(S(=O)(=O)n2ccc3nc(C#N)c(Br)cc32)cc1]

To a stirred solution of 6-bromo-1-tosyl-1H-pyrrolo[3,2-b]pyridine 4-oxide (0.160 g, 0.436 mmol) in DCE (4 mL) was added TEA (0.304 mL, 2.19 mmol), TMS-CN (0.292 mL, 2.18 mmol) at RT and the resulting reaction mixture was stirred at 80° C. overnight. The reaction mixture was diluted with water and extracted with DCM (2×20 mL). The combined organic layer was washed with water (10 mL), brine (10 mL), dried over anhydrous $Na_2SO_4$, filtered and the filtrate evaporated under reduced pressure. The crude product was purified by Combiflash chromatography (12 g Redisep® $SiO_2$ column, eluting with 10%-20% EtOAc in hexanes) to afford the title compound (0.13 g). LC/MS: m/z=376.3 [M+H]$^+$. $^1$H NMR (400 MHz, DMSO-$d_6$) δ ppm 8.74 (s, 1H), 8.45 (d, J=3.9 Hz, 1H), 8.09 (d, J=8.3 Hz, 2H), 7.47 (d, J=8.4 Hz, 2H), 7.12 (d, J=3.6 Hz, 1H), 2.39-2.30 (s, 3H).

methyl 6-bromo-1H-pyrrolo[3,2-b]pyridine-5-carboxylate (Int 11d)

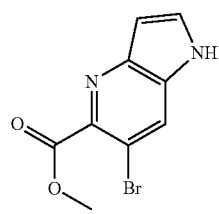

To a stirred solution of 6-bromo-1-tosyl-1H-pyrrolo[3,2-b]pyridine-5-carbonitrile (0.5 g, 1.33 mmol) in ethanol (10 mL) and water (4 mL) was added NaOH (0.213 g, 5.32 mmol) at RT and the resulting reaction mixture was refluxed at 90° C. overnight. The reaction mixture was concentrated under reduced pressure. To the resultant crude acid (0.28 g) in MeOH (5 mL) was added $H_2SO_4$ (0.31 mL) at RT and the reaction mixture was stirred at 65° C. overnight. The reaction mixture was concentrated, aqueous 10% sodium bicarbonate solution was added carefully and extracted with ethyl acetate (2×50 mL). The combined organic layer was washed with water, brine, dried over anhydrous sodium sulfate, filtered and concentrated under reduced pressure. The resultant crude material was purified by Combiflash chromatography (12 g Redisep® $SiO_2$ column, eluting with 60% ethyl acetate in hexanes) to afford the title compound (0.25 g) as brown color solid. LC/MS: m/z=255.3 [M+H]$^+$. $^1$H NMR (400 MHz, DMSO-$d_6$) δ ppm 12.00 (br. s., 1H), 8.14 (d, J=8.0 Hz, 1H), 7.73 (d, J=3.6 Hz, 1H), 6.69-6.68 (dd, J=8.0, 3.6 Hz, 1H), 4.09-3.73 (m, 3H)

methyl 6-bromo-1-((2-(trimethylsilyl)ethoxy)methyl)-1H-pyrrolo[3,2-b]pyridine-5-carboxylate (Int 11e)

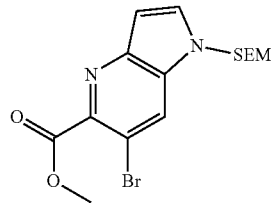 [SMILES: COC(=O)c1nc2ccn(COCC[Si](C)(C)C)c2cc1Br]

To a stirred solution of methyl 6-bromo-1H-pyrrolo[3,2-b]pyridine-5-carboxylate (0.23 g, 0.902 mmol) in DMF (4 mL) was added NaH (0.054 g, 1.353 mmol) at 0° C. and the resultant solution was stirred at RT for 5 min. SEM-Cl (0.239 mL, 1.353 mmol) was added and stirred further at RT for 1 h. The reaction mass was diluted with cold water and extracted with ethyl acetate (2×20 mL). The combined organic layer was washed with water, brine, dried over anhydrous sodium sulphate, filtered and the filtrate concentrated under reduced pressure. The crude compound was purified by ISCO (12 g Redisep® $SiO_2$ column, eluting with 50% ethyl acetate in pet ether) to afford the title compound (0.3 g). LC/MS: m/z=387.3 [M+H]$^+$. $^1$H NMR (400 MHz, DMSO-$d_6$) δ ppm 8.43 (s, 1H), 7.94 (d, J=3.5 Hz, 1H), 6.79-6.64 (m, 1H), 5.60 (s, 2H), 3.95 (s, 3H), 3.55-3.34 (m, 2H), 0.88-0.67 (m, 2H), −0.08 (s, 9H).

6-bromo-1-((2-(trimethylsilyl)ethoxy)methyl)-1H-pyrrolo[3,2-b]pyridine-5-carbaldehyde (Int 11f)

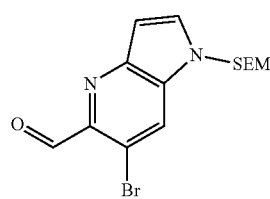 [SMILES: C[Si](C)(C)CCOCn1ccc2nc(C=O)c(Br)cc21]

To a stirred solution of methyl 6-bromo-1-((2-(trimethylsilyl)ethoxy)methyl)-1H-pyrrolo[3,2-b]pyridine-5-carboxylate (0.100 g, 0.260 mmol) in THF (2 mL) was added DIBAL-H (0.519 mL, 0.519 mmol) at −78° C. and stirred at the same temperature for 1 h. The reaction mixture was quenched with MeOH at −78° C., saturated potassium sodium tartrate solution was added and extracted with ethyl acetate (2×20 mL). The combined organic layer was washed with water (10 mL) and brine (10 mL), dried over anhydrous sodium sulphate, filtered and the filtrate concentrated under reduced pressure to afford the title compound (0.075 g). LC/MS: m/z=355.3 [M+H]$^+$. $^1$H NMR (400 MHz, DMSO-$d_6$) δ ppm 10.12 (s, 1H), 8.50 (s, 1H), 8.05 (d, J=3.5 Hz, 1H), 6.86 (d, J=3.5 Hz, 1H), 5.76-5.43 (m, 2H), 3.47-3.34 (m, 2H), 1.04-0.52 (m, 2H), −0.37 (s, 9H).

N-((6-bromo-1-((2-(trimethylsilyl)ethoxy)methyl)-1H-pyrrolo[3,2-b]pyridin-5-yl)methylene)-2-methylpropane-2-sulfinamide (Int 11g)

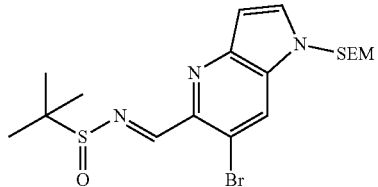 [SMILES: CC(C)(C)S(=O)/N=C/c1nc2ccn(COCC[Si](C)(C)C)c2cc1Br]

To a solution of 6-bromo-1-((2-(trimethylsilyl)ethoxy)methyl)-1H-pyrrolo[3,2-b]pyridine-5-carbaldehyde (1.50 g, 4.22 mmol) in dichloromethane (30 mL) was added copper (II) sulphate pentahydrate (2.11 g, 8.44 mmol), 2-methylpropane-2-sulfinamide (1.28 g, 10.55 mmol) and the resulting solution was stirred at RT overnight. The reaction mixture was filtered through Celite, washed with ethyl acetate and the combined filtrate was concentrated under reduced pressure. The crude compound was purified by ISCO (40 g Redisep® SiO$_2$ column, eluting with 60% ethyl acetate in pet ether) to afford the title compound (1.1 g). LC/MS: m/z=460.4 [M+H]$^+$. $^1$H NMR (400 MHz, DMSO-d$_6$) δ ppm 8.88 (s, 1H), 8.51 (s, 1H), 8.01 (d, J=3.4 Hz, 1H), 6.81 (d, J=3.2 Hz, 1H), 5.64 (s, 2H), 3.55-3.34 (m, 2H), 1.23 (s, 9H), 0.93-0.65 (m, 2H), −0.40 (m, 9H).

N-(1-(6-bromo-1-((2-(trimethylsilyl)ethoxy)methyl)-1H-pyrrolo[3,2-b]pyridin-5-yl)-2-(3,5-difluorophenyl)ethyl)-2-methylpropane-2-sulfinamide (Int 11h)

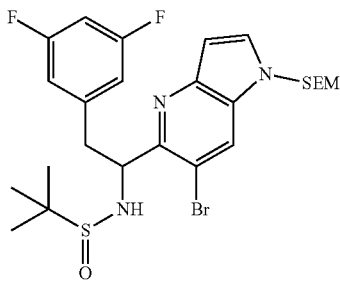 [SMILES: CC(C)(C)S(=O)NC(Cc1cc(F)cc(F)c1)c1nc2ccn(COCC[Si](C)(C)C)c2cc1Br]

To a stirred mixture of magnesium (0.099 g, 4.09 mmol) in diethyl ether (20 mL) was added 1-(bromomethyl)-3,5-difluorobenzene (0.423 mL, 3.27 mmol) drop wise at RT over 10 min and stirred further for 30 min to afford Grignard reagent. To a stirred solution of N-((6-bromo-1-((2-(trimethylsilyl)ethoxy)methyl)-1H-pyrrolo[3,2-b]pyridin-5-yl)methylene)-2-methylpropane-2-sulfinamide (0.750 g, 1.636 mmol) in THF (10 mL) was added the above Grignard reagent at −10° C. and the resulting solution was allowed to warm to RT and stirred for 2 h. The reaction mixture was quenched with aqueous saturated NH$_4$Cl solution and extracted with ethyl acetate (3×30 mL). The combined organic layer was washed with water (20 mL) and brine (20 mL), dried over anhydrous sodium sulphate, filtered and the filtrate concentrated to afford the title compound (0.80 g). The diastereomeric makeup was not determined. LC/MS: m/z=588.3 [M+H]$^+$. 1-(6-bromo-1-((2-(trimethylsilyl) ethoxy)methyl)-1H-pyrrolo[3,2-b]pyridin-5-yl)-2-(3,5-difluorophenyl)ethan-1-amine (Int 11i)

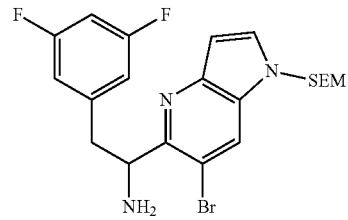 [SMILES: C[Si](C)(C)CCOCn1ccc2nc(C(N)Cc3cc(F)cc(F)c3)c(Br)cc21]

To a stirred solution of N-(1-(6-bromo-1-((2-(trimethylsilyl)ethoxy)methyl)-1H-pyrrolo[3,2-b]pyridin-5-yl)-2-(3,5-difluorophenyl)ethyl)-2-methylpropane-2-sulfinamide (0.900 g, 1.53 mmol) in 1,4-dioxane (10 mL) was added 4 M HCl in dioxane (0.47 mL, 15.3 mmol) at RT and stirred for 1 h. The reaction mass was concentrated to remove dioxane, diluted with 10% aqueous sodium bicarbonate solution and extracted with ethyl acetate (3×20 mL). The combined organic layer was washed with water (10 mL) and brine (10 mL), dried over anhydrous sodium sulphate, filtered and the filtrate concentrated under reduced pressure. The crude compound was purified by reverse phase prep-HPLC to afford the title compound (0.32 g) as brown solid. LC/MS: m/z=484.4 [M+H]$^+$.

tert-butyl (1-(6-bromo-1-((2-(trimethylsilyl)ethoxy)methyl)-1H-pyrrolo[3,2-b]pyridin-5-yl)-2-(3,5-difluorophenyl)ethyl)carbamate (Int 11j-E1 & Int 11j-E2 (Each is a Pure Enantiomer))

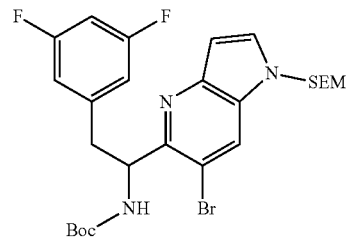 [SMILES: CC(C)(C)OC(=O)NC(Cc1cc(F)cc(F)c1)c1nc2ccn(COCC[Si](C)(C)C)c2cc1Br]

To a stirred solution of 1-(6-bromo-1-((2-(trimethylsilyl)ethoxy)methyl)-1H-pyrrolo[3,2-b]pyridin-5-yl)-2-(3,5-difluorophenyl)ethan-1-amine (0.300 g, 0.622 mmol) in DCM (5 mL) was added TEA (0.173 mL, 1.244 mmol) and Boc$_2$O (0.217 mL, 0.933 mmol) and resulting solution was stirred at RT for 1 h. The reaction mixture was diluted with water and extracted with DCM (3×20 mL). The combined organic layer was washed with water (10 mL) and brine (10 mL), dried over anhydrous sodium sulphate, filtered and the filtrate concentrated under reduced pressure to get crude compound (0.26 g). The individual enantiomers were separated by Chiral SFC separation (Whelk (R,R) (250×30) mm, 5 u; % Co-solvent 25% of IPA+ACN (1:1), Column temperature=30° C., % CO$_2$: 75%, % Co-solvent: 25% of IPA+ACN (1:1), Total Flow: 80.0 g/min, Back Pressure: 100 bars, UV absorbance: 225 nm).

Int 11j-E1: Chiral SFC retention time=4.53 min. LC/MS: m/z=584.4 [M+H]$^+$. $^1$H NMR (400 MHz, DMSO-d$_6$) δ ppm 8.40 (s, 1H), 7.95 (d, J=3.3 Hz, 1H), 7.31 (d, J=9.0 Hz, 1H), 7.20-6.93 (m, 3H), 6.75 (d, J=3.3 Hz, 1H), 5.68 (s, 2H), 5.37 (m, 1H), 3.54 (t, J=7.8 Hz, 2H), 3.21-2.91 (m, 2H), 1.34 (s, 9H), 0.90 (t, J=7.9 Hz, 2H), 0.05 (s, 9H).

Int 11j-E2: Chiral SFC retention time=6.23 min (Desired enantiomer).

tert-butyl (1-(6-(4-chloro-1-methyl-3-(methylsulfonamido)-1H-indazol-7-yl)-1-((2-(trimethylsilyl)ethoxy)methyl)-1H-pyrrolo[3,2-b]pyridin-5-yl)-2-(3,5-difluorophenyl)ethyl)carbamate (Int 11k (Single Enantiomer as a Mix of Atropisomers))

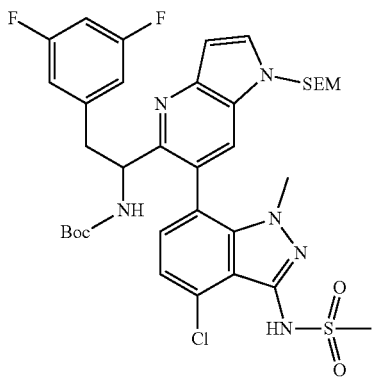 [SMILES: Cn1nc(NS(C)(=O)=O)c2c(Cl)ccc(-c3cc4c(ccn4COCC[Si](C)(C)C)nc3C(Cc3cc(F)cc(F)c3)NC(=O)OC(C)(C)C)c21]

To a stirred solution of tert-butyl (1-(6-bromo-1-((2-(trimethylsilyl)ethoxy)methyl)-1H-pyrrolo[3,2-b]pyridin-5-yl)-2-(3,5-difluorophenyl)ethyl)carbamate (Int 11j-E1, 0.050 g, 0.086 mmol) and N-(4-chloro-1-methyl-7-(4,4,5,5-tetramethyl-1,3,2-dioxaborolan-2-yl)-1H-indazol-3-yl)methanesulfonamide (0.066 g, 0.172 mmol) in 1,4-dioxane (2 mL) and water (0.1 mL) was added sodium bicarbonate (0.043 g, 0.515 mmol) and Pd(dppf)Cl$_2$.DCM complex (4.2 mg, 5.15 µmol). The reaction mixture was purged with nitrogen and heated under microwave irradiations at 130° C. for 1 h. The reaction mixture was filtered through Celite and the Celite pad was washed with ethyl acetate. The organic layer was concentrated and the crude was purified by reverse phase prep-HPLC to afford the title compound (0.06 g, brown gummy liquid) as mixture of atropisomers. LC/MS retention time=3.80 and 3.83 min, m/z=761.2 [M+H]$^+$. Column-KINETIX XB-C18, (3×75) mm, 2.6 µm; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4 min, then hold 0.5 min at 100% B with flow rate 1.5 mL/min; Detection: UV at 220 nm.

N-(7-(5-(1-amino-2-(3,5-difluorophenyl)ethyl)-1-((2-(trimethylsilyl)ethoxy)methyl)-1H-pyrrolo[3,2-b]pyridin-6-yl)-4-chloro-1-methyl-1H-indazol-3-yl)methanesulfonamide (Int 11l (Single Enantiomer as a Mix of Atropisomers))

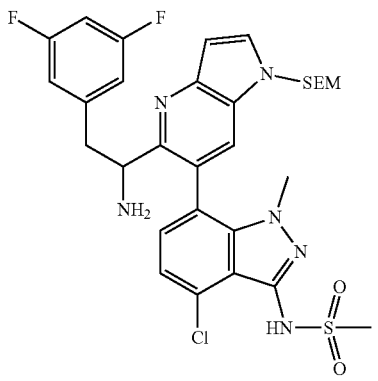 [SMILES: Cn1nc(NS(C)(=O)=O)c2c(Cl)ccc(-c3cc4c(ccn4COCC[Si](C)(C)C)nc3C(N)Cc3cc(F)cc(F)c3)c21]

To a stirred solution of tert-butyl (1-(6-(4-chloro-1-methyl-3-(methylsulfonamido)-1H-indazol-7-yl)-1-((2-(trimethylsilyl)ethoxy)methyl)-1H-pyrrolo[3,2-b]pyridin-5-yl)-2-(3,5-difluorophenyl)ethyl)carbamate (Int 11k, 0.090 g, 0.118 mmol) in 1,4-dioxane (2 mL) was added 4 M HCl in dioxane (0.014 mL, 0.473 mmol) and stirred further at RT for 1 h. The reaction mixture was concentrated, diluted with 10% sodium bicarbonate solution and extracted with ethyl acetate (3×10 mL). The combined organic layer was washed with water (10 mL) and brine (10 mL), dried over anhydrous sodium sulphate, filtered and the filtrate concentrated under reduced pressure to afford title compound (0.075 g) as mixture of atropisomers. Retention time=1.42 and 1.55 min, m/z=661.6 [M+H]$^+$. ACQUITY BEH C18 (3×50) mm, 1.7 µm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm.

N-(1-(6-(4-chloro-1-methyl-3-(methylsulfonamido)-1H-indazol-7-yl)-1-((2-(trimethylsilyl)ethoxy)methyl)-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 11m, (Homochiral Diastereomer as a Mix of Atropisomers))

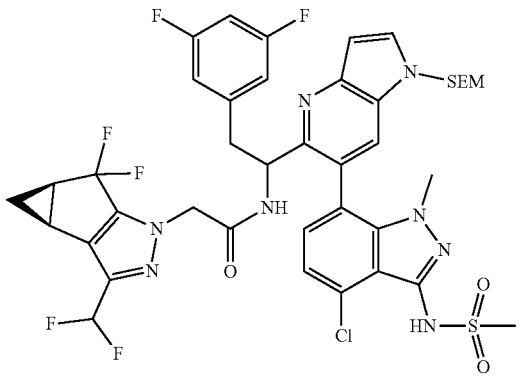 [SMILES: Cn1nc(NS(C)(=O)=O)c2c(Cl)ccc(-c3cc4c(ccn4COCC[Si](C)(C)C)nc3C(Cc3cc(F)cc(F)c3)NC(=O)Cn3nc(C(F)F)c4c3C(F)(F)[C@@H]3C[C@H]43)c21]

To a stirred solution of N-(7-(5-(1-amino-2-(3,5-difluorophenyl)ethyl)-1-((2-(trimethylsilyl)ethoxy)methyl)-1H-pyrrolo[3,2-b]pyridin-6-yl)-4-chloro-1-methyl-1H-indazol-3-yl)methanesulfonamide (Int. 11 µl, 0.080 g, 0.121 mmol) in DMF (2 mL) was added HATU (0.046 g, 0.121 mmol), DIPEA (10.6 µL, 0.060 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.038 g, 0.145 mmol) and the resulting reaction mixture was stirred at RT for 2 h. The reaction mixture was concentrated to remove DMF, 10% sodium bicarbonate solution was added and extracted with ethyl acetate (3×10 mL). The combined organic layer was washed with water (10 mL) and brine (10 mL), dried over anhydrous sodium sulphate, filtered and the filtrate concentrated to afford the title compound (0.1 g, brown gummy liquid) as mixture of atropisomers. LC/MS retention time=1.72 and 1.88 min, m/z=907.5 [M+H]$^+$. ACQUITY BEH C18 (3×50) mm, 1.7 µm; Flow rate: 0.7 mL/min; Mobile Phase A: 5 mmol NH$_4$OAc in 95% Water/5% ACN; Mobile Phase B: 5 mmol NH$_4$OAc in 5% Water/

95% ACN; 20% B to 100% B over 1 min, then hold for 0.6 min at 90% B; Detection: UV at 220 nm.

N-(1-(6-(4-chloro-1-methyl-3-(methylsulfonamido)-1H-indazol-7-yl)-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 5.1, 5.2, 5.3 & 5.4 (Each is a Homochiral Single Enatiomer)

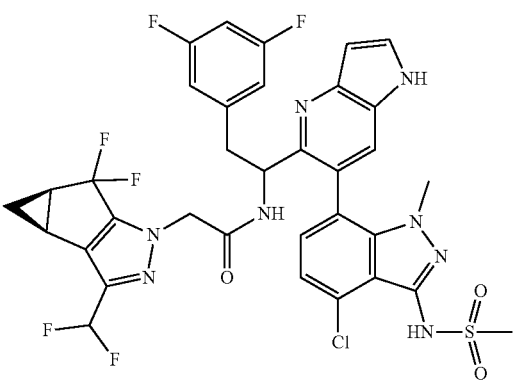 [SMILES: Cn1nc(NS(C)(=O)=O)c2c(Cl)ccc(-c3cc4[nH]ccc4nc3C(Cc3cc(F)cc(F)c3)NC(=O)Cn3nc(C(F)F)c4c3C(F)(F)[C@@H]3C[C@H]43)c21]

To a stirred solution of N-(1-(6-(4-chloro-1-methyl-3-(methylsulfonamido)-1H-indazol-7-yl)-1-((2-(trimethylsilyl)ethoxy)methyl)-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.10 g, 0.110 mmol) in THF (1 mL) was added TBAF (0.22 mL, 0.22 mmol), ethylenediamine (3.7 µL, 0.055 mmol) and the resulting solution was stirred at 70° C. for 2 h. The reaction mass was diluted with 10% sodium bicarbonate solution and extracted with ethyl acetate (3×10 mL). The combined organic layer was washed with water (10 mL) and brine (10 mL), dried over anhydrous sodium sulphate, filtered and the filtrate concentrated under reduced pressure. The crude compound was found to be a mixture of slowly interconverting atropisomers (in a 30:70 ratio) and were separated by reverse phase prep-HPLC and the fractions were concentrated immediately after the prep-HPLC for characterization purposes to afford Example 5.1 and 5.2.

Example 5.1 (Diast-1/Atrop-1)

LC/MS Retention time=2.69 min, m/z=777.0 [M+H]$^+$. KINETIX XB-C18, (3×75) mm, 2.6 µm; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4 min, then hold 0.5 min at 100% B with flow rate 1.5 mL/min; Detection: UV at 220 nm. $^1$H NMR (400 MHz, Methanol-d$_4$) δ ppm 7.40 (d, J=3.2 Hz, 1H), 7.1 (m, 1H), 7.19 (s, 2H), 6.80 (m, 1H), 6.74 (t, J=54 Hz, 1H), 6.67-6.56 (m, 1H), 6.43 (dd, J=8.3, 2.3 Hz, 2H), 5.25 (dd, J=9.0, 6.0 Hz, 1H), 4.78-4.72 (m, 2H), 3.42 (dd, J=13.3, 9.3 Hz, 1H), 3.28 (s, 3H), 3.07 (dd, J=13.3, 9.3 Hz, 1H), 2.89 (s, 3H), 2.49 (m, 2H), 1.41-1.25 (m, 1H), 1.08-0.97 (m, 1H).

Example 5.2 (Diast-1/Atrop-2)

LC/MS retention time=2.88 min, m/z=777.0 [M+H]$^+$. Column KINETIX XB-C18, (3×75) mm, 2.6 µm; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4 min, then hold 0.5 min at 100% B with flow rate 1.5 mL/min; Detection: UV at 220 nm. $^1$H NMR (400 MHz, Methanol-d$_4$) δ ppm 7.73 (d, J=3.2 Hz, 1H), 7.67 (s, 1H), 7.07 (d, J=7.1 Hz, 1H), 6.74 (t, J=54 Hz, 1H), 6.73 (m, 2H), 6.48 (d, J=7.6 Hz, 1H), 6.28 (d, J=7.1 Hz, 2H), 5.01 (t, J=7.1 Hz, 1H), 4.78-4.67 (m, 2H), 3.29 (s, 3H), 3.26 (s, 3H), 3.19 (dd, J=13.4, 7.6 Hz, 1H), 2.99 (dd, J=13.3, 9.3 Hz, 1H), 2.45 (br. s., 2H), 1.40-1.27 (m, 1H), 1.03 (br. s., 1H).

Example 5.3 and 5.4, with atropisomeric relation, were prepared from Int 11j-E2 according to the procedure described for the synthesis of Example 5.1 and 5.2.

Example 5.3 (Diast-2/Atrop-1)

LC/MS retention time=2.69 min, m/z=777.0 [M+H]$^+$. Column KINETIX XB-C18, (3×75) mm, 2.6 µm; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4 min, then hold 0.5 min at 100% B with flow rate 1.5 mL/min; Detection: UV at 220 nm. $^1$H NMR (400 MHz, Methanol-d$_4$) δ ppm 7.62 (d, J=3.2 Hz, 1H), 7.58 (s, 1H), 7.05 (s, 2H), 6.70 (m, 1H), 6.60 (t, J=56 Hz, 1H), 6.50 (m, 1H), 6.37 (m, 2H), 5.21 (dd, J=9.4, 5.5 Hz, 1H), 4.65 (s, 2H), 3.44 (dd, J=13.1, 9.2 Hz, 1H), 3.19 (s, 3H), 2.96 (dd, J=13.1, 9.2 Hz, 1H), 2.85 (s, 3H), 2.49 (br. s., 2H), 1.41 (d, J=6.1 Hz, 1H), 1.16-1.00 (m, 1H).

Example 5.4 (Diast-2/Atrop-2)

LC/MS retention time=2.88 min, m/z=777.0 [M+H]$^+$. Column KINETIX XB-C18, (3×75) mm, 2.6 µm; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4 min, then hold 0.5 min at 100% B with flow rate 1.5 mL/min; Detection: UV at 220 nm. $^1$H NMR (400 MHz, Methanol-d$_4$) δ ppm 7.73 (d, J=3.4 Hz, 1H), 7.65 (s, 1H), 7.05 (d, J=7.6 Hz, 1H), 6.70 (m, 1H), 6.65 (m, 1H), 6.60 (t, J=54 Hz, 1H), 6.40 (d, J=7.3 Hz, 1H), 6.28 (d, J=6.6 Hz, 2H), 4.99 (t, J=7.2 Hz, 1H), 4.81-4.70 (m, 2H), 3.16 (s, 3H), 3.14 (s, 3H), 3.21 (dd, J=13.4, 7.6 Hz, 1H), 2.98 (dd, J=13.1, 6.5 Hz, 1H), 2.53-2.31 (m, 2H), 1.45-1.26 (m, 1H), 1.12-0.98 (m, 1H).

5-bromo-1H-pyrazolo [3, 4-b] pyridine 7-oxide (Int 12a)

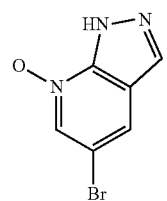

To a stirred solution of 5-bromo-1H-pyrazolo[3,4-b]pyridine (5.00 g, 25.2 mmol) in TFA (50 mL) was added hydrogen peroxide (11 mL, 126 mmol) at 0° C. The reaction mixture turns to hazy solution and the the resulting reaction mixture was stirred at 60° C. for 12 h. The volatiles were removed under vacuum to afford the crude title compound as yellow gummy solid which was processed to the next step as such. LC/MS: m/z=214.3 [M+H]$^+$. $^1$H NMR (400 MHz, DMSO-d$_6$) δ ppm 8.65 (d, J=1.5 Hz, 1H), 8.27 (s, 1H), 8.13 (s, 1H)

5-bromo-1H-pyrazolo [3, 4-b] pyridine-6-carbonitrile (Int 12b)

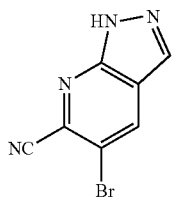 [SMILES: N#Cc1nc2[nH]ncc2cc1Br]

To a solution of 5-bromo-1H-pyrazolo[3,4-b]pyridine 7-oxide (5.40 g, 25.2 mmol) in DCE (25 mL) was added TEA (17.6 mL, 126 mmol) drop wise at 0° C. followed by TMS-CN (16.9 mL, 126 mmol). The reaction mixture was heated to 80° C. and stirred for 2 h. The reaction mixture was diluted with DCM (200 mL), washed with water (2×50 mL) and brine (2×50 mL), dried (Na$_2$SO$_4$), filtered, concentrated. The resultant crude material was then triturated with hexanes, filtered and dried to afford 5-bromo-1H-pyrazolo [3, 4-b] pyridine-6-carbonitrile (3.0 g), which was taken to the next step without any purification. LC/MS: m/z=221.0 [M−H]. $^1$H NMR (400 MHz, DMSO-d$_6$) δ ppm 14.0 (b.s, 1H), 8.87 (s, 1H), 8.33 (s, 1H).

5-bromo-1H-pyrazolo [3, 4-b] pyridine-6-carboxylic acid (Int 12c)

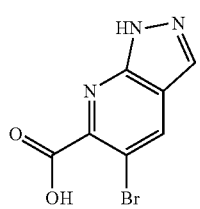 [SMILES: O=C(O)c1nc2[nH]ncc2cc1Br]

To a solution of 5-bromo-1H-pyrazolo[3,4-b]pyridine-6-carbonitrile (3.00 g, 13.45 mmol) in EtOH (50 mL) was added a solution of NaOH (2.15 g, 53.8 mmol) in water (20 mL) at RT and the resulting reaction mixture was heated to 100° C. and stirred for 4 h. The reaction mixture was cooled to RT and concentrated under reduced pressure to afford the sodium form of the desired product as yellow solid. The crude was taken to the next step without further purification. LC/MS: m/z=241.9 [M+H]$^+$.

Methyl 5-bromo-1H-pyrazolo [3, 4-b] pyridine-6-carboxylate (Int 12d)

To a suspension of 5-bromo-1H-pyrazolo[3,4-b]pyridine-6-carboxylic acid (sodium salt, 3.00 g, 12.4 mmol) in MeOH (80 mL) was added conc. sulfuric acid (2.64 mL, 49.6 mmol) drop wise at 0° C. and the resulting suspension was heated to 80° C. and stirred for 2 h. The volatiles were removed under reduced pressure, water (200 mL) was added and extracted with ethyl acetate (2×100 mL). The combined organic layer was washed with water and brine, dried over anhydrous sodium sulphate, filtered and concentrated to afford the title compound (2.8 g) as pale yellow solid. LC/MS: m/z=255.9 [M+H]$^+$. $^1$H NMR (400 MHz, CDCl$_3$) δ 11.98 (b.s, 1H), 8.45 (s, 1H), 8.12 (s, 1H), 4.08 (s, 3H).

Methyl 5-bromo-1-((2-(trimethylsilyl) ethoxy) methyl)-1H-pyrazolo [3, 4-b] pyridine-6-carboxylate (Int 12e)

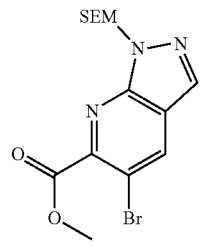

(+ SEM-regioisomer)

To a solution of methyl 5-bromo-1H-pyrazolo[3,4-b]pyridine-6-carboxylate (2.80 g, 10.93 mmol) in DMF (20 mL) was added NaH (0.547 g, 13.67 mmol) and stirred for 10 min at 0° C. SEM-Cl (2.33 mL, 13.12 mmol) was added and the resulting solution was allowed to warm to RT and stirred for 2 h. The reaction mass was cooled to 0° C., quenched with saturated NH$_4$Cl solution and extracted with ethyl acetate (2×100 mL). The combined organic layer was washed with water (50 mL) and brine (50 mL), dried over sodium sulphate, filtered and concentrated under reduced pressure to afford the title compound (3.8 g, brown liquid) as mixture of regio-isomers. LC/MS retention time=1.42 min and 1.56 min; m/z=386.4 [M+H]$^+$. ACQUITY BEH C18 (3×50) mm, 1.7 μm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm.

(5-bromo-1-((2-(trimethylsilyl) ethoxy) methyl)-1H-pyrazolo [3, 4-b] pyridin-6-yl) methanol (Int 12f)

N-((5-bromo-1-((2-(trimethylsilyl) ethoxy) methyl)-1H-pyrazolo [3, 4-b] pyridin-6-yl) methylene)-2-methylpropane-2-sulfinamide (Int 12h)

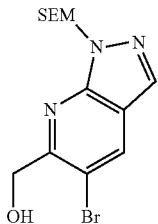 [SMILES: C[Si](C)(C)CCOCn1ncc2cc(Br)c(CO)nc21]

To a solution of methyl 5-bromo-1-((2-(trimethylsilyl)ethoxy)methyl)-1H-pyrazolo[3,4-b]pyridine-6-carboxylate (3.80 g, 9.84 mmol) in THF (60 mL) was added LiAlH$_4$ (2.05 mL, 4.92 mmol, 2.4 M in THF) at −78° C. and the resulting solution was stirred at the same temperature for 1 h. The reaction mixture was allowed to warm to RT and stirred further for 2 h. The reaction mixture is cooled to −50° C. and quenched with saturated sodium sulphate solution slowly and allowed the reaction mixture to warm to RT and extracted with ethyl acetate (2×100 mL). The combined organic layer was washed brine (100 mL), dried over anhydrous sodium sulphate, filtered and the filtrate concentrated under reduced pressure. The crude product was purified by combi flash chromatography (40 g Redisep® SiO$_2$ column, eluting with 10%-30% EtOAc in hexanes) to afford the desired compound (1.2 g) as pale yellow liquid. LC/MS: m/z=358.4 [M+H]$^+$. $^1$H NMR (400 MHz, CDCl$_3$) δ ppm 8.27 (s, 1H), 8.04 (s, 1H), 5.87 (s, 2H), 4.90 (s, 2H), 3.83-3.49 (m, 2H), 1.08-0.77 (m, 2H), 0.03-0.16 (s, 9H). [Note: The nature of the SEM-regiochemistry was not determined but it appears to be a single regioisomer here and for the relevant derivatives below.]

(5-bromo-1-((2-(trimethylsilyl) ethoxy) methyl)-1H-pyrazolo [3, 4-b] pyridine-6-carbaldehyde (Int 12g)

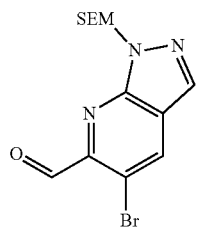 [SMILES: C[Si](C)(C)CCOCn1ncc2cc(Br)c(C=O)nc21]

To a solution of (5-bromo-1-((2-(trimethylsilyl)ethoxy)methyl)-1H-pyrazolo[3,4-b]pyridin-6-yl)methanol (1.20 g, 3.35 mmol) in DCM (30 mL) was added Dess-Martin periodinane (2.84 g, 6.70 mmol) at 0-5° C. and the resulting suspension was stirred at the same temperature for 1 h and allowed to warm to RT and stirred for 2 h. The reaction mixture was filtered through Celite pad, washed with DCM (3×50 mL) and the combined filtrate solution was washed with 10% aqueous sodium hydroxide (3×50 mL), water (2×50 mL) and brine (50 mL), dried over anhydrous sodium sulphate, filtered and concentrated to afford the title compound (1.0 g) as pale yellow liquid. $^1$H NMR (400 MHz, CDCl$_3$) δ ppm 10.30 (s, 1H), 8.43 (s, 1H), 8.14 (s, 1H), 5.94 (s, 2H), 3.91-3.40 (m, 2H), 1.10-0.64 (m, 2H), −0.16 (s, 9H).

To a stirred solution of 5-bromo-1-((2-(trimethylsilyl) ethoxy)methyl)-1H-pyrazolo[3,4-b]pyridine-6-carbaldehyde (900.0 mg, 2.53 mmol) in DCM (50 mL) was added 2-methylpropane-2-sulfinamide (337 mg, 2.78 mmol) and CuSO$_4$.5H$_2$O (806 mg, 5.05 mmol) and stirred at RT for 48 h. The reaction mixture was filtered through Celite pad, washed with DCM (2×50 mL) and the combined filtrate was washed with water (2×50 mL) and brine (50 mL), dried over anhydrous sodium sulphate and concentrated under reduced pressure. The resulting crude material was purified by combi flash chromatography (24 g Redisep® SiO$_2$ column, eluting with 0%-30% EtOAc in hexanes) to afford the title compound (1.0 g, pale yellow solid). LC/MS retention time=1.54 min and 1.66 min (56:28); m/z=459.4 [M+H]$^+$. ACQUITY BEH C18 (3×50) mm, 1.7 μm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm. $^1$H NMR (400 MHz, CDCl$_3$) δ ppm 8.89 (s, 1H), 8.79 (s, 1H), 8.34 (s, 1H), 5.80 (m, 2H), 3.62-3.57 (m, 2H), 1.19 (s, 9H), 1.10-0.64 (m, 2H), −0.136 (s, 9H).

N-(1-(5-bromo-1-((2-(trimethylsilyl) ethoxy) methyl)-1H-pyrazolo [3, 4-b] pyridin-6-yl)-2-(3, 5-difluorophenyl) ethyl)-2-methylpropane-2-sulfinamide (Int 12i)

To magnesium (0.095 g, 3.92 mmol) in diethyl ether (5 mL) was added 1-(bromomethyl)-3,5-difluorobenzene (0.507 mL, 3.92 mmol) drop wise over 15 min at RT and the mixture was stirred for 1 h to afford Grignard reagent. To a stirred solution of N-((5-bromo-1-((2-(trimethylsilyl) ethoxy)methyl)-1H-pyrazolo[3,4-b]pyridin-6-yl)methylene)-2-methylpropane-2-sulfinamide (900 mg, 1.959 mmol) in diethyl ether (20 mL) at −20° C. was added drop wise the above Grignard reagent and stirred at the same temperature for 10 min. The reaction mixture was then allowed to warm to RT and stirred for 2 h. The reaction mixture was cooled to 0° C., quenched with saturated NH$_4$Cl solution and extracted with ethyl acetate (2×100 mL). The combined organic layer was washed with water (2×50 mL) and brine, dried (Na$_2$SO$_4$), filtered and concentrated under reduced pressure to afford the crude compound as brown liquid. The crude product was purified by combi flash chromatography (40 g Redisep® SiO$_2$ column, eluting with 5-30% EtOAc in hexanes) to afford the title compound (1.0 g). LC/MS retention time=1.77 min m/z=587.4 [M+H]$^+$. ACQUITY BEH C18 (3×50) mm, 1.7 μm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm.

1-(5-bromo-1-((2-(trimethylsilyl) ethoxy) methyl)-1H-pyrazolo [3, 4-b] pyridin-6-yl)-2-(3,5-difluorophenyl)ethan-1-amine (Int 12j)

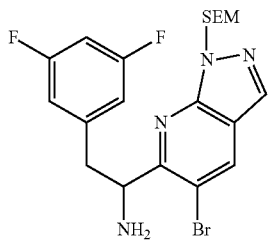

To a stirred solution of N-(1-(5-bromo-1-((2-(trimethylsilyl)ethoxy)methyl)-1H-pyrazolo[3,4-b]pyridin-6-yl)-2-(3,5-difluorophenyl)ethyl)-2-methylpropane-2-sulfinamide (1.20 g, 2.04 mmol) in 1,4-dioxane (10 mL) was added 4 M HCl in 1,4-dioxane (2.5 mL, 10 mmol) and stirred at RT for 2 h. Volatiles were removed under reduced pressure and the residue was treated with ether and evaporated two times to afford the title compound as HCl salt (600 mg), which was directly processed to next step without purification. LC/MS retention time=1.66 min; m/z=483.5 [M+H]$^+$. ACQUITY BEH C18 (3×50) mm, 1.7 μm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm. [Note: The nature of the SEM-regiochemical makeup was not determined.]

Tert-butyl (1-(5-bromo-1-((2-(trimethylsilyl) ethoxy) methyl)-1H-pyrazolo [3, 4-b]pyridin-6-yl)-2-(3, 5-difluorophenyl) ethyl) carbamate (Int 12k-E1 & Int 12k-E2 (Each is a Single Enantiomer))

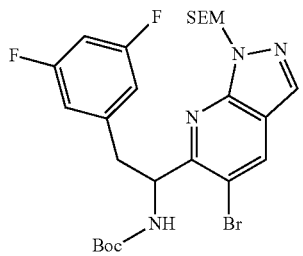 [SMILES: CC(C)(C)OC(=O)NC(Cc1cc(F)cc(F)c1)c1nc2c(cnn2COCC[Si](C)(C)C)cc1Br]

To a solution of 1-(5-bromo-1-((2-(trimethylsilyl)ethoxy)methyl)-1H-pyrazolo[3,4-b]pyridin-6-yl)-2-(3,5-difluorophenyl)ethan-1-amine, HCl (1.30 g, 1.296 mmol) in DCM (40 mL) was added Et$_3$N (0.45 mL, 3.24 mmol) and Boc$_2$O (0.36 mL, 1.56 mmol) and the resulting pale red colour solution was stirred at RT for 2 h. The reaction mixture diluted with DCM (2×20 mL), washed with water (2×10 mL), brine (20 mL), dried (Na$_2$SO$_4$), filtered, and concentrated. The crude product was then purified by combi flash chromatography (24 g Redisep® SiO$_2$ column, eluting with 5%-10% EtOAc in hexanes) to afford title compound (160 mg). The individual enantiomers were separated by Chiral SFC (Column: Whelk-01 (R,R) (250×21) mm, CO$_2$=75%; cosolvent=25% of 0.2% DEA in IPA; loadability/injection=5 mg/1.5 mL; column temp. 30.0° C., CO$_2$ flow rate: 70.0 g/min; back pressure=100 bar; detected at 220 n.m.

Int 12k-E1 (First-eluting enantiomer; retention time, 2.80 min): LC/MS: m/z=583.9 [M+H]$^+$. $^1$H NMR (400 MHz, Methanol-d$_4$) δ 8.49 (s, 1H), 8.14 (s, 1H), 6.86 (d, J=7.0 Hz, 2H), 6.79 (d, J=9.5 Hz, 2H), 5.98-5.82 (m, 2H), 5.62 (br. s., 1H), 3.70 (t, J=8.0 Hz, 2H), 3.30-3.19 (m, 1H), 2.99 (dd, J=13.6, 9.0 Hz, 1H), 1.39 (s, 9H), 1.01-0.78 (m, 2H), −0.17 (s, 9H).

Int 12k-E2 (Second-eluting enantiomer; retention time, 4.5 min): LC/MS: m/z=583.9 [M+H]$^+$. $^1$H NMR (400 MHz, Methanol-d$_4$) δ 8.49 (s, 1H), 8.14 (s, 1H), 6.86 (d, J=7.0 Hz, 2H), 6.79 (d, J=9.5 Hz, 2H), 5.98-5.82 (m, 2H), 5.62 (br. s., 1H), 3.70 (t, J=8.0 Hz, 2H), 3.30-3.19 (m, 1H), 2.99 (dd, J=13.6, 9.0 Hz, 1H), 1.39 (s, 9H), 1.01-0.78 (m, 2H), −0.17 (s, 9H).

tert-butyl (1-(5-(4-chloro-1-methyl-3-(methylsulfonamido)-1H-indazol-7-yl)-1-((2-(trimethylsilyl) ethoxy)methyl)-1H-pyrazolo[3,4-b]pyridin-6-yl)-2-(3,5-difluorophenyl)ethyl)carbamate (Int 12 (Single Enatiomer as a Mix of Atropisomers))

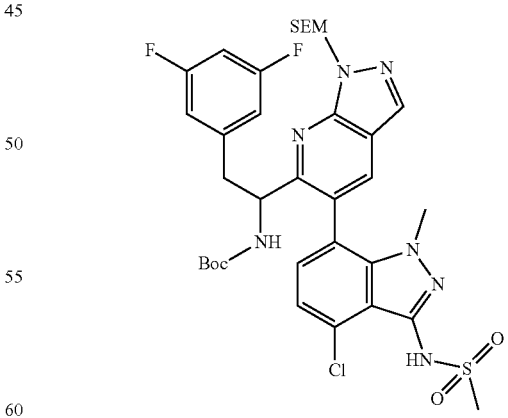

To a solution of tert-butyl (1-(5-bromo-1-((2-(trimethylsilyl)ethoxy)methyl)-1H-pyrazolo[3,4-b]pyridin-6-yl)-2-(3,5-difluorophenyl)ethyl)carbamate (Int 12k-E1, 80.0 mg, 0.137 mmol)) in 1,4-dioxane (2 mL) in a microwave vial was added N-(4-chloro-1-methyl-7-(4,4,5,5-tetramethyl-1,-

3,2-dioxaborolan-2-yl)-1Hindazol-3-yl)methanesulfonamide (106 mg, 0.274 mmol), sodium bicarbonate (69 mg, 0.82 mmol) and the mixture was degassed with nitrogen for 2 min. PdCl$_2$(dppf)-CH$_2$Cl$_2$ adduct (6.7 mg, 0.082 mmol) was added and the resulting reaction mixture was heated to 135° C. and stirred for 1 h in a microwave synthesizer. The reaction mixture was cooled to RT, extracted with ethyl acetate (100 mL), washed with water (50 mL) and brine (50 mL), dried (Na$_2$SO$_4$), filtered, and concentrated. The resultant crude material was purified by reverse phase HPLC to afford the title compound (160 mg) as mixture of atropisomers. LC/MS retention time=1.42 min and 1.56 min; m/z=760.5 [M−H]. ACQUITY BEH C18 (3×50) mm, 1.7 μm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm N-(7-(6-(1-amino-2-(3,5-difluorophenyl)ethyl)-1H-pyrazolo[3,4-b]pyridin-5-yl)-4-chloro-1-methyl-1H-indazol-3-yl)methanesulfonamide hydrochloride (Int 12m)

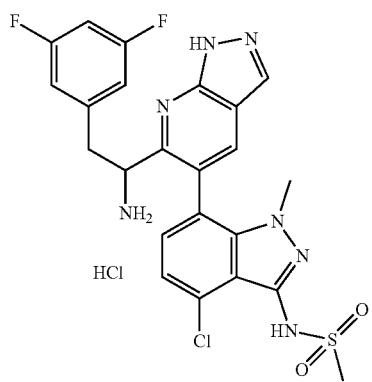 [SMILES: Cn1nc(NS(C)(=O)=O)c2c(Cl)ccc(-c3cc4cn[nH]c4nc3C(N)Cc3cc(F)cc(F)c3)c21 ; Cl]

To a stirred solution of tert-butyl (1-(5-(4-chloro-1-methyl-3-(methylsulfonamido)-1H-indazol-7-yl)-1-((2-(trimethylsilyl)ethoxy)methyl)-1H-pyrazolo[3,4-b]pyridin-6-yl)-2-(3,5-difluorophenyl)ethyl)carbamate (Int. 12l, 100 mg, 0.092 mmol) in 1,4-dioxane (2 mL) was added 4M HCl in 1,4-dioxane (1.0 mL, 33 mmol) drop wise at 0° C. The resulting solution was allowed to warm to RT and stirred for 6 h. The reaction mixture was then concentrated under reduced pressure to afford the title compound (70 mg, HCl salt) which was directly processed to next step without any purification. LC/MS retention time=0.84 min, 1.03 min; m/z=530.1 [M−H]. ACQUITY BEH C18 (2.1×50) mm, 1.7 μm; Flow rate: 1.1 mL/min; Mobile Phase A: 0.1% TFA in 95% Water/5% ACN; Mobile Phase B: 0.1% TFA in 5% Water/95% ACN; 0% B to 98% B over 1.6 min, then hold for 0.6 min at 90% B; Detection: UV at 220 nm.

N-(1-(5-(4-chloro-1-methyl-3-(methylsulfonamido)-1H-indazol-7-yl)-1H-pyrazolo[3,4-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 6.1 & 6.2 (Each is a Homochiral Diastereomer that was Observed to be a a Mix of Atropisomers)

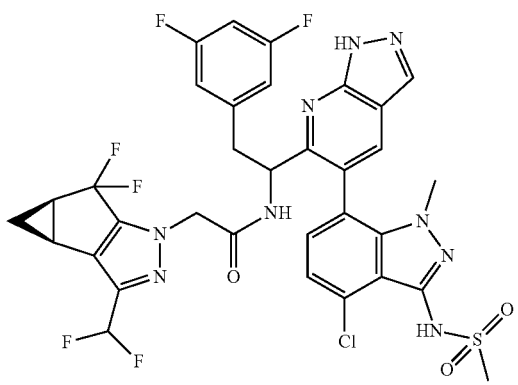 [SMILES: Cn1nc(NS(C)(=O)=O)c2c(Cl)ccc(-c3cc4cn[nH]c4nc3C(Cc3cc(F)cc(F)c3)NC(=O)Cn3nc(C(F)F)c4c3C(F)(F)[C@@H]3C[C@H]43)c21]

To a stirred solution of N-(7-(6-(1-amino-2-(3,5-difluorophenyl)ethyl)-1H-pyrazolo[3,4-b]pyridin-5-yl)-4-chloro-1-methyl-1H-indazol-3-yl)methanesulfonamide hydrochloride (Int. 12m, 8.0 mg) in DCM (2 mL) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (3.5 mg, 0.013 mmol), HATU (5.3 mg, 0.014 mmol) and the resulting solution was stirred at RT for 2 h. The reaction mixture was concentrated under reduced pressure and the resulting crude product was purified by prep-HPLC to afford the title compound (15 mg) as a mixture of atropisomers (7:3 ratio). LC/MS retention time=2.69 min, 2.86 min; m/z=776.0 [M−H]. KINETIX XB-C18, (3×75) mm, 2.6 μm; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4 min, then hold 0.5 min at 100% B with flow rate 1.5 mL/min; Detection: UV at 220 nm. HPLC retention time=15.18 and 15.74 min; X-Bridge Phenyl (4.6×150) mm, 3.5 μm; flow rate 1 mL/min; Mobile Phase A: 0.05% TFA in 95% Water/5% ACN; Mobile Phase B: 0.05% TFA in 5% Water/95% ACN; 10% B to 100% B over 25 min, then hold for 5 min at 100% B; Detection: UV at 254 and 220 nm.

Example 6.2, a mixture of atropisomers (7:3 ratio), was prepared from Int 12k-E2 in a similar as Example 6.1. LC/MS retention time=2.41 and 2.55 min; m/z=776.0 [M−H]⁻. KINETIX XB-C18, (3×75) mm, 2.6 μm; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4 min, then hold 0.5 min at 100% B with flow rate 1.5 mL/min; Detection: UV at 220 nm.

73

2,3-dibromopyridin-4-amine (Int 13a)

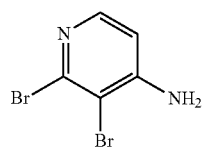

To a stirred solution of 2-bromopyridin-4-amine (2.00 g, 11.6 mmol) in acetic acid (20 mL) was added NBS (2.057 g, 11.56 mmol) and the the reaction mixture was stirred at RT for 16 h. The reaction mixture was concentrated and the crude product was purified by Combiflash chromatography (40 g Redisep® SiO$_2$ column, eluting with 22% EtOAc in hexanes) to afford the title compound (1.4 g) as an off-white solid. LC/MS: m/z=251.1 [M+H]$^+$. $^1$H NMR (400 MHz, CDCl$_3$) δ ppm 7.92 (d, J=3.60 Hz, 1H), 6.56 (d, J=4.00 Hz, 1H), 4.84 (bs, 2H).

2,3-dibromo-5-nitropyridin-4-amine (Int 13b)

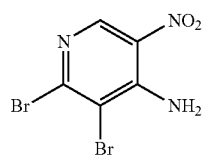 [SMILES: Nc1c([N+](=O)[O-])cnc(Br)c1Br]

To a stirred solution of 2,3-dibromopyridin-4-amine (1.4 g, 5.56 mmol) in concentrated sulphuric acid (12 mL, 225 mmol) was added potassium nitrate (0.674 g, 6.67 mmol) at −5° C. and the resulting reaction mixture was stirred at RT for 16 h. The reaction mixture was quenched with cold water (50 mL) and the yellow precipitate was filtered and dried under vacuum. To the yellow solid was added conc. H$_2$SO$_4$ (10 mL) at −5° C. and stirred at 90° C. for 2 h. The reaction mixture was cooled to RT, quenched with ice and the product was filtered and dried to afford the title compound (1.1 g) as yellow solid. LC/MS: m/z=296.1 [M+H]$^+$. $^1$H NMR (400 MHz, DMSO-d$_6$) δ 8.82 (s, 1H), 8.11 (very bs, 2H).

5,6-dibromopyridine-3,4-diamine (Int 13c)

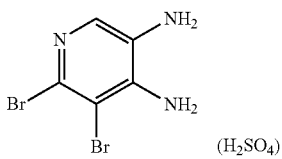

To a stirred solution of 2,3-dibromo-5-nitropyridin-4-amine (6.00 g, 16.6 mmol) in ethanol (120 mL) was added tin(II) chloride (19.16 g, 101 mmol) and the reaction mixture was heated at 65° C. for 16 h. The reaction mixture was cooled to 0° C., basified with 10% NaOH solution, and extracted with ethyl acetate (3×100 mL). The combined organic layer was dried over anhydrous sodium sulphate, filtered and concentrated to afford the title compound (4.8 g) as an off-white solid. LC/MS: m/z=266.1 [M+H]$^+$. $^1$H NMR (300 MHz, DMSO-d$_6$) δ ppm 7.39 (s, 1H), 5.92 (s, 2H), 5.04 (s, 2H).

74

6,7-dibromo-1H-imidazo[4,5-c]pyridine (Int 13d)

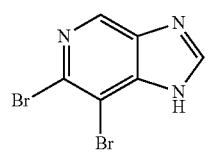

To a stirred solution of 5,6-dibromopyridine-3,4-diamine (0.500 g, 1.87 mmol) in acetonitrile (10 mL) was added triethyl orthoformate (1.56 mL, 9.37 mmol) and ytterbium (III) trifluoromethanesulfonate (5.8 mg, 9.4 μmol) and the reaction mixture was stirred at 80° C. for 16 h. The reaction mixture was concentrated and the crude product was purified by Combiflash chromatography (12 g Redisep® SiO$_2$ column, eluting with 95% EtOAc in hexanes) to afford the title compound (0.45 g) as an off-white solid. LC/MS: m/z=276.1 [M+H]$^+$. $^1$H NMR (300 MHz, DMSO-d$_6$) δ 13.51 (s, 1H), 8.74 (s, 1H), 8.55 (s, 1H).

7-bromo-6-vinyl-1H-imidazo[4,5-c]pyridine (Int 13e)

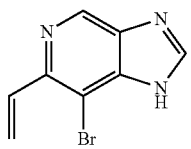

To a stirred solution of 6,7-dibromo-1H-imidazo[4,5-c] pyridine (0.50 g, 1.81 mmol) in DMF (5 mL) was added tributyl(vinyl)tin (0.583 mL, 1.98 mmol), Pd(PPh$_3$)$_4$ (0.104 g, 0.090 mmol) and the reaction mixture was purged with N$_2$ for 15 min and then stirred at 100° C. for 16 h. The reaction mixture was concentrated to remove DMF, the residue was added water (100 mL) and extracted with ethyl acetate (2×50 mL). The organic layer was combined, dried over anhydrous sodium sulphate, filtered, concentrated and the crude product was purified by Combiflash chromatography (12 g Redisep® SiO$_2$ column, eluting with 4.5% methanol in chloroform) to afford the title compound (0.25 g) as an off-white solid. LC/MS: m/z=224.2 [M+H]$^+$. $^1$H NMR (300 MHz, DMSO-d$_6$) δ 13.34 (bs, 1H), 8.88 (s, 1H), 8.47 (s, 1H), 7.28 (dd, J=16.8, 10.5 Hz, 1H), 6.37 (d, J=16.80 Hz, 1H), 5.52 (d, J=10.50 Hz, 1H).

7-bromo-1-((2-(trimethylsilyl)ethoxy)methyl)-6-vinyl-1H-imidazo[4,5-c]pyridine (Int 13f)

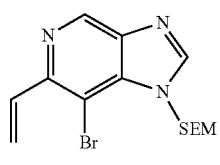

(+SEM-regioisomer)

To a stirred solution of 7-bromo-6-vinyl-1H-imidazo[4, 5-c]pyridine (1.70 g, 7.59 mmol) in DMF (20 mL) was added NaH (0.36 g, 9.1 mmol) at 0° C. and stirred at the same temperature for 30 min. SEM-Cl (1.48 mL, 8.35 mmol) was added and the reaction mixture was stirred at 0° C. for 2 h. The reaction mixture was quenched with ice cold water (100 mL) and extracted with ethyl acetate (3×100 mL). The combined organic layer was dried over anhydrous sodium sulphate, filtered, concentrated and the crude product was purified by Combiflash chromatography (24 g Redisep® SiO₂ column, eluting with 18% ethyl acetate in pet ether) to afford the title compound (2.1 g) as an off-white solid (mixture of regioisomers). LC/MS retention time=1.47 & 1.53 min, m/z=354 [M+H]⁺. ACQUITY BEH C18 (3×50) mm, 1.7 μm; Flow rate: 0.7 mL/min; Mobile Phase A: 5 mmol NH₄OAc in 95% Water/5% ACN; Mobile Phase B: 5 mmol NH₄OAc in 5% Water/95% ACN; 20% B to 100% B over 1 min, then hold for 0.6 min at 90% B; Detection: UV at 220 nm.

7-bromo-1-((2-(trimethylsilyl)ethoxy)methyl)-1H-imidazo[4,5-c]pyridine-6-carbaldehyde (Int 13g)

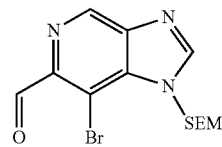

(+SEM-regioisomer)

To a stirred solution of 7-bromo-1-((2-(trimethylsilyl)ethoxy)methyl)-6-vinyl-1H-imidazo[4,5-c]pyridine (4.00 g, 11.29 mmol) in methanol (50 mL) and DCM (50 mL) was purged with ozone gas at −78° C. for 30 min. Dimethyl sulfide (1.67 mL, 22.6 mmol) was added at −78° C. and the reaction mixture was stirred at RT for 16 h. The reaction mixture was concentrated to remove the volatiles and the residue was treated with DCM (100 mL) and washed with water (3×100 mL). The organic layer was dried over anhydrous sodium sulphate, filtered and concentrated to afford the title compound (2.5 g, brown gummy solid) as a mixture of SEM regioisomer. The crude compound as such was taken for next step without further purification. LC/MS retention time=1.21 & 1.25 min, m/z=356.4 [M+H]⁺. ACQUITY BEH C18 (3×50) mm, 1.7 μm; Flow rate: 0.7 mL/min; Mobile Phase A: 5 mmol NH₄OAc in 95% Water/5% ACN; Mobile Phase B: 5 mmol NH₄OAc in 5% Water/95% ACN; 20% B to 100% B over 1 min, then hold for 0.6 min at 90% B; Detection: UV at 220 nm.

N-((7-bromo-1-((2-(trimethylsilyl)ethoxy)methyl)-1H-imidazo[4,5-c]pyridin-6-yl)methylene)-2-methylpropane-2-sulfinamide (Int 13h)

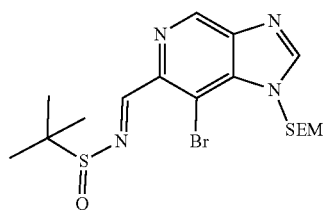 [SMILES: CC(C)(C)S(=O)/N=C/c1ncc2ncn(COCC[Si](C)(C)C)c2c1Br]

To a stirred solution of 7-bromo-1-((2-(trimethylsilyl)ethoxy)methyl)-1H-imidazo[4,5-c]pyridine-6-carbaldehyde (4.00 g, 11.23 mmol) in DCM (60 mL) was added 2-methylpropane-2-sulfinamide (1.50 g, 12.35 mmol), copper(II) sulfate (3.58 g, 22.45 mmol) and the reaction mixture was stirred at RT for 16 h. The reaction mixture was diluted with DCM (100 mL), filtered through Celite and the filtrate concentrated. The crude product was purified by Combiflash chromatography (40 g Redisep® SiO₂ column, eluting with 6% methanol in chloroform) to afford the title compound (3.5 g) as an off white gummy solid. LC/MS retention time=1.36 min, m/z=459.4 [M+H]⁺. ACQUITY BEH C18 (3×50) mm, 1.7 m; Flow rate: 0.7 mL/min; Mobile Phase A: 5 mmol NH₄OAc in 95% Water/5% ACN; Mobile Phase B: 5 mmol NH₄OAc in 5% Water/95% ACN; 20% B to 100% B over 1 min, then hold for 0.6 min at 90% B; Detection: UV at 220 nm. [Note: although a single peak was observed in LC/MS analysis, it was not apparent if the sample contained one SEM-regioisomer or not. Also, the SEM disposition for the dominant isomer, although ultimately inconsequential, was not established].

N-((7-(benzo[d]thiazol-5-yl)-1-((2-(trimethylsilyl)ethoxy)methyl)-1H-imidazo[4,5-c]pyridin-6-yl)methylene)-2-methylpropane-2-sulfinamide (Int 13i)

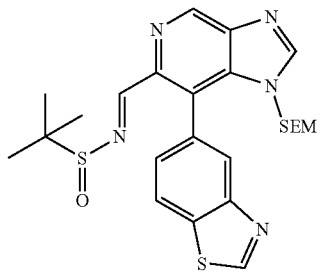 [SMILES: CC(C)(C)S(=O)/N=C/c1ncc2ncn(COCC[Si](C)(C)C)c2c1-c1ccc2scnc2c1]

To a stirred solution of N-((7-bromo-1-((2-(trimethylsilyl)ethoxy)methyl)-1H-imidazo[4,5-c]pyridin-6-yl)methylene)-2-methylpropane-2-sulfinamide (0.65 g, 1.42 mmol) in DMF (2 mL) was added 5-(4,4,5,5-tetramethyl-1,3,2-dioxaborolan-2-yl)benzo[d]thiazole (0.48 g, 1.84 mmol) and K₂CO₃ (0.59 g, 4.24 mmol) and the reaction mixture was purged with N₂ for 15 min. Pd(PPh₃)₄ (0.098 g, 0.085 mmol) was added and the reaction mixture was heated to 100° C. and stirred for 2 h. The reaction mixture was concentrated to remove DMF, the residue was treated with water (50 mL) and extracted with ethyl acetate. The organic layer was dried over anhydrous sodium sulphate, filtered, concentrated and the crude product was purified by Combiflash chromatography (40 g Redisep® SiO₂ column, eluting with 5% methanol in chloroform) to afford the title compound (0.80 g) as brown solid. LC/MS retention time=1.45 min, m/z=514.6 [M+H]⁺. ACQUITY BEH C18 (3×50) mm, 1.7 μm; Flow rate: 0.7 mL/min; Mobile Phase A: 5 mmol NH₄OAc in 95% Water/5% ACN; Mobile Phase B: 5 mmol NH₄OAc in 5% Water/95% ACN; 20% B to 100% B over 1 min, then hold for 0.6 min at 90% B; Detection: UV at 220 nm. [Note: although a single peak was observed in LC/MS analysis, it was not apparent if the sample contained one SEM-regioisomer or not. Also, the SEM disposition for the dominant isomer, although ultimately inconsequential, was not established].

N-(1-(7-(benzo[d]thiazol-5-yl)-1-((2-(trimethylsilyl)ethoxy)methyl)-1H-imidazo[4,5-c]pyridin-6-yl)-2-(3,5-difluorophenyl)ethyl)-2-methylpropane-2-sulfinamide (Int 13j)

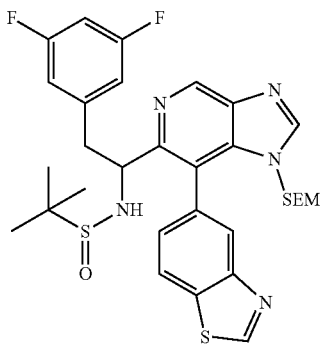 [SMILES: CC(C)(C)S(=O)NC(Cc1cc(F)cc(F)c1)c1ncc2ncn(COCC[Si](C)(C)C)c2c1-c1ccc2scnc2c1]

To a stirred mixture of magnesium turning (0.047 g, 1.95 mmol) in diethyl ether (5 mL) was added 1-(bromomethyl)-3,5-difluorobenzene (0.252 mL, 1.946 mmol) and the reaction mixture was stirred at RT for 1 h to afford the Grignard reagent. To a stirred solution of N-((7-(benzo[d]thiazol-5-yl)-1-((2-(trimethylsilyl)ethoxy)methyl)-1H-imidazo[4,5-c]pyridin-6-yl)methylene)-2-methylpropane-2-sulfinamide (0.5 g, 0.97 mmol) in diethyl ether (20 mL) at −30° C. was added drop wise the Grignard reagent prepared above and the reaction mixture was stirred at RT for 6 h. The reaction mixture was quenched with NH$_4$Cl solution and extracted with ethyl acetate (2×50 mL). The combined organic layer was dried over anhydrous sodium sulphate, filtered and concentrated to afford crude title compound (0.90 g) as brown gummy solid. The crude compound as such was taken for next step without further purification. LC/MS retention time=1.69 min, m/z=642.6 [M+H]$^+$. ACQUITY BEH C18 (3×50) mm, 1.7 µm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm. [Note: although a single peak was observed in LC/MS analysis, it was not apparent if the sample contained one SEM-regioisomer or not. Also, the SEM disposition for the dominant isomer, although ultimately inconsequential, was not established]

1-(7-(benzo[d]thiazol-5-yl)-1H-imidazo[4,5-c]pyridin-6-yl)-2-(3,5-difluorophenyl)ethanamine (Int 13k)

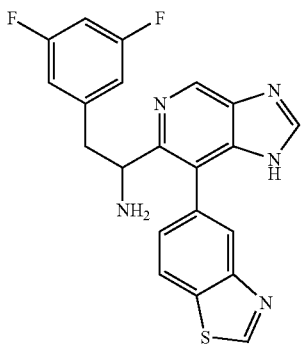 [SMILES: NC(Cc1cc(F)cc(F)c1)c1ncc2nc[nH]c2c1-c1ccc2scnc2c1]

To a solution of N-(1-(7-(benzo[d]thiazol-5-yl)-1-((2-(trimethylsilyl)ethoxy)methyl)-1H-imidazo[4,5-c]pyridin-6-yl)-2-(3,5-difluorophenyl)ethyl)-2-methylpropane-2-sulfinamide (0.80 g, 1.25 mmol) in 1,4-dioxane (10 mL) was added 4M HCl in 1,4-dioxane (5.2 mL, 24 mmol) and the reaction mixture was stirred at RT for 6 h. The reaction mixture was concentrated and the crude compound was purified by preparative HPLC to afford the title compound (0.08 g) as an off white solid. LC/MS retention time=0.70 min; m/z=408.2 [M+H]$^+$. ACQUITY BEH C18 (2.1×50) mm, 1.7 µm; Flow rate: 1.1 mL/min; Mobile Phase A: 0.1% TFA in 95% Water/5% ACN; Mobile Phase B: 0.1% TFA in 5% Water/95% ACN; 0% B to 98% B over 1.6 min, then hold for 0.6 min at 90% B; Detection: UV at 220 nm. $^1$H NMR (400 MHz, DMSO-d$_6$) δ ppm 9.50 (s, 1H), 9.17 (s, 1H), 8.46 (bs, 3H), 8.42 (s, 1H), 8.26 (d, J=8 Hz, 1H), 6.98 (m, 1H), 6.29 (d, J=6 Hz, 2H), 4.57 (bs, 1H), 3.18 (m, 2H).

N-(1-(7-(benzo[d]thiazol-5-yl)-1H-imidazo[4,5-c]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 7.1 and 7.2 Each is a Single Diastereomer)

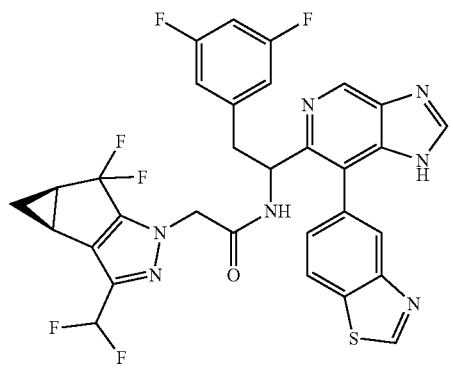 [SMILES: O=C(Cn1nc(C(F)F)c2c1C(F)(F)[C@@H]1C[C@H]21)NC(Cc1cc(F)cc(F)c1)c1ncc2nc[nH]c2c1-c1ccc2scnc2c1]

To a stirred solution of 1-(7-(benzo[d]thiazol-5-yl)-1H-imidazo[4,5-c]pyridin-6-yl)-2-(3,5-difluorophenyl)ethanamine (60 mg, 0.15 mmol) in DMF (2 mL) was added 2-((3bR,4aR)-3-(difluoromethyl)-5,5-difluoro-3b,4,4a,5-tetrahydro-1H-cyclopropa[3,4]cyclopenta[1,2-c]pyrazol-1-yl)acetic acid (38.9 mg, 0.147 mmol), DIPEA (0.026 mL, 0.15 mmol), HATU (56 mg, 0.15 mmol) and the reaction mixture was stirred at RT for 6 h. The reaction mixture was concentrated and the crude compound was purified by reverse phase HPLC followed by chiral SFC (Chiralpak IA (250×21) mm, 5 um; co-solvent, 30% of (0.2% DEA in IPA); column temperature. 30° C.; Loadability/Injection, 10 mg/mL; total flow, 70 g/min; back pressure, 100 bar; UV detection, 254 nM) to afford two diastereomers.

Example 7.1 (11 mg, First Eluting Diastereomer, Retention Time of 3.0 Min)

LC/MS: m/z=654.1 [M+H]$^+$. $^1$H NMR (400 MHz, Methanol-d$_4$) δ 9.29 (s, 1H), 9.07 (s, 1H), 8.22 (s, 1H), 8.15 (bs, 1H), 7.79 (s, 1H), 7.26 (s, 1H), 6.70 (t, J=54.8, 1H), 6.60 (m, 1H), 6.25 (bs, 2H), 5.44 (s, 1H), 4.81 (s, 2H), 3.18-3.02 (m, 2H), 2.56 (m, 2H), 1.36-1.31 (m, 1H), 0.99-0.91 (m, 1H).

Example 7.2 (12 mg, Second Eluting Diastereomer, Retention Time of 3.8 Min)

LC/MS: m/z=654.1 [M+H]$^+$. $^1$H NMR (400 MHz, DMSO-d$_6$) δ 9.46 (s, 1H), 9.07 (s, 1H), 8.87 (d, J=8.40 Hz,

1H), 8.31 (s, 1H), 8.24 (d, J=8.40 Hz, 1H), 7.79 (bs, 1H), 7.26 (bs, 1H), 6.70 (t, J=54.8, 1H), 6.60 (m, 1H), 6.26 (bs, 2H), 5.22 (m, 1H), 4.74 (dd, J=10.8, 6.4 Hz, 2H), 3.16-3.04 (m, 2H), 2.47 (m, 2H), 1.43-1.31 (m, 1H), 1.12-1.08 (m, 1H).

N-(1-(7-bromo-1-((2-(trimethylsilyl)ethoxy)methyl)-1H-imidazo[4,5-c]pyridin-6-yl)-2-(3,5-difluorophenyl)ethyl)-2-methylpropane-2-sulfinamide (Int 14a)

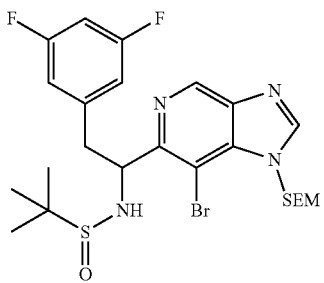 [SMILES: CC(C)(C)S(=O)NC(Cc1cc(F)cc(F)c1)c1ncc2ncn(COCC[Si](C)(C)C)c2c1Br]

To a stirred solution of magnesium (0.476 g, 19.59 mmol) in diethyl ether (5 mL) was added 1-(bromomethyl)-3,5-difluorobenzene (2.53 mL, 19.59 mmol) at RT and the reaction mixture was stirred at RT for 1 hour to afford the Grignard reagent. To a stirred solution of N-((7-bromo-1-((2-(trimethylsilyl)ethoxy)methyl)-1H-imidazo[4,5-c]pyridin-6-yl)methylene)-2-methylpropane-2-sulfinamide (1.50 g, 3.26 mmol) in diethyl ether (300 mL) at −20° C. was added slowly drop wise the Grignard reagent prepared above and the reaction mixture was stirred at RT for 2 h. The reaction mixture was quenched with ammonium chloride solution (100 mL) and the product was extracted with ethyl acetate (2×100 mL). The combined organic layer was dried over anhydrous sodium sulphate, filtered and concentrated to afford crude title compound (2.5 g), brown gummy solid as mixture of diastereomers with SEM group on different nitrogen atoms. The crude compound as such was taken for next step without further purification. LC/MS retention time=1.46, 1.51, 1.59 & 1.66 min; m/z=587.4 [M+H]$^+$. ACQUITY BEH C18 (3×50) mm, 1.7 μm; Flow rate: 0.7 mL/min; Mobile Phase A: 5 mmol NH$_4$OAc in 95% Water/5% ACN; Mobile Phase B: 5 mmol NH$_4$OAc in 5% Water/95% ACN; 20% B to 100% B over 1 min, then hold for 0.6 min at 90% B; Detection: UV at 220 nm.

1-(7-bromo-1H-imidazo [4, 5-c] pyridin-6-yl)-2-(3, 5-difluorophenyl) ethanamine (Int 14b-E1 and Int 14b-E2 (Each is a Single Enantiomer)

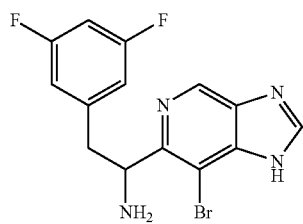 [SMILES: NC(Cc1cc(F)cc(F)c1)c1ncc2nc[nH]c2c1Br]

To a stirred solution of N-(1-(7-bromo-1-((2-(trimethylsilyl)ethoxy)methyl)-1H-imidazo[4,5-c]pyridin-6-yl)-2-(3, 5-difluorophenyl)ethyl)-2-methylpropane-2-sulfinamide (0.500 g, 0.851 mmol) in 1,4-dioxane (5 mL) was added HCl in 1,4-dioxane (4 M, 5 mL, 0.851 mmol) at RT and the reaction mixture was stirred for 2 h. The reaction mixture was concentrated and the crude product was purified by reverse phase HPLC. The individual enantiomers were separated by chiral SFC (Chiralpak AS-H (250×30) mm, 5 u, Co-solvent 0.2% DEA in IPA, Column temperature=30° C., % CO$_2$: 80%, % Co solvent: 20% of (0.2% DEA in IPA), Total Flow: 120.0 g/min, Back Pressure: 100 bars, UV absorbance: 254 nm) to afford the two enantiomers.

Int 14b-E1 (100 mg, first eluting isomer, off white solid). Chiral SFC retention time=2.87 min, LC/MS: m/z=353.3 [M+H]$^+$. $^1$H NMR (400 MHz, Methanol-d$_4$) δ ppm 8.89 (s, 1H), 8.32 (s, 1H), 6.69 (tt, J=2.26, 9.29 Hz, 1H), 6.57-6.65 (m, 2H), 5.13 (s, 1H), 3.34-3.40 (m, 1H), 3.04-3.19 (m, 2H).

Int 14b-E2 (100 mg, second eluting isomer, off white solid). Chiral SFC retention time=6.63 min.

tert-butyl 7-bromo-6-(1-((tert-butoxycarbonyl)amino)-2-(3,5-difluorophenyl)ethyl)-1H-imidazo[4,5-c]pyridine-1-carboxylate (Int 14c (a Single Enantiomer))

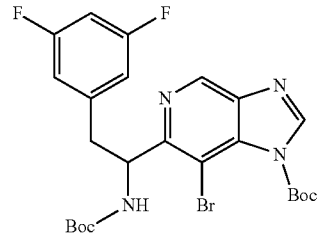 [SMILES: CC(C)(C)OC(=O)NC(Cc1cc(F)cc(F)c1)c1ncc2ncn(C(=O)OC(C)(C)C)c2c1Br]

To a stirred solution of 1-(7-bromo-1H-imidazo[4,5-c]pyridin-6-yl)-2-(3,5-difluorophenyl)ethan-1-amine (Int 14b-E1, 0.200 g, 0.566 mmol) in DCM (10 mL) was added TEA (0.158 mL, 1.133 mmol) and Boc$_2$O (0.263 mL, 1.133 mmol) at RT and the reaction mixture was stirred for 2 h. The reaction mixture was concentrated and the crude product was purified by Combiflash chromatography (120 g Redisep® SiO$_2$ column, eluting with 20% EtOAc in hexanes) to afford the title compound (0.22 g) as off white solid. LC/MS: m/z=553.4 [M+H]$^+$. $^1$H NMR (400 MHz, Methanol-d$_4$) δ ppm 9.24 (s, 1H), 8.84 (s, 1H), 6.73-6.81 (m, 3H), 5.63 (t, J=10.4 Hz, 1H), 3.37 (s, 1H), 3.02-3.09 (m, 2H), 1.76 (s, 9H), 1.32 (s, 9H).

tert-butyl (1-(7-(4-chloro-1-methyl-3-(methylsulfonamido)-1H-indazol-7-yl)-3H-imidazo[4,5-c]pyridin-6-yl)-2-(3,5-difluorophenyl)ethyl)carbamate (Int 14d-A1 and Int 14d-A2)

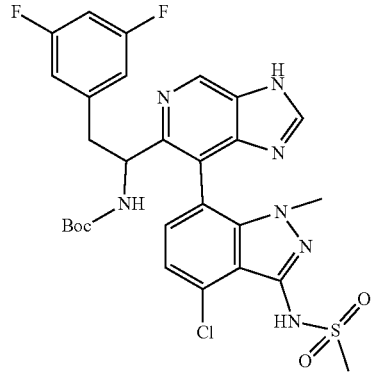 [SMILES: Cn1nc(NS(C)(=O)=O)c2c(Cl)ccc(-c3c(C(Cc4cc(F)cc(F)c4)NC(=O)OC(C)(C)C)ncc4[nH]cnc34)c21]

To a stirred solution of tert-butyl 7-bromo-6-(1-((tert-butoxycarbonyl)amino)-2-(3,5-difluorophenyl)ethyl)-1H-imidazo[4,5-c]pyridine-1-carboxylate (Int. 14c, 0.25 g, 0.452 mmol) in 1,4-dioxane (30 mL) was added N-(4-chloro-1-methyl-7-(4,4,5,5-tetramethyl-1,3,2-dioxaborolan-2-yl)-1H-indazol-3-yl)methanesulfonamide (0.348 g, 0.903 mmol) and sodium carbonate (0.072 g, 0.678 mmol) in water (2 mL) at RT and the reaction mixture was purged with $N_2$ for 15 min, $(Cy_3P)_2PdCl_2$ (0.017 g, 0.023 mmol) was added and the reaction mixture was heated at 135° C. for 2 h in microwave synthesizer. The reaction mixture was concentrated, to the residue was added water (25 mL) and extracted with ethyl acetate (2×25 mL). The combined organic layer was dried over anhydrous sodium sulphate, filtered, concentrated and the individual atropisomers were separated by prep-HPLC (XBridge phenyl (250*19) mm, 5 μm; Flow rate 15 mL/min; Mobile Phase A: 10 mM ammonium acetate in water; Mobile Phase B: Acetonitrile:Methanol (1:1); Gradient: Time (Min)/% B 0/30, 12/60, 18/70; detection: UV at 220 nm).

Int-14d-A1 (retention time 16.4 min, 80 mg, off white solid). LC/MS: m/z=632.0 [M+H]$^+$; $^1$H NMR (400 MHz, Methanol-d$_4$) δ ppm 9.15 (s, 1H), 8.31 (s, 1H), 7.32 (s, 2H), 6.63 (m, 1H), 6.45 (m, 2H), 5.05 (m, 1H), 3.32 (s, 3H), 3.03-3.08 (m, 2H), 2.76 (s, 3H), 1.41 (s, 9H).

Int-14d-A2 (retention time 17.6 min, 80 mg, off white solid). LC/MS: m/z=632.2 [M+H]$^+$; $^1$H NMR (400 MHz, Methanol-d$_4$) δ ppm 9.17 (s, 1H), 8.31 (s, 1H), 7.17-7.19 (m, 2H), 6.76 (d, J=8.40 Hz, 1H), 6.51 (t, J=14.40 Hz, 2H), 5.65 (m, 1H), 3.30 (s, 3H), 3.22 (s, 3H), 3.03-3.08 (m, 2H), 1.31 (s, 9H).

N-(7-(6-(1-amino-2-(3,5-difluorophenyl)ethyl)-3H-imidazo[4,5-c]pyridin-7-yl)-4-chloro-1-methyl-1H-indazol-3-yl)methanesulfonamide (Int-14e)

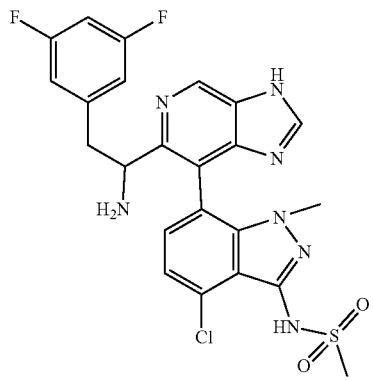 [SMILES: Cn1nc(NS(C)(=O)=O)c2c(Cl)ccc(-c3c(C(N)Cc4cc(F)cc(F)c4)ncc4[nH]cnc34)c21]

To a stirred solution of tert-butyl (1-(7-(4-chloro-1-methyl-3-(methylsulfonamido)-1H-indazol-7-yl)-3H-imidazo[4,5-c]pyridin-6-yl)-2-(3,5-difluorophenyl)ethyl)carbamate (Int-14d-A1, 0.060 g, 0.095 mmol) in 1,4-dioxane (5 mL) was added 4M HCl in 1,4-dioxane (2.0 mL, 8.0 mmol) at RT and stirred for 2 h. The reaction mixture was concentrated to afford the HCl salt of the title compound (0.045 g) as off white solid. LC/MS: m/z=532.3 [M+H]$^+$; $^1$H NMR (400 MHz, Methanol-d$_4$) δ ppm 9.27 (s, 1H), 8.39 (s, 1H), 7.46-7.54 (m, 1H), 7.37-7.46 (m, 1H), 6.72 (t, J=9.04 Hz, 1H), 6.42 (d, J=6.53 Hz, 2H), 4.54 (m, 1H), 3.44 (s, 3H), 3.35 (m, 1H), 3.11-3.23 (m, 1H), 2.71 (s, 3H).

N-(1-(7-(4-chloro-1-methyl-3-(methylsulfonamido)-1H-indazol-7-yl)-3H-imidazo[4,5-c]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Example 7.3, 7.4, 7.5 and 7.6

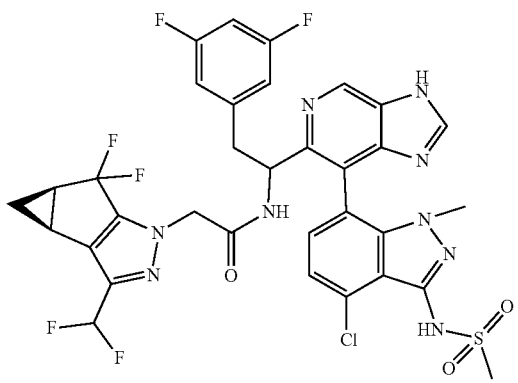 [SMILES: Cn1nc(NS(C)(=O)=O)c2c(Cl)ccc(-c3c(C(Cc4cc(F)cc(F)c4)NC(=O)Cn4nc(C(F)F)c5c4C(F)(F)[C@@H]4C[C@H]54)ncc4[nH]cnc34)c21]

To a stirred solution of N-(7-(6-(1-amino-2-(3,5-difluorophenyl)ethyl)-3H-imidazo[4,5-c]pyridin-7-yl)-4-chloro-1-methyl-1H-indazol-3-yl)methanesulfonamide/HC (0.030 g) in $CH_2Cl_2$ (4 mL) was added HATU (0.026 g, 0.068 mmol), DIPEA (0.020 mL, 0.113 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.015 g, 0.056 mmol) and the reaction mixture was stirred at RT for 2 h. The reaction mixture was concentrated and the crude compound was purified by reverse phase HPLC to afford Example 7.3 (17 mg) as an off white solid. LC/MS retention time=2.41 min, m/z=778.0 [M+H]$^+$, KINETIX XB-C18, (3×75) mm, 2.6 μm; Flow rate: 1 mL/min; Mobile Phase A: 0.1% HCOOH in 98% Water/2% ACN; Mobile Phase B: 0.1% HCOOH in 2% Water/98% ACN; 20% B to 100% B over 4 min, then hold 0.5 min at 100% B with flow rate 1.5 mL/min; Detection: UV at 220 nm. $^1$H NMR (400 MHz, Methanol-d$_4$) δ ppm 9.14 (s, 1H), 8.27 (s, 1H), 7.24 (s, 2H), 6.72 (t, J=54 Hz, 1H), 6.60 (m, 1H), 6.38 (d, J=6.53 Hz, 2H), 5.35 (dd, J=5.52, 9.54 Hz, 1H), 4.78 (m, 2H), 3.80 (m, 1H), 3.24 (s, 3H), 3.13 (m, 1H), 2.65 (s, 3H), 2.42-2.52 (m, 2H), 1.31-1.42 (m, 1H), 1.02 (br. s., 1H).

Example 7.4 was synthesized from Int-14d-A2 by using the same protocol noted for the synthesis of Example 7.3. LC/MS retention time=2.56 min, m/z=778.0 [M+H]$^+$, KINETIX XB-C18, (3×75) mm, 2.6 μm; Flow rate: 1 mL/min; Mobile Phase A: 0.1% HCOOH in 98% Water/2% ACN; Mobile Phase B: 0.1% HCOOH in 2% Water/98% ACN; 20% B to 100% B over 4 min, then hold 0.5 min at 100% B with flow rate 1.5 mL/min; Detection: UV at 220 nm. $^1$H NMR (400 MHz, Methanol-d$_4$) δ ppm 9.18 (s, 1H), 8.31 (s, 1H), 7.11 (d, J=7.50 Hz, 1H), 6.75 (m, 1H), 6.53 (t, J=54 Hz, 1H), 6.44 (t, J=6.25 Hz, 2H), 6.34 (d, J=8.0 Hz, 1H), 5.09 (t, J=7.25 Hz, 1H), 4.72 (s, 2H), 3.27-3.31 (m, 1H), 3.25 (s, 3H), 3.15 (s, 3H), 3.09 (dd, J=6.63, 13.13 Hz, 1H), 2.40-2.50 (m, 2H), 1.31-1.42 (m, 1H), 1.03 (br. s., 1H).

Int 14b-E2 was elaborated similarly to afford two more stereoisomers:

Example 7.5 LC/MS retention time=2.52 min, m/z=778.1 [M+H]$^+$, KINETIX XB-C18, (3×75) mm, 2.6 μm; Flow rate:

1 mL/min; Mobile Phase A: 0.1% HCOOH in 98% Water/ 2% ACN; Mobile Phase B: 0.1% HCOOH in 2% Water/98% ACN; 20% B to 100% B over 4 min, then hold 0.5 min at 100% B with flow rate 1.5 mL/min; Detection: UV at 220 nm. $^1$H NMR (400 MHz, CDCl$_3$) δ ppm 9.18 (s, 1H), 8.30 (s, 1H), 7.09-7.18 (m, 2H), 6.69 (t, J=54 Hz, 1H), 6.63 (m, 1H), 6.32 (d, J=6.50 Hz, 2H), 5.27 (dd, J=10.0, 5.75 Hz, 1H), 4.71 (m, 2H), 3.42 (dd, J=13.2, 10 Hz, 1H), 3.27 (s, 3H), 3.11 (dd, J=14.0, 6.0 Hz, 1H), 2.68 (s, 3H), 2.40 (m, 2H), 1.26-1.39 (m, 1H), 1.02 (m, 1H).

Example 7.6 LC/MS retention time=2.65 min, m/z=778.1 [M+H]$^+$, KINETIX XB-C18, (3×75) mm, 2.6 µm; Flow rate: 1 mL/min; Mobile Phase A: 0.1% HCOOH in 98% Water/ 2% ACN; Mobile Phase B: 0.1% HCOOH in 2% Water/98% ACN; 20% B to 100% B over 4 min, then hold 0.5 min at 100% B with flow rate 1.5 mL/min; Detection: UV at 220 nm. $^1$H NMR (400 MHz, Methanol-d$_4$) δ ppm 9.19 (s, 1H), 8.31 (s, 1H), 7.11 (d, J=7.53 Hz, 1H), 6.79 (m, 1H), 6.69 (t, J=54 Hz, 1H), 6.45 (d, J=6.02 Hz, 2H), 6.32 (d, J=7.53 Hz, 1H), 5.03-5.12 (m, 1H), 4.67-4.75 (s, 2H), 3.39-3.52 (m, 1H), 3.25 (s, 3H), 3.12-3.17 (s, 3H), 3.07-3.12 (m, 1H), 2.46 (m, 2H), 1.35-1.43 (m, 1H), 1.03 (m, 1H).

N-((3-bromoquinolin-2-yl)methylene)-2-methylpropane-2-sulfinamide (Int 15a)

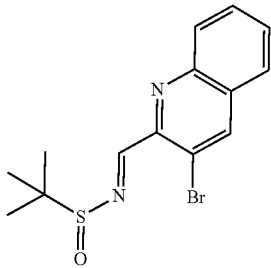 [SMILES: CC(C)(C)S(=O)/N=C/c1nc2ccccc2cc1Br]

Copper(II) sulfate (702 mg, 4.40 mmol) was added to a stirred solution of 3-bromoquinoline-2-carbaldehyde (519 mg, 2.20 mmol) and 2-methylpropane-2-sulfinamide (293 mg, 2.42 mmol) in DCM (20 mL) and the reaction mixture was stirred at rt overnight. The reaction mixture was diluted with water (60 mL) and extracted with EtOAc (100 mL). The organic component was washed with brine (50 mL), dried (MgSO$_4$), filtered and concentrated. The residue was purified by Biotage Horizon (40 g SiO$_2$, 25-50% EtOAc/hexanes) to afford the title compound (703 mg) as an off-white solid. LC-MS: m/z=338.9, 340.9 (1:1) [M+H]$^+$. $^1$H NMR (500 MHz, CDCl$_3$) δ 9.19 (s, 1H), 8.53 (s, 1H), 8.26 (d, J=9.0 Hz, 1H), 7.82 (dtd, J=8.4, 3.6, 1.3 Hz, 2H), 7.71-7.64 (m, 1H), 1.38 (s, 9H).

N-(1-(3-bromoquinolin-2-yl)-2-(3,5-difluorophenyl)ethyl)-2-methylpropane-2-sulfinamide (Int 15b)

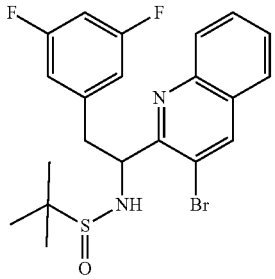 [SMILES: CC(C)(C)S(=O)NC(Cc1cc(F)cc(F)c1)c1nc2ccccc2cc1Br]

1-(Bromomethyl)-3,5-difluorobenzene (0.54 mL, 4.1 mmol) was added dropwise over 10 min. to a stirred mixture of magnesium (101 mg, 4.14 mmol) in diethyl ether (6 mL) under nitrogen. The reaction solution was stirred for 1.5 h and then added dropwise to a stirred solution of N-((3-bromoquinolin-2-yl)methylene)-2-methylpropane-2-sulfinamide (703 mg, 2.07 mmol) in THF (16 mL) at −78° C. The reaction mixture was then allowed to come to rt, stirred for 3 h, quenched with sat. NH$_4$Cl(aq.) and extracted with EtOAc. The organic component was washed with water and brine and then dried (MgSO$_4$), filtered and concentrated. The crude material was purified by Biotage Horizon (40 g SiO$_2$, 20-80% EtOAc/hexanes) to afford the title compound (860 mg) as a 1:3 mixture of diastereomers. LC/MS retention time=1.39 and 1.44 min; m/z=466.9, 468.9 (1:1) [M+H]$^+$. (Column: Water Aquity BEH C18 2.1×50 mm 1.7 µm. Solvent A=Water/0.05% TFA. Solvent B=Acetonitrile/ 0.05% TFA. Flow Rate=0.8 mL/min. Start % B=2. Final % B=98. Gradient Time=1.5 minutes, then a 0.5-minute hold at 98% B. Wavelength=220 nm). $^1$H NMR (500 MHz, CDCl$_3$) δ 8.41 (s, 0.33H), 8.35 (s, 1H), 8.08-8.00 (m, 1.33H), 7.81-7.72 (m, 2.66H), 7.63-7.55 (m, 1.33H), 6.85-6.81 (m, 0.66H), 6.74-6.64 (m, 2.33H), 6.64-6.58 (m, 1H), 5.61 (d, J=8.2 Hz, 0.33H), 5.41-5.33 (m, 1H), 5.25 (ddd, J=9.7, 8.2, 3.7 Hz, 0.33H), 4.75 (d, J=9.8 Hz, 1H), 3.50 (dd, J=13.5, 7.2 Hz, 1H), 3.38-3.25 (m, 1.33H), 2.87-2.76 (m, 0.33H), 1.21 (s, 3H), 1.17 (s, 9H).

tert-butyl (R)-(1-(3-bromoquinolin-2-yl)-2-(3,5-difluorophenyl)ethyl)carbamate (Int 15c-E1 and Int 15c-E2 (Each is a Single Enantiomer))

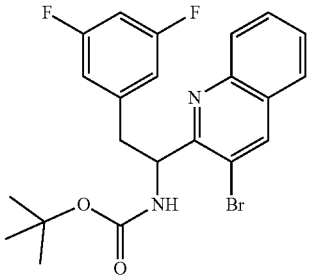 [SMILES: CC(C)(C)OC(=O)NC(Cc1cc(F)cc(F)c1)c1nc2ccccc2cc1Br]

A solution of 4M HCl (0.23 mL, 7.5 mmol) in dioxane was added to a stirred solution of N-(1-(3-bromoquinolin-2-yl)-2-(3,5-difluorophenyl)ethyl)-2-methylpropane-2-sulfinamide (350 mg, 0.75 mmol) in MeOH (2 mL) and the reaction mixture was stirred at rt for 3 h. The reaction mixture was concentrated under a stream of nitrogen. The residue was combined with di-tert-butyl dicarbonate (196 mg, 0.899 mmol) and DCM (3 mL), stirred and treated with TEA (0.26 mL, 1.9 mmol) and additional DCM (~2 mL) and then stirred at rt ON. The reaction mixture was diluted with water and EtOAc. The layers were separated and the organic component was washed with brine, dried (MgSO$_4$), filtered and concentrated to dryness. The residue was purified by Biotage Horizon (10-30% EtOAc/hexanes, 24 g SiO$_2$) to afford a racemic mixture of the title compound (287 mg). LC-MS retention time=1.56 min; m/z=463.0, 465.0 (1:1) [M+H]$^+$. (Column: Water Aquity BEH C18 2.1×50 mm 1.7 µm. Solvent A=Water/0.05% TFA. Solvent B=Acetonitrile/ 0.05% TFA. Flow Rate=0.8 mL/min. Start % B=2. Final % B=98. Gradient Time=1.5 minutes, then a 0.5-minute hold at 98% B. Wavelength=220 nm). $^1$H NMR (500 MHz, Methanol-$d_4$) δ 8.60 (s, 1H), 8.09 (d, J=8.5 Hz, 1H), 7.90 (br d, J=8.2 Hz, 1H), 7.82 (t, J=7.6 Hz, 1H), 7.67-7.60 (m, 1H), 6.95-6.74 (m, 3H), 5.62 (br dd, J=8.6, 5.0 Hz, 1H), 4.60 (br s, 1H), 3.01 (dd, J=13.6, 9.1 Hz, 1H), 1.40 (s, 9H).

The enantiomers were then separated using a Jasco Prep (Column: Lux Amylose-2, 21×250 mm, 5 mm. Mobile Phase: 5% IPA/95% $CO_2$. Pressure: 100 bar. Temperature: 40° C. Flow Rate: 80 mL/min. UV: 238 nm. Injection: 0.5 mL (~12 mg/mL in EtOH:$CHCl_3$ (1:1)) stacked @ 8.00'. Fraction Collection: Slope and Level-Make-up flow=7 mL/min EtOH) to afford: Int 15c-E1 (first eluting enantiomer, 120 mg): Peak 1 Window: 4.50'-7.00'.

Int 15c-E2 (second eluting enantiomer, 118 mg): Peak 2 Window: 6.50'-8.50'. This enantiomer afforded the more active final product.

tert-butyl (1-(3-(4-chloro-1-methyl-3-(methylsulfonamido)-1H-indazol-7-yl)quinolin-2-yl)-2-(3,5-difluorophenyl)ethyl)carbamate (Int 15d)

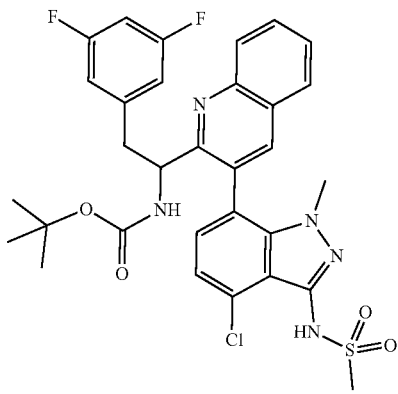 [SMILES: Cn1nc(NS(C)(=O)=O)c2c(Cl)ccc(-c3cc4ccccc4nc3C(Cc3cc(F)cc(F)c3)NC(=O)OC(C)(C)C)c21]

Nitrogen was bubbled through a slurry of tert-butyl (S)-(1-(3-bromoquinolin-2-yl)-2-(3,5-difluorophenyl)ethyl)carbamate (Int 15c-E2, 74 mg, 0.16 mmol) and N-(4-chloro-1-methyl-7-(4,4,5,5-tetramethyl-1,3,2-dioxaborolan-2-yl)-1H-indazol-3-yl)methanesulfonamide (77 mg, 0.199 mmol) in dioxane (2.7 mL) and 1M sodium bicarbonate (1.0 mL, 1.0 mmol) for 1 minute. Then $PdCl_2$(dppf)-$CH_2Cl_2$Adduct (13 mg, 0.016 mmol) was added to the reaction mixture, the reaction vessel was sealed and then heated at 140° C. for 1 h with microwave irradiation. The reaction mixture was allowed to cool to rt, filtered through Celite (flushing with EtOAc) and then partitioned between EtOAc and water. The aqueous component was extracted with additional EtOAc and then the combined organic components were washed with brine, dried ($MgSO_4$), filtered and concentrated. The residue was then purified using a Biotage Horizon (12 g $SiO_2$, 10-50% EtOAc/hexanes, loaded onto column with DCM) to afford the title compound (67 mg) as an amber glass and a 3:1 mixture of atropisomers. LC-MS (Major atropisomer) retention time=1.41 min; m/z=664.1 [M+Na]$^+$. (Column: Water Aquity BEH C18 2.1×50 mm 1.7 μm. Solvent A=Water/0.05% TFA. Solvent B=Acetonitrile/0.05% TFA. Flow Rate=0.8 mL/min. Start % B=2. Final % B=98. Gradient Time=1.5 minutes, then a 0.5-minute hold at 98% B. Wavelength=220 nm).

N-(7-(2-(1-amino-2-(3,5-difluorophenyl)ethyl)quinolin-3-yl)-4-chloro-1-methyl-1H-indazol-3-yl)methanesulfonamide (Int 15e)

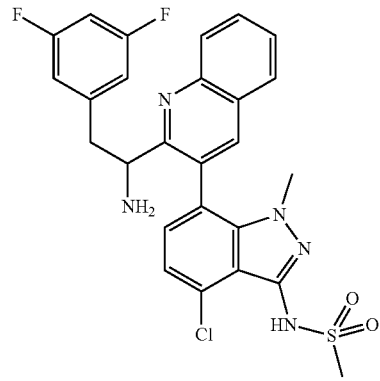 [SMILES: Cn1nc(NS(C)(=O)=O)c2c(Cl)ccc(-c3cc4ccccc4nc3C(N)Cc3cc(F)cc(F)c3)c21]

A solution of 4M HCl (0.52 mL, 2.1 mmol) in dioxane was added to a stirred solution of tert-butyl (S)-(1-(3-(4-chloro-1-methyl-3-(methylsulfonamido)-1H-indazol-7-yl)quinolin-2-yl)-2-(3,5-difluorophenyl)ethyl)carbamate (67 mg, 0.104 mmol) in MeOH (1.5 mL) and the reaction mixture was stirred ON. The reaction mixture was concentrated to dryness to afford an HCl salt of the title compound (74 mg) as a mixture (1:1) of atropisomers. The material was used without additional purification. LC-MS (1:1 mixture atropisomers) retention times=0.92 and 1.02 min; m/z=542.1 [M+H]$^+$ for each peak. (Column: Water Aquity BEH C18 2.1×50 mm 1.7 μm. Solvent A=Water/0.05% TFA. Solvent B=Acetonitrile/0.05% TFA. Flow Rate=0.8 mL/min. Start % B=2. Final % B=98. Gradient Time=1.5 minutes, then a 0.5-minute hold at 98% B. Wavelength=220 nm).

N-(1-(3-(4-chloro-1-methyl-3-(methylsulfonamido)-1H-indazol-7-yl)quinolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 8.1 & 8.2 (Each is a Single Homochiral Compound which is a Mix of Atropisomers)

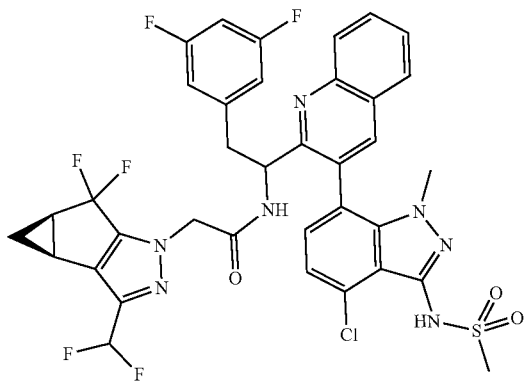 [SMILES: Cn1nc(NS(C)(=O)=O)c2c(Cl)ccc(-c3cc4ccccc4nc3C(Cc3cc(F)cc(F)c3)NC(=O)Cn3nc(C(F)F)c4c3C(F)(F)[C@@H]3C[C@H]43)c21]

HATU (25 mg, 0.064 mmol) was added to a stirred solution of an HCl salt of (S)—N-(7-(2-(1-amino-2-(3,5- difluorophenyl)ethyl)quinolin-3-yl)-4-chloro-1-methyl-1H-indazol-3-yl)methanesulfonamide (36 mg, 0.059 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (17 mg, 0.064 mmol) in DMF (0.7 mL) and DIPEA (0.06 mL, 0.4 mmol) and the reaction mixture was stirred at rt for 1d. The reaction was filtered and purified by preparative HPLC (collecting both atropisomers together) to afford Example 8.1 (12.8 mg). LC-MS (1:3 mixture of atropisomers) retention times=2.24 and 2.36 min; m/z=788.1 [M+H]+ for each peak. (Column: Waters XBridge C18, 2.1 mm×50 mm, 1.7 μm particles. Solvent A=5:95 acetonitrile:water with 0.1% trifluoroacetic acid. Solvent B=95:5 acetonitrile:water with 0.1% trifluoroacetic acid. Flow Rate=1 mL/min. Start % B=0. Final % B=100. Gradient Time=3.0 minutes, then a 0.75-minute hold at 98% B. Detection: MS and UV (220 nm)). $^1$H NMR (500 MHz, Methanol-$d_4$) δ 8.29-8.27 (m, 1H), 8.24 (d, J=7.9 Hz, 0.3H), 8.17 (d, J=8.5 Hz, 0.7H), 8.01-7.96 (m, 1H), 7.91-7.86 (m, 1H), 7.72-7.66 (m, 1H), 7.28-7.21 (m, 0.7H), 7.17 (d, J=7.3 Hz, 0.7H), 6.83-6.80 (m, 0.3H), 6.75 (d, J=7.3 Hz, 0.7H), 6.72-6.67 (m, 1.3H), 6.63-6.58 (m, 0.31H), 6.48 (br d, J=5.8 Hz, 0.7H), 6.30 (br d, J=6.1 Hz, 1.3H), 5.41 (dd, J=8.2, 6.1 Hz, 0.3H), 5.19 (t, J=6.9 Hz, 0.7H), 4.82-4.72 (m, 2H), 3.45 (dd, J=13.1, 8.5 Hz, 0.3H), 3.30 (s, 2H), 3.27 (s, 2H), 3.31-3.25 (m, 1H), 3.19 (dd, J=13.3, 6.6 Hz, 0.7H), 3.06 (dd, J=13.7, 6.1 Hz, 0.3H), 3.00-2.93 (m, 1.7H), 2.52-2.40 (m, 2H), 1.44-1.37 (m, 1H), 1.11-1.03 (m, 1H).

Example 8.2 was prepared similarly from Int 15-E1. LC-MS (1:3.5 mixture of atropisomers) retention times=2.24 and 2.36 min; m/z=788.1 [M+H]+ for each peak. (Column: Waters XBridge C18, 2.1 mm×50 mm, 1.7 μm particles. Solvent A=5:95 acetonitrile:water with 0.1% trifluoroacetic acid. Solvent B=95:5 acetonitrile:water with 0.1% trifluoroacetic acid. Flow Rate=1 mL/min. Start % B=0. Final % B=100. Gradient Time=3.0 minutes, then a 0.75-minute hold at 98% B. Detection: MS and UV (220 nm)).

tert-butyl (S)-(2-(3,5-difluorophenyl)-1-(3-(4-methoxyphenyl)-4-oxo-3,4-dihydropyrido[2,3-d]pyrimidin-2-yl)ethyl)carbamate (Int 16a)

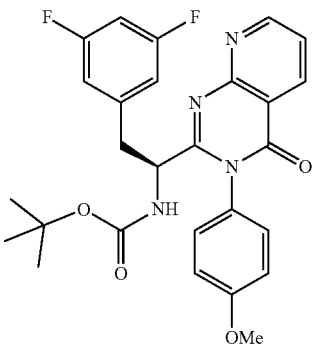 [SMILES: COc1ccc(-n2c([C@H](Cc3cc(F)cc(F)c3)NC(=O)OC(C)(C)C)nc3ncccc3c2=O)cc1]

Following a procedure from *Arch. Pharm. Chem. Life Sci.* 2006, 340, 281. To a solution of (S)-2-((tert-butoxycarbonyl)amino)-3-(3,5-difluorophenyl)propanoic acid (Int xx, 0.74 g, 2.46 mmol) in DCM (33 mL) was added N-methylmorpholine (0.68 mL, 6.14 mmol) followed by isobutyl chloroformate (0.65 mL, 4.91 mmol). The clear colorless reaction was then cooled to −20° C. (IPA, dry ice). 2-Aminonicotinic acid (0.34 g, 2.46 mmol) was then added and the slurry was allowed to slowly warm to ambient temperature over 2 h as cold bath thawed. The hazy orange pink solution was stirred 16 h. The reaction mixture was then heated at 45° C. for 2 h. After cooling to ambient temperature, the reaction was filtered and the filtrate was concentrated in vacuo. The crude addition product was taken up in DCM (25 mL) and cooled to −20° C. (IPA, dry ice). 4-Methoxyaniline (0.30 g, 2.46 mmol) was added and the reaction was allowed to slowly warm to ambient temperature over 2 h as cold bath thawed. After 20 h, the reaction was washed with 1 N HCl, saturated aqueous sodium bicarbonate, and brine. The DCM layer was then dried ($Na_2SO_4$) and concentrated in vacuo. The crude intermediate was then taken up in DCM (100 mL). N-methylmorpholine (0.32 mL, 2.95 mmol) was added and the reaction was then cooled to −20° C. (IPA, dry ice). Isobutyl chloroformate (0.39 mL, 2.95 mmol) was added. The reaction was allowed to slowly warm to ambient temperature over 2 h as cold bath thawed and then stirred 4 d. The reaction was washed with 1 N HCl, saturated aqueous sodium bicarbonate, and brine. The DCM layer was then dried ($Na_2SO_4$) and concentrated in vacuo. The crude product was taken up in a minimal amount of DCM and hexanes was added. The tan solid was filtered to provide the product (0.090 g). The filtrate was concentrated in vacuo and the resulting crude product was purified by silica gel flash chromatography to give a white solid (0.20 g). $^1$H NMR (500 MHz, DMSO-$d_6$) δ 9.10-8.90 (m, 1H), 8.61-8.48 (m, 1H), 7.60 (br dd, J=5.8, 2.4 Hz, 3H), 7.40-7.34 (m, 1H), 7.27-7.20 (m, 2H), 7.11-6.99 (m, 1H), 6.49 (br d, J=6.8 Hz, 2H), 4.41 (br t, J=8.6 Hz, 1H), 3.88 (s, 3H), 3.04 (br d, J=12.6 Hz, 1H), 2.92-2.82 (m, 1H), 1.27 (s, 9H). LC/MS (M+H)+: 509.10.

(S)-2-(1-amino-2-(3,5-difluorophenyl)ethyl)-3-(4-methoxyphenyl)pyrido[2,3-d]pyrimidin-4(3H)-one, Hydrochloride Salt (Int 16b)

Tert-butyl (S)-(2-(3,5-difluorophenyl)-1-(3-(4-methoxyphenyl)-4-oxo-3,4-dihydropyrido[2,3-d]pyrimidin-2-yl)ethyl)carbamate (80 mg, 0.157 mmol) was taken up in 4 N HCl in dioxane and stirred for 2 h. The reaction was then concentrated under a stream of nitrogen. The crude product was filtered to provide the product (80 mg). LC/MS (M+H)+: 409.15.

2-((3bS,4aR)-3-(difluoromethyl)-5,5-difluoro-3b,4,
4a,5-tetrahydro-1H-cyclopropa[3,4]cyclopenta[1,2-
c]pyrazol-1-yl)-N—((S)-2-(3,5-difluorophenyl)-1-
(3-(4-methoxyphenyl)-4-oxo-3,4-dihydropyrido[2,3-
d]pyrimidin-2-yl)ethyl)acetamide (Example 9.1)

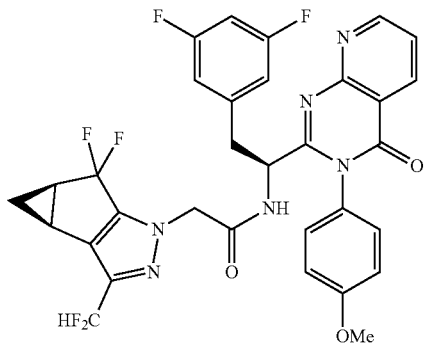

To a solution of (S)-2-(1-amino-2-(3,5-difluorophenyl) ethyl)-3-(4-methoxyphenyl)pyrido[2,3-d]pyrimidin-4(3H)-one, hydrochloride salt (40 mg), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (31 mg, 0.116 mmol), and DIPEA (0.044 mL, 0.249 mmol) in DMF (0.9 mL) was added HATU (44 mg, 0.116 mmol). The reaction was stirred for 2 h, filtered and purified by reverse phase HPLC to afford the product (12.8 mg). $^{1}$H NMR (600 MHz, DMSO-$d_6$) δ 9.22 (br d, J=2.6 Hz, 1H), 9.04 (br s, 1H), 8.54 (br d, J=7.7 Hz, 1H), 7.62 (dd, J=7.7, 4.8 Hz, 1H), 7.53-7.45 (m, 1H), 7.32 (br d, J=8.4 Hz, 1H), 7.22-7.17 (m, 1H), 7.13 (br dd, J=8.3, 2.8 Hz, 1H), 7.03 (br s, 1H), 7.01-6.82 (m, 1H), 6.52 (br d, J=5.5 Hz, 2H), 4.84-4.63 (m, 3H), 3.89-3.81 (m, 3H), 3.19 (br d, J=13.9 Hz, 1H), 2.87 (br dd, J=13.6, 10.6 Hz, 1H), 1.41-1.31 (m, 1H), 1.24 (br s, 2H), 0.90 (br s, 1H). LC/MS (M+H)$^{+}$: 655.2.

(S)—N-(2-(3,5-difluorophenyl)-1-(3-(4-methoxyphenyl)-4-oxo-3,4-dihydropyrido[2,3-d]pyrimidin-2-yl)ethyl)-2-(5-hydroxy-1H-indol-3-yl)acetamide Example 9.2

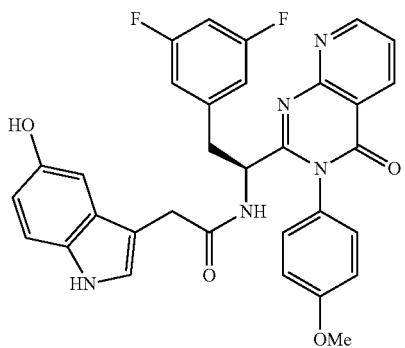 [SMILES: COc1ccc(-n2c([C@H](Cc3cc(F)cc(F)c3)NC(=O)Cc3c[nH]c4ccc(O)cc34)nc3ncccc3c2=O)cc1]

To a solution of (S)-2-(1-amino-2-(3,5-difluorophenyl) ethyl)-3-(4-methoxyphenyl)pyrido[2,3-d]pyrimidin-4(3H)-one, hydrochloride salt (40 mg), 2-(5-hydroxy-1H-indol-3-yl)acetic acid (24 mg, 0.116 mmol), and DIPEA (0.044 mL, 0.249 mmol) in DMF (0.9 mL) was added HATU (44 mg, 0.116 mmol). The reaction was stirred for 2 h, filtered and purified by reverse phase HPLC to afford the product (11.4 mg). $^{1}$H NMR (600 MHz, DMSO-$d_6$) δ 10.48 (br s, 1H), 9.03 (br s, 1H), 8.82 (br d, J=6.6 Hz, 1H), 8.53 (br d, J=7.7 Hz, 1H), 7.61 (dd, J=7.7, 4.8 Hz, 1H), 7.46-7.39 (m, 1H), 7.29 (br d, J=8.8 Hz, 1H), 7.19-7.13 (m, 1H), 7.07 (d, J=8.4 Hz, 1H), 7.04-6.93 (m, 3H), 6.77 (d, J=1.8 Hz, 1H), 6.58-6.45 (m, 3H), 4.66-4.56 (m, 1H), 3.81 (s, 3H), 3.45-3.41 (m, 2H), 3.16 (br d, J=13.6 Hz, 1H), 2.95-2.87 (m, 1H). LC/MS (M+H)$^{+}$: 582.1.

Examples 10.1 through 10.38 were prepared by adapting the procedures described above with the specific reagents needed to obtain products with the modified substitution patterns.

Examples 10.39 and 10.40

Tert-butyl (S)-(2-(3,5-difluorophenyl)-1-(4-oxo-4H-pyrido[2,3-d][1,3]oxazin-2-yl)ethyl)carbamate (Int 17a)

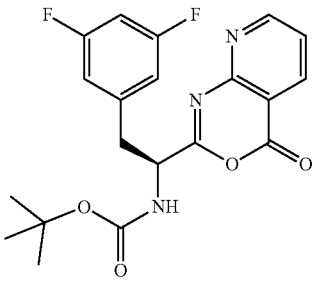 [SMILES: CC(C)(C)OC(=O)N[C@@H](Cc1cc(F)cc(F)c1)c1nc2ncccc2c(=O)o1]

Following a procedure from *Arch. Pharm. Chem. Life Sci.* 2006, 340, 281. To a solution of (S)-2-((tert-butoxycarbonyl) amino)-3-(3,5-difluorophenyl)propanoic acid (1.0 g, 3.32 mmol) in DCM (44 mL) was added N-methylmorpholine (0.84 mL, 8.30 mmol) followed by isobutyl chloroformate (0.91 mL, 6.64 mmol). The clear colorless reaction was then cooled to −20° C. (IPA, dry ice). 2-Aminonicotinic acid (0.46 g, 3.32 mmol) was then added and the slurry was allowed to slowly warm to ambient temperature over 2 h as cold bath thawed. The hazy orange pink solution was stirred for 18 h. The reaction was diluted with EtOAc. The organic mixture was washed with saturated aqueous sodium bicarbonate and brine. The organic layer was then dried (Na$_2$SO$_4$) and concentrated in vacuo. The crude product was triturated from hexane and filtered to provide the product (0.47 g) as a peach colored solid. $^{1}$H NMR (500 MHz, CDCl$_3$) δ 9.02 (br d, J=3.5 Hz, 1H), 8.58 (dd, J=7.8, 1.7 Hz, 1H), 7.57 (dd, J=7.9, 4.7 Hz, 1H), 6.73 (br s, 3H), 5.59-5.40 (m, 1H), 5.04 (br d, J=5.7 Hz, 1H), 3.50-3.36 (m, 1H), 3.18 (br dd, J=14.3, 6.9 Hz, 1H), 1.46 (br s, 9H).

N-(7-bromo-4-chloro-1-methyl-1H-indazol-3-yl)methanesulfonamide (Int 17b)

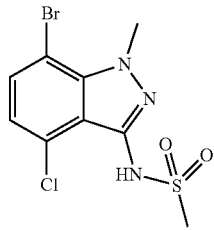 [SMILES: Cn1nc(NS(C)(=O)=O)c2c(Cl)ccc(Br)c21]

To a solution of 7-bromo-4-chloro-1-methyl-1H-indazol-3-amine (1.40 g, 5.37 mmol) in DCM (30 mL) was added Hunig's Base (3.75 mL, 21.5 mmol) and then the reaction was cooled in an ice bath and methanesulfonyl chloride (1.26 mL, 16.1 mmol) was added. The reaction mixture was stirred at this temperature for 1 h (precipitate formed). Mixture was then diluted with dichloromethane (100 mL) and washed with water, 1 M HCl and brine, dried ($Na_2SO_4$), filtered and concentrated in vacuo. The residue was taken up in EtOH (30 ml) and 10 ml of 20% aq. NaOH. The resulted mixture heated with a heat gun until it became a homogeneous solution and stirred at rt for 30 min. The mixture was diluted with water (80 mL) and acidified with 1 N HCl (60 mL). The precipitate was filtered, washed with water, and dried in vacuo to afford the title product (1.5 g) as an off-white solid. $^1$H NMR (500 MHz, $CDCl_3$) δ 7.48 (d, J=7.9 Hz, 1H), 7.24 (br s, 1H), 6.95 (d, J=7.9 Hz, 1H), 4.38 (s, 3H), 3.42 (s, 3H). LC/MS $(M+H)^+$=337.80.

N-(7-bromo-4-chloro-1-methyl-1H-indazol-3-yl)-N-(4-methoxy benzyl)methanesulfonamide (Int 17c)

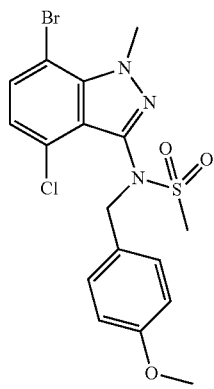 [SMILES: COc1ccc(CN(c2nn(C)c3c(Br)ccc(Cl)c23)S(C)(=O)=O)cc1]

To a mixture of N-(7-bromo-4-chloro-1-methyl-1H-indazol-3-yl)methanesulfonamide (1.3 g, 3.84 mmol) and 1-(chloromethyl)-4-methoxybenzene (0.625 mL, 4.61 mmol) in DMF (30 mL) was added cesium carbonate (1.626 g, 4.99 mmol) and the mixture was heated at 80° C. for 2 h. The mixture was poured into water (100 mL) and extracted with EtOAc (50 ml, 2×). The combined organic layer was washed with brine, dried over $MgSO_4$, filtered and concentrated in vacuo. The residue was purified by Biotage (0~35% EtOAc-hexanes) to afford the title product (1.5 g) as a white foam. $^1$H NMR (500 MHz, $CDCl_3$) δ 7.44 (d, J=7.9 Hz, 1H), 7.31 (d, J=8.5 Hz, 2H), 6.99 (d, J=7.9 Hz, 1H), 6.84 (d, J=8.5 Hz, 2H), 4.99 (br s, 1H), 4.76 (br s, 1H), 4.40 (s, 3H), 3.80 (s, 3H), 3.01 (s, 3H).

N-(7-amino-4-chloro-1-methyl-1H-indazol-3-yl)-N-(4-methoxybenzyl)methanesulfonamide (Int 17d)

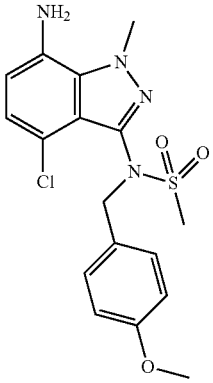 [SMILES: COc1ccc(CN(c2nn(C)c3c(N)ccc(Cl)c23)S(C)(=O)=O)cc1]

Following the reference: Andersen, Jacob et al, *Synlett* 2005 (14), 2209-2213. To a mixture of N-(7-bromo-4-chloro-1-methyl-1H-indazol-3-yl)-N-(4-methoxybenzyl)methane sulfonamide (600.0 mg, 1.308 mmol), copper(I) iodide (49.8 mg, 0.262 mmol), sodium ascorbate (518 mg, 2.62 mmol) and (1R,2R)—N1,N2-dimethylcyclohexane-1,2-diamine (46.5 mg, 0.327 mmol) in NMP (10 mL) was added a solution of sodium azide (255 mg, 3.92 mmol) in Water (2.0 mL). The mixture was then sealed and heated in a microwave system at 120° C. for 2.5 h. The mixture was then filtered through a pad of Celite and the pad was washed with EtOAc. The filtrate was poured into water (100 mL) and extracted with EtOAc (50 ml, 2×). The combined organic layer was washed with brine, dried over $MgSO_4$, filtered and evaporated in vacuo. The residue was purified by Biotage (5-100% EtOAc/hexanes) to afford the title product (400 mg) as an off-white solid. $^1$H NMR (400 MHz, $CDCl_3$) δ 7.33-7.29 (m, 2H), 6.89 (d, J=7.8 Hz, 1H), 6.85-6.79 (m, 2H), 6.48 (d, J=7.8 Hz, 1H), 5.11 (br.s, 1H), 4.81 (br.s, 1H), 4.30 (s, 3H), 3.80 (br s, 2H), 3.79 (s, 3H), 2.99 (s, 3H). LC/MS $(M+H)^+$=395.00.

N—((S)-1-(3-(4-chloro-1-methyl-3-(methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 10.39 & Example 10.40)

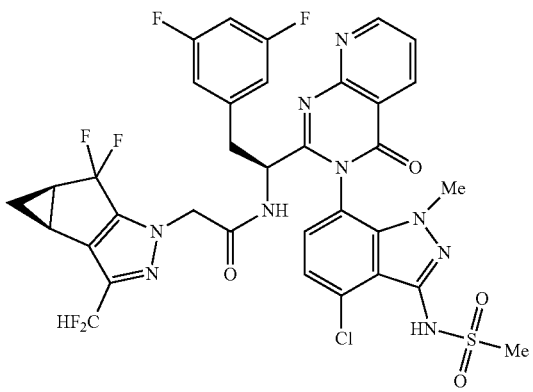

A slurry of tert-butyl (S)-(2-(3,5-difluorophenyl)-1-(4-oxo-4H-pyrido[2,3-d][1,3]oxazin-2-yl)ethyl)carbamate (Int 17a, 40 mg, 0.099 mmol) and N-(7-amino-1-methyl-1H-indazol-3-yl)-N-(4-methoxybenzyl)methanesulfonamide (Int 17d, 39 mg, 0.109 mmol) in DCE (0.50 mL) was stirred for 18 h. To the reaction was added N-methylmorpholine (0.013 mL, 0.119 mmol) followed by isobutyl chloroformate (0.016 mL, 0.119 mmol). After stirring for 1 h, the reaction was diluted with DCM and washed with saturated aqueous sodium bicarbonate. The organic layer was dried (Na$_2$SO$_4$) and concentrated in vacuo. The crude residue was treated with 4 N HCl in dioxane and stirred for 3 h. The reaction was then concentrated in vacuo and the crude amine was taken up in DMF (1 mL). To this solution was added DIPEA (0.052 mL, 0.397 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (37 mg, 0.139 mmol) followed by HATU (53 mg, 0.139 mmol). After stirring 1 h, the reaction was diluted with EtOAc and washed with brine. The EtOAc layer was dried (Na$_2$SO$_4$) and concentrated in vacuo. The crude residue was treated with TFA (3 mL) to provide an orange brown solution. After stirring 5 h, the reaction was concentrated under a stream of nitrogen. The crude product was purified by preparative HPLC (XBridge C18 column with a gradient with 5:95 acetonitrile:water with 0.1% trifluoroacetic acid and 95:5 acetonitrile:water with 0.1% trifluoroacetic acid) to afford the products: first eluting atropisomer 1 (7.2 mg) as Example 10.39 and second eluting atropisomer 2 (7.1 mg) as Example 10.40.

Atropisomer 2 required three purifications to reach high purity. Example 10.39: $^1$H NMR (500 MHz, CD$_3$OD) δ 9.13 (br d, J=3.4 Hz, 1H), 8.73 (dd, J=7.9, 1.5 Hz, 1H), 7.74 (dd, J=7.9, 4.6 Hz, 1H), 7.41-7.36 (m, 1H), 7.29-7.23 (m, 1H), 6.87-6.72 (m, 2H), 6.60-6.54 (m, 2H), 4.92-4.74 (m, 3H), 3.49-3.39 (m, 1H), 3.29 (s, 3H), 3.15 (s, 3H), 3.03-2.94 (m, 1H), 2.56-2.41 (m, 2H), 1.46-1.38 (m, 1H), 1.09 (br s, 1H). LC/MS (M+1): 806.1. Example 10.40: $^1$H NMR (500 MHz, DMSO-d$_6$) δ 9.67 (s, 1H), 9.20 (br d, J=7.9 Hz, 1H), 8.94 (br d, J=2.7 Hz, 1H), 8.45 (br d, J=7.6 Hz, 1H), 7.58 (br d, J=7.9 Hz, 1H), 7.52 (dd, J=7.8, 4.7 Hz, 1H), 7.29 (d, J=7.9 Hz, 1H), 7.08-6.59 (m, 3H), 6.48 (br d, J=6.7 Hz, 2H), 4.52-4.32 (m, 3H), 3.01 (s, 3H), 2.91-2.79 (m, 1H), 2.37 (s, 3H), 1.17 (br d, J=4.6 Hz, 1H), 1.12-1.04 (m, 2H), 0.67 (br s, 1H). LC/MS (M+1): 806.0.

tert-butyl (S)-(2-(3,5-difluorophenyl)-1-(4-oxo-7-(trifluoromethyl)-4H-pyrido[2,3-d][1,3]oxazin-2-yl)ethyl)carbamate (Int 18a)

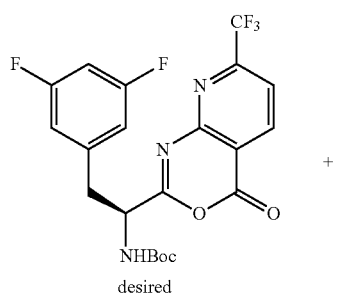

desired

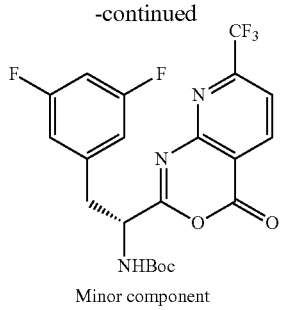

Minor component

To a solution of (S)-2-((tert-butoxycarbonyl)amino)-3-(3,5-difluorophenyl)propanoic acid (0.731 g, 2.426 mmol) in DCM (32 mL) was added N-methylmorpholine (0.670 mL, 6.06 mmol) followed by isobutyl chloroformate (0.640 mL, 4.85 mmol). The reaction was then cooled to −20° C. (IPA/dry ice) and 2-amino-6-(trifluoromethyl)nicotinic acid (0.50 g, 2.43 mmol) was added. The reaction slurry was allowed to slowly warm to ambient temperature overnight as bath thawed for 18 h. The reaction was heated to reflux for 2 h. Upon cooling to ambient temperature, the reaction was filtered. The filtrate was diluted with EtOAc. The organic layer was washed with saturated sodium bicarbonate, brine, dried (Na$_2$SO$_4$) and concentrated in vacuo. The crude product was triturated with hexanes and filtered to give the product which was a mixture due to some racemization as an orange solid (0.41 g, used as is). $^1$H NMR (500 MHz, CDCl$_3$) δ 8.80-8.75 (m, 1H), 7.95-7.89 (m, 1H), 6.74-6.71 (m, 3H), 5.52-5.44 (m, 1H), 5.08-5.01 (m, 1H), 3.44-3.37 (m, 1H), 3.19-3.15 (m, 1H), 1.47-1.44 (m, 9H)

tert-butyl (S)-(1-(3-(4-chloro-3-(N-(4-methoxybenzyl)methylsulfonamido)-1-methyl-1H-indazol-7-yl)-4-oxo-7-(trifluoromethyl)-3,4-dihydropyrido[2,3-d]pyrimidin-2-yl)-2-(3,5-difluorophenyl)ethyl)carbamate (Int 18b)

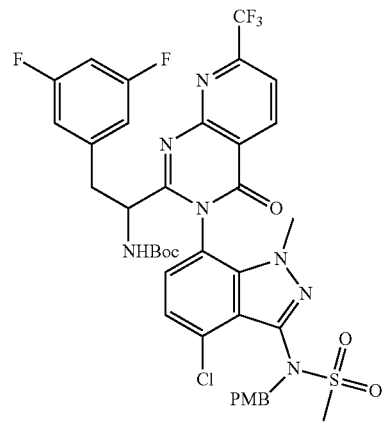

mixture of Int 18b and three other stereoisomers

A mixture of tert-butyl (S)-(2-(3,5-difluorophenyl)-1-(4-oxo-7-(trifluoromethyl)-4H-pyrido[2,3-d][1,3]oxazin-2-yl)ethyl)carbamate (Int 18a, 0.58 g, 1.23 mmol), N-(7-amino-4-chloro-1-methyl-1H-indazol-3-yl)-N-(4-methoxybenzyl)methanesulfonamide (Int 17d, 0.486 g, 1.230 mmol) and diphenyl phosphite (1.20 mL, 6.15 mmol) in pyridine (4.96 mL) was heated at 70° C. (oil bath) for 2 h and cooled to rt.

The reaction mixture was purified on silica gel (120 g Isco column) using 0-100% ethyl acetate in hexanes. The desired fractions were concentrated to give a yellow solid (0.41 g). LC/MS: m/z=870.2 [M+Na]$^+$.

(S)—N-(7-(2-(1-amino-2-(3,5-difluorophenyl)ethyl)-4-oxo-7-(trifluoromethyl)pyrido[2,3-d]pyrimidin-3(4H)-yl)-4-chloro-1-methyl-1H-indazol-3-yl)-N-(4-methoxybenzyl)methanesulfonamide hydrochloride (Int 18c)

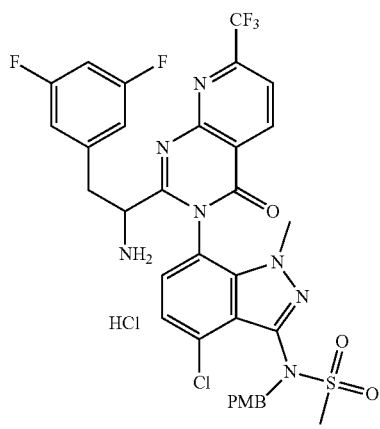

mixture of Int 18c and three other stereoisomers

HCl (7.30 mL, 29.3 mmol, 4N in dioxane) and tert-butyl (S)-(1-(3-(4-chloro-3-(N-(4-methoxybenzyl)methylsulfonamido)-1-methyl-1H-indazol-7-yl)-4-oxo-7-(trifluoromethyl)-3,4-dihydropyrido[2,3-d]pyrimidin-2-yl)-2-(3,5-difluorophenyl)ethyl) carbamate (Int 18b, 0.414 g, 0.488 mmol) was stirred at rt for 0.5 h and concentrated to give an off-white solid which was a mix of stereoisomers due to the racemization in a reaction earlier in the sequence and the stable atropisomers (used as is).

N—((S)-1-(3-(4-chloro-3-(N-(4-methoxybenzyl)methylsulfonamido)-1-methyl-1H-indazol-7-yl)-4-oxo-7-(trifluoromethyl)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 18d)

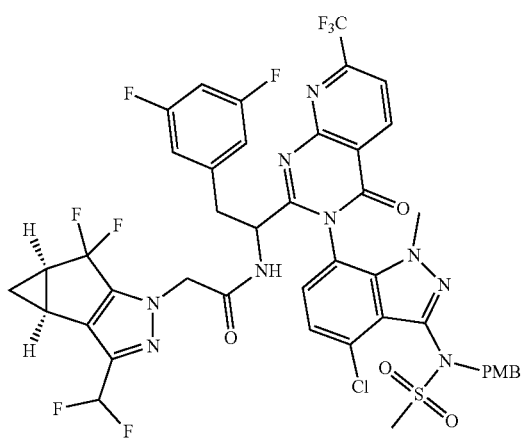

mixture of int 18d and three other stereoisomers

To a stirred solution of (S)—N-(7-(2-(1-amino-2-(3,5-difluorophenyl)ethyl)-4-oxo-7-(trifluoromethyl)pyrido[2,3-d]pyrimidin-3(4H)-yl)-4-chloro-1-methyl-1H-indazol-3-yl)-N-(4-methoxybenzyl)methanesulfonamide hydrochloride (Int 18c, 0.36 g, 0.459 mmol) in DMF (3.0 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.121 g, 0.459 mmol), HATU (0.183 g, 0.482 mmol) and DIPEA (0.16 mL, 0.92 mmol). The mixture was stirred for 2 h and purified on silica gel (120 g Isco column) using 0-100% ethyl acetate in hexanes. The desired fractions were concentrated to give a yellow oil (0.25 g) which was a mix of stereoisomers due to the racemization in a reaction earlier in the sequence and the stable atropisomers. LC/MS: m/z=994.1 [M+H]$^+$.

N—((S)-1-(3-(4-chloro-1-methyl-3-(methylsulfonamido)-1H-indazol-7-yl)-4-oxo-7-(trifluoromethyl)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 11.2) Along with Examples 11.1 and 11.3

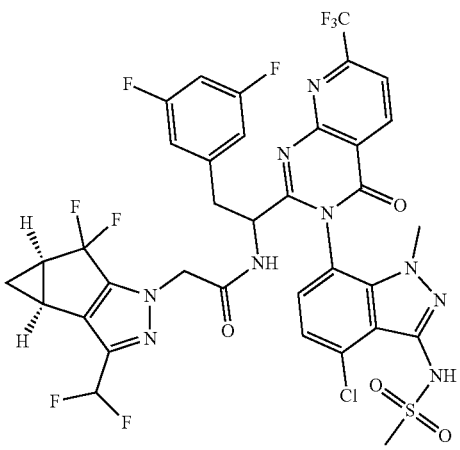

Example 11.1
two stereoisomers

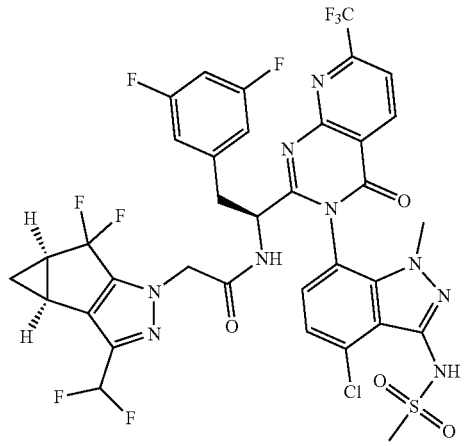

Example 11.2
homochiral

-continued

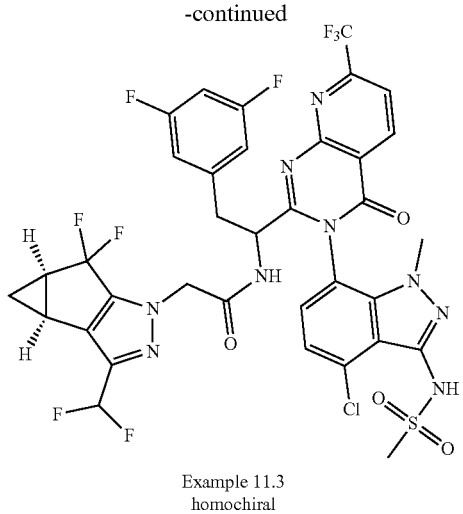

Example 11.3
homochiral

To a solution of N—((S)-1-(3-(4-chloro-3-(N-(4-methoxybenzyl)methylsulfonamido)-1-methyl-1H-indazol-7-yl)-4-oxo-7-(trifluoromethyl)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 18d, 0.250 g, 0.251 mmol) in DCM (0.84 mL) were added triflic acid (0.067 mL) and TFA (1.7 mL) and the mixture was stirred at rt for 1 h and concentrated. The crude material was purified under the following prep-HPLC condition to retrieve two isolates, each a mixture of stereoisomers. Prep-HPLC: XBridge C18, 200 mm×19 mm, 5-μm particles; Mobile Phase A: 5:95 acetonitrile:water with 10-mM ammonium acetate; Mobile Phase B: 95:5 acetonitrile:water with 10-Mm ammonium acetate; Gradient: a 0-minute hold at 32% B, 32-72% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. Detection: MS and UV (220 nm).

Example 11.1: First Elute (74 mg, Off White Solid)

LC/MS: m/z=874.0 [M+H]$^+$. This is actually a mixture of two stereoisomers due to some racemization at the chiral center that occurred earlier in the synthesis and the stable atropoisomer.

Second elute (159 mg, off white solid) was further purified by Chiralpak IC preparative column, 30×250 mm, 5 μm Mobile Phase: 20% IPA in CO$_2$, 150 bar Temp: 35° C., Flow rate: 70.0 mL/min. in 10 min. UV monitored @ 308 nm Injection: 0.5 mL of ~10 mg/mL in 1:1:1 IPA:MeOH:CHCl$_3$. Two elutes of stereoisomeric relation were isolated.

Example 11.2: First Elute (66 mg, Off White Solid)

$^1$H NMR (400 MHz, MeOH-d$_4$) δ 9.00-8.91 (m, 1H), 8.11-8.03 (m, 1H), 7.34 (s, 2H), 6.84-6.48 (m, 4H), 4.67-4.47 (m, 2H), 3.72-3.43 (m, 6H), 3.27-3.23 (m, 2H), 3.19-3.08 (m, 1H), 2.47-2.34 (m, 2H), 1.39-1.29 (m, 1H), 1.04-0.96 (m, 1H). LC/MS: m/z=874.0 [M+H]$^+$.

Example 11.3: Second Elute (71 mg, Off White Solid)

$^1$H NMR (400 MHz, MeOH-d$_4$) δ 9.02-8.85 (m, 1H), 8.14-8.00 (m, 1H), 7.44-7.25 (m, 2H), 6.86-6.36 (m, 4H), 4.70-4.48 (m, 2H), 3.97-3.88 (m, 1H), 3.70-3.62 (m, 2H), 3.59-3.54 (m, 1H), 3.51-3.43 (m, 2H), 3.28-3.22 (m, 3H), 3.18-3.08 (m, 1H), 2.46-2.35 (m, 2H), 1.37-1.28 (m, 1H), 1.05-0.97 (m, 1H). LC/MS: m/z=874.0 [M+H]$^+$.

Note that Example 11.2 converts slowly to one of the isomers in Example 11.1 when stored in MeOH at ambient condition. In a reverse set up, one of the isomers in Example 11.1 converts to Example 11.2.

tert-butyl (S)-(1-(7-chloro-4-oxo-4H-pyrido[2,3-d][1,3]oxazin-2-yl)-2-(3,5-difluorophenyl)ethyl)carbamate (Int 19a)

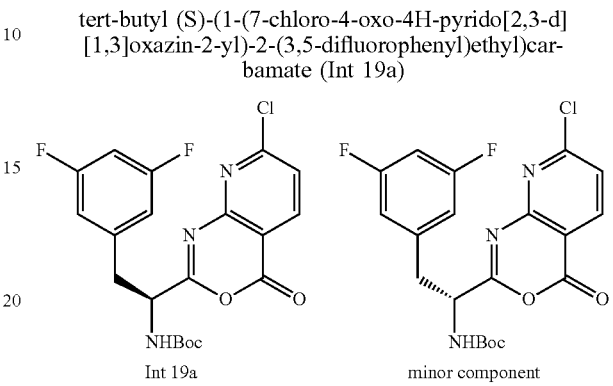

Int 19a        minor component

To a solution of (S)-2-((tert-butoxycarbonyl)amino)-3-(3,5-difluorophenyl)propanoic acid (1.746 g, 5.79 mmol) in DCM (77 mL) was added N-methylmorpholine (1.59 mL, 14.49 mmol) followed by isobutyl chloroformate (1.52 mL, 11.6 mmol). The reaction was then cooled to −20° C. (IPA/dry ice) and 2-amino-6-chloronicotinic acid (1.00 g, 5.79 mmol) was added. The reaction slurry was allowed to slowly warm to ambient temperature overnight as bath thawed for 18 h. The reaction was heated to reflux for 2 h. Upon cooling to ambient temperature, the mixture was filtered. The filtrate was diluted with EtOAc. The organic layer was washed with saturated sodium bicarbonate, brine, dried (Na$_2$SO$_4$) and concentrated in vacuo. The crude product was triturated with hexane and filtered to give the title product which contained some of the undesired enantiomer as a yellow solid (1.34 g, used as is). $^1$H NMR (500 MHz, CDCl$_3$) δ 8.51-8.44 (m, 1H), 7.60-7.54 (m, 1H), 6.73-6.68 (m, 3H), 5.50-5.43 (m, 1H), 5.03 (br d, J=5.5 Hz, 1H), 3.42-3.35 (m, 1H), 3.20-3.12 (m, 1H), 1.48-1.43 (m, 9H).

tert-Butyl (S)-(1-(7-chloro-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)carbamate (Int 19b)

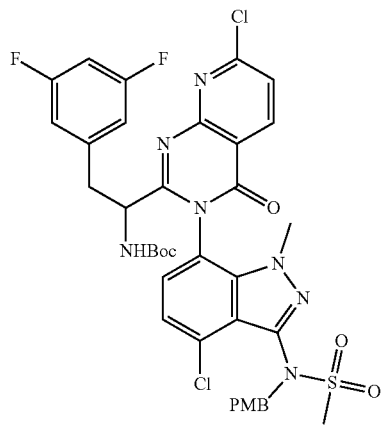

mixture of Int 19b and three other stereoisomers

A mixture of tert-butyl (S)-(1-(7-chloro-4-oxo-4H-pyrido[2,3-d][1,3]oxazin-2-yl)-2-(3,5-difluorophenyl)ethyl)carbamate (Int 19a, 0.25 g, 0.57 mmol) and N-(7-amino-4-chloro-1-methyl-1H-indazol-3-yl)-N-(4-methoxybenzyl)methanesulfonamide (Int 17d, 0.225 g, 0.571 mmol) in DCE (2.3 mL) was stirred at rt for 18 h. The reaction mixture was treated with isobutyl chloroformate (0.090 mL, 0.685 mmol) and N-methylmorpholine (0.075 mL, 0.685 mmol), then stirred at rt for 2 h and diluted with ethyl acetate, washed with sat NaHCO$_3$, dried over Na$_2$SO$_4$ and concentrated. The residue was purified on silica gel (40 g Isco column) using 0-100% ethyl acetate in hexanes. The desired fractions were concentrated to give a pale yellow solid (0.30 g) as the product which was a mixture of four stereoisomers due to some racemization and the existence of stable atropisomers. LC/MS: m/z=814.3 [M+H]$^+$.

N—((S)-1-(7-chloro-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 19d)

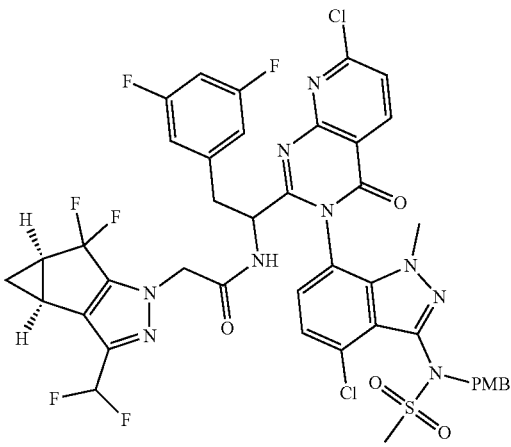

Mixture of Int 19d and three other stereoisomers (S)—N-(7-(2-(1-amino-2-(3,5-difluorophenyl)ethyl)-7-chloro-4-oxopyrido[2,3-d]pyrimidin-3(4H)-yl)-4-chloro-1-methyl-1H-indazol-3-yl)-N-(4-methoxybenzyl)methanesulfonamide hydrochloride (Int 19c)

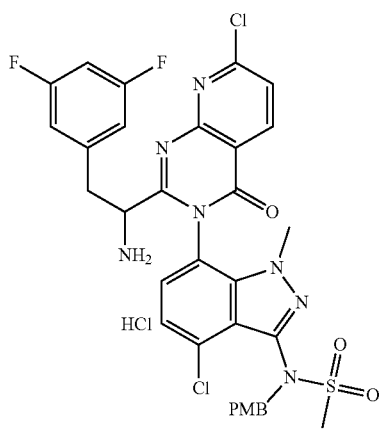

Mixture of Int 19c and three other stereoisomers

HCl (5.60 mL, 22.4 mmol, 4 N in dioxane) and tert-butyl (S)-(1-(7-chloro-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)carbamate (Int 19b, 0.304 g, 0.373 mmol) was stirred at rt for 0.5 h and concentrated to give an off-white solid (used as is) which was a mix of stereoisomers due to the racemization in a reaction earlier in the sequence and the stable atropisomers. LC/MS: m/z=714.3 [M+H]$^+$.

To a stirred solution of (S)—N-(7-(2-(1-amino-2-(3,5-difluorophenyl)ethyl)-7-chloro-4-oxopyrido[2,3-d]pyrimidin-3(4H)-yl)-4-chloro-1-methyl-1H-indazol-3-yl)-N-(4-methoxybenzyl)methanesulfonamide hydrochloride (Int 19c, 0.267 g, 0.356 mmol) in DMF (3 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.094 g, 0.356 mmol), HATU (0.142 g, 0.373 mmol) and DIPEA (0.12 mL, 0.71 mmol). The mixture was stirred for 2 h and purified on silica gel (80 g Isco column) using 0-100% ethyl acetate in hexanes. The desired fractions were concentrated to give a light yellow solid (0.26 g) which was a mix of stereoisomers due to the racemization in a reaction earlier in the sequence and the stable atropisomers. LC/MS: m/z=960.2 [M+H]$^+$.

N—((S)-1-(7-chloro-3-(4-chloro-1-methyl-3-(methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 12.1, 12.2, 12.3)

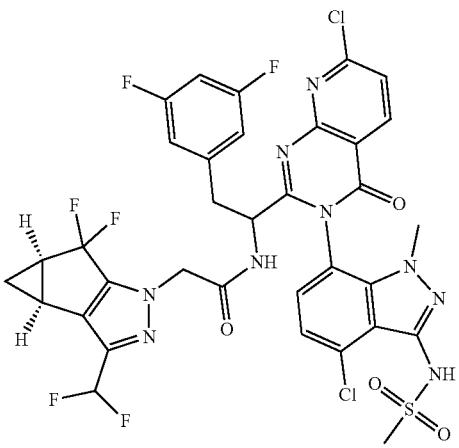

Example 12.1
Mixture of two stereoisomers

-continued

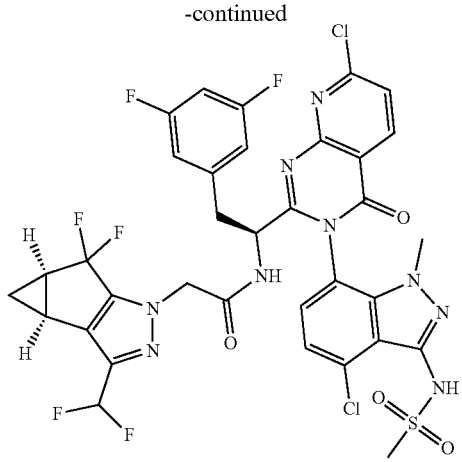

Example 12.2
homochiral

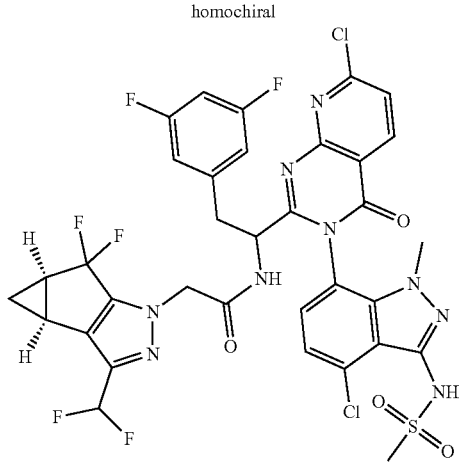

Example 12.3
homochiral

N—((S)-1-(7-chloro-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 19d, 0.256 g, 0.266 mmol) in DCM (1.1 mL) were added triflic acid (0.071 mL) and TFA (2.2 mL) and the mixture was stirred at rt for 1 h and concentrated. The crude material was purified under the following prep-HPLC condition to retrieve two isolates, each as a mixture of two stereoisomers. Prep-HPLC: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-70% B over 20 minutes, then a 5-minute hold at 100% B; Flow Rate: 20 mL/min; Column Temperature: 25° C. Fraction collection was triggered by UV signals. Fractions containing the desired product were combined and dried via centrifugal evaporation. Detection: MS and UV (220 nm).

Example 12.1: First Elute (59 mg, Off White Solid)

LC/MS: m/z=840.0 [M+H]$^+$. Second elute (64 mg, off white solid) was further purified by Chiral column to retrieve two elutes of stereoisomeric relation. Chiralpak IC preparative column, 30×250 mm, 5 μm Mobile Phase: 20% IPA in $CO_2$, 150 bar Temp: 35° C., Flow rate: 70.0 mL/min. in 25 min. UV monitored @ 308 nm. Injection: 0.75 mL of ~8 mg/mL in 1:1:1 IPA:MeOH:CHCl$_3$.

Example 12.2: First Elute (34 mg, Off White Solid)

$^1$H NMR (500 MHz, MeOH-d$_4$) δ 8.72-8.63 (m, 1H), 7.77-7.70 (m, 1H), 7.35-7.25 (m, 2H), 6.84-6.54 (m, 4H), 4.64-4.52 (m, 2H), 3.98-3.88 (m, 2H), 3.71-3.67 (m, 1H), 3.66-3.60 (m, 3H), 3.59-3.54 (m, 1H), 3.50-3.44 (m, 1H), 3.16-3.09 (m, 1H), 2.48-2.39 (m, 2H), 1.41-1.35 (m, 1H), 1.03-0.98 (m, 1H). LC/MS: m/z=840z.0 [M+H]$^+$.

Example 12.3: Second Elute (24 mg, Off White Solid)

$^1$H NMR (500 MHz, METHANOL-d$_4$) δ 8.73-8.63 (m, 1H), 7.74 (d, J=8.2 Hz, 1H), 7.35-7.23 (m, 2H), 6.83-6.56 (m, 4H), 4.63-4.52 (m, 2H), 3.64 (s, 3H), 3.48-3.42 (m, 2H), 3.27-3.22 (m, 3H), 3.15-3.07 (m, 1H), 2.48-2.37 (m, 2H), 1.39-1.33 (m, 1H), 1.06-0.98 (m, 1H). LC/MS: m/z=840.0 [M+H]$^+$.

Note that Example 12.2 converts slowly to one of the stereoisomers in Example 12.1 when stored in MeOH at ambient condition.

tert-butyl (S)-(2-(3,5-difluorophenyl)-1-(7-methoxy-4-oxo-4H-pyrido[2,3-d][1,3]oxazin-2-yl)ethyl)carbamate (Int 20a)

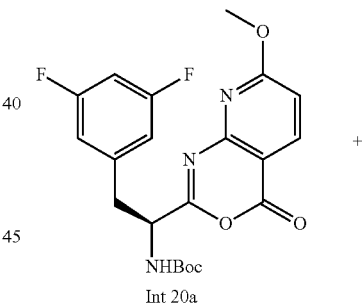

Int 20a

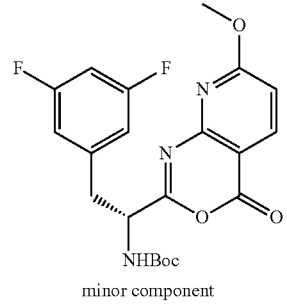

minor component

To a solution of (S)-2-((tert-butoxycarbonyl)amino)-3-(3,5-difluorophenyl)propanoic acid (0.408 g, 1.354 mmol) in DCM (18 mL) was added N-methylmorpholine (0.670 mL, 6.09 mmol) followed by isobutyl chloroformate (0.36 mL, 2.7 mmol). The reaction was then cooled to −20° C. (IPA/dry ice) and 2-amino-6-methoxynicotinic acid dihydrochloride (0.326 g, 1.354 mmol) was added. The reaction slurry was allowed to slowly warm to ambient temperature overnight as bath thawed for 18 h. The reaction was heated to reflux for 2 h. Upon cooling to ambient temperature, the reaction was filtered. The filtrate was diluted with EtOAc. The organic layer was washed with saturated sodium bicarbonate, brine, dried (Na$_2$SO$_4$) and concentrated in vacuo. The crude product was triturated with hexanes and filtered to give the product as a beige solid (0.25 g, used as is) which was a mixture due to some racemization. $^1$H NMR (500 MHz, CDCl$_3$) δ 8.40-8.27 (m, 1H), 7.01-6.89 (m, 1H), 6.75-6.69 (m, 3H), 5.47-5.39 (m, 11H), 5.06-4.95 (m, 1H), 4.17-4.09 (m, 3H), 3.42-3.33 (m, 1H), 3.19-3.12 (m, 1H), 1.47-1.42 (m, 9H), tert-butyl (S)-(1-(3-(4-chloro-3-(N-(4-methoxybenzyl)methylsulfonamido)-1-methyl-1H-indazol-7-yl)-7-methoxy-4-oxo-3,4-dihydropyrido[2,3-d]pyrimidin-2-yl)-2-(3,5-difluorophenyl)ethyl)carbamate (Int 20b)

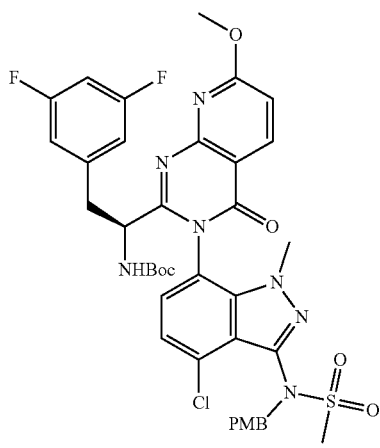

mix of int 20b and three other stereoisomers

A mixture of tert-butyl (S)-(2-(3,5-difluorophenyl)-1-(7-methoxy-4-oxo-4H-pyrido[2,3-d][1,3]oxazin-2-yl)ethyl) carbamate (Int 20a, 0.12 g, 0.277 mmol) and N-(7-amino-4-chloro-1-methyl-1H-indazol-3-yl)-N-(4-methoxybenzyl) methanesulfonamide (Int 17d, 0.109 g, 0.277 mmol) and diphenyl phosphite (0.27 mL, 1.38 mmol) in pyridine (1 mL) was heated at 70° C. for 2 h and purified on silica gel (24 g Isco column) using 0-100% ethyl acetate in hexanes. The desired fractions were concentrated to give a yellow solid (0.15 g) which was a mix of stereoisomers due to the racemization in a reaction earlier in the sequence and the stable atropisomers. LC/MS: m/z=810.3 [M+H]$^+$.

(S)—N-(7-(2-(1-amino-2-(3,5-difluorophenyl)ethyl)-7-methoxy-4-oxopyrido[2,3-d]pyrimidin-3(4H)-yl)-4-chloro-1-methyl-1H-indazol-3-yl)-N-(4-methoxybenzyl)methanesulfonamide hydrochloride (Int 20c)

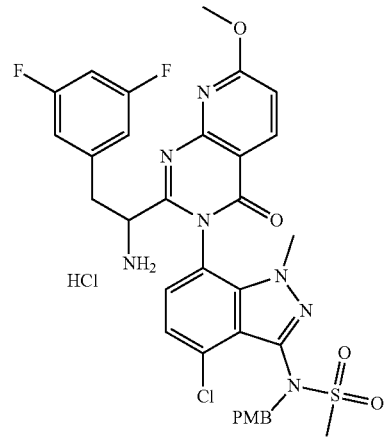

mixture of int 20c and three other stereoisomers

HCl (2.83 mL, 11.33 mmol, 4 N in dioxane) and tert-butyl (S)-(1-(3-(4-chloro-3-(N-(4-methoxybenzyl)methylsulfonamido)-1-methyl-1H-indazol-7-yl)-7-methoxy-4-oxo-3,4-dihydropyrido[2,3-d]pyrimidin-2-yl)-2-(3,5-difluorophenyl)ethyl)carbamate (Int 20b, 0.153 g, 0.189 mmol) was stirred at rt for 0.5 h and concentrated to give an off-white solid (used as is) which was a mix of stereoisomers due to the racemization in a reaction earlier in the sequence and the stable atropisomers. LC/MS: m/z=710.2 [M+H]$^+$.

N—((S)-1-(3-(4-chloro-3-(N-(4-methoxybenzyl) methylsulfonamido)-1-methyl-1H-indazol-7-yl)-7-methoxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide (Int 20d)

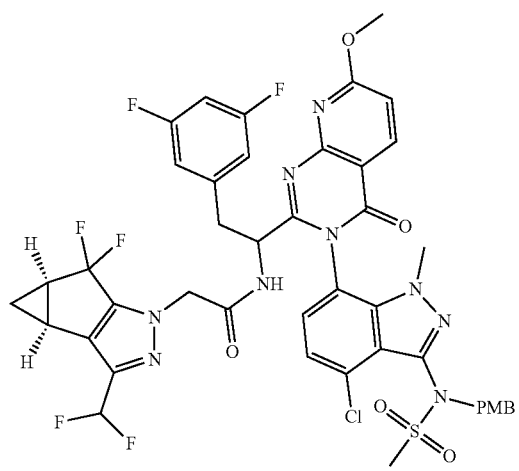

mixture of int 20d and three other stereoisomers

To a stirred solution of (S)—N-(7-(2-(1-amino-2-(3,5-difluorophenyl)ethyl)-7-methoxy-4-oxopyrido[2,3-d]pyrimidin-3(4H)-yl)-4-chloro-1-methyl-1H-indazol-3-yl)-N-(4-methoxybenzyl)methanesulfonamide hydrochloride (Int 20c, 0.134 g, 0.179 mmol) in DMF (1.8 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.047 g, 0.179 mmol), HATU (0.072 g, 0.188 mmol) and DIPEA (0.063 mL, 0.359 mmol). The mixture was stirred for 2 h and purified on silica gel (24 g Isco column) using 0-100% ethyl acetate in hexanes. The desired fractions were concentrated to give a yellow oil (0.19 g) which was a mix of stereoisomers due to the racemization in a reaction earlier in the sequence and the stable atropisomers. LC/MS: m/z=956.2 [M+H]$^+$.

N—((S)-1-(3-(4-chloro-1-methyl-3-(methylsulfonamido)-1H-indazol-7-yl)-7-methoxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 13.1, 13.2, 13.3)

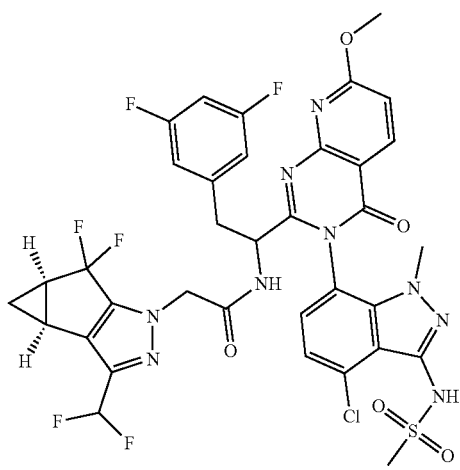

Example 13.1
Mixture of stereoisomers

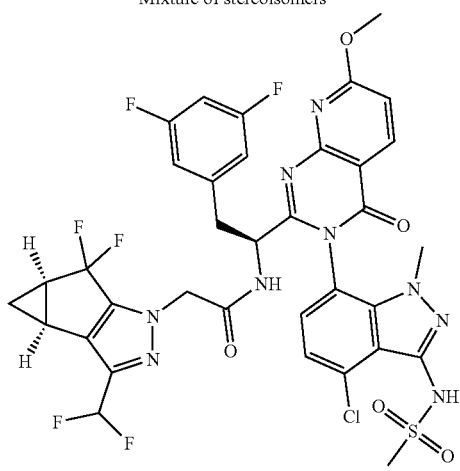

Example 13.2
homochiral

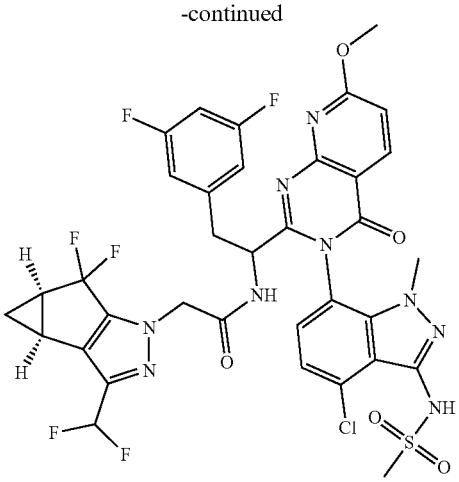

Example 13.3
homochiral

To a solution of N—((S)-1-(3-(4-chloro-3-(N-(4-methoxybenzyl)methylsulfonamido)-1-methyl-1H-indazol-7-yl)-7-methoxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 20d, 0.086 g, 0.090 mmol) in DCM (0.73 mL) were added triflic acid (0.024 mL) and TFA (1.46 mL) and the mixture was stirred at rt for 1 h and concentrated. The crude material was purified under the following prep-HPLC condition to retrieve two isolates, each as a mixture of stereoisomers. Prep-HPLC: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 28% B, 28-68% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Detection: MS and UV (220 nm).

Example 13.1: First Elute (22.3 mg, Off White Solid, a Mixture of Stereoisomers)

LC/MS: m/z=836.1 [M+H]$^+$.
Second elute (53 mg, off white solid, a mixture of stereoisomers) was further purified by Chiralpak IC preparative column, 30×250 mm, 5 m Mobile Phase: 25% IPA in CO$_2$, 150 bar Temp: 35° C., Flow rate: 70.0 mL/min. in 17 min. UV monitored @ 220 nm Injection: 1 mL of ~6 mg/mL in 1:1:1 IPA MeOH:CHCl$_3$. Two elutes of stereoisomeric relation were isolated.

Example 13.2: First Elute (30 mg, Off White Solid)

$^1$H NMR (500 MHz, MeOH-d$_4$) δ 8.52-8.45 (m, 1H), 7.33-7.27 (m, 1H), 7.22-7.17 (m, 1H), 7.10-7.05 (m, 1H), 6.84-6.56 (m, 4H), 4.63-4.52 (m, 2H), 4.20 (s, 3H), 3.64-3.59 (m, 3H), 3.49-3.44 (m, 2H), 3.25-3.22 (m, 3H), 3.16-3.10 (m, 1H), 2.47-2.39 (m, 2H), 1.41-1.34 (m, 1H), 1.05-0.98 (m, 1H). LC/MS: m/z=836.1[M+H]$^+$;
Not registered Example 13.3: Second elute (17 mg, off white solid, single stereoisomer). $^1$H NMR (500 MHz, MeOH-d$_4$) δ 8.53-8.44 (m, 1H), 7.37-7.27 (m, 1H), 7.26-

7.19 (m, 1H), 7.11-7.03 (m, 1H), 6.83-6.50 (m, 4H), 4.64-4.49 (m, 2H), 4.19-4.14 (m, 3H), 3.66-3.59 (m, 3H), 3.50-3.42 (m, 2H), 3.26-3.22 (m, 3H), 3.15-3.08 (m, 1H), 2.47-2.35 (m, 2H), 1.37-1.33 (m, 1H), 1.06-1.00 (m, 1H). LC/MS: m/z=836.1 [M+H]$^+$.

N-(4-chloro-1-(2,2-difluoroethyl)-7-(4,4,5,5-tetramethyl-1,3,2-dioxaborolan-2-yl)-1H-indazol-3-yl)methanesulfonamide (Int 21a)

Overall Synthetic Scheme:

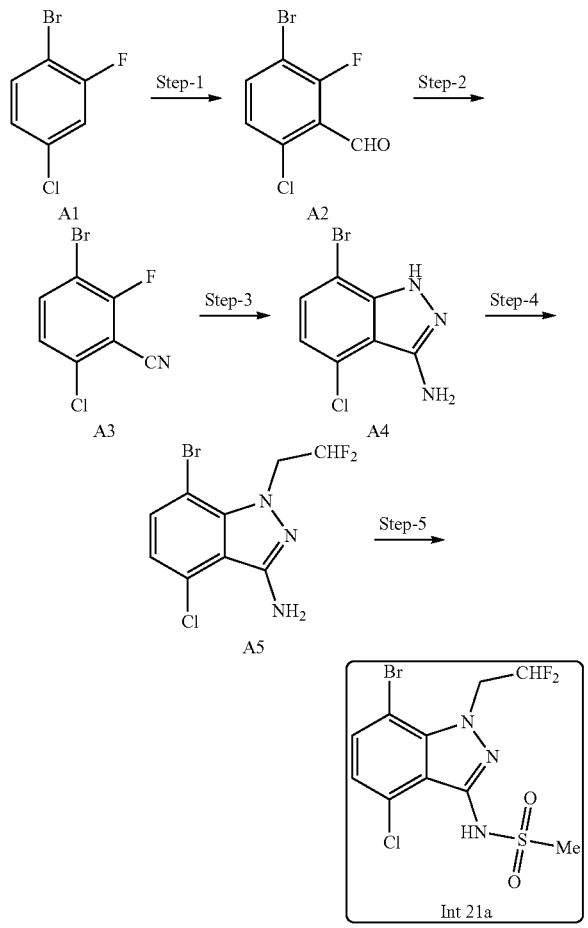

Step-1: Synthesis of 3-bromo-6-chloro-2-fluorobenzaldehyde 2

Reaction Scheme:

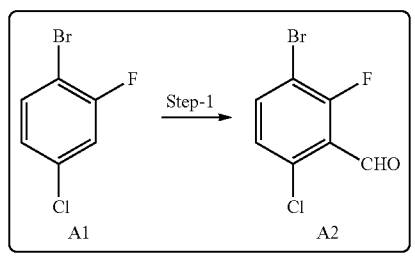

To a stirred solution of 1-Bromo-4-chloro-2-fluorobenzene A1 (200 g, 0.955 mol, 1.0 equiv.) in anhydrous THF (2.0 L) was added 2.0 M lithium diisopropylamide (LDA) in THF (620 mL, 1.24 mol, 1.3 equiv.) at −50° C., the reaction mixture was allowed to −20° C. and stirred for 1 h. Then it was re-cooled to −50° C. and slowly added DMF (184.8 mL, 2.48 mol, 2.6 equiv.) at the same temperature. The mixture was allowed to 0° C. and stirred for 30-45 min. After completion of the reaction (monitored by TLC), it was quenched with the slow addition of ice cold water (2.0 L); then diluted with ethyl acetate (2.0 L) and stirred for 15 min at room temperature. The organic layer was separated and aqueous layer was extracted with ethyl acetate (2×1.0 L). The combined organic layers were washed with water (2×1.0 L); 1.0 N HCl (1.0 L) and 15% NaCl solution (2.0 L). The organic layer was dried over anhydrous Na$_2$SO$_4$, concentrated under vacuum. The resultant crude solid was directly used for next step without further purification. Yield: 210.0 g, 93% (reported 78%). $^1$H NMR (400 MHz, CDCl$_3$): δ 10.39 (d, J=0.8 Hz, 1H), 7.69 (dd, J$_1$=7.2 Hz, J$_2$=8.8 Hz, 1H), 7.19 (dd, J=1.2 Hz, J$_2$=8.4 Hz, 1H).

Step-2: Synthesis of 3-bromo-6-chloro-2-fluorobenzonitrile A3

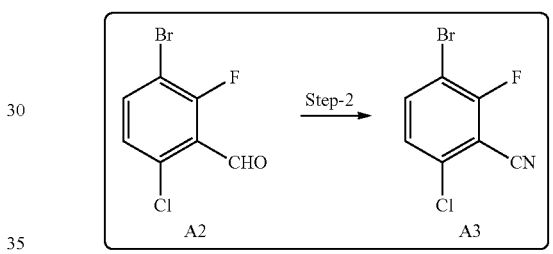

To a solution of 3-Bromo-6-chloro-2-fluorobenzaldehyde A2 (210.0 g, 0.89 mol, 1.0 equiv.) in water (2.1 L) was charged with Hydroxylamine-O-sulfonic acid (175.15 g, 1.55 mol, 1.75 equiv.) at room temperature. The reaction mixture was heated to 50° C. and stirred for 18 h. After reaction completion (the reaction progress was monitored by TLC), it was cooled to room temperature and stirred for 1-1.5 h. The solids were filtered and washed with water. The wet solid was dried at 50° C. under vacuum for 12-15 h to afford the crude 3-Bromo-6-chloro-2-fluorobenzonitrile A3 as a solid; which can be directly used for the next reaction without further purification. Yield: 190.0 g, 91% (reported 92%). $^1$H NMR (400 MHz, CDCl$_3$): δ 7.50 (dd, J$_1$=7.1 Hz, J$_2$=8.6 Hz, 1H), 7.15 (dd, J$_1$=1.4 Hz, J$_2$=8.7 Hz, 1H).

Step-3: Synthesis of 7-bromo-4-chloro-1H-indazol-3-amine A4

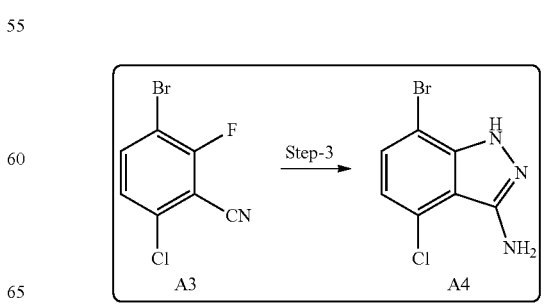

To a stirred solution of 3-Bromo-6-chloro-2-fluorobenzonitrile A3 (10.0 g, 0.043 mol, 1.0 equiv.) in ethanol (50 mL) was added hydrazine hydrate (10.42 mL, 0.21 mol, 5.0 equiv.) at room temperature. The reaction mixture was heated to 110° C. and stirred for 15 h. After completion of the reaction (monitored by TLC), it was cooled to room temperature and water (100 mL) was added and stirred for 1 h at room temperature. The obtained solids were filtered and washed with water (100 mL). The wet solid was dried under vacuum at 50° C. for 12-15 hours. The crude solid was purified by column chromatography (eluting with 10% EA/Hexanes to 40% EA/Hexanes) to afford 7-Bromo-4-chloro-1H-indazol-3-amine A4 as a dull white solid. Yield: 8.4 g, 80%; $^1$H NMR (400 MHz, DMSO-$d_6$): δ 12.21 (bs, 1H), 7.41 (d, J=7.8 Hz, 1H), 6.84 (d, J=7.8 Hz, 1H), 5.34 (bs, 2H) ppm.

Step-4: Synthesis of 7-bromo-4-chloro-1-(2,2-difluoroethyl)-1H-indazol-3-amine A5

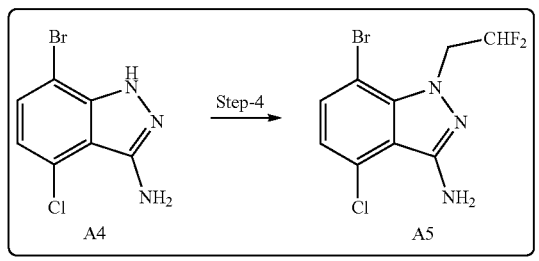

To a stirred solution of 7-Bromo-4-chloro-1H-indazol-3-amine A4 (2.0 g, 8.16 mmol, 1.0 equiv.) in dry THF (20 mL) at 0° C. was added $^t$BuOK (1.20 g, 10.61 mmol, 1.3 equiv.) in portions. After being stirred for 10 min at 0° C., 2,2-Difluoroethyl trifluoromethanesulfonate (1.92 g, 8.98 mmol, 1.10 equiv.) was added slowly at the same temperature. Then it was slowly raised to room temperature and stirred for 2 h. After completion of the reaction (monitored by TLC), it was diluted with ice cold water (20 mL) and MTBE (40 mL). The organic layer was separated, washed with water (2×20 mL), dried over Na$_2$SO$_4$, filtered and concentrated in vacuum. Column chromatographic purification (eluting with 5% EA/hexanes to 10% EA/hexanes) of this crude led to 7-Bromo-4-chloro-1-(2,2-difluoroethyl)-1H-indazol-3-amine A5 as a light yellow solid. Yield: 1.8 g, 71%. $^1$H NMR (400 MHz, DMSO-$d_6$): δ 7.53 (d, J=8.0 Hz, 1H), 6.94 (d, J=8.0 Hz, 1H), 6.30 (tt, $J_1$=3.9 Hz, $J_2$=7.7 Hz, $J_3$=55.2 Hz, 1H), 5.61 (s, 2H), 4.92 (td, $J_1$=3.8 Hz, $J_2$=14.1 Hz, 2H).

Step-5: Synthesis of N-(7-bromo-4-chloro-1-(2,2-difluoroethyl)-1H-indazol-3-yl)methane Sulphonamide (Int-21a)

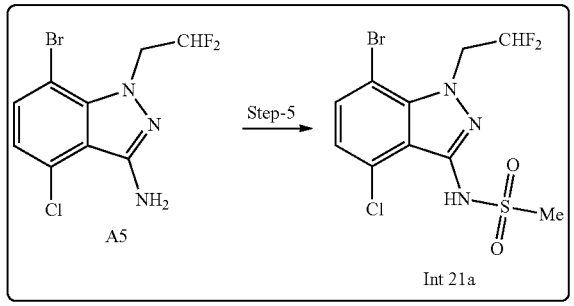

To a stirred solution of 7-Bromo-4-chloro-1-(2,2-difluoroethyl)-1H-indazol-3-amine A5 (0.5 g, 1.61 mmol, 1.0 equiv.) in dry DCM (5 mL) was added DIPEA (0.84 mL, 4.83 mmol, 3.0 equiv.) and DMAP (0.98 mg, 0.08 mmol, 0.05 equiv.). After being stirred for 10-15 min, the reaction mixture was cooled to 0° C. and methanesulfonyl chloride (0.38 mL, 4.83 mmol, 3.0 equiv.) was added slowly. Then it was stirred at room temperature for 2 h. After completion of the reaction (monitored by TLC), it was diluted with DCM (2×10 mL) and water (10 mL). The organic layer was separated and washed with water (2×10 mL), brine (5 mL), dried over Na$_2$SO$_4$, filtered and concentrated in vacuum. The residue obtained was dissolved in ethanol (8 mL) and added with 10 N NaOH (10 mL) solution. The reaction mixture was stirred at room temperature for 2 h. After the removal of one of two mesyl groups (monitored by TLC), it was diluted with water (10 mL) and acidified with 1.0 N HCl (pH 2-3). The obtained solids were filtered, washed with water and dried under vacuum. Column chromatographic purification (eluting with 20% EA/hexanes to 40% EA/hexanes) of this crude material afforded the pure N-(7-Bromo-4-chloro-1-(2,2-difluoroethyl)-1H-indazol-3-yl) methane sulfonamide Int-21a as a light yellow solid. Yield: 0.40 g, 64%

N-(7-bromo-4-chloro-1-(2,2-difluoroethyl)-1H-indazol-3-yl)-N-(4-methoxybenzyl)methanesulfonamide (Int 21b)

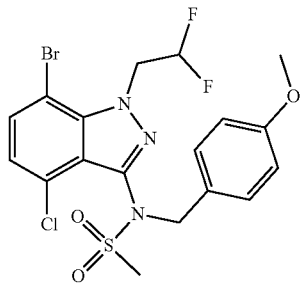 [SMILES: COc1ccc(CN(c2nn(CC(F)F)c3c(Br)ccc(Cl)c23)S(C)(=O)=O)cc1]

4-methoxybenzyl chloride (0.250 ml, 1.853 mmol) was added to a mixture of N-(7-bromo-4-chloro-1-(2,2-difluoroethyl)-1H-indazol-3-yl)methanesulfonamide (Int 21a, 0.600 g, 1.54 mmol) and Cs$_2$CO$_3$ (1.006 g, 3.09 mmol) in DMF (6.2 ml). The mixture was stirred at rt overnight. The mixture was diluted with ethyl acetate, washed with brine, dried over Na$_2$SO$_4$ and concentrated. The residue was purified on silica (80 g Isco column) using 0-60% ethyl acetate in hexanes to give a viscous yellow oil (0.73 g). $^1$H NMR (400 MHz, CDCl$_3$) δ 7.54-7.48 (m, 1H), 7.25-7.21 (m, 2H), 7.10-7.04 (m, 1H), 6.83-6.77 (m, 2H), 6.26-5.92 (m, 1H), 5.43-5.28 (m, 1H), 5.08-4.91 (m, 2H), 4.83-4.69 (m, 1H), 3.80-3.76 (m, 3H), 3.03-2.98 (m, 3H). LC/MS: m/z=531.9 [M+Na]$^+$.

111

N-(4-chloro-1-(2,2-difluoroethyl)-7-((diphenylmethylene)amino)-1H-indazol-3-yl)-N-(4-methoxybenzyl)methanesulfonamide (Int 21c)

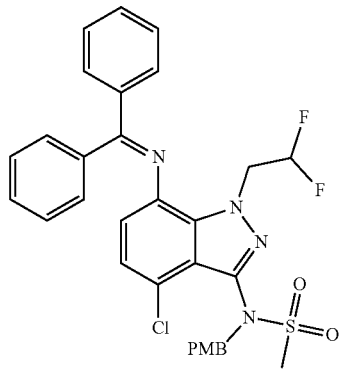

A mixture of N-(7-bromo-4-chloro-1-(2,2-difluoroethyl)-1H-indazol-3-yl)-N-(4-methoxybenzyl)methanesulfonamide (Int 21b, 0.73 g, 1.435 mmol), diphenylmethanimine (0.266 mL, 1.583 mmol), PdOAc$_2$ (0.016 g, 0.072 mmol), R-(+)-BINAP (0.134 g, 0.215 mmol) and Cs$_2$CO$_3$ (0.701 g, 2.152 mmol) in Dioxane (14.4 mL) was degassed for 5 min and heated (heating block) at 95° C. for 2 h, filtered through a plug of Celite and concentrated. The residue was purified on silica gel (220 g Isco column) using 0-40% ethyl acetate, the desired fractions were concentrated to give a bright yellow solid (0.74 g). LC/MS: m/z=609.1 [M+H]$^+$.

N-(7-amino-4-chloro-1-(2,2-difluoroethyl)-1H-indazol-3-yl)-N-(4-methoxybenzyl)methanesulfonamide (Int 21d)

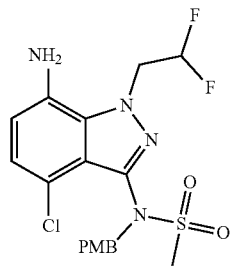

To a bright yellow solution of N-(4-chloro-1-(2,2-difluoroethyl)-7-((diphenylmethylene)amino)-1H-indazol-3-yl)-N-(4-methoxybenzyl)methanesulfonamide (Int 21c, 0.74 g, 1.215 mmol) in THF (12 mL) was added HCl (3.0 mL, 12 mmol) and water (0.11 mL) (it was slightly exothermic at rt). The resulting dark orange solution was stirred at rt for 2 h, at which point it turned into a light-yellow solution. The reaction mixture was concentrated and the residue was taken up in ethyl acetate, washed with 2 M K$_3$PO$_4$, dried over MgSO$_4$ and concentrated. The residue was purified on silica (80 g Isco column) using 0-60% ethyl acetate in hexanes. The desired fractions were concentrated to give a brown foamy solid (0.48 g). LC/MS: m/z=445.1 [M+H]$^+$.

112 tert-Butyl (S)-(1-(3-(4-chloro-1-(2,2-difluoroethyl)-3-(N-(4-methoxybenzyl)methylsulfonamido)-1H-indazol-7-yl)-4-oxo-3,4-dihydropyrido[2,3-d]pyrimidin-2-yl)-2-(3,5-difluorophenyl)ethyl)carbamate (Int 21e)

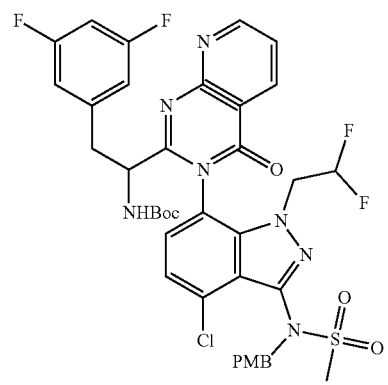

mixture of int 21e and several stereoisomers

A mixture of tert-butyl (S)-(2-(3,5-difluorophenyl)-1-(4-oxo-4H-pyrido[2,3-d][1,3]oxazin-2-yl)ethyl)carbamate (Int 17a, 0.30 g, 0.744 mmol), N-(7-amino-4-chloro-1-(2,2-difluoroethyl)-1H-indazol-3-yl)-N-(4-methoxybenzyl)methanesulfonamide (Int 21d, 0.331 g, 0.744 mmol) and diphenyl phosphite (0.720 mL, 3.72 mmol) in pyridine (3.0 mL) was heated at 70° C. (heating block) for 2 h and purified on silica gel (80 g Isco column) using 0-100% ethyl acetate in hexanes. The desired fractions were concentrated to give a yellow solid which was a mix of stereoisomers (0.33 g). LC/MS: m/z=830.4 [M+H]$^+$.

(S)-N-(7-(2-(1-amino-2-(3,5-difluorophenyl)ethyl)-4-oxopyrido[2,3-d]pyrimidin-3(4H)-yl)-4-chloro-1-(2,2-difluoroethyl)-1H-indazol-3-yl)-N-(4-methoxybenzyl)methanesulfonamide hydrochloride (Int 21f)

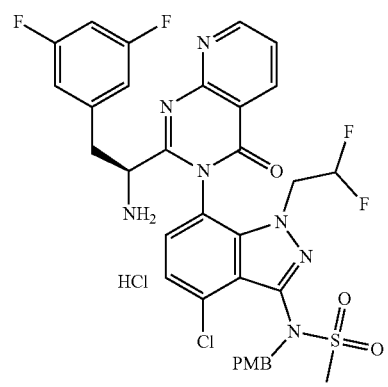

HCl (6.0 mL, 24 mmol, 4 N in dioxane) and tert-butyl (S)-(1-(3-(4-chloro-1-(2,2-difluoroethyl)-3-(N-(4-methoxybenzyl)methylsulfonamido)-1H-indazol-7-yl)-4-oxo-3,4-dihydropyrido[2,3-d]pyrimidin-2-yl)-2-(3,5-difluorophenyl)ethyl)carbamate (Int 21e, 0.33 g, 0.397 mmol) was stirred at rt for 0.5 h and concentrated to give an off-white solid as a mixture of stereoisomers (used as is). LC/MS: m/z=730.2 [M+H]$^+$.

113

N—((S)-1-(3-(4-chloro-1-(2,2-difluoroethyl)-3-(N-(4-methoxybenzyl)methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 21g)

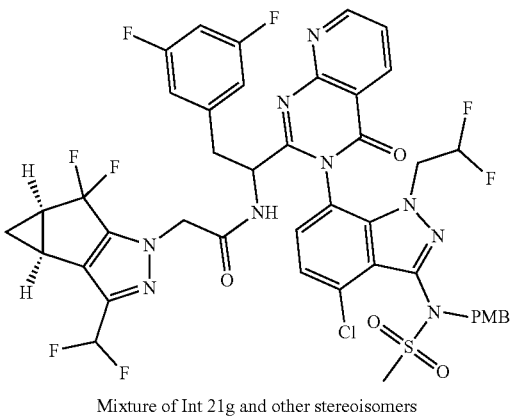

Mixture of Int 21g and other stereoisomers

To a stirred solution of (S)—N-(7-(2-(1-amino-2-(3,5-difluorophenyl)ethyl)-4-oxopyrido[2,3-d]pyrimidin-3(4H)-yl)-4-chloro-1-(2,2-difluoroethyl)-1H-indazol-3-yl)-N-(4-methoxybenzyl)methanesulfonamide hydrochloride (Int 21f, 0.154 g, 0.201 mmol) in DMF (1 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.053 g, 0.201 mmol), HATU (0.080 g, 0.211 mmol) and DIPEA (0.070 mL, 0.402 mmol). The mixture was stirred for 2 h and purified on silica gel (24 g Isco column) using 0-100% ethyl acetate in hexanes to afford the title product as a light brown oil (0.19 g) as a mixture of stereoisomers. LC/MS: m/z=976.4 [M+H]⁺.

N—((S)-1-(3-(4-chloro-1-(2,2-difluoroethyl)-3-(methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 14.1, 14.2)

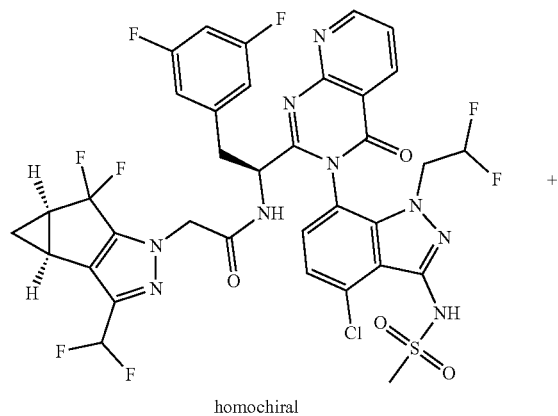

homochiral

114

-continued

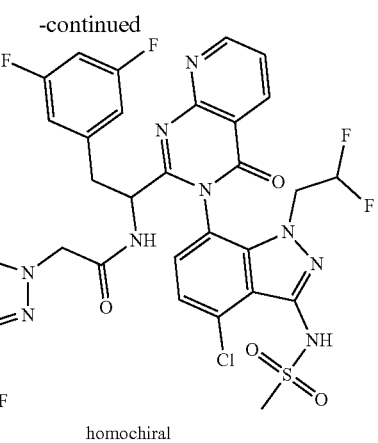

homochiral

To a solution of N—((S)-1-(3-(4-chloro-1-(2,2-difluoroethyl)-3-(N-(4-methoxybenzyl)methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 21g, 0.19 g, 0.195 mmol) in DCM (1.6 mL) were added TFA (3.2 mL) and triflic acid (0.044 mL) and the mixture was stirred at rt for 1 h and concentrated. The crude was purified by prep-HPLC using XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 26% B, 26-66% B over 23 minutes, then a 5-minute hold at 100% B; Flow Rate: 20 mL/min; Column Temperature: 25° C. Fraction collection was triggered by MS and UV signals. The retrieved material was further purified under the following condition: Chiralpak AD-H preparative column, 30×250 mm, 5 μm Mobile Phase: 20% IPA in CO₂, 150 bar Temp: 35° C., Flow rate: 70.0 mL/min. in 15 min. UV monitored @ 306 nm. Injection: 0.5 mL of ~10 mg/mL in 1:1:1 IPA:MeOH:CHCl₃. Two elutes, each a single stereoisomer were isolated Example 14.1: First Elute (70 mg, Off-White Solid)

¹H NMR (400 MHz, MeOH-d₄) δ 9.18-9.07 (m, 1H), 8.79-8.67 (m, 1H), 7.77-7.67 (m, 1H), 7.46-7.30 (m, 2H), 6.84-6.47 (m, 4H), 6.18-5.84 (m, 1H), 4.82-4.75 (m, 1H), 4.71-4.54 (m, 2H), 4.49-4.31 (m, 1H), 4.04-3.88 (m, 1H), 3.75-3.59 (m, 1H), 3.29-3.24 (m, 3H), 3.16-3.05 (m, 1H), 2.47-2.34 (m, 2H), 1.42-1.27 (m, 1H), 1.03-0.93 (m, 1H). LC/MS: m/z=856.0 [M+H]⁺.

Example 14.2: Second Elute (25 mg, Off-White Solid)

¹H NMR (400 MHz, MeOH-d₄) δ 9.15-9.08 (m, 1H), 8.77-8.70 (m, 1H), 7.76-7.69 (m, 1H), 7.43-7.38 (m, 1H), 7.37-7.37 (m, 1H), 7.38-7.30 (m, 1H), 6.82-6.51 (m, 4H), 6.20-5.84 (m, 1H), 4.79 (dd, J=9.4, 4.4 Hz, 1H), 4.70-4.56 (m, 2H), 4.42-4.30 (m, 1H), 3.68-3.67 (m, 2H), 3.55 (br s, 1H), 3.27 (s, 3H), 3.15-3.07 (m, 1H), 2.46-2.29 (m, 2H), 1.35-1.32 (m, 1H), 1.05-0.95 (m, 1H). LC/MS: m/z=856.0 [M+H]⁺.

tert-butyl (S)-(1-(3-(4-chloro-3-(N-(4-methoxyben-zyl)methylsulfonamido)-1-methyl-1H-indazol-7-yl)-4-oxo-3,4-dihydropyrido[2,3-d]pyrimidin-2-yl)-2-(3,5-difluorophenyl)ethyl)carbamate (Int 22a)

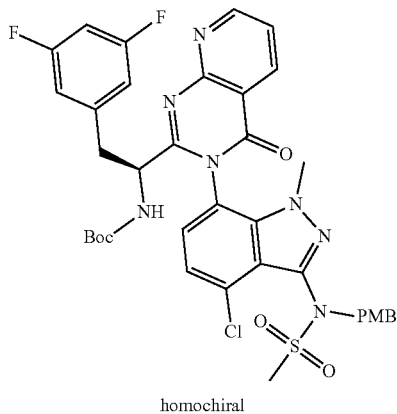

homochiral

A sample of Int 22a was prepared in a similar fashion to the procedure provided in the synthesis of Example 10.39/Example 10.40. Chiral column analysis indicated the sample is a mixture of 4 stereoisomers (2 major and 2 minor), consistent with some chiral erosion at the benzylic center and the presence of atropisomers. The sample was purified by OD-H column (mobile phase $CO_2$/MeOH, 7:3; 35° C.; 100 bars; 220 nM detection) and of the two major peaks the one eluting later was retrieved.

(S)—N-(7-(2-(1-amino-2-(3,5-difluorophenyl)ethyl)-4-oxopyrido[2,3-d]pyrimidin-3(4H)-yl)-4-chloro-1-methyl-1H-indazol-3-yl)-N-(4-methoxybenzyl)methanesulfonamide (Int 22b)

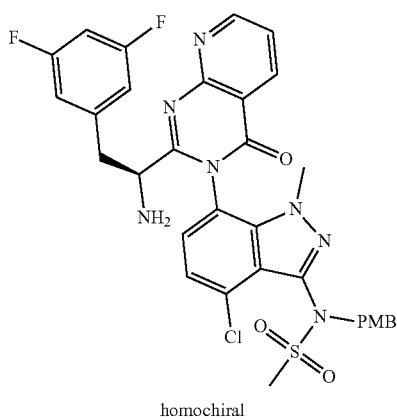

homochiral

HCl (16.2 mL, 65 mmol) was added to a solution of tert-butyl (S)-(1-(3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)carbamate (Int 22a, 1.69 g, 2.17 mmol) in DCM (5 mL) and the mixture was stirred at rt for 0.5 hr and the volatile component was removed in vacuo to afford Int 22b which was confirmed to be homochiral and was used as is.

(S)—N-(1-(3-(4-chloro-1-methyl-3-(methylsulfona-mido)-1H-indazol-7-yl)-4-oxo-3,4-dihydropyrido[2,3-d]pyrimidin-2-yl)-2-(3,5-difluorophenyl)ethyl)-2-(3-cyclopropyl-1H-pyrazol-1-yl)acetamide
(Example 15)

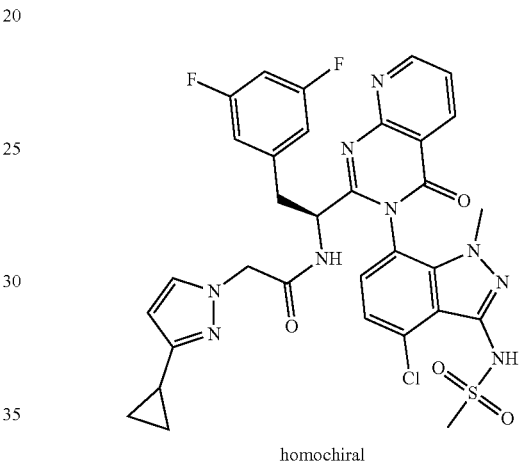

homochiral

To a stirred solution of (S)—N-(7-(2-(1-amino-2-(3,5-difluorophenyl)ethyl)-4-oxopyrido[2,3-d]pyrimidin-3(4H)-yl)-4-chloro-1-methyl-1H-indazol-3-yl)-N-(4-methoxybenzyl)methanesulfonamide hydrochloride (Int 22b, 0.05 g, 0.070 mmol) in THF (1 mL) were added 2-(3-cyclopropyl-1H-pyrazol-1-yl)acetic acid (0.012 g, 0.070 mmol), HATU (0.028 g, 0.073 mmol) and DIPEA (0.024 mL, 0.14 mmol). The mixture was stirred for 2 h. The residue was taken up in DCM (0.5 mL) and triflic acid (0.05 mL) and TFA (1 mL) were added. The mixture was stirred at rt for 1 h and concentrated. The crude was purified by XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 23% B, 23-63% B over 20 minutes, then a 5-minute hold at 100% B; Flow Rate: 20 mL/min; Column Temperature: 25° C. Fraction collection was triggered by MS and UV signals. Title product was isolated as an off-white solid (34 mg). $^1$H NMR (400 MHz, MeOH-$d_4$) δ 9.15-9.05 (m, 1H), 8.78-8.67 (m, 1H), 7.77-7.66 (m, 1H), 7.36-7.21 (m, 3H), 6.81-6.63 (m, 3H), 5.93-5.85 (m, 1H), 5.02-4.96 (m, 2H), 4.45-4.26 (m, 2H), 3.56-3.50 (m, 2H), 3.28-3.26 (m, 3H), 3.16-3.08 (m, 1H), 1.87-1.79 (m, 1H), 0.88-0.82 (m, 2H), 0.65-0.59 (m, 2H). LC/MS: m/z=708.1 [M+H]$^+$.

tert-Butyl (S)-(1-(3-(4-chloro-3-(N-(4-methoxyben-zyl)methylsulfonamido)-1-methyl-1H-indazol-7-yl)-4-oxo-3,4-dihydroquinazolin-2-yl)-2-(3,5-difluoro-phenyl)ethyl)carbamate (Int 23a)

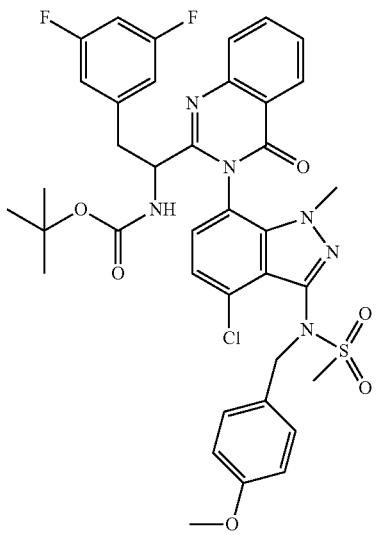

mixture of int 23a and other stereo isomers

A pressure vessel containing a mixture of (S)-2-((tert-butoxycarbonyl)amino)-3-(3,5-difluorophenyl)propanoic acid (70 mg, 0.23 mmol), 2-aminobenzoic acid (32 mg, 0.23 mmol) and diphenyl phosphite (0.16 mL, 0.77 mmol) in pyridine (1.5 mL) was sealed in a pressure vessel and heated in an oil bath at 70° C. for 2 h. N-(7-amino-4-chloro-1-methyl-1H-indazol-3-yl)-N-(4-methoxybenzyl)methane-sulfonamide (Int 17d, 101 mg, 0.26 mmol) was then added to the reaction mixture and the vessel was resealed and heated again in the bath at 70° C. for an additional 2 h. The solvent was removed with a steady stream of nitrogen. The residue was partitioned between water (20 mL) and EtOAc (10 mL). The organic component was washed with 5% citric acid, 1.5 M $K_3PO_4$ and brine, dried over $MgSO_4$, filtered, and evaporated in vacuo. The residue was purified by flash column chromatography (12 g silica gel cartridge), eluted with gradient 0-50% EtOAc-hexanes to afford the title product (91 mg) as a colorless foam as a mix of stereoisomers. LC-MS retention time=1.13 min; m/z=779.08 [M+H]$^+$, (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm). $^1$H NMR (500 MHz, CDCl$_3$) 8.54-8.20 (m, 1H), 7.98-7.88 (m, 1H), 7.89-7.80 (m, 1H), 7.61 (br t, J=7.4 Hz, 1H), 7.34 (br d, J=8.0 Hz, 2H), 7.25-7.09 (m, 1H), 6.84 (br t, J=8.7 Hz, 2H), 6.72 (br t, J=8.8 Hz, 1H), 6.66-6.24 (m, 3H), 5.48-5.17 (m, 1H), 5.12-4.92 (m, 1H), 4.88-4.68 (m, 1H), 4.71-4.46 (m, 1H), 3.80 (br d, J=4.7 Hz, 3H), 3.67 (s, 2H), 3.34-3.14 (m, 2H), 2.96 (br d, J=11.0 Hz, 3.6H), 2.80 (br dd, J=13.1, 6.0 Hz, 0.4H), 1.46-1.30 (m, 8H), 1.13-0.93 (m, 1H).

(S)—N-(7-(2-(1-amino-2-(3,5-difluorophenyl)ethyl)-4-oxoquinazolin-3(4H)-yl)-4-chloro-1-methyl-1H-indazol-3-yl)methanesulfonamide (Int 23b)

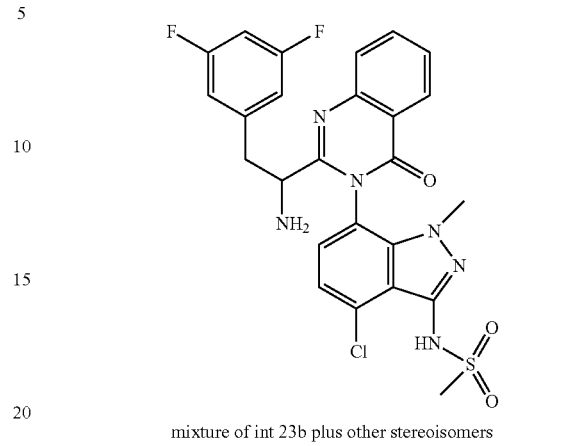

mixture of int 23b plus other stereoisomers

To an ice bath cooled solution of tert-Butyl (S)-(1-(3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int 23a, 91 mg, 0.12 mmol) in DCM (0.8 mL) was added TFA (0.8 mL) and triflic acid (0.10 mL). The resultant orange solution was stirred at rt for 1 h. The volatiles were removed with a steady stream of nitrogen. The residue was partitioned between EtOAc (5 mL) and sat. NaHCO$_3$ (10 mL). The organic component was washed with brine, dried over MgSO$_4$, filtered, and evaporated in vacuo to afford the desired product (off-white foam, 85 mg) as a mixture of stereoisomers, which was used as is. LC-MS retention time=0.65, 0.77 min; m/z=559.08 [M+H]$^+$, (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

N—((S)-1-(3-(4-chloro-1-methyl-3-(methylsulfona-mido)-1H-indazol-7-yl)-4-oxo-3,4-dihydroquinazo-lin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 16)

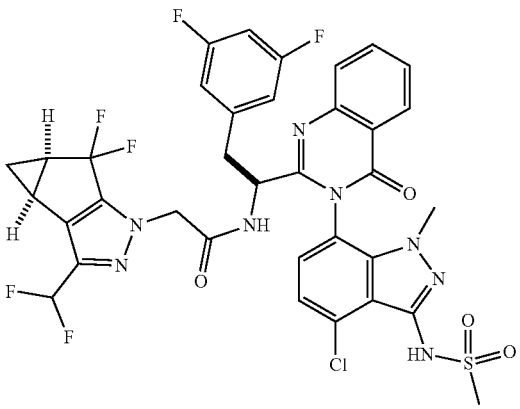 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4ccccc4c3=O)c21]

To a solution of (S)—N-(7-(2-(1-amino-2-(3,5-difluoro-phenyl)ethyl)-4-oxoquinazolin-3(4H)-yl)-4-chloro-1- methyl-1H-indazol-3-yl)methanesulfonamide (Int 23b, 65 mg, 0.12 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (32 mg, 0.12 mmol), HOAT (7.9 mg, 0.058 mmol) and EDC (24 mg, 0.13 mmol) in DMF (1.0 mL) was added N-methylmorpholine (125 μL, 1.14 mmol). The reaction mixture was stirred at rt for 2 h and purified via preparative HPLC (Column: XBridge C18, 19×200 mm, 5 μm particles; Mobile Phase A: 10 mM ammonium acetate in 5:95 acetonitrile:water; Mobile Phase B: 10 mM ammonium acetate in 95:5 acetonitrile:water; Gradient: 50-90% B over 15 min, then a 5 min hold at 100% B; Flow: 20 mL/min) to afford two fractions, each as a mixture of stereoisomers which was apparent from $^{19}$F NMR analysis. The title compound was the dominant component and eluted second (29.2 mg). LC-MS retention time=1.00 min; m/z=805.2. [M+H]$^+$, (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm). $^1$H NMR (500 MHz, MeOH-d$_4$) δ 8.30 (d, J=7.9 Hz, 1H), 8.02-7.95 (m, 1H), 7.93-7.87 (m, 1H), 7.68 (t, J=7.6 Hz, 1H), 7.37-7.26 (m, 1H), 7.24-7.11 (m, 1H), 6.98-6.65 (m, 1H), 6.66-6.54 (m, 3H), 4.85 (br d, J=5.2 Hz, 2H), 3.60 (s, 3H), 3.47 (dd, J=13.9, 5.0 Hz, 1H), 3.33 (s, 3H), 3.14-2.99 (m, 1H), 2.59-2.30 (m, 2H), 1.52-1.30 (m, 3H), 1.01 (br d, J=3.1 Hz, 1H). $^{19}$F NMR (376 MHz, MeOH-d$_4$) δ −82.2 (d, J=254.6 Hz, 1F), −105.1 (d, J=254.6 Hz, 1F), −111.7 (s, 2F), −113.3 (d, J=311.9 Hz, 1F), −114.5 (d, J=311.9 Hz, 1F).

tert-butyl (S)-(1-(3-(4-chloro-3-(N-(4-methoxybenzyl)methylsulfonamido)-1-methyl-1H-indazol-7-yl)-7-methoxy-4-oxo-3,4-dihydroquinazolin-2-yl)-2-(3,5-difluorophenyl)ethyl)carbamate (Int 24a)

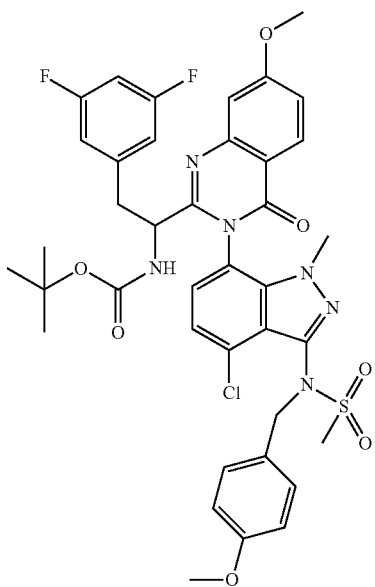

mixture of int 24a and other stereoisomers

In an oven dried pressure vessel, (S)-2-((tert-butoxycarbonyl)amino)-3-(3,5-difluorophenyl)propanoic acid (100 mg, 0.332 mmol) and 2-amino-4-methoxybenzoic acid (57 mg, 0.34 mmol) in pyridine (1.7 mL) were treated with diphenyl phosphite (225 μl, 1.16 mmol). The vessel was flushed with argon, sealed and placed in 70-75° C. sand bath shaker for 2 h. The reaction mixture was cooled to rt, treated with N-(7-amino-4-chloro-1-methyl-1H-indazol-3-yl)-N-(4-methoxybenzyl)methanesulfonamide (Int 17d, 144 mg, 0.363 mmol), resealed and heated at 70-75° C. in a sand bath shaker overnight. The reaction was concentrated and the residue purified using a Biotage Horizon (80 g Teledyne Isco Silica Flash Column, gradient from 100% hexanes to 100% EtOAc over 10 column volumes) to afford title product (140 mg) as a colorless solid and a mixture of stereoisomers. LC-MS retention time=1.74 min; m/z=753.20 [M+H-t-Bu]$^+$, 809.20 [M+H]$^+$, (Column: Acquity UPLC BEH, 2.1×50 mm, 1.7 μm particles; Solvent A=0.05% TFA in 100% Water. Solvent B=0.05% TFA in 100% Acetonitrile. Flow Rate=0.8 mL/min. Start % B=2. Final % B=98. Gradient Time=1.5 min, then a 1.5 min hold at 100% B. Wavelength=220 nm).

(S)—N-(7-(2-(1-amino-2-(3,5-difluorophenyl)ethyl)-7-methoxy-4-oxoquinazolin-3(4H)-yl)-4-chloro-1-methyl-1H-indazol-3-yl)methanesulfonamide (Int 24b)

Intermediate A14BA-243

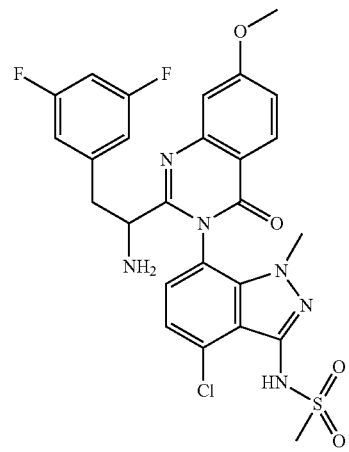

Mixture of Int 24b and other stereoisomers

To a solution of tert-butyl (S)-(1-(3-(4-chloro-3-(N-(4-methoxybenzyl)methylsulfonamido)-1-methyl-1H-indazol-7-yl)-7-methoxy-4-oxo-3,4-dihydroquinazolin-2-yl)-2-(3,5-difluorophenyl)ethyl)carbamate (Int 24a, 138 mg, 0.171 mmol) in anhydrous DCM (3 mL) was added neat TFA (6 mL, 80 mmol). The resulting pale yellow solution was allowed to stand at rt for 4 min and then treated with neat triflic acid (75 μL). The resulting purple solution was allowed to stand at rt for 30 min. The solvent was removed under a gentle stream of nitrogen. The residue was dissolved in EtOAc (80 mL) and the organic layer was extracted with aq saturated NaHCO$_3$ (2×15 mL), brine (1×10 mL), dried over Na$_2$SO$_4$, filtered and evaporated to dryness to afford the title product (white solid, 123 mg) as a mixture of stereoisomers. LC-MS retention time=1.26, 1.32 min; m/z=589.15 [M+H]$^+$ (Column: Acquity UPLC BEH, 2.1×50 mm, 1.7 μm particles; Solvent A=0.05% TFA in 100% Water. Solvent B=0.05% TFA in 100% Acetonitrile. Flow Rate=0.8 mL/min. Start % B=2. Final % B=98. Gradient Time=1.5 min, then a 1.5 min hold at 100% B. Wavelength=220 nm).

N—((S)-1-(3-(4-chloro-1-methyl-3-(methylsulfonamido)-1H-indazol-7-yl)-7-methoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 17)

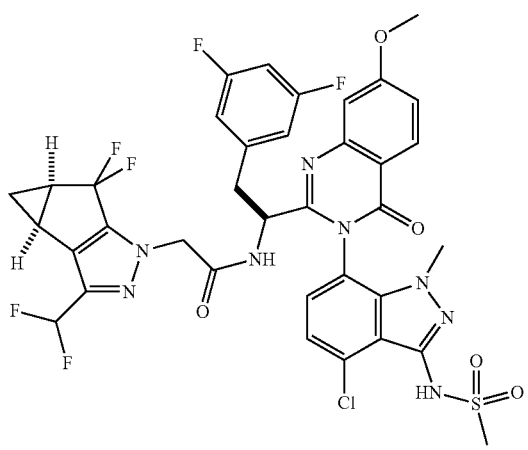 [SMILES: COc1ccc2c(=O)n(-c3ccc(Cl)c4c(NS(C)(=O)=O)nn(C)c34)c([C@H](Cc3cc(F)cc(F)c3)NC(=O)Cn3nc(C(F)F)c4c3C(F)(F)[C@@H]3C[C@H]43)nc2c1]

N-methylmorpholine (125 µL, 1.14 mmol) and EDC (32.0 mg, 0.167 mmol) were added to a solution of (S)—N-(7-(2-(1-amino-2-(3,5-difluorophenyl)ethyl)-7-methoxy-4-oxoquinazolin-3(4H)-yl)-4-chloro-1-methyl-1H-indazol-3-yl)methanesulfonamide (Int 24b, 83 mg, 0.141 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (41.7 mg, 0.158 mmol), and 1-hydroxy-7-azabenzotriazole (9.7 mg, 0.071 mmol) in anhydrous DMF (1.0 mL). The reaction mixture was flushed with N₂, capped and allowed to stand at rt. After 45 min, additional 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (4 mg) and EDC (3 mg) were added to the reaction and let stand at rt for an additional 45 min. The reaction mixture was purified via preparative HPLC (Column: XBridge C18, 19×200 mm, 5 µm particles; Mobile Phase A: 10 mM ammonium acetate in 5:95 acetonitrile:water; Mobile Phase B: 10 mM ammonium acetate in 95:5 acetonitrile:water; Gradient: 50-90% B over 15 min, then a 5 min hold at 100% B; Flow: 20 mL/min) to afford two fractions, each as a mixture of stereoisomers which was apparent from $^{19}$F NMR analysis. The title compound was the dominant component and eluted second (47.4 mg). LC-MS retention time=1.62 min; m/z=835.20 [M+H]⁺ (Column: Acquity UPLC BEH, 2.1×50 mm, 1.7 µm particles; Solvent A=0.05% TFA in 100% Water. Solvent B=0.05% TFA in 100% Acetonitrile. Flow Rate=0.8 mL/min. Start % B=2. Final % B=98. Gradient Time=1.5 min, then a 1.5 min hold at 100% B. Wavelength=220 nm). $^1$H NMR (500 MHz, DMSO-d₆) δ 9.83 (br s, 1H), 9.10 (br d, J=8.2 Hz, 1H), 8.13 (d, J=8.7 Hz, 1H), 7.65 (br d, J=7.2 Hz, 1H), 7.40 (br d, J=4.3 Hz, 1H), 7.25 (d, J=8.7 Hz, 1H), 7.21 (s, 1H), 7.07-7.00 (m, 1H), 6.92 (t, $J_{HF}$=54.3 Hz, 1H), 6.65 (br d, J=6.3 Hz, 2H), 4.67-4.57 (m, 1H), 4.57-4.47 (m, 2H), 3.98 (s, 3H), 3.49 (s, 3H), 3.45-3.34 (m, 1H), 3.17 (s, 3H), 3.00 (br dd, J=14.1, 10.6 Hz, 2H), 2.47-2.40 (m, 2H), 1.39-1.32 (m, 1H), 0.86 (br d, J=3.2 Hz, 1H). $^{19}$F NMR (470 MHz, DMSO-d₆) δ −79.5 (d, J=253.1 Hz, 1F), −102.9 (d, J=254.6 Hz, 1F), −110.1 (s, 2F), −110.9 (d, J=308.1 Hz, 1F), −112.7 (d, J=308.1 Hz, 1F).

tert-Butyl (S)-(1-(3-(4-chloro-3-(N-(4-methoxybenzyl)methylsulfonamido)-1-methyl-1H-indazol-7-yl)-7-fluoro-4-oxo-3,4-dihydroquinazolin-2-yl)-2-(3,5-difluorophenyl)ethyl)carbamate (Int 25a)

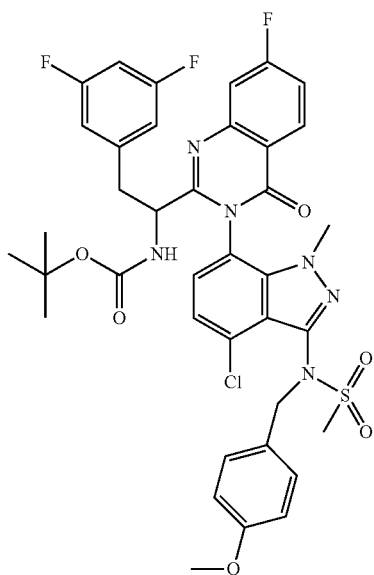

Mixture of int 25a and other stereoisomers

A mixture of (S)-2-((tert-butoxycarbonyl)amino)-3-(3,5-difluorophenyl)propanoic acid (150 mg, 0.498 mmol), 2-amino-4-fluorobenzoic acid (77 mg, 0.50 mmol) and diphenyl phosphite (0.35 mL, 1.6 mmol) in pyridine (2 mL) was sealed in a pressure vessel and heated in an oil bath at 70° C. for 2 h. The reaction was cooled to rt and then N-(7-amino-4-chloro-1-methyl-1H-indazol-3-yl)-N-(4-methoxybenzyl)methanesulfonamide (Int 17d, 216 mg, 0.548 mmol) was added and the reaction was resealed and heated again at 70° C. for an additional 2 h. The volatile component was removed by a steady stream of nitrogen. The residue was partitioned between water (20 mL) and EtOAc (10 mL). The organic component was washed with 5% citric acid, 1.5 M K₃PO₄ and brine, dried over MgSO₄, filtered, evaporated in vacuo. The residue was purified by flash column chromatography (24 g silica gel cartridge, eluted (S)—N-(7-(2-(1-amino-2-(3,5-difluorophenyl)ethyl)-7-fluoro-4-oxoquinazolin-3(4H)-yl)-4-chloro-1-methyl-1H-indazol-3-yl)-N-(4-methoxybenzyl)methanesulfonamide (Int 25b)

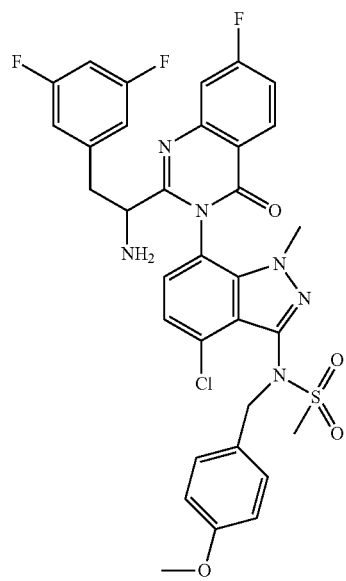

mixture of int 24b and other stereoisomers

To a solution of tert-Butyl (S)-(1-(3-(4-chloro-3-(N-(4-methoxybenzyl)methylsulfonamido)-1-methyl-1H-indazol-7-yl)-7-fluoro-4-oxo-3,4-dihydroquinazolin-2-yl)-2-(3,5-difluorophenyl)ethyl)carbamate (Int 25a, 208 mg, 0.261 mmol) in DCM (1.3 mL) was added 4 M HCl in 1,4-dioxane (1.30 mL, 5.22 mmol). The resulting light yellow solution was stirred at rt overnight and then concentrated in vacuo. The residue was triturated with diethyl ether, filtered, and evaporated in vacuo to afford an HCl salt of title product (white solid, 174 mg) as a mixture of stereoisomers. LC-MS retention time=0.83, 0.85 min; m/z=697.08 [M+H]$^+$ (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

with gradient 0-40% EtOAc-hexanes) to afford title product (210 mg) as a white foam and mixture of stereoisomers. LC-MS retention time=1.15 min; m/z=797.08 [M+H]$^+$ (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

N—((S)-1-(3-(4-chloro-3-(N-(4-methoxybenzyl)methylsulfonamido)-1-methyl-1H-indazol-7-yl)-7-fluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 25c)

To a solution of an HCl salt of (S)—N-(7-(2-(1-amino-2-(3,5-difluorophenyl)ethyl)-7-fluoro-4-oxoquinazolin-3(4H)-yl)-4-chloro-1-methyl-1H-indazol-3-yl)-N-(4-methoxybenzyl)methanesulfonamide (Int 25b, 174 mg, 0.237 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (65.8 mg, 0.249 mmol) and EDC (50.0 mg, 0.26 mmol) in DMF (2 mL) was added 1M HOAT in DMA (119 μL, 0.119 mmol) and N-methylmorpholine (125 μL, 1.14 mmol). The reaction mixture was stirred at rt for 4 h. The reaction mixture was poured into 5% citric acid (20 mL) and extracted with EtOAc (2×10 mL). The organic component was washed with brine, dried over MgSO$_4$, and evaporated in vacuo. The residue was purified by flash column chromatography (24 g silica gel cartridge, eluted with gradient 0-50% EtOAc-Hexanes) to afford title product (204 mg) as a white foam. LC-MS retention time=1.10 min; m/z=943.4 [M+H]$^+$ (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

N—((S)-1-(3-(4-chloro-1-methyl-3-(methylsulfona-mido)-1H-indazol-7-yl)-7-fluoro-4-oxo-3,4-dihydro-quinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 18)

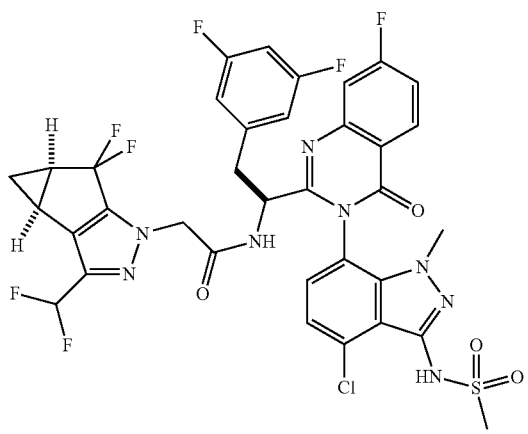 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(F)ccc4c3=O)c21]

To an ice bath cooled solution of N—((S)-1-(3-(4-chloro-3-(N-(4-methoxybenzyl)methylsulfonamido)-1-methyl-1H-indazol-7-yl)-7-fluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int 25c, 204 mg, 0.216 mmol) in DCM (0.8 mL) was added TFA (0.80 mL) and triflic acid (0.10 mL). The resulting orange solution was stirred at rt for 1 h. The solvent was removed with a steady stream of nitrogen. The residue was partitioned between EtOAc (5 mL) and sat. NaHCO$_3$ (10 mL). The organic component was washed with brine, dried over MgSO$_4$, filtered, and evaporated in vacuo. The residue (209 mg) was taken up into DMF (1.5 mL) and purified via preparative HPLC (Column: XBridge C18, 19×200 mm, 5 μm particles; Mobile Phase A: 10 mM ammonium acetate in 5:95 acetonitrile:water; Mobile Phase B: 10 mM ammonium acetate in 95:5 acetonitrile:water; Gradient: 50-90% B over 15 min, then a 5 min hold at 100% B; Flow: 20 mL/min) to afford two fractions, each as a mixture of stereoisomers which was apparent from $^{19}$F NMR analysis. The second elute (50 mg), which was the dominant component, was further purified by chiral preparative HPLC (Column: Chiralpak IC preparative, 30×250 mm, 5 μm particles; Mobile Phase: 20% IPA in CO$_2$, 150 bar; Flow rate: 70.0 mL/min. for 17 min; Temp: 35° C.; Wavelength=308 nm; Injection: 0.25 mL of ~25 mg/mL solution in 1:1 EtOH:CHCl$_3$ by stacked injection) to afford the title compound, which is the dominant stereoisomer and eluted first (24 mg). LC-MS retention time=1.01 min; m/z=823.08 [M+H], (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm). $^{19}$F NMR (471 MHz, DMSO-d$_6$) δ −79.5 (br d, J=253.2 Hz, 1F), −102.2 (s, 1F), −103.0 (br d, J=253.2 Hz, 1F), −110.1 (s, 2F), −110.8 (d, J=307.6 Hz, 1F), −112.8 (d, J=307.6 Hz, 1F).

tert-butyl (S)-(1-(3-(4-chloro-3-(N-(4-methoxybenzyl)methylsulfonamido)-1-methyl-1H-indazol-7-yl)-5-fluoro-4-oxo-3,4-dihydroquinazolin-2-yl)-2-(3,5-difluorophenyl)ethyl)carbamate (Int 26a)

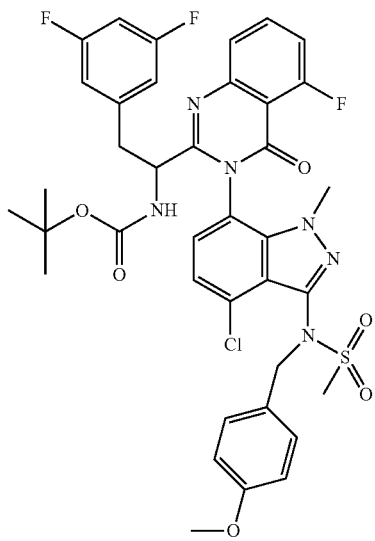

mixture of Int 26a and stereoisomers

A mixture of (S)-2-((tert-butoxycarbonyl)amino)-3-(3,5-difluorophenyl)propanoic acid (150 mg, 0.498 mmol), 2-amino-6-fluorobenzoic acid (77 mg, 0.50 mmol) and diphenyl phosphite (0.35 mL, 1.6 mmol) in pyridine (3 mL) was sealed in a pressure vessel and heated in an oil bath at 70° C. for 2 h. N-(7-amino-4-chloro-1-methyl-1H-indazol-3-yl)-N-(4-methoxybenzyl)methanesulfonamide (Int 17d, 216 mg, 0.548 mmol) was added to the reaction mixture and it was again heated in the bath at 70° C. for an additional 2 h. The solvent was removed by a steady stream of nitrogen. The residue was partitioned between water (20 mL) and EtOAc (10 mL). The organic component was washed with 5% citric acid, 1.5 M K$_3$PO$_4$ and brine, dried over MgSO$_4$, filtered, and evaporated in vacuo. The residue was purified by flash column chromatography (24 g silica gel cartridge, eluted with gradient 0-40% EtOAc-hexanes) to afford title product (242 mg) as a white foam which was a mixture of stereoisomers. LC-MS retention time=1.12 min; m/z=797.08 [M+H]$^+$, (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

(S)—N-(7-(2-(1-amino-2-(3,5-difluorophenyl)ethyl)-5-fluoro-4-oxoquinazolin-3(4H)-yl)-4-chloro-1-methyl-1H-indazol-3-yl)methanesulfonamide (Int 26b)

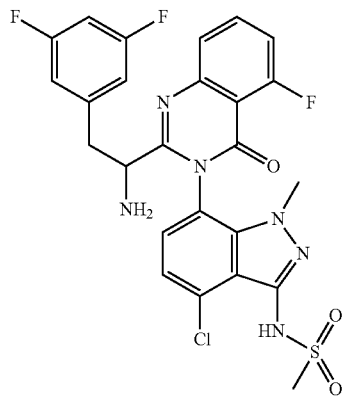

mixture of Int 26b and other stereoisomers

To an ice bath cooled solution of tert-butyl (S)-(1-(3-(4-chloro-3-(N-(4-methoxybenzyl)methylsulfonamido)-1-methyl-1H-indazol-7-yl)-5-fluoro-4-oxo-3,4-dihydroquinazolin-2-yl)-2-(3,5-difluorophenyl)ethyl)carbamate (Int 26a, 242 mg, 0.304 mmol) in DCM (0.8 mL) was added TFA (0.80 mL) and triflic acid (0.14 mL). The resulted orange solution was stirred at rt for 1 h. The solvent was removed by a steady stream of $N_2$. The residue was partitioned between EtOAc (5 mL) and sat. $NaHCO_3$ (10 mL). The organic component was washed with brine, dried over $MgSO_4$, filtered, and evaporated in vacuo to afford title product (white foam, 214 mg) as a mixture of stereoisomers. LC-MS retention time=0.65. 0.67 min; m/z=577.08 [M+H]$^+$, (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

N—((S)-1-(3-(4-chloro-1-methyl-3-(methylsulfonamido)-1H-indazol-7-yl)-5-fluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 19)

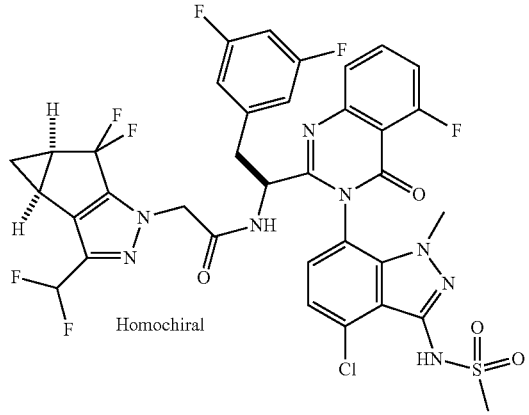 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cccc(F)c4c3=O)c21]

To a solution of (S)—N-(7-(2-(1-amino-2-(3,5-difluorophenyl)ethyl)-5-fluoro-4-oxoquinazolin-3(4H)-yl)-4-chloro-1-methyl-1H-indazol-3-yl)methanesulfonamide (Int 26b, 175 mg, 0.303 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (72.1 mg, 0.273 mmol) and HOAT (1 M in DMA, 0.15 mL, 0.15 mmol) in DMF (3 mL) was added EDC (64.0 mg, 0.33 mmol) and N-methylmorpholine (0.105 mL, 0.952 mmol). The reaction mixture was stirred at rt for 4 h. The reaction mixture was poured into 5% citric acid (20 mL), extracted with EtOAc (2×10 mL). The combined organic components were washed with brine, dried over $MgSO_4$, and evaporated in vacuo. The residue (220 mg) was taken up into DMF (1.5 mL) and purified via preparative HPLC (Column: XBridge C18, 19×200 mm, 5 μm particles; Mobile Phase A: 10 mM ammonium acetate in 5:95 acetonitrile:water ; Mobile Phase B: 10 mM ammonium acetate in 95:5 acetonitrile:water; Gradient: 50-90% B over 15 min, then a 5 min hold at 100% B; Flow: 20 mL/min) to afford two fractions, each as a mixture of stereoisomers exhibiting targeted molecular weight. The second elute (80 mg), which was also the dominant component, was further purified by chiral preparative HPLC (Column: Chiralpak IC preparative, 30×250 mm, 5 μm particles; Mobile Phase: 20% IPA in $CO_2$, 140 bar; Flow rate: 70.0 mL/min. for 17 min; Temp: 35° C.; Wavelength=308 nm; Injection: 0.25 mL of ~25 mg/mL solution in 1:1 EtOH:$CHCl_3$ by stacked injection) to afford the title compound as the first eluting stereoisomer which was also the dominant component (65.8 mg). LC-MS retention time=1.01 min; m/z=823.08 [M+H]$^+$, (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm). $^1$H NMR (400 MHz, MeOH-$d_4$) δ 7.94 (td, J=8.3, 5.5 Hz, 1H), 7.71 (d, J=8.3 Hz, 1H), 7.38-7.32 (m, 1H), 7.31 (d, J=7.8 Hz, 1H), 7.22 (d, J=7.8 Hz, 1H), 6.78 (tt, J=9.3, 2.4 Hz, 1H), 6.68 (t, $J_{HF}$=54.7 Hz, 1H), 6.63-6.57 (m, 2H), 4.51 (s, 2H), 3.65 (s, 3H), 3.57 (dd, J=5.4, 4.1 Hz, 2H), 3.24 (s, 3H), 3.07 (dd, J=14.1, 9.5 Hz, 1H), 2.48-2.38 (m, 2H), 1.36 (br d, J=7.8 Hz, 1H), 1.02-0.96 (m, 1H). $^{19}$F NMR (376 MHz, $CD_3OD$) δ -82.2 (d, J=254.9 Hz, 1F), -105.1 (d, J=254.9 Hz, 1F), -111.3 (s, 1F), -111.7 (s, 2F), -113.3 (d, J=312.1 Hz, 1F), -114.6 (d, J=312.1 Hz, 1F).

tert-Butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int 27a)

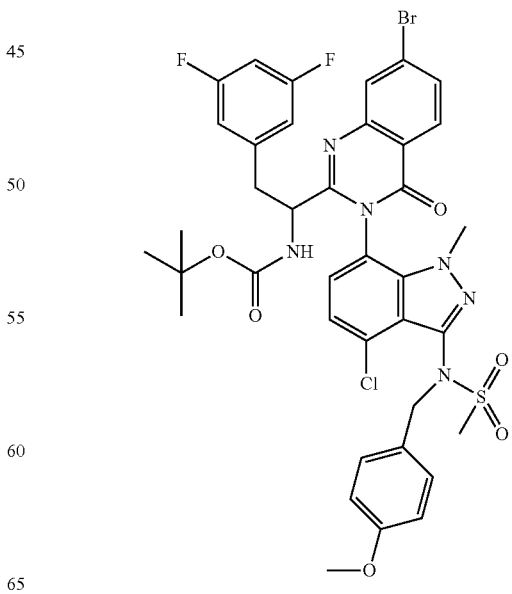

mixture of Int 27a and stereoisomers

A mixture of (S)-2-((tert-butoxycarbonyl)amino)-3-(3,5-difluorophenyl)propanoic acid (420 mg, 1.39 mmol), 2-amino-4-bromobenzoic acid (301 mg, 1.39 mmol) and diphenyl phosphite (0.99 mL, 4.6 mmol) in pyridine (5 mL) was sealed and heated in an oil bath at 70° C. for 2 h. N-(7-amino-4-chloro-1-methyl-1H-indazol-3-yl)-N-(4-methoxybenzyl)methanesulfonamide (Int 17d, 606 mg, 1.53 mmol) was added, and the reaction mixture was heated again in the oil bath at 80° C. for another 2 h. The solvent was removed with a steady stream of $N_2$. The residue was partitioned between water (20 mL) and EtOAc (20 mL). The organic component was washed with 5% citric acid, 1.5 M $K_3PO_4$, and brine, dried over $MgSO_4$, filtered, and evaporated in vacuo. The residue was purified by flash column chromatography (80 g silica gel cartridge, eluted with gradient 0-40% EtOAc-hexanes) to afford title product (608 mg) as a white foam which was a mixture of stereoisomers. LC-MS retention time=1.20 min; m/z=857.08 [M+H]+(Column: Acquity UPLC BEH, 2.1×50 mm, 1.7 µm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

tert-butyl (S)-(1-(3-(4-chloro-3-(N-(4-methoxybenzyl)methylsulfonamido)-1-methyl-1H-indazol-7-yl)-7-cyano-4-oxo-3,4-dihydroquinazolin-2-yl)-2-(3,5-difluorophenyl)ethyl)carbamate (Int 27b)

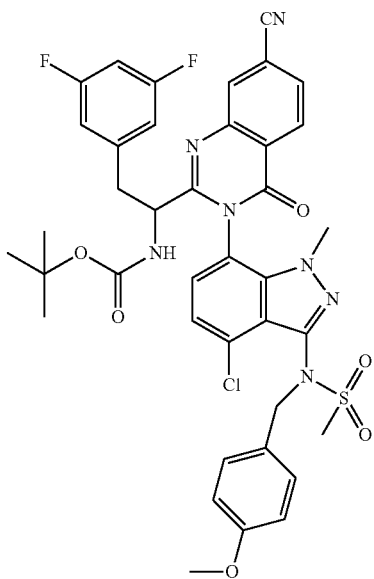

Int 27b and mixture of stereoisomers

A vial was charged with tert-Butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int 27a, 374 mg, 0.436 mmol), zinc cyanide (35.8 mg, 0.305 mmol), t-BuXPhos Pd G3 (34.6 mg, 0.044 mmol), THF (4 mL) and water (16 mL). The vial was sealed, evacuated under vacuum and back-filled with $N_2$ three times. The vial was heated in a microwave system at 60° C. for 2 h. The reaction mixture was poured into water (20 mL) and extracted with EtOAc (10 mL). The organic component was washed with brine, dried over $MgSO_4$, filtered, concentrated in vacuo. The residue was purified by flash column chromatography (24 g silica gel cartridge, eluted with gradient 0-40% EtOAc-hexanes) to afford title product (192 mg) as an off-white foam which was a mixture of stereoisomers. LC-MS retention time=1.12 min; m/z=748.2 [M+H-t-Bu]+. Column: Acquity UPLC BEH, 2.1×50 mm, 1.7 µm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm.

(S)—N-(7-(2-(1-amino-2-(3,5-difluorophenyl)ethyl)-7-cyano-4-oxoquinazolin-3(4H)-yl)-4-chloro-1-methyl-1H-indazol-3-yl)methanesulfonamide (Int 27c)

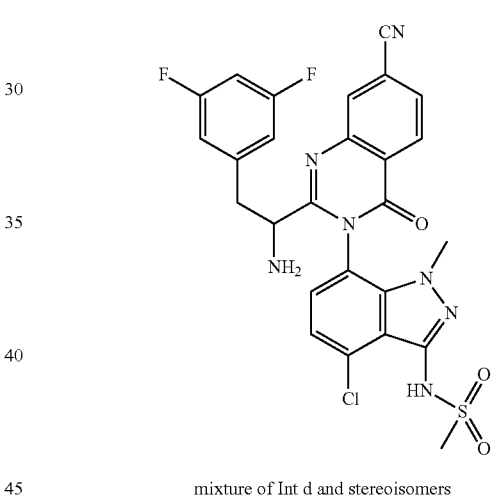

mixture of Int d and stereoisomers

To an ice bath cooled solution of tert-butyl (S)-(1-(3-(4-chloro-3-(N-(4-methoxybenzyl)methylsulfonamido)-1-methyl-1H-indazol-7-yl)-7-cyano-4-oxo-3,4-dihydroquinazolin-2-yl)-2-(3,5-difluorophenyl)ethyl)carbamate (Int 27b, 192 mg, 0.239 mmol) in DCM (0.8 mL) was added TFA (0.800 mL) and triflic acid (0.11 mL). The reaction mixture was stirred at rt for 1 h. The volatiles were removed with a steady stream of $N_2$. The residue was partitioned between EtOAc (15 mL) and sat. $NaHCO_3$ (20 mL). The organic component was washed with brine, dried over $MgSO_4$, filtered, evaporated in vacuo to afford title product (white foam, 139 mg) as a mixture of stereoisomers. LC-MS retention time=0.66, 0.72 min; m/z=584.08 [M+H]+ (Column: Acquity UPLC BEH, 2.1×50 mm, 1.7 µm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

131

N—((S)-1-(3-(4-chloro-1-methyl-3-(methylsulfonamido)-1H-indazol-7-yl)-7-cyano-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Example 20

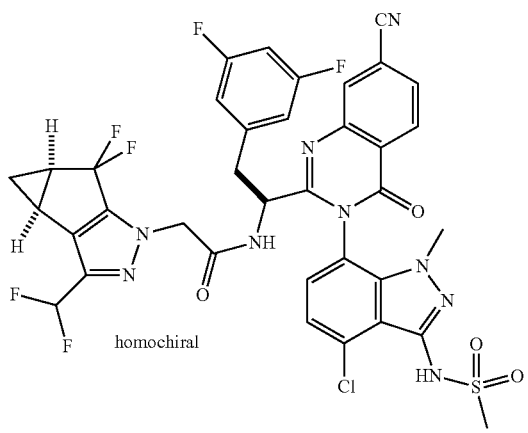 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(C#N)ccc4c3=O)c21]

homochiral

To an ice bath cooled solution of (S)—N-(7-(2-(1-amino-2-(3,5-difluorophenyl)ethyl)-7-cyano-4-oxoquinazolin-3(4H)-yl)-4-chloro-1-methyl-1H-indazol-3-yl)methanesulfonamide (Int 27c, 139 mg, 0.238 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (62.9 mg, 0.238 mmol) and HOAT (1 M in DMA, 0.12 mL, 0.12 mmol) in DMF (4 mL) were added EDC (50.2 mg, 0.262 mmol) and N-methylmorpholine (0.105 mL, 0.952 mmol). The reaction mixture was stirred at rt overnight, poured into 5% citric acid (20 mL) and extracted with EtOAc (2×10 mL). The combined organic component was washed with brine, dried it over MgSO$_4$, and evaporated in vacuo. The residue (220 mg) was taken up into DMF (2 mL) and purified via preparative HPLC (Column: XBridge C18, 19×200 mm, 5 μm particles; Mobile Phase A: 10 mM ammonium acetate in 5:95 acetonitrile:water; Mobile Phase B: 10 mM ammonium acetate in 95:5 acetonitrile:water; Gradient: 50-90% B over 15 min, then a 5 min hold at 100% B; Flow: 20 mL/min) to afford two fractions, each as a mixture of stereoisomers which was apparent from $^{19}$F NMR analysis. The second eluting fraction (30 mg), which was also the dominant one was further purified by chiral preparative HPLC (Column: Chiralpak IC preparative, 30×250 mm, 5 μm particles; Mobile Phase: 20% IPA in CO$_2$, 140 bar; Flow rate: 70.0 mL/min. for 17 min; Temp: 35° C.; Wavelength=308 nm; Injection: 0.25 ml of ~25 mg/mL solution in 1:1 EtOH:CHCl$_3$ by stacked injection) to afford the title compound as the first eluting stereoisomer (13 mg), which was also relatively dominant. LC-MS retention time=0.99 min; m/z=830.08 [M+H]$^+$ (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm). $^1$H NMR (400 MHz, MeOH-d$_4$) δ 8.42 (d, J=8.3 Hz, 1H), 8.26 (d, J=0.8 Hz, 1H), 7.92 (dd, J=8.2, 1.4 Hz, 1H), 7.31 (d, J=8.0 Hz, 1H), 7.26 (d, J=8.0 Hz, 1H), 6.81-6.75 (m, 1H), 6.68 (t, J$_{HF}$=54.7 Hz, 1H), 6.64-6.58 (m, 2H), 4.51 (d, J=2.5 Hz, 2H), 3.60 (s, 3H), 3.24 (s, 3H), 3.46 (br dd, J=14.1, 4.8 Hz, 2H), 3.09 (dd, J=14.3, 9.5 Hz, 1H), 2.43 (ddd, J=1.4, 7.7, 4.0 Hz, 2H), 1.36 (q, J=6.6 Hz, 1H), 1.02-0.95 (m, 1H). $^{19}$F NMR (376 MHz, MeOH-d$_4$) δ −82.2 (d, J=254.9 Hz, 1F), −105.0 (d, J=254.9 Hz, 1F), −111.7 (s, 2F), −113.2 (d, J=312.1 Hz, 1F), −114.6 (d, J=312.1 Hz, 1F).

tert-butyl (S)-(1-(3-(4-chloro-3-(N-(4-methoxybenzyl)methylsulfonamido)-1-methyl-1H-indazol-7-yl)-6-fluoro-4-oxo-3,4-dihydroquinazolin-2-yl)-2-(3,5-difluorophenyl)ethyl)carbamate (Int 28a)

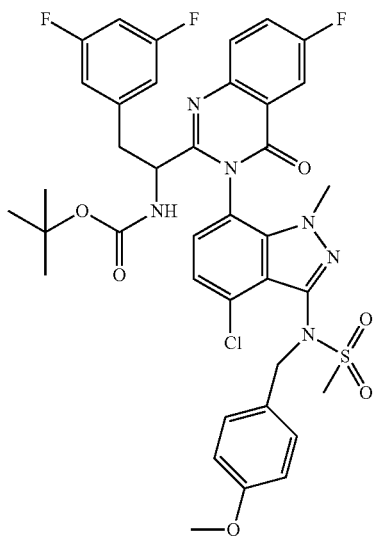

mixture of Int 28a and stereoisomers

A mixture of (S)-2-((tert-butoxycarbonyl)amino)-3-(3,5-difluorophenyl)propanoic acid (140 mg, 0.465 mmol), 2-amino-5-fluorobenzoic acid (72.1 mg, 0.465 mmol) and diphenyl phosphite (0.33 mL, 1.5 mmol) in pyridine (3 mL) was sealed into a pressure vessel and heated in an oil bath at 70° C. for 2 h. After cooling to rt, N-(7-amino-4-chloro-1-methyl-1H-indazol-3-yl)-N-(4-methoxybenzyl)methanesulfonamide (Int 17d, 202 mg, 0.511 mmol) was added and the reaction mixture was sealed and heated again in an oil bath at 70° C. for another 2 h. The solvent was removed by a steady stream of nitrogen. The residue was partitioned between water (20 mL) and EtOAc (10 mL). The organic component was washed with 5% citric acid, 1.5 M K$_3$PO$_4$ and brine, dried over MgSO$_4$, filtered, and evaporated in vacuo. The residue was purified by flash column chromatography (24 g silica gel cartridge, eluted with gradient 0~40% EtOAc-hexanes) to afford title product (187 mg) as a white foam which was a mix of stereoisomers. LC-MS retention time=1.14 min; m/z=797.08 [M+H]$^+$, 741.20 [M+H-t-Bu]$^+$, (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

133

(S)—N-(7-(2-(1-amino-2-(3,5-difluorophenyl)ethyl)-6-fluoro-4-oxoquinazolin-3(4H)-yl)-4-chloro-1-methyl-1H-indazol-3-yl)methanesulfonamide (Int 28b)

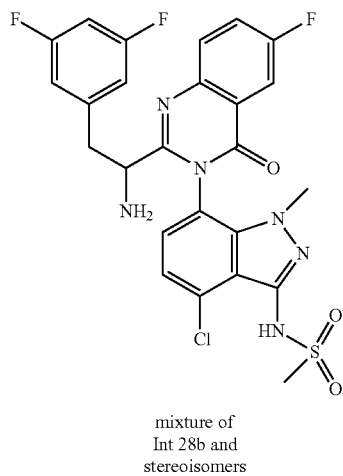 [SMILES: Cn1nc(NS(C)(=O)=O)c2c(Cl)ccc(-n3c(C(N)Cc4cc(F)cc(F)c4)nc4ccc(F)cc4c3=O)c21]

mixture of
Int 28b and
stereoisomers

To an ice bath cooled solution of tert-butyl (S)-(1-(3-(4-chloro-3-(N-(4-methoxybenzyl)methylsulfonamido)-1-methyl-1H-indazol-7-yl)-6-fluoro-4-oxo-3,4-dihydroquinazolin-2-yl)-2-(3,5-difluorophenyl)ethyl)carbamate (Int 28a, 187 mg, 0.235 mmol) in DCM (0.8 mL) was added TFA (0.8 mL) and triflic acid (0.10 mL). The reaction mixture was stirred at rt for 1 h. The volatiles were removed by a steady stream of nitrogen. The residue was partitioned between EtOAc (15 mL) and sat. NaHCO₃ (20 mL). The organic component was washed with brine, dried over MgSO₄, filtered, and evaporated in vacuo to afford title product (white foam, 176 mg) as a mixture of stereoisomers. LC-MS retention time=0.68, 0.73 min; m/z=577.08 [M+H]⁺ (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

N—((S)-1-(3-(4-chloro-1-methyl-3-(methylsulfonamido)-1H-indazol-7-yl)-6-fluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 21)

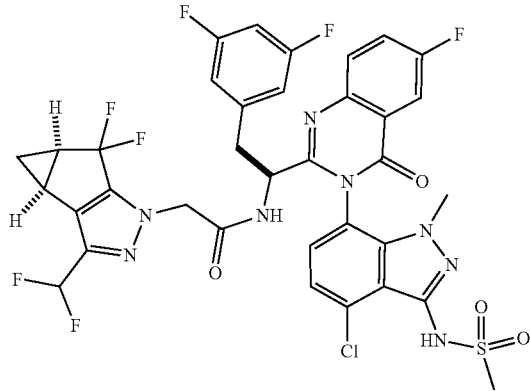 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4ccc(F)cc4c3=O)c21]

134

To a solution of (S)—N-(7-(2-(1-amino-2-(3,5-difluorophenyl)ethyl)-6-fluoro-4-oxoquinazolin-3(4H)-yl)-4-chloro-1-methyl-1H-indazol-3-yl)methanesulfonamide (Int 28b, 176 mg, 0.235 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (62.1 mg, 0.235 mmol) and HOAT (1 M in DMA, 0.12 mL, 0.12 mmol) in DMF (3 mL) was added EDC (49.5 mg, 0.258 mmol) and N-methylmorpholine (0.10 mL, 0.94 mmol). The reaction mixture was stirred at rt overnight, poured into 5% citric acid (20 mL) and extracted with EtOAc (2×10 mL). The combined organic components were washed with brine, dried over MgSO₄, and evaporated in vacuo. The residue (200 mg) was taken up into DMF (2 mL) and purified via preparative HPLC (Column: XBridge C18, 19×200 mm, 5 μm particles; Mobile Phase A: 10 mM ammonium acetate in 5:95 acetonitrile:water; Mobile Phase B: 10 mM ammonium acetate in 95:5 acetonitrile:water; Gradient: 50-90% B over 15 min, then a 5 min hold at 100% B; Flow: 20 mL/min) to afford the title compound (70 mg) as the second eluting peak, which was also relatively dominant. LC-MS retention time=0.99 min; m/z=823.08 [M+H]⁺ (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm). ¹H NMR (400 MHz, MeOH-d₄) δ 8.01-7.90 (m, 2H), 7.76 (td, J=8.5, 3.0 Hz, 1H), 7.30 (d, J=8.0 Hz, 1H), 7.20 (d, J=7.8 Hz, 1H), 6.81-6.74 (m, 1H), 6.68 (t, $J_{HF}$=54.7 Hz, 1H), 6.65-6.57 (m, 2H), 4.50 (s, 2H), 3.59 (s, 3H), 3.45 (br dd, J=14.2, 5.1 Hz, 2H), 3.24 (s, 3H), 3.08 (dd, J=14.1, 9.3 Hz, 1H), 2.42 (ddd, J=11.5, 7.6, 4.0 Hz, 2H), 1.36 (br d, J=7.5 Hz, 1H), 0.99 (br dd, J=5.5, 2.3 Hz, 1H). ¹⁹F NMR (376 MHz, CD₃OD) δ −82.2 (d, J=254.9 Hz, 1F), −105.1 (d, J=254.9 Hz, 1F), −111.7 (s, 2F), −113.2 (s, 1F), −113.3 (d, J=312.1 Hz, 1F), −114.6 (d, J=312.1 Hz, 1F).

tert-butyl (S)-(1-(5-choro-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int 29a)

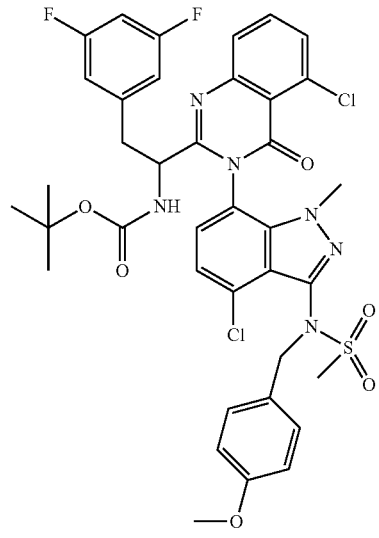

mixture of Int 29a
and stereoisomers

A mixture of (S)-2-((tert-butoxycarbonyl)amino)-3-(3,5-difluorophenyl)propanoic acid (100 mg, 0.332 mmol), 2-amino-6-chlorobenzoic acid (56.9 mg, 0.332 mmol) and diphenyl phosphite (0.24 mL, 1.1 mmol) in pyridine (3 mL) was sealed in a pressure vessel and heated in an oil bath at 70° C. for 2 h. The reaction mixture was allowed to cool to rt, then N-(7-amino-4-chloro-1-methyl-1H-indazol-3-yl)-N-(4-methoxybenzyl)methane sulfonamide (Int 17d, 144 mg, 0.365 mmol) was added and the pressure vessel was heated again in the oil bath at 70° C. for another 2 h. The solvent was removed with a steady stream of $N_2$. The residue was partitioned between water (20 mL) and EtOAc (20 mL). The organic component was washed with 5% citric acid, 1.5 M $K_3PO_4$, and brine, dried over $MgSO_4$, filtered, and evaporated in vacuo. The residue was purified by flash column chromatography (80 g silica gel cartridge, eluted with gradient 0-50% EtOAc-hexanes) to afford title product (181 mg) as a white foam which was a mixture of stereoisomers. LC-MS retention time=1.15 min; m/z=813.08 [M+H]$^+$ (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

(S)—N-(7-(2-(1-amino-2-(3,5-difluorophenyl)ethyl)-5-chloro-4-oxoquinazolin-3(4H)-yl)-4-chloro-1-methyl-1H-indazol-3-yl)methanesulfonamide (Int 29b)

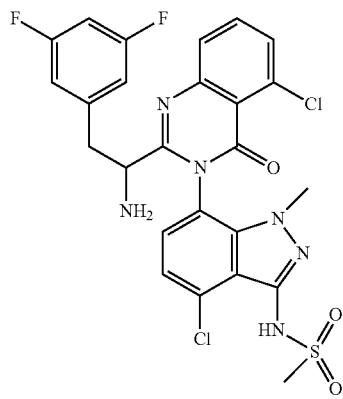

mixture of Int 29b and stereoisomers

To an ice bath cooled solution of tert-butyl (S)-(1-(5-chloro-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int 29a, 181 mg, 0.222 mmol) in DCM (0.8 mL) was added TFA (0.80 mL) and triflic acid (0.10 mL). The reaction mixture was stirred at rt for 1 h. The volatile component was removed with a steady stream of $N_2$. The residue was partitioned between EtOAc (15 mL) and sat. $NaHCO_3$ (10 mL). The organic component was washed with brine, dried over $MgSO_4$, filtered, and evaporated in vacuo to afford the title product (144 mg) as a mixture of stereoisomers. LC-MS retention time=0.69, 0.75 min; m/z=593.08 [M+H]$^+$ (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

N—((S)-1-(5-chloro-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 22.1 and 22.2)

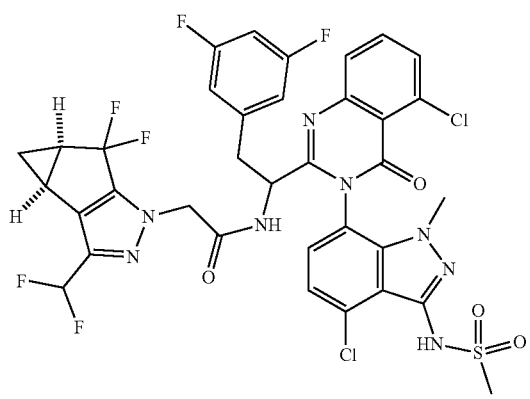

Example 22.1

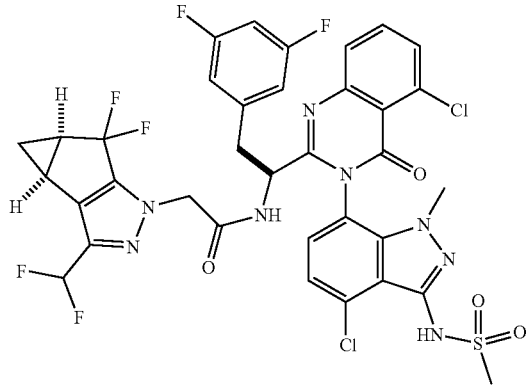

Example 22.2
homochiral

To a solution of (S)—N-(7-(2-(1-amino-2-(3,5-difluorophenyl)ethyl)-5-chloro-4-oxoquinazolin-3(4H)-yl)-4-chloro-1-methyl-1H-indazol-3-yl)methanesulfonamide (Int 29b, 160 mg, 0.23 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (61 mg, 0.23 mmol) and HOAt (1 M in DMA, 0.12 mL, 0.12 mmol) in DMF (2.5 mL) was added EDC (48 mg, 0.25 mmol) and N-methylmorpholine (0.10 mL, 0.92 mmol). The reaction mixture was stirred at rt ON, poured into 5% citric acid (20 mL), and extracted with EtOAc (2×10 mL). The combined organic component was washed with brine, dried over $MgSO_4$, and evaporated in vacuo. The residue was taken up in DMF (2 mL) and purified via preparative HPLC (Column: XBridge C18, 19×200 mm, 5 μm particles; Mobile Phase A: 10 mM ammonium acetate in 5:95 acetonitrile:water; Mobile Phase B: 10 mM ammonium acetate in 95:5 acetonitrile:water; Gradient: 50-90% B over 15 min, then a 5 min hold at 100% B; Flow: 20 mL/min) to afford two fractions, each as a mixture of stereoisomers which was apparent from $^{19}$F NMR analysis.

First Eluting Fraction.

The second eluting fraction (82.6 mg), which was also the dominant one was further purified by chiral preparative HPLC (Column: Chiralpak IC preparative, 30×250 mm, 5 μm particles; Mobile Phase: 30% IPA in $CO_2$, 150 bar; Flow rate: 70.0 mL/min. for 12 min; Temp: 35° C.; Wavelength=318 nm; Injection: 0.5 mL of 20 mg/mL solution in 1:1 IPA:MeOH; by stacked injection) to retrieve the first eluting stereoisomer, which was also relatively dominant. By $^1$H NMR this material was shown to contain an impurity and was thus repurified via preparative HPLC (Column: XBridge C18, 19×200 mm, 5 μm particles; Mobile Phase A: 10 mM ammonium acetate in 5:95 acetonitrile:water; Mobile Phase B: 10 mM ammonium acetate in 95:5 acetonitrile:water; Gradient: 37-77% B over 22 min, then a 5 min hold at 100% B; Flow: 20 mL/min) to afford Example 22.2 (49.6 mg). LC-MS retention time=2.16 min; m/z=839.00 [M+H]$^+$ (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm)). $^1$H NMR (400 MHz, $CD_3OD$) δ 7.89-7.79 (m, 2H), 7.66 (dd, J=7.3, 1.8 Hz, 1H), 7.31 (d, J=7.9 Hz, 1H), 7.22 (d, J=7.9 Hz, 1H), 6.81-6.74 (m, 1H), 6.68 (t, $J_{HF}$=54.7 Hz, 1H), 6.61 (dd, J=8.3, 2.3 Hz, 2H), 4.80 (dd, J=9.3, 4.8 Hz, 1H), 4.50 (s, 2H), 3.65 (s, 3H), 3.45 (br dd, J=14.1, 5.0 Hz, 1H), 3.24 (s, 3H), 3.08 (dd, J=14.1, 9.3 Hz, 1H), 2.42 (ddd, J=11.8, 7.8, 4.0 Hz, 2H), 1.40-1.31 (m, 1H), 0.99 (dt, J=3.6, 1.9 Hz, 1H). $^{19}$F NMR (471 MHz, $CD_3OD$) δ −82.2 (br d, J=254.9 Hz, 1F), −105.1 (br d, J=254.9 Hz, 1F), −111.7 (s, 2F), −113.3 (d, J=312.1 Hz, 1F), −114.6 (d, J=312.1 Hz, 1F).

Tert-butyl (S)-(1-(6-(3-cyanophenyl)-1-((2-(trimethylsilyl)ethoxy)methyl)-1H-pyrazolo[4,3-b]pyridin-5-yl)-2-(3,5-difluorophenyl)ethyl)carbamate (Int CI1a)

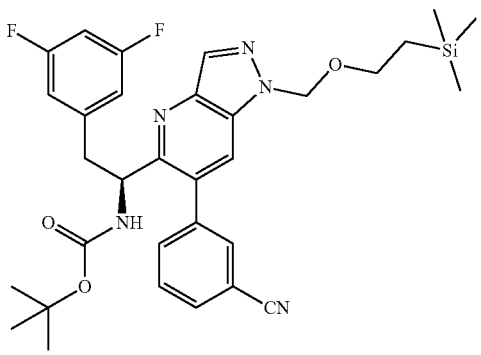 [SMILES: CC(C)(C)OC(=O)N[C@@H](Cc1cc(F)cc(F)c1)c1nc2cnn(COCC[Si](C)(C)C)c2cc1-c1cccc(C#N)c1]

A mixture of tert-butyl (S)-(1-(6-bromo-1-((2-(trimethylsilyl)ethoxy)methyl)-1H-pyrazolo[4,3-b]pyridin-5-yl)-2-(3,5-difluorophenyl)ethyl)carbamate (Int 4JE2, 0.15 g, 0.257 mmol), (3-cyanophenyl)boronic acid (0.057 g, 0.386 mmol), Pd(Ph$_3$P)$_4$ (0.018 g, 0.015 mmol) and K$_2$CO$_3$ (0.11 g, 0.77 mmol) in DMF (2 mL) was degassed for 5 min and heated at 100° C. for 2 h and cooled to rt. The reaction mixture was purified on silica gel (40 g Isco column) using 0-30% ethyl acetate in hexanes. The desired fractions were concentrated to afford title product as a pale yellow foamy solid (0.14 g). $^1$H NMR (500 MHz, CDCl$_3$) δ 8.39-8.28 (m, 1H), 7.78-7.52 (m, 3H), 7.51-7.38 (m, 1H), 7.26-7.16 (m, 1H), 6.68-6.58 (m, 1H), 6.17 (br d, J=6.1 Hz, 2H), 5.88-5.70 (m, 3H), 5.25-5.13 (m, 1H), 3.59 (t, J=8.2 Hz, 2H), 3.09-2.96 (m, 2H), 1.49-1.33 (m, 9H), 0.98-0.81 (m, 2H), −0.03-0.10 (m, 9H). LC/MS: m/z=606.2 [M+H]$^+$.

(S)-3-(5-(1-amino-2-(3,5-difluorophenyl)ethyl)-1-((2-(trimethylsilyl)ethoxy)methyl)-1H-pyrazolo[4,3-b]pyridin-6-yl)benzonitrile hydrochloride (Int CI1b)

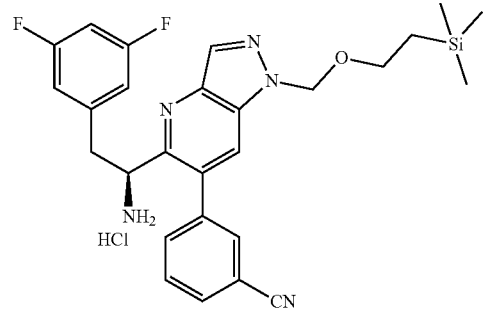 [SMILES: C[Si](C)(C)CCOCn1ncc2nc([C@@H](N)Cc3cc(F)cc(F)c3)c(-c3cccc(C#N)c3)cc21 ; Cl]

HCl (0.57 mL, 2.28 mmol) was added to a solution of tert-butyl (S)-(1-(6-(3-cyanophenyl)-1-((2-(trimethylsilyl)ethoxy)methyl)-1H-pyrazolo[4,3-b]pyridin-5-yl)-2-(3,5-difluorophenyl)ethyl)carbamate (Int CI1a, 0.138 g, 0.228 mmol) in DCM (2 mL) and the mixture was stirred at rt for 2 h and concentrated to give a pale yellow solid (used as is).

N—((S)-1-(6-(3-cyanophenyl)-1-((2-(trimethylsilyl)ethoxy)methyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI1c)

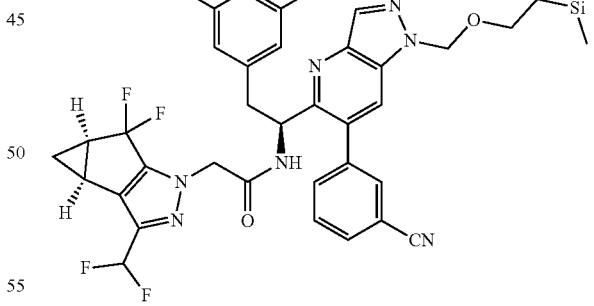

To a stirred solution of (S)-3-(5-(1-amino-2-(3,5-difluorophenyl)ethyl)-1-((2-(trimethylsilyl)ethoxy)methyl)-1H-pyrazolo[4,3-b]pyridin-6-yl)benzonitrile hydrochloride (Int CI1b, 0.05 g, 0.092 mmol) in DMF (1 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.024 g, 0.092 mmol), HATU (0.037 g, 0.097 mmol) and DIPEA (0.03 mL, 0.184 mmol). The reaction mixture was stirred at rt for 2 h. The reaction mixture was purified on silica gel (24 g Isco column) using 0-30% ethyl acetate in hexanes. The desired fractions were concentrated to give a yellow viscous oil (0.04 g). LC/MS: m/z=752.1 [M+H]+.

N—((S)-1-(6-(3-cyanophenyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 10.2)

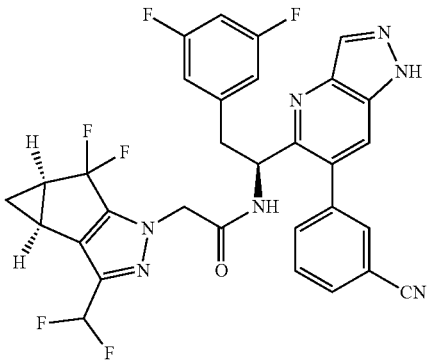 [SMILES: N#Cc1cccc(-c2cc3[nH]ncc3nc2[C@H](Cc2cc(F)cc(F)c2)NC(=O)Cn2nc(C(F)F)c3c2C(F)(F)[C@@H]2C[C@H]32)c1]

TFA (0.155 mL, 2.007 mmol) was added to a solution of N—((S)-1-(6-(3-cyanophenyl)-1-((2-(trimethylsilyl)ethoxy)methyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI1b, 0.039 g, 0.052 mmol) in DCM (1 mL) and the mixture was stirred at rt for 2.25 h and concentrated. The residue was taken up in DCM (1 mL) and ethylene diamine (0.2 mL, 3.2 mmol) was added and the mixture was stirred at rt for 1 h and concentrated. The residue was dissolved in methanol and filtered.
Preparative LC/MS Method A The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 32-72% B over 20 minutes, then a 6-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 622.08; Retention Time: 1.94 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 622.1; Retention Time: 1.93 min. $^1$H NMR (500 MHz, MeOH-d$_4$) δ 8.36-8.29 (m, 1H), 7.79-7.73 (m, 2H), 7.59 (t, J=7.7 Hz, 1H), 7.49 (br d, J=7.0 Hz, 1H), 7.37-7.32 (m, 1H), 6.83-6.57 (m, 2H), 6.28 (br d, J=6.2 Hz, 2H), 5.41 (dd, J=8.4, 6.2 Hz, 1H), 4.83 (s, 2H), 3.20-3.12 (m, 1H), 3.10-3.01 (m, 1H), 2.52-2.42 (m, 2H), 1.40 (q, J=7.1 Hz, 1H), 1.14-1.06 (m, 1H).

Examples 10.3 to 10.7 were prepared and purified according to the general procedure described for Example 10.2

2-Chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)benzamide Example 10.3

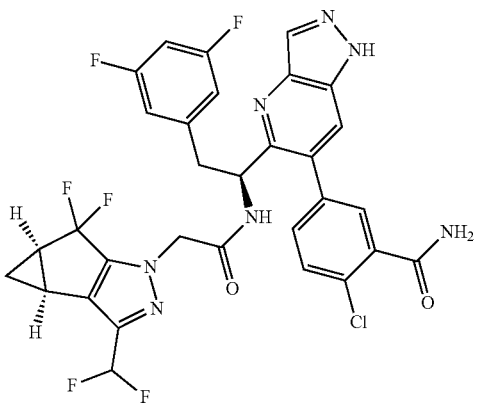

Purity: 100.0%; Observed Mass: 674.0; Retention Time: 1.81 min. $^1$H NMR (500 MHz, MeOH-d$_4$) δ 8.34-8.28 (m, 1H), 7.77 (s, 1H), 7.50 (d, J=8.4 Hz, H), 7.30 (d, J=2.2 Hz, 1H), 7.14 (br d, J=7.7 Hz, 1H), 6.84-6.57 (m, 2H), 6.41-6.34 (m, 2H), 5.47 (dd, J=7.9, 6.8 Hz, 1H), 4.80 (d, J=1.5 Hz, 1H), 3.27-3.19 (m, 1H), 3.07 (dd, J=13.2, 6.2 Hz, 1H), 2.52-2.41 (m, 2H), 1.43-1.36 (m, 1H), 1.10-1.03 (m, 1H).

N—((S)-1-(6-(4-cyano-3-fluorophenyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 10.4)

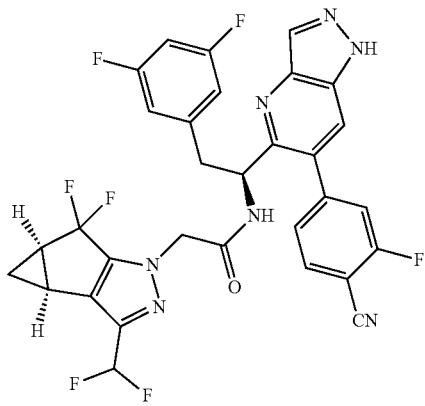 [SMILES: N#Cc1ccc(-c2cc3[nH]ncc3nc2[C@H](Cc2cc(F)cc(F)c2)NC(=O)Cn2nc(C(F)F)c3c2C(F)(F)[C@@H]2C[C@H]32)cc1F]

Purity: 100.0%; Observed Mass: 640.0; Retention Time: 1.99 min. $^1$H NMR (500 MHz, MeOH-d$_4$) δ 8.51-8.31 (m, 1H), 7.99-7.77 (m, 2H), 7.37-7.01 (m, 2H), 6.92-6.53 (m, 2H), 6.48-6.28 (m, 2H), 5.57-5.33 (m, 1H), 3.25-3.01 (m, 2H), 2.63-2.40 (m, 2H), 2.15-1.92 (m, 2H), 1.52-1.35 (m, 1H), 1.19-1.00 (m, 1H).

N—((S)-1-(6-(4-cyanophenyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 10.5)

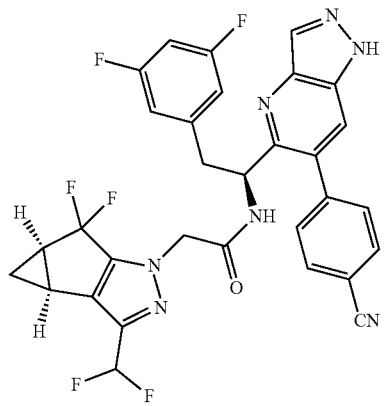 [SMILES: N#Cc1ccc(-c2cc3[nH]ncc3nc2[C@H](Cc2cc(F)cc(F)c2)NC(=O)Cn2nc(C(F)F)c3c2C(F)(F)[C@@H]2C[C@H]32)cc1]

Purity: 100.0%; Observed Mass: 622.1; Retention Time: 1.96 min. ¹H NMR (500 MHz, MeOH-d₄) δ 8.37-8.27 (m, 1H), 7.81-7.73 (m, 3H), 7.34 (br d, J=7.3 Hz, 2H), 6.83-6.55 (m, 2H), 6.29 (br d, J=6.6 Hz, 2H), 5.48-5.41 (m, 1H), 4.92-4.72 (m, 2H), 3.15 (dd, J=13.0, 7.9 Hz, 1H), 3.09-3.00 (m, 1H), 2.52-2.43 (m, 2H), 1.44-1.35 (m, 1H), 1.12-1.06 (m, 1H).

5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-2-fluorobenzamide (Example 10.6)

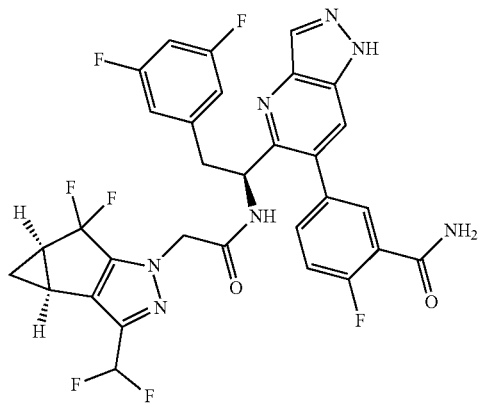 [SMILES: NC(=O)c1cc(-c2cc3[nH]ncc3nc2[C@H](Cc2cc(F)cc(F)c2)NC(=O)Cn2nc(C(F)F)c3c2C(F)(F)[C@@H]2C[C@H]32)ccc1F]

Purity: 100.0%; Observed Mass: 658.2; Retention Time: 1.75 min. ¹H NMR (500 MHz, MeOH-d₄) δ 8.38-8.30 (m, 1H), 7.77 (s, 1H), 7.56-7.21 (m, 3H), 6.87 (s, 2H), 6.43-6.26 (m, 2H), 5.47 (t, J=7.3 Hz, 1H), 4.58 (br s, 2H), 3.25-3.01 (m, 2H), 2.52-2.42 (m, 2H), 2.13-2.12 (m, 1H), 1.44-1.38 (m, 1H), 1.09 (br d, J=3.4 Hz, 1H).

5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-2-fluoro-N-methylbenzamide (Example 10.7)

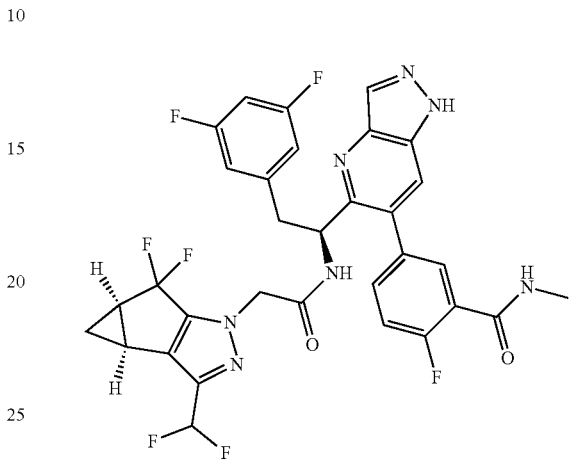

Purity: 100.0%; Observed Mass: 672.1; Retention Time: 1.87 min. ¹H NMR (500 MHz, MeOH-d₄) δ 8.38-8.30 (m, 1H), 7.76 (s, 1H), 7.21 (s, 3H), 6.84-6.57 (m, 2H), 6.33 (br d, J=6.4 Hz, 2H), 5.45 (dd, J=8.2, 6.4 Hz, 1H), 4.62-4.52 (m, 2H), 3.21 (dd, J=13.1, 8.2 Hz, 1H), 3.07 (dd, J=13.1, 6.4 Hz, 1H), 2.92 (s, 3H), 2.48 (ddd, J=11.3, 7.6, 4.3 Hz, 2H), 1.41 (q, J=6.9 Hz, 1H), 1.12-1.04 (m, 1H).

Methyl (S)-3-(5-(1-((tert-butoxycarbonyl)amino)-2-(3,5-difluorophenyl)ethyl)-1-((2-(trimethylsilyl)ethoxy)methyl)-1H-pyrazolo[4,3-b]pyridin-6-yl)benzoate (Int CI1d)

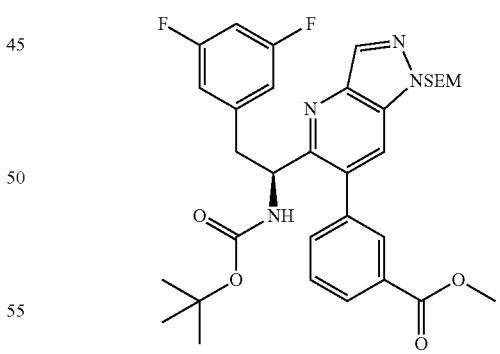

A mixture of tert-butyl (S)-(1-(6-bromo-1-((2-(trimethylsilyl)ethoxy)methyl)-1H-pyrazolo[4,3-b]pyridin-5-yl)-2-(3,5-difluorophenyl)ethyl)carbamate (Int 4JE2, 0.08 g, 0.137 mmol), (3-(methoxycarbonyl)phenyl)boronic acid (0.037 g, 0.206 mmol), Tetrakis (9.51 mg, 8.23 µmol) and K₂CO₃ (0.057 g, 0.411 mmol) in DMF (1 mL) was degassed for 5 min and heated at 100° C. for 2 h and cooled to rt. The reaction mixture was purified on silica gel (24 g Isco column) using 20-100% ethyl acetate in hexanes. The desired fractions were concentrated to afford a yellow solid (0.05 g). LC/MS: m/z=639.2 [M+H]+.

Methyl (S)-3-(5-(1-amino-2-(3,5-difluorophenyl)ethyl)-1-((2-(trimethylsilyl)ethoxy)methyl)-1H-pyrazolo[4,3-b]pyridin-6-yl)benzoate hydrochloride (Int CI1e)

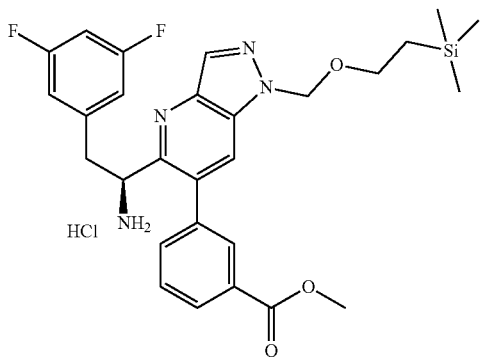 [SMILES: COC(=O)c1cccc(-c2cc3c(cnn3COCC[Si](C)(C)C)nc2[C@@H](N)Cc2cc(F)cc(F)c2)c1 ; Cl]

HCl (0.18 mL, 0.736 mmol) was added to a solution of methyl (S)-3-(5-(1-((tert-butoxycarbonyl)amino)-2-(3,5-difluorophenyl)ethyl)-1-((2-(trimethylsilyl)ethoxy)methyl)-1H-pyrazolo[4,3-b]pyridin-6-yl)benzoate (Int CI1d, 0.047 g, 0.074 mmol) in DCM (1.5 mL) and the mixture was stirred at rt for 2 h and concentrated to give a pale yellow solid (used in the next step as is). LC/MS: m/z=539.1 [M+H]+.

Methyl 3-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1-((2-(trimethylsilyl)ethoxy)methyl)-1H-pyrazolo[4,3-b]pyridin-6-yl)benzoate (Int CI1f)

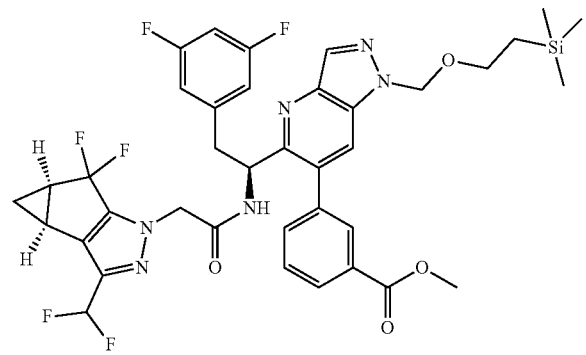 [SMILES: COC(=O)c1cccc(-c2cc3c(cnn3COCC[Si](C)(C)C)nc2[C@H](Cc2cc(F)cc(F)c2)NC(=O)Cn2nc(C(F)F)c3c2C(F)(F)[C@@H]2C[C@H]32)c1]

To a stirred solution of methyl (S)-3-(5-(1-amino-2-(3,5-difluorophenyl)ethyl)-1-((2-(trimethylsilyl)ethoxy)methyl)-1H-pyrazolo[4,3-b]pyridin-6-yl)benzoate hydrochloride (Int CI1e, 0.042 g, 0.073 mmol) in DMF (1.5 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.019 g, 0.073 mmol), HATU (0.029 g, 0.077 mmol) and DIPEA (0.03 mL, 0.146 mmol). The reaction mixture was stirred at rt for 2 h while being monitored by 1 cms. The reaction mixture was purified on silica gel (24 g Isco column) using 0-100% ethyl acetate in hexanes. The desired fractions were concentrated to give a pale yellow solid (0.05 g). LC/MS: m/z=785.1 [M+H]+.

Methyl 3-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)benzoate (Example 10.8); 3-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)benzoic acid (Example 10.10)

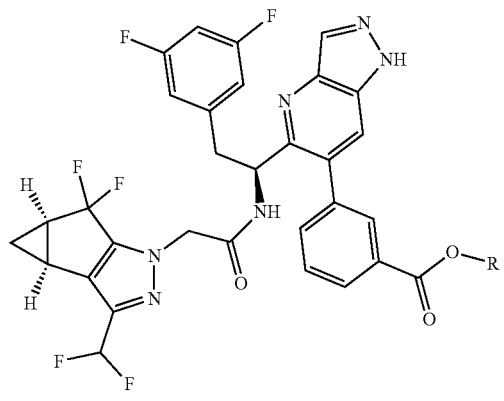

R = Me (Example 10.8)
R = H (Example 10.10)

TFA (0.15 mL, 1.91 mmol) was added to a solution of methyl 3-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1-((2-(trimethylsilyl)ethoxy)methyl)-1H-pyrazolo[4,3-b]pyridin-6-yl)benzoate (Int CI1f, 0.03 g, 0.038 mmol) in DCM (1 mL) and the mixture was stirred at rt for 3 h and concentrated. The residue was taken up in DCM (1 mL) and ethylene diamine (0.16 mL, 2.313 mmol) was added and the mixture was stirred at rt for 1 h and concentrated. The residue was dissolved in methanol, NaOH (0.08 mL, 0.38 mmol) was added to the other half and the mixture was stirred at rt for 2 h. The crude material was purified via preparative LC/MS method A. Two elutes (Examples 10.8 and 10.10) were isolated.

Example 10.8

Purity: 100.0%; Observed Mass: 655.1; Retention Time: 2 min. $^1$H NMR (600 MHz, DMSO-$d_6$) δ 9.12-8.94 (m, 1H), 8.48-8.35 (m, 1H), 8.01 (br d, J=7.3 Hz, 1H), 7.87-7.81 (m, 1H), 7.78-7.68 (m, 1H), 7.65-7.55 (m, 2H), 7.26-6.79 (m, 5H), 6.43 (br d, J=7.7 Hz, 2H), 5.29-5.19 (m, 1H), 4.81-4.66 (m, 2H), 3.11-2.93 (m, 2H), 1.38 (q, J=7.0 Hz, 1H), 0.91 (br s, 1H).

Example 10.10

Purity: 100.0%; Observed Mass: 641.1; Retention Time: 1.57 min. ¹H NMR (600 MHz, DMSO-$d_6$) δ 9.12-8.94 (m, 1H), 8.48-8.35 (m, 1H), 8.01 (br d, J=7.3 Hz, 1H), 7.87-7.81 (m, 1H), 7.78-7.68 (m, 1H), 7.65-7.55 (m, 2H), 7.26-6.79 (m, 5H), 6.43 (br d, J=7.7 Hz, 2H), 5.29-5.19 (m, 1H), 4.81-4.66 (m, 2H), 3.11-2.93 (m, 2H), 1.38 (q, J=7.0 Hz, 1H), 0.91 (br s, 1H).

methyl (S)-5-(5-(1-(((tert-butoxycarbonyl)amino)-2-(3,5-difluorophenyl)ethyl)-1-((2-(trimethylsilyl)ethoxy)methyl)-1H-pyrazolo[4,3-b]pyridin-6-yl)-2-chlorobenzoate (Int CI1g)

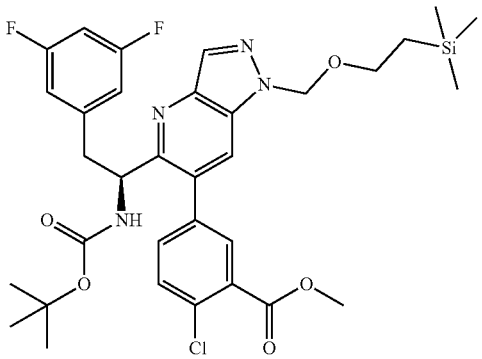 [SMILES: COC(=O)c1cc(-c2cc3c(cnn3COCC[Si](C)(C)C)nc2[C@H](Cc2cc(F)cc(F)c2)NC(=O)OC(C)(C)C)ccc1Cl]

Prepared just like Int CI1d. ¹H NMR (500 MHz, CDCl₃) δ 7.97 (s, 1H), 7.92 (s, 1H), 7.71 (s, 1H), 7.57 (d, J=8.4 Hz, 1H), 7.43 (d, J=8.4 Hz, 1H), 7.03 (dd, J=7.5, 2.9 Hz, 1H), 7.03 (dd, J=7.5, 2.9 Hz, 1H), 6.70 (t, J=9.5 Hz, 1H), 5.78 (s, 2H), 4.98 (ddd, J=9.2, 5.9, 5.5 Hz, 1H), 3.91 (s, 3H), 3.54 (t, J=8.0 Hz, 2H), 3.35 (dd, J=13.9, 5.5 Hz, 1H), 3.05 (dd, J=13.9, 9.2 Hz, 1H), 1.40 (s, 9H), 0.87 (t, J=8.0 Hz, 2H), -0.07 (s, 9H). LC/MS: m/z=673.1 [M+H]⁺.

Methyl (S)-5-(5-(1-amino-2-(3,5-difluorophenyl)ethyl)-1-((2-(trimethylsilyl)ethoxy)methyl)-1H-pyrazolo[4,3-b]pyridin-6-yl)-2-chlorobenzoate hydrochloride (Int CI1h)

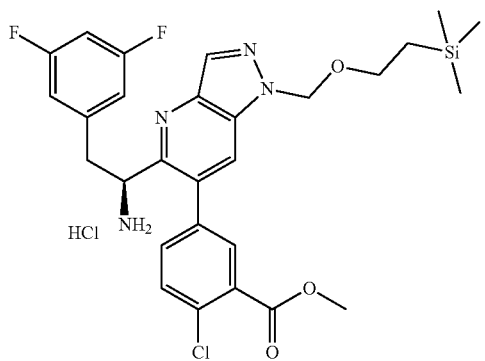 [SMILES: COC(=O)c1cc(-c2cc3c(cnn3COCC[Si](C)(C)C)nc2[C@@H](N)Cc2cc(F)cc(F)c2)ccc1Cl ; Cl]

Prepared just like Int CI1e using Int CI1g. LC/MS: m/z=573.3 [M+H]⁺.

Methyl 2-chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1-((2-(trimethylsilyl)ethoxy)methyl)-1H-pyrazolo[4,3-b]pyridin-6-yl)benzoate (Int CI1i)

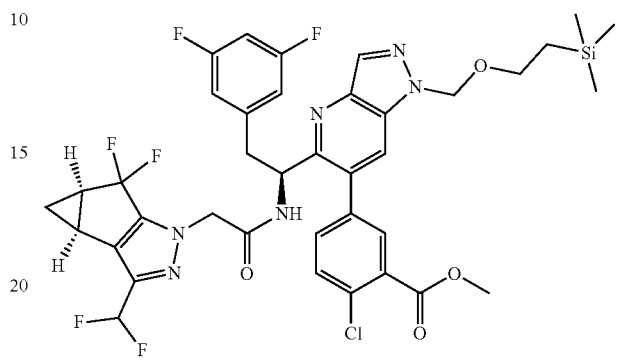

Prepared just like Int CI1f using Int CI1h. LC/MS: m/z=819.2 [M+H]⁺.

2-chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1-((2-(trimethylsilyl)ethoxy)methyl)-1H-pyrazolo[4,3-b]pyridin-6-yl)benzoic acid (Int CI1j)

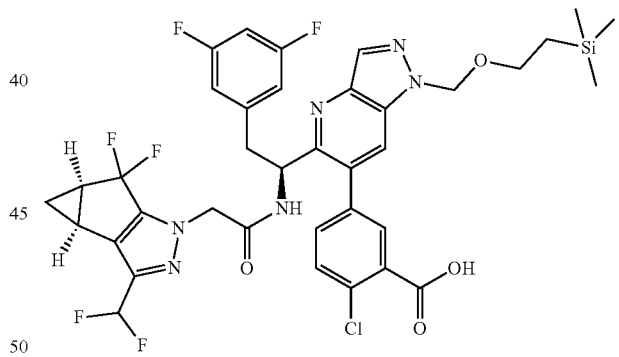

NaOH (0.12 mL, 0.610 mmol) was added to a solution of methyl 2-chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1-((2-(trimethylsilyl)ethoxy)methyl)-1H-pyrazolo[4,3-b]pyridin-6-yl)benzoate (Int CI1i, 0.05 g, 0.061 mmol) in methanol (1 mL) and the mixture was stirred at rt for 2 h and concentrated. The residue was taken up in water, acidified with 2 N HCl and extracted with ethyl acetate. The ethyl acetate extract was dried over Na₂SO₄, filtered and concentrated to give a white solid (0.05 g, used as is in the next step). LC/MS: m/z=805.3 [M+H]⁺.

Examples 10.9 and 10.11 were prepared and purified according to the general procedure described for Examples 10.8 and 10.10.

Methyl 2-chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)benzoate (Example 10.9);
2-Chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)benzoic acid (Example 10.11)

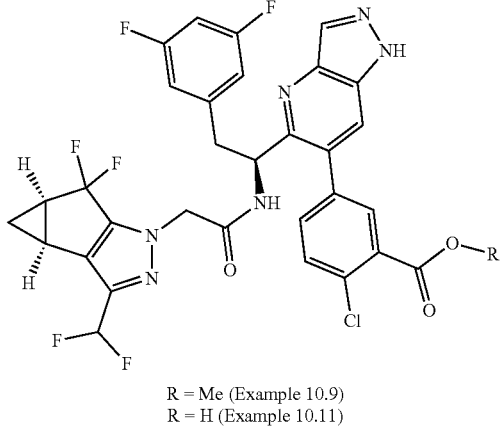

R = Me (Example 10.9)
R = H (Example 10.11)

Example 10.9

Purity: 95.3%; Observed Mass: 689.1; Retention Time: 2.12 min.

Example 10.11

Purity: 99.0%; Observed Mass: 675.0; Retention Time: 1.83 min. 1H NMR (600 MHz, DMSO-$d_6$) δ 9.01-8.92 (m, 1H), 8.36 (s, 1H), 7.75-7.62 (m, 1H), 7.46-7.32 (m, 2H), 7.17 (br d, J=7.7 Hz, 1H), 7.05-6.78 (m, 2H), 6.63 (br s, 2H), 5.23 (br d, J=4.8 Hz, 1H), 4.82-4.61 (m, 2H), 3.08-2.88 (m, 2H), 2.46 (br d, J=4.8 Hz, 1H), 1.40-1.31 (m, 1H), 0.91 (br s, 1H).

Examples 10.12 to 10.15 were prepared and purified according to the general procedure described for Example 10.2.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(1-oxoisoindolin-5-yl)-1H-pyrazolo[4,3-b]pyridin-5-yl)ethyl)acetamide (Example 10.12)

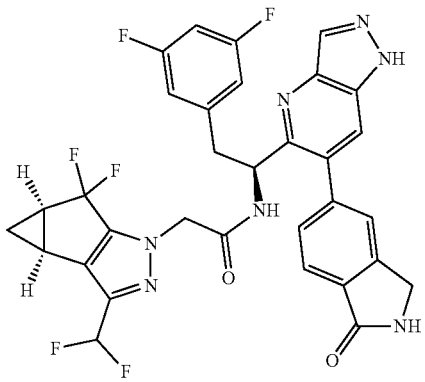 [SMILES: O=C(Cn1nc(C(F)F)c2c1C(F)(F)[C@@H]1C[C@H]21)N[C@@H](Cc1cc(F)cc(F)c1)c1nc2cn[nH]c2cc1-c1ccc2c(c1)CNC2=O]

Purity: 100.0%; Observed Mass: 652.1; Retention Time: 1.66 min. 1H NMR (600 MHz, DMSO-$d_6$) δ 9.09-8.93 (m, 1H), 8.65 (s, 1H), 8.42 (s, 1H), 7.82 (s, 1H), 7.71 (d, J=7.7 Hz, 1H), 7.51-7.09 (m, 2H), 7.07-6.83 (m, 2H), 7.28-6.81 (m, 1H), 7.47-6.78 (m, 1H), 6.42 (br d, J=6.6 Hz, 2H), 5.24 (q, J=7.5 Hz, 1H), 4.84-4.65 (m, 2H), 3.17-2.92 (m, 2H), 1.39 (q, J=6.7 Hz, 1H), 0.92 (br s, 1H).

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(1-oxoisoindolin-4-yl)-1H-pyrazolo[4,3-b]pyridin-5-yl)ethyl)acetamide (Example 10.13)

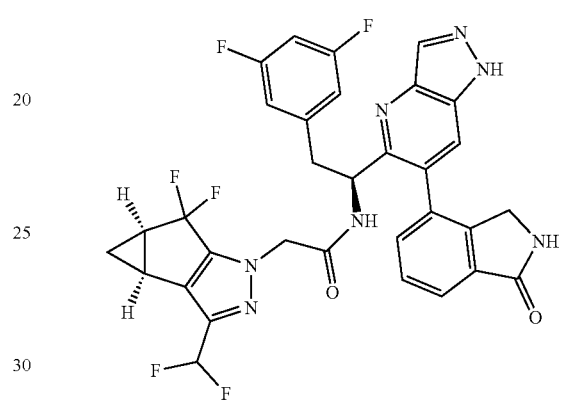

Purity: 100.0%; Observed Mass: 652.1; Retention Time: 1.72 min. 1H NMR (500 MHz, MeOH-$d_4$) δ 8.41-8.32 (m, 1H), 7.96-7.82 (m, 2H), 7.69-7.54 (m, 2H), 7.05 (d, J=7.3 Hz, 1H), 6.86-6.55 (m, 2H), 6.40-6.25 (m, 2H), 4.80-4.70 (m, 1H), 4.37-4.03 (m, 1H), 3.28-3.14 (m, 1H), 3.06-2.91 (m, 2H), 2.55 (br d, J=1.2 Hz, 2H), 1.47-1.35 (m, 1H), 1.16-1.02 (m, 1H).

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3-oxoisoindolin-5-yl)-1H-pyrazolo[4,3-b]pyridin-5-yl)ethyl)acetamide (Example 10.14)

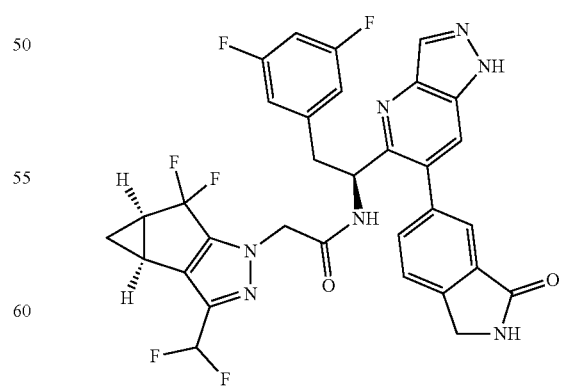

Purity: 100.0%; Observed Mass: 652.1; Retention Time: 1.66 min. 1H NMR (500 MHz, MeOH-$d_4$) δ 8.38-8.29 (m, 1H), 7.79 (s, 1H), 7.65 (d, J=7.9 Hz, 1H), 7.57-7.38 (m, 2H), 6.87-6.56 (m, 2H), 6.28 (br d, J=6.7 Hz, 2H), 5.51 (t, J=7.3 Hz, 1H), 4.64-4.49 (m, 3H), 3.22-2.99 (m, 2H), 2.53-2.40 (m, 2H), 2.03-1.96 (m, 1H), 1.40 (q, J=7.2 Hz, 1H), 1.16-1.05 (m, 1H).

N—((S)-1-(6-(4-chloro-3-cyanophenyl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 10.15)

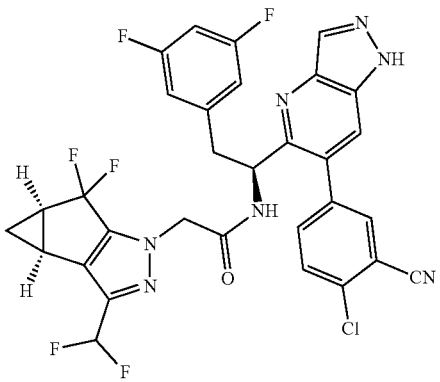 [SMILES: N#Cc1cc(-c2cc3[nH]ncc3nc2[C@H](Cc2cc(F)cc(F)c2)NC(=O)Cn2nc(C(F)F)c3c2C(F)(F)[C@@H]2C[C@H]32)ccc1Cl]

Purity: 100.0%; Observed Mass: 656.1; Retention Time: 2.09 min. $^1$H NMR (500 MHz, MeOH-$d_4$) δ 8.39-8.31 (m, 1H), 7.77 (s, 1H), 7.66 (d, J=8.5 Hz, 1H), 7.55-7.45 (m, 1H), 7.42-7.32 (m, 1H), 6.85-6.55 (m, 2H), 6.36-6.26 (m, 2H), 5.38 (dd, J=8.9, 5.8 Hz, 1H), 3.23-3.06 (m, 2H), 2.53-2.41 (m, 2H), 1.44-1.36 (m, 1H), 1.45-1.22 (m, 1H), 1.35-1.15 (m, 1H), 1.14-1.05 (m, 1H).

2-Chloro-N-(cyclopropylsulfonyl)-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)benzamide (Example 10.16)

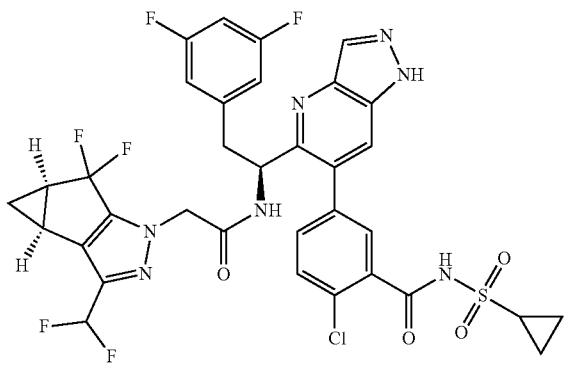

A mixture of 2-chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1-((2-(trimethylsilyl)ethoxy)methyl)-1H-pyrazolo[4,3-b]pyridin-6-yl)benzoic acid (Int CI1j, 0.03 g, 0.037 mmol), cyclopropane sulfonamide (5.42 mg, 0.045 mmol), DMAP (6.83 mg, 0.056 mmol) in THF (1 mL) was stirred at rt and 1-(3-dimethylaminopropyl)-3-ethylcarbodiimide hydrochloride (10.71 mg, 0.056 mmol) was added and the mixture was stirred at rt for 3 h and concentrated. The residue was taken up in DCM (1 mL) and TFA (0.5 mL) was added and the mixture was stirred for 1.5 h and concentrated. The residue was taken up in DCM (0.6 mL) and ethylene diamine (0.5 mL) was added, the mixture was stirred at rt for 1 h, concentrated, taken up in methanol and filtered. The crude material was purified via preparative LC/MS method A. Purity: 100.0%; Observed Mass: 778.1; Retention Time: 1.97 min. $^1$H NMR (500 MHz, MeOH-$d_4$) δ 8.40-8.30 (m, 1H), 7.80-7.76 (m, 1H), 7.54 (d, J=8.2 Hz, 1H), 7.41-7.18 (m, 2H), 6.85-6.56 (m, 2H), 6.38 (br d, J=6.4 Hz, 2H), 5.46 (t, J=7.5 Hz, 1H), 3.23 (dd, J=13.1, 8.2 Hz, 1H), 3.13-3.05 (m, 2H), 2.50-2.42 (m, 2H), 1.44-1.26 (m, 5H), 1.20-1.03 (m, 3H). Examples 10.18 to 10.21 were prepared and purified according to the general procedure described for Example 10.16.

2-Chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-N-(methylsulfonyl)benzamide (Example 10.18)

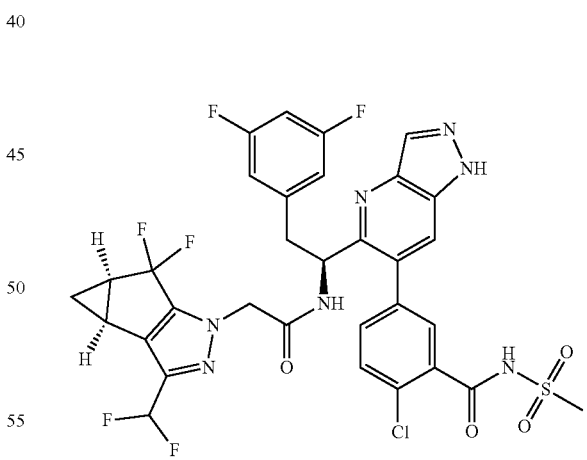

Purity: 97%; Observed Mass: 752.0; Retention Time: 1.57 min. $^1$H NMR (500 MHz, MeOH-$d_4$) δ 8.34-8.24 (m, 1H), 7.89-7.79 (m, 1H), 7.45 (br d, J=8.2 Hz, 2H), 7.30-7.20 (m, 1H), 6.87-6.57 (m, 2H), 6.37 (br d, J=6.1 Hz, 2H), 5.57 (t, J=7.2 Hz, 1H), 3.18-3.09 (m, 4H), 3.00 (dd, J=13.4, 7.3 Hz, 1H), 2.52-2.44 (m, 2H), 2.03-1.94 (m, 14H), 1.40 (q, J=7.0 Hz, 1H), 1.36-1.31 (m, 2H), 1.09 (br d, J=2.7 Hz, 1H).

151

2-chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-N-(isopropylsulfonyl)benzamide (Example 10.19)

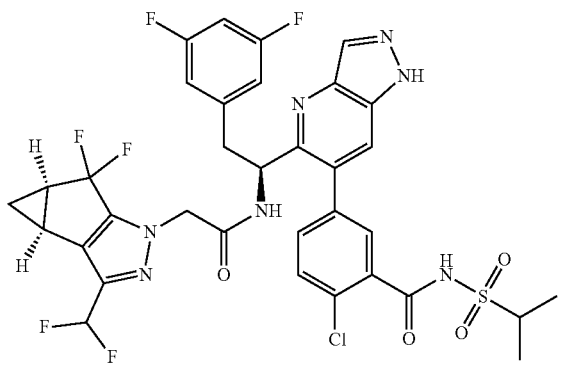

Purity: 98%; Observed Mass: 780.1; Retention Time: 2.01 min. $^1$H NMR (500 MHz, MeOH-d$_4$) δ 8.38-8.29 (m, 1H), 7.82-7.75 (m, 1H), 7.54 (d, J=8.2 Hz, 1H), 7.40-7.18 (m, 2H), 6.84-6.57 (m, 2H), 6.43-6.34 (m, 2H), 5.46 (t, J=7.3 Hz, 1H), 3.92-3.80 (m, 1H), 3.26-3.18 (m, 1H), 3.14 (s, 1H), 2.51-2.42 (m, 2H), 1.50-1.27 (m, 9H), 1.12-1.04 (m, 1H).

2-Chloro-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-N-((1-methylcyclopropyl)sulfonyl)benzamide (Example 10.20)

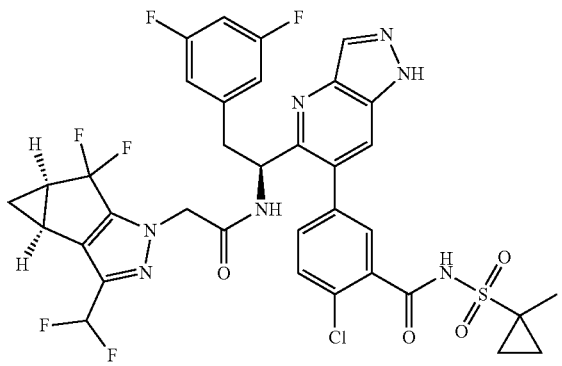 [SMILES: CC1(S(=O)(=O)NC(=O)c2cc(-c3cc4[nH]ncc4nc3[C@H](Cc3cc(F)cc(F)c3)NC(=O)Cn3nc(C(F)F)c4c3C(F)(F)[C@@H]3C[C@H]43)ccc2Cl)CC1]

Purity: 100.0%; Observed Mass: 792.0; Retention Time: 1.68 min. $^1$H NMR (500 MHz, MeOH-d$_4$) δ 8.38-8.29 (m, 1H), 7.82-7.76 (m, 1H), 7.59-7.50 (m, 1H), 7.42-7.15 (m, 2H), 6.85-6.55 (m, 2H), 6.40 (br d, J=6.1 Hz, 2H), 5.46 (t, J=7.5 Hz, 1H), 3.27-3.19 (m, 1H), 3.14-3.06 (m, 1H), 2.47 (ddd, J=11.2, 7.7, 4.0 Hz, 2H), 1.72-1.57 (m, 5H), 1.44-1.26 (m, 3H), 1.11-1.04 (m, 1H), 1.02-0.95 (m, 2H).

152

2-Chloro-N-(cyclopentylsulfonyl)-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)benzamide Example (10.21)

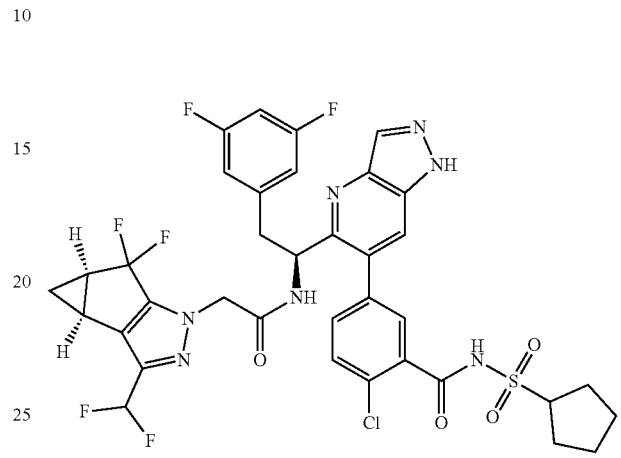

Purity: 100.0%; Observed Mass: 806.1; Retention Time: 2.16 min. $^1$H NMR (500 MHz, MeOH-d$_4$) δ 8.39-8.28 (m, 1H), 7.82-7.75 (m, 1H), 7.57-7.49 (m, 1H), 7.38-7.20 (m, 2H), 6.85-6.54 (m, 2H), 6.45-6.34 (m, 2H), 5.46 (t, J=7.2 Hz, 1H), 4.27-4.12 (m, 1H), 3.23 (dd, J=13.3, 7.8 Hz, 1H), 3.13 (s, 1H), 2.54-2.41 (m, 2H), 2.20-2.09 (m, 4H), 1.89-1.66 (m, 4H), 1.45-1.37 (m, 1H), 1.36-1.31 (m, 1H), 1.12-1.04 (m, 1H).

methyl 5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1-((2-(trimethylsilyl)ethoxy)methyl)-1H-pyrazolo[4,3-b]pyridin-6-yl)-2-fluorobenzoate (Int Cl 1k)

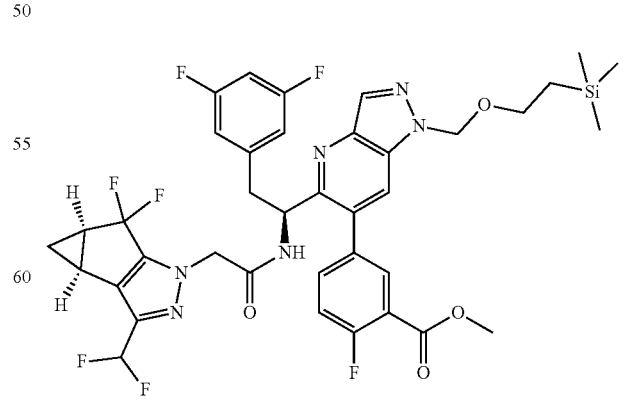

Prepared just like Int Cl1i. LC/MS: m/z=803.1 [M+H]$^+$.

methyl 5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-2-fluorobenzoate (Int CI1l)

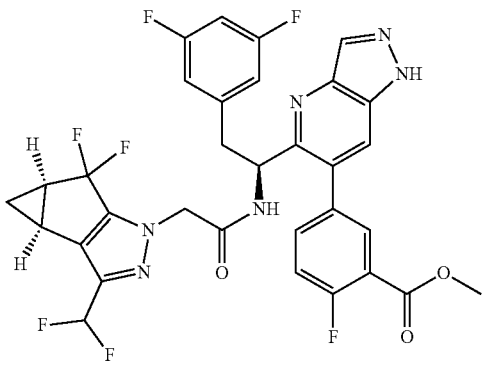 [SMILES: COC(=O)c1cc(-c2cc3[nH]ncc3nc2[C@H](Cc2cc(F)cc(F)c2)NC(=O)Cn2nc(C(F)F)c3c2C(F)(F)[C@@H]2C[C@H]32)ccc1F]

Prepared just like Example 10.2 using Int CI1k. LC/MS: m/z=673.3 [M+H]+.

5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-2-fluorobenzoic acid (Example 10.25)

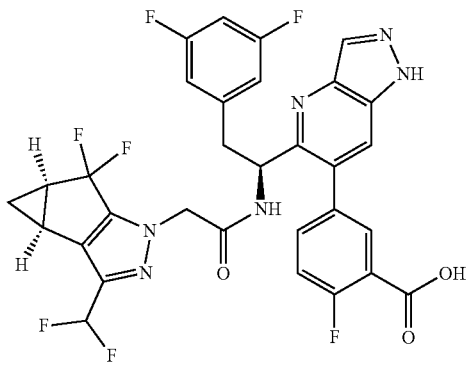 [SMILES: O=C(Cn1nc(C(F)F)c2c1C(F)(F)[C@@H]1C[C@H]21)N[C@@H](Cc1cc(F)cc(F)c1)c1nc2cn[nH]c2cc1-c1ccc(F)c(C(=O)O)c1]

NaOH (0.26 mL, 1.31 mmol) was added to a solution of methyl 5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-2-fluorobenzoate (Int CI1, 0.088 g, 0.131 mmol) in methanol (1 mL) and the mixture was stirred at rt for 2 h and concentrated. The residue was taken up in water, acidified with 2 N HCl and extracted with ethyl acetate. The ethyl acetate extract was dried over Na$_2$SO$_4$, filtered and concentrated. The crude material was purified via preparative LC/MS method A. Purity: 100.0%; Observed Mass: 659.1; Retention Time: 1.49 min. $^1$H NMR (500 MHz, MeOH-d$_4$) δ 8.35-8.23 (m, 1H), 7.85-7.76 (m, 1H), 7.58 (s, 1H), 7.39 (br d, J=5.2 Hz, 1H), 7.17 (t, J=9.3 Hz, 1H), 6.86-6.57 (m, 2H), 6.36 (br d, J=6.7 Hz, 2H), 5.56 (t, J=7.0 Hz, 1H), 3.16-3.07 (m, 1H), 3.03 (s, 1H), 2.53 (br d, J=3.4 Hz, 1H), 1.96 (br d, J=0.9 Hz, 2H), 1.46-1.36 (m, 1H), 1.09 (br d, J=1.5 Hz, 1H).

5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1-((2-(trimethylsilyl)ethoxy)methyl)-1H-pyrazolo[4,3-b]pyridin-6-yl)-2-fluorobenzoic acid (Int CI1m)

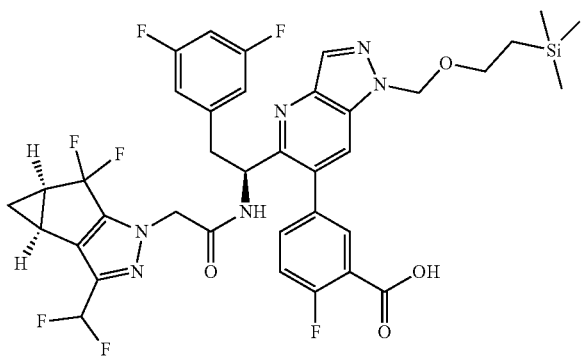 [SMILES: C[Si](C)(C)CCOCn1ncc2nc([C@H](Cc3cc(F)cc(F)c3)NC(=O)Cn3nc(C(F)F)c4c3C(F)(F)[C@@H]3C[C@H]43)c(-c3ccc(F)c(C(=O)O)c3)cc21]

Prepared just like Int CI1j using Int CI1k. LC/MS: m/z=789.4 [M+H]+.

Examples 10.26 to 10.29 were prepared and purified according to the general procedure described for Example 10.16.

5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-2-fluoro-N-(methylsulfonyl)benzamide (Example 10.26)

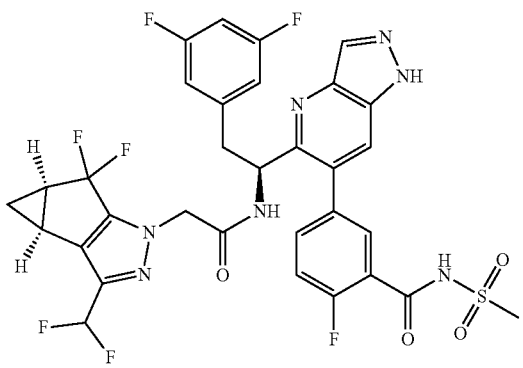 [SMILES: CS(=O)(=O)NC(=O)c1cc(-c2cc3[nH]ncc3nc2[C@H](Cc2cc(F)cc(F)c2)NC(=O)Cn2nc(C(F)F)c3c2C(F)(F)[C@@H]2C[C@H]32)ccc1F]

155

Purity: 100.0%; Observed Mass: 736.1; Retention Time: 1.52 min. $^1$H NMR (400 MHz, MeOH-d$_4$) δ 8.41-8.30 (m, 1H), 7.77 (s, 1H), 7.51-7.19 (m, 3H), 6.89-6.53 (m, 2H), 6.38-6.29 (m, 2H), 5.49 (s, 1H), 3.37 (s, 3H), 3.23 (dd, J=12.8, 8.7 Hz, 1H), 3.13-3.01 (m, 1H), 2.54-2.39 (m, 2H), 1.48-1.36 (m, 1H), 1.16-1.06 (m, 1H).

5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-2-fluoro-N-(isopropylsulfonyl)benzamide (Example 10.27)

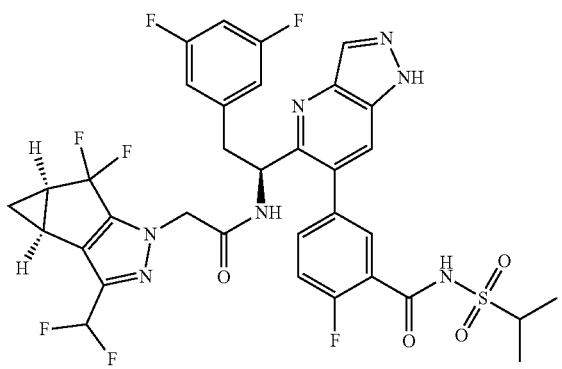 [SMILES: CC(C)S(=O)(=O)NC(=O)c1cc(-c2cc3[nH]ncc3nc2[C@H](Cc2cc(F)cc(F)c2)NC(=O)Cn2nc(C(F)F)c3c2C(F)(F)[C@@H]2C[C@H]32)ccc1F]

Purity: 100.0%; Observed Mass: 764.1; Retention Time: 1.6 min.

N-(cyclopropylsulfonyl)-5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-2-fluorobenzamide (Example 10.28)

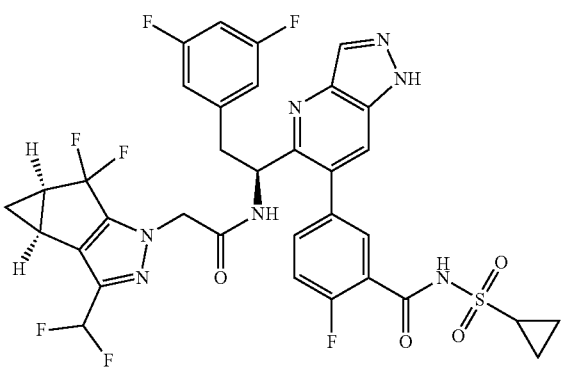 [SMILES: O=C(Cn1nc(C(F)F)c2c1C(F)(F)[C@@H]1C[C@H]21)N[C@@H](Cc1cc(F)cc(F)c1)c1nc2cn[nH]c2cc1-c1ccc(F)c(C(=O)NS(=O)(=O)C2CC2)c1]

Purity: 97%; Observed Mass: 762.1; Retention Time: 1.96 min.

156

5-(5-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrazolo[4,3-b]pyridin-6-yl)-2-fluoro-N-((1-methylcyclopropyl)sulfonyl)benzamide (Example 10.29)

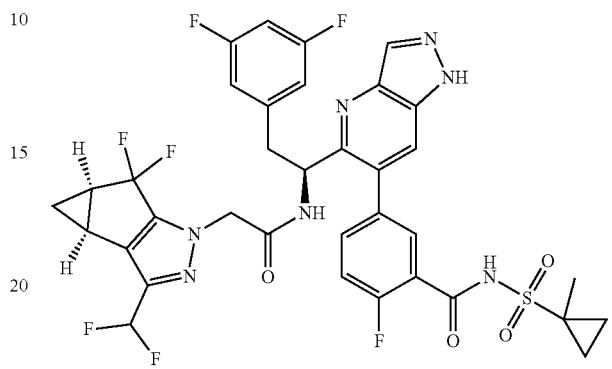

Purity: 100.0%; Observed Mass: 736.1; Retention Time: 1.52 min. $^1$H NMR (400 MHz, MeOH-d$_4$) δ 8.35-8.23 (m, 1H), 7.82 (s, 1H), 7.58 (dd, J=6.7, 2.1 Hz, 1H), 7.43-7.30 (m, 1H), 7.19 (dd, J=10.0, 8.6 Hz, 1H), 6.89-6.52 (m, 2H), 6.44-6.29 (m, 2H), 5.62-5.52 (m, 1H), 3.20-3.08 (m, 1H), 3.05-2.95 (m, 1H), 2.54-2.42 (m, 2H), 1.96 (s, 2H), 1.60-1.46 (m, 5H), 1.45-1.35 (m, 1H), 1.13-1.06 (m, 1H), 0.85-0.64 (m, 2H).

6-(4,4,5,5-tetramethyl-1,3,2-dioxaborolan-2-yl)pyrazolo[1,5-a]pyridine (Int CI2a)

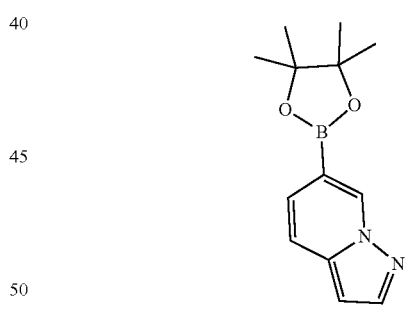

A mixture of 6-bromopyrazolo[1,5-a]pyridine (0.2 g, 1.015 mmol), 4,4,4',4',5,5,5',5'-octamethyl-2,2'-bi(1,3,2-dioxaborolane) (0.31 g, 1.22 mmol), potassium acetate (0.3 g, 3.05 mmol) and PdCl$_2$(dppf) (0.074 g, 0.102 mmol) in 1,4-Dioxane (3 mL) was purged with nitrogen and was heated at 85° C. for 6 h. The reaction mixture was filtered through Celite, diluted with ethyl acetate, washed with brine, dried over Na$_2$SO$_4$, concentrated and purified on silica gel (40 g, Isco column) using 0-50% ethyl acetate in hexanes. The desired fractions were concentrated to give a viscous oil which solidified upon standing to an off-white waxy solid (0.21 g). $^1$H NMR (500 MHz, CDCl$_3$) δ 8.91-8.84 (m, 1H), 8.01 (d, J=2.2 Hz, 1H), 7.52 (dd, J=8.8, 1.1 Hz, 1H), 7.39 (dd, J=8.9, 1.0 Hz, 1H), 6.51 (dd, J=2.2, 0.8 Hz, 1H), 1.41-1.35 (m, 12H)

2-((3bS,4aR)-3-(difluoromethyl)-5,5-difluoro-3b,4,
4a,5-tetrahydro-1H-cyclopropa[3,4]cyclopenta[1,2-
c]pyrazol-1-yl)-N—((S)-2-(3,5-difluorophenyl)-1-
(6-(pyrazolo[1,5-a]pyridin-6-yl)-1H-pyrazolo[4,3-b]
pyridin-5-yl)ethyl)acetamide (Example 10.36)

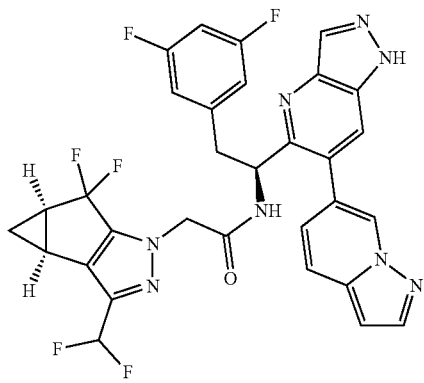 [SMILES: O=C(Cn1nc(C(F)F)c2c1C(F)(F)[C@@H]1C[C@H]21)N[C@@H](Cc1cc(F)cc(F)c1)c1nc2cn[nH]c2cc1-c1ccc2ccnn2c1]

Prepared and purified according to the general procedure described for example 10.2 using Int CI2a. Purity: 100.0%; Observed Mass: 637.1; Retention Time: 1.9 min. $^1$H NMR (500 MHz, MeOH-d$_4$) δ 8.41-8.30 (m, 1H), 8.18 (br s, 1H), 8.02 (d, J=2.1 Hz, 1H), 7.87 (s, 1H), 7.69 (d, J=8.9 Hz, 1H), 7.18-7.04 (m, 1H), 6.86-6.54 (m, 3H), 6.35-6.25 (m, 2H), 5.55 (dd, J=8.2, 6.4 Hz, 1H), 3.23-3.04 (m, 2H), 2.53-2.40 (m, 2H), 1.45-1.34 (m, 1H), 1.13-1.04 (m, 1H).

2-((3bS,4aR)-3-(difluoromethyl)-5,5-difluoro-3b,4,
4a,5-tetrahydro-1H-cyclopropa[3,4]cyclopenta[1,2-
c]pyrazol-1-yl)-N—((S)-2-(3,5-difluorophenyl)-1-
(6-(2-methyl-3-oxoisoindolin-5-yl)-1H-pyrazolo[4,
3-b]pyridin-5-yl)ethyl)acetamide (Example 23)

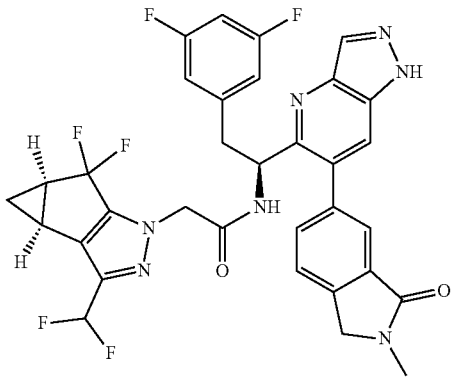 [SMILES: CN1Cc2ccc(-c3cc4[nH]ncc4nc3[C@H](Cc3cc(F)cc(F)c3)NC(=O)Cn3nc(C(F)F)c4c3C(F)(F)[C@@H]3C[C@H]43)cc2C1=O]

Prepared and purified according to the general procedure described for Example 10.2 Purity: 100.0%; Observed Mass: 666.1; Retention Time: 1.8 min. $^1$H NMR (500 MHz, MeOH-d$_4$) δ 8.39-8.29 (m, 1H), 7.79 (s, 1H), 7.68-7.31 (m, 3H), 6.88-6.52 (m, 2H), 6.29 (br d, J=6.4 Hz, 2H), 5.50 (br t, J=7.2 Hz, 1H), 3.26 (s, 3H), 3.19-3.01 (m, 2H), 2.56-2.42 (m, 2H), 1.95 (s, 3H), 1.46-1.37 (m, 1H), 1.10 (br s, 1H).

Examples 24 to CI8 were prepared and purified according to the general procedure described for Example 10.2

2-((3bS,4aR)-3-(difluoromethyl)-5,5-difluoro-3b,4,
4a,5-tetrahydro-1H-cyclopropa[3,4]cyclopenta[1,2-
c]pyrazol-1-yl)-N—((S)-2-(3,5-difluorophenyl)-1-
(6-(4-sulfamoylphenyl)-1H-pyrazolo[4,3-b]pyridin-
5-yl)ethyl)acetamide (Example 24)

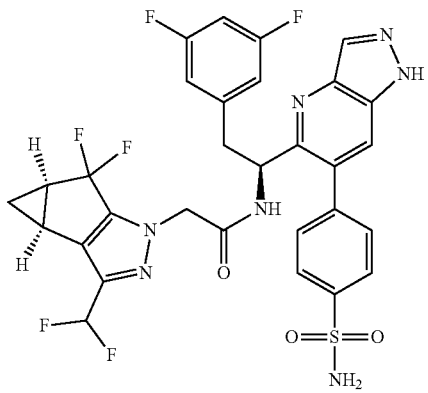 [SMILES: NS(=O)(=O)c1ccc(-c2cc3[nH]ncc3nc2[C@H](Cc2cc(F)cc(F)c2)NC(=O)Cn2nc(C(F)F)c3c2C(F)(F)[C@@H]2C[C@H]32)cc1]

The crude material was purified via preparative LC/MS method A. Purity: 100.0%; Observed Mass: 676.0; Retention Time: 1.72 min. $^1$H NMR (500 MHz, MeOH-d$_4$) δ 8.40-8.30 (m, 1H), 7.96 (d, J=8.5 Hz, 2H), 7.79 (s, 1H), 7.34 (br d, J=6.7 Hz, 2H), 6.88-6.56 (m, 2H), 6.32 (br d, J=6.4 Hz, 2H), 5.51-5.42 (m, 1H), 3.19 (dd, J=13.1, 7.9 Hz, 1H), 3.10-2.99 (m, 1H), 2.49 (ddd, J=10.9, 7.6, 3.8 Hz, 2H), 1.47-1.36 (m, 1H), 1.15-1.04 (m, 1H).

2-((3bS,4aR)-3-(difluoromethyl)-5,5-difluoro-3b,4,
4a,5-tetrahydro-1H-cyclopropa[3,4]cyclopenta[1,2-
c]pyrazol-1-yl)-N—((S)-2-(3,5-difluorophenyl)-1-
(6-(4-(morpholinosulfonyl)phenyl)-1H-pyrazolo[4,3-
b]pyridin-5-yl)ethyl)acetamide (Example 25)

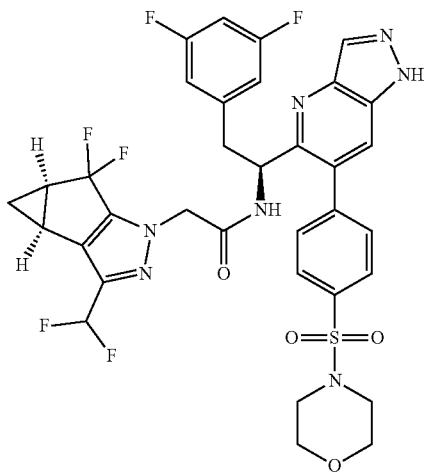 [SMILES: O=C(Cn1nc(C(F)F)c2c1C(F)(F)[C@@H]1C[C@H]21)N[C@@H](Cc1cc(F)cc(F)c1)c1nc2cn[nH]c2cc1-c1ccc(S(=O)(=O)N2CCOCC2)cc1]

The crude material was purified via preparative LC/MS method A. Purity: 100.0%; Observed Mass: 746.1; Retention Time: 1.91 min. $^1$H NMR (500 MHz, MeOH-d$_4$) δ 8.44-8.18 (m, 1H), 7.88-7.66 (m, 3H), 7.51-7.20 (m, 2H), 6.86-6.48 (m, 2H), 6.27 (br d, J=6.4 Hz, 2H), 5.48-5.33 (m, 1H), 3.72 (t, J=4.6 Hz, 4H), 3.22-2.92 (m, 6H), 2.45 (ddd, J=11.0, 7.6, 4.0 Hz, 2H), 2.05-1.87 (m, 1H), 1.37 (q, J=7.0 Hz, 1H), 1.05 (br d, J=3.1 Hz, 1H).

2-((3bS,4aR)-3-(difluoromethyl)-5,5-difluoro-3b,4, 4a,5-tetrahydro-1H-cyclopropa[3,4]cyclopenta[1,2-c]pyrazol-1-yl)-N—((S)-2-(3,5-difluorophenyl)-1-(6-(4-(N,N-dimethylsulfamoyl)phenyl)-1H-pyrazolo[4,3-b]pyridin-5-yl)ethyl)acetamide (Example 26)

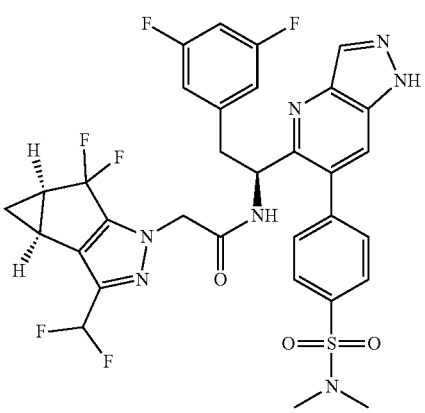 [SMILES: CN(C)S(=O)(=O)c1ccc(-c2cc3[nH]ncc3nc2[C@H](Cc2cc(F)cc(F)c2)NC(=O)Cn2nc(C(F)F)c3c2C(F)(F)[C@@H]2C[C@H]32)cc1]

The crude material was purified via preparative LC/MS method A. Purity: 97%; Observed Mass: 704.1; Retention Time: 1.99 min. $^1$H NMR (500 MHz, MeOH-d$_4$) δ 8.43-8.30 (m, 1H), 7.87-7.77 (m, 3H), 7.45-7.37 (m, 2H), 6.87-6.58 (m, 2H), 6.35-6.26 (m, 2H), 5.42 (t, J=7.3 Hz, 1H), 4.90-4.81 (m, 1H), 4.62 (br s, 1H), 3.17 (dd, J=13.0, 8.4 Hz, 1H), 3.09-2.99 (m, 1H), 2.79-2.74 (m, 6H), 2.53-2.44 (m, 2H), 1.46-1.35 (m, 1H), 1.13-1.03 (m, 1H).

2-((3bS,4aR)-3-(difluoromethyl)-5,5-difluoro-3b,4, 4a,5-tetrahydro-1H-cyclopropa[3,4]cyclopenta[1,2-c]pyrazol-1-yl)-N—((S)-2-(3,5-difluorophenyl)-1-(6-(4-(thiomorpholinosulfonyl)phenyl)-1H-pyrazolo[4,3-b]pyridin-5-yl)ethyl)acetamide (Example 27)

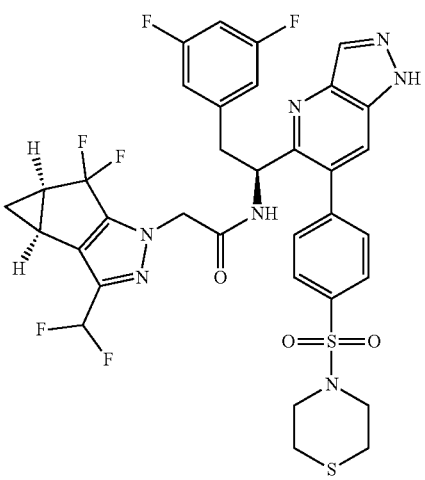 [SMILES: O=C(Cn1nc(C(F)F)c2c1C(F)(F)[C@@H]1C[C@H]21)N[C@@H](Cc1cc(F)cc(F)c1)c1nc2cn[nH]c2cc1-c1ccc(S(=O)(=O)N2CCSCC2)cc1]

The crude material was purified via preparative LC/MS method A. Purity: 100.0%; Observed Mass: 762.1; Retention Time: 2.1 min. $^1$H NMR (500 MHz, MeOH-d$_4$) δ 8.40-8.31 (m, 1H), 7.84-7.77 (m, 3H), 7.49-7.33 (m, 2H), 6.87-6.59 (m, 2H), 6.33-6.27 (m, 2H), 5.43 (t, J=7.3 Hz, 1H), 4.90 (s, 1H), 4.57 (s, 1H), 3.43-3.36 (m, 4H), 3.18 (dd, J=13.1, 8.5 Hz, 1H), 3.10-3.02 (m, 1H), 2.80-2.70 (m, 4H), 2.49 (ddd, J=11.1, 7.6, 3.8 Hz, 2H), 1.46-1.37 (m, 1H), 1.13-1.06 (m, 1H).

2-((3bS,4aR)-3-(difluoromethyl)-5,5-difluoro-3b,4, 4a,5-tetrahydro-1H-cyclopropa[3,4]cyclopenta[1,2-c]pyrazol-1-yl)-N—((S)-2-(3,5-difluorophenyl)-1-(6-(4-((4-methylpiperazin-1-yl)sulfonyl)phenyl)-1H-pyrazolo[4,3-b]pyridin-5-yl)ethyl)acetamide (Example 28)

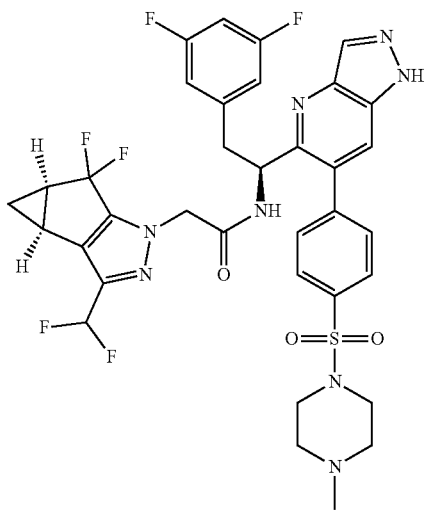 [SMILES: CN1CCN(S(=O)(=O)c2ccc(-c3cc4[nH]ncc4nc3[C@H](Cc3cc(F)cc(F)c3)NC(=O)Cn3nc(C(F)F)c4c3C(F)(F)[C@@H]3C[C@H]43)cc2)CC1]

The crude material was purified via preparative LC/MS method A Purity: 100.0%; Observed Mass: 759.2; Retention Time: 1.93 min. $^1$H NMR (500 MHz, MeOH-d$_4$) δ 8.39-8.32 (m, 1H), 7.87-7.74 (m, 3H), 7.44-7.31 (m, 2H), 6.89-6.57 (m, 2H), 6.36-6.23 (m, 2H), 5.47-5.34 (m, 1H), 3.23-3.01 (m, 7H), 2.61-2.44 (m, 6H), 2.35-2.26 (m, 3H), 2.00 (br s, 1H), 1.42 (q, J=6.7 Hz, 1H), 1.15-1.03 (m, 1H).

Tert-butyl (S)-(2-(3,5-difluorophenyl)-1-(3-(6-methoxypyridin-3-yl)-4-oxo-3,4-dihydropyrido[2,3-d]pyrimidin-2-yl)ethyl)carbamate (Int CI4b)

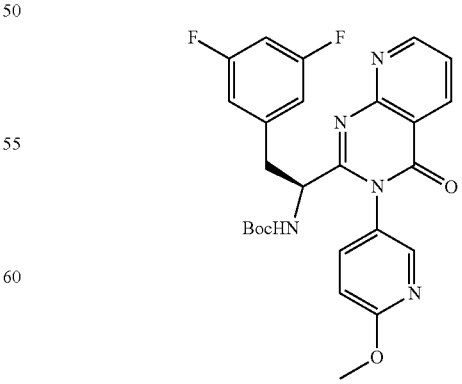

A mixture of tert-butyl (S)-(2-(3,5-difluorophenyl)-1-(4-oxo-4H-pyrido[2,3-d][1,3]oxazin-2-yl)ethyl)carbamate (Int 17a, 0.1 g, 0.248 mmol) and 6-methoxypyridin-3-amine (0.034 g, 0.273 mmol) in DCE (1 mL) was stirred at rt for 18 h. The reaction mixture was treated with mL, 0.119 mmol) followed by isobutyl chloroformate (0.04 mL, 0.297 mmol) and N-methylmorpholine (0.033 mL, 0.297 mmol), then stirred at rt for 2 h, diluted with ethyl acetate, washed with sat NaHCO$_3$, dried over Na$_2$SO$_4$ and concentrated. The residue was purified on silica gel (40 g Isco column) using 0-60% ethyl acetate in hexanes. The desired fractions were concentrated to give a pink solid (60 mg) which was a mix of stereoisomers due to the racemization in a reaction earlier in the sequence. LC/MS: m/z=510.3 [M+H]$^+$.

(S)-2-(1-amino-2-(3,5-difluorophenyl)ethyl)-3-(6-methoxypyridin-3-yl)pyrido[2,3-d]pyrimidin-4(3H)-one hydrochloride (Int CI4c)

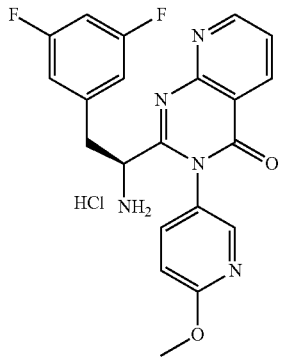 [SMILES: COc1ccc(-n2c([C@@H](N)Cc3cc(F)cc(F)c3)nc3ncccc3c2=O)cn1 ; Cl]

HCl (1.6 mL, 6.24 mmol) was added to a solution of tert-butyl (S)-(2-(3,5-difluorophenyl)-1-(3-(6-methoxypyridin-3-yl)-4-oxo-3,4-dihydropyrido[2,3-d]pyrimidin-2-yl)ethyl)carbamate (Int CI4b, 0.053 g, 0.104 mmol) in DCM (0.4 mL) and the mixture was stirred at rt for 0.5 h and concentrated to give a pale yellow solid (used as is) which was a mix of stereoisomers due to the racemization in a reaction earlier in the sequence. LC/MS: m/z=410.0 [M+H]$^+$ 2-[(2S,4R)-9-(difluoromethyl)-5,5-difluoro-7,8-diazatricyclo[4.3.0.0$^{2,4}$]nona-1(6),8-dien-7-yl]-N-[(1S)-2-(3,5-difluorophenyl)-1-[3-(6-methoxypyridin-3-yl)-4-oxo-3H,4H-pyrido[2,3-d]pyrimidin-2-yl]ethyl]acetamide: (Example 29)

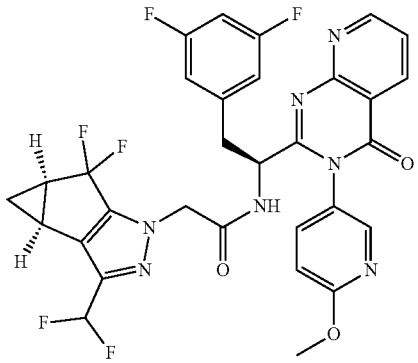 [SMILES: COc1ccc(-n2c([C@H](Cc3cc(F)cc(F)c3)NC(=O)Cn3nc(C(F)F)c4c3C(F)(F)[C@@H]3C[C@H]43)nc3ncccc3c2=O)cn1]

To a stirred solution of (S)-2-(1-amino-2-(3,5-difluorophenyl)ethyl)-3-(6-methoxypyridin-3-yl)pyrido[2,3-d]pyrimidin-4(3H)-one hydrochloride (Int CI4c, 0.046 mg, 0.103 mmol) in DMF (1.5 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.027 g, 0.103 mmol), HATU (0.041 g, 0.108 µmol) and DIPEA (0.04 mL, 0.206 mmol). The reaction mixture was stirred for 2 h and filtered. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 34-74% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 656.13; Retention Time: 1.96 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 656.1; Retention Time: 1.93 min. $^1$H NMR (500 MHz, MeOH-d$_4$) δ 9.11-9.00 (m, 1H), 8.73-8.63 (m, 1H), 8.24-8.15 (m, 1H), 7.89 (dd, J=5.3, 2.6 Hz, 1H), 7.80-7.63 (m, 2H), 7.43-7.37 (m, 1H), 6.99 (td, J=8.6, 2.9 Hz, 1H), 6.83-6.74 (m, 1H), 6.64-6.64 (m, 1H), 6.67-6.56 (m, 1H), 5.00-4.56 (m, 2H), 4.08-3.94 (m, 3H), 3.42-3.35 (m, 1H), 3.15 (s, 1H), 2.51-2.39 (m, 2H), 1.41-1.33 (m, 1H), 1.14-0.99 (m, 1H) which was a mix of stereoisomers due to the racemization in a reaction earlier in the sequence.

Examples 30 to CI38 were prepared and purified according to the general procedure described for Example 29 and by using appropriate reagents.

N-[(1S)-1-{3-[4-(difluoromethoxy)phenyl]-4-oxo-3H,4H-pyrido[2,3-d]pyrimidin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide: (Example 30)

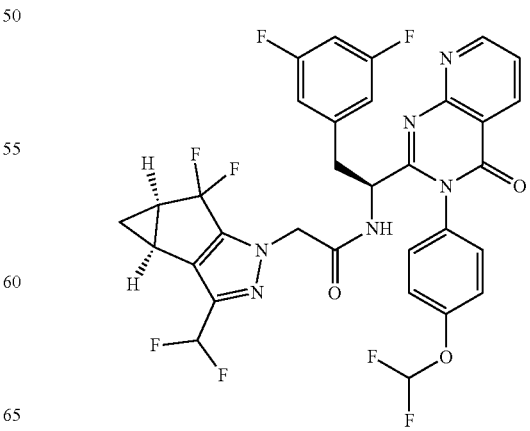

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 37-77% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 691.08; Retention Time: 2.06 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 691.1; Retention Time: 2.03 min. $^1$H NMR (500 MHz, MeOH-d$_4$) δ 9.10-9.01 (m, 1H), 8.68 (br d, J=7.6 Hz, 1H), 7.68 (dd, J=7.9, 4.6 Hz, 1H), 7.55-7.46 (m, 1H), 7.40-7.32 (m, 2H), 7.29-7.19 (m, 1H), 7.13-6.66 (m, 3H), 6.61-6.49 (m, 2H), 5.10-4.51 (m, 1H), 3.11-2.97 (m, 1H), 2.53-2.39 (m, 2H), 1.98 (s, 2H), 1.41-1.30 (m, 1H), 1.08 (s, 1H) which was a mix of stereoisomers due to the racemization in a reaction earlier in the sequence.

2-[(2S,4R)-9-(difluoromethyl)-5,5-difluoro-7,8-diazatricyclo[4.3.0.0$^{2,4}$]nona-1(6),8-dien-7-yl]-N-[(1S)-2-(3,5-difluorophenyl)-1-[4-oxo-3-(3-oxo-2,3-dihydro-1H-isoindol-5-yl)-3H,4H-pyrido[2,3-d]pyrimidin-2-yl]ethyl]acetamide: (Example 31)

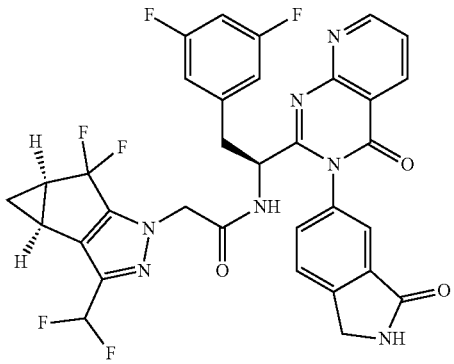 [SMILES: O=C(Cn1nc(C(F)F)c2c1C(F)(F)[C@@H]1C[C@H]21)N[C@@H](Cc1cc(F)cc(F)c1)c1nc2ncccc2c(=O)n1-c1ccc2c(c1)C(=O)NC2]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 24-64% B over 22 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 680.13, 680.13; Retention Time: 1.6, 1.64 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 680.1; Retention Time: 1.62 min. $^1$H NMR (500 MHz, MeOH-d$_4$) δ 9.11-9.03 (m, 1H), 8.70 (br d, J=7.9 Hz, 1H), 7.86-7.77 (m, 1H), 7.65 (s, 2H), 7.42 (br d, J=6.7 Hz, 1H), 6.82-6.46 (m, 4H), 4.92-4.53 (m, 5H), 3.51-3.40 (m, 1H), 3.11-3.03 (m, 1H), 2.49-2.38 (m, 2H), 1.42-1.30 (m, 1H), 1.10-0.99 (m, 1H) which was a mix of stereoisomers due to the racemization in a reaction earlier in the sequence.

2-[(2S,4R)-9-(difluoromethyl)-5,5-difluoro-7,8-diazatricyclo[4.3.0.0$^{2,4}$]nona-1(6),8-dien-7-yl]-N-[(1S)-2-(3,5-difluorophenyl)-1-{3-[4-(dimethylsulfamoyl)phenyl]-4-oxo-3H,4H-pyrido[2,3-d]pyrimidin-2-yl}ethyl]acetamide (Example 32)

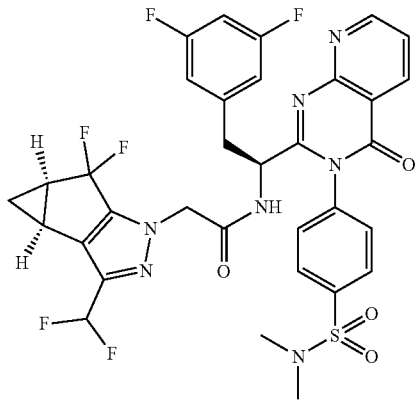 [SMILES: CN(C)S(=O)(=O)c1ccc(-n2c([C@H](Cc3cc(F)cc(F)c3)NC(=O)Cn3nc(C(F)F)c4c3C(F)(F)[C@@H]3C[C@H]43)nc3ncccc3c2=O)cc1]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 34-74% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 732.12; Retention Time: 1.96 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 732.1; Retention Time: 1.93 min. $^1$H NMR (500 MHz, DMSO-$d_6$) δ 9.07-8.94 (m, 1H), 8.90-8.82 (m, 1H), 8.38-8.31 (m, 1H), 7.83-7.59 (m, 3H), 7.53-7.40 (m, 2H), 6.88-6.57 (m, 2H), 6.39 (br d, J=6.7 Hz, 2H), 4.62-4.28 (m, 3H), 3.09-3.00 (m, 1H), 2.82-2.70 (m, 1H), 2.43-2.38 (m, 6H), 2.29 (br s, 8H), 1.16 (br d, J=6.1 Hz, 1H), 0.73-0.62 (m, 1H) Sample is a mix of stereoisomers.

5-{2-[(1S)-1-{2-[(2S,4R)-9-(difluoromethyl)-5,5-difluoro-7,8-diazatricyclo[4.3.0.0$^{2,4}$]nona-1(6),8-dien-7-yl]acetamido}-2-(3,5-difluorophenyl)ethyl]-4-oxo-3H,4H-pyrido[2,3-d]pyrimidin-3-yl}-2-fluorobenzamide (Example 33)

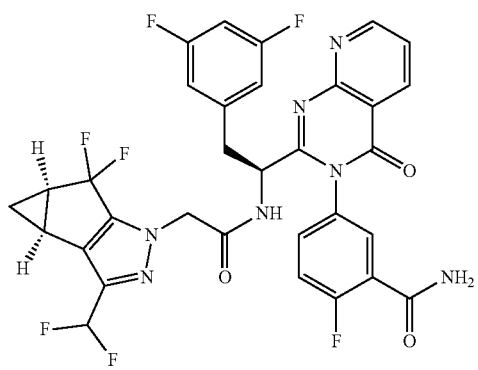 [SMILES: NC(=O)c1cc(-n2c([C@H](Cc3cc(F)cc(F)c3)NC(=O)Cn3nc(C(F)F)c4c3C(F)(F)[C@@H]3C[C@H]43)nc3ncccc3c2=O)ccc1F]

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 14-54% B over 27 minutes, then a 6-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 686.11, 686.11; Retention Time: 1.66, 1.71 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 686.11, 686.11; Retention Time: 1.62, 1.67 min. $^1$H NMR (500 MHz, MeOH-$d_4$) δ9.15-8.97 (m, 1H), 8.67 (br d, J=7.9 Hz, 1H), 7.86-7.55 (m, 3H), 7.86-7.21 (m, 4H), 6.85-6.52 (m, 4H), 4.99-4.62 (m, 1H), 3.49-3.35 (m, 1H), 3.16-3.04 (m, 1H), 2.51-2.39 (m, 2H), 1.42-1.31 (m, 1H), 1.12-0.99 (m, 1H) [some peaks may be under the solvent peak].

2-Chloro-5-{2-[(1S)-1-{2-[(2S,4R)-9-(difluoromethyl)-5,5-difluoro-7,8-diazatricyclo[4.3.0.0$^{2,4}$]nona-1(6),8-dien-7-yl]acetamido}-2-(3,5-difluorophenyl)ethyl]-4-oxo-3H,4H-pyrido[2,3-d]pyrimidin-3-yl}benzamide: (Example 34)

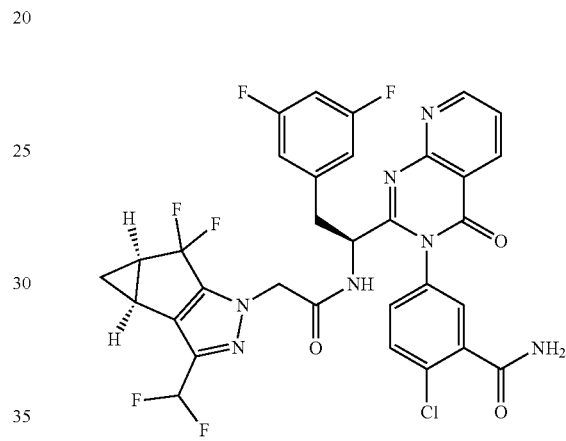

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 28-68% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 702.14, 702.14; Retention Time: 1.77, 1.85 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 702.11, 702.11; Retention Time: 1.77, 1.85 min.

167

2-[(2S,4R)-9-(difluoromethyl)-5,5-difluoro-7,8-diazatricyclo[4.3.0.0²,⁴]nona-1(6),8-dien-7-yl]-N-[(1S)-2-(3,5-difluorophenyl)-1-{4-oxo-3-[4-(propan-2-yl)phenyl]-3H,4H-pyrido[2,3-d]pyrimidin-2-yl}ethyl]acetamide (Example 35)

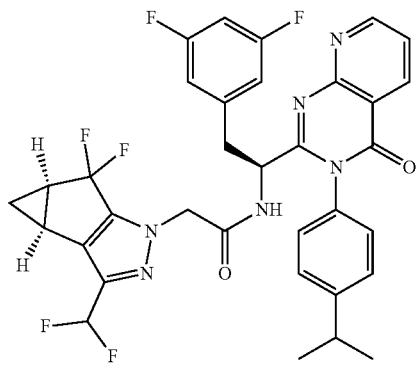

Mixture of indicated and other stereoisomers

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 43-83% B over 20 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 667.23; Retention Time: 2.3 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 667.23; Retention Time: 2.31 min. $^1$H NMR (500 MHz, MeOH-$d_4$) δ 9.07-8.96 (m, 1H), 8.72-8.63 (m, 1H), 7.66 (dd, J=7.9, 4.6 Hz, 1H), 7.54 (br d, J=7.9 Hz, 2H), 7.47-7.40 (m, 1H), 7.29-7.24 (m, 1H), 6.81-6.53 (m, 2H), 6.40 (br d, J=6.4 Hz, 2H), 5.10-4.50 (m, 2H), 3.25 (br dd, J=14.2, 4.1 Hz, 1H), 3.08 (dt, J=13.7, 6.9 Hz, 1H), 2.96-2.88 (m, 1H), 2.49-2.38 (m, 2H), 1.36 (br d, J=6.7 Hz, 7H), 1.08-1.03 (m, 1H).

168

N-[(1S)-1-[3-(1,3-benzothiazol-6-yl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0²,⁴]nona-1(6),8-dien-7-yl]acetamide (Example 36)

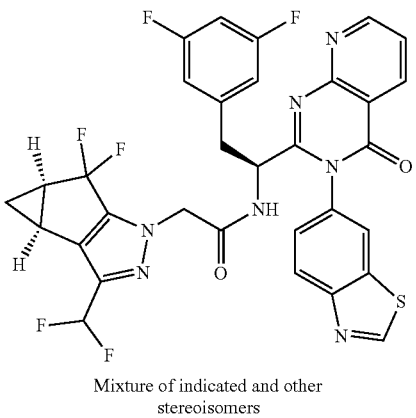 [SMILES: O=C(Cn1nc(C(F)F)c2c1C(F)(F)[C@@H]1C[C@H]21)N[C@@H](Cc1cc(F)cc(F)c1)c1nc2ncccc2c(=O)n1-c1ccc2ncsc2c1]

Mixture of indicated and other stereoisomers

The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 25% B, 25-65% B over 23 minutes, then a 5-minute hold at 100% B; Flow Rate: 20 mL/min; Column Temperature: 25° C. Fraction collection was triggered by UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 682.1; Retention Time: 1.84 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 682.09; Retention Time: 1.91 min. Final Product: (66 mg, a mixture of stereoisomers): $^1$H NMR (500 MHz, MeOH-$d_4$) δ 9.11-8.99 (m, 1H), 8.73-8.65 (m, 1H), 8.43-8.33 (m, 1H), 7.88-7.55 (m, 3H), 7.39-7.04 (m, 1H), 6.84-6.53 (m, 2H), 6.47-6.31 (m, 2H), 4.91-4.71 (m, 1H), 3.37 (br s, 1H), 3.03-2.91 (m, 1H), 2.71-2.62 (m, 1H), 2.50-2.37 (m, 2H), 1.41-1.30 (m, 2H), 1.08-1.00 (m, 1H). LC/MS: m/z=682.1 [M+H]$^+$.

Tert-butyl (S)-(1-(6-bromo-4-oxo-4H-pyrido[2,3-d][1,3]oxazin-2-yl)-2-(3,5-difluorophenyl)ethyl)carbamate (Int CI6a)

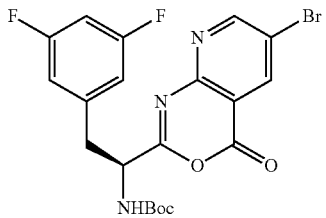 [SMILES: CC(C)(C)OC(=O)N[C@@H](Cc1cc(F)cc(F)c1)c1nc2ncc(Br)cc2c(=O)o1]

To a solution of (S)-2-((tert-butoxycarbonyl)amino)-3-(3,5-difluorophenyl)propanoic acid (2.4 g, 7.97 mmol) in DCM (106 mL) was added N-methylmorpholine (2.2 mL, 19.91 mmol) followed by isobutyl chloroformate (2.1 mL, 15.93 mmol). The clear colorless reaction was then cooled to −20° C. (IPA, dry ice). 2-amino-5-bromonicotinic acid (1.73 g, 7.97 mmol) was then added and the slurry was allowed to slowly warm to ambient temperature over 2 h as cold bath thawed. The hazy orange solution was stirred for 18 h, then heated at 45° C. for 2 h and cooled to rt. The reaction was diluted with EtOAc. The organic mixture was washed with saturated aqueous sodium bicarbonate and brine. The organic layer was then dried (Na$_2$SO$_4$) and concentrated. The crude product was triturated from ether and filtered to provide the product as an off-white colored solid (1.4 g). $^1$H NMR (500 MHz, CDCl$_3$) δ 9.04 (d, J=2.2 Hz, 1H), 8.67 (d, J=2.4 Hz, 1H), 6.72 (br d, J=7.6 Hz, 3H), 5.43 (br d, J=7.6 Hz, 1H), 5.02 (br d, J=5.7 Hz, 1H), 3.38 (br dd, J=13.8, 4.8 Hz, 1H), 3.17 (br dd, J=13.5, 7.5 Hz, 1H), 1.45 (s, 9H).

Tert-butyl (S)-(1-(6-bromo-3-(4-cyclopropylphenyl)-4-oxo-3,4-dihydropyrido[2,3-d]pyrimidin-2-yl)-2-(3,5-difluorophenyl)ethyl)carbamate (Int CI6b)

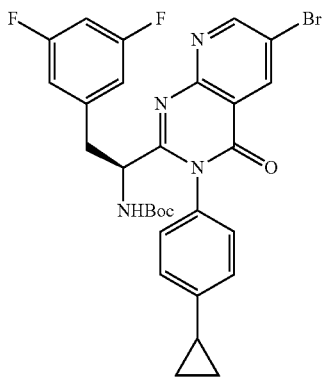 [SMILES: CC(C)(C)OC(=O)N[C@@H](Cc1cc(F)cc(F)c1)c1nc2ncc(Br)cc2c(=O)n1-c1ccc(C2CC2)cc1]

A mixture of tert-butyl (S)-(1-(6-bromo-4-oxo-4H-pyrido[2,3-d][1,3]oxazin-2-yl)-2-(3,5-difluorophenyl)ethyl)carbamate (Int CI6a, 0.35 g, 0.726 mmol) and 4-cyclopropylaniline (0.106 g, 0.798 mmol) in DCE (2.9 mL) was stirred at rt for 18 h. The reaction mixture was treated with isobutyl chloroformate (0.1 ml, 0.87 mmol) and N-methylmorpholine (0.1 ml, 0.87 mmol), then stirred at rt for 2 h and diluted with ethyl acetate, washed with sat NaHCO$_3$, dried over Na$_2$SO$_4$ and concentrated. The residue was purified on silica gel (40 g Isco column) using 0-60% ethyl acetate in hexanes. The desired fractions were concentrated to give a yellow solid (0.37 g) which was a mix of stereoisomers due to the racemization in a reaction earlier in the sequence. LC/MS: m/z=597.3 [M+H]$^+$.

Tert-butyl (S)-(1-(6-bromo-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)carbamate (Int CI6c)

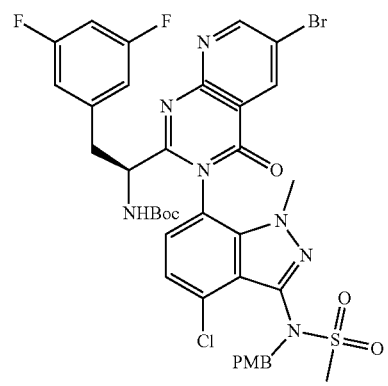

A mixture of stereoisomers due to the racemization in a reaction earlier in the sequence. LC/MS: m/z=880.3 [M+Na].

(S)-2-(1-amino-2-(3,5-difluorophenyl)ethyl)-6-bromo-3-(4-cyclopropylphenyl)pyrido[2,3-d]pyrimidin-4(3H)-one hydrochloride (Int CI6d)

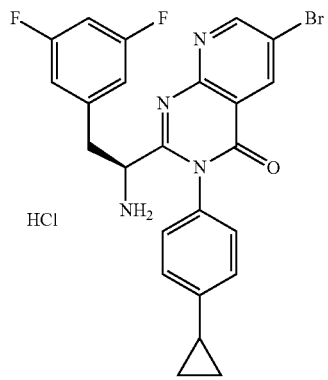 [SMILES: N[C@@H](Cc1cc(F)cc(F)c1)c1nc2ncc(Br)cc2c(=O)n1-c1ccc(C2CC2)cc1 ; Cl]

HCl (9.4 mL, 37.5 mmol) was added to a solution of tert-butyl (S)-(1-(6-bromo-3-(4-cyclopropylphenyl)-4-oxo-3,4-dihydropyrido[2,3-d]pyrimidin-2-yl)-2-(3,5-difluorophenyl)ethyl) carbamate (Int CI6b, 0.373 g, 0.624 mmol) in DCM (0.5 mL) and the mixture was stirred at rt for 0.5 h and concentrated to give a pale yellow solid (used as is) which was a mix of stereoisomers due to the racemization in a reaction earlier in the sequence. LC/MS: m/z=499.0 [M+H]$^+$.

171

(S)—N-(7-(2-(1-amino-2-(3,5-difluorophenyl)ethyl)-6-bromo-4-oxopyrido[2,3-d]pyrimidin-3(4H)-yl)-4-chloro-1-methyl-1H-indazol-3-yl)-N-(4-methoxybenzyl)methanesulfonamide hydrochloride (Int CI6e)

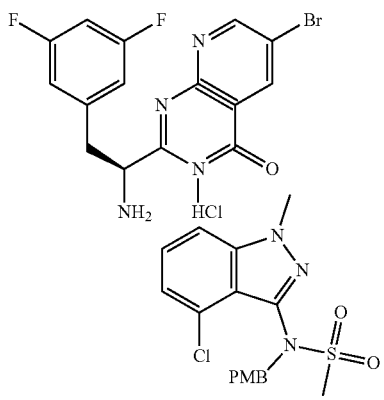

A mixture of stereoisomers due to the racemization in a reaction earlier in the sequence. LC/MS: m/z=758.3 [M+H]⁺.

N—((S)-1-(6-bromo-3-(4-cyclopropylphenyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI6f)

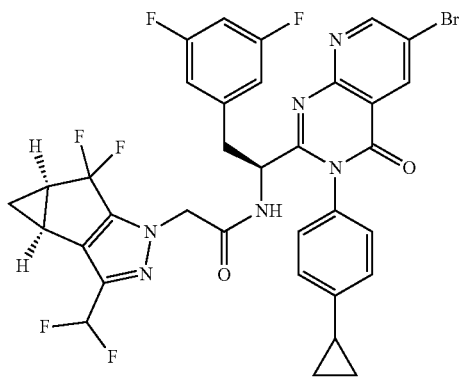 [SMILES: O=C(Cn1nc(C(F)F)c2c1C(F)(F)[C@@H]1C[C@H]21)N[C@@H](Cc1cc(F)cc(F)c1)c1nc2ncc(Br)cc2c(=O)n1-c1ccc(C2CC2)cc1]

To a stirred solution of 2-((3bS,4aR)-3-(difluoromethyl)-5,5-difluoro-3b,4,4a,5-tetrahydro-1H-cyclopropa[1,2-c]pyrazol-1-yl)acetic acid (0.074 g, 0.281 mmol) in DMF (2 mL) were added (S)-2-(1-amino-2-(3,5-difluorophenyl)ethyl)-6-bromo-3-(4-cyclopropylphenyl)pyrido[2,3-d]pyrimidin-4(3H)-one hydrochloride (Int CI6d, 0.15 g, 0.281 mmol), 2-(3H-[1,2,3]triazolo[4,5-b]pyridin-3-yl)-1,1,3,3-tetramethylisouronium hexafluorophosphate(V) (0.107 g, 0.281 mmol) and DIPEA (0.1 mL, 0.562 mmol). The reaction mixture was stirred at rt for 2 h and purified on silica (40 g Isco column) using 5-100% ethyl acetate in hexanes. The desired fractions were concentrated to give an off-white solid (0.17 g) which was a mix of stereoisomers due to the racemization in a reaction earlier in the sequence. LC/MS: m/z=743.1 [M+H]⁺.

172

N—((S)-1-(6-bromo-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI6g)

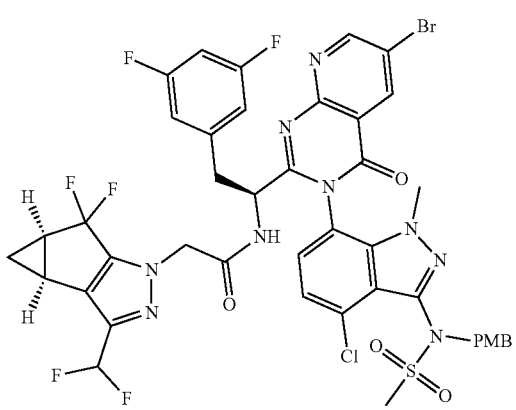

Mixture of indicated and other stereoisomers

To a stirred solution of (S)—N-(7-(2-(1-amino-2-(3,5-difluorophenyl)ethyl)-6-bromo-4-oxopyrido[2,3-d]pyrimidin-3(4H)-yl)-4-chloro-1-methyl-1H-indazol-3-yl)-N-(4-methoxybenzyl)methanesulfonamide hydrochloride (Int CI6e, 0.090 g, 0.114 mmol) in DMF (1 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.030 g, 0.114 mmol), HATU (0.045 g, 0.119 mmol) and DIPEA (0.040 mL, 0.227 mmol). The mixture was stirred for 2 h and purified on silica gel (40 g Isco column) using 0-100% ethyl acetate in hexanes. The desired fractions were concentrated to give a light brown oil (0.13 g). A mixture of stereoisomers. LC/MS: m/z=1004.3 [M+H]⁺.

N—((S)-1-(3-(4-chloro-3-(N-(4-methoxybenzyl)methylsulfonamido)-1-methyl-1H-indazol-7-yl)-6-cyano-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI6h)

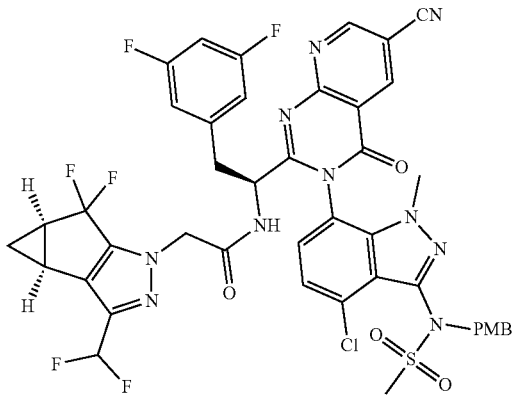

A mixture of indicated and other stereoisomers

A mixture of N—((S)-1-(6-bromo-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI6g, 0.05 g, 0.050 mmol), dicyanozine (4.09 mg, 0.035 mmol) and t-BuXPhos Pd G3 (1.976 mg, 2.487 μmol) in THF (0.4 mL)/water (1.6 mL) was degassed for 5 min, and heated in a microwave at 60 C for 2 h. The reaction mixture was diluted with DCM. The organic layer was dried over $Na_2SO_4$ and concentrated (the residue was used in the next step without purification).

N-(1-(3-(4-chloro-1-methyl-3-(methylsulfonamido)-1H-indazol-7-yl)-6-cyano-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 37.1 & 37.2);
N-(1-(6-bromo-3-(4-chloro-1-methyl-3-(methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 38.1 & 38.2)

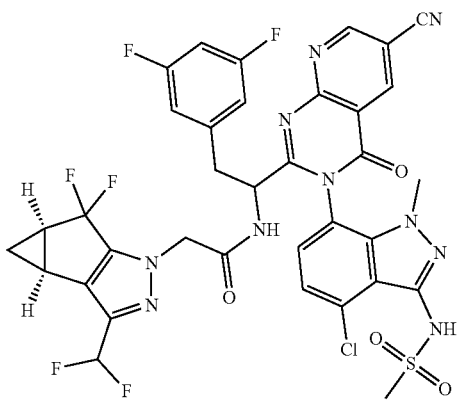

Two elutes, each as a mixture of stereoiosmer, isolated
Example 37.1 & 37.2

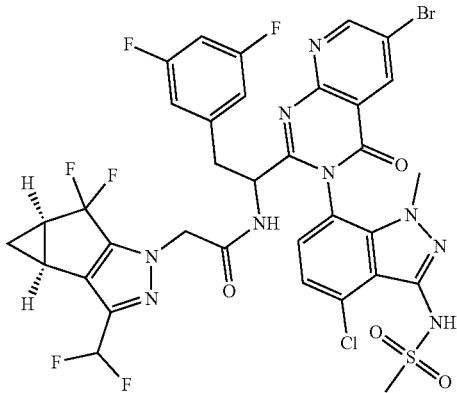

Two elutes, each as a mixture of stereoiosmer, isolated
Example 38.1 & 38.2

N—((S)-1-(3-(4-chloro-3-(N-(4-methoxybenzyl)methylsulfonamido)-1-methyl-1H-indazol-7-yl)-6-cyano-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.047 g, 0.049 mmol) in DCM were added triflic acid (0.013 ml, 0.148 mmol) and TFA (0.66 ml) and the mixture was stirred at rt for 1 h and concentrated. The crude material was purified by XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.1%; Observed Mass: 831.06; Retention Time: 1.88 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.4%; Observed Mass: 831.05; Retention Time: 1.9 min. Detection: MS and UV (220 nm). Two elutes were isolated.

Example 37.1 First Elute (6 mg, a Mixture of Stereoisomers)

LC/MS: m/z=831.1[M+H]$^+$.

Example 37.2 Second Elute (5 mg, a Mixture of Stereoisomers)

$^1$H NMR (500 MHz, MeOH-d$_4$) δ 9.41-9.33 (m, 1H), 9.14-9.07 (m, 1H), 7.39-7.32 (m, 2H), 6.84-6.51 (m, 4H), 4.66-4.50 (m, 2H), 3.70-3.63 (m, 3H), 3.52-3.45 (m, 1H), 3.30-3.22 (m, 4H), 3.18-3.11 (m, 1H), 2.47-2.38 (m, 2H), 1.40-1.32 (m, 2H), 1.04-0.97 (m, 1H). LC/MS: m/z=831.1 [M+H]$^+$.

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 883.97; Retention Time: 2.06 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 884.11; Retention Time: 2.07 min. Two elutes were isolated.

Example 38.1

Third elute (4 mg, a mixture of stereoisomers). $^1$H NMR (500 MHz, MeOH-$d_4$) δ 9.27-9.15 (m, 1H), 8.90-8.82 (m, 1H), 7.46-7.20 (m, 2H), 6.90-6.47 (m, 4H), 4.86-4.71 (m, 1H), 3.42-3.35 (m, 2H), 3.29 (s, 3H), 3.20-3.17 (m, 3H), 3.01-2.94 (m, 1H), 2.55-2.47 (m, 2H), 2.03-1.90 (m, 1H), 1.45-1.37 (m, 1H), 1.12-1.06 (m, 1H). LC/MS: m/z=884.0 [M+H]$^+$.

Example 38.2

Fourth elute (4 mg, a mixture of stereoisomers). $^1$H NMR (500 MHz, MeOH-$d_4$) δ 9.22-9.12 (m, 1H), 8.89-8.81 (m, 1H), 7.38-7.26 (m, 2H), 6.83-6.53 (m, 4H), 4.60-4.49 (m, 2H), 3.70-3.59 (m, 3H), 3.51-3.41 (m, 1H), 3.29-3.23 (m, 3H), 3.17-3.03 (m, 1H), 2.48-2.36 (m, 2H), 1.40-1.30 (m, 2H), 1.05-0.96 (m, 1H). LC/MS: m/z=884.0 [M+H]$^+$.

N-[(1S)-1-[6-cyano-3-(4-cyclopropylphenyl)-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Example 39)

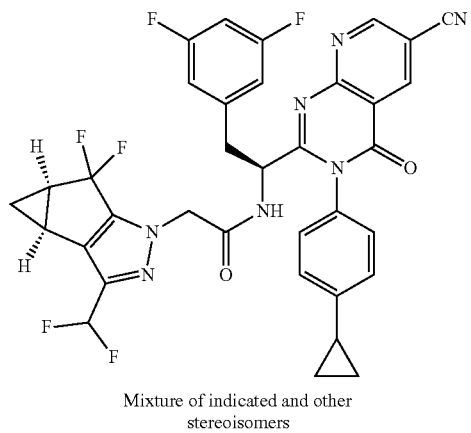 [SMILES: N#Cc1cnc2nc([C@H](Cc3cc(F)cc(F)c3)NC(=O)Cn3nc(C(F)F)c4c3C(F)(F)[C@@H]3C[C@H]43)n(-c3ccc(C4CC4)cc3)c(=O)c2c1]

Mixture of indicated and other stereoisomers ((S)-1-(6-bromo-3-(4-cyclopropylphenyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI6f, 0.05 g, 0.067 mmol), dicyanozine (5.53 mg, 0.047 mmol) and t-BuXPhos Pd G3 (2.67 mg, 3.36 µmol) in THF (0.3 mL)/water (1.1 mL) was degassed for 5 min, and heated in a microwave at 60° C. for 2 h. The reaction mixture was diluted with DMF and filtered. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 38-83% B over 20 minutes, then a 5-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 690.12; Retention Time: 2.27 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 690.14; Retention Time: 2.28 min. $^1$H NMR (500 MHz, MeOH-$d_4$) δ 9.36-9.23 (m, 1H), 9.05-8.93 (m, 1H), 7.42-7.29 (m, 3H), 7.20 (br t, J=6.1 Hz, 1H), 6.83-6.52 (m, 2H), 6.40 (br t, J=6.9 Hz, 2H), 5.03-4.46 (m, 2H), 3.27-3.16 (m, 1H), 2.93 (ddd, J=14.1, 9.7, 4.6 Hz, 1H), 2.50-2.38 (m, 2H), 2.13-1.92 (m, 1H), 1.42-1.28 (m, 1H), 1.14-0.98 (m, 3H), 0.90-0.75 (m, 2H).

Tert-butyl(S)-(1-(7-chloro-4-oxo-4H-pyrido[2,3-d][1,3]oxazin-2-yl)-2-(3,5-difluorophenyl)ethyl)carbamate (Int CI7a)

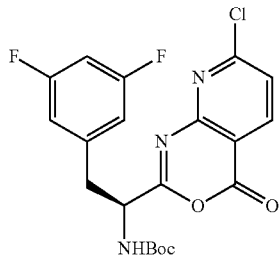 [SMILES: CC(C)(C)OC(=O)N[C@@H](Cc1cc(F)cc(F)c1)c1nc2nc(Cl)ccc2c(=O)o1]

Int CI7a was prepared according to the general procedure described for Int CI6a.

N—((S)-1-(7-chloro-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI7b)

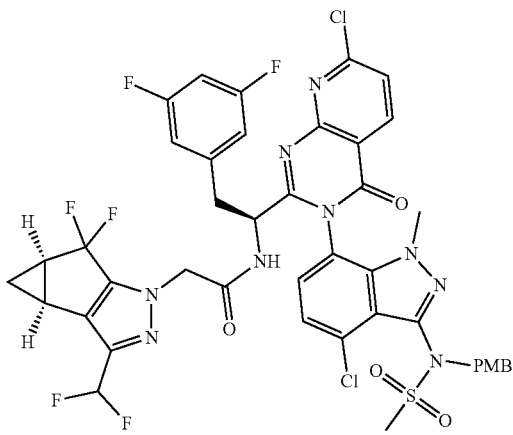

Mixture of indicated and other stereoisomers

Int CI7b was prepared according to the general procedure described for Int CI6g using Int CI7a. LC/MS: m/z=960.4 [M+H]+.

N—((S)-1-(3-(4-chloro-3-(N-(4-methoxybenzyl)methylsulfonamido)-1-methyl-1H-indazol-7-yl)-7-cyano-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI7c)

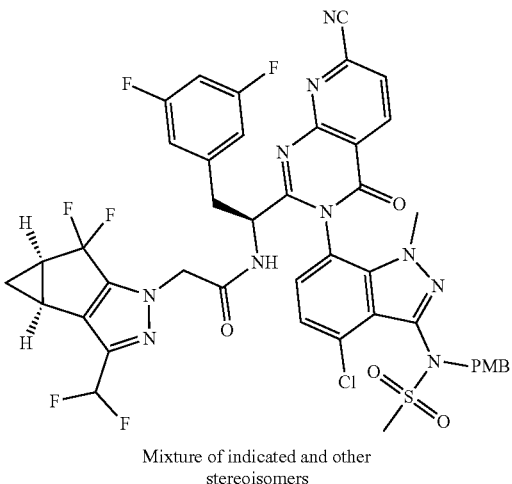

Mixture of indicated and other stereoisomers

N—((S)-1-(7-chloro-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI7b, 0.05 g, 0.052 mmol), dicyanozine (4.28 mg, 0.036 mmol) and t-BuXPhos Pd G3 (2.08 mg, 2.60 μmol) in DMF (2.1 mL) was degassed for 5 min, and heated in a microwave at 70 C for 2 h. The reaction mixture was concentrated (the residue was used in the next step without purification). LC/MS: m/z=951.3 [M+H]+.

N-(1-(3-(4-chloro-1l-methyl-3-(methylsulfonamido)-1H-indazol-7-yl)-7-cyano-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 40.1 & Example 40.2)

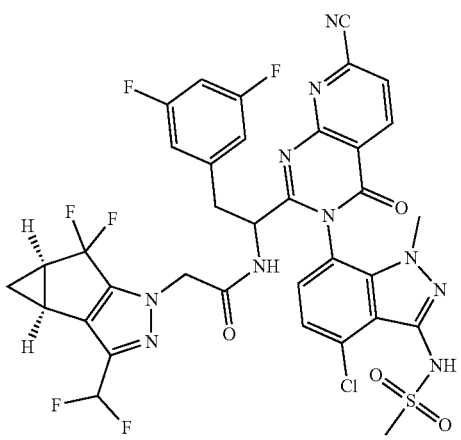

Two elutes, each as a mixture of stereoisomers

Prepared according to the general procedure described for Example 38.1 and 38.2 using Int CI7c. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 25 minutes, then a 4-minute hold at 100% B; Flow: 20 mL/min. Fractions containing the desired product were combined and dried via centrifugal evaporation. Detection: MS and UV (220 nm). Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 90.5%; Observed Mass: 831.04; Retention Time: 1.88 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 93.7%; Observed Mass: 831.03; Retention Time: 1.89 min. Two elutes of stereo isomeric relation were isolated. LC/MS: m/z=831.0[M+H]+.

Example 40.1 First Elute (3 mg, a Mixture of Stereoisomers)

Example 40.2 Second Elute (6 mg, a Mixture of Stereoisomers)

$^1$H NMR (500 MHz, MeOH-d$_4$) δ 8.70-8.60 (m, 1H), 7.79-7.71 (m, 1H), 7.43-7.36 (m, 1H), 7.32-7.24 (m, 1H), 6.88-6.44 (m, 4H), 4.92-4.61 (m, 2H), 3.40-3.36 (m, 1H), 3.30 (s, 4H), 3.20 (br s, 3H), 3.03-2.93 (m, 1H), 2.56-2.46 (m, 2H), 1.48-1.38 (m, 1H), 1.12-1.06 (m, 1H).

Tert-butyl (S)-(2-(3,5-difluorophenyl)-1-(7-methyl-4-oxo-4H-pyrido[2,3-d][1,3]oxazin-2-yl)ethyl)carbamate (Int CI8a)

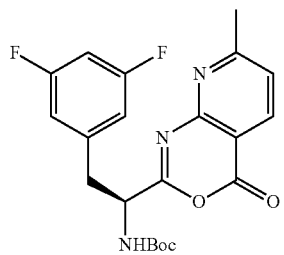 [SMILES: Cc1ccc2c(=O)oc([C@H](Cc3cc(F)cc(F)c3)NC(=O)OC(C)(C)C)nc2n1]

To a solution of (S)-2-((tert-butoxycarbonyl)amino)-3-(3, 5-difluorophenyl)propanoic acid (0.990 g, 3.29 mmol) in DCM (44 mL) was added N-methylmorpholine (0.9 ml, 8.22 mmol) followed by isobutyl chloroformate (0.86 ml, 6.57 mmol). The reaction was then cooled to −20° C. (IPA/dry ice) and 2-amino-6-methylnicotinic acid (0.5 g, 3.29 mmol) was added. The reaction slurry was allowed to slowly warm to ambient temperature overnight as bath thawed for 18 h. The reaction was heated to reflux for 2 h. Upon cooling to ambient temperature, the reaction was filtered. The filtrate was diluted with EtOAc. The organic layer was washed with saturated sodium bicarbonate, brine, dried (Na$_2$SO$_4$) and concentrated. The crude product was triturated with hexane and filtered to give the product as an off-white solid. (0.68 g).

Tert-butyl (S)-(1-(3-(4-chloro-3-(N-(4-methoxybenzyl)methylsulfonamido)-1-methyl-1H-indazol-7-yl)-7-methyl-4-oxo-3,4-dihydropyrido[2,3-d]pyrimidin-2-yl)-2-(3,5-difluorophenyl)ethyl)carbamate (Int CI8b)

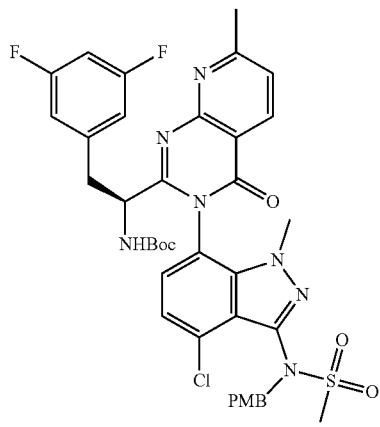

A mixture of tert-buty (S)-(2-(3,5-difluorophenyl)-1-(7-methyl-4-oxo-4H-pyrido[2,3-d][1,3]oxazin-2-yl)ethyl)carbamate (Int CI8a, 0.1 g, 0.240 mmol) and N-(7-amino-4-chloro-1-methyl-1H-indazol-3-yl)-N-(4-methoxybenzyl)methanesulfonamide (0.095 g, 0.240 mmol) in DCE (1 mL) was stirred at rt for 18 h. The reaction mixture was treated with isobutyl chloroformate (0.04 ml, 0.287 mmol) and N-methylmorpholine (0.03 ml, 0.287 mmol), then stirred at rt for 2 h and diluted with ethyl acetate, washed with sat NaHCO$_3$, dried over Na$_2$SO$_4$ and concentrated. The residue was purified on silica gel (40 g Isco column) using 5-100% ethyl acetate in hexanes. The desired fractions were concentrated to give a pink solid (0.11 g). LC/MS: m/z=794.4 [M+H]$^+$.

(S)—N-(7-(2-(1-amino-2-(3,5-difluorophenyl)ethyl)-7-methyl-4-oxopyrido[2,3-d]pyrimidin-3(4H)-yl)-4-chloro-1-methyl-1H-indazol-3-yl)-N-(4-methoxybenzyl)methanesulfonamide hydrochloride (Int CI8c)

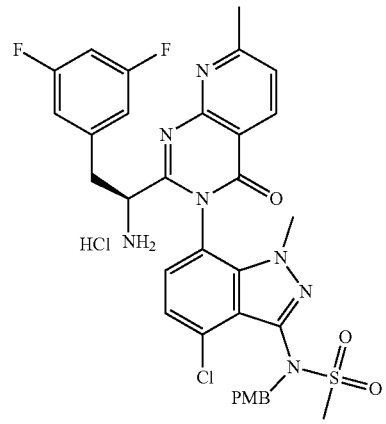

HCl (2.1 ml, 8.23 mmol) and tert-butyl (S)-(1-(3-(4-chloro-3-(N-(4-methoxybenzyl)methylsulfonamido)-1-methyl-1H-indazol-7-yl)-7-methyl-4-oxo-3,4-dihydropyrido[2,3-d]pyrimidin-2-yl)-2-(3,5-difluorophenyl)ethyl)carbamate (Int CI8b, 0.11 g, 0.137 mmol) was stirred at rt for 0.5 h and concentrated to give a pale yellow solid (used as is). LC/MS: m/z=694.4 [M+H]$^+$.

N-(1-(3-(4-chloro-3-(N-(4-methoxybenzyl)methylsulfonamido)-1-methyl-1H-indazol-7-yl)-7-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI8d)

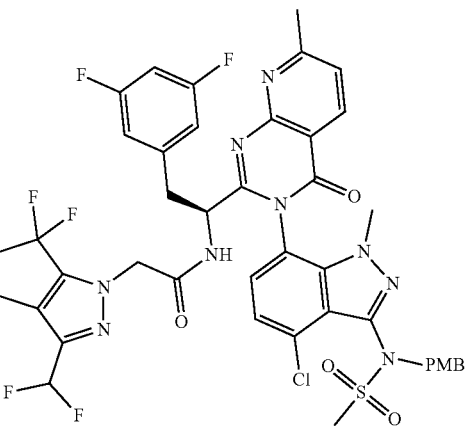

mixture of stereoisomers

To a stirred solution of (S)—N-(7-(2-(1-amino-2-(3,5-difluorophenyl)ethyl)-7-methyl-4-oxopyrido[2,3-d]pyrimidin-3(4H)-yl)-4-chloro-1-methyl-1H-indazol-3-yl)-N-(4-methoxybenzyl)methanesulfonamide hydrochloride (Int CI8c, 0.041 g, 0.057 mmol) in DMF (1.5 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetic acid (0.015 g, 0.057 mmol), HATU (0.023 g, 0.060 mmol) and DIPEA (0.020 mL, 0.114 mmol). The mixture was stirred for 2 h and purified on silica gel (12 g Isco column) using 0-100% ethyl acetate in hexanes. The desired fractions were concentrated to give a light brown oil (0.047 g). LC/MS: m/z=940.4 [M+H]$^+$.

N-[(1S)-1-[3-(4-chloro-3-methanesulfonamido-1-methyl-1H-indazol-7-yl)-7-methyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl] acetamide (Example 41.2) and Example 41.1

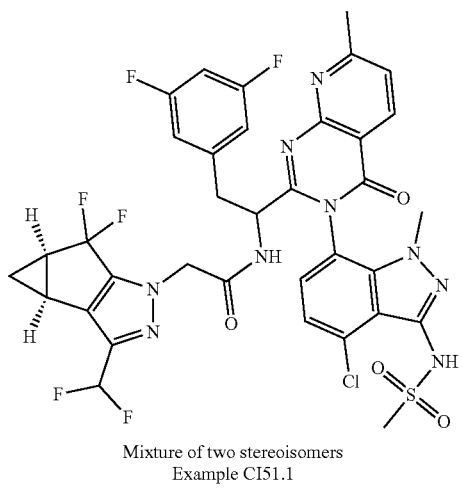

Mixture of two stereoisomers
Example CI51.1

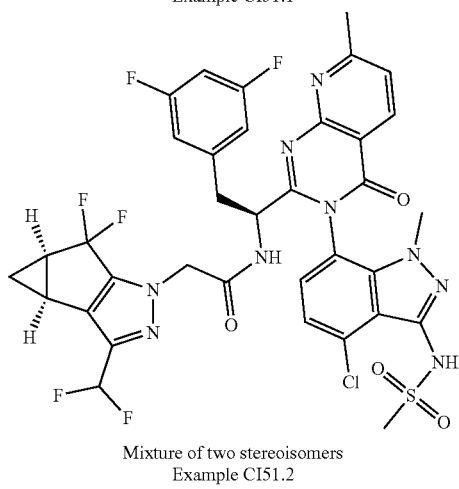

Mixture of two stereoisomers
Example CI51.2

To a solution of N—((S)-1-(3-(4-chloro-3-(N-(4-methoxybenzyl)methylsulfonamido)-1-methyl-1H-indazol-7-yl)-7-methyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI8d, 0.047 g, 0.050 mmol) in DCM (0.33 mL) were added triflic acid (0.013 ml, 0.150 mmol) and TFA (0.67 mL) and the mixture was stirred at rt for 1 h and concentrated. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 26-66% B over 25 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 820.04; Retention Time: 1.89 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 820.02; Retention Time: 1.91 min. Two elutes were isolated.

Example 41.1 First Elute (a Mixture of Stereoisomers)

$^1$H NMR (500 MHz, MeOH-d$_4$) δ 8.66-8.51 (m, 1H), 7.62 (d, J=7.9 Hz, 1H), 7.43-7.31 (m, 1H), 7.29-7.21 (m, 1H), 6.89-6.51 (m, 4H), 4.90-4.73 (m, 1H), 3.45 (br dd, J=13.6, 8.4 Hz, 1H), 3.29 (s, 3H), 3.15-3.10 (m, 3H), 3.03-2.91 (m, 1H), 2.87-2.79 (m, 3H), 2.56-2.45 (m, 2H), 2.04-1.91 (m, 1H), 1.45-1.27 (m, 1H), 1.45-1.26 (m, 1H), 1.15-1.06 (m, 1H).

Example 41.2 Second Elute, (a Mixture of Stereoisomers)

$^1$H NMR (500 MHz, MeOH-d$_4$) δ 8.64-8.54 (m, 1H), 7.65-7.56 (m, 1H), 7.34-7.19 (m, 2H), 6.85-6.53 (m, 4H), 3.70-3.59 (m, 3H), 3.52-3.46 (m, 1H), 3.29-3.24 (m, 3H), 3.19-3.09 (m, 1H), 2.82 (s, 3H), 2.47-2.38 (m, 2H), 2.07-1.92 (m, 1H), 1.49-1.19 (m, 3H), 1.01 (br s, 1H).

Tert-butyl (S)-(2-(3,5-difluorophenyl)-1-(5,7-dimethyl-4-oxo-4H-pyrido[2,3-d][1,3]oxazin-2-yl)ethyl) carbamate (Int CI9a)

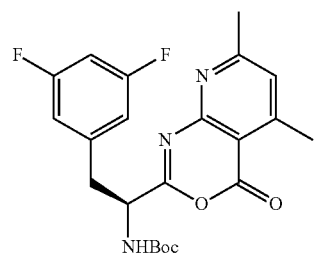

To a solution of (S)-2-((tert-butoxycarbonyl)amino)-3-(3,5-difluorophenyl)propanoic acid (0.907 g, 3.01 mmol) in DCM (40 mL) was added N-methylmorpholine (0.83 mL, 7.52 mmol) followed by isobutyl chloroformate (0.790 mL, 6.02 mmol). The reaction was then cooled to −20° C.

(IPA/dry ice) and 2-amino-4,6-dimethylnicotinic acid (0.5 g, 3.01 mmol) was added. The reaction slurry was allowed to slowly warm to ambient temperature overnight as bath thawed for 18 h. The reaction was heated to reflux for 2 h. Upon cooling to ambient temperature, the reaction was filtered. The filtrate was diluted with EtOAc. The organic layer was washed with saturated sodium bicarbonate, brine, dried (Na$_2$SO$_4$) and concentrated in vacuo. The crude product was triturated with hexane and filtered to give the product as an off-white solid. (0.46 g).

Tert-butyl (S)-(1-(3-(4-chloro-3-(N-(4-methoxybenzyl)methylsulfonamido)-1-methyl-1H-indazol-7-yl)-5,7-dimethyl-4-oxo-3,4-dihydropyrido[2,3-d]pyrimidin-2-yl)-2-(3,5-difluorophenyl)ethyl)carbamate (Int CI9b)

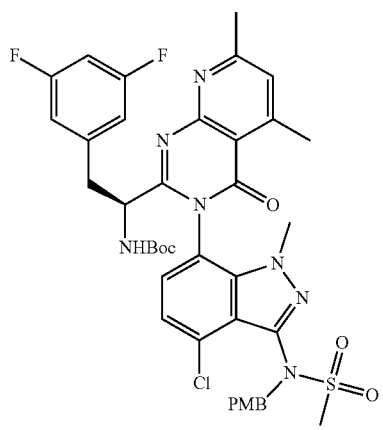

A mixture of tert-butyl (S)-(2-(3,5-difluorophenyl)-1-(5,7-dimethyl-4-oxo-4H-pyrido[2,3-d][1,3]oxazin-2-yl)ethyl)carbamate (Int CI9a, 0.079 g, 0.182 mmol) and N-(7-amino-4-chloro-1-methyl-1H-indazol-3-yl)-N-(4-methoxybenzyl)methanesulfonamide (0.072 g, 0.182 mmol) in Pyridine (0.74 ml) was heated at 70° C. for 2 h and purified on silica gel (40 g Isco column) using 0-100% ethyl acetate in hexanes. The desired fractions were concentrated to give a yellow solid (0.057 g). LC/MS: m/z=808.5 [M+H]$^+$.

(S)—N-(7-(2-(1-amino-2-(3,5-difluorophenyl)ethyl)-5,7-dimethyl-4-oxopyrido[2,3-d]pyrimidin-3(4H)-yl)-4-chloro-1-methyl-1H-indazol-3-yl)-N-(4-methoxybenzyl)methanesulfonamide hydrochloride (Int CI9c)

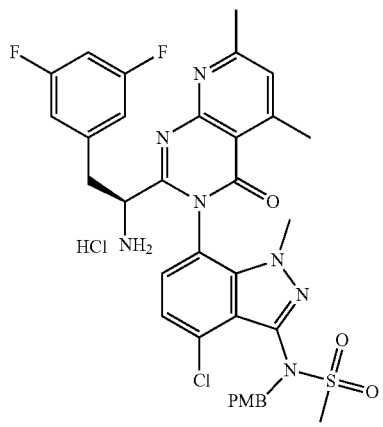

HCl (0.71 ml, 2.82 mmol) and tert-butyl (S)-(1-(3-(4-chloro-3-(N-(4-methoxybenzyl)methylsulfonamido)-1-methyl-1H-indazol-7-yl)-5,7-dimethyl-4-oxo-3,4-dihydropyrido[2,3-d]pyrimidin-2-yl)-2-(3,5-difluorophenyl)ethyl)carbamate (Int CI9b, 0.038 g, 0.047 mmol) was stirred at rt for 0.5 h and concentrated to give a pale yellow solid (used as is). LC/MS: m/z=708.4 [M+H]$^+$.

N-[(1S)-1-[3-(4-chloro-3-methanesulfonamido-1-methyl-1H-indazol-7-yl)-5,7-dimethyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Int CI9d)

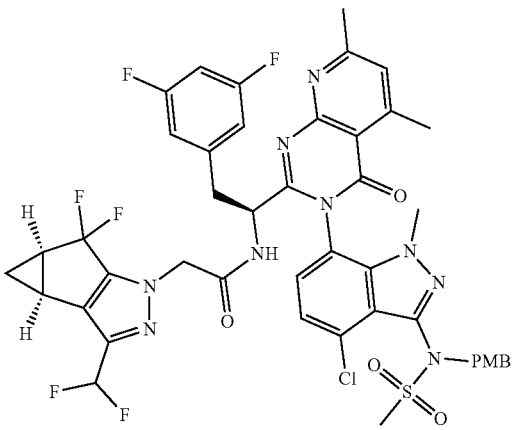

Mixture of indicated and other stereoisomers

To a stirred solution of (S)—N-(7-(2-(1-amino-2-(3,5-difluorophenyl)ethyl)-5,7-dimethyl-4-oxopyrido[2,3-d]pyrimidin-3(4H)-yl)-4-chloro-1-methyl-1H-indazol-3-yl)-N-(4-methoxybenzyl)methanesulfonamide hydrochloride (Int CI9c, 0.116 g, 0.156 mmol) in DMF (1.5 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.041 g, 0.156 mmol), HATU (0.062 g, 0.164 mmol) and DIPEA (0.06 mL, 0.312 mmol). The mixture was stirred for 2 h and purified on silica gel (40 g Isco column) using 0-100% ethyl acetate in hexanes. The desired fractions were concentrated to give a light brown oil (0.16 g). LC/MS: m/z=954.5 [M+H]$^+$.

N-[(1S)-1-[3-(4-chloro-3-methanesulfonamido-1-methyl-1H-indazol-7-yl)-5,7-dimethyl-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0²,⁴]nona-1(6),8-dien-7-yl]acetamide (Example 42.2) and Examples 42.1 & 42.3

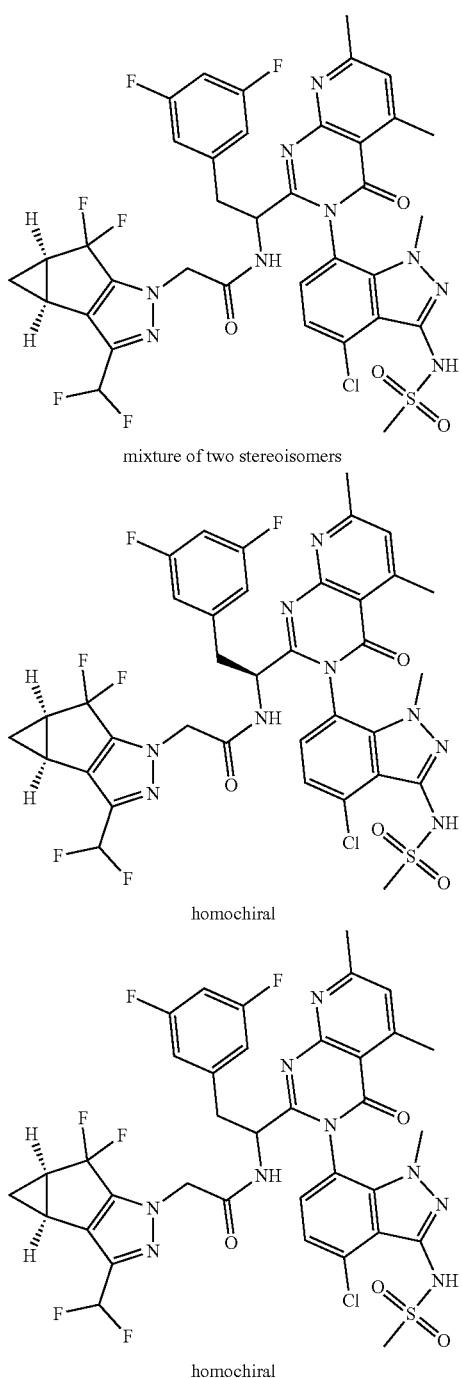

mixture of two stereoisomers homochiral homochiral

To a solution of N—((S)-1-(3-(4-chloro-3-(N-(4-methoxybenzyl)methylsulfonamido)-1-methyl-1H-indazol-7-yl)-5,7-dimethyl-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int CI9d, 0.08 g, 0.084 mmol)) in DCM (0.55 mL) were added triflic acid (0.022 ml, 0.251 mmol) and TFA (1.1 ml) and the mixture was stirred at rt for 1 h and concentrated. The crude material was purified under the following prep-HPLC condition to retrieve two isolates, each as a mixture of stereoisomers. Prep-HPLC: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-78% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 834.1; Retention Time: 1.84 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 834.07; Retention Time: 1.99 min.

Example 42.1 First Elute (32 mg, Off White Solid, a Mixture of Stereoisomers)

$^1$H NMR (500 MHz, MeOH-$d_4$) δ 7.43-7.37 (m, 1H), 7.35-7.30 (m, 1H), 7.24-7.18 (m, 1H), 6.89-6.51 (m, 4H), 4.94-4.89 (m, 1H), 4.85-4.74 (m, 2H), 3.45-3.38 (m, 1H), 3.28-3.23 (m, 3H), 3.13 (s, 3H), 3.00-2.91 (m, 1H), 2.83-2.77 (m, 3H), 2.77-2.73 (m, 3H), 2.57-2.45 (m, 2H), 1.48-1.39 (m, 1H), 1.12-1.06 (m, 1H). LC/MS: m/z=834.4 [M+H]$^+$.

Second elute (39 mg, off white solid, a mixture of stereoisomers) was further purified by Chiralpak IC preparative column, 30×250 mm, 5 μm Mobile Phase: 25% IPA in CO$_2$, 150 bar, Temp: 35° C. Flow rate: 70.0 mL/min. for 20 min. UV monitored @ 220 nm Injection: 0.5 ml of ~11 mg/mL in IPA. Two elutes were isolated.

Example 42.2 First Elute (25 mg, Off White Solid)

$^1$H NMR (500 MHz, MeOH-$d_4$) δ 7.43-7.38 (m, 1H), 7.33-7.28 (m, 1H), 7.20-7.16 (m, 1H), 6.83-6.53 (m, 4H), 4.60-4.52 (m, 2H), 3.66-3.62 (m, 3H), 3.51-3.45 (m, 2H), 3.26-3.23 (m, 3H), 3.16-3.08 (m, 1H), 2.85-2.81 (m, 3H), 2.75-2.72 (m, 3H), 2.47-2.40 (m, 2H), 1.40-1.34 (m, 1H), 1.04-0.99 (m, 1H). LC/MS: m/z=834.4 [M+H]$^+$.

Example 42.3 Second Elute (10 mg, Off White Solid, Single Stereoisomer)

$^1$H NMR (500 MHz, MeOH-$d_4$) δ 7.43-7.38 (m, 1H), 7.36-7.28 (m, 1H), 7.23-7.17 (m, 1H), 6.84-6.55 (m, 4H), 4.61-4.54 (m, 2H), 3.72-3.56 (m, 4H), 3.51-3.44 (m, 1H), 3.29-3.23 (m, 3H), 3.15-3.06 (m, 1H), 2.85-2.78 (m, 3H), 2.76-2.70 (m, 3H), 2.47-2.38 (m, 2H), 1.40-1.36 (m, 1H), 1.05-1.00 (m, 1H). LC/MS: m/z=834.4 [M+H]+.

7-bromo-4-chloro-1H-indazol-3-amine (Int CI10a)

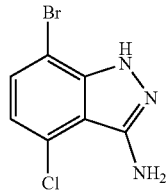 [SMILES: Nc1n[nH]c2c(Br)ccc(Cl)c12]

A solution of 3-bromo-6-chloro-2-fluorobenzonitrile (1.50 g, 6.40 mmol) in Ethanol (12.80 ml) in a microwave vial was treated with hydrazine (1.3 mL, 40.6 mmol), the mixture was heated at 120° C. in a microwave reactor for 35 min. The reaction mixture (pale yellow solid) was taken up in ethyl acetate, washed with water, brine, dried over $Na_2SO_4$ and concentrated. The residue taken up in methanol (just enough ti dissolve it), some DCM was added, then hexanes was added till a precipitate formed. Air was blown into the mixture to remove some of the DCM. The suspension was filtered and suction dried to give an off-white fluffy solid (1.5 g). $^1$H NMR (500 MHz, DMSO-$d_6$) δ 12.51-12.05 (m, 1H), 7.44 (d, J=7.9 Hz, 1H), 6.87 (d, J=7.9 Hz, 1H), 5.33 (s, 2H).

2-(7-bromo-4-chloro-1H-indazol-3-yl)isoindoline-1,3-dione (Int CI10b)

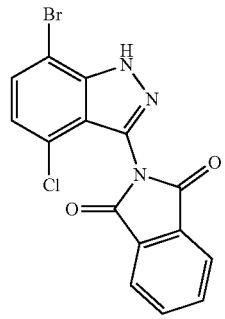 [SMILES: O=C1c2ccccc2C(=O)N1c1n[nH]c2c(Br)ccc(Cl)c12]

Phthalic anhydride (1.352 g, 9.13 mmol) was added to a solution of 7-bromo-4-chloro-1H-indazol-3-amine (Int CI 10a, 1.5 g, 6.09 mmol) in Dioxane (20 mL) in a microwave vial and heated at 150° C. for 2 h in a microwave reactor. The reaction mixture was concentrated. The beige solid was purified on silica gel (220 g, Isco column) using 0-40% ethyl acetate in hexanes. The desired fractions were concentrated to give a light pink solid (1.2 g). $^1$H NMR (500 MHz, DMSO-$d_6$) δ 14.57-14.29 (m, 1H), 8.14-8.08 (m, 2H), 8.05-7.99 (m, 2H), 7.76-7.72 (m, 1H), 7.26-7.21 (m, 1H). LC/MS: m/z=377.9 [M+2H]+.

2-(7-bromo-4-chloro-1-cyclopropyl-1H-indazol-3-yl)isoindoline-1,3-dione (Int CI10c)

A round bottom flask was charged with 2-(7-bromo-4-chloro-1H-indazol-3-yl)isoindoline-1,3-dione (Int CI10b, 0.988 g, 2.62 mmol), cyclopropylboronic acid (0.676 g, 7.87 mmol), sodium carbonate (0.834 g, 7.87 mmol), copper (II) acetate (0.477 g, 2.62 mmol) and 2,2'-bipyridine (0.410 g, 2.62 mmol) which were suspended in DCE (26.2 ml), flushed with nitrogen and heated at 80° C. for 6h. The reaction mixture was filtered and concentrated. The residue was purified on silica (220 g Isco column) using 0-40% ethyl acetate in hexanes. The desired fractions were concentrated to give a pale yellow solid (0.52 g). LC/MS: m/z=415.8 [M+H]+.

7-bromo-4-chloro-1-cyclopropyl-1H-indazol-3-amine (CIInt 10d)

A mixture of 2-(7-bromo-4-chloro-1-cyclopropyl-1H-indazol-3-yl)isoindoline-1,3-dione (Int CI10c, 0.92 g, 2.208 mmol) and hydrazine hydrate (0.54 mL, 11.04 mmol) in Ethanol (18.40 mL)/THF (18.40 mL) was stirred at rt for 3 h and concentrated. The residue was dissolved in DMSO and purified on silica gel (120 g Isco column) using 10-100% ethyl acetate. The desired fraction were concentrated to give a pale yellow solid (0.5 g). $^1$H NMR (500 MHz, CDCl$_3$) δ 7.47-7.36 (m, 1H), 6.83-6.70 (m, 1H), 4.62-4.40 (m, 2H), 3.89-3.74 (m, 1H), 1.35-1.30 (m, 2H), 1.16-1.11 (m, 2H).

N-(7-bromo-4-chloro-1-cyclopropyl-1H-indazol-3-yl)methanesulfonamide (Int CI10e)

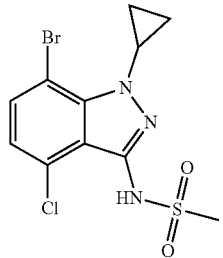 [SMILES: CS(=O)(=O)Nc1nn(C2CC2)c2c(Br)ccc(Cl)c12]

To a solution of 7-bromo-4-chloro-1-cyclopropyl-1H-indazol-3-amine (Int CI10d, 0.250 g, 0.872 mmol) in DCM (4.4 mL) was added DIPEA (0.610 ml, 3.49 mmol) then the reaction was cooled in an ice bath and methane sulfonyl chloride (0.14 ml, 1.745 mmol) was added. The reaction mixture was stirred at this temperature for 1 h (precipitate formed). Mixture was then diluted with dichloromethane (10 mL) and washed with water, 1 M HCl and brine, dried ($Na_2SO_4$), filtered and concentrated in vacuo to give a light yellow solid. The residue was taken up in EtOH (10 mL) and 5 ml of 20% aq. NaOH. The resulted mixture heated with a heat gun until it became a homogeneous solution and stirred at rt for 30 min. The mixture was diluted with water (20 mL) and acidified with 2 M HCl and the resultant precipitates was collected by filtration to afford the desired product as an off-white solid (0.27 g). $^1$H NMR (500 MHz, $CDCl_3$) δ 7.55-7.42 (m, 1H), 7.26-7.14 (m, 1H), 7.06-6.87 (m, 1H), 4.16-3.96 (m, 1H), 3.51-3.32 (m, 3H), 1.43-1.38 (m, 2H), 1.24-1.17 (m, 2H).

N-(7-bromo-4-chloro-1-cyclopropyl-1H-indazol-3-yl)-N-(4-methoxybenzyl)methanesulfonamide (Int CI10f)

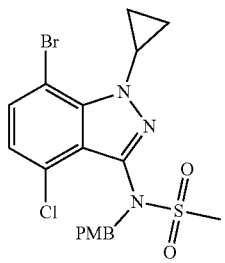

4-Methoxybenzyl chloride (0.120 ml, 0.889 mmol) was added to a mixture of N-(7-bromo-4-chloro-1-cyclopropyl-1H-indazol-3-yl)methanesulfonamide (Int CI10e, 0.27 g, 0.740 mmol) and $Cs_2CO_3$ (0.483 g, 1.481 mmol) in DMF (5.3 ml). The mixture was stirred at rt overnight. The mixture was diluted with ethyl acetate, washed with brine, dried over $Na_2SO_4$ and concentrated. The residue was purified on silica (24 g Isco column) using 0-60% ethyl acetate in hexanes. The desired fractions were concentrated to give a colorless viscous oil (0.38 g). LC/MS: m/z=484 [M+H]$^+$.

N-(4-chloro-1-cyclopropyl-7-((diphenylmethylene)amino)-1H-indazol-3-yl)-N-(4-methoxybenzyl)methanesulfonamide (Int CI10g)

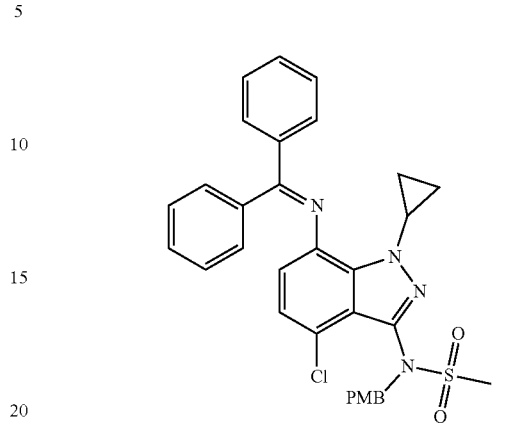

A mixture of N-(7-bromo-4-chloro-1-cyclopropyl-1H-indazol-3-yl)-N-(4-methoxybenzyl)methanesulfonamide (Int CI10f, 0.36 g, 0.743 mmol), diphenylmethanimine (0.137 ml, 0.819 mmol), $PdOAc_2$ (8.34 mg, 0.037 mmol), R-(+)-BINAP (0.069 g, 0.111 mmol) and $Cs_2CO_3$ (0.363 g, 1.114 mmol) in Dioxane (7.43 ml) was degassed for 5 min and heated in a microwave at 120° C. for 2 h. The reaction mixture filtered through Celite and concentrated. The residue was purified on silica gel (80 g Isco column) using 0-30% ethyl acetate, the desired fractions were concentrated to give a bright yellow solid (0.28 g). $^1$H NMR (400 MHz, $CDCl_3$) δ 7.87-7.76 (m, 2H), 7.58-7.32 (m, 7H), 7.26-7.20 (m, 2H), 7.16-7.10 (m, 2H), 6.85-6.79 (m, 1H), 6.75-6.69 (m, 1H), 6.09-6.01 (m, 1H), 5.04-4.61 (m, 2H), 4.18-4.08 (m, 1H), 3.80 (s, 1H), 3.84-3.74 (m, 1H), 3.01-3.00 (m, 1H), 2.97 (s, 1H), 1.24-1.15 (m, 2H), 0.95-0.84 (m, 2H). LC/MS: m/z=585.2 [M+H]$^+$.

N-(7-amino-4-chloro-1-cyclopropyl-1H-indazol-3-yl)-N-(4-methoxybenzyl)methanesulfonamide (Int CI10h)

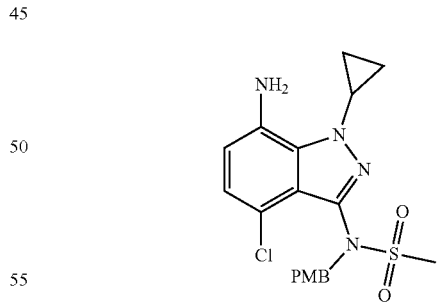

To a bright yellow solution of N-(4-chloro-1-cyclopropyl-7-((diphenylmethylene)amino)-1H-indazol-3-yl)-N-(4-methoxybenzyl)methanesulfonamide (Int CI10g, 0.284 g, 0.485 mmol) in THF (4.9 ml) was added HCl (1.2 ml, 4.85 mmol) and water (0.044 ml, 2.427 mmol)). The resulting dark orange solution was stirred at rt for 2 h and concentrated. The residue was taken up in ethyl acetate, washed with 2 M $K_3PO_4$, dried over $MgSO_4$ and concentrated. The residue was purified on silica (80 g Isco column) using 0-60% ethyl acetate in hexanes. The desired fractions were concentrated to give a pink foamy solid (0.1 g). $^1$H NMR (400 MHz, CDCl$_3$) δ 7.26 (br d, J=2.8 Hz, 2H), 6.93-6.88 (m, 1H), 6.83-6.77 (m, 2H), 6.52-6.44 (m, 1H), 5.12-4.89 (m, 1H), 4.82-4.62 (m, 1H), 3.95-3.87 (m, 1H), 3.79 (s, 3H), 3.67-3.48 (m, 2H), 2.98 (s, 3H), 1.43-1.36 (m, 2H), 1.30-1.30 (m, 1H), 1.20 (br dd, J=7.2, 1.4 Hz, 2H). LC/MS: m/z=420.9 [M+H]$^+$.

7-bromo-4-chloro-1-isopropyl-1H-indazol-3-amine (Int CI11a)

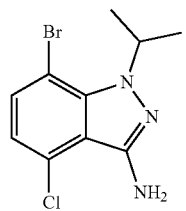

Sodium methoxide (0.54 g, 9.47 mmol) was added to a solution of 3-bromo-6-chloro-2-fluorobenzonitrile (0.5 g, 2.133 mmol) and isopropyl hydrazine hydrochloride (0.524 g, 4.73 mmol) in ethanol (5 mL), the mixture was heated at 120° C. in a microwave reactor for 35 min. The reaction mixture (pale yellow solid) was taken up in ethyl acetate, washed with water, brine, dried over Na$_2$SO$_4$ and concentrated. The residue was purified on silica gel (40 g Isco column) using 5-100% ethyl acetate in hexanes. The desired fractions were concentrated to give a light brown solid (0.29 g). $^1$H NMR (500 MHz, CDCl$_3$) δ 7.30 (s, 1H), 6.76-6.56 (m, 1H), 4.73-4.32 (m, 3H), 1.65 (d, J=6.8 Hz, 6H). LC/MS: m/z=290.0 [M+H]$^+$.

N-(7-bromo-4-chloro-1-isopropyl-1H-indazol-3-yl) methanesulfonamide (Int CI1b)

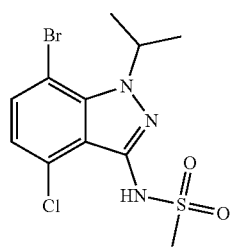 [SMILES: CC(C)n1nc(NS(C)(=O)=O)c2c(Cl)ccc(Br)c21]

To a solution of 7-bromo-4-chloro-1-isopropyl-1H-indazol-3-amine (Int CI11 a, 0.159 g, 0.551 mmol) in CH$_2$Cl$_2$(2 mL) was added DIPEA (0.385 mL, 2.204 mmol) then the reaction was cooled in an ice bath and methanesulfonyl chloride (0.19 g, 1.653 mmol) was added. The reaction mixture was stirred at this temperature for 1 h (precipitate formed). The reaction mixture was then diluted with dichloromethane (10 mL) and washed with water, 1 M HC and brine, dried (Na$_2$SO$_4$), filtered and concentrated. The residue was purified on silica (24 g Isco column). The desired fractions were concentrated to give a light yellow solid (nmr suggests a bis-sulfonation). The residue was taken up in EtOH (4 mL) and 2 mL of 20% aq. NaOH. The resulted mixture heated with a heat gun until it became a homogeneous solution and stirred at rt for 30 min. The reaction mixture was diluted with water (5 mL) and acidified with 2 M HCl (60 mL). The resultant cloudy mixture was extracted with DCM, dried over Na$_2$SO$_4$ and concentrated to give the desired product as a pink solid (0.12 g). $^1$H NMR (500 MHz, CDCl$_3$) δ 7.53-7.38 (m, 1H), 7.01 (d, J=7.7 Hz, 1H), 6.72 (s, 1H), 5.45-5.29 (m, 1H), 3.16 (s, 3H), 1.66 (d, J=6.5 Hz, 6H). LC/MS: m/z=366.0 [M+H]$^+$.

N-(7-bromo-4-chloro-1-isopropyl-1H-indazol-3-yl)-N-(4-methoxybenzyl)methanesulfonamide (Int CI11c)

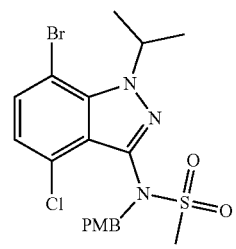

4-Methoxybenzyl chloride (0.07 ml, 0.524 mmol) was added to a mixture of N-(7-bromo-4-chloro-1-isopropyl-1H-indazol-3-yl)methanesulfonamide (Int CI1b, 0.16 g, 0.436 mmol) and Cs$_2$CO$_3$ (0.284 g, 0.873 mmol) in DMF (3.1 ml). The reaction mixture was stirred at rt overnight, then, diluted with ethyl acetate, washed with brine, dried over Na$_2$SO$_4$ and concentrated. The residue was purified on silica (24 g Isco column) using 0-60% ethyl acetate in hexanes. The desired fractions were concentrated to give a white solid (0.18 g). LC/MS: m/z=486.2 [M+H]$^+$.

N-(4-chloro-7-((diphenylmethylene)amino)-1-isopropyl-1H-indazol-3-yl)-N-(4-methoxybenzyl)methanesulfonamide (Int CI11d)

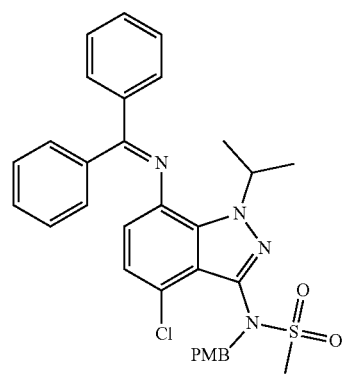

A mixture of N-(7-bromo-4-chloro-1-isopropyl-1H-indazol-3-yl)-N-(4-methoxybenzyl)methanesulfonamide (Int CI11c, 0.181 g, 0.372 mmol), diphenylmethanimine (0.074 g, 0.410 mmol), PdOAc$_2$ (4.17 mg, 0.019 mmol), R-(+)-BINAP (0.035 g, 0.056 mmol) and Cs$_2$CO$_3$ (0.182 g, 0.558 mmol) in Dioxane (3.7 mL) was degassed for 5 min and heated in the microwave at 120° C. for 2 h. The reaction mixture was purified on silica (40 g Isco column) using 0-40% ethyl acetate in hexanes. The desired fractions were concentrated to give a bright yellow solid (0.14 g). LC/MS: m/z=587.4 [M+H]$^+$.

N-(7-amino-4-chloro-1-isopropyl-1H-indazol-3-yl)-N-(4-methoxybenzyl)methanesulfonamide (Int CI11e)

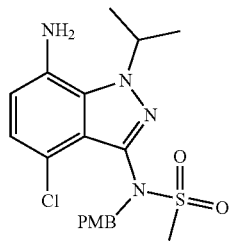

To a bright yellow solution of N-(4-chloro-7-(((diphenylmethylene)amino)-1-isopropyl-1H-indazol-3-yl)-N-(4-methoxybenzyl)methanesulfonamide (Int CI11d, 0.14 g, 0.232 mmol) in THF (2.316 ml) was added HCl (0.6 ml, 2.316 mmol) and water (0.02 ml, 1.158 mmol) (it was slightly exothermic at rt). The resulting dark orange solution was stirred at rt for 2 h (it turned into a light yellow solution). The reaction mixture was concentrated and the residue was taken up in ethyl acetate, washed with 2 M K$_3$PO$_4$, dried over MgSO$_4$ and concentrated. The residue was purified on silica (24 g Isco column) using 0-40% ethyl acetate in hexanes. The desired fractions were concentrated to give an off-white sticky solid (66 mg). LC/MS: m/z=423.2 [M+H]$^+$.

tert-butyl (S)-(2-(3,5-difluorophenyl)-1-(7-methoxy-4-oxo-4H-pyrido[2,3-d][1,3]oxazin-2-yl)ethyl)carbamate (Int CI11f)

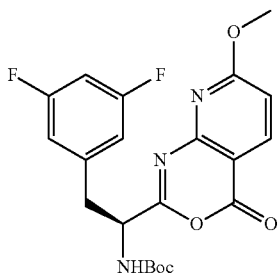 [SMILES: COc1ccc2c(=O)oc([C@H](Cc3cc(F)cc(F)c3)NC(=O)OC(C)(C)C)nc2n1]

Prepared according to the general procedure described for Int CI9a.

N-[(1S)-1-{3-[4-chloro-3-methanesulfonamido-1-(propan-2-yl)-1H-indazol-7-yl]-4-oxo-3H,4H-pyrido[2,3-d]pyrimidin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Example 43.2) and Example 43.1

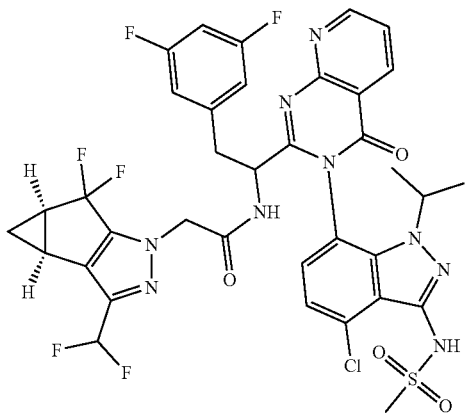

Mixture of stereoisomers
Example 43.1

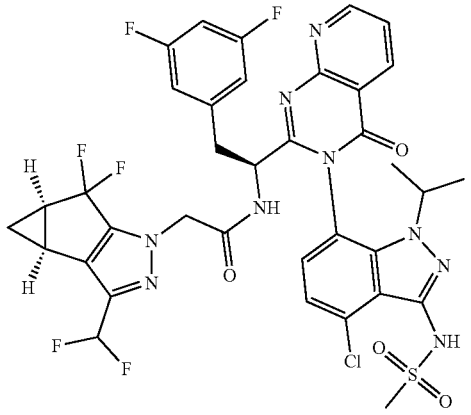

Mixture of stereoisomers
Example 43.2

Prepared according to the general procedure described for Int CI9d using Int CI11e. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.8%; Observed Mass: 834.09; Retention Time: 1.88 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.2%; Observed Mass: 834.07; Retention Time: 1.92 min. Two elutes were isolated Example 43.1 First Elute (12 mg, a Mixture of Stereoisomers)

$^1$H NMR (500 MHz, MeOH-d$_4$) δ 9.14-9.00 (m, 1H), 8.77-8.67 (m, 1H), 7.73-7.65 (m, 1H), 7.49-7.29 (m, 2H), 6.82-6.49 (m, 2H), 6.24-6.10 (m, 2H), 5.38-5.26 (m, 1H), 4.82-4.66 (m, 1H), 3.26-3.17 (m, 3H), 3.03 (s, 1H), 2.43 (br s, 2H), 1.53-1.27 (m, 8H), 1.03 (br s, 1H)[some peaks may be under solvent peak]

Example 43.2 Second Elute (4 mg, a Mixture of Stereoisomers)

$^1$H NMR (500 MHz, MeOH-d$_4$) δ 9.13-9.02 (m, 1H), 8.68 (s, 1H), 7.76-7.64 (m, 1H), 7.33 (br d, J=7.6 Hz, 1H), 7.20 (br d, J=7.6 Hz, 1H), 6.81-6.47 (m, 4H), 5.30-5.21 (m, 1H), 4.66-4.41 (m, 2H), 3.20 (s, 3H), 3.03-2.94 (m, 1H), 2.42 (br s, 2H), 1.48-1.22 (m, 10H), 1.00 (br s, 1H).

N-(7-bromo-4-chloro-1-(2,2-difluoroethyl)-1H-indazol-3-yl)methanesulfonamide (Int CI12a)

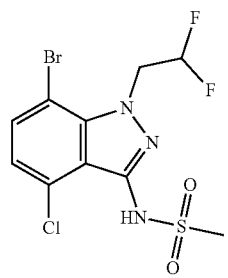 [SMILES: CS(=O)(=O)Nc1nn(CC(F)F)c2c(Br)ccc(Cl)c12]

To a 100 mL pressure bottle under N$_2$ was added N-(4-chloro-1-(2,2-difluoroethyl)-7-(4,4,5,5-tetramethyl-1,3,2-dioxaborolan-2-yl)-1H-indazol-3-yl)methanesulfonamide (0.4 g, 0.918 mmol) and Methanol (16.8 mL). The resulting suspension was then treated with a solution of copper(II) bromide (0.619 g, 2.77 mmol) dissolved in Water (5.1 mL). The reaction was sealed and placed in an oil bath and heated at 80° C. for 10 h. The reaction mixture was diluted with water and extracted with EtOAc, dried with MgSO$_4$, filtered and concentrated to produce a brown solid. The residue was purified on silica (40 g Isco column) using 0-50% ethyl acetate in hexanes. The desired fractions were concentrated to give a light pink solid (0.3 g). $^1$H NMR (500 MHz, CDCl$_3$) δ 7.60-7.49 (m, 1H), 7.48-7.36 (m, 1H), 7.08-6.94 (m, 1H), 6.40-5.99 (m, 1H), 5.25-5.04 (m, 2H), 3.51-3.35 (m, 3H). LC/MS: m/z=387.7[M+H]$^+$.

N-(7-bromo-4-chloro-1-(2,2-difluoroethyl)-1H-indazol-3-yl)cyclopropanesulfonamide (Int CI13a)

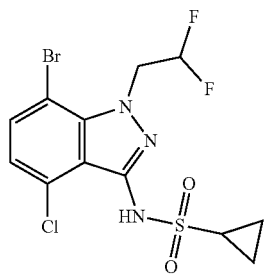 [SMILES: O=S(=O)(Nc1nn(CC(F)F)c2c(Br)ccc(Cl)c12)C1CC1]

To a 100 mL pressure bottle under N$_2$ was added N-(4-chloro-1-(2,2-difluoroethyl)-7-(4,4,5,5-tetramethyl-1,3,2-dioxaborolan-2-yl)-1H-indazol-3-yl)cyclopropanesulfonamide (1.9 g, 4.12 mmol) and Methanol (34 mL). The resulting suspension was then treated with a solution of copper(II) bromide (2.78 g, 12.43 mmol) dissolved in Water (10 mL). The reaction was sealed and placed in an oil bath and heated at 80° C. for 10 h. The reaction mixture was diluted with water and extracted with EtOAc, dried with MgSO$_4$, filtered, then concentrated give a light pink solid (1.71 g, used as is). $^1$H NMR (400 MHz, CDCl$_3$) δ 7.61-7.49 (m, 1H), 7.44-7.35 (m, 1H), 7.02 (d, J=8.1 Hz, 1H), 6.37-5.98 (m, 1H), 5.26-5.07 (m, 2H), 3.07-2.91 (m, 1H), 1.45-1.37 (m, 2H), 1.18-1.06 (m, 2H). LC/MS: m/z=414.0[M+H]$^+$.

N-(7-bromo-4-chloro-1-(2,2-difluoroethyl)-1H-indazol-3-yl)-N-(4-methoxybenzyl)methanesulfonamide (Int CI12b)

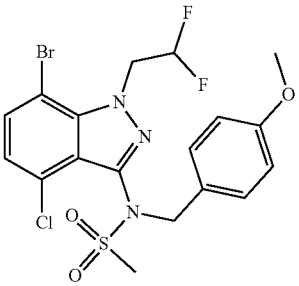 [SMILES: COc1ccc(CN(c2nn(CC(F)F)c3c(Br)ccc(Cl)c23)S(C)(=O)=O)cc1]

4-Methoxybenzyl chloride (0.250 ml, 1.853 mmol) was added to a mixture of N-(7-bromo-4-chloro-1-(2,2-difluoroethyl)-1H-indazol-3-yl)methanesulfonamide (Int CI12a, 0.6 g, 1.544 mmol) and Cs$_2$CO$_3$ (1.006 g, 3.09 mmol) in DMF (6.2 mL). The mixture was stirred at rt overnight. The mixture was diluted with ethyl acetate, washed with brine, dried over Na$_2$SO$_4$ and concentrated. The residue was purified on silica (80 g Isco column) using 0-60% ethyl acetate in hexanes. The desired fractions were concentrated to give a viscous yellow oil (0.73 g). LC/MS: m/z=507.9 [M+H]$^+$.

197

N-(7-bromo-4-chloro-1-(2,2-difluoroethyl)-1H-indazol-3-yl)-N-(4-methoxybenzyl)cyclopropanesulfonamide (Int CI13b)

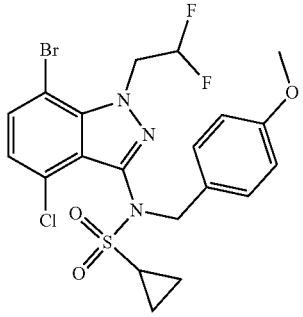 [SMILES: COc1ccc(CN(c2nn(CC(F)F)c3c(Br)ccc(Cl)c23)S(=O)(=O)C2CC2)cc1]

4-Methoxybenzyl chloride (0.668 ml, 4.95 mmol) was added to a mixture of N-(7-bromo-4-chloro-1-(2,2-difluoroethyl)-1H-indazol-3-yl)cyclopropanesulfonamide (Int CI13a, 1.71 g, 4.12 mmol) and $Cs_2CO_3$ (2.69 g, 8.25 mmol) in DMF (16.50 mL). The mixture was stirred at rt overnight. The mixture was diluted with ethyl acetate, washed with brine, dried over $Na_2SO_4$ and concentrated. The residue was purified on silica (220 g Isco column) using 0-60% ethyl acetate in hexanes. The desired fractions were concentrated to give a sticky white solid. $^1$H NMR (400 MHz, $CDCl_3$) δ 7.51-7.44 (m, 1H), 7.27-7.23 (m, 2H), 7.06-7.00 (m, 1H), 6.80-6.73 (m, 2H), 6.24-5.88 (m, 1H), 5.37-4.82 (m, 4H), 3.79-3.72 (m, 3H), 2.69-2.58 (m, 1H), 1.24-1.13 (m, 2H), 1.08-0.99 (m, 2H). LC/MS: m/z=535.7 $[M+2H]^+$.

N-(4-chloro-1-(2,2-difluoroethyl)-7-((diphenylmethylene)amino)-1H-indazol-3-yl)-N-(4-methoxybenzyl)methanesulfonamide (Int CI12c)

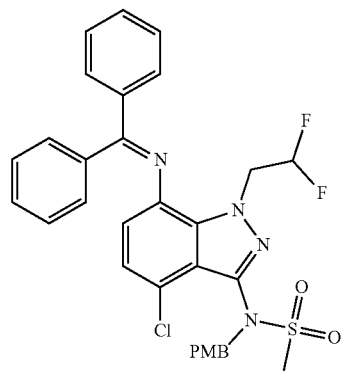

A mixture of N-(7-bromo-4-chloro-1-(2,2-difluoroethyl)-1H-indazol-3-yl)-N-(4-methoxybenzyl)methanesulfonamide (Int $CI_{12}b$, 0.73 g, 1.435 mmol), diphenylmethanimine (0.27 ml, 1.583 mmol), $PdOAc_2$ (0.016 g, 0.072 mmol), R-(+)-BINAP (0.134 g, 0.215 mmol) and $Cs_2CO_3$ (0.701 g, 2.152 mmol) in Dioxane (14.4 mL) was degassed for 5 min and heated (heating block) at 95° C. for 2 h. The reaction mixture was purified on silica gel (220 g Isco column) using 0-40% ethyl acetate, the desired fractions were concentrated to give a bright yellow solid (0.74 g). LC/MS: m/z=609.1 $[M+H]^+$.

198

N-(4-chloro-1-(2,2-difluoroethyl)-7-((diphenylmethylene)amino)-1H-indazol-3-yl)-N-(4-methoxybenzyl)cyclopropanesulfonamide (Int CI13c)

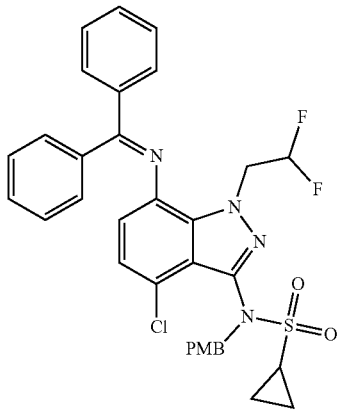

A mixture of N-(7-bromo-4-chloro-1-(2,2-difluoroethyl)-1H-indazol-3-yl)-N-(4-methoxybenzyl)cyclopropanesulfonamide (Int CI13b, 0.83 g, 1.552 mmol), diphenylmethanimine (0.287 ml, 1.712 mmol), $PdOAc_2$ (0.017 g, 0.078 mmol), R-(+)-BINAP (0.145 g, 0.233 mmol) and $Cs_2CO_3$ (0.758 g, 2.328 mmol) in Dioxane (13 mL) was degassed for 5 min and heated in a microwave at 120° C. for 2 h. The reaction mixture filtered through Celite and concentrated. The residue was purified on silica gel (220 g Isco column) using 0-30% ethyl acetate, the desired fractions were concentrated to give a bright yellow solid (0.85 g). LC/MS: m/z=635.3 $[M+H]^+$.

N-(7-amino-4-chloro-1-(2,2-difluoroethyl)-1H-indazol-3-yl)-N-(4-methoxybenzyl)methanesulfonamide (Int CI12d)

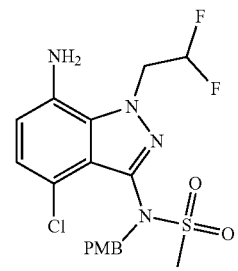

To a bright yellow solution of N-(4-chloro-1-(2,2-difluoroethyl)-7-((diphenylmethylene)amino)-1H-indazol-3-yl)-N-(4-methoxybenzyl)methanesulfonamide (Int CI12c, 0.74 g, 1.215 mmol) in THF (12.15 ml) was added HC (3 mL, 12.15 mmol) and water (0.11 mL, 6.07 mmol) (it was slightly exothermic at rt). The resulting dark orange solution was stirred at rt for 2 h (it turned into a light yellow solution). The reaction mixture was concentrated and the residue was taken up in ethyl acetate, washed with 2 M $K_3PO_4$, dried over $MgSO_4$ and concentrated. The residue was purified on silica (80 g Isco column) using 0-60% ethyl acetate in hexanes. The desired fractions were concentrated to give a brown foamy solid (0.48 g).

N-(7-amino-4-chloro-1-(2,2-difluoroethyl)-1H-indazol-3-yl)-N-(4-methoxybenzyl)cyclopropanesulfonamide (Int CI13d)

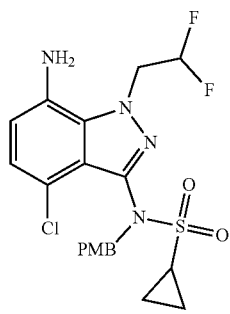

Prepared according to the general procedure described for Int CI12d using Int CI13c. LC/MS: m/z=471.1 [M+H]$^+$.

N—((S)-1-(3-(4-chloro-1-(2,2-difluoroethyl)-3-(methylsulfonamido)-1H-indazol-7-yl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 44.1) and Example 44.2

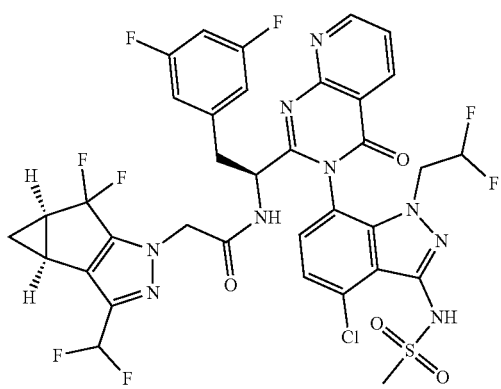

Homochiral
Example 44.1

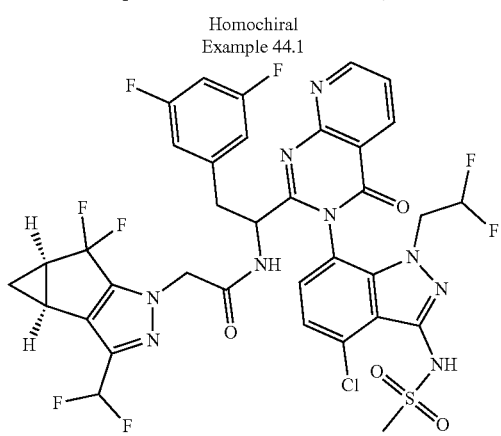

Homochiral
Example 44.2

Prepared according to the general procedure described for Example 38.1 and 38.2 using Int 17a and Int CI12d. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 26-66% B over 25 minutes, then a 4-minute hold at 100% B; Flow: 20 mL/min. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 856; Retention Time: 1.96 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 856.06; Retention Time: 1.93 min. The resultant mixture of stereoisomers (102 mg) was further purified by Chiralpak IC preparative column, 30×250 mm, 5 µm Mobile Phase: 20% IPA in CO$_2$, 150 bar Temp: 35° C., Flow rate: 70.0 mL/min. in 15 min. UV monitored @ 220 nm. Injection: 0.5 mL of ~10 mg/mL in 1:1:1 IPA MeOH:CHCl$_3$. Two elutes were isolated.

Example 44.1 First Elute (70 mg, Homochiral)

$^1$H NMR (400 MHz, MeOH-d$_4$) δ 9.17-9.06 (m, 1H), 8.77-8.66 (m, 1H), 7.77-7.67 (m, 1H), 7.47-7.29 (m, 2H), 6.84-6.45 (m, 4H), 6.19-5.85 (m, 1H), 4.82-4.72 (m, 1H), 4.70-4.54 (m, 2H), 4.47-4.30 (m, 1H), 4.04-3.88 (m, 1H), 3.70-3.56 (m, 1H), 3.29-3.23 (m, 3H), 3.17-3.04 (m, 1H), 2.50-2.33 (m, 2H), 1.42-1.30 (m, 1H), 1.03-0.93 (m, 1H)

Example 44.2 Second Elute (25 mg, Homochiral)

$^1$H NMR (400 MHz, MeOH-d$_4$) δ 9.18-9.06 (m, 1H), 8.78-8.69 (m, 1H), 7.77-7.69 (m, 1H), 7.44-7.27 (m, 2H), 6.83-6.45 (m, 4H), 6.18-5.82 (m, 1H), 4.82-4.74 (m, 1H), 4.71-4.56 (m, 2H), 4.43-4.29 (m, 1H), 3.98-3.93 (m, 1H), 3.27-3.23 (m, 3H), 3.15-3.04 (m, 2H), 2.47-2.33 (m, 2H), 1.40-1.34 (m, 1H), 1.03-0.94 (m, 1H).

N-[(1S)-1-{3-[4-chloro-3-cyclopropanesulfonamido-1-(2,2-difluoroethyl)-1H-indazol-7-yl]-4-oxo-3H,4H-pyrido[2,3-d]pyrimidin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Example 45.2) and Example 45.1

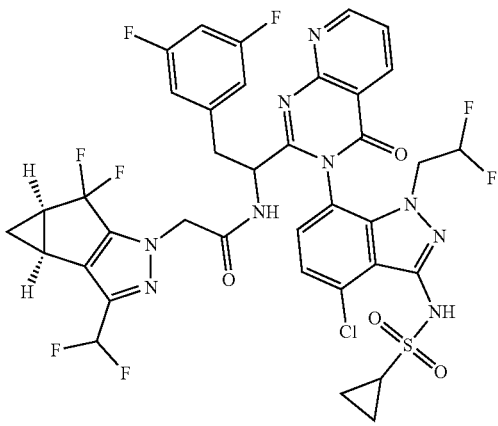

Mixture of stereoisomers
Example 45.1

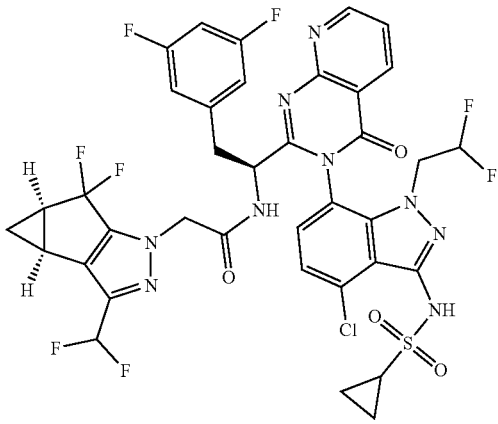

Mixture of indicated and another stereoisomers
Example 45.2

Prepared according to the general procedure described for Example 38.1 and 38.2 using Int 17a and 13d. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 28% B, 28-68% B over 25 minutes, then a 5-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 882.08; Retention Time: 1.97 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 882.05; Retention Time: 1.98 min. Two elutes were isolated.

Example 45.1 First Elute (4 mg, a Mixture of Stereoisomers)

$^1$H NMR (500 MHz, MeOH-d$_4$) δ 9.19-9.10 (m, 1H), 8.79-8.69 (m, 1H), 7.80-7.70 (m, 1H), 7.44-7.38 (m, 1H), 7.34-7.24 (m, 1H), 6.87-6.57 (m, 4H), 6.19-5.90 (m, 1H), 4.85-4.60 (m, 2H), 4.01-3.72 (m, 2H), 3.41-3.35 (m, 1H), 3.16-3.08 (m, 1H), 3.00-2.92 (m, 1H), 2.70-2.66 (m, 1H), 2.54-2.43 (m, 2H), 1.44-1.36 (m, 1H), 1.34-1.28 (m, 1H), 1.18-1.11 (m, 2H), 1.09-1.04 (m, 3H).

Example 45.2 Second Elute (69 mg, a Mixture of Stereoisomers)

$^1$H NMR (500 MHz, MeOH-d$_4$) δ 9.18-9.07 (m, 1H), 8.81-8.65 (m, 1H), 7.79-7.69 (m, 1H), 7.48-7.29 (m, 2H), 6.84-6.73 (m, 1H), 6.71-6.64 (m, 1H), 6.60-6.49 (m, 2H), 6.18-5.85 (m, 1H), 4.83-4.57 (m, 2H), 4.46-4.32 (m, 1H), 4.01-3.87 (m, 1H), 3.44-3.35 (m, 1H), 3.14-3.06 (m, 1H), 2.96-2.87 (m, 1H), 2.47-2.37 (m, 2H), 1.40-1.25 (m, 2H), 1.13-1.06 (m, 2H), 1.02-0.96 (m, 3H)

Examples 46 through CI72 were prepared according to the general procedure described for Example 41.1 and Example 41.2 using Int 17a.

N-[(1S)-1-[3-(4-chloro-3-methanesulfonamido-1-methyl-1H-indazol-7-yl)-4-oxo-3H,4H-pyrido[2,3-d]pyrimidin-2-yl]-2-(3,5-difluorophenyl)ethyl]-2-[3-(difluoromethyl)-1H,4H,5H,6H-cyclopenta[c]pyrazol-1-yl]acetamide (Example 46.1 & 46.2)

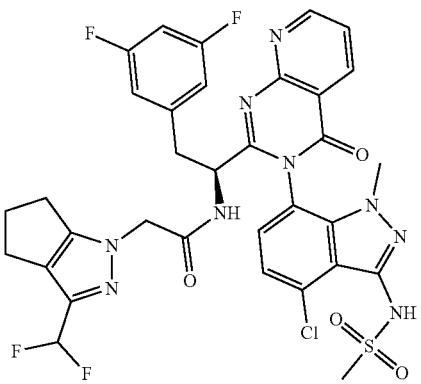

Mixture of indicated isomer and its enantiomer

-continued

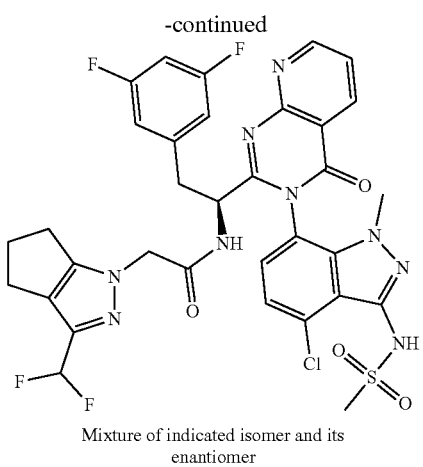

Mixture of indicated isomer and its enantiomer

The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 32% B, 32-72% B over 23 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.7%; Observed Mass: 758.1; Retention Time: 1.73 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.3%; Observed Mass: 758.1; Retention Time: 1.74 min. Two elutes were isolated.

Example 46.1 First Elute (3 mg, a Mixture of Enantiomers of Unknown Proportion)

Example 46.2 Second Elute (21 mg, a Mixture of Enantiomers of Unknown Proportion)

$^1$H NMR (500 MHz, MeOH-d$_4$) δ 9.16-9.09 (m, 1H), 8.80-8.71 (m, 1H), 7.78-7.69 (m, 1H), 7.37-7.28 (m, 2H), 6.82-6.41 (m, 4H), 5.10-4.84 (m, 1H), 4.67-4.57 (m, 1H), 4.48-4.25 (m, 2H), 3.70-3.63 (m, 3H), 3.58-3.48 (m, 1H), 3.28 (s, 3H), 3.21-3.13 (m, 1H), 2.68-2.62 (m, 2H), 2.58-2.47 (m, 4H).

N-[(1S)-1-[3-(4-chloro-3-methanesulfonamido-1-methyl-1H-indazol-7-yl)-4-oxo-3H,4H-pyrido[2,3-d]pyrimidin-2-yl]-2-(3,5-difluorophenyl)ethyl]-2-(3-methyl-1H-pyrazol-1-yl)acetamide (Example 47.1 & Example 47.2)

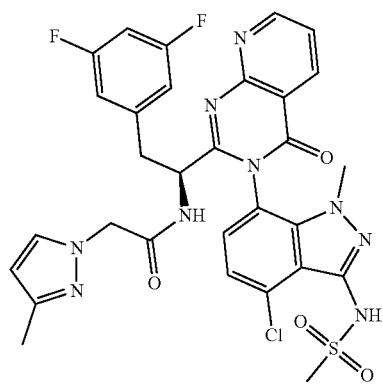

Mixture of enantiomers of unknown proportion


Mixture of enantiomers of unknown proportion

The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 26% B, 26-66% B over 23 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 682.1; Retention Time: 1.58 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 682.08; Retention Time: 1.55 min. Two elutes were isolated.

Example 47.1 First Elute (2 mg, a Mixture of Enantiomers)

$^1$H NMR (500 MHz, MeOH-d$_4$) δ 9.19-9.09 (m, 1H), 8.77-8.69 (m, 1H), 7.77-7.67 (m, 1H), 7.54-7.47 (m, 1H), 7.42-7.35 (m, 1H), 7.26-7.18 (m, 1H), 6.81-6.74 (m, 1H), 6.61-6.52 (m, 2H), 6.19-6.09 (m, 1H), 4.93-4.60 (m, 2H), 3.47-3.39 (m, 1H), 3.31-3.27 (m, 3H), 3.18-3.12 (m, 3H), 2.98 (br dd, J=13.3, 6.3 Hz, 1H), 2.27 (s, 3H), 1.40-1.29 (m, 1H)

Example 47.2 Second Elute (28 mg, a Mixture of Enantiomers)

$^1$H NMR (500 MHz, MeOH-d$_4$) δ 9.15-9.05 (m, 1H), 8.79-8.70 (m, 1H), 7.77-7.68 (m, 1H), 7.37-7.23 (m, 3H), 6.80-6.60 (m, 3H), 6.07-5.97 (m, 1H), 4.48-4.25 (m, 2H), 3.72-3.61 (m, 3H), 3.56-3.46 (m, 11H), 3.30-3.26 (m, 3H), 3.18-3.07 (m, 1H), 2.20-2.11 (m, 3H), 1.35-1.31 (m, 1H).

N-[(1S)-1-[3-(4-chloro-3-methanesulfonamido-1-methyl-1H-indazol-7-yl)-4-oxo-3H,4H-pyrido[2,3-d]pyrimidin-2-yl]-2-(3,5-difluorophenyl)ethyl]-2-[3-(difluoromethyl)-2H,4H,5H,6H-cyclopenta[c]pyrazol-2-yl]acetamide (Example 48.1 & 48.2)

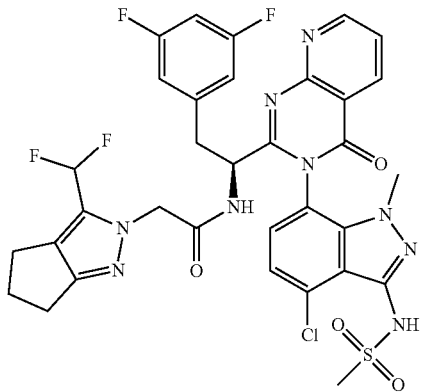

Mixture of enantiomers of unknown proportion

The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 34% B, 34-74% B over 22 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.8%; Observed Mass: 758.11; Retention Time: 1.73 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 92.6%; Observed Mass: 758.08; Retention Time: 1.73 min. Two elutes, each as a mixture of enantiomers of unknown proportion were isolated.

Example 48.1 First Elute (6 mg, a Mixture of Enantiomers)

Example 48.2 Second Elute (23 mg, a Mixture of Enantiomers)

$^1$H NMR (500 MHz, MeOH-d$_4$) δ 9.19-9.04 (m, 1H), 8.79-8.66 (m, 1H), 7.79-7.66 (m, 1H), 7.38-7.20 (m, 2H), 6.84-6.47 (m, 4H), 4.67-4.17 (m, 2H), 3.71-3.59 (m, 3H), 3.51-3.43 (m, 1H), 3.29-3.24 (m, 3H), 3.18-3.05 (m, 1H), 2.72-2.58 (m, 4H), 2.46-2.35 (m, 2H), 1.37-1.29 (m, 1H).

N-[(1S)-1-[3-(4-chloro-3-methanesulfonamido-1-methyl-1H-indazol-7-yl)-4-oxo-3H,4H-pyrido[2,3-d]pyrimidin-2-yl]-2-(3,5-difluorophenyl)ethyl]-2-(5-hydroxy-1H-indazol-3-yl)acetamide (Example 49.1 & Example 49.2)

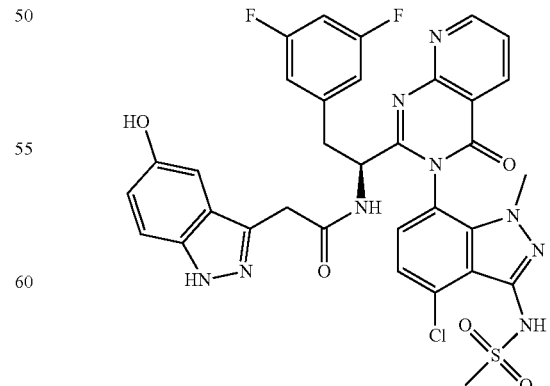

Mixture of enantiomers of unknown proportion

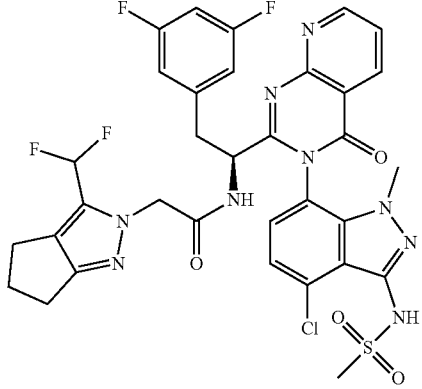

Mixture of enantiomers of unknown proportion

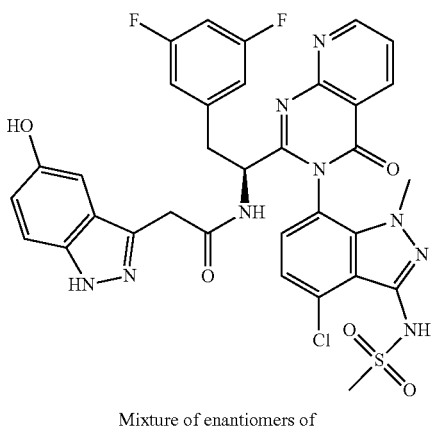

Mixture of enantiomers of
unknown proportion

The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 18% B, 18-59% B over 26 minutes, then a 5-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.7%; Observed Mass: 734.07; Retention Time: 1.43 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.4%; Observed Mass: 734.09; Retention Time: 1.44 min. Two elutes were isolated.

Example 49.1 First Elute (3 mg, a Mixture of Enantiomers)

Example 49.2 Second Elute (6 mg, a Mixture of Enantiomers)

$^1$H NMR (500 MHz, DMSO-$d_6$) δ 9.13-9.03 (m, 2H), 8.66-8.57 (m, 1H), 7.77-7.65 (m, 2H), 7.48-7.40 (m, 1H), 7.26-7.17 (m, 1H), 6.95-6.77 (m, 2H), 6.69-6.58 (m, 3H), 4.62-4.50 (m, 1H), 3.67-3.33 (m, 3H), 3.09-2.99 (m, 1H), 2.58-2.44 (m, 20H).

2-(3-amino-1H-pyrazol-1-yl)-N-[(1S)-1-[3-(4-chloro-3-methanesulfonamido-1-methyl-1H-indazol-7-yl)-4-oxo-3H,4H-pyrido[2,3-d]pyrimidin-2-yl]-2-(3,5-difluorophenyl)ethyl]acetamide (Example 50.1 & Example 50.2)

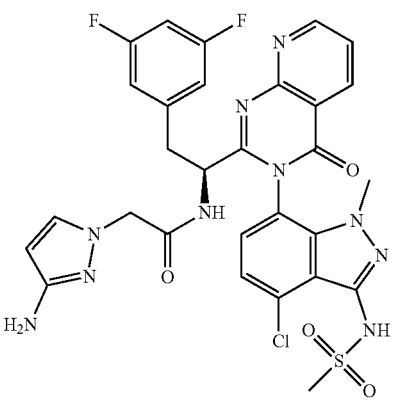

Mixture of enantiomers of
unknown proportion

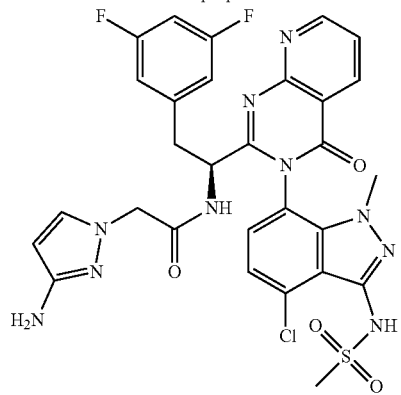

Mixture of enantiomers of
unknown proportion

The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 13% B, 13-56% B over 26 minutes, then a 5-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 88.7%; Observed Mass: 683.09; Retention Time: 1.41 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 89.3%; Observed Mass: 683.09; Retention Time: 1.31 min. Two elutes were isolated.

Example 50.1 First Elute (2 mg, a Mixture of Enantiomers)

$^1$H NMR (500 MHz, MeOH-d$_4$) δ 9.23-9.09 (m, 1H), 8.78-8.68 (m, 1H), 7.78-7.57 (m, 2H), 7.43-7.18 (m, 2H), 6.82-6.74 (m, 1H), 6.59-6.47 (m, 2H), 4.94-4.59 (m, 1H), 3.49-3.38 (m, 1H), 3.30 (s, 3H), 3.18 (s, 3H), 3.02-2.92 (m, 1H), 1.69-1.56 (m, 1H).

Example 50.2 Second Elute (11 mg, a Mixture of Enantiomers)

$^1$H NMR (500 MHz, MeOH-d$_4$) δ 9.16-9.05 (m, 1H), 8.81-8.70 (m, 1H), 7.77-7.70 (m, 1H), 7.49-7.27 (m, 3H), 6.83-6.64 (m, 3H), 4.50-4.29 (m, 2H), 3.72-3.62 (m, 3H), 3.60-3.45 (m, 2H), 3.28 (s, 3H), 3.19-3.09 (m, 1H), 1.72-1.57 (m, 1H).

N-[(1S)-1-[3-(4-chloro-3-methanesulfonamido-1-methyl-1H-indazol-7-yl)-4-oxo-3H,4H-pyrido[2,3-d]pyrimidin-2-yl]-2-(3,5-difluorophenyl)ethyl]-2-(5-fluoro-1H-indol-3-yl)acetamide (Example 51)

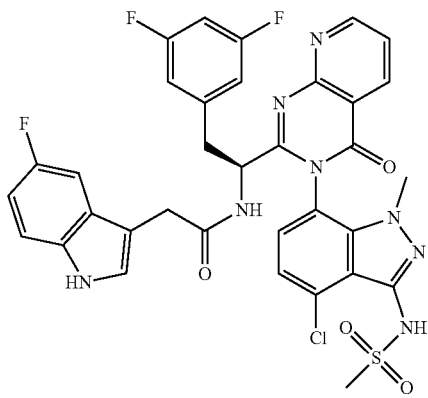

Mixture of indicated and other stereoisomers

The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 30% B, 30-70% B over 22 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.8%; Observed Mass: 735.07; Retention Time: 1.7 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.0%; Observed Mass: 735.1; Retention Time: 1.71 min. Product: (5 mg, a mixture of stereoisomers): $^1$H NMR (500 MHz, MeOH-d$_4$) δ 9.19-9.03 (m, 1H), 8.77-8.69 (m, 1H), 7.77-7.66 (m, 1H), 7.39-7.17 (m, 3H), 7.06-6.91 (m, 2H), 6.80-6.51 (m, 4H), 5.08-4.98 (m, 1H), 3.50-3.41 (m, 4H), 3.28 (s, 3H), 3.20-3.10 (m, 1H), 2.74-2.65 (m, 2H), 1.36-1.26 (m, 2H). LC/MS: m/z=735.1[M+H]$^+$.

N-[(1S)-1-[3-(4-chloro-3-methanesulfonamido-1-methyl-1H-indazol-7-yl)-4-oxo-3H,4H-pyrido[2,3-d]pyrimidin-2-yl]-2-(3,5-difluorophenyl)ethyl]-2-[3-(trifluoromethyl)-1H,4H,5H,6H-cyclopenta[c]pyrazol-1-yl]acetamide (Example 52)

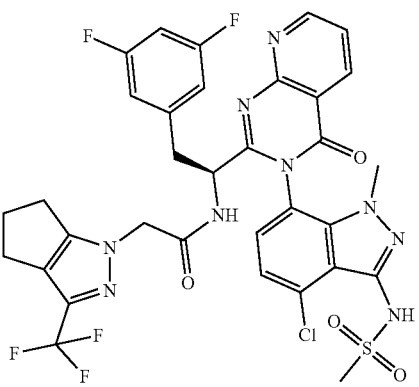

A mixture of indicated and other stereoisomers

The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: a 0-minute hold at 35% B, 35-75% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 776.11; Retention Time: 1.93 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B;

Flow: 1 mL/min; Detection: MS and UV (220 nm). Injection 2 results: Purity: 100.0%; Observed Mass: 776.06; Retention Time: 1. 92 min. Product: (17 mg, a mixture of stereoisomers): $^1$H NMR (500 MHz, MeOH-d$_4$) δ 9.15-9.05 (m, 1H), 8.80-8.70 (m, 1H), 7.79-7.70 (m, 1H), 7.37-7.24 (m, 2H), 6.82-6.60 (m, 3H), 4.95 (br d, J=3.1 Hz, 1H), 4.55-4.29 (m, 2H), 3.67-3.61 (m, 3H), 3.57-3.47 (m, 1H), 3.29 (s, 3H), 3.16 (br dd, J=14.0, 9.8 Hz, 1H), 2.70-2.61 (m, 2H), 2.58-2.47 (m, 4H).

N-[(1S)-1-[3-(4-chloro-3-methanesulfonamido-1-methyl-1H-indazol-7-yl]-4-oxo-3H,4H-pyrido[2,3-d]pyrimidin-2-yl]-2-(3,5-difluorophenyl)ethyl]-2-(5-hydroxy-1H-indol-3-yl)acetamide (Example 53)

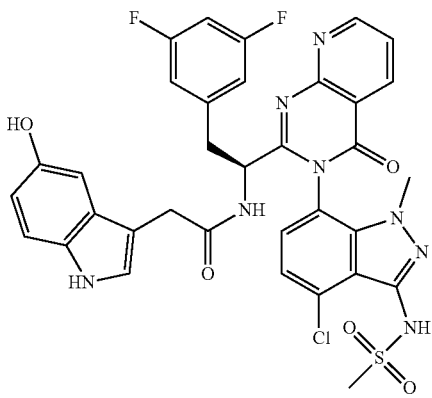

A mixture of indicated and other stereoisomers

The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 19% B, 19-63% B over 25 minutes, then a 5-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.9%; Observed Mass: 733.16; Retention Time: 1.49 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.6%; Observed Mass: 733.14; Retention Time: 1.5 min. Product: (2 mg, a mixture of stereoisomers).

N-[(1S)-1-{3-[4-chloro-1-(2,2-difluoroethyl)-3-methanesulfonamido-1H-indazol-7-yl]-7-methoxy-4-oxo-3H,4H-pyrido[2,3-d]pyrimidin-2-yl}-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Example 54.2) and Example 54.1

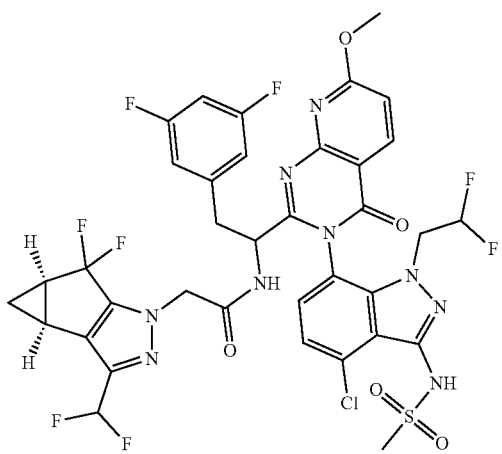

Mixture of stereoisomers
Example 54.1

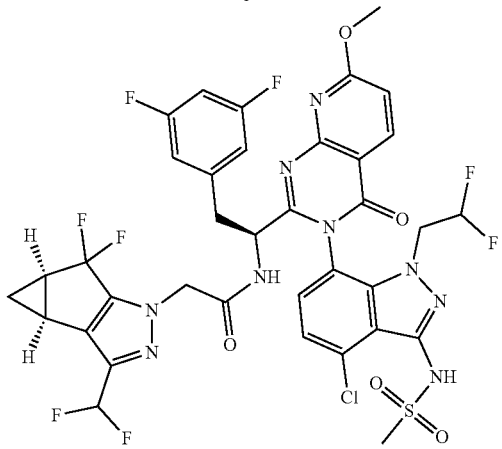

Mixture of indicated and an alternate stereoisomers
Example 54.2

Prepared according to the general procedure described for Example 38.1 and 38.2 and using Int CI12d. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-70% B over 25 minutes, then a 5-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 886.06; Retention Time: 2.01 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 886.07; Retention Time: 2 min. Two elutes were isolated.

Example 54.1 First Elute (5 mg, a Mixture of Stereoisomers)

$^1$H NMR (500 MHz, MeOH-d$_4$) δ 8.50-8.42 (m, 1H), 7.45-7.36 (m, 1H), 7.32-7.24 (m, 1H), 7.15-7.05 (m, 1H), 6.89-6.51 (m, 4H), 6.20-5.95 (m, 1H), 4.89-4.63 (m, 2H), 4.23-4.15 (m, 3H), 4.01-3.76 (m, 2H), 3.29 (br s, 4H), 3.16-3.05 (m, 1H), 2.54-2.43 (m, 2H), 1.46-1.38 (m, 1H), 1.12-1.03 (m, 1H).

Example 54.2 Second Elute (18 mg, a Mixture of Stereoisomers)

$^1$H NMR (500 MHz, MeOH-d$_4$) δ 8.52-8.44 (m, 1H), 7.44-7.35 (m, 1H), 7.32-7.26 (m, 1H), 7.12-7.04 (m, 1H), 6.83-6.51 (m, 4H), 6.19-5.88 (m, 1H), 4.79-4.58 (m, 2H), 4.43-4.29 (m, 1H), 4.21-4.14 (m, 3H), 4.01-3.89 (m, 1H), 3.46-3.35 (m, 2H), 3.29-3.25 (m, 3H), 3.15-3.04 (m, 1H), 2.48-2.40 (m, 2H), 1.40-1.33 (m, 1H), 1.08-0.97 (m, 1H).

N-[(1S)-1-{3-[4-chloro-1-(2,2-difluoroethyl)-3-methanesulfonamido-1H-indazol-7-yl]-7-methoxy-4-oxo-3H,4H-pyrido[2,3-d]pyrimidin-2-yl}-2-(3,5-difluorophenyl)ethyl]-2-(3-cyclopropyl-1H-pyrazol-1-yl)acetamide (Example 55.1 & Example 55.2)

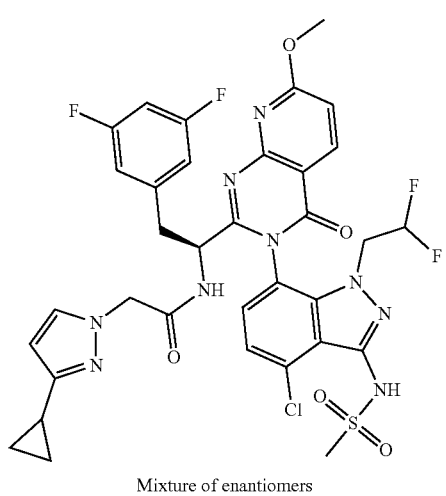

Mixture of enantiomers

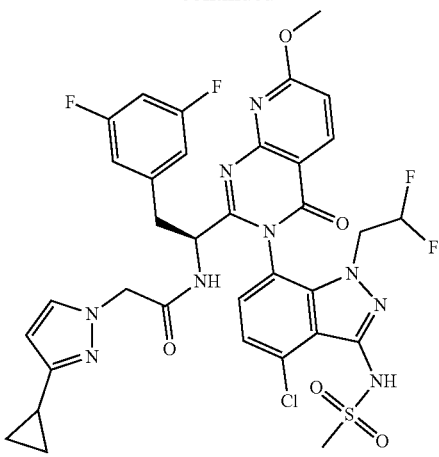

Mixture of enantiomers

Prepared according to the general procedure described for Example 38.1 and 38.2 using Int CI12d. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 26% B, 26-66% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 788.07; Retention Time: 1.95 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 788.06; Retention Time: 1.92 min. Two elutes were isolated.

Example 55.1 First Elute (9 mg, a Mixture of Stereoisomers)

$^1$H NMR (500 MHz, MeOH-d$_4$) δ 8.55-8.39 (m, 1H), 7.43-7.36 (m, 2H), 7.25-7.19 (m, 1H), 7.14-7.08 (m, 1H), 6.81-6.73 (m, 1H), 6.63-6.54 (m, 2H), 6.18-5.90 (m, 2H), 4.73-4.54 (m, 2H), 4.20 (s, 3H), 3.99-3.72 (m, 2H), 3.30 (br s, 5H), 3.14-3.06 (m, 1H), 1.95-1.89 (m, 1H), 0.96-0.87 (m, 2H), 0.73-0.66 (m, 2H)

Example 55.2 Second Elute (24 mg, a Mixture of Stereoisomers)

N-[(1S)-1-{3-[4-chloro-3-cyclopropanesulfonamido-1-(2,2-difluoroethyl)-1H-indazol-7-yl]-7-methoxy-4-oxo-3H,4H-pyrido[2,3-d]pyrimidin-2-yl}-2-(3,5-difluorophenyl)ethyl]-2-[(2S,4R)-9-(difluoromethyl)-5,85-difluoro-7,8-diazatricyclo[4.3.0.0$^{2,4}$]nona-1(6),8-dien-7-yl]acetamide (Example 56.2) and Example 56.1

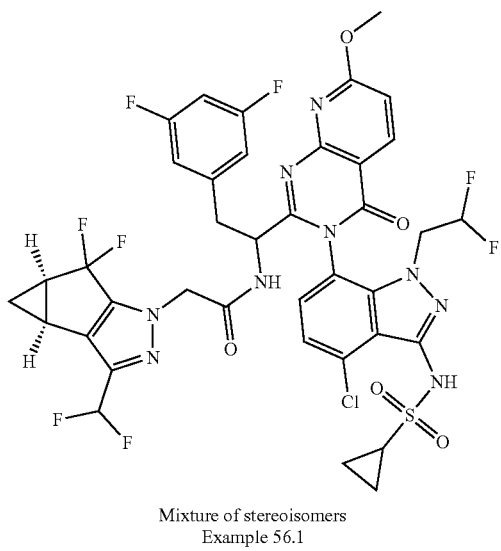

Mixture of stereoisomers
Example 56.1

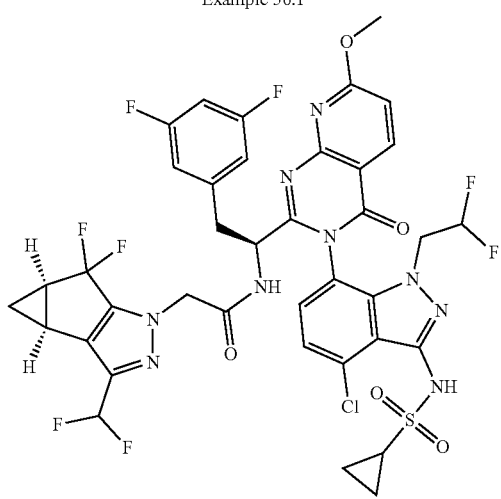

Mixture of indicated and alternate stereoisomers
Example 56.2

Prepared according to the general procedure described for Example 38.1 and 38.2 using Int CI13d. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 32% B, 32-72% B over 25 minutes, then a 5-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 912.02; Retention Time: 2.09 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 912.05; Retention Time: 2.11 min. Two elutes were isolated.

Example 56.1 First Elute (3 mg, a Mixture of Stereoisomers)

$^{1}$H NMR (500 MHz, MeOH-d$_4$) δ 8.52-8.42 (m, 1H), 7.42-7.34 (m, 1H), 7.29 (br dd, J=7.8, 5.0 Hz, 1H), 7.14-7.06 (m, 1H), 6.49 (s, 4H), 6.23-5.94 (m, 1H), 4.93-4.60 (m, 3H), 4.24-4.14 (m, 3H), 4.00-3.79 (m, 2H), 3.18-3.06 (m, 1H), 3.02-2.91 (m, 1H), 2.54-2.42 (m, 2H), 1.43-1.37 (m, 1H), 1.17-1.10 (m, 1H), 1.19-0.94 (m, 5H).

Example 56.2 Second Elute (21 mg, a Mixture of Stereoisomers)

$^{1}$H NMR (500 MHz, MeOH-d$_4$) δ 8.52-8.42 (m, 1H), 7.43-7.35 (m, 1H), 7.32-7.25 (m, 1H), 7.12-7.05 (m, 1H), 6.85-6.49 (m, 4H), 6.18-5.89 (m, 1H), 4.80-4.56 (m, 3H), 4.43-4.29 (m, 1H), 4.22-4.13 (m, 3H), 4.01-3.86 (m, 1H), 3.47-3.37 (m, 1H), 3.15-3.03 (m, 1H), 2.97-2.86 (m, 1H), 2.50-2.38 (m, 2H), 1.42-1.33 (m, 1H), 1.14-1.07 (m, 2H), 1.05-0.97 (m, 3H).

N-[(1S)-1-{3-[4-chloro-3-cyclopropanesulfonamido-1-(2,2-difluoroethyl)-1H-indazol-7-yl]-7-methoxy-4-oxo-3H,4H-pyrido[2,3-d]pyrimidin-2-yl}-2-(3,5-difluorophenyl)ethyl]-2-(3-cyclopropyl-1H-pyrazol-1-yl)acetamide (Example 57.1 and Example 57.2)

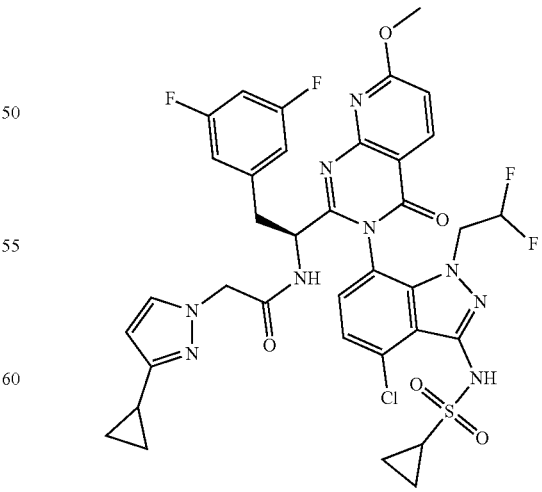

A mixture of enantiomers of unknown proportion

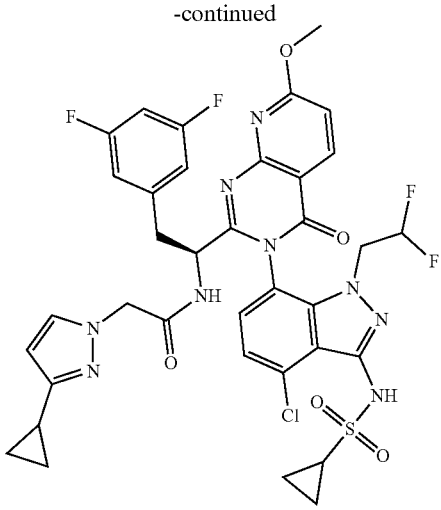

A mixture of enantiomers
of unknown proportion

Prepared according to the general procedure described for Example 38.1 and 38.2 using Int CI13d. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 29% B, 29-69% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 814.03; Retention Time: 1.96 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 814.05; Retention Time: 1. 95 min. Two elutes were isolated.

Example 57.1 First Elute (4 mg, a Mixture of Enantiomers)

$^1$H NMR (500 MHz, MeOH-d$_4$) δ 8.54-8.38 (m, 1H), 7.47-7.32 (m, 2H), 7.27-7.06 (m, 2H), 6.83-6.44 (m, 3H), 6.11-5.91 (m, 2H), 4.73-4.56 (m, 2H), 4.24-4.17 (m, 3H), 3.98-3.76 (m, 2H), 3.15-2.94 (m, 2H), 1.20-1.00 (m, 4H), 0.99-0.83 (m, 4H), 0.75-0.63 (m, 2H).

Example 57.2 Second Elute (22 mg, a Mixture of Enantiomers)

$^1$H NMR (500 MHz, MeOH-d$_4$) δ 8.54-8.42 (m, 1H), 7.45-7.26 (m, 3H), 7.13-7.07 (m, 1H), 6.85-6.76 (m, 1H), 6.63-6.56 (m, 2H), 6.17-5.90 (m, 2H), 4.93-4.88 (m, 1H), 4.93-4.87 (m, 2H), 4.69-4.60 (m, 2H), 4.56-4.48 (m, 2H), 4.42-4.29 (m, 1H), 4.22-4.15 (m, 3H), 3.49-3.41 (m, 1H), 3.37 (s, 3H), 3.36-3.36 (m, 1H), 3.14-3.04 (m, 1H), 2.98-2.92 (m, 1H), 1.19-1.09 (m, 3H), 1.08-1.00 (m, 2H), 0.89-0.85 (m, 2H), 0.72-0.61 (m, 2H).

N-[(1S)-1-[3-(4-chloro-3-methanesulfonamido-1-methyl-1H-indazol-7-yl)-7-methoxy-4-oxo-3H,4H-pyrido[2,3-d]pyrimidin-2-yl]-2-(3,5-difluorophenyl)ethyl]-2-(3-cyclopropyl-1H-pyrazol-1-yl)acetamide (Examples 58.1 & 58.2)

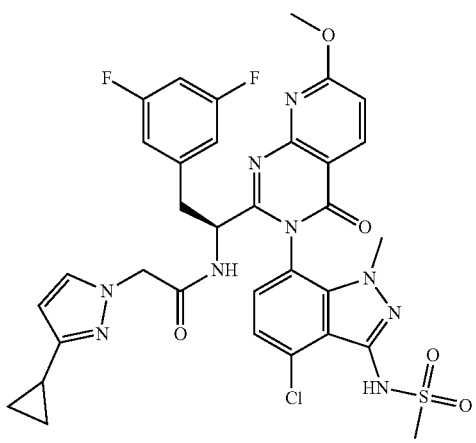

A mixture of enantiomers
of unknown proportion

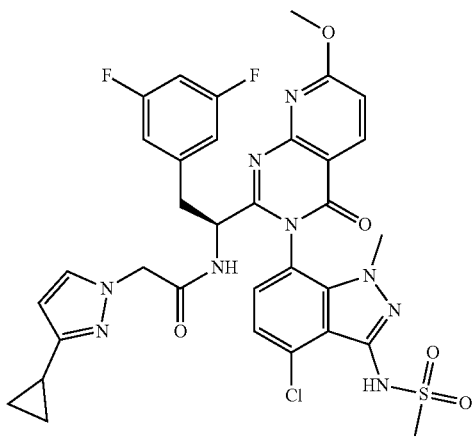

A mixture of enantiomers
of unknown proportion

Prepared according to the general procedure described for Example 38.1 and 38.2 using Int CI11d. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 24% B, 24-64% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 738.1; Retention Time: 1.79 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 738.11; Retention Time: 1.74 min. Two elutes were isolated.

Example 58.1 First Elute (10 mg, a Mixture of Stereoisomers)

$^1$H NMR (500 MHz, MeOH-$d_4$) δ 8.50-8.41 (m, 1H), 7.48 (d, J=2.1 Hz, 1H), 7.38-7.32 (m, 1H), 7.25-7.18 (m, 1H), 7.12-7.05 (m, 1H), 6.82-6.72 (m, 1H), 6.57-6.51 (m, 2H), 6.05-5.98 (m, 1H), 4.79-4.65 (m, 1H), 4.24-4.16 (m, 3H), 3.42-3.34 (m, 2H), 3.30-3.27 (m, 3H), 3.20-3.16 (m, 3H), 3.01-2.94 (m, 1H), 2.03-1.86 (m, 2H), 0.98-0.85 (m, 2H), 0.74-0.62 (m, 2H).

Example 58.2 Second Elute (18 mg, a Mixture of Stereoisomers)

$^1$H NMR (500 MHz, MeOH-$d_4$) δ 8.52-8.42 (m, 1H), 7.35-7.28 (m, 2H), 7.25-7.17 (m, 1H), 7.10-7.02 (m, 1H), 6.82-6.71 (m, 1H), 6.68-6.59 (m, 2H), 5.97-5.88 (m, 1H), 4.50-4.32 (m, 2H), 4.22-4.13 (m, 3H), 3.65-3.56 (m, 3H), 3.52-3.44 (m, 1H), 3.28 (s, 3H), 3.17-3.05 (m, 1H), 2.01-1.92 (m, 2H), 1.90-1.80 (m, 1H), 0.90-0.81 (m, 2H), 0.70-0.58 (m, 2H).

2-Amino-6-ethoxynicotinic acid (Int CI17a)

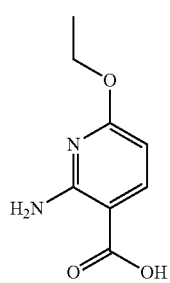

Sodium hydride (1.16 g, 29.0 mmol) was added to ethanol (8.33 ml), copper(I) iodide (0.055 g, 0.290 mmol) and 2-amino-6-chloronicotinic acid (0.5 g, 2.90 mmol) were added. The reaction mixture was then stirred for 3 h at 110° C., then overnight at 80° C. and cooled to rt. Diethyl ether and aqueous ammonia were added to the reaction mixture. The aqueous layer was isolated and neutralized with citric acid (0.5 M), then extracted with DCM. The organic layer was washed with brine, dried over MgSO$_4$ and concentrated to give a reddish brown solid (0.34 g, used as is). LC/MS: m/z=183.1 [M+H]$^+$.

tert-butyl (S)-(1-(3-(4-chloro-3-(N-(4-methoxybenzyl)methylsulfonamido)-1-methyl-1H-indazol-7-yl)-7-ethoxy-4-oxo-3,4-dihydropyrido[2,3-d]pyrimidin-2-yl)-2-(3,5-difluorophenyl)ethyl)carbamate (Int CI17b)

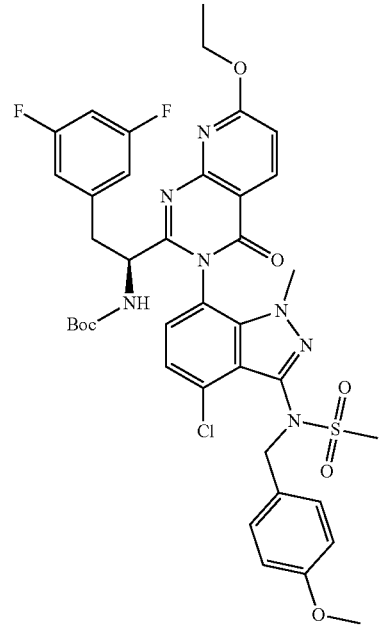 [SMILES: CCOc1ccc2c(=O)n(-c3ccc(Cl)c4c(N(Cc5ccc(OC)cc5)S(C)(=O)=O)nn(C)c34)c([C@H](Cc3cc(F)cc(F)c3)NC(=O)OC(C)(C)C)nc2n1]

A mixture of (S)-2-((tert-butoxycarbonyl)amino)-3-(3,5-difluorophenyl)propanoic acid (0.1 g, 0.332 mmol), 2-amino-6-ethoxynicotinic acid (Int CI17a, 0.060 g, 0.332 mmol), N-(7-amino-4-chloro-1-methyl-1H-indazol-3-yl)-N-(4-methoxybenzyl)methanesulfonamide (0.131 g, 0.332 mmol) and diphenyl phosphite (0.26 ml, 1.328 mmol) in Pyridine (1.3 ml) in a pressure vial was heated in an aluminum block for 2.5 hours at 70° C. and cooled to rt. The reaction mixture was purified on silica gel (40 g Isco column) using 0-100% ethyl acetate in hexanes. The desired fractions were concentrated to give an orange solid as the product (0.14 g). LC/MS: m/z=824.3 [M+H]$^+$.

221

(S)—N-(7-(2-(1-amino-2-(3,5-difluorophenyl)ethyl)-7-ethoxy-4-oxopyrido[2,3-d]pyrimidin-3(4H)-yl)-4-chloro-1-methyl-1H-indazol-3-yl)-N-(4-methoxy-benzyl)methanesulfonamide hydrochloride (Int CI17c)

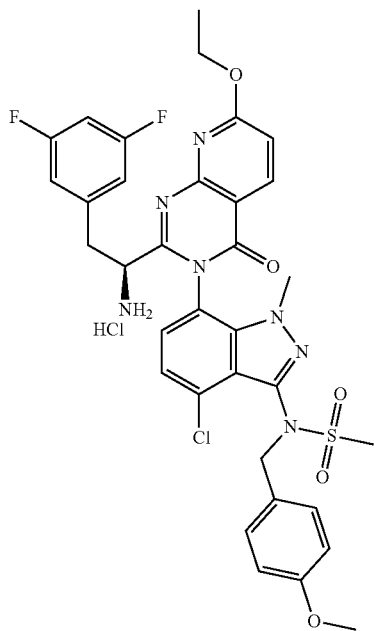 [SMILES: CCOc1ccc2c(=O)n(-c3ccc(Cl)c4c(N(Cc5ccc(OC)cc5)S(C)(=O)=O)nn(C)c34)c([C@@H](N)Cc3cc(F)cc(F)c3)nc2n1 ; Cl]

HCl (2.60 ml, 10.41 mmol) and tert-butyl (S)-(1-(3-(4-chloro-3-(N-(4-methoxybenzyl)methylsulfonamido)-1-methyl-1H-indazol-7-yl)-7-ethoxy-4-oxo-3,4-dihydro-pyrido[2,3-d]pyrimidin-2-yl)-2-(3,5-difluorophenyl)ethyl)carbamate (Int CI17b, 0.143 g, 0.173 mmol) was stirred at rt for 0.5 h and concentrated to give an off-white solid (used as is).

N-[(1S)-1-[3-(4-chloro-3-methanesulfonamido-1-methyl-1H-indazol-7-yl)-7-ethoxy-4-oxo-3H,4H-pyrido[2,3-d]pyrimidin-2-yl]-2-(3,5-difluorophenyl)ethyl]-2-(3-cyclopropyl-1H-pyrazol-1-yl)acetamide (Example 59)

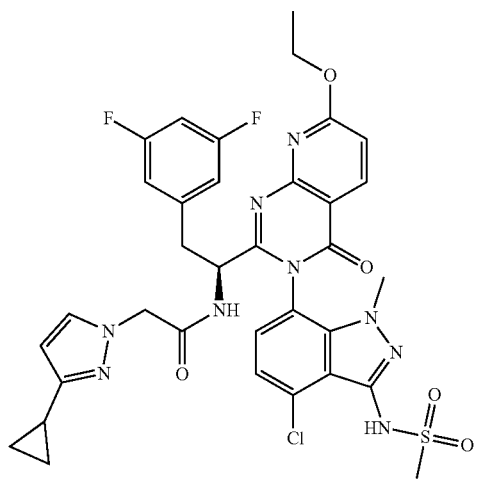

mixture of enantiomers of unknown proportion

222

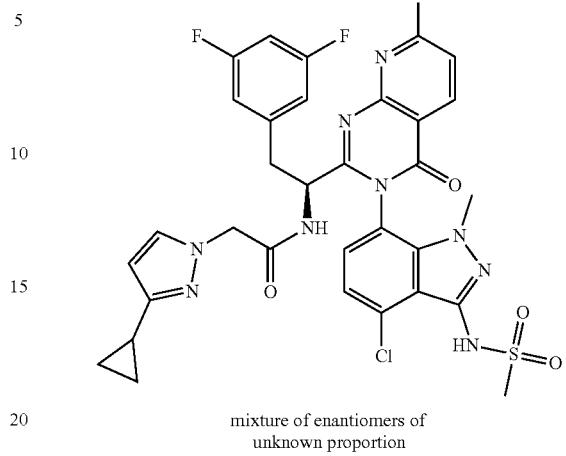

mixture of enantiomers of unknown proportion

Prepared according to the general procedure described for Example 38.1 and 38.2 using Int CI17c. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 25% B, 25-65% B over 27 minutes, then a 7-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 752.11; Retention Time: 1.89 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 752.06; Retention Time: 1.85 min. Two elutes were isolated.

Example 59.1 First Elute (9 mg, a Mixture of Enantiomers of Unknown Proportion)

$^1$H NMR (500 MHz, MeOH-d$_4$) δ 8.50-8.41 (m, 1H), 7.58-7.47 (m, 1H), 7.37-7.31 (m, 1H), 7.25-7.17 (m, 1H), 7.07-7.01 (m, 1H), 6.81-6.71 (m, 1H), 6.59-6.48 (m, 2H), 6.10-5.98 (m, 1H), 4.79-4.61 (m, 2H), 3.43-3.35 (m, 1H), 3.34-3.33 (m, 3H), 3.30-3.26 (m, 3H), 3.20-3.15 (m, 3H), 3.02-2.93 (m, 1H), 1.97-1.89 (m, 1H), 1.56-1.49 (m, 3H), 0.95-0.88 (m, 2H), 0.74-0.67 (m, 2H).

Example 59.2 Second Elute (16 mg, a Mixture of Enantiomers of Unknown Proportion)

$^1$H NMR (500 MHz, MeOH-d$_4$) δ 8.51-8.41 (m, 1H), 7.36-7.28 (m, 2H), 7.25-7.18 (m, 1H), 7.08-7.01 (m, 1H), 6.82-6.73 (m, 1H), 6.68-6.61 (m, 2H), 5.96-5.86 (m, 1H), 4.69-4.52 (m, 2H), 4.49-4.28 (m, 2H), 3.65-3.56 (m, 3H), 3.52-3.40 (m, 1H), 3.32-3.24 (m, 4H), 3.14-3.03 (m, 1H), 1.90-1.78 (m, 1H), 1.55-1.45 (m, 3H), 0.89-0.82 (m, 2H), 0.71-0.58 (m, 2H).

N-[(1S)-1-[3-(4-chloro-3-methanesulfonamido-1-methyl-1H-indazol-7-yl)-7-ethoxy-4-oxo-3H,4H-pyrido[2,3-d]pyrimidin-2-yl]-2-(3,5-difluorophenyl)ethyl]-2-[(2S,4R)-9-(difluoromethyl)-5,5-difluoro-7,8-diazatricyclo[4.3.0.0$^{2,4}$]nona-1(6),8-dien-7-yl]acetamide (Example 60.2) and Example 60.1

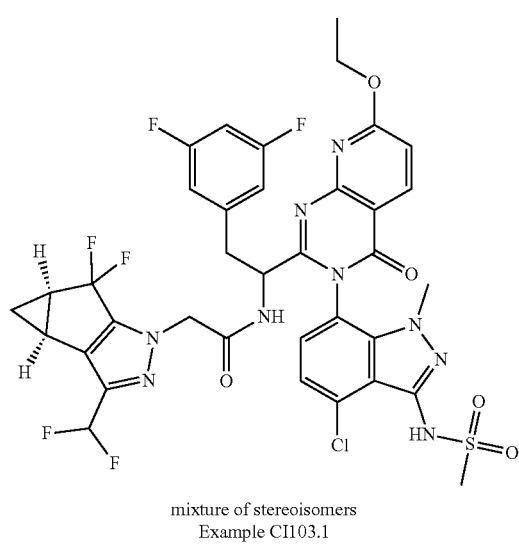

mixture of stereoisomers
Example CI103.1

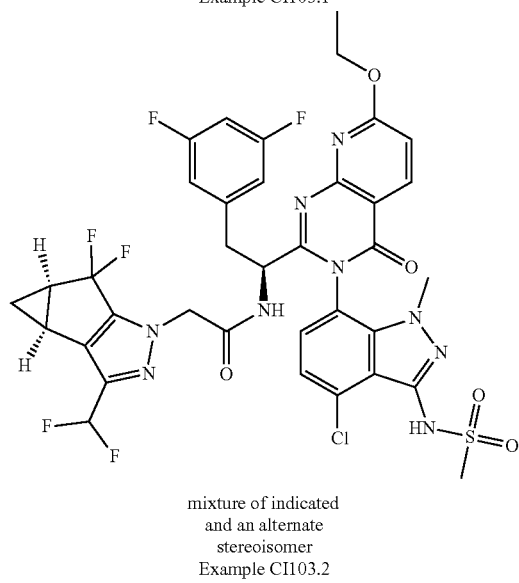

mixture of indicated
and an alternate
stereoisomer
Example CI103.2

Prepared according to the general procedure described for Example 38.1 and 38.2 using Int CI17c. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 32% B, 32-72% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.2%; Observed Mass: 850.12; Retention Time: 2.07 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.6%; Observed Mass: 850.09; Retention Time: 2.1 min. Two elutes were isolated.

Example 60.1 First Elute (15 mg, a Mixture of Stereoisomers)

Example 60.2 Second Elute (15 mg, a Mixture of Stereoisomers)

$^1$H NMR (500 MHz, MeOH-d$_4$) δ 8.47 (br d, J=8.5 Hz, 1H), 7.34-7.26 (m, 1H), 7.25-7.17 (m, 1H), 7.10-7.01 (m, 11H), 6.89-6.47 (m, 4H), 4.71-4.49 (m, 4H), 3.65-3.56 (m, 3H), 3.49-3.42 (m, 1H), 3.29-3.22 (m, 3H), 3.15-3.06 (m, 1H), 2.48-2.38 (m, 2H), 1.55-1.46 (m, 3H), 1.41-1.25 (m, 3H), 1.03-0.97 (m, 1H).

tert-butyl (S)-(1-(7-amino-6-(3-oxoisoindolin-5-yl)-[1,2,4]triazolo[1,5-a]pyrimidin-5-yl)-2-(3,5-difluorophenyl)ethyl)carbamate (Int 10.32a)

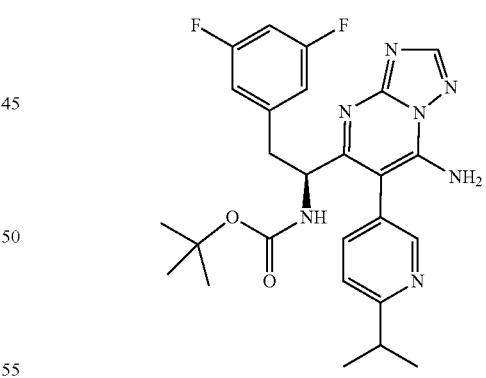

To a dry reaction vial under nitrogen was added with tert-butyl (S)-(1-(7-amino-6-bromo-[1,2,4]triazolo[1,5-a]pyrimidin-5-yl)-2-(3,5-difluorophenyl)ethyl)carbamate (58.7 mg, 0.125 mmol) (Int DF7b), (6-isopropyl-3-pyridinyl)boronic acid (31 mg, 0.188 mmol), toluene (2.75 mL), Dioxane (3.5 mL) and sodium carbonate, 2M in water (200 μL, 0.400 mmol). The reaction was flushed very well with argon, treated with tetrakis(triphenylphosphine)palladium (0) (22.3 mg, 0.019 mmol), flushed with argon again, capped and heated at 130° C. for 18h. The reaction was treated with additional dioxane (1.0 mL), (6-isopropyl-3-pyridinyl)boronic acid (19 mg, 0.115 mmol) and a small amount of tetrakis Pd (did not weigh), flushed with argon and heated at 130° C. for 48 h. The reaction was diluted with ethyl acetate (80 mL) and water (8 mL), the organic layer was washed with brine (1×5 mL), dried over sodium sulfate, filtered and evaporated to dryness. The crude residue was purified via silica gel chromatography (24 g SiO$_2$ column, 0-100% dichloromethane:ACN) to afford the title compound, 67.4 mg. LC/MS m/z 510.3 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.29 min.

(S)-5-(1-amino-2-(3,5-difluorophenyl)ethyl)-6-(6-isopropylpyridin-3-yl)-[1,2,4]triazolo[1,5-a]pyrimidin-7-amine (Int 10.32b)

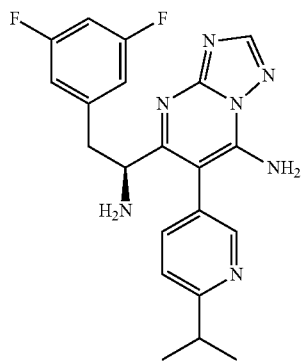 [SMILES: CC(C)c1ccc(-c2c([C@@H](N)Cc3cc(F)cc(F)c3)nc3ncnn3c2N)cn1]

To a solution of tert-butyl (S)-(1-(7-amino-6-(6-isopropylpyridin-3-yl)-[1,2,4]triazolo[1,5-a]pyrimidin-5-yl)-2-(3,5-difluorophenyl)ethyl)carbamate (46.5 mg, 0.091 mmol) (Int 10.32a) in anhydrous dichloromethane (10 mL) was added TFA (4.0 mL, 51.9 mmol) with rapid swirling. The reaction was allowed to stand at room temp for 20 min, then the solvent was slowly removed under a gentle stream of nitrogen for 18 h. The residue was redissolved in additional dichloromethane (10 mL), treated with additional TFA (4 mL) and allowed to stand at room temp for 30 min, then the volatiles were removed under a gentle stream of N$_2$ for 36 h. The residue was dissolved in ethyl acetate (60 mL) and the organic layer was washed with saturated aqueous sodium bicarbonate (1×10 mL), brine (1×5 mL), dried over sodium sulfate, filter and evaporated to dryness to give the desired product, 30 mg, that was used ":as is' in subsequent reaction (s). LC/MS m/z 410.2 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.03 min.

N—((S)-1-(7-amino-6-(6-isopropylpyridin-3-yl)-[1,2,4]triazolo[1,5-a]pyrimidin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 10.32)

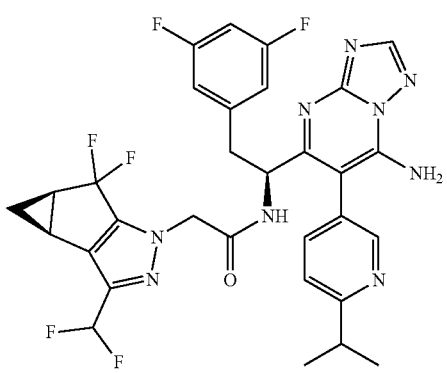 [SMILES: CC(C)c1ccc(-c2c([C@H](Cc3cc(F)cc(F)c3)NC(=O)Cn3nc(C(F)F)c4c3C(F)(F)[C@@H]3C[C@H]43)nc3ncnn3c2N)cn1]

To a solution of (S)-5-(1-amino-2-(3,5-difluorophenyl)ethyl)-6-(6-isopropylpyridin-3-yl)-[1,2,4]triazolo[1,5-a]pyrimidin-7-amine (30 mg, 0.073 mmol) (Int 10.32b) in anhydrous DMF (1.0 mL) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (18 mg, 0.068 mmol) and 1-hydroxy-7-azabenzotriazole (3 mg, 0.022 mmol). The reaction was flushed briefly with N2, then treated with N-methylmorpholine (50 µL, 0.455 mmol) followed by EDC (13 mg, 0.068 mmol) and allowed to stir at room temp for 35 min. The crude material was purified via preparative LC/MS to afford the title compound, 11.2 mg, likely as a mixture of stereoisomers. LC/MS m/z 656.2 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.92 min.

2-(3,5-difluorophenyl)-N-methoxy-N-methylacetamide (Int DF6a)

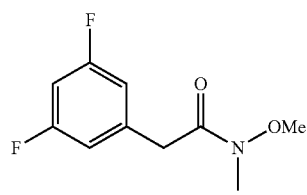

To a 500 mL round bottom flask under nitrogen was added 2-(3,5-difluorophenyl)acetic acid (10.05 g, 58.4 mmol), 1-hydroxy-7-azabenzotriazole (800 mg, 5.88 mmol), N,O-dimethylhydroxylamine hydrochloride (5.92 g, 60.7 mmol) and anhydrous dichloromethane (350 mL). The reaction was then treated with N-methylmorpholine (21 ml, 191 mmol), followed by EDC (11.85 g, 61.8 mmol) and allowed to stir for 36 h. The reaction was diluted with dichloromethane (75 mL) and partitioned in a 1 L separatory funnel versus saturated aqueous NaHCO₃ (200 mL), water (50 mL). The organic layer was then extracted 0.3 N HCl (250 mL), water (300 mL), brine (300 mL), dried over $Na_2SO_4/MgSO_4$, filtered and evaporated to dryness to give the title compound, 11.91 g. LC/MS m/z 216.0 (M+H)⁺. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.23 min. ¹H NMR (500 MHz, CDCl3-d) δ 6.91-6.82 (m, 2H), 6.72 (tt, J=9.0, 2.3 Hz, 1H), 3.76 (s, 2H), 3.69 (s, 3H), 3.23 (s, 3H)

6-bromo-1-(triisopropylsilyl)-1H-pyrrolo[3,2-b]pyridine (Int DF6b)

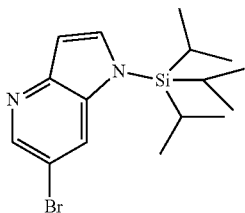 [SMILES: CC(C)[Si](C(C)C)(C(C)C)n1ccc2ncc(Br)cc21]

To a 250 mL round bottom flask under nitrogen was added 6-bromo-1H-pyrrolo[3,2-b]pyridine (2.5 g, 12.69 mmol) and anhydrous THF (50 mL) The reaction was cooled to 0° C., treated with potassium tert-butoxide, 1.0 M in THF (15.23 mL, 15.23 mmol) and stirred at 0° C. for 30 min. The reaction was then treated with TIPS-Cl (2.96 mL, 13.96 mmol), the bath was removed and the reaction allowed to warm to room temp over 18h. The reaction was recooled to 0° C., quenched with 6 mL of saturated aq. NH₄Cl and allowed to warm to room temp over 18h. The solvent was removed under a stream of nitrogen and the residue was dissolved in ethyl acetate. The organic layer was washed with water, dried over MgSO₄, filtered and evaporated to dryness. The crude residue was purified via silica gel chromatography (80 g SiO₂ column, 0-100% hexanes:ethyl acetate) to afford the title compound, 3.62 g. LC/MS m/z 353.0, 355.0 (M+H)⁺. Column: Waters Aquity UPLC BEH C18, 2.1 mm×50 mm, 1.7 μm particles; Mobile Phase A: 10% MeOH: 90% water: 0.1% TFA; Mobile Phase B: 90% MeOH: 10% water: with 0.1% TFA; Temperature: 40° C.; Gradient: 0% B to 100% B over 2 min, then a 1 min hold at 100% B; Flow: 0.8 mL/min; Detection: UV (254 nm); Retention Time: 2.12 min. ¹H NMR (400 MHz, CDCl₃) δ 8.51 (d, J=2.0 Hz, 11H), 7.89 (dd, J=1.9, 0.9 Hz, 1H), 7.48 (d, J=3.3 Hz, 1H), 6.83 (dd, J=3.4, 0.9 Hz, 1H), 1.68 (quin, J=7.5 Hz, 3H), 1.17 (d, J=7.5 Hz, 18H)

1-(6-bromo-1-(triisopropylsilyl)-1H-pyrrolo[3,2-b]pyridin-5-yl)-2-(3,5-difluorophenyl)ethan-1-one (Int DF6c)

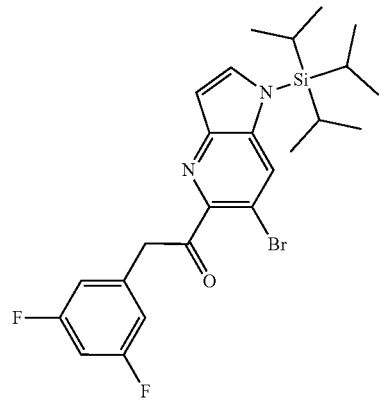 [SMILES: CC(C)[Si](C(C)C)(C(C)C)n1ccc2nc(C(=O)Cc3cc(F)cc(F)c3)c(Br)cc21]

To a solution of solution of 6-bromo-1-(triisopropylsilyl)-1H-pyrrolo[3,2-b]pyridine (2.57 g, 7.27 mmol) (Int DF6b) in distilled THF (75 mL) [hereafter, the phrase "distilled THF" means that the THF was distilled over sodium benzophenone ketyl under a nitrogen atmosphere] under argon at −30° C. was added 2,2,6,6-tetramethylpiperidinylmagnesium chloride lithium chloride complex 1.0 M in THF/toluene (15 mL, 15.00 mmol) over 3 min. The reaction was stirred at a range of −30° C. to −7° C. (optimal temp is −10° C.) for 2.25 h, cooled to −40° C., then treated with neat 2-(3,5-difluorophenyl)-N-methoxy-N-methylacetamide (3.3 g, 15.33 mmol) (Int DF6a). The reaction was stirred at a range of −40° C. to −25° C. for 15 min, then stored at −20° C. for 18h. The reaction was then stirred at a range of −15° C. to 0° C. for 3h, cooled to −40° C. and quenched with saturated aqueous NH4Cl (200 mL). The reaction was diluted with ethyl acetate (400 mL) and the organic layer was washed with brine. The aqueous layer was extracted with additional ethyl acetate (300 mL) and the organic layer was washed with brine. The organic layers were combined, dried over Na₂SO₄, filtered and evaporated to dryness. The crude residue was purified via silica gel chromatography (120 g SiO₂ column, 0-40% dichloromethane:ethyl acetate) to afford the title compound, 1.83 g. LC/MS m/z 507.2, 509.2 (M+H)⁺. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.23 min. ¹H NMR (500 MHz, CDCl₃) δ 8.02 (d, J=0.8 Hz, 1H), 7.60 (d, J=3.4 Hz, 1H), 6.96-6.87 (m, 3H), 6.70 (tt, J=9.1, 2.4 Hz, 1H), 4.59 (s, 2H), 1.69 (quin, J=7.6 Hz, 3H), 1.17 (d, J=7.5 Hz, 18H).

(E)-1-(6-bromo-1H-pyrrolo[3,2-b]pyridin-5-yl)-2-(3, 5-difluorophenyl)ethan-1-one oxime (Int DF6d)

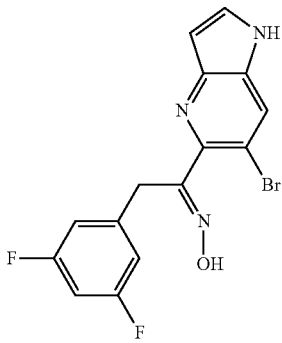 [SMILES: O/N=C(\Cc1cc(F)cc(F)c1)c1nc2cc[nH]c2cc1Br]

To a solution of 1-(6-bromo-1-(triisopropylsilyl)-1H-pyrrolo[3,2-b]pyridin-5-yl)-2-(3,5-difluorophenyl)ethan-1-one (212.2 mg, 0.418 mmol) (Int DF6c) in anhydrous MeOH (3 mL) was added hydroxylamine hydrochloride (90.5 mg, 1.302 mmol). The reaction was flushed with argon, capped and stirred at room temp for 18h. The solvent was removed under a gentle stream of nitrogen and the residue was dissolved in ethyl acetate (75 mL). The organic layer was washed with saturated aqueous $NaHCO_3$ (15 mL). The aqueous layer was back extracted with additional ethyl acetate (20 mL), the organic layers were combined, washed with brine (1×15 mL), dried over $Na_2SO_4$, filtered and evaporated to dryness to give the title compound, 132.8 mg. LC/MS m/z 366, 368 $(M+H)^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.27 min.

1-(6-bromo-1H-pyrrolo[3,2-b]pyridin-5-yl)-2-(3,5-difluorophenyl)ethan-1-amine (Int DF 6e)

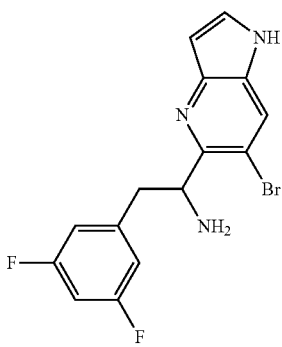 [SMILES: NC(Cc1cc(F)cc(F)c1)c1nc2cc[nH]c2cc1Br]

Bioorg. & Med. Chem., vol 24 (2016), pp 2257-2272.

To a solution of (E)-1-(6-bromo-1H-pyrrolo[3,2-b]pyridin-5-yl)-2-(3,5-difluorophenyl)ethan-1-one oxime (132.8 mg, 0.363 mmol) (Int DF6d) in TFA (2.0 mL) at −10° C. was added zinc (241.8 mg, 3.70 mmol) in 3 portions. The reaction was stirred at −10° C. for 1 min, then the bath was removed and the reaction was allowed to slowly warm to room temp over 18h. The reaction was treated with additional zinc (200 mg, 3.06 mmol) (nanoparticle size) and allowed to stir at room temp for 90 min, or until judged to be complete by LC/MS. The reaction was filtered thru a small plug of glass wool, rinsed with a small amount of TFA and the volatiles were evaporated off under a gentle stream of nitrogen. The residue was Dissolved residue in ethyl acetate (65 mL) and the organic layer was extracted with aqueous saturated $NaHCO_3$ (35 mL). The water layer was back extracted with ethyl acetate (2×30 mL), the organic layers were combined, washed with brine (1×15 mL), dry over $Na_2SO_4$, filtered and evaporated to dryness to give the title compound, 158 mg. LC/MS m/z 352,354 $(M+H)^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.17 min.

Note that this reaction can be quite difficult in that complete debromination can occur if the reaction is allowed to go too long. Care must be taken when adding the zinc reagent and the reaction should be monitored frequently, by LC/MS to avoid the debrominated side product.

N-(1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF6f), N—((S)-1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF6f.1) and N—((R)-1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF6f.2)

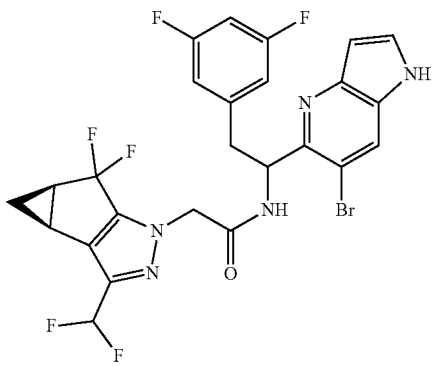

Int DF6f

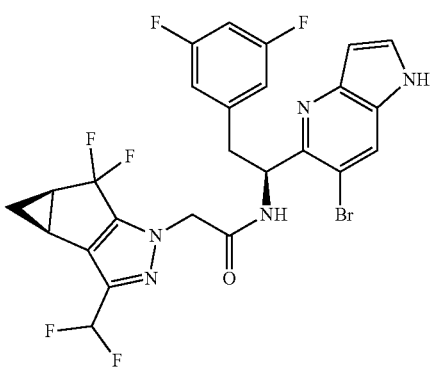

Int DF6f.1

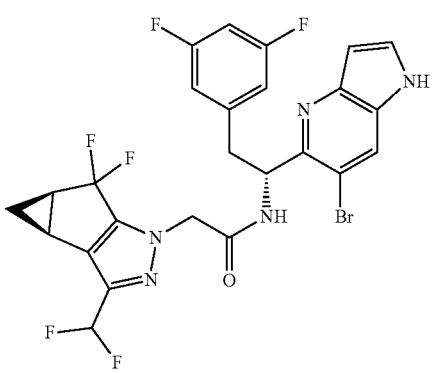

Int DF6f.2

To a suspension of 1-(6-bromo-1H-pyrrolo[3,2-b]pyridin-5-yl)-2-(3,5-difluorophenyl)ethan-1-amine (125 mg, 0.355 mmol) (Int DF6e), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (94 mg, 0.355 mmol) and 1-hydroxy-7-azabenzotriazole (11.8 mg, 0.087 mmol) in anhydrous dichloromethane (15 mL) was added N-methylmorpholine (200 µl, 1.819 mmol), followed by EDC (79 mg, 0.412 mmol). The reaction was stirred at room temp for 5 min, then distilled THF (10 mL) was added and the reaction was allowed to stir at room temp for 45 min. The solvent was removed under a gentle stream of nitrogen and the crude residue was purified via silica gel chromatography (80 g SiO$_2$ column, 0-40% dichloromethane:ethyl acetate) then further purified by chiral SCF chromatography (Chiralpak AS-H column, 10% methanol, 0.1% DEA in CO$_2$, 150 bar, 220/254 nm) to afford the pure stereoisomers: Int DF6f: 390 mg. LC/MS m/z 598.2, 600.2 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.52 min. Int DF6f.1: 112.5 mg. Int DF6f.2: 140.7 mg.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-(2-(3,5-difluorophenyl)-1-(6-(3-oxoisoindolin-5-yl)-1H-pyrrolo[3,2-b]pyridin-5-yl)ethyl)acetamide (Example 61)

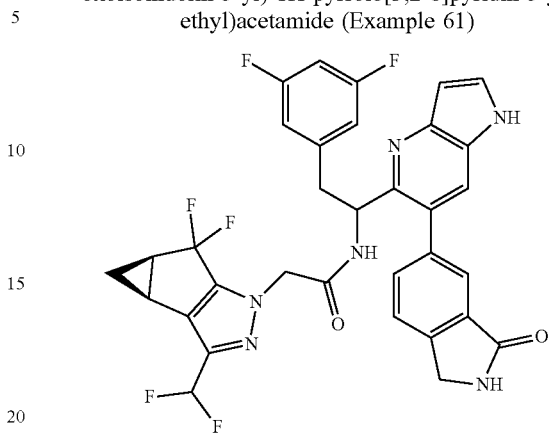

To a dry reaction vial under nitrogen was added N-(1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (29.7 mg, 0.050 mmol) (Int DF6f), 6-(4,4,5,5-tetramethyl-1,3,2-dioxaborolan-2-yl)isoindolin-1-one (38.6 mg, 0.149 mmol) and degassed Dioxane (4 mL). The reaction flushed with argon for, treated with sodium carbonate, 2.0M in water (112 µL, 0.224 mmol) followed by tetrakis(triphenylphosphine)palladium(0) (6 mg, 5.19 µmol), flushed with argon again, capped and heated at 130° C. for 18h. The reaction was treated with additional 6-(4,4,5,5-tetramethyl-1,3,2-dioxaborolan-2-yl)isoindolin-1-one (16 mg, 0.06 mmol) and tetrakis Pd, flushed with argon and heated at 130° C. for 24 h. The reaction diluted with ethyl acetate (50 mL), washed with brine (10 mL), dried over Na$_2$SO$_4$, filtered and evaporate to dryness. The crude material was purified via preparative LC/MS to afford the title compound, likely a mixture of stereoisomers, 8.8 mg. LC/MS m/z 651.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.79 min.

tert-butyl (S)-(1-(7-amino-[1,2,4]triazolo[1,5-a]pyrimidin-5-yl)-2-(3,5-difluorophenyl)ethyl)carbamate (Int DF7a)

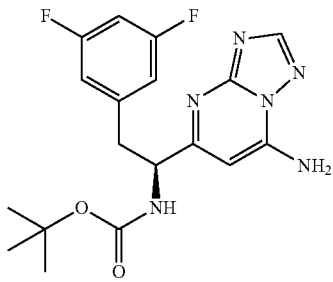 [SMILES: CC(C)(C)OC(=O)N[C@@H](Cc1cc(F)cc(F)c1)c1cc(N)n2ncnc2n1]

To a 150 mL pressure bottle under nitrogen was added tert-butyl (S)-(4-cyano-1-(3,5-difluorophenyl)-3-oxobutan-2-yl)carbamate (1.694 g, 5.22 mmol) (Int DF3b), 1H-1,2,4- triazol-3-amine (967.4 mg, 11.51 mmol) and anhydrous Toluene (55.3 mL). The reaction was flushed with nitrogen, treated with acetic acid (1.1 mL, 19.22 mmol), capped, and heated at 125° C. for 8h. The solvent was evaporated off under a gentle stream of nitrogen and the residue was dissolved in a THF/dichloromethane mixture (roughly 2:1) and diluted with ethyl acetate. The organic layer is washed with aqueous saturated NaHCO3 (1×35 mL), brine (1×35 mL), dried over $Na_2SO_4$, filtered and evaporated to dryness. The aqueous layer is back extracted with ethyl acetate (1×75 mL) and the organic layer is washed with brine (1×10 mL), dried over $Na_2SO_4$ and combined with the bulk organic layer. The residue was twice treated with dichloromethane (75 mL) and evaporated to dryness. The reside was suspended in dichloromethane (35 mL) and the solid was collected by vacuum filtration to afford the title compound, 747 mg. LC/MS m/z 391.1 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.21 min tert-butyl (S)-(1-(7-amino-6-bromo-[1,2,4]triazolo [1,5-a]pyrimidin-5-yl)-2-(3,5-difluorophenyl)ethyl) carbamate (Int DF7b)

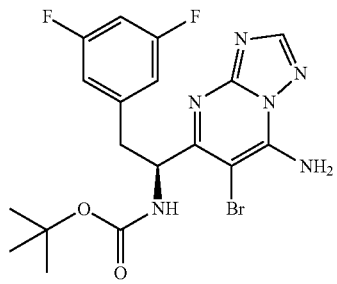 [SMILES: CC(C)(C)OC(=O)N[C@@H](Cc1cc(F)cc(F)c1)c1nc2ncnn2c(N)c1Br]

To a suspension of tert-butyl (S)-(1-(7-amino-[1,2,4]triazolo[1,5-a]pyrimidin-5-yl)-2-(3,5-difluorophenyl)ethyl) carbamate (300 mg, 0.768 mmol) (Int DF7a) in anhydrous Acetonitrile (9.5 mL) was added N-bromosuccinimide (48.2 mg, 0.271 mmol). The resulting tan suspension was stirred at room temp for 15 min. After 15 min, added additional NBS (48 mg, 0.27 mmol) in 3 portions (more or less equal) over 15 min. The reaction was checked by LC/MS and judged to be partially complete. Additional NBS (40.8 mg, 0.229 mmol) was added in 3 portions (more or less equal) over 15 min and the reaction was stirred at room temp for 20 min. The reaction (a suspension) was filtered thru a small frit to afford the title compound, 319.5 mg (includes a second crop). LC/MS m/z 469.1, 471.1 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.36 min tert-butyl (S)-(1-(7-amino-6-(3-oxoisoindolin-5-yl)-[1,2,4]triazolo[1,5-a]pyrimidin-5-yl)-2-(3,5-difluorophenyl)ethyl)carbamate (Int DF7c)

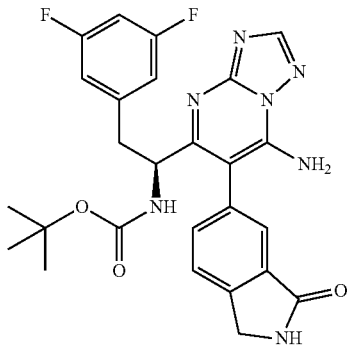 [SMILES: CC(C)(C)OC(=O)N[C@@H](Cc1cc(F)cc(F)c1)c1nc2ncnn2c(N)c1-c1ccc2c(c1)C(=O)NC2]

To a dry reaction vial under nitrogen was added with tert-butyl (S)-(1-(7-amino-6-bromo-[1,2,4]triazolo[1,5-a]pyrimidin-5-yl)-2-(3,5-difluorophenyl)ethyl)carbamate (40 mg, 0.085 mmol) (Int DF7b), 6-(4,4,5,5-tetramethyl-1,3,2-dioxaborolan-2-yl)isoindolin-1-one (35 mg, 0.135 mmol) and degassed dioxane (2.5 mL). The reaction was flushed with argon, then treated with sodium carbonate 2 M in water (0.20 mL, 0.400 mmol), followed by tetrakis(triphenylphosphine)palladium(0) (5 mg, 4.33 μmol). The reaction was flushed with argon, capped, stirred at room temp for 10 min, then heated at 135° C. for 44h. The reaction was partitioned with Ethyl acetate and brine and the organic layer was dried over Na2SO4, filtered and evaporated to dryness. The crude residue was purified via silica gel chromatography (24 g $SiO_2$ column, 0-100% dichloromethane:ACN) to afford the title compound, 27 mg. LC/MS m/z 522.3 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.27 min (S)-6-(7-amino-5-(1-amino-2-(3,5-difluorophenyl) ethyl)-[1,2,4]triazolo[1,5-a]pyrimidin-6-yl)isoindolin-1-one (Int DF7d)

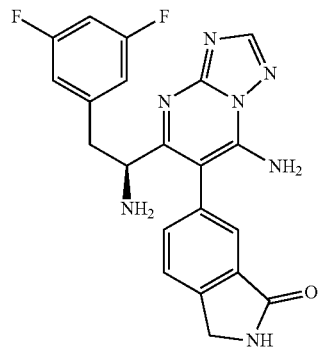 [SMILES: Nc1c(-c2ccc3c(c2)C(=O)NC3)c([C@@H](N)Cc2cc(F)cc(F)c2)nc2ncnn12]

To a solution of tert-butyl (S)-(1-(7-amino-6-(3-oxoisoindolin-5-yl)-[1,2,4]triazolo[1,5-a]pyrimidin-5-yl)-2-(3,5-difluorophenyl)ethyl)carbamate (27 mg, 0.052 mmol) in anhydrous dichloromethane (3 mL) was added TFA (10 mL, 130 mmol) with rapid swirling. The reaction was allowed to stand at room temp for 45 min and then the volatiles were removed under a gentle stream of nitrogen. The residue was dissolved in ethyl acetate (45 mL) and the organic layer was washed with aqueous saturated NaHCO$_3$ (2×15 mL), brine (1×10 mL), dried over Na$_2$SO$_4$, filtered and evaporated to dryness. Transfer to 20 mL reaction vial with dichloromethane and evaporate to dryness again to afford the title compound, 22 mg. LC/MS m/z 422.2 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.10 min N—((S)-1-(7-amino-6-(3-oxoisoindolin-5-yl)-[1,2,4]triazolo[1,5-a]pyrimidin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 62)

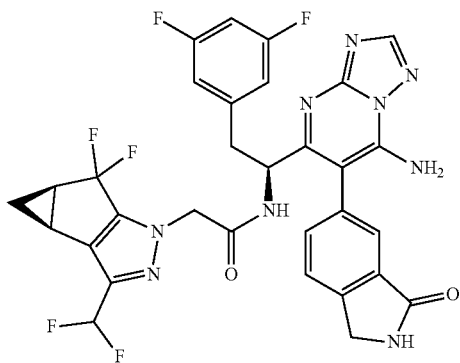 [SMILES: Nc1c(-c2ccc3c(c2)C(=O)NC3)c([C@H](Cc2cc(F)cc(F)c2)NC(=O)Cn2nc(C(F)F)c3c2C(F)(F)[C@@H]2C[C@H]32)nc2ncnn12]

To a solution of (S)-6-(7-amino-5-(1-amino-2-(3,5-difluorophenyl)ethyl)-[1,2,4]triazolo[1,5-a]pyrimidin-6-yl)isoindolin-1-one (21.91 mg, 0.052 mmol) (Int DF7d) in anhydrous DMF (2.5 mL) was added 1-hydroxy-7-azabenzotriazole (1 mg, 7.35 µmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (3.5 mg, 0.013 mmol). The reaction is flushed briefly with nitrogen, then treated with N-methylmorpholine (30 µL, 0.273 mmol) followed by EDC (2.5 mg, 0.013 mmol) and stirred at room temp for 20 min. The reaction was treated with additional 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (3.5 mg, 0.013 mmol) and allowed to stir at room temp until judged to be complete. The crude material was purified via preparative LC/MS to afford the title compound, 3.8 mg, likely as a mixture of stereoisomers. LC/MS m/z 668.2 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.56 min.

N-(1-(6-(4-chloro-1-methyl-3-(methylsulfonamido)-1H-indazol-7-yl)-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF8a)

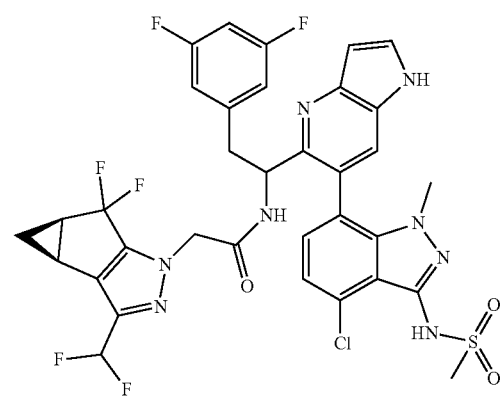 [SMILES: Cn1nc(NS(C)(=O)=O)c2c(Cl)ccc(-c3cc4[nH]ccc4nc3C(Cc3cc(F)cc(F)c3)NC(=O)Cn3nc(C(F)F)c4c3C(F)(F)[C@@H]3C[C@H]43)c21]

To a dry reaction vial under nitrogen was added N-(1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (24 mg, 0.040 mmol) (Int DF6f), N-(4-chloro-1-methyl-7-(4,4,5,5-tetramethyl-1,3,2-dioxaborolan-2-yl)-1H-indazol-3-yl)methanesulfonamide (47 mg, 0.122 mmol) and degassed Dioxane (4 mL). The reaction was purged with argon, treated with sodium carbonate, 2.0M in water (100 µL, 0.200 mmol) followed by tetrakis(triphenylphosphine)palladium(0) (6 mg, 5.19 µmol). The reaction was again purged with argon, capped and heated at 135° C. for 18h. The reaction was diluted with ethyl acetate (50 mL) and the organic layer was washed with water (5 mL), brine (8 mL), dried over Na2SO4, filtered and evaporated to dryness to give the title compound, 31.2 mg. LC/MS m/z 777.3 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.37 min N—((S)-1-(6-(4-chloro-1-methyl-3-(N-methylmethylsulfonamido)-1H-indazol-7-yl)-1-methyl-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 64) and Example 63

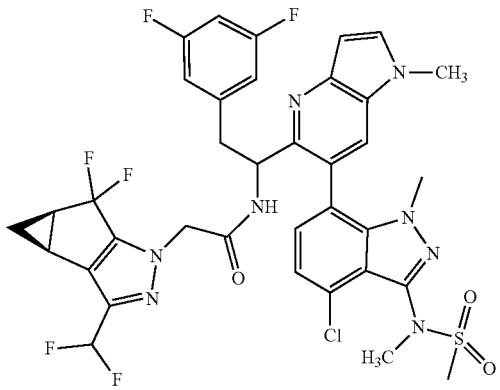

Example DF8
Mix of two steroisomers

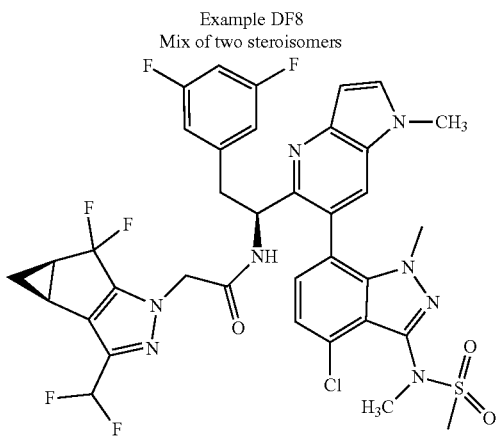

Example DF9
A mixture of indicated isomer and a steroisomer

To a solution of N-(1-(6-(4-chloro-1-methyl-3-(methylsulfonamido)-1H-indazol-7-yl)-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (31.2 mg, 0.040 mmol) (Int DF8a, crude material) in THF (5 mL) was added triphenylphosphine (42 mg, 0.160 mmol). The reaction was flushed with nitrogen, capped, then treated with methanol (31.6 µL, 0.780 mmol), followed by DIAD (35 µL, 0.180 mmol) and allowed to stir at room temp for 4.5h. The solvent was removed under a gentle stream of nitrogen and the residue was dissolved in acetone, treated with K2CO3 (300 mg, 2.17 mmol) and iodomethane (50 µlit, 0.8 mmol) and heated at 55° C. for 18h. The reaction was treated with additional iodomethane (75 µlit, 1.2 mmol) and heated at 55° C. for 18h. The reaction was filtered thru a frit and the crude material was purified via preparative LC/MS to afford two elutes.

Example 63: First Eluting Peak, 1.2 mg

LC/MS m/z=811.0 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Retention Time: 2.17 min.

Example 64: Second Eluting Peak, 4.6 mg

LC/MS m/z=805.1 (M+H)$^+$. Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100.0%; Retention Time: 2.27 min.

tert-butyl (R)-(1-(6-bromo-1H-pyrrolo[3,2-b]pyridin-5-yl)-2-(3,5-difluorophenyl)ethyl)carbamate and tert-butyl (S)-(1-(6-bromo-1H-pyrrolo[3,2-b]pyridin-5-yl)-2-(3,5-difluorophenyl)ethyl)carbamate (Int DF10a and Int DF10b)

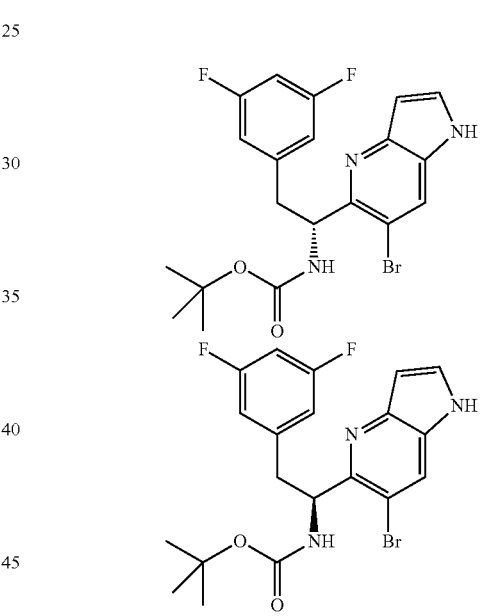

To a suspension of 1-(6-bromo-1H-pyrrolo[3,2-b]pyridin-5-yl)-2-(3,5-difluorophenyl)ethan-1-amine (690 mg, 1.959 mmol) (Int DF6e) in dichloromethane (100 mL) was added di-tert-butyl dicarbonate (428 mg, 1.959 mmol) in 2 equal portion, 90 min apart. The reaction was stirred at room temp for 30 min, then treated with additional di-tert-butyl dicarbonate (380 mg, 1.74 mmol) and the reaction was stirred at room temp for 90 min. The reaction was then treated with N-methylmorpholine (100 µL, 0.910 mmol) and stirred at room temp for 18. The reaction was then treated with additional di-tert-butyl dicarbonate (249 mg, 1.14 mmol) and N-methylmorpholine (210 µL, 1.91 mmol) and stirred at room temp for 5h. The reaction was treated with additional di-tert-butyl dicarbonate (320 mg, 1.47 mmol) and N-methylmorpholine (300 µL, 2.73 mmol), stirred at room temp for 18h and the solvent was removed in vacuo. The crude material was purified via silica gel chromatography (120 g SiO$_2$ column, 0-100% ethyl acetate/dichloromethane), then further purified by chiral SCF chromatography (Chiralpak AS-H column, 15% methanol, 0.1% DEA in CO2, 150 bar, 220/254 nm) to afford the pure stereoisomers. Int DF10a: 116 mg. LC/MS m/z=452.1, 454.1 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.61 min Int DF10b: 120.3 mg. LC/MS m/z 452.1, 454.1 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.61 min tert-butyl (S)-(2-(3,5-difluorophenyl)-1-(6-(4-(morpholinosulfonyl)phenyl)-1H-pyrrolo[3,2-b]pyridin-5-yl)ethyl)carbamate (Int DF10c)

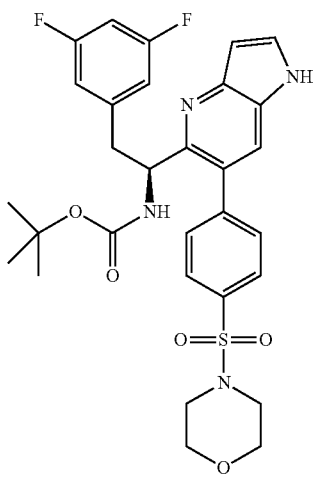

To a reaction vial under nitrogen was added tert-butyl (S)-(1-(6-bromo-1H-pyrrolo[3,2-b]pyridin-5-yl)-2-(3,5-difluorophenyl)ethyl)carbamate (32.8 mg, 0.073 mmol) (Int DF10b) 4-(morpholinosulfonyl)phenylboronic acid (60 mg, 0.221 mmol), degassed dioxane (6 mL) and degassed sodium carbonate, 2.0M in water (265 μL, 0.530 mmol). The reaction was flushed with argon, treated with tetrakis(triphenylphosphine)palladium(0)(5 mg, 4.33 μmol), flushed with argon again, capped heated at 130° C. for 24h. The reaction was diluted with ethyl acetate (85 mL) and the organic layer was washed with water (1×6 mL), brine (1×4 mL), dried over Na2SO4, filtered and evaporated to dryness. The crude material was purified via silica gel chromatography (24 g SiO2 column, 0-100% ethyl acetate/dichloromethane) to afford the title compound, 39.5 mg. LC/MS m/z 599.3 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.53 min.

(S)-2-(3,5-difluorophenyl)-1-(6-(4-(morpholinosulfonyl)phenyl)-1H-pyrrolo[3,2-b]pyridin-5-yl)ethan-1-amine (Int DF10d)

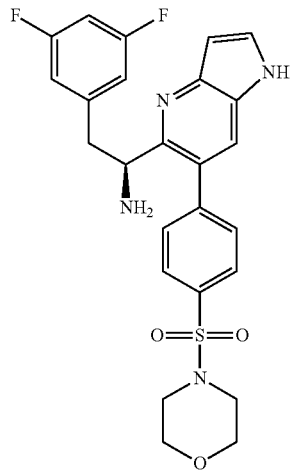

To a solution of tert-butyl (S)-(2-(3,5-difluorophenyl)-1-(6-(4-(morpholinosulfonyl)phenyl)-1H-pyrrolo[3,2-b]pyridin-5-yl)ethyl)carbamate (35 mg, 0.058 mmol) (Int DF10c) in dichloromethane (10 mL) was added TFA (6 mL, 78 mmol) with rapid swirling. The resulting solution was allowed to stand at room temp for 30 min, then the solvent was removed under a gentle stream of nitrogen. The residue was dissolved in ethyl acetate (35 mL), and the organic layer was washed with aqueous saturated NaHCO3 (2×10 mL), brine (1×10 mL), dried over Na2SO4 and evaporated to dryness to give the title compound, 29 mg. LC/MS m/z=499.3 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.40 min.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(4-(morpholinosulfonyl)phenyl)-1H-pyrrolo[3,2-b]pyridin-5-yl)ethyl)acetamide (Example 65)

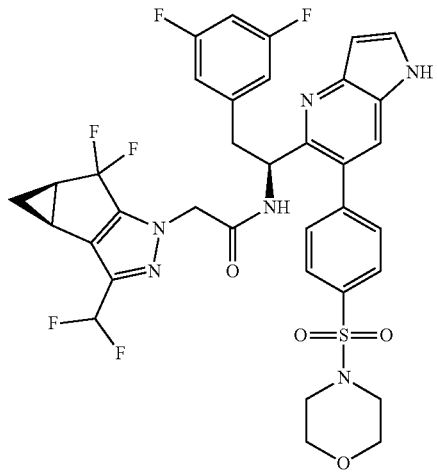

To a dry reaction vial containing (S)-2-(3,5-difluorophenyl)-1-(6-(4-(morpholinosulfonyl)phenyl)-1H-pyrrolo[3,2-b]pyridin-5-yl)ethan-1-amine (29 mg, 0.058 mmol) (Int DF10c) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (15.37 mg, 0.058 mmol), 1-hydroxy-7-azabenzotriazole (1.6 mg, 0.012 mmol) and anhydrous DMF (1.0 mL). The reaction was flushed with nitrogen, then treated with N-methylmorpholine (35 µL, 0.318 mmol), followed by EDC (13.4 mg, 0.070 mmol). The reaction was capped and allowed to stir at room temp for 18h. The reaction was purified via preparative LC/MS to afford the title compound, 24.3 mg. LC/MS m/z=745.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.03 min.

methyl 5-bromo-1H-pyrrolo[2,3-b]pyridine-6-carboxylate (Int DF11a)

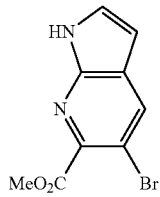

To a dry flask under nitrogen was added 5-bromo-1H-pyrrolo[2,3-b]pyridine-6-carboxylic acid (1 g, 4.15 mmol), Toluene (15 mL) and MeOH (102 mL). The resulting suspension was treated with TMS-diazomethane 2 M in hexanes in multiple portions until the reaction was judged to be complete by LC/MS. The solvent was removed in vacuo to give the title compound, 1.05g. LC/MS m/z=254.9, 256.9 (M+H). Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.16 min.

methyl 5-bromo-1-((2-(trimethylsilyl)ethoxy)methyl)-1H-pyrrolo[2,3-b]pyridine-6-carboxylate (Int DF11b)

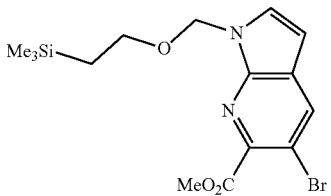 [SMILES: COC(=O)c1nc2c(ccn2COCC[Si](C)(C)C)cc1Br]

To a solution of methyl 5-bromo-1H-pyrrolo[2,3-b]pyridine-6-carboxylate (1.05 g, 4.12 mmol) (Int DF11a) in distilled THF (50 mL) under a continuous nitrogen flush was added potassium tert-butoxide 1M in THF (4.8 ml, 4.80 mmol) over 1 min via syringe. The reaction was stirred for 2 min then treated with SEM-Cl (0.90 ml, 5.07 mmol) and allowed to stir at room temp for 1.5 h. The reaction was poured into a mixture of water and aqueous NH4Cl, diluted with ethyl acetate and the organic layer was washed with brine, dried over Na2SO4, filtered and evaporated to dryness. The crude material was purified via silica gel chromatography (80 g SiO$_2$ column, 0-100% hexanes:dichloromethane) to afford the title compound, 983 mg. LC/MS m/z=385, 387 (M+H)$^+$; 805.3 (M+Na). Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.63 min.

(5-bromo-1-((2-(trimethylsilyl)ethoxy)methyl)-1H-pyrrolo[2,3-b]pyridin-6-yl)methanol (Int DF11c)

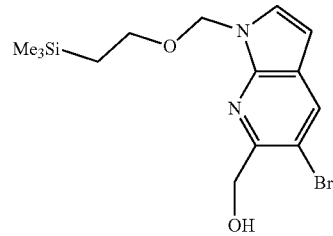 [SMILES: C[Si](C)(C)CCOCn1ccc2cc(Br)c(CO)nc21]

To a dry 250 mL round bottom flask was added methyl 5-bromo-1-((2-(trimethylsilyl)ethoxy)methyl)-1H-pyrrolo[2,3-b]pyridine-6-carboxylate (983 mg, 2.55 mmol) (Int DF11b) and distilled THF (30 mL). The reaction was flushed with argon, cooled −40° C. and treated with DIBAL-H, 1 M in heptane (11 mL, 11 mmol) over 2 h, keeping the temp between −40° C. and −15° C. The reaction was cooled to −15° C., treated with MeOH (6 mL) and allowed to warm to room temp. The reaction mixture was quenched saturated potassium sodium tartrate solution (23 g in ~200 mL water) and diluted with ethyl acetate. The organic layer was washed with water, brine, dried over Na2SO4, filtered and evaporated to dryness to give the title compound, 850 mg. LC/MS m/z=357, 359 (M+H)$^+$; Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.61 min.

5-bromo-1-((2-(trimethylsilyl)ethoxy)methyl)-1H-pyrrolo[2,3-b]pyridine-6-carbaldehyde (Int DF11d)

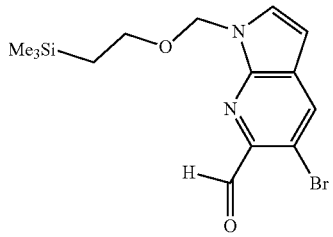 [SMILES: C[Si](C)(C)CCOCn1ccc2cc(Br)c(C=O)nc21]

To a solution of (5-bromo-1-((2-(trimethylsilyl)ethoxy)methyl)-1H-pyrrolo[2,3-b]pyridin-6-yl)methanol (850 mg, 2.379 mmol) (Int DF11c) in dichloromethane (15 mL) under nitrogen was added solid Dess-Martin periodinane (1.3 g, 3.07 mmol). The reaction was stirred at room temp for 3 h, then the solvent was removed under a gentle stream of nitrogen. The residue diluted with ethyl acetate (100 mL) and aqueous 0.5 M sodium hydroxide (50 mL) and the organic layer was extracted with water (1×30 mL), brine (1×30 mL), dried over Na2SO4/MgSO4, filtered and evaporated to dryness to give the title compound, 930 mg. LC/MS m/z=355, 357 (M+H)$^+$; Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.66 min.

1-(5-bromo-1-((2-(trimethylsilyl)ethoxy)methyl)-1H-pyrrolo[2,3-b]pyridin-6-yl)-2-(3,5-difluorophenyl)ethan-1-ol (Int DF11e)

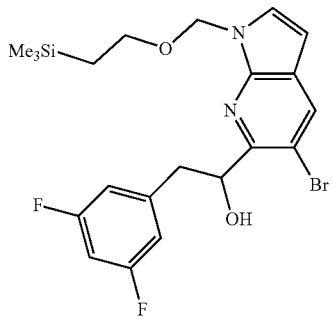 [SMILES: C[Si](C)(C)CCOCn1ccc2cc(Br)c(C(O)Cc3cc(F)cc(F)c3)nc21]

To a solution of 5-bromo-1-((2-(trimethylsilyl)ethoxy)methyl)-1H-pyrrolo[2,3-b]pyridine-6-carbaldehyde (930 mg, 2.62 mmol) (Int DF11d) in distilled THF (20 mL) under a continuous argon flow was added (3,5-difluorobenzyl)zinc(II) bromide 0.5 M in THF (8 mL, 4.00 mmol). The reaction was stirred for 15 min, then treated with additional (3,5-difluorobenzyl)zinc(II) bromide 0.5 M in THF (0.8 mL, 0.4 mmol). The reaction was stirred cold for 45 min, then poured into a mixture of aqueous saturated NH4Cl and ethyl acetate. The aqueous layer was back extracted with ethyl acetate, the organic layers were combined, washed with brine, dried over Na2SO4, and filtered. The crude material was purified via silica gel chromatography (80 g SiO$_2$ column, 0-100% ethyl acetate/dichloromethane) to afford the title compound, 900 mg. LC/MS m/z=483.1, 485.1 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.84 min.

$^1$H NMR (500 MHz, CDCl$_3$) δ 8.15 (s, 1H), 7.38 (d, J=3.5 Hz, 1H), 6.83 (dd, J=8.3, 2.2 Hz, 2H), 6.67 (s, 1H), 6.52 (d, J=3.5 Hz, 1H), 5.62 (q, J=10.9 Hz, 2H), 5.36-5.29 (m, 1H), 4.45-4.38 (m, 1H), 3.55-3.46 (m, 2H), 3.28 (dd, J=13.8, 3.0 Hz, 1H), 2.82 (dd, J=13.9, 8.2 Hz, 1H), 0.90 (ddd, J=9.6, 6.5, 2.4 Hz, 2H), −0.03 (s, 9H)

2-(1-(5-bromo-1-((2-(trimethylsilyl)ethoxy)methyl)-1H-pyrrolo[2,3-b]pyridin-6-yl)-2-(3,5-difluorophenyl)ethyl)isoindoline-1,3-dione (Int DF11f)

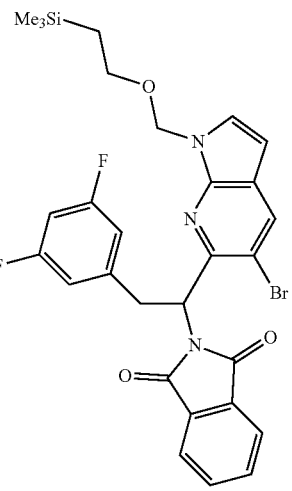

To a magnetically stirred solution of 1-(5-bromo-1-((2-(trimethylsilyl)ethoxy)methyl)-1H-pyrrolo[2,3-b]pyridin-6-yl)-2-(3,5-difluorophenyl)ethan-1-ol (731 mg, 1.512 mmol) (Int DF11e), isoindoline-,3-dione (253 mg, 1.720 mmol) and triphenylphosphine (509 mg, 1.941 mmol) in distilled THE (25 mL) under a continuous argon flush was DIAD (0.32 mL, 1.646 mmol) and the reaction was stirred cold for 30 min. The solvent was removed under a gentle stream of nitrogen and the crude material was purified via silica gel chromatography (80 g SiO$_2$ column, 0-100% ethyl acetate:

dichloromethane) to afford the title compound, 678 mg. LC/MS m/z=612.2, 614.2 (M+H)+. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.94 min.

1-(5-bromo-1-((2-(trimethylsilyl)ethoxy)methyl)-1H-pyrrolo[2,3-b]pyridin-6-yl)-2-(3,5-difluorophenyl)ethan-1-amine (Int DF11g)

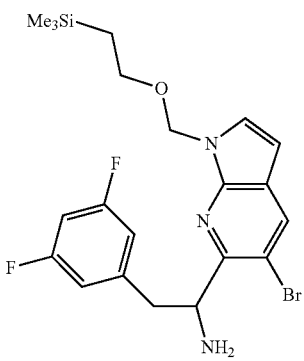 [SMILES: C[Si](C)(C)CCOCn1ccc2cc(Br)c(C(N)Cc3cc(F)cc(F)c3)nc21]

To a solution of 2-(1-(5-bromo-1-((2-(trimethylsilyl)ethoxy)methyl)-1H-pyrrolo[2,3-b]pyridin-6-yl)-2-(3,5-difluorophenyl)ethyl)isoindoline-1,3-dione (Int DF11f) (520 mg, 0.849 mmol) in EtOH (20 mL) was added hydrazine hydrate (460 µl, 9.48 mmol). The reaction was stirred and warmed slightly until all the solids dissolved, then the reaction was heated at 80° C. for 6h. The reaction was cooled to room temp, during which time some solid precipitated out of the reaction. The reaction was diluted with MeOH (30-40 mL) and heated until all the solids were in solution. The solution was concentrated to a volume of ~50 mL and allowed to stand while slowly cooling to room temp, then placed in a −20° C. freezer for 18h. The solution was triturated with EtOH (10 mL), ether (10 mL) and hexanes (10 mL) and the resulting solid was collected by filtration and discarded. The filtrated was concentrated in vacuo to give the title compound, 408 mg. LC/MS m/z=482.1, 484.1 (M+H)+. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.84 min.

N—((R)-1-(5-bromo-1-((2-(trimethylsilyl)ethoxy)methyl)-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide and N—((S)-1-(5-bromo-1-((2-(trimethylsilyl)ethoxy)methyl)-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF11h.1 and Int DF11h.2)

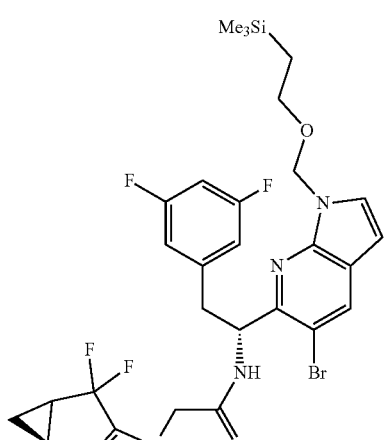

Int DF11h.1

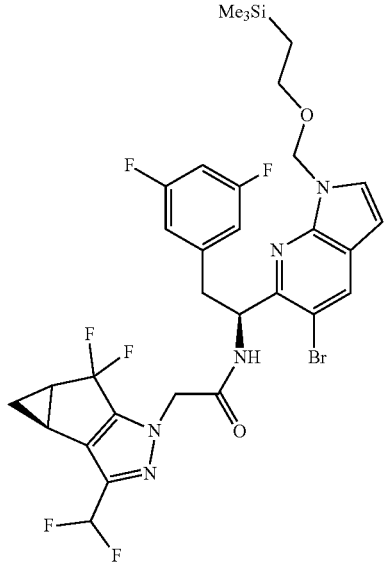

Int DF11h.2

To a suspension of 1-(5-bromo-1-((2-(trimethylsilyl)ethoxy)methyl)-1H-pyrrolo[2,3-b]pyridin-6-yl)-2-(3,5-difluorophenyl)ethan-1-amine (Int DF11g) (408 mg, 0.846 mmol), 2-((3bS,4aR)-3-(difluoromethyl)-5,5-difluoro-3b,4, 4a,5-tetrahydro-1H-cyclopropa[3,4]cyclopenta[1,2-c]pyrazol-1-yl)acetic acid (224 mg, 0.848 mmol), and 1-hydroxy-7-azabenzotriazole (25 mg, 0.184 mmol) in dichloromethane (15 mL) and THF (10 mL) under argon was treated with N-methylmorpholine (500 µl, 4.55 mmol), followed by EDC (212 mg, 1.106 mmol). The reaction was capped and stirred at room temp for 18h, then treated with additional 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (20 mg, 0.08 mmol), EDC (40 mg, 0.21 mmol) and N-methylmorpholine and allowed to stir at room temp for 5h. The solvent was removed in vacuo and the crude residue was purified via silica gel chromatography (24 g SiO$_2$ column, 0-100% ethyl acetate/dichloromethane) and then further purified by chiral SCF chromatography (Chiralpak AS-H column, 15% 2-Propanol, 0.1% DEA in CO$_2$, 150 bar, 220/254 nm) to afford the pure chiral compound, Int DF11h.1 187.2 mg and the pure chiral compound, Int DF1 h.2 190 mg. Int DF11h.2: LC/MS m/z=728.2, 730.2 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.99 min N—((S)-1-(5-(4-chloro-1-methyl-3-(methylsulfonamido)-1H-indazol-7-yl)-1-((2-(trimethylsilyl)ethoxy)methyl)-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF12) and Int DF11

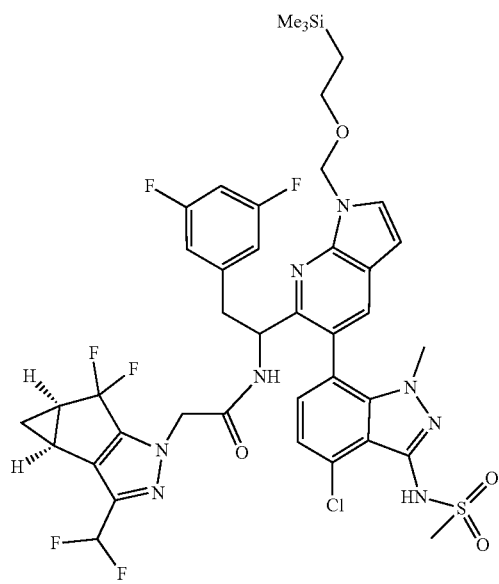

Example DF11
Mix of two steroisimers

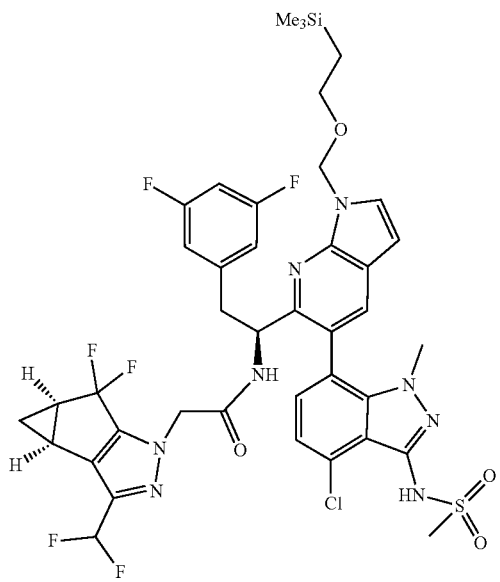

Example DF12
A mixture of indicated isomer and a stereoisomer

To a reaction vial under argon was added N—((S)-1-(5-bromo-1-((2-(trimethylsilyl)ethoxy)methyl)-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (30 mg, 0.041 mmol) (Int DF11h.2), N-(4-chloro-1-methyl-7-(4,4,5,5-tetramethyl-1,3,2-dioxaborolan-2-yl)-1H-indazol-3-yl)methanesulfonamide (50 mg, 0.130 mmol) and dioxane (4 mL). The reaction was flushed with argon, treated with sodium carbonate, 2.0M in water (105 µL, 0.210 mmol), followed by tetrakis(triphenylphosphine)palladium (0)(5 mg, 4.33 µmol), flushed with argon again, capped and heated at 130° C. for 18h. The reaction was diluted with ethyl acetate (30 mL) and the organic layer was washed with water (1×5 mL), brine (1×5 mL), dried over Na2SO4, filtered and evaporated to dryness. The crude residue was purified via preparative HPLC to retrieve two fractions, each likely a mixture of stereoisomers. Int DF11: First eluting peak, 4.9 mg. LC/MS m/z=907.2 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.6 min.

Int DF12: Second eluting peak, 22.5 mg. LC/MS m/z=907.2 (M+H Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Retention time: 2.72 min ethyl (S)-4-((tert-butoxycarbonyl)amino)-5-(3,5-difluorophenyl)-3-oxopentanoate (Int DF15a)

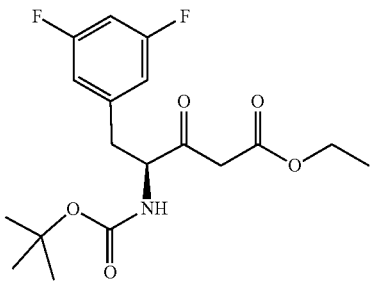 [SMILES: CCOC(=O)CC(=O)[C@H](Cc1cc(F)cc(F)c1)NC(=O)OC(C)(C)C]

To a dry 500 mL round bottom flask under nitrogen was added THF (125 mL). The reaction was flushed with argon, cooled to −78° C., treated with lithium bis(trimethylsilyl) amide, 1.0M in THF (52 mL, 52.0 mmol), stirred at −78° C. for 3 min, then treated with ethyl acetate (6.2 mL, 63.3 mmol) (previously dried over 4A mol sieves). The reaction was then treated with solid methyl (S)-2-((tert-butoxycarbonyl)amino)-3-(3,5-difluorophenyl)propanoate (5 g, 15.86 mmol) (Int DF3a) in a single portion and the reaction was stirred at −75° C. for 10 min, slowly allowed to warm to −50° C. over 35 min, then allowed to warm to room temp over 20 min. The reaction was cooled to −50° C., quenched with cold saturated NH4Cl (100 mL), diluted with ethyl acetate (700 mL) and the organic layer was washed with brine (1×30 mL), dried over Na2SO4, filtered and evaporated to dryness. LC/MS m/z=394.0 (M+Na). Column: Waters Aquity UPLC BEH C18, 2.1 mm×50 mm, 1.7 μm particles; Mobile Phase A: 10% MeOH: 90% water with 0.1% TFA; Mobile Phase B: 90% MeOH: 10% water with 0.1% TFA; Temperature: 40° C.; Gradient: 0% B to 100% B over 2 min, then a 1 min hold at 100% B; Flow: 0.8 mL/min; Detection: UV (220 nm); Retention Time: 1.97 min tert-butyl (S)-(2-(3,5-difluorophenyl)-1-(7-hydroxypyrazolo[1,5-a]pyrimidin-5-yl)ethyl)carbamate (Int DF15b)

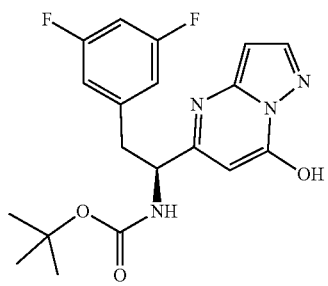 [SMILES: CC(C)(C)OC(=O)N[C@@H](Cc1cc(F)cc(F)c1)c1cc(O)n2nccc2n1]

To a 250 mL round bottom flask under nitrogen was added ethyl (S)-4-((tert-butoxycarbonyl)amino)-5-(3,5-difluorophenyl)-3-oxopentanoate (2.13 g, 5.74 mmol) (Int DF15a), 3-aminopyrazole (760 mg, 9.15 mmol) and anhydrous p-Xylene (40 mL). The reaction was flushed with nitrogen and heated at 130° C. for 18 h. The reaction was diluted with hexanes (200 mL) and the resulting solid was collected by filtration to afford the title compound, 2.18 g. LC/MS m/z=391.0 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.17 min tert-butyl (S)-(1-(6-bromo-7-hydroxypyrazolo[1,5-a]pyrimidin-5-yl)-2-(3,5-difluorophenyl)ethyl)carbamate (Int DF15c)

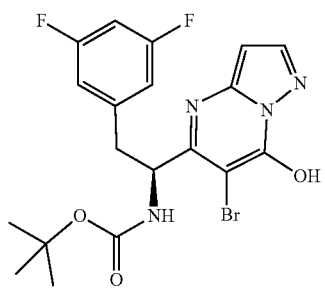 [SMILES: CC(C)(C)OC(=O)N[C@@H](Cc1cc(F)cc(F)c1)c1nc2ccnn2c(O)c1Br]

To a solution of tert-butyl (S)-(2-(3,5-difluorophenyl)-1-(7-hydroxypyrazolo[1,5-a]pyrimidin-5-yl)ethyl)carbamate (2.21 g, 5.66 mmol) in t-butylamine (40 mL) and dichloromethane (100 mL) was added Br2 stock solution (10 mL, 423 mg, 2.65 mmol, 0.47 eq) [1.27 g Br2 in dichloromethane (30 mL)]. The reaction was monitored by LC/MS and additional Br2 stock solution was added until the reaction was judged to be complete. The reaction was quenched with saturated aqueous Na2S2O3 (0.5 g/mL, 40 mL), diluted with dichloromethane (400 mL). and the organic layer was washed with saturated Na2S2O3 (1×30 mL), water (1×15 mL), brine (1×15 mL), dried over Na2SO4, filtered and evaporated to dryness to give the title compound, 2.85 g. LC/MS m/z=469.0, 471 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.24 min.

tert-butyl (S)-(1-(7-(benzyloxy)-6-bromopyrazolo[1,5-a]pyrimidin-5-yl)-2-(3,5-difluorophenyl)ethyl)carbamate (Int DF15d)

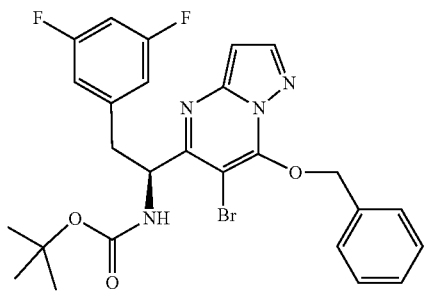 [SMILES: CC(C)(C)OC(=O)N[C@@H](Cc1cc(F)cc(F)c1)c1nc2ccnn2c(OCc2ccccc2)c1Br]

To a solution of tert-butyl (S)-(1-(6-bromo-7-hydroxypyrazolo[1,5-a]pyrimidin-5-yl)-2-(3,5-difluorophenyl)ethyl)carbamate (300 mg, 0.639 mmol) (Int DF15c) in distilled THF (6 mL) was added triphenylphosphine (420 mg, 1.601 mmol). The reaction was flushed with nitrogen, capped and treated with benzyl alcohol (167 μL, 1.618 mmol). The reaction was then cooled to 0° C. and slowly (over 5 min) treated with DIAD (260 μL, 1.337 mmol) at 12:15 PM, stirred cold for 5 min, then the bath was removed and the reaction was allowed to warm to room temp over 30 min. The reaction was diluted with ethyl acetate (200 mL) and the organic layer was extracted with water (1×30 mL), brine (1×30 mL), dried over Na2SO4, filtered and evaporated to dryness. The crude material was purified via silica gel chromatography (40 g SiO$_2$ column, 0-100% ethyl acetate:dichloromethane) to afford the title compound, 309 mg. LC/MS m/z=559, 561 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.54 min.

tert-butyl (S)-(2-(3,5-difluorophenyl)-1-(7-hydroxy-6-(6-isopropylpyridin-3-yl)pyrazolo[1,5-a]pyrimidin-5-yl)ethyl)carbamate (Int DF15e)

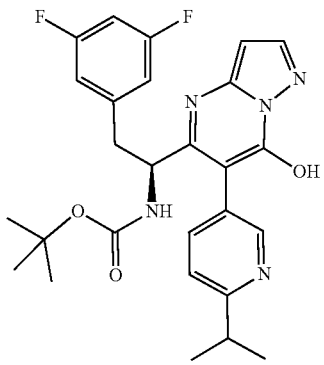 [SMILES: CC(C)c1ccc(-c2c([C@H](Cc3cc(F)cc(F)c3)NC(=O)OC(C)(C)C)nc3ccnn3c2O)cn1]

To a dry reaction vial under nitrogen was added tert-butyl (S)-(1-(7-(benzyloxy)-6-bromopyrazolo[1,5-a]pyrimidin-5-yl)-2-(3,5-difluorophenyl)ethyl)carbamate (30 mg, 0.054 mmol) (Int DF15d), (6-isopropylpyridin-3-yl)boronic acid (30 mg, 0.182 mmol) and degassed dioxane (4 mL). The reaction was purged with argon, treated with sodium carbonate, 2.0M in water (150 μL, 0.300 mmol), tetrakis(triphenylphosphine)palladium(0) (6 mg, 5.19 μmol), flushed with argon again, and heated at 130° C. for 18h. The solvent was removed under a gentle stream of nitrogen, the crude residue was dissolved in ethyl acetate, and the organic layer was washed with water (1×8 mL), brine (1×8 mL), dried over Na2SO4, filtered and evaporated to dryness to give the title compound, 59 mg.

LC/MS m/z=510.3 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.46 min.

(S)-5-(1-amino-2-(3,5-difluorophenyl)ethyl)-6-(6-isopropylpyridin-3-yl)pyrazolo[1,5-a]pyrimidin-7-ol (Int DF15f)

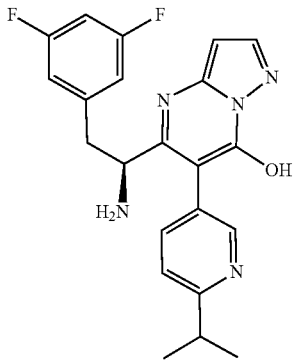 [SMILES: CC(C)c1ccc(-c2c([C@@H](N)Cc3cc(F)cc(F)c3)nc3ccnn3c2O)cn1]

To a solution of tert-butyl (S)-(2-(3,5-difluorophenyl)-1-(7-hydroxy-6-(6-isopropylpyridin-3-yl)pyrazolo[1,5-a]pyrimidin-5-yl)ethyl)carbamate (27.2 mg, 0.053 mmol) (Int DF15e) in dichloromethane (5 mL) was added TFA and the reaction was allowed to stand at room temp for 30 min. The solvent was removed under a gentle stream of nitrogen and the residue was dissolved in ethyl acetate (50 mL) and the organic layer was washed with aqueous saturated NaHCO$_3$ (1×10 mL), brine (1×10 mL), dried over Na2SO4, filtered and evaporated to dryness to give the title compound, 51.7 mg. LC/MS m/z=410.2 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.20 min.

tert-butyl (R)-(2-(3,5-difluorophenyl)-1-(6-(4-(morpholinosulfonyl)phenyl)-1H-pyrrolo[3,2-b]pyridin-5-yl)ethyl)carbamate (Int DF16a)

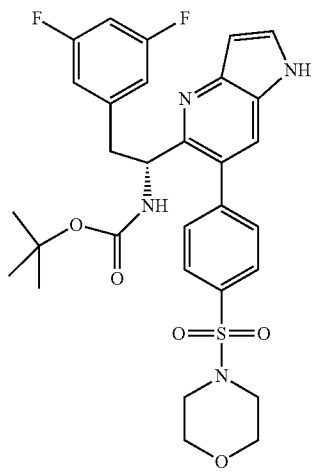

To a reaction vial was added tert-butyl (R)-(1-(6-bromo-1H-pyrrolo[3,2-b]pyridin-5-yl)-2-(3,5-difluorophenyl)ethyl)carbamate (18.8 mg, 0.042 mmol) (Int DF10a),

253

4-(morpholinosulfonyl)phenylboronic acid (35 mg, 0.129 mmol) and degassed Dioxane (4 mL). The reaction was flushed with argon, treated with sodium carbonate, 2.0M in water (150 μL, 0.300 mmol), tetrakis(triphenylphosphine)palladium(0) (3 mg, 2.60 μmol), flushed with argon again, capped and heated at 130° C. for 18h. The solvent was removed under a gentle stream of nitrogen and the crude product was dissolved in ethyl acetate (40 mL), washed with water (1×6 mL), brine (1×6 mL), dried over Na2SO4, filtered and evaporated to dryness. The crude material was purified via silica gel chromatography (12 g SiO$_2$ column, 0-100% ethyl acetate:dichloromethane) to afford the title compound, 33.9 mg. LC/MS m/z=599.3 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.63 min.

(R)-2-(3,5-difluorophenyl)-1-(6-(4-(morpholinosulfonyl)phenyl)-1H-pyrrolo[3,2-b]pyridin-5-yl)ethan-1-amine (Int DF16b)

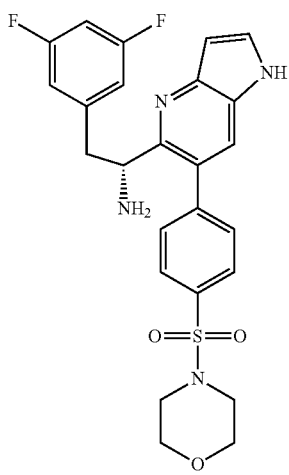

To a solution of tert-butyl (R)-(2-(3,5-difluorophenyl)-1-(6-(4-(morpholinosulfonyl)phenyl)-1H-pyrrolo[3,2-b]pyridin-5-yl)ethyl)carbamate (22 mg, 0.037 mmol) (Int DF16a) in anhydrous dichloromethane (4 mL) was added TFA (4 mL, 51.9 mmol) and the resulting solution was stirred at room temp for 30 min. The volatiles were removed under gentle stream of nitrogen and the residue was dissolved in in ethyl acetate (35 mL), washed with aqueous saturated NaHCO$_3$ (1×10 mL), water (1×5 mL), brine (1×5 mL), dried over Na2SO4, filtered and evaporated to dryness to give the title compound, 29.5 mg. LC/MS m/z=499.2 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.45 min.

254

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((R)-2-(3,5-difluorophenyl)-1-(6-(4-(morpholinosulfonyl)phenyl)-1H-pyrrolo[3,2-b]pyridin-5-yl)ethyl)acetamide (Example 66)

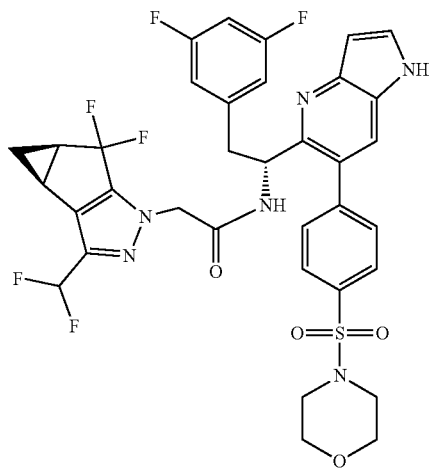

To a reaction vial was added (R)-2-(3,5-difluorophenyl)-1-(6-(4-(morpholinosulfonyl)phenyl)-1H-pyrrolo[3,2-b]pyridin-5-yl)ethan-1-amine (18 mg, 0.036 mmol) (Int DF16b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (9.54 mg, 0.036 mmol), 1-hydroxy-7-azabenzotriazole (1 mg, 7.35 μmol) and DMF (800 μL). The reaction was flushed briefly with nitrogen, then treated with N-methylmorpholine (20 μL, 0.182 mmol), followed by EDC (7.5 mg, 0.039 mmol). The reaction was capped and allowed to stir at room temp for 18h. The crude reaction was purified via preparative HPLC to afford the title compound, 16.7 mg. LC/MS m/z=645.1 (M+H)$^+$. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.09 min. I (S)-2-(2-(3-(difluoromethyl)-5,6-dihydrocyclopenta[c]pyrazol-1(4H)-yl)acetamido)-3-(3,5-difluorophenyl)propanoic acid (Int DF17a)

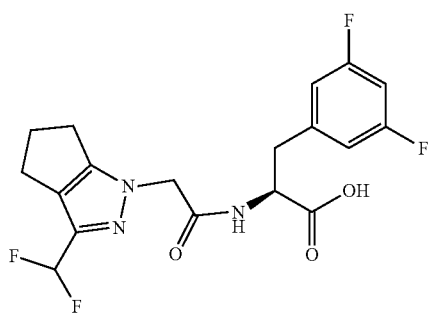 [SMILES: O=C(Cn1nc(C(F)F)c2c1CCC2)N[C@@H](Cc1cc(F)cc(F)c1)C(=O)O]

To a solution of methyl (S)-2-(2-(3-(difluoromethyl)-5,6-dihydrocyclopenta[c]pyrazol-1(4H)-yl)acetamido)-3-(3,5-difluorophenyl)propanoate (885 mg, 2.141 mmol) (Int DF4a) in anhydrous ClCH2CH2Cl (25 mL) was added trimethyltin hydroxide (1.17 g, 6.47 mmol). The reaction was flushed with argon, capped and heated at 80° C. for 90 min. The solvent was removed in vacuo and the residue was dissolved in ethyl acetate (220 mL). The organic layer was washed with 1.0 M aqueous HCl (4×20 mL), brine (1×20 mL), dried over Na2SO4, filtered and evaporated to dryness to give the title compound, 910 mg. LC/MS m/z=400.1 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.3 min.

(S)-2-(3-(difluoromethyl)-5,6-dihydrocyclopenta[c]pyrazol-1(4H)-yl)-N-(2-(3,5-difluorophenyl)-1-(4-oxo-4H-benzo[d][1,3]oxazin-2-yl)ethyl)acetamideide (Int DF22a)

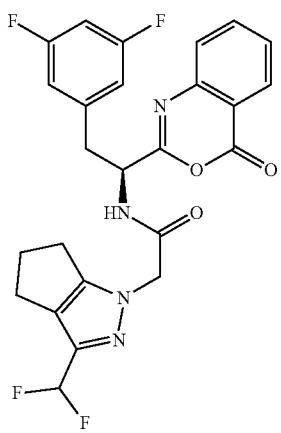 [SMILES: O=C(Cn1nc(C(F)F)c2c1CCC2)N[C@@H](Cc1cc(F)cc(F)c1)c1nc2ccccc2c(=O)o1]

To a dry reaction vial under nitrogen was added (S)-2-(2-(3-(difluoromethyl)-5,6-dihydrocyclopenta[c]pyrazol-1(4H)-yl)acetamido)-3-(3,5-difluorophenyl)propanoic acid (400 mg, 1.002 mmol) (Int DF17a), anthranilic acid (137 mg, 1.002 mmol) and anhydrous Pyridine (6.4 mL). The reaction was flushed with argon, treated with diphenyl phosphite (680 μL, 3.51 mmol), capped and heated at 70° C. for 2.5 h to afford the title compound that was used "as is" without purification in subsequent steps. LC/MS m/z=501.2 (M+H)$^+$: Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.48 min.

(S)—N-(1-(6,8-difluoro-4-oxo-4H-benzo[d][1,3]oxazin-2-yl)-2-(3,5-difluorophenyl)ethyl)-2-(3-(difluoromethyl)-5,6-dihydrocyclopenta[c]pyrazol-1(4H)-yl)acetamide (Int DF27a)

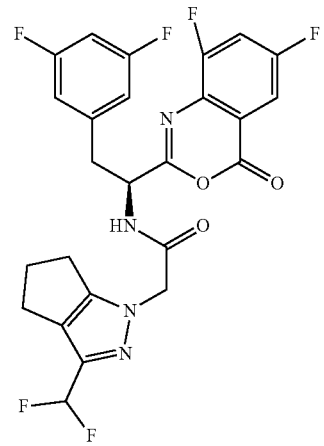 [SMILES: O=C(Cn1nc(C(F)F)c2c1CCC2)N[C@@H](Cc1cc(F)cc(F)c1)c1nc2c(F)cc(F)cc2c(=O)o1]

To a dry reaction vial under nitrogen was added (S)-2-(2-(3-(difluoromethyl)-5,6-dihydrocyclopenta[c]pyrazol-1(4H)-yl)acetamido)-3-(3,5-difluorophenyl)propanoic acid (135 mg, 0.338 mmol) (Int DF17a), 2-amino-3,5-difluorobenzoic acid (60 mg, 0.347 mmol), and anhydrous Pyridine (2.1 mL). The reaction was with argon, treated with diphenyl phosphite (240 μL, 1.240 mmol), capped heated at 70° C. for 110 min to afford the title compound that was used "as is" without purification in subsequent steps. LC/MS m/z=537.2 (M+H)$^+$: Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.49 min.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(5,8-dimethyl-4-oxo-4H-benzo[d][1,3]oxazin-2-yl)ethyl)acetamide (Int DF29a)

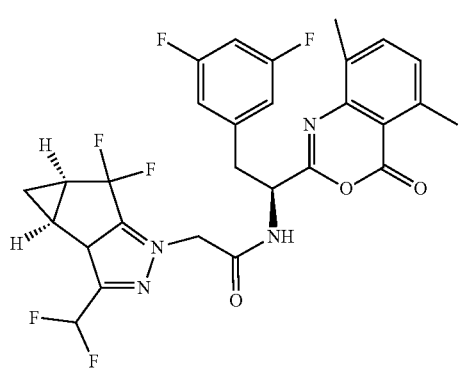

To a dry reaction vial under nitrogen was added (S)-2-(2-((3bS,4aR)-3-(difluoromethyl)-5,5-difluoro-3b,4,4a,5- tetrahydro-1H-cyclopropa[3,4]cyclopenta[1,2-c]pyrazol-1-yl)acetamido)-3-(3,5-difluorophenyl)propanoic acid (90 mg, 0.201 mmol) (Int MS301b), 2-amino-3,6-dimethylbenzoic acid (33.2 mg, 0.201 mmol) and anhydrous Pyridine (1.4 mL). The reaction was flushed with argon, treated with diphenyl phosphite (137 µL, 0.708 mmol), capped and heated at 75° C. for 3 h to afford the title compound that was used "as is" without purification in subsequent steps. LC/MS m/z=577.2 (M+H)$^+$: Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.65 min.

N—((S)-1-(3-(4-chloro-1-methyl-3-(methylsulfonamido)-1H-indazol-7-yl)-5,8-dimethyl-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 68) and Example 67

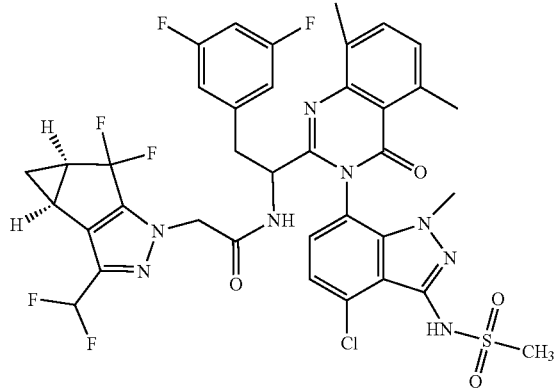

Example 67
Mix of two stereoisomers

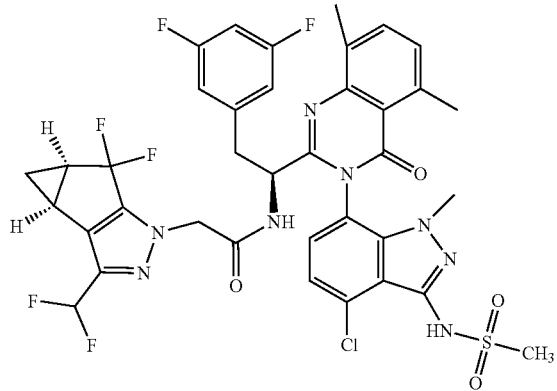

Example 68
A mixture of indicated isomer
and a stereoisomer

To the reaction vial containing a solution of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-(2-(3,5-difluorophenyl)-1-(5,8-dimethyl-4-oxo-4H-benzo[d][1,3]oxazin-2-yl)ethyl)acetamide (57.6 mg, 0.100 mmol) (Int DF29a) in Pyridine (700 µL) was added N-(7-amino-4-chloro-1-methyl-1H-indazol-3-yl)-N-(4-methoxybenzyl)methanesulfonamide (Int 17d, 47 mg, 0.119 mmol). The reaction was flushed briefly with argon, capped and heated at 75° C. for 12h. The solvent was removed under a gentle stream of nitrogen and the reside was dissolved in dichloromethane (2 mL) trated with TFA (2.0 mL, 26.0 mmol). The reaction was allowed to stand at room temp for 5 min, then neat triflic acid (55 µL, 0.619 mmol) was added. The reaction was allowed to stand at room temp for 30 min and the solvent was evaporated off under a gentle stream of nitrogen. The residue was dissolved in dichloromethane (1 mL) and treated with a solution of 10% N-methylmorpholine in dichloromethane (3 mL). The solvent was removed under a gentle stream of nitrogen, the residue was dissolved in DMF (1.2 mL) and purified via preparative LC/MS to afford two fractions, each as a mixture of two stereoisomers.

Example 67: First Eluting Peak, 5.8 mg

LC/MS m/z=833.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.27 min.

Example 68: Second Eluting Peak, 19.1 mg

LC/MS m/z=833.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.33 min.

N-(7-amino-1-methyl-1H-indazol-3-yl)-N-(4-methoxybenzyl)methanesulfonamide (Int DF34a)

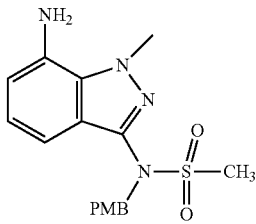

To a suspension of N-(7-amino-4-chloro-1-methyl-1H-indazol-3-yl)-N-(4-methoxybenzyl)methanesulfonamide (Int 17d, 100 mg, 0.253 mmol) in MeOH (20 mL) was added palladium hydroxide on carbon (22 mg, 0.157 mmol). The reaction was flushed with nitrogen, capped and then purged with nitrogen for 10 min. The reaction was stirred at room temp under a balloon of H2 for 18h. The catalyst was filtered off thru a small pad of celite, washed well with MeOH and evaporated to dryness to give the title compound, 91 mg, that was used "as is" without further purification in subsequent step(s). LC/MS m/z=743.4 (2M+Na): Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.31 min.

(S)—N-(7-(2-(1-amino-2-(3,5-difluorophenyl)ethyl)-4-oxoquinazolin-3(4H)-yl)-1-methyl-1H-indazol-3-yl)methanesulfonamide (Int DF34b)

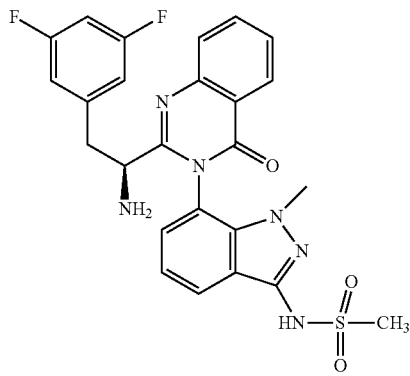 [SMILES: Cn1nc(NS(C)(=O)=O)c2cccc(-n3c([C@@H](N)Cc4cc(F)cc(F)c4)nc4ccccc4c3=O)c21]

To a dry reaction vial under nitrogen was added (S)-2-((tert-butoxycarbonyl)amino)-3-(3,5-difluorophenyl)propanoic acid (65 mg, 0.216 mmol), 2-aminobenzoic acid (29.6 mg, 0.216 mmol), and anhydrous Pyridine (700 µL). The reaction was flushed with argon, treated with diphenyl phosphite (150 µL, 0.775 mmol), capped and heated at 75° C. for 2h. The reaction was then treated with N-(7-amino-1-methyl-1H-indazol-3-yl)-N-(4-methoxybenzyl)methanesulfonamide (91 mg, 0.252 mmol) (Int DF34a), flushed with argon and heated 75° C. for 4.5 h. The solvent was removed under a gentle stream of nitrogen, the residue was dissolved in dichloromethane (1 mL) and treated with TFA (2 mL). The reaction was allowed to stand at room temp for 4 min, then neat triflic acid (115 µL, 1.295 mmol) was added and the reaction was allowed to stand at room temp for 40 min. The solvent was removed under a gentle stream of nitrogen to give the title compound, 113 mg, that was used "as is" without further purification in subsequent reaction(s). LC/MS m/z=525.2 (M+H)+: Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.24 min.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(1-methyl-3-(methylsulfonamido)-1H-indazol-7-yl)-4-oxo-3,4-dihydroquinazolin-2-yl)ethyl)acetamide (Example 70) and Example 69

Example 69

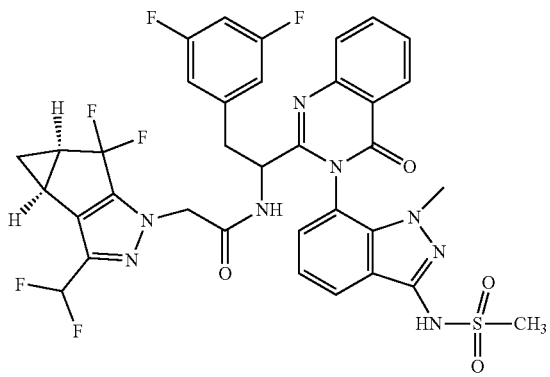

Mix of two stereoisomers

Example 70

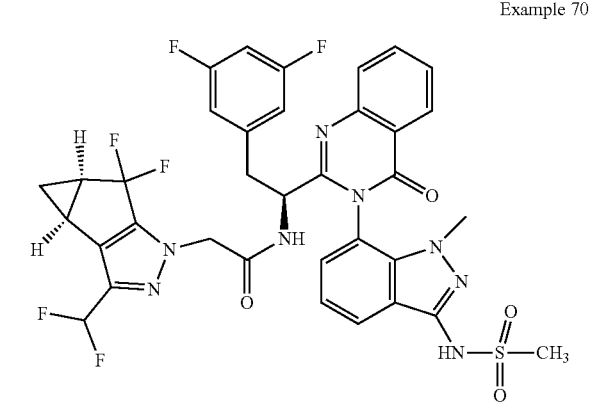

A mixture of indicated isomer and a stereoisomer

To a reaction vial containing (S)—N-(7-(2-(1-amino-2-(3,5-difluorophenyl)ethyl)-4-oxoquinazolin-3(4H)-yl)-1-methyl-1H-indazol-3-yl)methanesulfonamide (56.5 mg, 0.108 mmol) (Int DF34b) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (28.5 mg, 0.108 mmol), 1-hydroxy-7-azabenzotriazole (1 mg, 7.35 µmol) and anhydrous DMF (750 µL). The reaction was flushed with nitrogen, then treated with N-methylmorpholine (65 µL, 0.591 mmol) followed by EDC (27.3 mg, 0.142 mmol), capped and allowed to stand at room temp for 18h. The reaction was treated with 7MNH3/MeOH (100 µL) and was purified via preparative LC/MS to afford two fractions.

Example 69: First Eluting Peak, 4.3 mg

LC/MS m/z=771.1 (M+H)+. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.09 min.

Example 70: Second Eluting Peak, 13.4 mg

LC/MS m/z=771.1 (M+H)+. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.15 min.

tert-butyl(S)-(1-(3-(4-chloro-3-(N-(4-methoxyben-zyl)methylsulfonamido)-1-methyl-1H-indazol-7-yl)-7-methoxy-4-oxo-3,4-dihydroquinazolin-2-yl)-2-(3,5-difluorophenyl)ethyl)carbamate (Int DF36a)

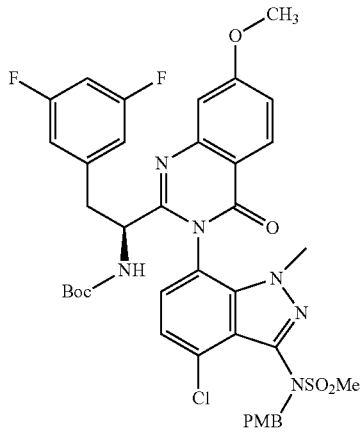

To a dry vial under nitrogen was added (S)-2-((tert-butoxycarbonyl)amino)-3-(3,5-difluorophenyl)propanoic acid (100 mg, 0.332 mmol) and 2-amino-4-methoxybenzoic acid (57 mg, 0.341 mmol) and pyridine (1.7 mL). The reaction was flushed with argon, treated with diphenyl phosphite (225 µl, 1.163 mmol), capped and heated at 70-65° C. for 2 h. The reaction was then treated with N-(7-amino-4-chloro-1-methyl-1H-indazol-3-yl)-N-(4-methoxybenzyl)methanesulfonamide (Int 17d, 143.5 mg, 0.363 mmol) and heated at 70-75° C. for 18h. The solvent was removed under a gentle stream of nitrogen and the crude material was purified via silica gel chromatography (80 g SiO$_2$ column, 0-100% ethyl acetate:hexanes) to afford the title compound, 140 mg. LC/MS m/z=753.2 (M-55); 831.3 (M+Na). Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.74 min.

(S)—N-(7-(2-(1-amino-2-(3,5-difluorophenyl)ethyl)-7-methoxy-4-oxoquinazolin-3(4H)-yl)-4-chloro-1-methyl-1H-indazol-3-yl)methanesulfonamide (Int DF36b)

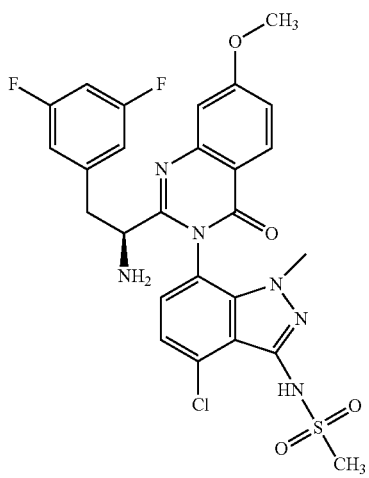 [SMILES: COc1ccc2c(=O)n(-c3ccc(Cl)c4c(NS(C)(=O)=O)nn(C)c34)c([C@@H](N)Cc3cc(F)cc(F)c3)nc2c1]

To a solution of tert-butyl (S)-(1-(3-(4-chloro-3-(N-(4-methoxybenzyl)methylsulfonamido)-1-methyl-1H-indazol-7-yl)-7-methoxy-4-oxo-3,4-dihydroquinazolin-2-yl)-2-(3,5-difluorophenyl)ethyl)carbamate (138 mg, 0.171 mmol) (Int DF36a) in anhydrous dichloromethane (3 mL) was added neat TFA (6 mL, 78 mmol). The reaction was allowed to stand at room temp for 4 min, then treated with neat triflic acid (75 µL, 0.845 mmol). The reaction was allowed to stand at room temp for 30 min, then the solvent was removed under a gentle stream of nitrogen. The residue was dissolved in ethyl acetate (80 mL) and the organic layer was washed with aqueous saturated NaHCO3 (2×15 mL), brine (1×10 mL), dried over Na2SO4, filtered and evaporated to dryness to give the title compound, 123 mg, as a stereoisomer mixture that was used "as is" without further purification in subsequent step(s). LC/MS m/z=589.2 (M+H)$^+$; Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.27, 1.32 min.

(S)—N-(7-(2-(1-amino-2-(3,5-difluorophenyl)ethyl)-8-fluoro-4-oxoquinazolin-3(4H)-yl)-4-chloro-1-methyl-1H-indazol-3-yl)methanesulfonamide (Int DF40a)

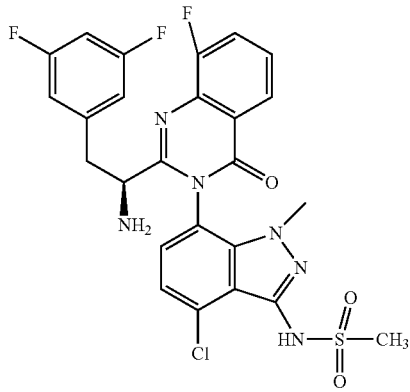 [SMILES: Cn1nc(NS(C)(=O)=O)c2c(Cl)ccc(-n3c([C@@H](N)Cc4cc(F)cc(F)c4)nc4c(F)cccc4c3=O)c21]

To a dry reaction vial under nitrogen was added (S)-2-((tert-butoxycarbonyl)amino)-3-(3,5-difluorophenyl)propanoic acid (90 mg, 0.299 mmol), 2-amino-3-fluorobenzoic acid (46.3 mg, 0.299 mmol) and anhydrous pyridine. The reaction was flushed with argon, treated with diphenyl phosphite (202.5 µl, 1.046 mmol), capped and heated at 75° C. for 3 h. The reaction was treated with N-(7-amino-4-chloro-1-methyl-1H-indazol-3-yl)-N-(4-methoxybenzyl)methanesulfonamide (Int 17d, 125 mg, 0.317 mmol), heated at 75° C. for 18 h and the solvent was removed under a gentle stream of nitrogen. The residue was dissolved in dichloromethane and the solvent again was removed under a gentle stream of nitrogen. The residue was redissolved in dichloromethane (1 mL), treated with TFA (2 mL) and allowed to stand at room temp for 30 min. The reaction was then treated with triflic acid (135 µl, 1.520 mmol), allowed to stand at room temp for 40 min and the volatiles were removed under a gentle stream of nitrogen. The residue was dissolved in ethyl acetate (50 mL) and the organic layer was washed with saturated aqueous NaHCO$_3$ (2×5 mL), brine (1×5 mL), dried over Na2SO4, filtered and evaporated to dryness to give the title compound, 86 mg, as a stereoisomer mixture that was used "as is" without further purification in subsequent step(s). LC/MS m/z=577.2, 579.2 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.33, 1.39 min.

N—((S)-1-(3-(4-chloro-1-methyl-3-(methylsulfonamido)-1H-indazol-7-yl)-8-fluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 71) and Example 70

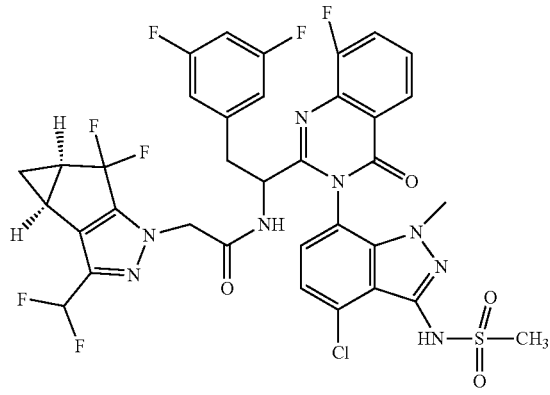

Example 70

Mix of two stereoisomers

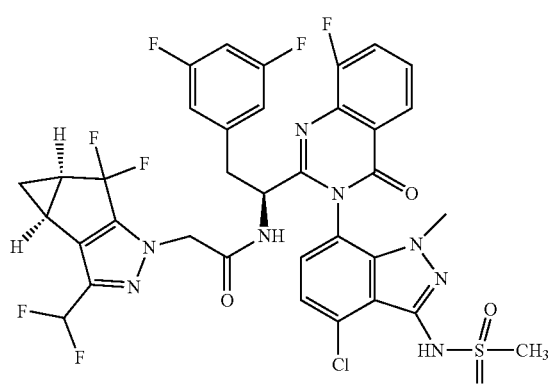

Example 71

A mixture of indicated isomer and a stereoisomer

To a dry reaction vial under nitrogen was added N-(7-(2-(1-amino-2-(3,5-difluorophenyl)ethyl)-8-fluoro-4-oxoquinazolin-3(4H)-yl)-4-chloro-1-methyl-1H-indazol-3-yl)methanesulfonamide (86 mg, 0.149 mmol) (Int DF40a), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (39.4 mg, 0.149 mmol), 1-hydroxy-7-azabenzotriazole (2 mg, 0.015 mmol) and anhydrous DMF (1.0 mL). The reaction was flushed with nitrogen, treated with N-methylmorpholine (150 μL, 1.364 mmol), EDC (45 mg, 0.235 mmol) and allowed to stand at room temp for 40 min. The reaction was treated with additional 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (4 mg, 0.015 mmol) and allowed to stand at room temp for 90 min. The reaction was treated with additional 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (10 mg, 0.038 mmol) and allowed to stand at room temp for 2 h. The reaction was treated with additional 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (30 mg, 0.114 mmol), N-methylmorpholine (150 μL, 1.364 mmol) and EDC (45 mg, 1.57 mmol), and allowed to stand at room temp for 18h. The reaction was treated with 7MNH3/MeOH (100 μL) and was purified via preparative LC/MS to afford two elutes.

Example 70: First Eluting Peak, 30.1 mg

LC/MS m/z=823.1 (M+H)+. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.14 min.

Example 71: Second Eluting Peak, 77.6 mg

LC/MS m/z=823.1 (M+H)+. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.2 min.

(S)—N-(7-(2-(1-amino-2-(3,5-difluorophenyl)ethyl)-6,8-difluoro-4-oxoquinazolin-3(4H)-yl)-4-chloro-1-methyl-1H-indazol-3-yl)methanesulfonamide (Int DF42a)

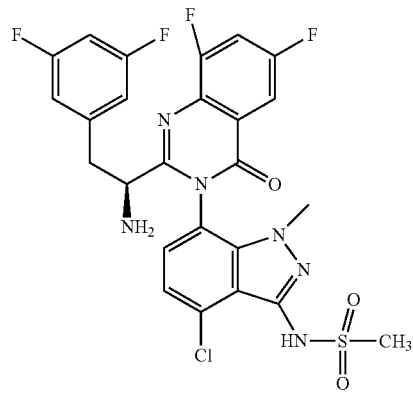 [SMILES: Cn1nc(NS(C)(=O)=O)c2c(Cl)ccc(-n3c([C@@H](N)Cc4cc(F)cc(F)c4)nc4c(F)cc(F)cc4c3=O)c21]

To a dry reaction vial under nitrogen was added (S)-2-((tert-butoxycarbonyl)amino)-3-(3,5-difluorophenyl)propanoic acid (90 mg, 0.299 mmol), 2-amino-3,5-difluorobenzoic acid (51.7 mg, 0.299 mmol) and anhydrous Pyridine (700 µL). The reaction was flushed with argon, treated with diphenyl phosphite (202 µL, 1.044 mmol), and heated at 75° C. for 3 h. The reaction was treated with N-(7-amino-4-chloro-1-methyl-1H-indazol-3-yl)-N-(4-methoxybenzyl) methanesulfonamide (Int 17d, 121.5 mg, 0.308 mmol), heated at 80° C. for 24 h and then the solvent was removed under a gentle stream of nitrogen. The residue was dissolved in dichloromethane and the solvent again was removed under a gentle stream of nitrogen. The residue was redissolved in dichloromethane (1 mL), treated with TFA (2 mL) and allowed to stand at room temp for 5 min. The reaction was then treated with triflic acid (135 µl, 1.520 mmol) and allowed to stand at room temp for 45 min. The reaction was treated with additional triflic acid (67 µL), allowed to stand at room temp for 90 and the volatiles were removed under a gentle stream of nitrogen. The residue was dissolved in ethyl acetate (50 mL) and the organic layer was washed with saturated aqueous NaHCO$_3$ (2×5 mL), brine (1×5 mL), dried over Na2SO4, filtered and evaporated to dryness to give the title compound, 89 mg, as a stereoisomer mixture that was used "as is" without further purification in subsequent step(s). LC/MS m/z=595.2, 597.2 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.34, 1.41 min.

N—((S)-1-(3-(4-chloro-1-methyl-3-(methylsulfonamido)-1H-indazol-7-yl)-6,8-difluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 74) and Example 73

Example 73

Mix of two stereoisomers

Example 74

A mixture of indicated isomer and a stereoisomer

To a dry reaction vial under nitrogen was added (S)—N-(7-(2-(1-amino-2-(3,5-difluorophenyl)ethyl)-6,8-difluoro-4-oxoquinazolin-3(4H)-yl)-4-chloro-1-methyl-1H-indazol-3-yl)methanesulfonamide (56 mg, 0.094 mmol) (Int DF42a), 2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetic acid (24.87 mg, 0.094 mmol), 1-hydroxy-7-azabenzotriazole (2 mg, 0.015 mmol) and anhydrous DMF (1.0 mL). The reaction was flushed with nitrogen, treated with N-methylmorpholine (165 µL, 1.501 mmol), EDC (43 mg, 0.224 mmol), and allowed to stand at room temp for 2h. The reaction was treated with additional 2-((3bS,4aR)-3-(difluoromethyl)-5,5-difluoro-3b,4,4a,5-tetrahydro-1H-cyclopropa [3,4]cyclopenta[1,2-c]pyrazol-1-yl)acetic acid (15 mg, 0.057 mmol) and stand at room temp for 30 min. The reaction was treated with additional 2-((3bS,4aR)-3-(difluoromethyl)-5,5-difluoro-3b,4,4a,5-tetrahydro-1H-cyclopropa [3,4]cyclopenta[1,2-c]pyrazol-1-yl)acetic acid (30 mg, 0.114 mmol), N-methylmorpholine (150 µL, 1.364 mmol), EDC (45 mg, 1.57 mmol), and allowed to stand at room temp for 18 h. The reaction was treated with 7MNH3/MeOH (100 µL) and was purified via preparative LC/MS to afford two elutes.

Example 73: First Eluting Peak, 16.1 mg

LC/MS m/z=841.0 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.19 min.

Example 74: Second Eluting Peak, 47.2 mg

LC/MS m/z=841.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.24 min.

267

(S)—N-(7-(2-(1-amino-2-(3,5-difluorophenyl)ethyl)-8-fluoro-7-methoxy-4-oxoquinazolin-3(4H)-yl)-4-chloro-1-methyl-1H-indazol-3-yl)methanesulfonamide (Int DF47a)

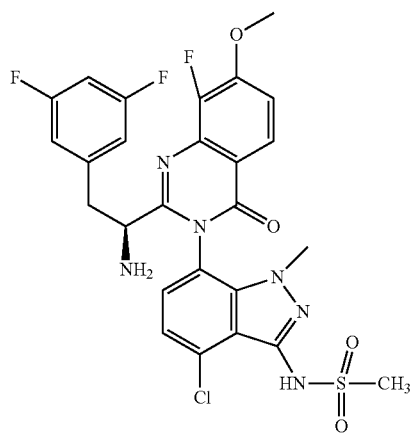 [SMILES: COc1ccc2c(=O)n(-c3ccc(Cl)c4c(NS(C)(=O)=O)nn(C)c34)c([C@@H](N)Cc3cc(F)cc(F)c3)nc2c1F]

To a dry reaction vial under nitrogen was added (S)-2-((tert-butoxycarbonyl)amino)-3-(3,5-difluorophenyl)propanoic acid (80 mg, 0.266 mmol), 2-amino-3-fluoro-4-methoxybenzoic acid (49.2 mg, 0.266 mmol) and anhydrous Pyridine (700 μL). The reaction was flushed with argon, treated with diphenyl phosphite (180 μL, 0.930 mmol), and heated at 75° C. for 2 h. The reaction was treated with N-(7-amino-4-chloro-1-methyl-1H-indazol-3-yl)-N-(4-methoxybenzyl)methanesulfonamide (Int 17d, 116 mg, 0.294 mmol), heated at 75° C. for 18h and the solvent was removed under a gentle stream of nitrogen. The residue was dissolved in dichloromethane and evaporated to dryness under a gentle stream of nitrogen. The residue was dissolved in dichloromethane (1 mL), treated with TFA (2 mL) and allowed to stand at room temp for 5 min. The reaction was then treated with triflic acid (240 μl, 2.82 mmol), allowed to stand at room temp for 15 min and the volatiles were removed under a gentle stream of nitrogen. The residue was dissolved in ethyl acetate (45 mL) and the organic layer was washed with saturated aqueous $NaHCO_3$ (2×5 mL), brine (1×5 mL), dried over Na2SO4, filtered and evaporated to dryness to give the title compound, 80 mg, as a stereoisomer mixture that was used "as is" without further purification in subsequent step(s). LC/MS m/z=607.1, 609.1 (M+H). Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.05, 1.10 min.

268

N—((S)-1-(3-(4-chloro-1-methyl-3-(methylsulfonamido)-1H-indazol-7-yl)-8-fluoro-7-methoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 76) and Example 75

Exmaple 75

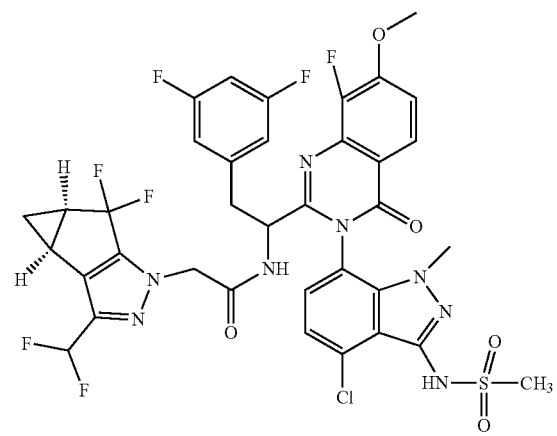

Mix of two stereoisomers

Example 76

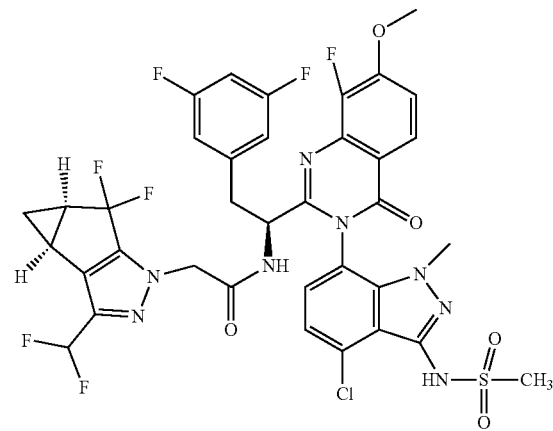

A mixture of indicated isomer and a stereoisomer

To a dry reaction vial under nitrogen was added (S)—N-(7-(2-(1-amino-2-(3,5-difluorophenyl)ethyl)-8-fluoro-7-methoxy-4-oxoquinazolin-3(4H)-yl)-4-chloro-1-methyl-1H-indazol-3-yl)methanesulfonamide (80 mg, 0.132 mmol) (Int DF47a), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (65 mg, 0.246 mmol), 1-hydroxy-7-azabenzotriazole (15 mg, 0.110 mmol) and anhydrous DMF (1 mL). The reaction was flushed with nitrogen, treated with N-methylmorpholine (120 μL, 1.091 mmol), EDC (65 mg, 0.339 mmol) and allowed to stand at room temp for 1 h. The reaction was treated with 7MNH3/MeOH (100 μL) and was purified via preparative LC/MS to afford two elutes.

Example 75: First Eluting Peak, 7.2 mg

LC/MS m/z=853.1 (M+H)⁺. Column: Waters XBridge C18, 2.1 mm×50 mm, 1.7 μm particles; Mobile Phase A:

5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.07 min.

Example 76: Second Eluting Peak, 37.2 mg

LC/MS m/z=853.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.15 min.

(S)—N-(1-(3-(4-chloro-1-methyl-3-(methylsulfonamido)-1H-indazol-7-yl)-7-methoxy-4-oxo-3,4-dihydroquinazolin-2-yl)-2-(3,5-difluorophenyl)ethyl)-2-(3-cyclopropyl-1H-pyrazol-1-yl)acetamide (Example 78 and Example 77)

Example DF69

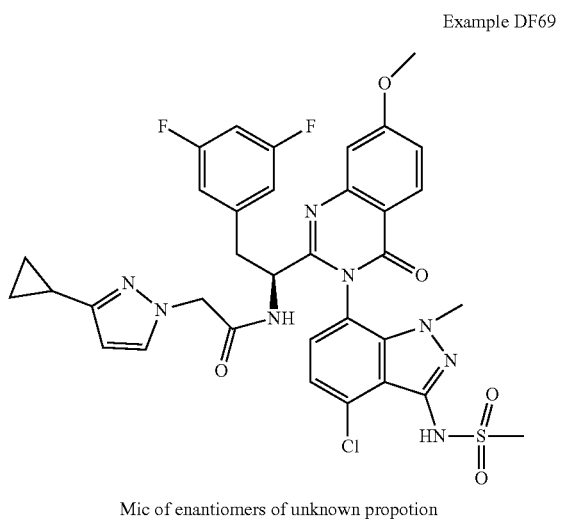

Mic of enantiomers of unknown propotion

Example DF70

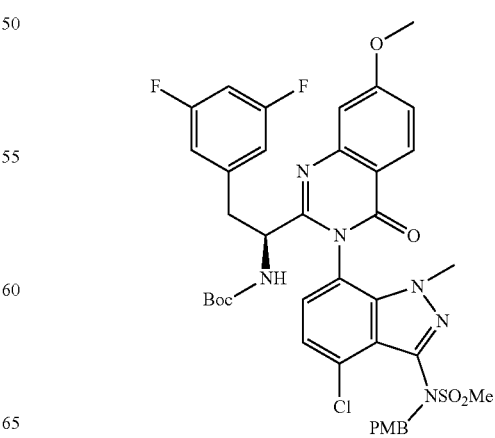

Mic of enantiomers of unknown propotion

To a solution of (S)—N-(7-(2-(1-amino-2-(3,5-difluorophenyl)ethyl)-7-methoxy-4-oxoquinazolin-3(4H)-yl)-4-chloro-1-methyl-1H-indazol-3-yl)methanesulfonamide (43 mg, 0.073 mmol) (Int DF36b) in anhydrous DMF (1.0 mL) was added 2-(3-cyclopropyl-1h-pyrazol-1-yl)acetic acid (12.7 mg, 0.076 mmol), 1-hydroxy-7-azabenzotriazole (3.5 mg, 0.026 mmol) and N-methylmorpholine (70 μL, 0.637 mmol). The reaction was flushed with nitrogen, treated, EDC (20.2 mg, 0.105 mmol), allowed to stand at room temp for 5 h, and the crude reaction was purified via preparative HPLC to retrieve two fractions, each as a mixture of stereoisomers but where one was dominant.

Example 77: First Eluting Peak, 8.1 mg

LC/MS m/z=737.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1. 9 min. $^{19}$F NMR (471 MHz, DMSO-d$_6$) δ −109.72 (s, 2F)

Example 78: Second Eluting Peak, 39.1 mg

LC/MS m/z=737.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.02 min. $^1$H NMR (500 MHz, DMSO-d$_6$, water suppression) δ 8.86 (br d, J=8.2 Hz, 1H), 8.13 (d, J=8.5 Hz, 1H), 7.67 (d, J=7.9 Hz, 1H), 7.40 (br d, J=7.6 Hz, 1H), 7.31-7.19 (m, 3H), 7.03 (br t, J=9.3 Hz, 1H), 6.69 (br d, J=6.4 Hz, 2H), 5.84 (d, J=1.8 Hz, 1H), 4.63-4.52 (m, 1H), 4.42-4.34 (m, 1H), 4.31-4.23 (m, 1H), 3.98 (s, 3H), 3.54 (s), 3.20 (s), 3.01 (br dd, J=14.0, 10.7 Hz, 1H), 1.74 (td, J=8.5, 4.3 Hz, 1H), 0.80-0.72 (m, 2H), 0.59-0.40 (m, 2H).

$^{19}$F NMR (471 MHz, DMSO-d$_6$) δ −110.07 (s, 2F)

tert-butyl (S)-(1-(3-(4-chloro-3-(N-(4-methoxybenzyl)methylsulfonamido)-1-methyl-1H-indazol-7-yl)-7-methoxy-4-oxo-3,4-dihydroquinazolin-2-yl)-2-(3,5-difluorophenyl)ethyl)carbamate (Int DF71a)

To a dry reaction vial under nitrogen was added (in this order) (S)-2-((tert-butoxycarbonyl)amino)-3-(3,5-difluorophenyl)propanoic acid (432.8 mg, 1.436 mmol), 2-amino-4-methoxybenzoic acid (240 mg, 1.436 mmol), N-(7-amino-4-chloro-1-methyl-1H-indazol-3-yl)-N-(4-methoxybenzyl)methanesulfonamide (Int 17d, 567 mg, 1.436 mmol), diphenyl phosphite (1.1 mL, 5.68 mmol) and anhydrous Pyridine (5.5 mL). The reaction was flushed with argon, sonicated for 30 sec. to dissolve all the solids and heated at 70° C. for 3.5h. The solvent was removed under a gentle stream of nitrogen and the the crude material was purified via silica gel chromatography (120 g SiO₂ column, 0-100% ethyl acetate:hexanes) to the title compound, 780 mg. LC/MS m/z=753.2, 755.2 (M-55); Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.71 min.

(S)—N-(7-(2-(1-amino-2-(3,5-difluorophenyl)ethyl)-7-methoxy-4-oxoquinazolin-3(4H)-yl)-4-chloro-1-methyl-1H-indazol-3-yl)methanesulfonamide (Int DF71b)

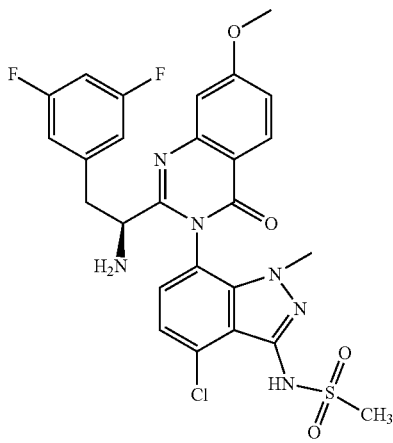 [SMILES: COc1ccc2c(=O)n(-c3ccc(Cl)c4c(NS(C)(=O)=O)nn(C)c34)c([C@@H](N)Cc3cc(F)cc(F)c3)nc2c1]

To a solution of tert-butyl (S)-(1-(3-(4-chloro-3-(N-(4-methoxybenzyl)methylsulfonamido)-1-methyl-1H-indazol-7-yl)-7-methoxy-4-oxo-3,4-dihydroquinazolin-2-yl)-2-(3,5-difluorophenyl)ethyl)carbamate (780 mg, 0.964 mmol) (Int DF71a) in anhydrous dichloromethane (10 mL) was added TFA (15 mL, 195 mmol). The resulting solution was swirled rapidly for 2-3 min, allowed to stand at room temp for 5 min, treated with triflic acid (1.0 mL, 11.26 mmol) and allowed to stand at room temp for 30 min. The solvent was removed under a gentle stream of nitrogen, the residue suspended dichloromethane (15 mL), and quenched a solution of sodium carbonate (1.5 g, 14.15 mmol) in water (15 mL). The reaction was diluted with ethyl acetate (400 mL) and the organic layer was washed with saturated aqueous NaHCO₃ (2×20 mL), brine (1×20 mL), dried over Na₂S04, filtered and evaporated to dryness to to afford the title compound, 787.8 mg. LC/MS m/z=589.2 (M+H)⁺; Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.32 min.

tert-butyl (S)-(2-(3,5-difluorophenyl)-1-(7-methoxy-3-(3-(N-(4-methoxybenzyl)methylsulfonamido)-1-methyl-1H-indazol-7-yl)-4-oxo-3,4-dihydroquinazolin-2-yl)ethyl)carbamate (Int DF79a)

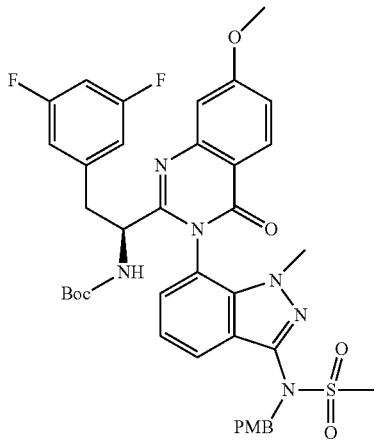

To a dry reaction vial under nitrogen was added (S)-2-((tert-butoxycarbonyl)amino)-3-(3,5-difluorophenyl)propanoic acid (118 mg, 0.392 mmol), 2-amino-4-methoxybenzoic acid (65.5 mg, 0.392 mmol) and anhydrous Pyridine (2.0 mL). The reaction was flushed with argon, treated with diphenyl phosphite and heated at 80° C. for 160 min. The reaction was treated with N-(7-amino-1-methyl-1H-indazol-3-yl)-N-(4-methoxybenzyl)methanesulfonamide (141.4 mg, 0.392 mmol) (Int DF34a) and heated at 75-80° C. for 18h. The solvent was removed under a gentle stream of nitrogen and the crude material was purified via silica gel chromatography (24 g SiO₂ column, 0-100% ethyl acetate:dichloromethane) to afford the title compound, 132 mg. LC/MS M/Z=775.3 (M-55); 797.3 (M+Na). Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.69 min.

(S)—N-(7-(2-(1-amino-2-(3,5-difluorophenyl)ethyl)-7-methoxy-4-oxoquinazolin-3(4H)-yl)-1-methyl-1H-indazol-3-yl)methanesulfonamide (Int DF79b)

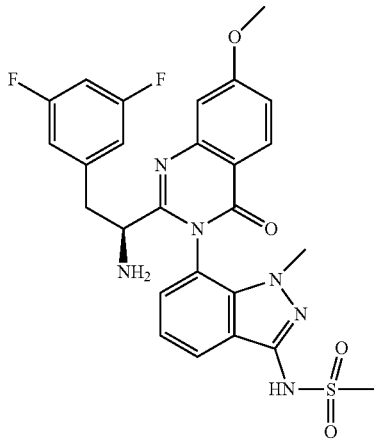 [SMILES: COc1ccc2c(=O)n(-c3cccc4c(NS(C)(=O)=O)nn(C)c34)c([C@@H](N)Cc3cc(F)cc(F)c3)nc2c1]

To a reaction vial containing a solution of tert-butyl (S)-(2-(3,5-difluorophenyl)-1-(7-methoxy-3-(3-(N-(4-methoxybenzyl)methylsulfonamido)-1-methyl-1H-indazol-7-yl)-4-oxo-3,4-dihydroquinazolin-2-yl)ethyl)carbamate (132 mg, 0.170 mmol) in dichloromethane (3 mL) was added TFA (6 mL, 78 mmol) with rapid swirling. The resulting solution was allowed to stand at room temp for 4 min, treated with triflic acid (150 µL, 1.689 mmol), allowed to stand at room temp for 15 min and the solvent was evaporated off gentle stream of nitrogen. The residue was suspended in dichloromethane (5 mL), quenched with saturated aqueous NaHCO$_3$ (10 mL), diluted with ethyl acetate (50 mL) and the organic layer was washed with aqueous saturated NaHCO$_3$ (1×5 mL), brine (1×5 mL), dried over Na2SO4, filtered and evaporated to dryness to give the title compound, 255 mg. LC/MS m/z=555.2 (M+H)$^+$; 797.3 (M+Na). Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.46 min.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(7-methoxy-3-(1-methyl-3-(methylsulfonamido)-1H-indazol-7-yl)-4-oxo-3,4-dihydroquinazolin-2-yl)ethyl)acetamide (Example 80) and Example 79

To a solution of (S)—N-(7-(2-(1-amino-2-(3,5-difluorophenyl)ethyl)-7-methoxy-4-oxoquinazolin-3(4H)-yl)-1-methyl-1H-indazol-3-yl)methanesulfonamide (94 mg, 0.169 mmol) (Int DF79b) in anhydrous DMF (850 µL) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (41 mg, 0.155 mmol) and 1-hydroxy-7-azabenzotriazole (4 mg, 0.029 mmol). The reaction was flushed with nitrogen, treated with N-methylmorpholine (70 µL, 0.637 mmol), EDC (20.2 mg, 0.105 mmol), allowed to stand at room temp for 100 min, and the crude reaction was purified via preparative HPLC to retrieve two fractions, each as a mixture of stereoisomers but where one stereoisomer dominates.

Example 79: First Eluting Peak, 3.2 mg

LC/MS m/z=801.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.99 min. Proton Example 80: Second Eluting Peak, 17.3 mg LC/MS m/z=801.2 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.06 min.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(6-isopropylpyridin-3-yl)-1H-pyrrolo[3,2-b]pyridin-5-yl)ethyl)acetamide (Example 81)

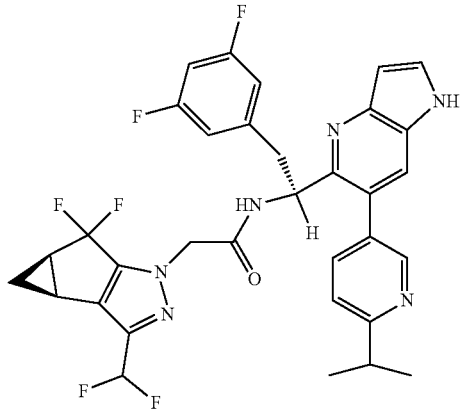 [SMILES: CC(C)c1ccc(-c2cc3[nH]ccc3nc2[C@H](Cc2cc(F)cc(F)c2)NC(=O)Cn2nc(C(F)F)c3c2C(F)(F)[C@@H]2C[C@H]32)cn1]

To a dry reaction vial under nitrogen was added N—((S)-1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (43 mg, 0.072 mmol) (Int DF6f.1), (6-isopropylpyridin-3-yl)boronic acid (19 mg, 0.115 mmol) and degassed Dioxane (4 mL). The reaction was purged with argon for 4 min, treated with sodium carbonate, 2.0M in water (100 µL, 0.200 mmol), tetrakis(triphenylphosphine)palladium(0) (6 mg, 5.19 µmol), flushed with argon again, and heated at 130° C. for 18h. The reaction was diluted with ethyl acetate, washed with brine, dried over Na2SO4, filtered, evaporated to dryness and the crude material was purified via preparative LC/MS to afford the title compound, 26.5 mg. LC/MS m/z=639.2 (M+H)$^+$. Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Retention Time: 2.14 min.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(6-isopropylpyridin-3-yl)-1H-pyrrolo[3,2-b]pyridin-5-yl)ethyl)acetamide (Example 82)

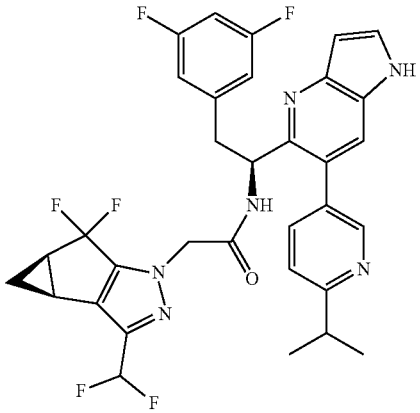 [SMILES: CC(C)c1ccc(-c2cc3[nH]ccc3nc2[C@H](Cc2cc(F)cc(F)c2)NC(=O)Cn2nc(C(F)F)c3c2C(F)(F)[C@@H]2C[C@H]32)cn1]

To a solution of N—((S)-1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (13.8 mg, 0.023 mmol) (Int DF6f.1) and (6-isopropylpyridin-3-yl)boronic acid (14 mg, 0.085 mmol) in distilled THF (3 mL) under argon was added potassium phosphate tribasic 0.5 M in water (0.23 mL, 0.115 mmol), $2^{nd}$ generation xphos precatalyst (14 mg, 0.018 mmol) and the reaction was stirred at room temp for 18h. The reaction was treated with additional (6-isopropylpyridin-3-yl)boronic acid (50 mg, 0.30 mmol), dioxane (3 mL), aqueous 2 M Na2CO3 (0.2 mL) and tetrakis(triphenylphosphine)palladium(0) (4 mg, 3.46 μmol), flushed with argon again, and heated at 132° C. for 18h. The reaction was diluted with ethyl acetate, washed with brine, dried over Na2SO4, filtered, evaporated to dryness and the crude material was purified via preparative LC/MS to afford the title compound, 26.5 mg. LC/MS m/z=639.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.12 min.

N-(4-chloro-7-(6-(2-(3,5-difluorophenyl)-1-(1,3-dioxoisoindolin-2-yl)ethyl)-1-((2-(trimethylsilyl)ethoxy)methyl)-1H-pyrrolo[2,3-b]pyridin-5-yl)-1-methyl-1H-indazol-3-yl)methanesulfonamide (Int DF104b)

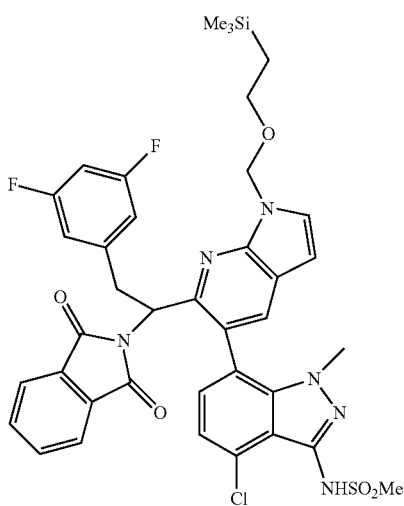

To a dry reaction vial under nitrogen was added 2-(1-(5-bromo-1-((2-(trimethylsilyl)ethoxy)methyl)-1H-pyrrolo[2,3-b]pyridin-6-yl)-2-(3,5-difluorophenyl)ethyl)isoindoline-, 3-dione (150 mg, 0.245 mmol) (Int DF1If), N-(4-chloro-1-methyl-7-(4,4,5,5-tetramethyl-1,3,2-dioxaborolan-2-yl)-1H-indazol-3-yl)methanesulfonamide (Int 17d, 100 mg, 0.259 mmol) and THF (12 mL). The reaction was flushed with argon, treated with potassium phosphate tribasic 0.5 M in water (2 mL, 1.000 mmol), $2^{nd}$ generation xphos precatalyst (14 mg, 0.018 mmol), and stirred at room temp for 18h. The reaction was diluted with ethyl acetate and the organic layer was washed with brine, dried over Na2SO4, filtered, evaporated to dryness and the crude material was purified via silica gel chromatography (80 g SiO$_2$ column, 0-100% ethyl acetate:dichloromethane) to afford the title compound, 67.2 mg, as a mixture of stereoisomers. LC/MS m/z=791.4, 793.4 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.83 min.

N-(7-(6-(1-amino-2-(3,5-difluorophenyl)ethyl)-1-((2-(trimethylsilyl)ethoxy)methyl)-1H-pyrrolo[2,3-b]pyridin-5-yl)-4-chloro-1-methyl-1H-indazol-3-yl)methanesulfonamide (Int DF104c)

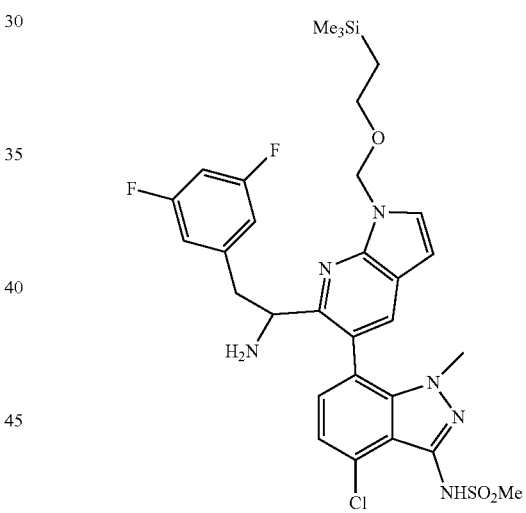

To a suspension of N-(4-chloro-7-(6-(2-(3,5-difluorophenyl)-1-(1,3-dioxoisoindolin-2-yl)ethyl)-1-((2-(trimethylsilyl)ethoxy)methy)-1H-pyrrolo[2,3-b]pyridin-5-yl)-1-methyl-1H-indazol-3-yl)methanesulfonamide (43.3 mg, 0.055 mmol) (Int DF104b) in EtOH (11 mL) under argon was treated with hydrazine hydrate (30 μl, 0.618 mmol). The reaction was stirred at room temp for 5 min, heated at 75° C. for 10 min, heated at 80° C. for 18h and the solvent was removed under a gentle stream of nitrogen to give the title compound, 36.2 mg. LC/MS m/z=661.3 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.57 min.

N—((S)-1-(5-(4-chloro-1-methyl-3-(methylsulfonamido)-1H-indazol-7-yl)-1-((2-(trimethylsilyl)ethoxy)methyl)-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF105) and Int DF104

Int DF104

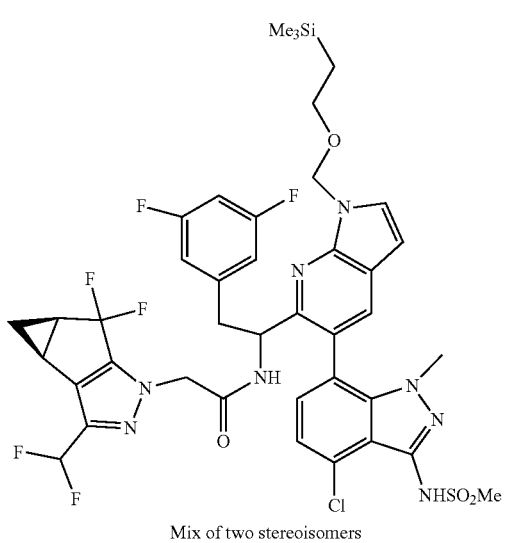

Mix of two stereoisomers

Int DF105

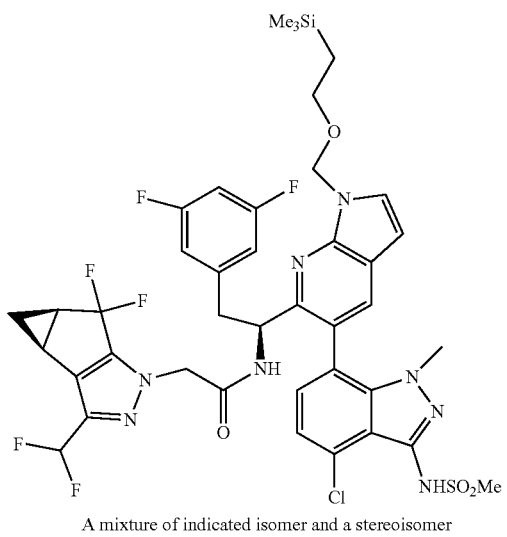

A mixture of indicated isomer and a stereoisomer

A magnetically stirred suspension of N-(7-(6-(1-amino-2-(3,5-difluorophenyl)ethyl)-1-((2-(trimethylsilyl)ethoxy)methyl)-1H-pyrrolo[2,3-b]pyridin-5-yl)-4-chloro-1-methyl-1H-indazol-3-yl)methanesulfonamide (Int DF104c) (36 mg, 0.054 mmol), 1-hydroxy-7-azabenzotriazole (1.5 mg, 0.011 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (16 mg, 0.061 mmol) in dichloromethane (5 mL) under argon was treated with N-methylmorpholine (50 μl, 0.455 mmol) and EDC (12 mg, 0.063 mmol). The resulting suspension was treated with distilled THF (4 mL) and stirred at room temp for 4.5 h. The reaction was treated with additional 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (7.4 mg, 0.03 mmol), EDC (7.4 mg), stirred at room temp for 18h and the crude reaction was purified via preparative LC/MS to afford two elutes, each as a mixture of stereoisomers exhibiting targeted molecule weight.

Int DF104: First eluting peak, 4.6 mg. LC/MS m/z=907.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.56 min. Int DF105: second eluting peak, 8.2 mg. LC/MS m/z=907.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.67 min.

N—((S)-1-(5-(4-chloro-1-methyl-3-(methylsulfonamido)-1H-indazol-7-yl)-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 84) and Example 83

Example 83

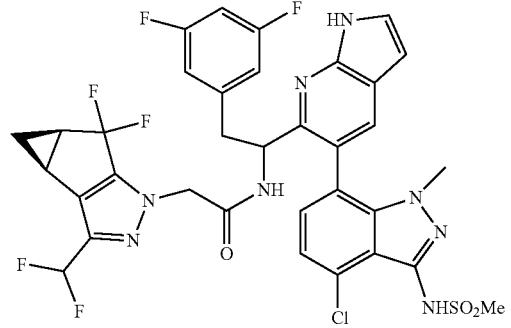

Mix of two stereoisomers

Example 84

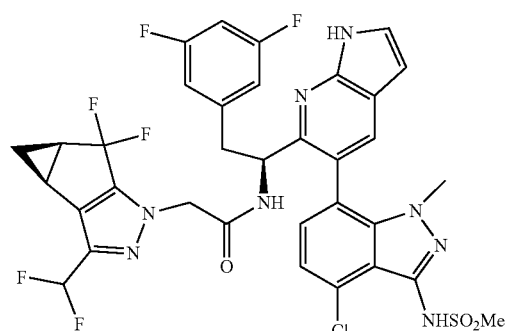

A mixture of indicated isomer and a stereoisomer

To a reaction vial containing crude N-(1-(5-(4-chloro-1-methyl-3-(methylsulfonamido)-1H-indazol-7-yl)-1-((2-(trimethylsilyl)ethoxy)methyl)-1H-pyrrolo[2,3-b]pyridin-6- yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (a mixture of Int DF104 and Int DF105) was added neat TFA (2 mL) and the reaction was allowed to stand at room temp for 30 min. The volatiles were removed under a gentle stream of nitrogen and the reside was dissolved in 7M NH3/MeOH (9 mL), heated at 70° C. for 40 min and allowed to stand at room temp for 18h. The solvent was removed under a gentle stream of nitrogen, the residue was redissolved in MeOH (4 mL), treated with 50 µlit ethylenediamine (50 µL) and the crude product was purified via preparative LC/MS to afford two elutes, each as a mixture of stereoisomers but where one stereoisomer dominates, exhibiting targeted molecule weight.

Example 83: First Eluting Peak, 2.9 mg

LC/MS m/z=777.0 (M+H)+. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.95 min.

Example 84: Second Eluting Peak, 5.4 mg

LC/MS m/z=777.0 (M+H)+. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.07 min.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((R)-2-(3,5-difluorophenyl)-1-(6-(6-isopropylpyridin-3-yl)-1H-pyrrolo[3,2-b]pyridin-5-yl)ethyl)acetamide (Example 85)

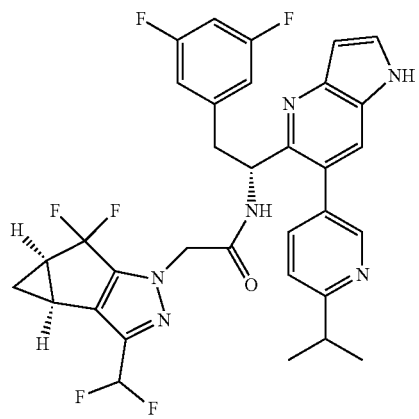 [SMILES: CC(C)c1ccc(-c2cc3[nH]ccc3nc2[C@@H](Cc2cc(F)cc(F)c2)NC(=O)Cn2nc(C(F)F)c3c2C(F)(F)[C@@H]2C[C@H]32)cn1]

To a dry vial under nitrogen was added N—((R)-1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (21 mg, 0.035 mmol) (Int DF6f.2), (6-isopropylpyridin-3-yl)boronic acid (25 mg, 0.152 mmol), degassed Dioxane (4 mL) and degassed sodium carbonate 2 M in water (0.12 mL, 0.240 mmol). The reaction was flushed with argon, treated with tetrakis(triphenylphosphine)palladium(0) (5 mg, 4.33 µmol), flushed with argon again, and heated at 132° C. for 18 h. The reaction was diluted with ethyl acetate (15 mL), the organic layer was washed with brine (10 mL), dried over Na2SO4, filtered, evaporated to dryness and the crude material was purified via preparative LC/MS to afford the title compound, 14.3 mg. LC/MS m/z=639.2 (M+H)+. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.15 min.

tert-butyl 2-(6-bromo-5-((R)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrrolo[3,2-b]pyridin-1-yl)acetate (Int DF109 a)

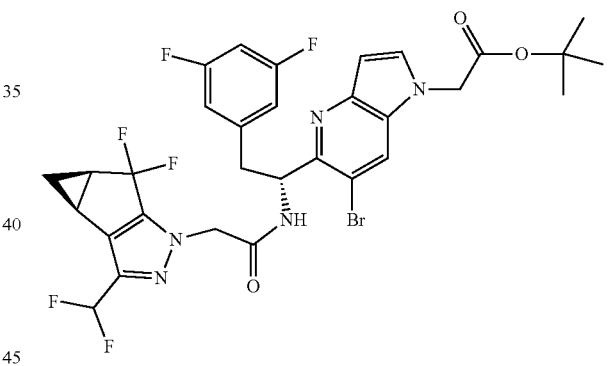

To a magnetically stirred solution of N—((R)-1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (32.9 mg, 0.055 mmol) (Int DF6f.2) in Acetone (3 mL) was added solid potassium carbonate (183 mg, 1.324 mmol), tert-butyl 2-bromoacetate (79 mg, 0.405 mmol) and the reaction was heated at 55-60° C. oil bath for 36-40 h. The solids were filtered off through a 45 micron frit and the solvent was removed under a gentle stream of nitrogen to give the title compound, 39.2 mg that was used "as is" in subsequent reaction(s). LC/MS m/z=712.3, 714.3 (M+H)+. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.75 min.

tert-butyl 2-(6-(4-chloro-1-methyl-3-(methylsulfonamido)-1H-indazol-7-yl)-5-((R)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-1H-pyrrolo[3,2-b]pyridin-1-yl)acetate (Int DF109b)

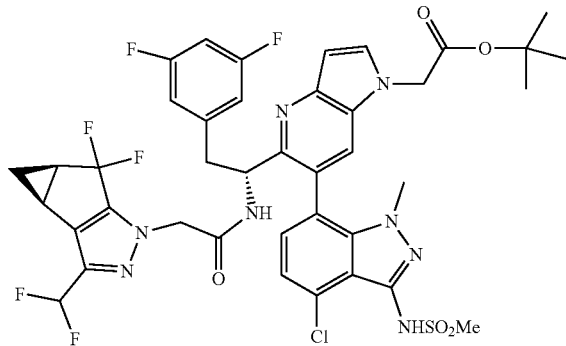

To a reaction vial under nitrogen was added tert-butyl 2-(6-bromo-5-((R)-1-(2-((3bS,4aR)-3-(difluoromethyl)-5,5-difluoro-3b,4,4a,5-tetrahydro-1H-cyclopenta[1,2-c]pyrazol-1-yl)acetamido)-2-(3,5-difluorophenyl)ethyl)-1H-pyrrolo[3,2-b]pyridin-1-yl)acetate (39 mg, 0.055 mmol) (Int DF109a), N-(4-chloro-1-methyl-7-(4,4,5,5-tetramethyl-1,3,2-dioxaborolan-2-yl)-1H-indazol-3-yl)methanesulfonamide (Int 17d, 65 mg, 0.169 mmol), degassed dioxane (6 mL) and degassed sodium carbonate 2 M in water (0.2 mL, 0.400 mmol). The reaction was flushed with argon, treated with tetrakis(triphenylphosphine)palladium(0) (5 mg, 4.33 μmol), flushed with argon again, and heated at 132° C. for 18h. The reaction was diluted with ethyl acetate (20 mL), the organic layer was washed with 1 N HC (4 mL), brine, dried over Na$_2$SO$_4$ and evaporated to dryness to give the title compound, 48.8 mg, that was used "as is" in subsequent reaction(s). LC/MS m/z=891.4, 714.3 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.66 min.

N—((R)-1-(5-bromo-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF111a)

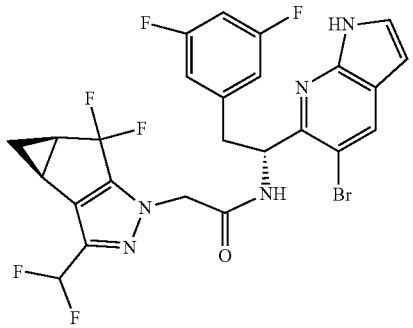 [SMILES: O=C(Cn1nc(C(F)F)c2c1C(F)(F)[C@@H]1C[C@H]21)N[C@H](Cc1cc(F)cc(F)c1)c1nc2[nH]ccc2cc1Br]

To a reaction vial containing N—((R)-1-(5-bromo-1-((2-(trimethylsilyl)ethoxy)methyl)-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (41 mg, 0.056 mmol) (Int DF11g.1) was added neat TFA (3 mL) and the reaction was allowed to stand at room temp for 2.25h. The reaction was treated with TFA (1.0 mL) and the reaction was heated at 70° C. for 45 min. The reaction was treated with additional TFA (4 mL) and allowed to stand at room temp for 18h. The volatiles were removed under a gentle stream of nitrogen and the residue was dissolved in 7 M NH$_3$/MeOH (8 mL) and heated at 70° C. for 1.5h. The reaction was evaporated to dryness under a gentle stream of nitrogen to give the title compound, 34 mg, that was used "as is" in subsequent reaction(s). LC/MS m/z=598.1, 600.1 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.47 min.

N—((R)-1-(5-(4-chloro-1-methyl-3-(methylsulfonamido)-1H-indazol-7-yl)-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 87) and Example 86

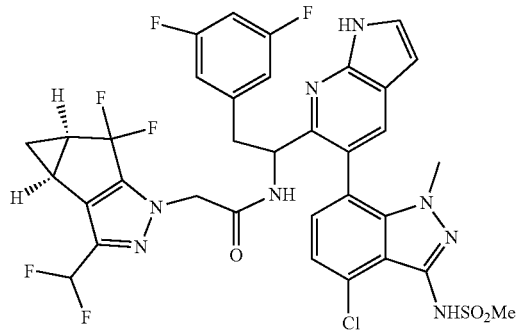

Example 86
Mix of two stereoisomers

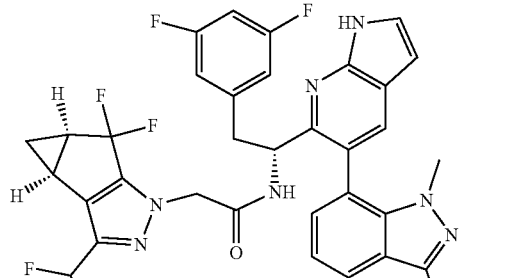

Example 87
A mixture of indicated isomer
and a stereoisomer

To a reaction vial under nitrogen was added N—((R)-1-(5-bromo-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (33 mg, 0.055 mmol) (Int DF111a), N-(4-chloro-1-methyl-7-(4,4,5,5-tetramethyl-1,3,2-dioxaborolan-2-yl)-1H-indazol-3-yl)methanesulfonamide (Int 17d, 70 mg, 0.182 mmol), degassed Dioxane (6 mL) and sodium carbonate 2 M in water (0.21 mL, 0.420 mmol). The reaction was flushed with argon, treated with tetrakis(triphenylphosphine)palladium(0) (5 mg, 4.33 µmol), flushed with argon again, and heated at 132° C. for 18h. The reaction was diluted with ethyl acetate (15 mL) and the organic layer was washed with brine (10 mL). dried over Na2SO4, filtered thru 0.45 micron and the crude product was purified via preparative LC/MS to afford two elutes.

Example 86: First Eluting Peak, 6.8 mg

LC/MS m/z=777.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.96 min.

Example 87: Second Eluting Peak, 7.8 mg

LC/MS m/z=777.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.07 min.

N—((S)-1-(6-bromo-3-chloro-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF113a)

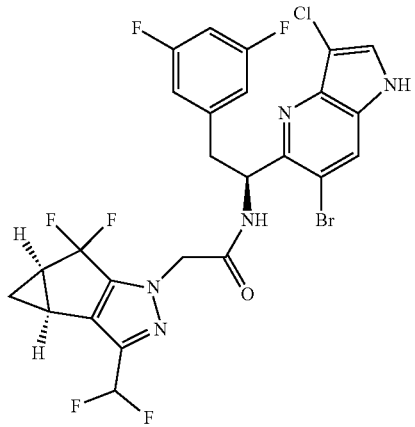 [SMILES: O=C(Cn1nc(C(F)F)c2c1C(F)(F)[C@@H]1C[C@H]21)N[C@@H](Cc1cc(F)cc(F)c1)c1nc2c(Cl)c[nH]c2cc1Br]

To a solution of N—((S)-1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (34.7 mg, 0.058 mmol) (Int DF6f.1) in distilled THF (4 mL) was added NCS (10 mg, 0.075 mmol). The reaction was heated at 70° C. for 18h and the solvent was removed under a gentle stream of nitrogen to give the title compound, 36.7 mg, that was used "as is" in subsequent reaction(s). LC/MS m/z=632.1, 634.1 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.47 min.

N—((S)-1-(3-chloro-6-(4-chloro-1-methyl-3-(methylsulfonamido)-1H-indazol-7-yl)-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 89) and Example 88

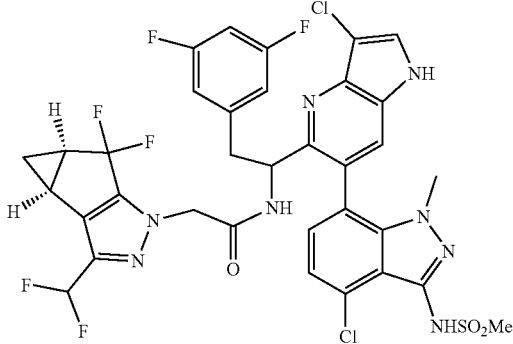

Example 88
Mix of two stereoisomers

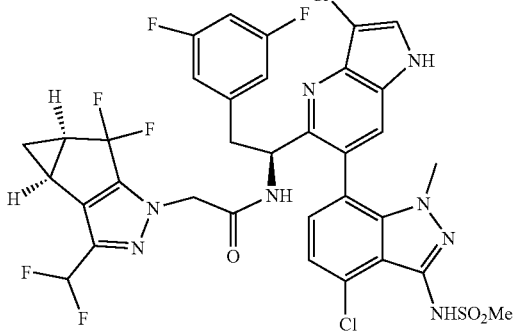

Example 89
A mixture of indicated isomer
and a stereoisomer

To a reaction vial under nitrogen was added N—((S)-1-(6-bromo-3-chloro-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF113a) (36 mg, 0.057 mmol), N-(4-chloro-1-methyl-7-(4,4,5,5-tetramethyl-1,3,2-dioxaborolan-2-yl)-1H-indazol-3-yl)methanesulfonamide (71 mg, 0.184 mmol), degassed dioxane (6 mL) and sodium carbonate 2 M in water (0.22 mL, 0.440 mmol). The reaction was treated with tetrakis(triphenylphosphine) palladium(0) (5 mg, 4.33 µmol), flushed with argon, and heated at 132° C. for 5.25 h. The reaction was diluted with ethyl acetate (15 mL) and the organic layer was washed with brine (10 mL), dried over Na2SO4, filtered thru 0.45 micron frit, evaporated to dryness under a gentle stream of nitrogen and the crude product was purified via preparative LC/MS to afford two elutes.

Example 88: First Eluting Peak, 3.5 mg

LC/MS m/z=811.0 (M+H)+. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.06 min.

Example 89: Second Eluting Peak, 7.8 mg

LC/MS m/z=811.0 (M+H)+. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.13 min.

N—((S)-1-(6-(4-chloro-3-(methylsulfonamido)-1H-indazol-7-yl)-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 90)

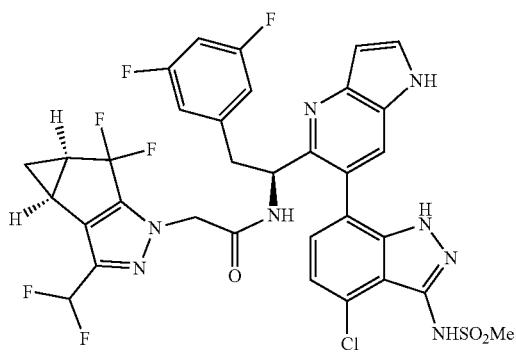

To a reaction vial under nitrogen was added N—((S)-1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (32.4 mg, 0.054 mmol) (Int DF6f.1), N-(4-chloro-7-(4,4,5,5-tetramethyl-1,3,2-dioxaborolan-2-yl)-1H-indazol-3-yl)methanesulfonamide (Int 17d, 62 mg, 0.167 mmol), degassed (argon) Dioxane (4 mL) and sodium carbonate 2 M in water (0.2 mL, 0.400 mmol). The reaction was treated with tetrakis(triphenylphosphine)palladium(0) (5 mg, 4.33 mol), flushed with argon and heated at 132° C. for 18h. The solvent was removed under a gentle stream of nitrogen, the residue was diluted with ethyl acetate (15 mL) and the organic layer was washed with brine (10 mL), dried over Na2SO4, and filtered thru 0.45 uM frit. The solvent was removed under a gentle stream of nitrogen and the crude product was purified via preparative LC/MS to afford the title compound, 15.4 mg. LC/MS m/z=763.0.0 (M+H)+. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.9 min.

N—((R)-1-(5-bromo-1-(mesitylsulfonyl)-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int DF116a)

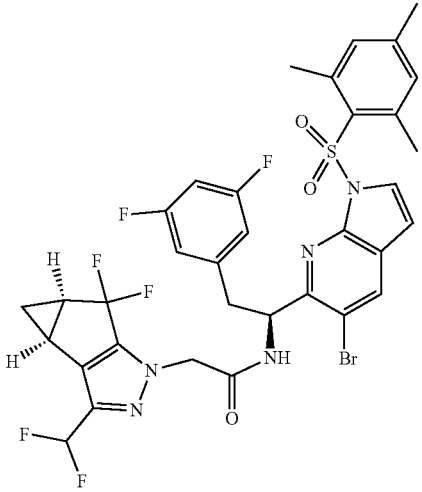 [SMILES: Cc1cc(C)c(S(=O)(=O)n2ccc3cc(Br)c([C@H](Cc4cc(F)cc(F)c4)NC(=O)Cn4nc(C(F)F)c5c4C(F)(F)[C@@H]4C[C@H]54)nc32)c(C)c1]

To a magnetically stirred solution of N—((S)-1-(5-bromo-1H-pyrrolo[2,3-b]pyridin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (22 mg, 0.037 mmol) (Int DF11a) and DMAP (5.3 mg, 0.043 mmol) in distilled THF (5 mL) under a continuous argon flush was added potassium tert-butoxide 1 M in THF (150 μL, 0.150 mmol). The reaction was stirred cold for 1 min, treated with solid 2,4,6-trimethylbenzenesulfonyl chloride (12.4 mg, 0.057 mmol) and stirred cold for 10 min while concentrating the reaction to a volume of ~2 mL. The reaction was capped, allowed to warm to room temp over 10 min, evaporated to almost dryness under a gentle stream of nitrogen and stored at −20° C. for 18. The solvent was removed under a gentle stream of argon and the solid residue was treated with dioxane (3 mL), followed by acetic acid (7 μL, 0.122 mmol) to afford the title compound, 28 mg, that was used "as is" without further purification in subsequent step(s). LC/MS m/z=802.2, 804.2 (M+Na). Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.72 min.

N-(4-chloro-1-(2,2-difluoroethyl)-7-(4,4,5,5-tetramethyl-1,3,2-dioxaborolan-2-yl)-1H-indazol-3-yl)methanesulfonamide (Int DF117a)

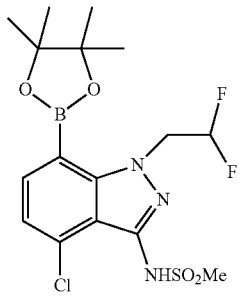

To a dry vial under a continuous argon flush was added N-(4-chloro-7-(4,4,5,5-tetramethyl-1,3,2-dioxaborolan-2-yl)-1H-indazol-3-yl)methanesulfonamide (ELS-90-Target 2, 87.4 mg, 0.235 mmol), distilled THF (4 mL) and potassium-tert-butoxide, 1 M in THF (0.23 mL, 0.230 mmol) slowly over 1 min. The reaction was stirred at room temp for 2 min, then treated with TIPS-Cl (55 µL, 0.260 mmol) and allowed to stir at room temp for 55 min. The reaction was treated with additional potassium-tert-butoxide, 1.0 M in THF (0.25 mL, 0.250 mmol), stirred for 1 min, treated with 2,2-difluoroethyl trifluoromethanesulfonate (54 mg, 0.252 mmol) and stirred at room temp for 53 min. The reaction was cooled under a continuous argon flush, treated with acetic acid (10 µL, 0.175 mmol), the solvent was removed under a gentle stream of nitrogen and the crude material was purified via silica gel chromatography (24 g SiO$_2$ column, 0-100% ethyl acetate:dichloromethane) to afford the title compound, 23 mg. LC/MS m/z=436, 438 (M+H)$^+$; Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 5 min, then a 2.0 min hold at 100% B; Flow: 0.8 mL/min; Detection: UV (220 nm); Retention Time: 3.28 min. $^1$H NMR (500 MHz, CHLOROFORM-d) δ 7.90 (d, J=7.6 Hz, 1H), 7.41 (br s, 1H), 7.14 (d, J=7.6 Hz, 1H), 6.23-5.94 (m, 1H), 5.24 (td, J=13.2, 4.4 Hz, 2H), 3.42 (s, 3H), 1.42 (s, 12H)

N-((S)-1-(6-(4-chloro-1-(2,2-difluoroethyl)-3-(methylsulfonamido)-1H-indazol-7-yl)-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 91)

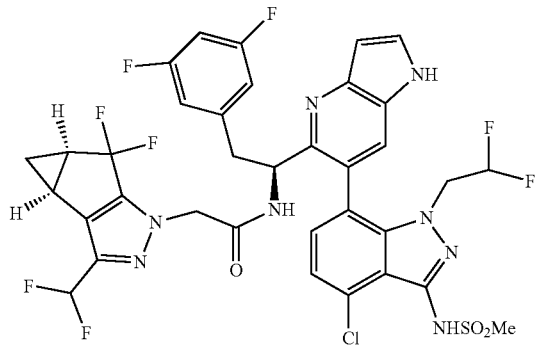

To a dry reaction vial under nitrogen was added N—((S)-1-(6-bromo-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (19.2 mg, 0.032 mmol) (Int DF6f.1), N-(4-chloro-1-(2,2-difluoroethyl)-7-(4,4,5,5-tetramethyl-1,3,2-dioxaborolan-2-yl)-1H-indazol-3-yl)methanesulfonamide (18 mg, 0.041 mmol) (Int DF117a) and degassed (argon) dioxane (4 mL). The reaction was treated with sodium carbonate 2 M in water (0.1 mL, 0.200 mmol), tetrakis(triphenylphosphine)palladium(0) (4 mg, 3.46 mol), flushed with argon again, and heated at 132° C. for 18h. The reaction was diluted with ethyl acetate (20 mL) and the organic layer was washed with water (5 mL) and brine (10 mL). The aqueous layer was back extracted with ethyl acetate (15 mL), the organic layers were dried over Na2SO4, filtered, evaporated to dryness and the crude material was purified via preparative LC/MS to afford the title compound, 1.6 mg. LC/MS m/z=827.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.07, 2.11 min.

tert-butyl 2-(4-chloro-3-(methylsulfonamido)-7-(4,4,5,5-tetramethyl-1,3,2-dioxaborolan-2-yl)-1H-indazol-1-yl)acetate (Int DF118a)

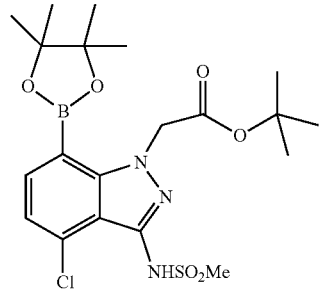

To a solution of N-(4-chloro-7-(4,4,5,5-tetramethyl-1,3,2-dioxaborolan-2-yl)-1H-indazol-3-yl)methanesulfonamide (ELS-90-Target 2, 400 mg, 1.076 mmol) in distilled THF (17 mL) under a continuous argon flow (serves to cool the reaction slightly) was added potassium-tert-butoxide, 1 M in THF (1.08 mL, 1.080 mmol) slowly over 1 min. The reaction was stirred for 2 min, treated with TIPS-Cl (0.25 mL, 1.180 mmol) and stirred at room temp for 52 min. The reaction was again cooled slightly under a continuous argon flow, treated with potassium-tert-butoxide, 1 M in THF (1.08 mL, 1.080 mmol), stirred for 1 min, then treated with tert-butyl 2-bromoacetate (162 µL, 1.097 mmol). The reaction was stirred at room temp for 30 min, cooled to −78° C., quenched with acetic acid (40 µL, 0.699 mmol), the solvent was removed under a gentle stream of nitrogen and the crude material was purified via silica gel chromatography (80 g SiO$_2$ column, 0-100% ethyl acetate:dichloromethane) to afford the title compound, 320 mg. LC/MS m/z=486.2, 488.2 (M+H)+; Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.8 min.

$^1$H NMR (500 MHz, CDCl$_3$) δ 7.88 (d, J=7.6 Hz, 1H), 7.35 (s, 1H), 7.12 (d, J=7.5 Hz, 1H), 5.56 (s, 2H), 3.37 (s, 3H), 1.405 (s, 9H), 1.395 (s, 12H).

tert-butyl (S)-(1-(6-(4-chloro-1-(2,2-difluoroethyl)-3-(methylsulfonamido)-1H-indazol-7-yl)-1-((2-(trimethylsilyl)ethoxy)methyl)-1H-pyrazolo[4,3-b]pyridin-5-yl)-2-(3,5-difluorophenyl)ethyl)carbamate (Int DF120a)

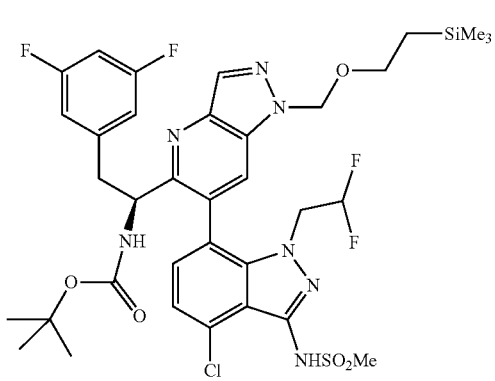

To a dry reaction vial under nitrogen was added tert-butyl (S)-(1-(6-bromo-1-((2-(trimethylsilyl)ethoxy)methyl)-1H-pyrazolo[4,3-b]pyridin-5-yl)-2-(3,5-difluorophenyl)ethyl)carbamate (Int 7a, 159 mg, 0.273 mmol), N-(4-chloro-1-(2,2-difluoroethyl)-7-(4,4,5,5-tetramethyl-1,3,2-dioxaborolan-2-yl)-1H-indazol-3-yl)methanesulfonamide (170 mg, 0.390 mmol) (Int DF117a) and degassed (argon) dioxane (4 mL). The reaction was flushed with argon, treated sodium carbonate, 2 M in water (0.6 mL, 1.200 mmol), tetrakis(triphenylphosphine)palladium(0) (15 mg, 0.013 mmol), flushed with argon again, and heated at 132° C. for 24h. The reaction was diluted with ethyl acetate (20 mL) and the organic layer was washed with water (1×5 mL) and brine (1×10 mL). The aqueous layers were back extracted with ethyl acetate (15 mL), the organic layers were combined, dried over Na2SO4, filtered, evaporated to dryness and the crude residue was purified via silica gel chromatography (80 g SiO$_2$ column, 0-100% ethyl acetate:dichloromethane) to afford the title compound, 140 mg. LC/MS m/z=756.3, 758.3 (M-55). Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 2.03 min.

(S)—N-(7-(5-(1-amino-2-(3,5-difluorophenyl)ethyl)-1H-pyrazolo[4,3-b]pyridin-6-yl)-4-chloro-1-(2,2-difluoroethyl)-1H-indazol-3-yl)methanesulfonamide (Int DF120b)

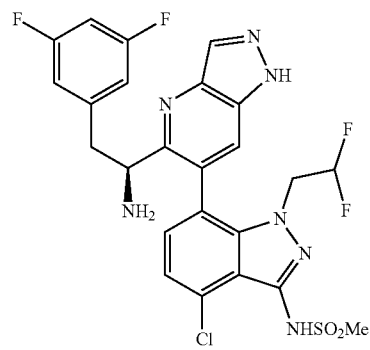

To a cold solution of tert-butyl (S)-(1-(6-(4-chloro-1-(2,2-difluoroethyl)-3-(methylsulfonamido)-1H-indazol-7-yl)-1-((2-(trimethylsilyl)ethoxy)methyl)-1H-pyrazolo[4,3-b]pyridin-5-yl)-2-(3,5-difluorophenyl)ethyl)carbamate (140 mg, 0.172 mmol) (Int DF120a) in dichloromethane (3 mL) was added HCl, 4 M in dioxane (1.5 mL, 6.00 mmol). The reaction was allowed to stand at room temp for 30 min, then treated with additional HC, 4 M in dioxane (0.8 mL, 3.2 mmol) and allowed to stand at room temp for 18h. The volatiles were removed under a gentle stream of nitrogen while warming to 70° C. and the residue was suspended in dichloromethane (4 mL). The solvent was removed under a gentle stream of nitrogen to give the title compound, 127 mg, as a stereoisomer mixture. LC/MS m/z=582.1, 584.1 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 0.5 min hold at 100% B; Flow: 0.8 mL/min; Detection: UV (220 nm); Retention Time: 1.01, 1.07 min.

N—((S)-1-(6-(4-chloro-1-(2,2-difluoroethyl)-3-(methylsulfonamido)-1H-indazol-7-yl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 93) and Example 92

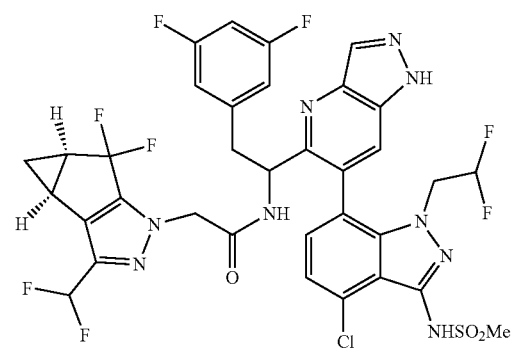

Example DF120
Mix of two stereoisomers

291
-continued

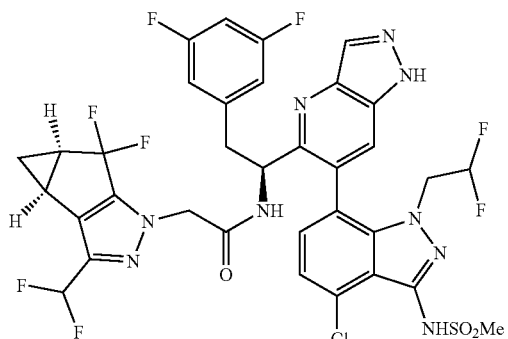

Example DF121
A mixture of indicated
isomer and a stereoisomer

To a dry reaction vial under nitrogen was added (S)—N-(7-(5-(1-amino-2-(3,5-difluorophenyl)ethyl)-1H-pyrazolo[4,3-b]pyridin-6-yl)-4-chloro-1-(2,2-difluoroethyl)-1H-indazol-3-yl)methanesulfonamide (46 mg, 0.079 mmol) (Int DF120b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (24 mg, 0.091 mmol), 1-hydroxy-7-azabenzotriazole (5.1 mg, 0.037 mmol) and DMF (1.5 mL). The reaction was flushed with nitrogen, treated with N-methylmorpholine (90 µl, 0.819 mmol), EDC (16.8 mg, 0.088 mmol) and allowed to stand at room temp for 2h. The solvent was removed under a gentle stream of nitrogen, the residue was dissolved in dichloromethane (2 mL), evaporated to dryness, treated with TFA (3 mL) and the reaction was allowed to stand at room temp for 40 min. The solvent was removed under a gentle stream of nitrogen, the residue was redissolved in 7 M $NH_3$/MeOH (5 mL) and the reaction was heated at 70° C. for 25 min. The solvent was removed and the crude residue was purified via preparative HPLC to retrieve two fractions, each as a mixture of stereoisomer but where one was dominant.

Example 92: First Eluting Peak, 6.8 mg

LC/MS m/z=828.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.94 min.

Example 93: Second Eluting Peak, 13.1 mg

LC/MS m/z=828.0 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.99 min.

N-(4-chloro-7-(4,4,5,5-tetramethyl-1,3,2-dioxaborolan-2-yl)-1-(2,2,2-trifluoroethyl)-1H-indazol-3-yl)methanesulfonamide (Int DF125a)

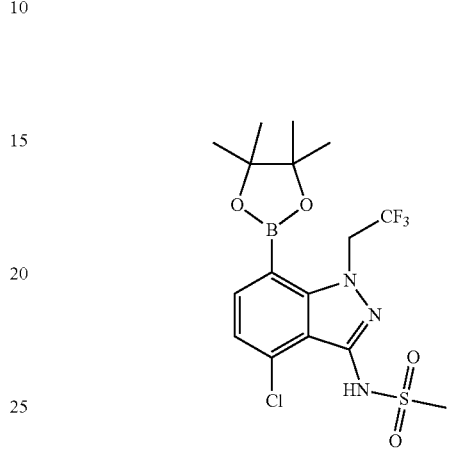

To a dry 100 mL round bottom flask under nitrogen was added N-(4-chloro-7-(4,4,5,5-tetramethyl-1,3,2-dioxaborolan-2-yl)-1H-indazol-3-yl)methanesulfonamide (ELS-90-target 2, 1.0 g, 2.69 mmol) and distilled THF (45 mL). The reaction was flushed under a continuous stream of argon (reaction gets cold), treated with potassium tert-butoxide, 1.0M in THF (2.70 mL, 2.70 mmol) over 90 seconds, stirred under a continuous argon stream for 2 min, treated with TIPS-Cl (625 µL, 2.95 mmol) and stirred at room temp for 1 h. The reaction was treated with additional potassium tert-butoxide, 1.0M in THF (2.70 mL, 2.70 mmol) over 90 seconds while maintaining an argon flush, capped, treated with 2,2,2-trifluoroethyl trifluoromethanesulfonate (640 mg, 2.76 mmol) and stirred at room temp for 22 min. The reaction was monitored by LC/MS and additional 2,2,2-trifluoroethyl trifluoromethanesulfonate was added in small portions until the reaction was judged to be complete. The solvent was evaporated off under a gentle stream of nitrogen, the residue was diluted with saturated aqueous $NH_4Cl$ (60 mL) and ethyl acetate (400 mL), the organic layer was extracted with water (1×25 mL), brine (1×25 mL), dried over $Na_2SO_4$, filtered, evaporated to dryness and the crude material was purified via silica gel chromatography (80 g $SiO_2$ column, 0-100% ethyl acetate:dichloromethane) to afford the title compound, 640 mg. LC/MS m/z=454.1, 456.1 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.96 min. $^1$H NMR (500 MHz, CDCl3) δ 7.95 (d, J=7.6 Hz, 1H), 7.46 (s, 1H), 7.16 (d, J=7.6 Hz, 1H), 5.63 (q, J=8.5 Hz, 2H), 3.44 (s, 3H), 1.41 (s, 12H).

tert-butyl (S)-(1-(6-(4-chloro-3-(methylsulfona-mido)-1-(2,2,2-trifluoroethyl)-1H-indazol-7-yl)-1-((2-(trimethylsilyl)ethoxy)methyl)-1H-pyrazolo[4,3-b]pyridin-5-yl)-2-(3,5-difluorophenyl)ethyl) carbamate (Int DF125b)

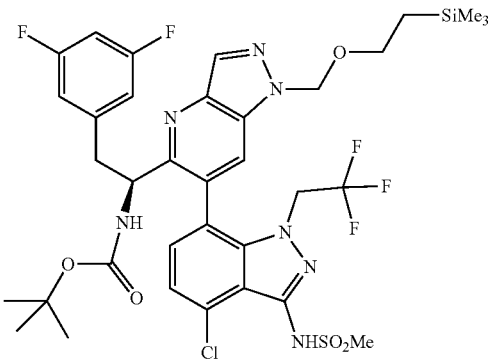

To a dry reaction vial under n2 was added tert-butyl (S)-(1-(6-bromo-1-((2-(trimethylsilyl)ethoxy)methyl)-1H-pyrazolo[4,3-b]pyridin-5-yl)-2-(3,5-difluorophenyl)ethyl) carbamate (Int 7a, 101 mg, 0.173 mmol) and N-(4-chloro-7-(4,4,5,5-tetramethyl-1,3,2-dioxaborolan-2-yl)-1-(2,2,2-trifluoroethyl)-1H-indazol-3-yl)methanesulfonamide (115 mg, 0.253 mmol) (Int DF125a) and degassed (argon) dioxane (4 mL). The reaction was flushed with argon, treated with sodium carbonate 2 M in water (0.40 mL, 0.800 mmol), tetrakis(triphenylphosphine)palladium(0) (12 mg, 10.38 μmol), flushed with argon again, and heated at 132° C. for 24 h. The reaction was diluted with ethyl acetate (20 mL), the organic layer was washed with water (1×5 mL), brine (1×10 mL) and the water layers were back extracted with ethyl acetate (1×15 mL). The organic layers were combined, dried over Na2SO4, filtered, evaporated to dryness and the crude material was purified via silica gel chromatography (80 g SiO2 column, 0-100% ethyl acetate:dichloromethane) to afford the title compound, 125 mg. LC/MS m/z=830.3, 832.3 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 2.20 min.

(S)—N-(7-(5-(1-amino-2-(3,5-difluorophenyl)ethyl)-1H-pyrazolo[4,3-b]pyridin-6-yl)-4-chloro-1-(2,2,2-trifluoroethyl)-1H-indazol-3-yl)methanesulfonamide (Int DF125c)

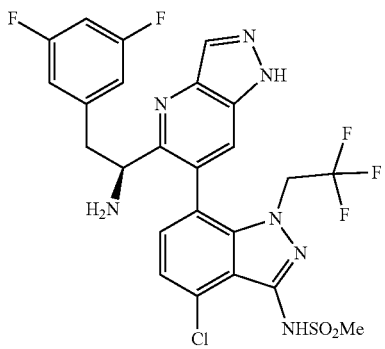

To a reaction vial containing was added tert-butyl (S)-(1-(6-(4-chloro-3-(methylsulfonamido)-1-(2,2,2-trifluoroethyl)-1H-indazol-7-yl)-1-((2-(trimethylsilyl)ethoxy)methyl)-1H-pyrazolo[4,3-b]pyridin-5-yl)-2-(3,5-difluorophenyl)ethyl)carbamate (125 mg, 0.151 mmol) (Int DF125b), neat TFA (5 mL) and the reaction was allowed to stand at room temp for 2 h. The volatiles were removed under a gentle stream of nitrogen, the residue was dissolved in ethyl acetate, the organic layer was washed sat aqueous NaHCO3, and brine, dried over Na2SO4, filtered and concentrated to give the title compound, 90 mg, that was used "as is" in subsequent reaction(s). LC/MS m/z=600.1 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.07 min.

N—((S)-1-(6-(4-chloro-3-(methylsulfonamido)-1-(2,2,2-trifluoroethyl)-1H-indazol-7-yl)-1H-pyrazolo[4,3-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 95) and Example 94

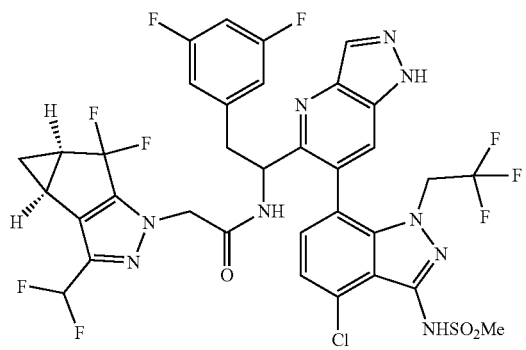

Example 94
Mix of two stereoisomers

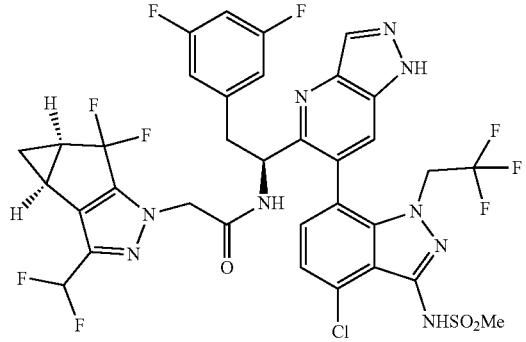

Example 95
A mixture of indicated isomer and a stereoisomer

To a solution of (S)—N-(7-(5-(1-amino-2-(3,5-difluorophenyl)ethyl)-1H-pyrazolo[4,3-b]pyridin-6-yl)-4-chloro-1-(2,2,2-trifluoroethyl)-1H-indazol-3-yl)methanesulfonamide (54 mg, 0.090 mmol) (Int DF125c) in dichloromethane (1.5 mL) and THF (1 mL) was added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (29 mg, 0.110 mmol), 1-hydroxy-7-azabenzotriazole (5.4 mg, 0.040 mmol), N-methylmorpholine (85 µl, 0.773 mmol) and finally EDC (21.8 mg, 0.114 mmol). The reaction was allowed to stand at room temp for 30 min, then the solvent was removed under a gentle stream of nitrogen. The residue was dissolved in DMF (1 mL), treated with N-methylmorpholie (90 µL), allowed to stand for 15 min at room temp and the crude material was purified via preparative LC/MS to afford two elutes.

Example 94: First Eluting Peak, 1.9 mg

LC/MS m/z=846.1 (M+H)$^+$. Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.94, 1.98 min.

Example 95: Second Eluting Peak, 7.2 mg

LC/MS m/z=846.0 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.98 min.

tert-butyl(S)-(1-(3-(4-chloro-1-(2,2-difluoroethyl)-3-(methylsulfonamido)-1H-indazol-7-yl)quinoxalin-2-yl)-2-(3,5-difluorophenyl)ethyl)carbamate (Int DF129a)

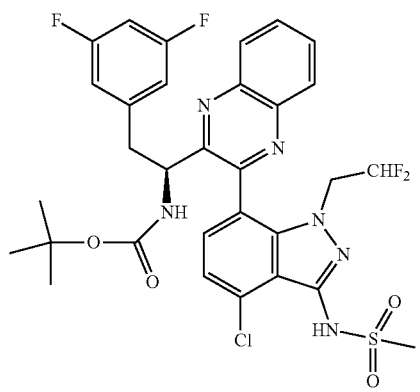 [SMILES: CC(C)(C)OC(=O)N[C@@H](Cc1cc(F)cc(F)c1)c1nc2ccccc2nc1-c1ccc(Cl)c2c(NS(C)(=O)=O)nn(CC(F)F)c12]

To a dry reaction vial under nitrogen was added tert-butyl (S)-(1-(3-bromoquinoxalin-2-yl)-2-(3,5-difluorophenyl)ethyl)carbamate (30 mg, 0.065 mmol) (Int JB1d), N-(4-chloro-1-(2,2-difluoroethyl)-7-(4,4,5,5-tetramethyl-1,3,2-dioxaborolan-2-yl)-1H-indazol-3-yl)methanesulfonamide (31.5 mg, 0.072 mmol) (Int DF117a) and degassed (argon) dioxane (3 mL). The reaction is flushed well with argon, treated sodium carbonate 2 M in water (0.18 mL, 0.360 mmol), tetrakis(triphenylphosphine)palladium(0) (5 mg, 4.33 µmol), flushed with argon again, and heated at 132° C. for 30 h. The reaction was partitioned with ethyl acetate (30 mL), water (10 mL) and the organic layer was washed with brine (1×5 mL). The water layers were back extracted with ethyl acetate (1×15 mL), the organic layers were combined, dried over Na2SO4, filtered and evaporated to dryness to give the title compound, 44 mg, that was used "as is" in subsequent reaction(s). LC/MS m/z=715.3, 717.3 (M+Na). Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.57 min.

(S)—N-(7-(3-(1-amino-2-(3,5-difluorophenyl)ethyl)quinoxalin-2-yl)-4-chloro-1-(2,2-difluoroethyl)-1H-indazol-3-yl)methanesulfonamide (Int DF129b)

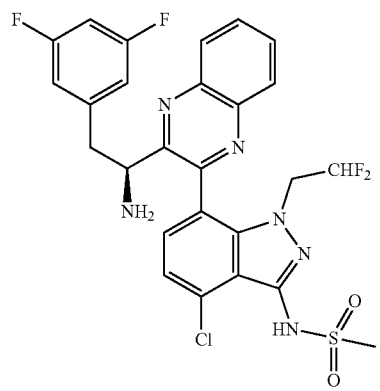 [SMILES: CS(=O)(=O)Nc1nn(CC(F)F)c2c(-c3nc4ccccc4nc3[C@@H](N)Cc3cc(F)cc(F)c3)ccc(Cl)c12]

To a dry vial containing tert-butyl (S)-(1-(3-(4-chloro-1-(2,2-difluoroethyl)-3-(methylsulfonamido)-1H-indazol-7-yl)quinoxalin-2-yl)-2-(3,5-difluorophenyl)ethyl)carbamate (44 mg, 0.063 mmol) (Int DF129a) was added TFA (8 mL). The reaction was allowed to stand at room temp for 75 min, then the volatiles were removed under a gentle stream of nitrogen. The residue was dissolved in ethyl acetate (30 mL) and the organic layer was washed with saturated aqueous NaHCO3 (1×20 mL), and brine (1×5 mL). The water layers were back extracted with ethyl acetate (1×10 mL), the organic layers were combined, dried over na2SO4, filtered and evaporated to dryness to afford the title compound, 37 mg, that was used "as is" without further purification in subsequent reaction(s). LC/MS m/z=593.2 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.18 min.

N—((S)-1-(3-(4-chloro-1-(2,2-difluoroethyl)-3-(methylsulfonamido)-1H-indazol-7-yl)quinoxalin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 96)

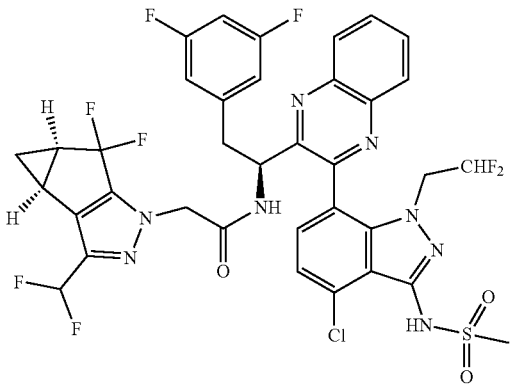 [SMILES: CS(=O)(=O)Nc1nn(CC(F)F)c2c(-c3nc4ccccc4nc3[C@H](Cc3cc(F)cc(F)c3)NC(=O)Cn3nc(C(F)F)c4c3C(F)(F)[C@@H]3C[C@H]43)ccc(Cl)c12]

To a dry reaction vial under nitrogen was added (S)—N-(7-(3-(1-amino-2-(3,5-difluorophenyl)ethyl)quinoxalin-2-yl)-4-chloro-1-(2,2-difluoroethyl)-1H-indazol-3-yl)methanesulfonamide (35 mg, 0.059 mmol) (Int DF129b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetic acid (18 mg, 0.068 mmol), 1-hydroxy-7-azabenzotriazole (6 mg, 0.044 mmol) and DMF (1 mL). The reaction was flushed with nitrogen, treated with N-methylmorpholine (70 µl, 0.637 mmol), EDC (13 mg, 0.068 mmol), allowed to stand at room temp for 1.5 h, and the crude reaction was purified via preparative HPLC to afford the title compound, 28.8 mg. LC/MS m/z=839.1 (M+H)⁺. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.2 min.

tert-butyl (1-(3-(4-chloro-3-(N-(4-methoxybenzyl)methylsulfonamido)-1-methyl-1H-indazol-7-yl)-8-methyl-4-oxo-3,4-dihydroquinazolin-2-yl)-2-(3,5-difluorophenyl)ethyl)carbamate (Int DF130a)

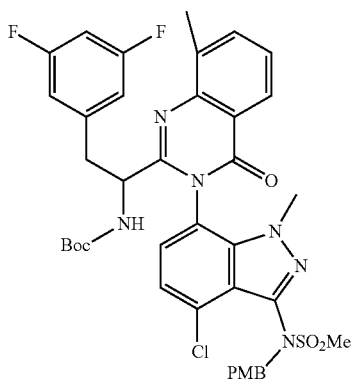

To a dry reaction vial under nitrogen was added (S)-2-((tert-butoxycarbonyl)amino)-3-(3,5-difluorophenyl)propanoic acid (100 mg, 0.332 mmol), 2-amino-3-methylbenzoic acid (51 mg, 0.337 mmol) and anhydrous pyridine (1.7 mL). The reaction was flushed with argon, treated with diphenyl phosphite (225 µl, 1.163 mmol), flushed with argon again and heated at 80° C. for 85 min. The reaction was then treated with N-(7-amino-4-chloro-1-methyl-1H-indazol-3-yl)-N-(4-methoxybenzyl)methanesulfonamide (Int 17d, 140 mg, 0.355 mmol) and heated at 80° C. for 5 h. The solvent was removed under a gentle stream of nitrogen while warming slightly and the crude material was purified via silica gel chromatography (80 g SiO₂ column, 0-100% ethyl acetate:hexanes) to afford the title compound, 163 mg. LC/MS m/z=793.3 (M+H)⁺. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.72 min.

(S)—N-(7-(2-(1-amino-2-(3,5-difluorophenyl)ethyl)-8-methyl-4-oxoquinazolin-3(4H)-yl)-4-chloro-1-methyl-1H-indazol-3-yl)methanesulfonamide (Int DF130b)

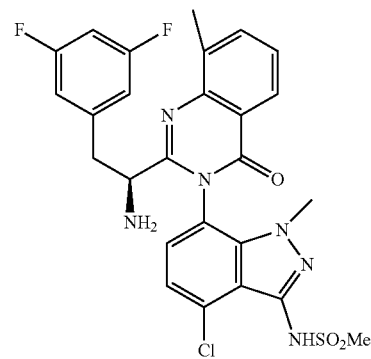

To a reaction vial containing tert-butyl (S)-(1-(3-(4-chloro-3-(N-(4-methoxybenzyl)methylsulfonamido)-1-methyl-1H-indazol-7-yl)-8-methyl-4-oxo-3,4-dihydroquinazolin-2-yl)-2-(3,5-difluorophenyl)ethyl)carbamate (163 mg, 0.205 mmol) (Int DF130a) and dichloromethane (3 mL) under argon was treated with TFA (6 mL) and the reaction was allowed to stand at room temp for 5 min. The reaction was treated with triflic acid (60 µL, 0.676 mmol), allowed to stand at room temp for 30 min and the volatiles were removed under a gentle stream of nitrogen. The residue was dissolved in ethyl acetate, the organic layer was washed with sat aqueous NaHCO3, brine and the water layers were back extracted with additional ethyl acetate. The organic layers were combined, dried over Na2SO4, filtered and evaporated to dryness to afford the title compound, 130 mg, as a stereoisomer mixture, that was used "as is" in subsequent reaction(s). LC/MS m/z=573.2, 575.2 (M+H)⁺. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.13, 1.19 min.

N—((S)-1-(3-(4-chloro-1-methyl-3-(methylsulfonamido)-1H-indazol-7-yl)-8-methyl-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 98) and Example 97

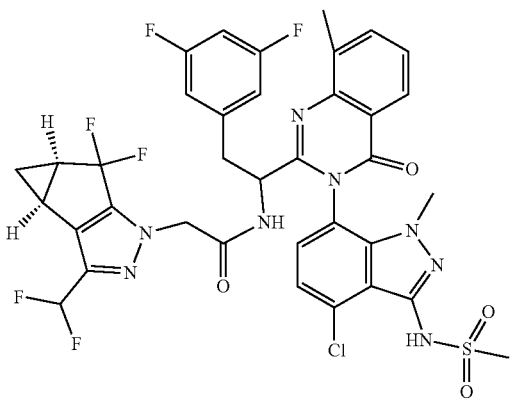

Example 97
Mix of two stereoisomers

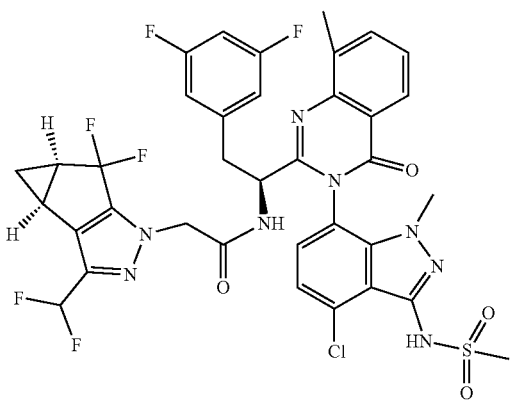

Example 98
A mixture of indicated isomer
and a stereoisomer

To a dry reaction vial under nitrogen was added (S)—N-(7-(2-(1-amino-2-(3,5-difluorophenyl)ethyl)-8-methyl-4-oxoquinazolin-3(4H)-yl)-4-chloro-1-methyl-1H-indazol-3-yl)methanesulfonamide (58 mg, 0.101 mmol) (Int DF130b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (30 mg, 0.114 mmol), 1-hydroxy-7-azabenzotriazole (7 mg, 0.051 mmol) and DMF (1 mL). The reaction was flushed with argon, treated with N-methylmorpholine (90 µl, 0.819 mmol), EDC (23 mg, 0.120 mmol), allowed to stir at room temp for 1.5 h and the crude reaction was purified via preparative HPLC to retrieve two fractions, each as a mixture of stereoisomers but where one stereoisomer dominates.

Example 97: First Eluting Peak, 13 mg

LC/MS m/z=819.1 (M+H)+. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.14 min.

Example 98: Second Eluting Peak, 30.4 mg

LC/MS m/z=819.1 (M+H)+. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.2 min. Analytical SCF chromatography indicates a single stereoisomer.
$^{19}$F NMR (471 MHz, DMSO-d$_6$) δ −79.59 (br d, J=253.2 Hz, 1F), −102.95 (br d, J=253.2 Hz, 1F), −110.16 (s, 2F), −110.38−−111.31 (d, 1F), −112.24−−113.18 (d, 1F).

(S)—N-(1-(3-(4-chloro-1-methyl-3-(methylsulfonamido)-1H-indazol-7-yl)-6,8-difluoro-4-oxo-3,4-dihydroquinazolin-2-yl)-2-(3,5-difluorophenyl)ethyl)-2-(3-(difluoromethyl)-5,6-dihydrocyclopenta[c]pyrazol-1(4H)-yl)acetamide (Example 100 and Example 99)

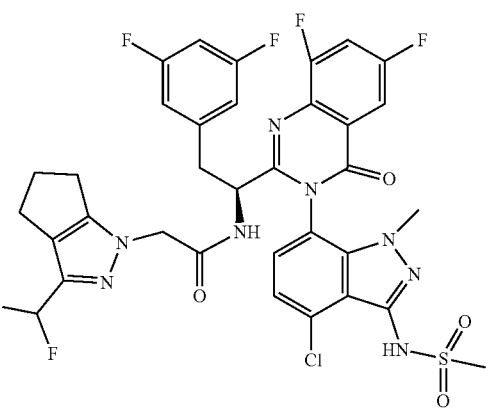

Example 99
Mix of enantiomers of unknown proportion

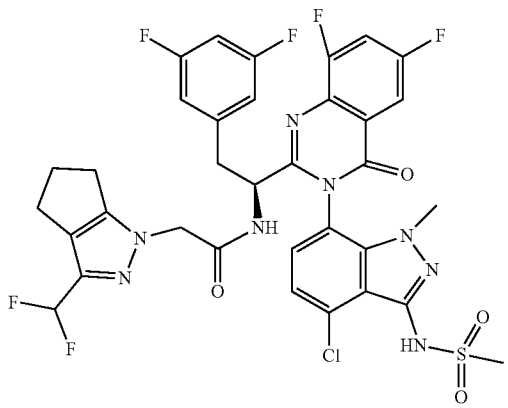

Example 100
Mix of enantiomers of unknown proportion

To a dry vial under nitrogen was added N-(7-amino-4-chloro-1-methyl-1H-indazol-3-yl)-N-(4-methoxybenzyl)methanesulfonamide (Int 17d, 50 mg, 0.127 mmol) and 800 □lit of the reaction solution from Int DF27a which contained N-(1-(6,8-difluoro-4-oxo-4H-benzo[d][1,3]oxazin-2-yl)-2-(3,5-difluorophenyl)ethyl)-2-(3-(difluoromethyl)-5,6-dihydrocyclopenta[c]pyrazol-1(4H)-yl)acetamide (60 mg, 0.112 mmol). The reaction was flushed briefly with argon, capped and heated at 80° C. for 5 h. The crude reaction was evaporated to dryness under a gentle stream of nitrogen while warming at 70° C., the residue was dissolved in dichloromethane (1 mL) and treated with TFA (2 mL). The reaction was allowed to stand at room temp for 5 min, then treated with triflic acid (90 μl, 1.014 mmol) and allowed to stand at room temp for 45 min. The solvent was removed under a gentle stream of nitrogen, and the residue was dissolved in a solution of N-methylmorpholine (120 μl, 1.091 mmol) in CH2CL2 (2 mL). The solvent was removed under a gentle stream of nitrogen and the crude reside was redissolved in DMF (1.2 mL) and purified via preparative HPLC to afford two elutes.

Example 99: First Eluting Peak, 10.4 mg

LC/MS m/z=793.1 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.05 min.

Example 100: Second Eluting Peak, 19.5 mg

LC/MS m/z=793.1 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.13 min.

N—((S)-1-(8-chloro-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 102) and Example DF101

Example 101

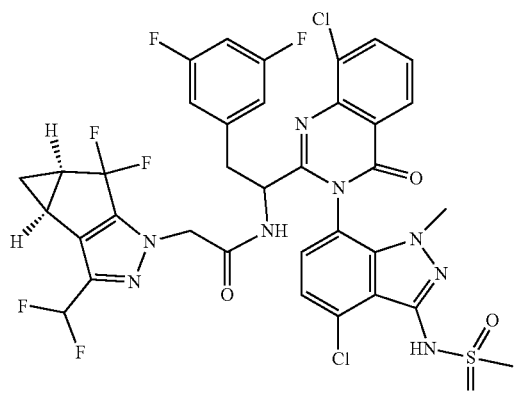

Mix of two stereoisomers

Example 102

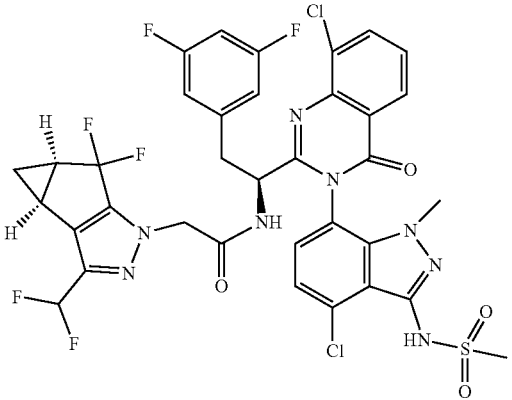

A mixture of indicated isomer and a stereoisomer

To a dry reaction vial under nitrogen was added (S)-2-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-3-(3,5-difluorophenyl)propanoic acid (47 mg, 0.105 mmol) (Int MS301b), 2-amino-3-chlorobenzoic acid (18.03 mg, 0.105 mmol) and anhydrous pyridine (0.8 mL). The reaction was flushed with argon, treated with diphenyl phosphite (73 μL, 0.377 mmol) and heated at 80° C. for 90 min. The reaction was treated with N-(7-amino-4-chloro-1-methyl-1H-indazol-3-yl)-N-(4-methoxybenzyl)methanesulfonamide (Int 17d, 50 mg, 0.127 mmol), heated at 80° C. for 12 h and the solvent was removed under a gentle stream of nitrogen while warming at 70° C. The residue was dissolved in dichloromethane (1.5 mL), evaporated to dryness, redissolved in dichloromethane (1 mL), treated with TFA (1.5 mL) and allowed to stand at room temp for 2 min. The reaction was then treated with triflic acid (60 μL, 0.676 mmol) and allowed to stand at room temp for 1.5 h. The reaction was treated with additional triflic acid (50 μL, 0.563 mmol), allowed to stand at room temp for 70 min and the volatiles were removed under a gentle stream of nitrogen. The residue was dissolved in dichloromethane (3 mL), treated with N-methylmorpholine (250 μL), evaporated to dryness and the crude residue was dissolved in DMF (1.5 mL) and purified via preparative HPLC to afford the title compound each as a mixture of stereoisomers but where one stereoisomer dominates, exhibiting targeted molecule weight.

Example 101: First Eluting Peak, 23.0 mg

LC/MS m/z=839.0 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.15 min.

Example 102: Second Eluting Peak, 26.2 mg

LC/MS m/z=839.0 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100%

B over 3 min, then a 0.75 min hold at 100% B; Flow: 1 mL/min; Detection: MS and UV (220 nm). Retention Time: 2.2 min.

N—((S)-1-(3-(4-chloro-1-methyl-3-(methylsulfonamido)-1H-indazol-7-yl)-8-methoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example DF104) and Example 103

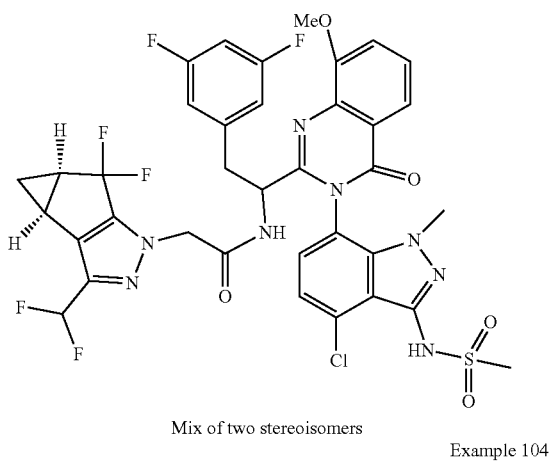

Mix of two stereoisomers

Example 103

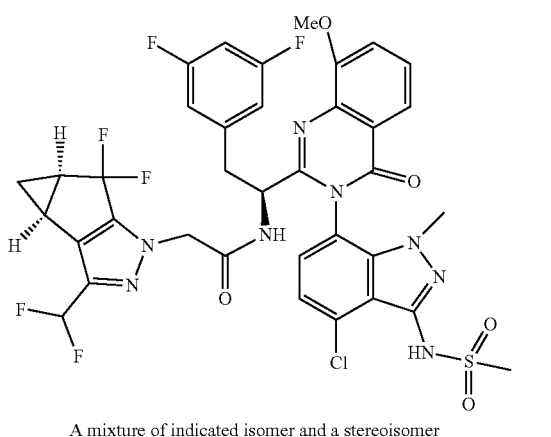

A mixture of indicated isomer and a stereoisomer

Example 104

To a dry reaction vial under nitrogen was added (S)-2-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-3-(3,5-difluorophenyl)propanoic acid (40 mg, 0.089 mmol) (Int MS301b), 2-amino-3-methoxybenzoic acid (18 mg, 0.108 mmol) and anhydrous Pyridine (0.8 mL). The reaction was flushed with argon, treated with diphenyl phosphite (73 µl, 0.377 mmol), and heated at 70-75° C. for 1.5 h. The reaction was treated with N-(7-amino-4-chloro-1-methyl-1H-indazol-3-yl)-N-(4-methoxybenzyl)methanesulfonamide (Int 17d, 45.6 mg, 0.115 mmol), heated at 70° C. for 18 h and the solvent was removed under a gentle stream of nitrogen while warming at 70° C. The reside was dissolved in dichloromethane (1 mL), treated with TFA (2 mL), allowed to stand at room temp for 5 min, treated with triflic acid (95 µl, 1.070 mmol) and allowed to stand at room temp for 20 min. The reaction was treated with additional triflic acid (50 µl, 0.563 mmol), allowed to stand at room temp for 1 h and the volatiles were removed under a gentle stream of nitrogen. The crude residue was treated with a solution of N-methylmorpholine (120 µl, 1.091 mmol) in CH₂CL2 (2 mL) and then the volatiles were again removed under a gentle stream of nitrogen. The crude residue was dissolved in DMF (1 mL) and the crude material was purified via preparative LC/MS to afford two elutes.

Example 103: First Eluting Peak, 14.8 mg

LC/MS m/z=835.1 (M+H)⁺. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.97 min.

Example 104: Second Eluting Peak, 23.2 mg

LC/MS m/z=835.1 (M+H)⁺. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.02 min.

3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazoline-8-carboxamide (Example 106) and Example 105

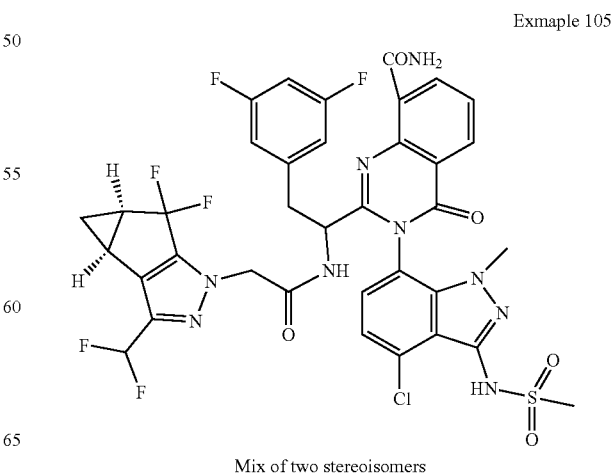

Exmaple 105

Mix of two stereoisomers

Example 106

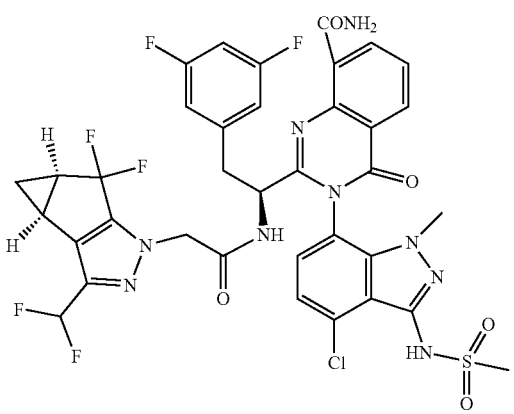

A mixture of indicated isomer and a stereoisomer

To a dry reaction vial under nitrogen was added (S)-2-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-3-(3,5-difluorophenyl)propanoic acid (68.7 mg, 0.154 mmol) (Int MS301b), 2-aminoisophthalic acid (28.7 mg, 0.158 mmol) and anhydrous Pyridine (1 mL). The reaction was flushed with argon, treated with diphenyl phosphite (105 µl, 0.543 mmol) and heated at 75-80° C. for 140 min. The reaction was treated with N-(7-amino-4-chloro-1-methyl-1H-indazol-3-yl)-N-(4-methoxybenzyl)methanesulfonamide (Int 17d, 62 mg, 0.157 mmol), heated at 70-75° C. for 18 h, and the solvent was removed under a gentle stream of nitrogen. The residue was dissolved in dichloromethane and one half of the solution (75 mg, 0.077 mmol) was evaporated to dryness. The residue was dissolved in distilled THF (2 mL), treated with 1-hydroxy-7-azabenzotriazole (15 mg, 0.110 mmol), EDC (40 mg, 0.209 mmol) ammonia, 2 M in i-PrOH (30 µl, 0.06 mmol) and the reaction was allowed to stir at room temp for 18 h. The reaction was treated with additional ammonia, 2 M in i-PrOH (100 µl, 0.2 mmol) and allowed to stir at room temp for 18h. The solvent was removed under a gentle stream of nitrogen while warming at 60° C., the residue was dissolved in dichloromethane (1.5 mL) and treated with TFA (3 mL), followed by triflic acid (160 µl, 1.802 mmol) and the reaction was allowed to stand at room temp for 90 min. The volatiles were removed under a gentle stream of nitrogen and the residue was partitioned with ethyl acetate vs aqueous NaHCO3. The organic layer was washed with brine, dried sodium sulfate, evaporated and the crude residue was dissolved in DMF (1 mL) and the crude material was purified via preparative LC/MS to afford two elutes.

Example 105: First Eluting Peak, 5.0 mg

LC/MS m/z=848.1 (M+H)+. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.82 min.

Example 106: Second Eluting Peak, 6.2 mg

LC/MS m/z=848.0 (M+H)+. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.87 min.

(S)—N-(7-(2-(1-amino-2-(3,5-difluorophenyl)ethyl)-5,8-dichloro-4-oxoquinazolin-3(4H)-yl)-4-chloro-1-methyl-1H-indazol-3-yl)methanesulfonamide (Int DF157a)

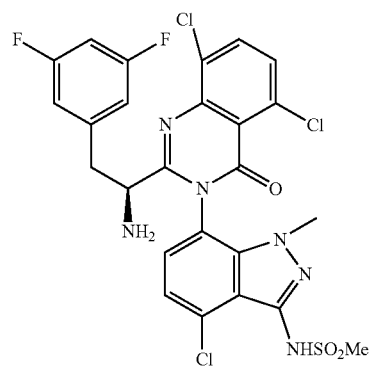

To a dry reaction vial under nitrogen was added (S)-2-((tert-butoxycarbonyl)amino)-3-(3,5-difluorophenyl)propanoic acid (45 mg, 0.149 mmol), 2-amino-3,6-dichlorobenzoic acid (31 mg, 0.150 mmol), N-(7-amino-4-chloro-1-methyl-1H-indazol-3-yl)-N-(4-methoxybenzyl)methanesulfonamide (Int 17d, 59 mg, 0.149 mmol) and anhydrous Pyridine (0.9 mL). The reaction was flushed with argon, treated with diphenyl phosphite (28.9 µL, 0.149 mmol) and heated at 70-75° C. for 40 h. The solvent was removed under a gentle stream of nitrogen while warming at 70° C. and the residue was dissolved in TFA (4 mL), treated with triflic acid (300 µL, 3.38 mmol) and allowed to stand at room temp for 1.75 h. The volatiles were removed under a gentle stream of nitrogen, the reside dissolved in dichloromethane (50 mL) and the reaction was treated with a mixture of saturated aqueous NaHCO3 and saturated aqueous Na2CO3 (50 mL). The reaction was further diluted with dichloromethane (50 mL) and the organic layer was washed with brine, dried over Na2SO4, filtered and evaporated to dryness to afford the title compound, 47 mg, that was used "as is" without further purification in subsequent reaction(s). LC/MS m/z=627.1, 629.1 (M+H)+. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.54 min.

307 tert-butyl (S)-(1-(3-(4-chloro-3-(N-(4-methoxybenzyl)methylsulfonamido)-1-methyl-1H-indazol-7-yl)-7-fluoro-8-methyl-4-oxo-3,4-dihydroquinazolin-2-yl)-2-(3,5-difluorophenyl)ethyl)carbamate (Int DF159a)

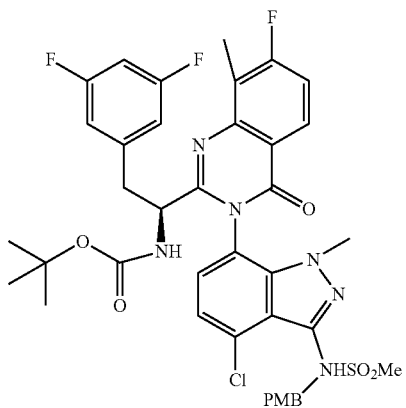

To a dry reaction vial under nitrogen was added (S)-2-((tert-butoxycarbonyl)amino)-3-(3,5-difluorophenyl)propanoic acid (45 mg, 0.149 mmol), 2-amino-4-fluoro-3-methylbenzoic acid (25.2 mg, 0.149 mmol) and anhydrous Pyridine (0.9 mL). The reaction was flushed with argon, treated with diphenyl phosphite (125 μL, 0.646 mmol) and heated at 75° C. for 80 min. The reaction was treated with N-(7-amino-4-chloro-1-methyl-1H-indazol-3-yl)-N-(4-methoxybenzyl)methanesulfonamide (Int 17d, 59 mg, 0.149 mmol) and heated at 75° C. for 18 h. The solvent was removed under a gentle stream of nitrogen and the crude material was purified via silica gel chromatography (80 g SiO₂ column, 0-100% ethyl acetate:hexanes) to afford the title compound, 120 mg. LC/MS m/z=755.3 (M-55); 833.3 (M+Na). Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.94 min.

(S)—N-(7-(2-(1-amino-2-(3,5-difluorophenyl)ethyl)-7-fluoro-8-methyl-4-oxoquinazolin-3(4H)-yl)-1,4-dimethyl-1H-indazol-3-yl)methanesulfonamide (Int DF159b)

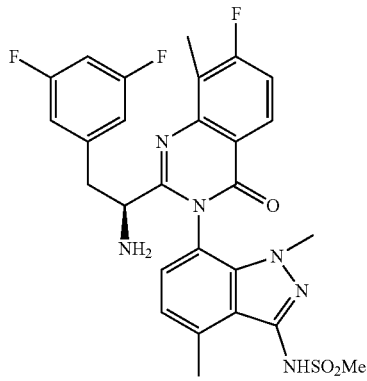

308

To a solution of tert-butyl (S)-(1-(3-(4-chloro-3-(N-(4-methoxybenzyl)methylsulfonamido)-1-methyl-1H-indazol-7-yl)-7-fluoro-8-methyl-4-oxo-3,4-dihydroquinazolin-2-yl)-2-(3,5-difluorophenyl)ethyl)carbamate (120 mg, 0.148 mmol) (Int DF159a) in TFA (8 mL) was added triflic acid (110 μl, 1.239 mmol) and the reaction was allowed to stand at room temp until judged to be complete by LC/MS. The solvent was removed under a gentle stream of nitrogen and the residue was taken up in dichloromethane (small amount) and added to aqueous sat Na2CO3 (50 mL). The reaction was diluted with ethyl acetate (75 mL), the organic layer was washed with water (1×10 mL) and brine (1×20 mL), dried over Na2SO4 and evaporated to dryness to give the title compound, 83 mg, as a mixture of stereoisomers. LC/MS m/z=591.2, 593.2 (M+H)⁺. Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.48, 1.55 min.

N—((S)-1-(3-(4-chloro-1-methyl-3-(methylsulfonamido)-1H-indazol-7-yl)-7-fluoro-8-methyl-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 108) and Example 107

Example 107

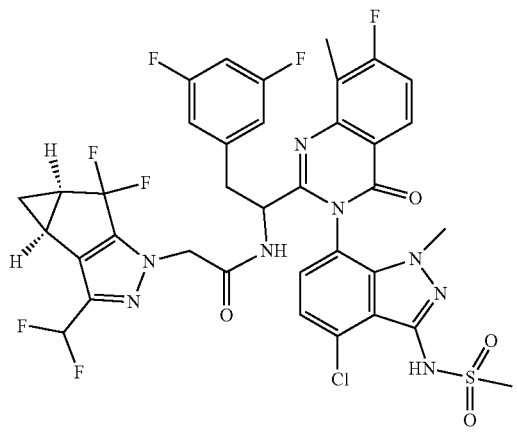

Mix of two stereoisomers

Example 108

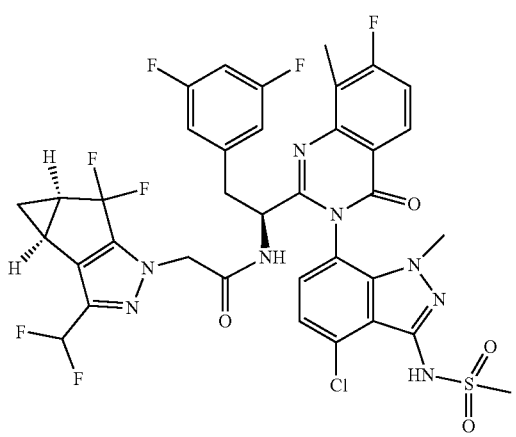

A mixture of indicated isomer and a stereoisomer

To a mixture of (S)—N-(7-(2-(1-amino-2-(3,5-difluorophenyl)ethyl)-7-fluoro-8-methyl-4-oxoquinazolin-3(4H)-yl)-4-chloro-1-methyl-1H-indazol-3-yl)methanesulfonamide (64.5 mg, 0.109 mmol) (Int DF159a), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (40 mg, 0.151 mmol), and 1-hydroxy-7-azabenzotriazole (6.2 mg, 0.046 mmol) in DMF (1 mL) under argon was added N-methylmorpholine (105 µL, 0.955 mmol) and EDC (34.5 mg, 0.180 mmol). The reaction was stirred at room temp for 75 min, treated with 7 M NH$_3$/MeOH (100 µL) and the crude reaction was purified via preparative LC/MS to afford two elutes.

Example 107: First Eluting Peak, 15.8 mg

LC/MS m/z=837.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.22 min.

Example 108: Second Eluting Peak, 29.0 mg

LC/MS m/z=837.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.28 min.

tert-butyl (S)-(1-(3-(4-chloro-3-(N-(4-methoxybenzyl)methylsulfonamido)-1-methyl-1H-indazol-7-yl)-7-fluoro-8-methoxy-4-oxo-3,4-dihydroquinazolin-2-yl)-2-(3,5-difluorophenyl)ethyl)carbamate (Int DF161a)

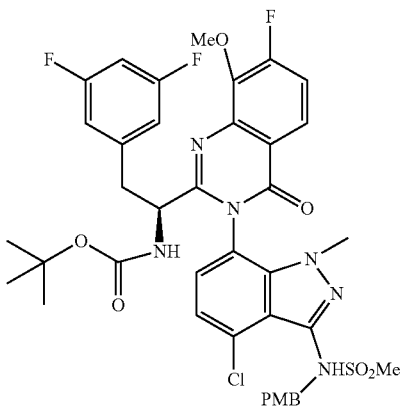

To a dry reaction vial under nitrogen was added (S)-2-((tert-butoxycarbonyl)amino)-3-(3,5-difluorophenyl)propanoic acid (100 mg, 0.332 mmol), 2-amino-4-fluoro-3-methoxybenzoic acid (62 mg, 0.335 mmol) and anhydrous pyridine (1.4 mL). The reaction was flushed with argon, treated with diphenyl phosphite (250 µL, 1.292 mmol) and heated at 75° C. for 100 min. The reaction was treated with N-(7-amino-4-chloro-1-methyl-1H-indazol-3-yl)-N-(4-methoxybenzyl)methanesulfonamide (Int 17d, 131 mg, 0.332 mmol) and heated at 75° C. for 18 h. The solvent was removed under a gentle stream of nitrogen and the crude material was purified via silica gel chromatography (80 g SiO$_2$ column, 0-100% ethyl acetate:hexanes) to afford the title compound, 250 mg. LC/MS m/z=771.2, 773.2 (M-55); 827.3 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.89 min.

(S)—N-(7-(2-(1-amino-2-(3,5-difluorophenyl)ethyl)-7-fluoro-8-methoxy-4-oxoquinazolin-3(4H)-yl)-4-chloro-1-methyl-1H-indazol-3-yl)methanesulfonamide (Int DF161b)

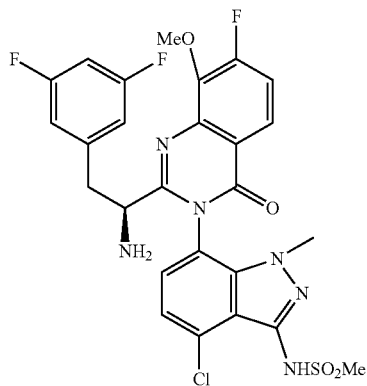

To a solution of tert-butyl (S)-(1-(3-(4-chloro-3-(N-(4-methoxybenzyl)methylsulfonamido)-1-methyl-1H-indazol-7-yl)-7-fluoro-8-methoxy-4-oxo-3,4-dihydroquinazolin-2- yl)-2-(3,5-difluorophenyl)ethyl)carbamate (250 mg, 0.302 mmol) (Int DF161a) in TFA (15 mL) was added triflic acid (350 μL, 3.94 mmol) and the reaction was allowed to stand at room temp for 15 min. The solvent was removed under a gentle stream of nitrogen and the residue was taken up in dichloromethane (small amount) and added to a mixture of sat aqueous NaHCO3 and sat K2CO3 (100 mL). The reaction was diluted with ethyl acetate (100 mL) and the organic layer was washed with water (1×10 mL) and brine (1×20 mL). The water layers were back extracted with ethyl acetate (1×50 mL), the organic layers were combined, dried over na2S)4, filtered and evaporated to dryness to afford the title compound, 148 mg, as a mixture of stereoisomers. LC/MS m/z=607.2, 609.2 (M+H)⁺. Column: Waters Aquity UPLC BEH C18, 2.1 mm×50 mm, 1.7 m particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.44, 1.52 min.

N—((S)-1-(3-(4-chloro-1-methyl-3-(methylsulfonamido)-1H-indazol-7-yl)-7-fluoro-8-methoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 110) and Example 109

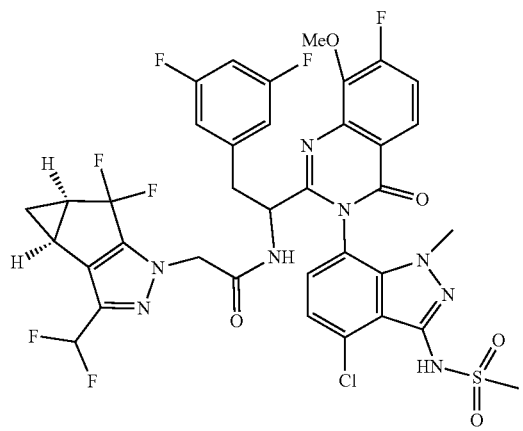

Example 109
Mix of two stereoisomers

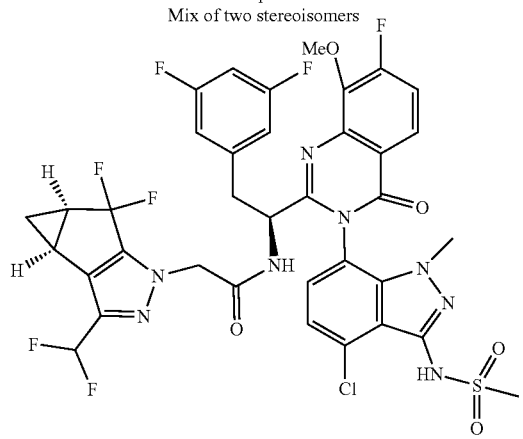

Example 110
A mixture of indicated isomer and a stereoisomer

To a mixture of (S)—N-(7-(2-(1-amino-2-(3,5-difluorophenyl)ethyl)-7-fluoro-8-methoxy-4-oxoquinazolin-3(4H)-yl)-4-chloro-1-methyl-1H-indazol-3-yl)methanesulfonamide (74 mg, 0.122 mmol) (Int DF161b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (36.8 mg, 0.139 mmol), and 1-hydroxy-7-azabenzotriazole (6.3 mg, 0.046 mmol) in DMF (1 mL) under argon was added N-methylmorpholine (115 μL, 1.046 mmol) and EDC (30 mg, 0.156 mmol). The reaction was stirred at room temp for 5 h, treated with 7 M NH₃/MeOH (100 μL) and the crude reaction was purified via preparative LC/MS to afford two elutes.

Example 109: First Eluting Peak, 11.7 mg

LC/MS m/z=853.1 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.1 min.

Example 110: Second Eluting Peak, 37.1 mg

LC/MS m/z=853.1 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.15 min.

(S)—N-(1-(3-(4-chloro-1-methyl-3-(methylsulfonamido)-1H-indazol-7-yl)-7-fluoro-8-methoxy-4-oxo-3,4-dihydroquinazolin-2-yl)-2-(3,5-difluorophenyl)ethyl)-2-(3-cyclopropyl-1H-pyrazol-1-yl)acetamide (Example 112 and Example 111)

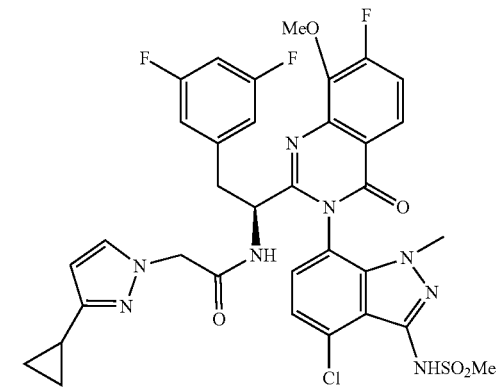

Example 111
Mix of enantiomers of unknown proportion

313

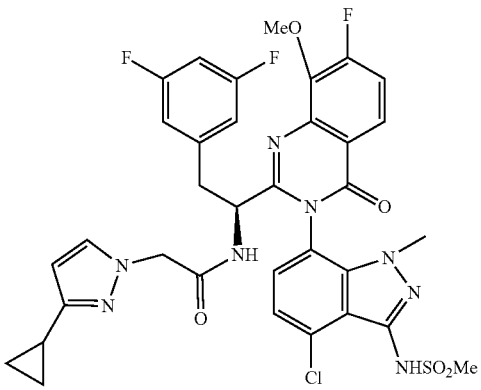

Example 112
Mix of enantiomers of
unknown proportion

To a mixture of (S)—N-(7-(2-(1-amino-2-(3,5-difluorophenyl)ethyl)-7-fluoro-8-methoxy-4-oxoquinazolin-3(4H)-yl)-4-chloro-1-methyl-1H-indazol-3-yl)methanesulfonamide (40 mg, 0.66 mmol) (Int DF161b), 2-(3-cyclopropyl-1H-pyrazol-1-yl)acetic acid (14 mg, 0.084 mmol), and 1-hydroxy-7-azabenzotriazole (4 mg, 0.029 mmol) in DMF (1 mL) was added N-methylmorpholine (80 µL, 0.728 mmol). The reaction was stirred at room temp for 18 h, treated with 7 M $NH_3$/MeOH (100 µL) and the crude reaction was purified via preparative LC/MS to afford two elutes.

Example 111: First Eluting Peak, 8.2 mg

LC/MS m/z=755.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 1.94 min.

Example 112: Second Eluting Peak, 16.2 mg

LC/MS m/z=755.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.05 min

314 tert-butyl (S)-(1-(3-(4-chloro-3-(N-(4-methoxybenzyl)methylsulfonamido)-1-methyl-1H-indazol-7-yl)-6,8-difluoro-7-methoxy-4-oxo-3,4-dihydroquinazolin-2-yl)-2-(3,5-difluorophenyl)ethyl)carbamate (Int DF192a)

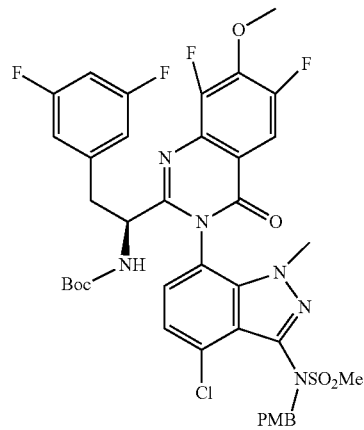

To a dry reaction vial under N2 was added 2-amino-3,5-difluoro-4-methoxybenzoic acid (107 mg, 0.527 mmol), (S)-2-((tert-butoxycarbonyl)amino)-3-(3,5-difluorophenyl)propanoic acid (159 mg, 0.527 mmol), N-(7-amino-4-chloro-1-methyl-1H-indazol-3-yl)-N-(4-methoxybenzyl)methanesulfonamide (208 mg, 0.527 mmol) and last anhydrous Pyridine (2 mL). The reaction was capped, flushed with argon, sonnicated for 15 sec. until all the solids dissolved and heated at 75-80° C. for 18 h. The solvent was removed under a gentle stream of N2 and the crude residue was purified via silica gel chromatography (80 g $SiO_2$ column, 0-100% ethyl acetate:dichloromethane) to afford the title compound, 253 mg. LC/MS m/z=789.2, 791.2 (M-55); 867.3, 869.4 (M+Na). Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 2.13 min.

(S)—N-(7-(2-(1-amino-2-(3,5-difluorophenyl)ethyl)-6,8-difluoro-7-methoxy-4-oxoquinazolin-3(4H)-yl)-4-chloro-1-methyl-1H-indazol-3-yl)methanesulfonamide (Int DF 192b)

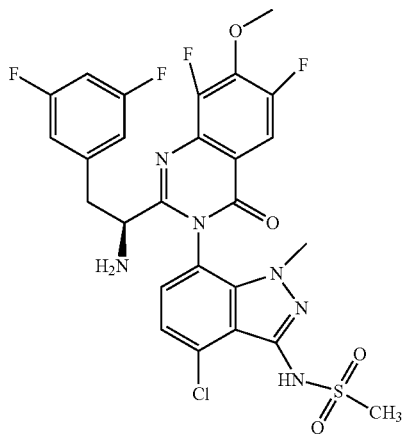 [SMILES: COc1c(F)cc2c(=O)n(-c3ccc(Cl)c4c(NS(C)(=O)=O)nn(C)c34)c([C@@H](N)Cc3cc(F)cc(F)c3)nc2c1F]

To a solution of tert-butyl (S)-(1-(3-(4-chloro-3-(N-(4-methoxybenzyl)methylsulfonamido)-1-methyl-1H-indazol-7-yl)-6,8-difluoro-7-methoxy-4-oxo-3,4-dihydroquinazolin-2-yl)-2-(3,5-difluorophenyl)ethyl)carbamate (253 mg, 0.299 mmol) (Int DF192a) in anhydrous dichloromethane (4 mL) was added TFA (8 mL, 104 mmol). The reaction was stirred at room temp for 5 min, treated with triflic acid (190 µL, 2.140 mmol) and allowed to stand at room temp for 20 min. The volatiles were removed under a gentle stream of nitrogen and the residue was suspended in dichloromethane (5 mL) and quenched with aqueous saturated sodium bicarbonate (10 mL). The reaction was diluted with ethyl acetate (80 mL) and the organic layer was washed with saturated aqueous sodium bicarbonate (1×10 mL) and brine (1×5 mL). The aqueous layers were back extracted with ethyl acetate (20 mL), the organic layers were combined, dried over sodium sulfate, filtered and evaporated to dryness to give the title compound, 291.6 mg, as a stereoisomer mixture. LC/MS m/z=625.2, 627.2 (M+H)+. Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.56 min.

Following the general procedure as described earlier in the patent, the compounds in the table below were prepared from Int DF192b and appropriate substrate: Note: LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm)

| Ex # | Structure | LC/MS ret. Time (min) | Obs MW (M + H)+ | Purity |
|---|---|---|---|---|
| 113 | 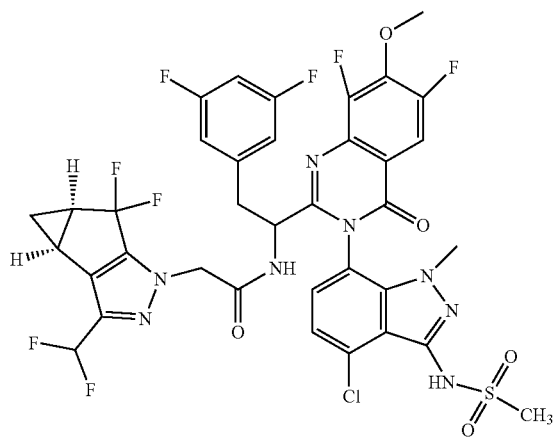<br>Mix of two stereoisomers | 2.34 | 871.1 | 97% |
| 114 | 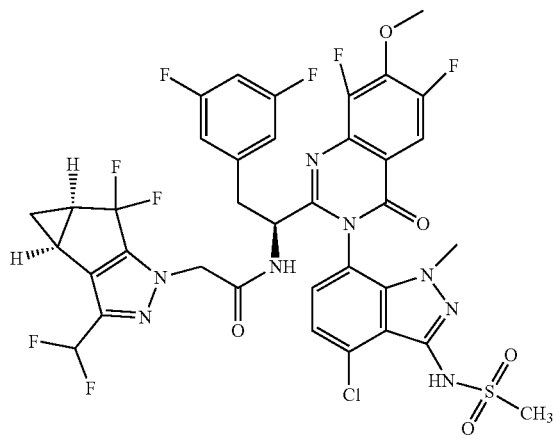<br>A mixture of indicated isomer and a stereoisomer | 2.38 | 871.1 | 98% |

| Ex # | Structure | LC/MS ret. Time (min) | Obs MW (M + H)+ | Purity |
|---|---|---|---|---|
| 115 | 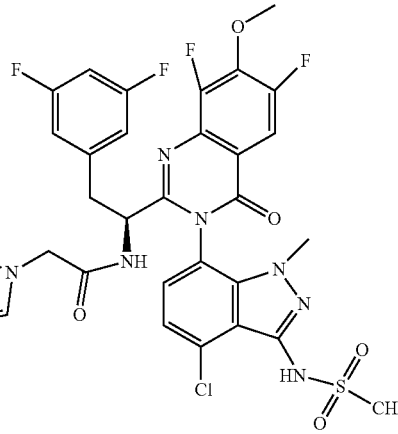<br>Mix of enantiomers of unknown proportion | 2.19 | 773.0 | 86% |
| 116 | 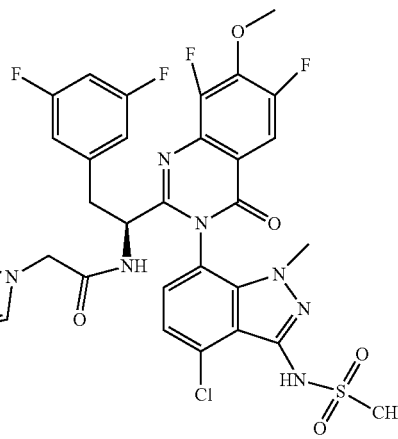<br>Mix of enantiomers of unknown proportion | 2.29 | 773.0 | 99% |

Methyl 6-bromo-1-methyl-1H-pyrrolo[3,2-b]pyridine-5-carboxylate (Int JD1a)

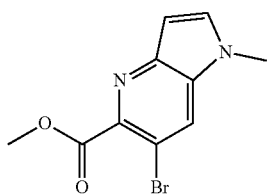

Within a round bottom flask fitted with a septum and equipped with a magnetic stirring bar was added methyl 6-bromo-1H-pyrrolo[3,2-b]pyridine-5-carboxylate (1 g, 3.92 mmol) in THF (35 mL) under a nitrogen atmosphere. The solution was stirred and cooled to 0° C. in an ice-water bath and potassium tert-butoxide (4.70 mL, 4.70 mmol) (1 M in THF) was added giving a thick yellow suspension. After stirring for 15 minutes at 0° C., methyl iodide (0.270 mL, 4.31 mmol) was added, which eventually gave a thick white suspension. The bath was removed and the reaction was allowed to warm to RT. The reaction was slowly quenched with sat. NH4Cl solution while stirring at RT to give a yellow clear solution. The mixture was concentrated down under a stream of nitrogen overnight. The residue was taken up in water and ethyl acetate, organic layer washed with brine, then the organic layer was dried over MgSO4, filtered and concentrated down under vacuum to give 1.01g of the title product. Used material as is for next reaction as purity by LC/MS was >90%. LC/MS m/z=268.9/270.9 (M+H)+. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.56 min. $^1$H NMR (400 MHz, CDCl$_3$-d) δ 7.94 (d, J=0.8 Hz, 1H), 7.39 (d, J=3.3 Hz, 1H), 6.80 (dd, J=3.3, 0.8 Hz, 1H), 4.05 (s, 3H), 3.85 (s, 3H).

6-bromo-1-methyl-1H-pyrrolo[3,2-b]pyridine-5-carbaldehyde (Int JD1b)

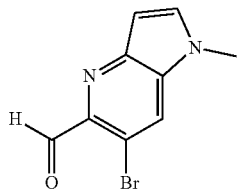

Within a septum topped round bottom flask equipped with a magnetic stirring bar was added methyl 6-bromo-1-methyl-1H-pyrrolo[3,2-b]pyridine-5-carboxylate (500 mg, 1.858 mmol) (Int JD1a) in THF (20 mL) under a nitrogen atmosphere. The solution was stirred and cooled to −78° C. in a dry ice-acetone bath and DIBAL-H (3.72 mL, 3.72 mmol) (1 M in hexanes) was added portion-wise. Stirring was continued for 1 hour at −78° C. The entire reaction was quenched with 1 mL of methanol while still very cold. The bath was removed and the reaction was allowed to warm to RT. The reaction mixture was diluted with ethyl acetate and was washed with saturated potassium sodium tartrate solution (10 mL) and stirred at RT. The mixture was transferred to a separatory funnel and the water layer was removed. The organic layer was dried over $MgSO_4$, filtered, and concentrated down under vacuum to give 395 mg of material which was used as is for next step. LC/MS m/z=238.9/240.9 (M+H)[+]. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.58 min. $^1$H NMR (400 MHz, $CDCl_3$-d) δ 10.39 (s, 1H), 7.94 (s, 1H), 7.45 (d, J=3.3 Hz, 1H), 6.88 (dd, J=3.3, 0.8 Hz, 1H), 3.87 (s, 3H).

1-(6-bromo-1-methyl-1H-pyrrolo[3,2-b]pyridin-5-yl)-2-(3,5-difluorophenyl)ethan-1-ol (Int JD1c)

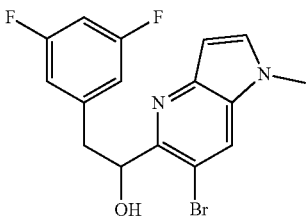 [SMILES: Cn1ccc2nc(C(O)Cc3cc(F)cc(F)c3)c(Br)cc21]

While under nitrogen, within a round bottom flask equipped with a magnetic stirrer bar was added 6-bromo-1-methyl-1H-pyrrolo[3,2-b]pyridine-5-carbaldehyde (640 mg, 2.68 mmol) (Int JD1b), and anhydrous THF (25 mL). While stirring at 0° C., (3,5-difluorobenzyl)zinc(II) bromide (8.03 mL, 4.02 mmol) (0.5M in THF) was added dropwise over 5 minutes and the mixture was allowed to continue stirring at 0° C. for 5-10 minutes, then warmed to RT over 15 minutes. While still stirring at RT, 0.5 equiv. (2.7 mL) of (3,5-difluorobenzyl)zinc(II) bromide was added. After 15 minutes, the entire reaction was quenched with sat. $NH_4Cl$ solution and the solvents were removed under a stream of nitrogen. The residue was taken up in ethyl acetate and water and a yellow solid formed. The yellow solid was removed by filtration the washed with ethyl acetate. The remaining water and organic mixture was washed with brine, and the combined organic layers were dried over $MgSO_4$, filtered, and concentrated down to give a residue. The residue was dissolved in DCM and was transferred to the top of an 80 g silica flash chromatography column. The desired product was eluted with 0-100% ethyl acetate/hexanes over 1.3 L of total solvent. Like fractions (TLC $R_f$=0.66; 50% ethyl acetate/hexanes) gave 650 mg of material with >85% purity and was used as such in next step. LC/MS m/z=366.9/368.9 (M+H)[+]. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.09 min. $^1$H NMR (400 MHz, $CDCl_3$-d) δ 7.89 (s, 1H), 7.33 (br d, J=2.5 Hz, 1H), 6.85 (br d, J=6.8 Hz, 2H), 6.77-6.53 (m, 2H), 5.30 (br s, 1H), 4.78 (br d, J=7.5 Hz, 1H), 3.85 (s, 3H), 3.27 (br d, J=12.5 Hz, 1H), 2.81 (br dd, J=13.7, 8.4 Hz, 1H).

2-(1-(6-bromo-1-methyl-1H-pyrrolo[3,2-b]pyridin-5-yl)-2-(3,5-difluorophenyl)ethyl)isoindoline-1,3-dione (Int JD1d)

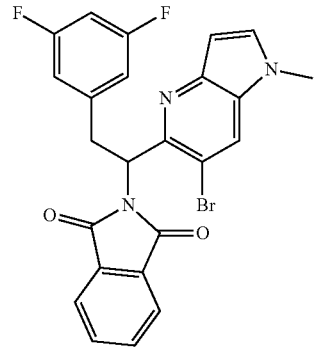 [SMILES: Cn1ccc2nc(C(Cc3cc(F)cc(F)c3)N3C(=O)c4ccccc4C3=O)c(Br)cc21]

While under nitrogen, within a round bottom flask equipped with a magnetic stirrer bar was added 1-(6-bromo-1-methyl-1H-pyrrolo[3,2-b]pyridin-5-yl)-2-(3,5-difluorophenyl)ethan-1-ol (650 mg, 1.770 mmol)(Int JD1c), isoindoline-1,3-dione (260 mg, 1.770 mmol), triphenylphosphine (511 mg, 1.947 mmol) and anhydrous, dry (distilled from sodium) THF (20 mL). While stirring at 0° C., DIAD (0.379 mL, 1.947 mmol) was added dropwise over 5 minutes and the yellow solution was allowed to continue stirring at 0° C., then slowly warm to RT. LC/MS after 1 hour (reaction still cold) showed no remaining starting material and the desired product as major. THF was removed under a stream of nitrogen. The remaining residue was dissolved in DCM and was transferred to the top of an 80 g silica flash chromatography column. The desired product was eluted with 0-100% ethyl acetate/hexanes over 1.2 L of total solvent. Like fractions (TLC: $R_f$=0.57; 50% ethyl acetate/hexanes) gave 890 mg of material with >75% purity which was used in the next step as such. LC/MS=495.9/497.9 (M+1) LC/MS m/z=791.1 (M+H)[+]. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.;

Gradient: 2% B to 98% B over 2 min, then a 1 min hold at 100% B; Flow: 0.8 mL/min; Detection: UV (254 nm); Retention Time: 1.52 min.

N-(4-chloro-7-(5-(2-(3,5-difluorophenyl)-1-(1,3-dioxoisoindolin-2-yl)ethyl)-1-methyl-1H-pyrrolo[3,2-b]pyridin-6-yl)-1-methyl-1H-indazol-3-yl)methanesulfonamide (Int JD1e)

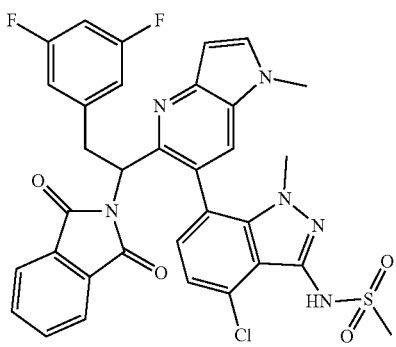 [SMILES: Cn1ccc2nc(C(Cc3cc(F)cc(F)c3)N3C(=O)c4ccccc4C3=O)c(-c3ccc(Cl)c4c(NS(C)(=O)=O)nn(C)c34)cc21]

In a septum top pressure vial equipped with a magnetic stirring bar was added 2-(1-(6-bromo-1-methyl-1H-pyrrolo[3,2-b]pyridin-5-yl)-2-(3,5-difluorophenyl)ethyl)isoindoline-1,3-dione (Int JD1d, 400 mg, 0.645 mmol) and N-(4-chloro-1-methyl-7-(4,4,5,5-tetramethyl-1,3,2-dioxaborolan-2-yl)-1H-indazol-3-yl)methanesulfonamide (311 mg, 0.806 mmol). The solids were suspended in distilled THF (25 mL). The mixture was treated with 0.5 M K$_3$PO$_4$ (5.16 mL, 2.58 mmol) and X-Phos precatalyst G2 (54.8 mg, 0.055 mmol). Argon was streamed over and bubbled into the mixture for 5 minutes with sonication. The vial was capped and stirred at RT for 48 hours. LC/MS showed formation of the desired product. The reaction mixture was transferred to a separatory funnel to remove the aqueous layer, using brine to help break up the layers. The organic layer was dried over MgSO$_4$, filtered and concentrated under vacuum to give a residue. The residue was dissolved in DCM and was transferred to the top of a 40 g silica flash chromatography column. The desired product was eluted with 0-100% ethyl acetate/hexanes over 1.2 L of total solvent (then hold at 90-100% ethyl acetate/hexanes to force this material off the column). Like fractions (TLC: R=0.19; 50% ethyl acetate/hexanes) gave 75 mg of material with >80%, which was used as is for next step. LC/MS m/z=674.95 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.30 min.

N-(7-(5-(1-amino-2-(3,5-difluorophenyl)ethyl)-1-methyl-1H-pyrrolo[3,2-b]pyridin-6-yl)-4-chloro-1-methyl-1H-indazol-3-yl)methanesulfonamide (Int JD1f)

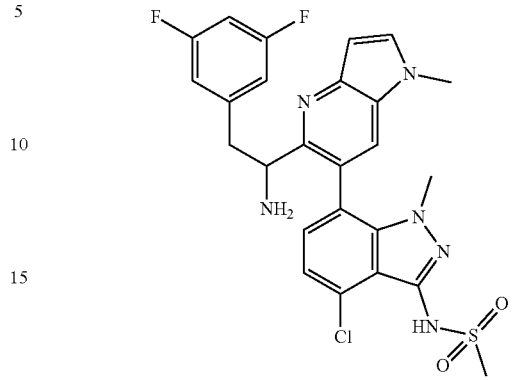

Within a septum topped vial equipped with a magnetic stirrer bar was added N-(4-chloro-7-(5-(2-(3,5-difluorophenyl)-1-(1,3-dioxoisoindolin-2-yl)ethyl)-1-methyl-1H-pyrrolo[3,2-b]pyridin-6-yl)-1-methyl-1H-indazol-3-yl)methanesulfonamide (35 mg, 0.052 mmol) (Int JD1d) and EtOH (2 mL). The substrate had limited solubility in ethanol, so dichloroethane (1 mL) was added. While stirring the cloudy solution at 20° C., hydrazine mono hydrate (0.046 mL, 0.933 mmol) was added dropwise and the solution was heated with stirring at 70° C. for 2 hours. The cloudy mixture became clear on heating. LC/MS after 16 hours at 70° C. showed less polar major and minor peaks with the desired mass. The reaction mixture was cooled and some off-white solid formed as the solvents were removed under a stream of nitrogen. The residue that remained was taken up in DCM and water then transferred to a separatory funnel. The layers were separated, and the organic layer was dried over MgSO$_4$, filtered and concentrated down to a residue. Used this residue as is for the next step. LC/MS m/z=545.2 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.31 min.

N-(1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 117 and Example 118)

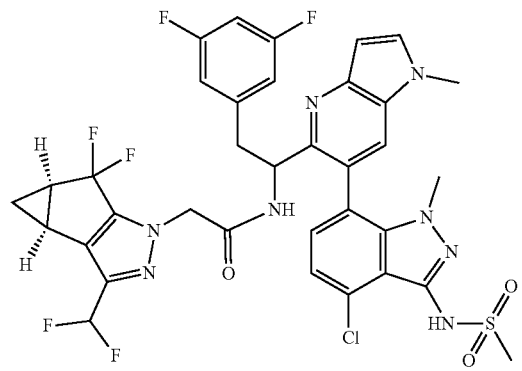 [SMILES: Cn1ccc2nc(C(Cc3cc(F)cc(F)c3)NC(=O)Cn3nc(C(F)F)c4c3C(F)(F)[C@@H]3C[C@H]43)c(-c3ccc(Cl)c4c(NS(C)(=O)=O)nn(C)c34)cc21]

Within a septum top vial equipped with a magnetic stirring bar was added N-(7-(5-(1-amino-2-(3,5-difluorophenyl)ethyl)-1-methyl-1H-pyrrolo[3,2-b]pyridin-6-yl)-4-chloro-1-methyl-1H-indazol-3-yl)methanesulfonamide (28 mg, 0.051 mmol) (Int JD1f), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (14.25 mg, 0.054 mmol) and 3H-[1,2,3]triazolo[4,5-b]pyridin-3-ol (1.888 mg, 0.014 mmol) in DCM (2 mL). Triethylamine (0.043 mL, 0.308 mmol), followed by EDC (25.6 mg, 0.134 mmol) was added. The vial was capped and the suspension was stirred at RT. LC/MS after 16 hours of stirring at RT suggests that the starting material is consumed and two desired molecular weight peaks are present but not in equal quantity. The reaction mixture was concentrated down under a stream of nitrogen, then taken up in 1.5 mL of DMF, filtered and purified via preparative HPLC to N-(1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide, as two compounds.

Example 117 First Eluting Peak, 6.2 mg

LC/MS m/z=791.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 96%; Retention Time: 2.02 min.

Example 118 Second Eluting Peak, 11.3 mg

LC/MS m/z=791.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 98.5%; Retention Time: 2.15 min. $^1$H NMR (600 MHz, DMSO-d$_6$; WS (water suppression)) 9.78 (br d, J=5.9 Hz, 1H), 9.02-8.90 (m, 1H), 7.90 (br s, 1H), 7.79 (br s, 1H), 7.24 (s, 1H), 7.19 (d, J=7.3 Hz, 1H), 7.16 (s, 1H), 7.07 (s, 1H), 7.03-6.95 (m, 1H), 6.91 (s, 1H), 6.89-6.80 (m, 1H), 6.71 (br s, 1H), 6.47 (br d, J=7.0 Hz, 2H), 4.93-4.81 (m, 1H), 4.80-4.71 (m, 1H), 4.69 (s, 1H), 4.67-4.58 (m, 1H), 3.50-3.37 (m, 2H), 3.24-3.15 (m, 4H), 3.14-3.02 (m, 1H), 3.02-2.90 (m, 1H), 2.48-2.37 (m, 1H), 1.41-1.29 (m, 1H), 0.86 (br d, J=4.8 Hz, 1H).

tert-butyl (1-(6-bromo-1-methyl-1H-pyrrolo[3,2-b]pyridin-5-yl)-2-(3,5-difluorophenyl)ethyl)carbamate (Int JD2a)

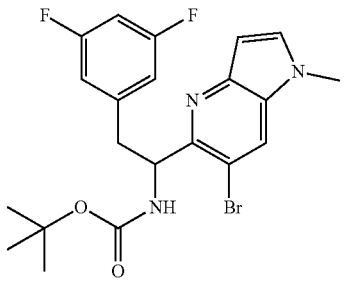 [SMILES: Cn1ccc2nc(C(Cc3cc(F)cc(F)c3)NC(=O)OC(C)(C)C)c(Br)cc21]

Within a round bottom flask equipped with a magnetic stirrer bar was added 1-(6-bromo-1-methyl-1H-pyrrolo[3,2-b]pyridin-5-yl)-2-(3,5-difluorophenyl)ethan-1-amine (255 mg, 0.696 mmol) in anhydrous DCM (2 mL). BOC-anhydride (0.162 mL, 0.696 mmol) (152 mg dissolved in 5 mL of DCM) was added. The reaction was allowed to stir at RT overnight. Reduced reaction solvent volume down to about 10 mL and loaded directly on to a 40 g silica gel chromatography column eluting with 0-100% ethyl acetate/hexanes over 1.1 L total solvent. Like fractions (TLC: R$_f$=0.48; 30% ethyl acetate/hexanes) gave 250 mg of tert-butyl (1-(6-bromo-1-methyl-1H-pyrrolo[3,2-b]pyridin-5-yl)-2-(3,5-difluorophenyl)ethyl)carbamate as an off-white solid after concentration under vacuum. Purity >90%. The material was separated into enantiomers by preparative chiral SFC purification (Chiralpak AS-H prep 30×250 mm, 5 μm; 15% methanol (0.1% DEA) in CO$_2$, 150 bar; temp. 35° C.; flow 70 mL/min for 7 minutes; UV @ 304 nm; injection: 0.5 mL of 28 mg/mL in 1:1 methanol/chloroform; peak 1 at 3.34 min, peak 2 at 5.54 min.) to give 110 mg of enantiomer peak 1 and 100 mg of enantiomer peak 2 after concentration, each as a colorless residue. LC/MS m/z=466.0/468.05 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 2.03 min. $^1$H NMR (400 MHz, CDCl$_3$-d) δ 7.82 (s, 1H), 7.35-7.30 (m, 1H), 6.71-6.57 (m, 2H), 6.34 (br d, J=1.0 Hz, 1H), 6.05 (br d, J=7.8 Hz, 1H), 5.60 (br d, J=7.3 Hz, 1H), 5.01 (dt, J=12.4, 6.2 Hz, 1H), 3.82 (s, 3H), 3.22 (br dd, J=13.3, 5.5 Hz, 1H), 3.01 (br dd, J=13.3, 7.0 Hz, 1H), 1.29 (d, J=6.3 Hz, 9H).

tert-butyl (S)-(1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)carbamate (Int JD2b)

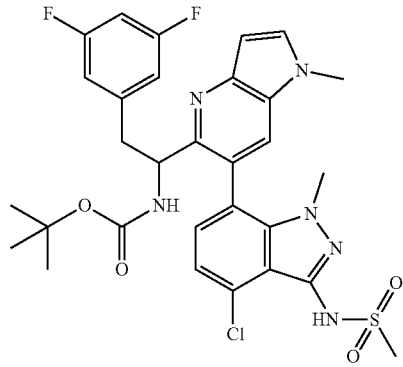 [SMILES: Cn1ccc2nc(C(Cc3cc(F)cc(F)c3)NC(=O)OC(C)(C)C)c(-c3ccc(Cl)c4c(NS(C)(=O)=O)nn(C)c34)cc21]

In a septum top pressure vial equipped with a magnetic stirring bar was added tert-butyl (1-(6-bromo-1-methyl-1H-pyrrolo[3,2-b]pyridin-5-yl)-2-(3,5-difluorophenyl)ethyl)carbamate (100 mg, 0.214 mmol, enantiomer peak 2 from previous SFC separation) (Int JD2a) and N-(4-chloro-1-methyl-7-(4,4,5,5-tetramethyl-1,3,2-dioxaborolan-2-yl)-1H-indazol-3-yl)methanesulfonamide (103 mg, 0.268 mmol). The solids were suspended in dry (distilled from sodium) THF (5 mL). The mixture was treated with 0.5M K$_3$PO$_4$ (1.716 mL, 0.858 mmol) and X-Phos precatalyst G2 (18.23 mg, 0.018 mmol). Argon was streamed over and bubbled into the mixture for 5 minutes with sonication. The vial was capped and stirred at RT for 48 hours. Additional 0.6 equiv. (51 mg) of N-(4-chloro-1-methyl-7-(4,4,5,5-tetramethyl-1,3,2-dioxaborolan-2-yl)-1H-indazol-3-yl)methanesulfonamide was added along with 6 mg of X-Phos precatalyst. Argon was bubbled into the reaction mixture for 5 minutes with sonication and the vial capped and sealed with film to be stirred for several days at RT. The reaction mixture was concentrated down to remove THF under a stream of nitrogen. N-(4-chloro-1-methyl-7-(4,4,5,5-tetramethyl-1,3,2-dioxaborolan-2-yl)-1H-indazol-3-yl)methanesulfonamide (103 mg, 0.268 mmol), Pd tetrakis (20 mg), sodium carbonate (0.429 mL, 0.858 mmol) and dioxane (5 mL) were added and the mixture was flushed with Argon, sealed and heated at 120° C. overnight. LC/MS showed that the starting material was consumed, and desired product was a major peak. Removed solvents under a stream of nitrogen. Took up material in ethyl acetate and water and transferred mixture to separatory funnel to remove aqueous layer, using brine to help break up the layers. Dried organic layer over $MgSO_4$, filtered and concentrated under vacuum to give a residue. The residue was dissolved in DCM and was transferred to the top of an 40 g silica gel chromatography column. The desired product was eluted with 0-100% ethyl acetate/hexanes over 1.4 L of total solvent. Like fractions (TLC: $R_f$=0.21; 50% ethyl acetate/hexanes) gave 80 mg of tert-butyl (S)-(1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)carbamate as an off-white residue. LC/MS shows two isomers, combined purity of both isomers >90%. LC/MS m/z=645.15 (M+H)$^+$; 667.2 (M+Na)$^+$. Column: Waters Aquity UPLC BEH C18, 2.1 mm×50 mm, 1.7 m particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.93/1.99 min. (1:3 ratio).

(S)—N-(7-(5-(1-amino-2-(3,5-difluorophenyl)ethyl)-1-methyl-1H-pyrrolo[3,2-b]pyridin-6-yl)-4-chloro-1-methyl-1H-indazol-3-yl)methanesulfonamide, HC (Int JD2c)

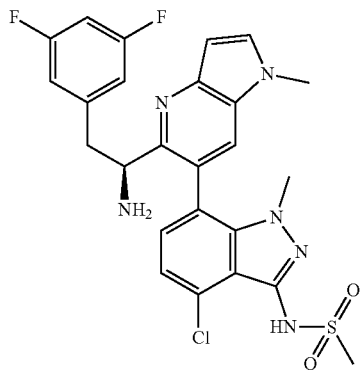 [SMILES: Cn1ccc2nc([C@@H](N)Cc3cc(F)cc(F)c3)c(-c3ccc(Cl)c4c(NS(C)(=O)=O)nn(C)c34)cc21]

In a septum top pressure vial equipped with a magnetic stirring bar was added tert-butyl (S)-(1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)carbamate (80 mg, 0.124 mmol) (Int JD2b). The solid was dissolved in anhydrous dioxane (5 mL). The mixture was treated with 4 M HCl (0.620 mL, 2.480 mmol) in dioxane. The vial was capped and stirred at RT for 2 hours. LC/MS showed reaction complete with no remaining starting material. Removed all solvent under a stream of nitrogen to give 70 mg of (S)—N-(7-(5-(1-amino-2-(3,5-difluorophenyl)ethyl)-1-methyl-1H-pyrrolo[3,2-b]pyridin-6-yl)-4-chloro-1-methyl-1H-indazol-3-yl)methanesulfonamide, HCl as an off-white solid. Use as is without further purification. LC/MS shows isomers, combined purity of both isomers ~80%. LC/MS m/z=545.15 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.55/1.82 min. (1:3 ratio).

N—((S)-1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Example 119 and Example 120

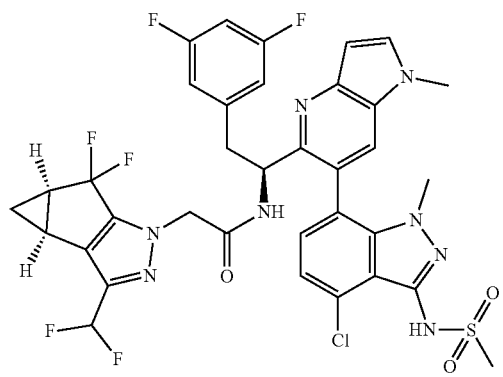 [SMILES: Cn1ccc2nc([C@H](Cc3cc(F)cc(F)c3)NC(=O)Cn3nc(C(F)F)c4c3C(F)(F)[C@@H]3C[C@H]43)c(-c3ccc(Cl)c4c(NS(C)(=O)=O)nn(C)c34)cc21]

Within a septum top vial equipped with a magnetic stirring bar was added (S)—N-(7-(5-(1-amino-2-(3,5-difluorophenyl)ethyl)-1-methyl-1H-pyrrolo[3,2-b]pyridin-6-yl)-4-chloro-1-methyl-1H-indazol-3-yl)methanesulfonamide, HCl (30 mg, 0.052 mmol) (Int JD2c); 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (14.31 mg, 0.054 mmol) and 3H-[1,2,3]triazolo[4,5-b]pyridin-3-ol (1.896 mg, 0.014 mmol) in DCM (2 mL). Triethylamine (0.050 mL, 0.361 mmol) followed by EDC (25.7 mg, 0.134 mmol) was added. The vial was capped under a nitrogen atmosphere, and the solution was stirred at RT overnight. The reaction mixture was concentrated down under a stream of nitrogen, then taken up in 1.5 mL of DMF, filtered and purified via preparative HPLC to retrieve N—((S)-1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide, as two homochiral compounds.

Example 119 First Eluting Peak, 3.8 mg

LC/MS m/z=791.1 (M+H)$^+$. Column: Waters XBridge C18, 2.1 mm×50 mm, 1.7 μm particles; Mobile Phase A: 5:95 acetonitrile:water with 10 mM ammonium acetate;

Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 95%; Retention Time: 2.02 min.

Example 120 Second Eluting Peak, 9.3 mg

LC/MS m/z=791.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 97%; Retention Time: 2.13 min. $^1$H NMR (500 MHz, DMSO-d6; WS) δ 9.00 (d, J=8.5 Hz, 1H), 7.90 (s, 1H), 7.80 (d, J=3.1 Hz, 1H), 7.19 (d, J=7.3 Hz, 1H), 7.07-6.97 (m, 1H), 6.86 (d, J=7.3 Hz, 1H), 6.71 (d, J=3.1 Hz, 1H), 6.48 (br d, J=6.4 Hz, 2H), 4.94-4.82 (m, 1H), 4.75 (br d, J=16.5 Hz, 1H), 4.64 (d, J=16.5 Hz, 1H), 3.87-3.78 (m, 3H), 3.23-3.15 (m, 4H), 3.10 (br dd, J=13.7, 5.2 Hz, 1H), 2.96 (br dd, J=13.3, 9.0 Hz, 1H), 1.91 (s, 6H), 1.42-1.32 (m, 1H), 0.86 (br s, 1H).

tert-butyl (R)-(1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl) carbamate (Int JD2d)

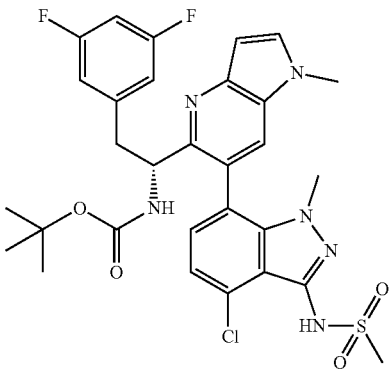 [SMILES: Cn1ccc2nc([C@@H](Cc3cc(F)cc(F)c3)NC(=O)OC(C)(C)C)c(-c3ccc(Cl)c4c(NS(C)(=O)=O)nn(C)c34)cc21]

In a septum top pressure vial equipped with a magnetic stirring bar was added tert-butyl (1-(6-bromo-1-methyl-1H-pyrrolo[3,2-b]pyridin-5-yl)-2-(3,5-difluorophenyl)ethyl) carbamate (110 mg, 0.236 mmol; enantiomer peak 1 from previous SFC separation) and N-(4-chloro-1-methyl-7-(4,4,5,5-tetramethyl-1,3,2-dioxaborolan-2-yl)-1H-indazol-3-yl) methanesulfonamide (182 mg, 0.472 mmol). The solids were suspended in dioxane (5 mL). The mixture was treated with 2 M sodium carbonate (0.590 mL, 1.179 mmol) and palladium tetrakis (23.17 mg, 0.020 mmol). Argon was streamed over and bubbled into the mixture for 5 minutes with sonication. The vial was capped then stirred at 120° C. for 16 hours within a preheated oil bath. LC/MS showed clean conversion to desired product as two isomers. Removed solvent under a stream of nitrogen, took up the residue in ethyl acetate and water. Transferred mixture to separatory funnel to remove aqueous layer, using brine to help break up the layers. Dried organic layer over MgSO$_4$, filtered and concentrated under vacuum to give a residue. The residue was dissolved in DCM and was transferred to the top of an 40 g silica gel chromatography column. The desired product was eluted with 0-100% ethyl acetate/hexanes over 1.3 L of total solvent. Like fractions (TLC: R$_f$=0.20/0.24 (isomers); 50% ethyl acetate/hexanes) gave 110 mg of tert-butyl (R)-(1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)carbamate as an off-white solid. LC/MS shows isomers, combined purity of both isomers >90%. LC/MS m/z=667.15 (M+Na)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.91/1.98 min. (1:3 ratio).

(R)—N-(7-(5-(1-amino-2-(3,5-difluorophenyl) ethyl)-1-methyl-1H-pyrrolo[3,2-b]pyridin-6-yl)-4-chloro-1-methyl-1H-indazol-3-yl)methanesulfonamide, HCl (Int JD2e)

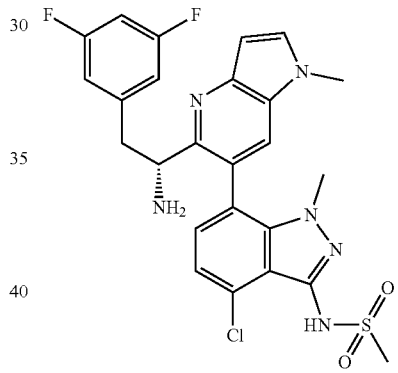

In a septum top pressure vial equipped with a magnetic stirring bar was added tert-butyl (R)-(1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl) ethyl)carbamate (110 mg, 0.171 mmol) (Int JD2d). The solid was dissolved in anhydrous dioxane (8 mL). The mixture was treated with 4 M HCl (0.853 mL, 3.41 mmol) in dioxane. The vial was capped and stirred at RT for 2 hours. LC/MS showed reaction complete with no remaining starting material. Removed all solvent under a stream of nitrogen to give 100 mg of (R)—N-(7-(5-(1-amino-2-(3,5-difluorophenyl)ethyl)-1-methyl-1H-pyrrolo[3,2-b]pyridin-6-yl)-4-chloro-1-methyl-1H-indazol-3-yl)methanesulfonamide, HCl as an off-white solid. Use as is without further purification. LC/MS shows isomers; combined purity of both isomers >85%. LC/MS m/z=545.1 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.54/1.81 min. (1:3 ratio).

N—((R)-1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 121 and Example 122)

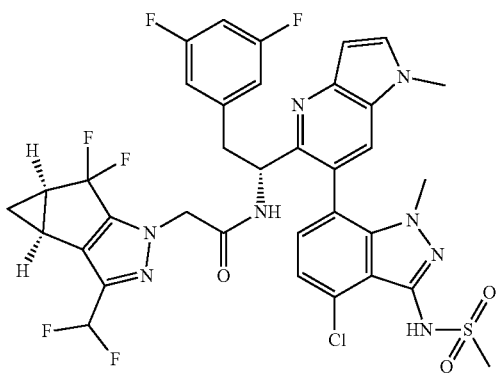 [SMILES: Cn1ccc2nc([C@@H](Cc3cc(F)cc(F)c3)NC(=O)Cn3nc(C(F)F)c4c3C(F)(F)[C@@H]3C[C@H]43)c(-c3ccc(Cl)c4c(NS(C)(=O)=O)nn(C)c34)cc21]

Within a septum top vial equipped with a magnetic stirring bar was added (R)—N-(7-(5-(1-amino-2-(3,5-difluorophenyl)ethyl)-1-methyl-1H-pyrrolo[3,2-b]pyridin-6-y)-4-chloro-1-methyl-1H-indazol-3-yl)methanesulfonamide, HCl (30 mg, 0.052 mmol) (Int JD2e); 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (14.31 mg, 0.054 mmol) and 3H-[1,2,3]triazolo[4,5-b]pyridin-3-ol (1.896 mg, 0.014 mmol) in DCM (2 mL). Triethylamine (0.050 mL, 0.361 mmol) followed by EDC (25.7 mg, 0.134 mmol) was added. The vial was capped under a nitrogen atmosphere, and the solution was stirred at RT. The reaction mixture was concentrated down under a stream of nitrogen, then taken up in 1.5 mL of DMF, filtered and purified via preparative HPLC to give N—((R)-1-(6-(4-chloro-1-methyl-3-(methylsulfonamido)-1H-indazol-7-yl)-1-methyl-1H-pyrrolo[3,2-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide, as two homochiral compounds.

Example 121 First Eluting Peak, 6.8 mg

LC/MS m/z=791.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 96%; Retention Time: 2.02 min.

Example 122 Second Eluting Peak, 12.1 mg

LC/MS m/z=791.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 98%; Retention Time: 2.13 min. $^1$H NMR (500 MHz, DMSO-d$_6$; WS) δ 9.00 (d, J=8.5 Hz, 1H), 7.90 (s, 1H), 7.80 (d, J=3.1 Hz, 1H), 7.19 (d, J=7.3 Hz, 1H), 7.07-6.97 (m, 1H), 6.86 (d, J=7.3 Hz, 1H), 6.71 (d, J=3.1 Hz, 1H), 6.48 (br d, J=6.4 Hz, 2H), 4.94-4.82 (m, 1H), 4.75 (br d, J=16.5 Hz, 1H), 4.64 (d, J=16.5 Hz, 1H), 3.87-3.78 (m, 3H), 3.23-3.15 (m, 4H), 3.10 (br dd, J=13.7, 5.2 Hz, 1H), 2.96 (br dd, J=13.3, 9.0 Hz, 1H), 1.91 (s, 6H), 1.42-1.32 (m, 1H), 0.86 (br s, 1H).

tert-butyl (1-((3-carbamoylpyridin-2-yl)amino)-3-(3,5-difluorophenyl)-1-oxopropan-2-yl)carbamate (Int JD3a)

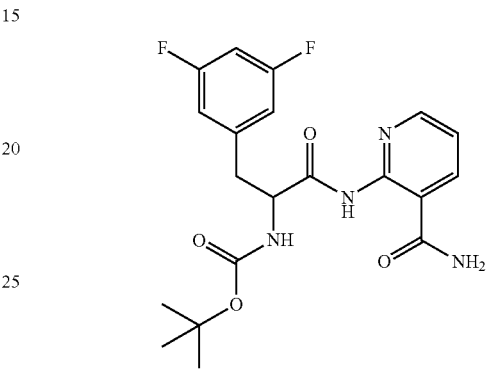

Within a round bottom flask equipped with a magnetic stirrer bar was added (S)-2-((tert-butoxycarbonyl)amino)-3-(3,5-difluorophenyl)propanoic acid (4.95 g, 16.43 mmol) in DCM (100 mL). N-methylmorpholine (4.52 mL, 41.1 mmol) and then isobutyl chloroformate (4.32 mL, 32.9 mmol) was added, and the flask was cooled to −70° C. in an IPA/CO$_2$ bath while stirring. 2-aminonicotinic acid (2.269 g, 16.43 mmol) was then added to the mixture. The resulting slurry was stirred cold and allowed to continue stirring overnight as the bath warmed slowly. The entire reaction was quenched by adding reaction mixture portion wise into a rapidly stirring solution of 150 mL of 7 N ammonia in methanol to give primary amide and methyl ester products simultaneously. The slightly colored solution was concentrated down under vacuum to give a pink solid. The solids were triturated with DCM, and the solid filtered to give 3.99 g of tert-butyl (1-((3-carbamoylpyridin-2-yl)amino)-3-(3,5-difluorophenyl)-1-oxopropan-2-yl)carbamate as an off-white solid. The methyl ester product remained in the filtrate. This material was analyzed by chiral SFC analytical HPLC and showed two peaks of similar areas, suggesting racemization had occurred under these reaction conditions. This material was used as is without further purification. LC/MS m/z=421.25 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.065 min. $^1$H NMR (500 MHz, DMSO-d$_6$) δ 8.95 (br d, J=2.6 Hz, 1H), 8.50 (d, J=7.8 Hz, 1H), 7.53 (dd, J=7.9, 4.5 Hz, 1H), 7.47 (br d, J=8.2 Hz, 1H), 7.20-7.01 (m, 4H), 4.68 (br t, J=7.1 Hz, 1H), 3.22-3.09 (m, 1H), 3.03-2.86 (m, 2H), 1.30 (s, 10H).

tert-butyl (2-(3,5-difluorophenyl)-1-(4-oxo-3,4-dihydropyrido[2,3-d]pyrimidin-2-yl)ethyl)carbamate (Int JD3b)

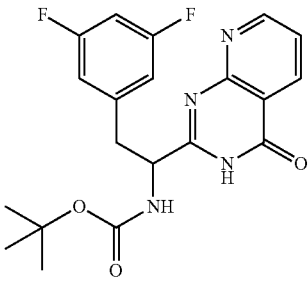 [SMILES: CC(C)(C)OC(=O)NC(Cc1cc(F)cc(F)c1)c1nc2ncccc2c(=O)[nH]1]

Within a round bottom flask equipped with a magnetic stirrer bar was added tert-butyl (1-((3-carbamoylpyridin-2-yl)amino)-3-(3,5-difluorophenyl)-1-oxopropan-2-yl)carbamate (1 g, 2.379 mmol) (Int JD3a) in THF (100 mL). Iodine (1.056 g, 4.16 mmol) and then HMDS (1.496 mL, 7.14 mmol) was added, and the vial was capped and stirred at RT. Within 15 minutes, LC/MS showed reaction complete, only desired product with no starting material left. The reaction mixture was dumped into a water solution of 3.8g of Na2S2O3 (250 mL water) and 250 mL of ethyl acetate. The organic layer was separated, washed with brine, dried over sodium sulfate, filtered and concentrated down to 560 mg of tert-butyl (2-(3,5-difluorophenyl)-1-(4-oxo-3,4-dihydropyrido[2,3-d]pyrimidin-2-yl)ethyl)carbamate as a yellow residue then solidified to an off-white solid. This material was analyzed by chiral SFC analytical HPLC and showed two peaks, again confirming racemization had occurred under the previous reaction conditions. This material was used as is without further purification. LC/MS m/z=403.15 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.615 min.

tert-butyl(1-(3-(4-chlorophenyl)-4-oxo-3,4-dihydropyrido[2,3-d]pyrimidin-2-yl)-2-(3,5-difluorophenyl)ethyl)carbamate (Int JD3c)

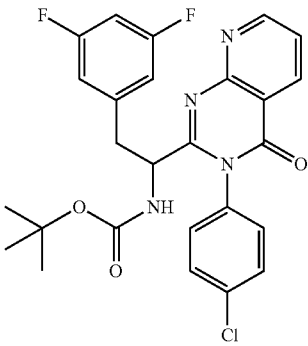 [SMILES: CC(C)(C)OC(=O)NC(Cc1cc(F)cc(F)c1)c1nc2ncccc2c(=O)n1-c1ccc(Cl)cc1]

Within a microwave pressure vial equipped with a magnetic stirring bar was added tert-butyl (2-(3,5-difluorophenyl)-1-(4-oxo-3,4-dihydropyrido[2,3-d]pyrimidin-2-yl)ethyl)carbamate (100 mg, 0.249 mmol) (Int JD3b) and 1-bromo-4-chlorobenzene (105 mg, 0.547 mmol) in anhydrous dioxane (2.5 mL) and DMF (5 mL). N1,N2-dimethylethane-1,2-diamine (32.9 mg, 0.373 mmol), K$_3$PO$_4$ (158 mg, 0.746 mmol) followed by copper(I) iodide (71.0 mg, 0.373 mmol) was added. The reaction mixture was degassed with Argon (bubbled into mixture), and the vial was capped and stirred at 110° C. for 5 hours in the microwave reactor. LC/MS showed formation of the desired product and unreacted starting material. The reaction mixture was diluted with ethyl acetate and washed with water. The organic layer was dried over MgSO$_4$, filtered and concentrated down under vacuum to give an oil. The oil was diluted in DCM and transferred on to a 40 g silica gel chromatography column. The desired product and remaining starting material were eluted with 0-100% ethyl acetate/hexanes over 1.2 L of total solvent. Desired product was detected by TLC: R$_f$=0.52 in 50% ethyl acetate/hexanes. Like fractions were combined and concentrated to give 40 mg of the title product as a red oil. This material was used as is without further purification. LC/MS m/z=513.15 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 2 min, then a 1 min hold at 100% B; Flow: 0.8 mL/min; Detection: UV (254 nm); Retention Time: 1.43 min.

2-(1-amino-2-(3,5-difluorophenyl)ethyl)-3-(4-chlorophenyl)pyrido[2,3-d]pyrimidin-4(3H)-one, HCl (Int JD3d)

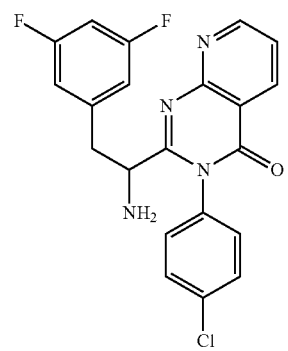 [SMILES: NC(Cc1cc(F)cc(F)c1)c1nc2ncccc2c(=O)n1-c1ccc(Cl)cc1]

Within a round bottom flask equipped with a magnetic stirring bar was added tert-butyl (1-(3-(4-chlorophenyl)-4-oxo-3,4-dihydropyrido[2,3-d]pyrimidin-2-yl)-2-(3,5-difluorophenyl)ethyl)carbamate (40 mg, 0.078 mmol) (Int JD3c) and in anhydrous dioxane (3 mL). HCl (0.390 mL, 1.560 mmol) (4 M in dioxane) was added. The reaction mixture was stirred at 20° C. for 16 hours. The reaction mixture was dried down under a stream of nitrogen to give a residue, which was used as is in the next step. LC/MS m/z=413.10 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water N-(1-(3-(4-chlorophenyl)-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 123)

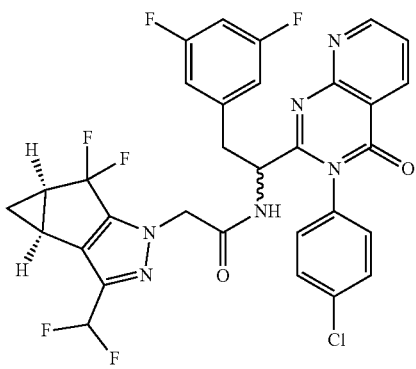

Within a round bottom flask equipped with a magnetic stirring bar was added 2-(1-amino-2-(3,5-difluorophenyl)ethyl)-3-(4-chlorophenyl)pyrido[2,3-d]pyrimidin-4(3H)-one, HCl (35 mg, 0.078 mmol) (Int JD3d); 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (21.61 mg, 0.082 mmol) and 3H-[1,2,3]triazolo[4,5-b]pyridin-3-ol (3.18 mg, 0.023 mmol) in DCM (3 mL). TEA (0.065 mL, 0.467 mmol) followed by EDC (38.8 mg, 0.203 mmol) was added. The flask was capped under a nitrogen atmosphere, and the suspension was stirred at RT for 16 hours. LC/MS showed of mixture of starting material and desired product. The reaction mixture was concentrated down under a stream of nitrogen, then taken up in 1.5 mL of DMF, filtered and purified via preparative HPLC to give 2.3 mg of the title product as a mixture of diastereomers. LC/MS m/z=659.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 97%; Retention Time: 2.15 min. $^1$H NMR (500 MHz, DMSO-d$_6$; WS) δ 8.95 (br s, 1H), 8.47 (br d, J=7.6 Hz, 1H), 7.59-7.54 (m, 1H), 7.51 (br s, 3H), 7.02 (br d, J=7.3 Hz, 1H), 6.84-6.70 (m, 2H), 5.64 (br d, J=8.2 Hz, 1H), 4.70 (br d, J=17.1 Hz, 1H), 4.50 (br d, J=16.5 Hz, 1H), 3.88 (s, 1H), 3.21-3.11 (m, 2H), 3.08-2.96 (m, 1H), 1.40-1.29 (m, 1H), 1.21 (br s, 2H), 1.10 (s, 1H), 0.83 (br s, 1H).

N—((S)-1-(3-(4-chlorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 124)

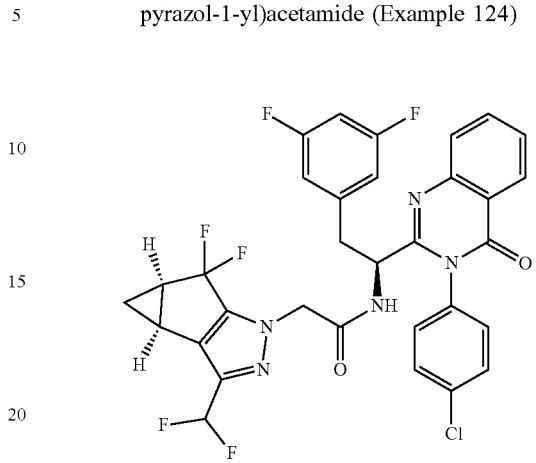

Within a septum cap vial equipped with a magnetic stirrer bar was added (S)-2-((tert-butoxycarbonyl)amino)-3-(3,5-difluorophenyl)propanoic acid (25 mg, 0.083 mmol), 2-aminobenzoic acid (11.38 mg, 0.083 mmol), and diphenyl phosphite (0.056 mL, 0.290 mmol) in pyridine (0.5 mL). The vial was capped and the mixture was heated in a oil bath for 1.5 hours at 70° C. 4-chloroaniline (11.64 mg, 0.091 mmol) was then added to the mixture and the cap replaced on the vial, and the reaction was again heated to 70° C. for an additional 1.5 hours. Removed the pyridine under a stream of nitrogen to give a thick yellow oil. The oil was taken up in DCM (2 mL) and treated with HC (0.622 mL, 2.489 mmol) (4 M in dioxane) and stirred at RT for several hours. The reaction mixture was dried down under a stream of nitrogen to a yellow residue. To this residue was added 2-(1-amino-2-(3,5-difluorophenyl)ethyl)-3-(4-chlorophenyl)quinazolin-4(3H)-one, HCl, tert-butyl (1-(3-(4-chlorophenyl)-4-oxo-3,4-dihydroquinazolin-2-yl)-2-(3,5-difluorophenyl)ethyl)carbamate, HOAT (3.39 mg, 0.025 mmol) and DMF (1.5 mL). TEA (0.081 mL, 0.581 mmol) followed by EDC (39.8 mg, 0.207 mmol) was then added. The flask was capped and the suspension was stirred at RT overnight. Filtered reaction mixture and purified material by preparative HPLC to give 24.7 mg of the title product. LC/MS m/z=658.09 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.26 min. $^1$H NMR (500 MHz, DMSO-d6; WS (water suppression)) δ 9.07 (br d, J=7.9 Hz, 1H), 8.16 (br d, J=7.9 Hz, 1H), 7.94 (br t, J=7.5 Hz, 1H), 7.79 (d, J=8.2 Hz, 1H), 7.70 (br d, J=8.2 Hz, 1H), 7.66-7.58 (m, 2H), 7.56 (br d, J=8.5 Hz, 1H), 7.40 (br d, J=8.5 Hz, 1H), 7.09-6.98 (m, 1H), 6.95 (s, 1H), 6.84 (s, 1H), 6.57 (br d, J=6.7 Hz, 2H), 4.82-4.69 (m, 1H), 4.69-4.50 (m, 2H), 3.27-3.13 (m, 1H), 2.90 (br dd, J=13.6, 10.2 Hz, 1H), 2.48-2.38 (m, 1H), 1.37 (q, J=6.6 Hz, 1H), 1.23 (s, 1H), 0.90 (br s, 1H). $^{19}$F NMR (471 MHz, DMSO-d$_6$) δ −79.74 (d, J=253.2 Hz, 1H), −102.56 (d, J=253.2 Hz, 1H), −110.31 (s, 2F), −110.91 (d, J=308.9 Hz, 1H), −112.45 (d, J=308.9 Hz, 1H).

methyl (S)-2-(1-((tert-butoxycarbonyl)amino)-2-(3,5-difluorophenyl)ethyl)-3-(4-chloro-3-(N-(4-methoxybenzyl)methylsulfonamido)-1-methyl-1H-indazol-7-yl)-4-oxo-3,4-dihydroquinazoline-8-carboxylate (Int JD6a)

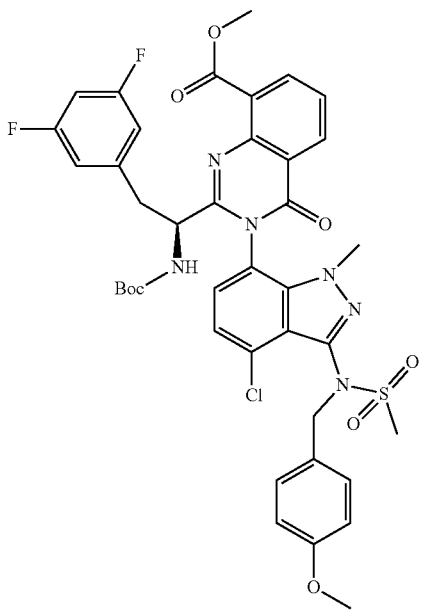 [SMILES: COC(=O)c1cccc2c(=O)n(-c3ccc(Cl)c4c(N(Cc5ccc(OC)cc5)S(C)(=O)=O)nn(C)c34)c([C@H](Cc3cc(F)cc(F)c3)NC(=O)OC(C)(C)C)nc12]

Within a septum top vial equipped with a magnetic stirrer bar was added (S)-2-((tert-butoxycarbonyl)amino)-3-(3,5-difluorophenyl)propanoic acid (200 mg, 0.664 mmol), 2-amino-3-(methoxycarbonyl)benzoic acid (130 mg, 0.664 mmol), and diphenyl phosphite (0.449 mL, 2.323 mmol) in pyridine (2 mL). The vial was capped and the mixture was heated in an aluminum block for 1.5 hours at 70° C. N-(7-amino-4-chloro-1-methyl-1H-indazol-3-yl)-N-(4-methoxybenzyl)methanesulfonamide (288 mg, 0.730 mmol) (Int 17d) was then added to the mixture and the cap placed on the vial, and the reaction was again heated to 70° C. for an additional 2+ hours. Dried down the reaction slowly under a stream of nitrogen to give a residue. The residue was dissolved in DCM and was transferred to the top of an 80 g silica gel flash chromatography column. The desired product was eluted with 0-100% ethyl acetate/hexanes over 1.4 L of total solvent. Like fractions (TLC: $R_f$=0.18; 30% ethyl acetate/hexanes) were combined and concentrated down to give 360 mg of title product as a pale yellow foam. LC/MS m/z=837.25 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 0.5 min hold at 100% B; Flow: 0.8 mL/min; Detection: UV (254 nm); Retention Time: 1.63 min.

methyl (S)-2-(1-amino-2-(3,5-difluorophenyl)ethyl)-3-(4-chloro-1-methyl-3-(methylsulfonamido)-1H-indazol-7-yl)-4-oxo-3,4-dihydroquinazoline-8-carboxylate (Int JD6b)

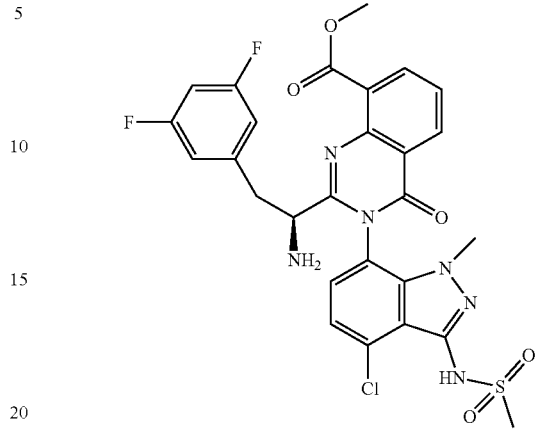

At RT, within a septum top vial equipped with a magnetic stirrer bar was added methyl (S)-2-(1-((tert-butoxycarbonyl)amino)-2-(3,5-difluorophenyl)ethyl)-3-(4-chloro-3-(N-(4-methoxybenzyl)methylsulfonamido)-1-methyl-1H-indazol-7-yl)-4-oxo-3,4-dihydroquinazoline-8-carboxylate (80 mg, 0.096 mmol) (Int JD6a) in TFA (0.552 mL, 7.17 mmol). triflic acid (0.051 mL, 0.573 mmol) was added to the reaction and rapidly stirred for 30 minutes. Dried down the reaction slowly under a stream of nitrogen to remove TFA, then diluted the remaining residue in DCM (3 mL). Partitioned the organic layer with 20 mL saturated aqueous NaHCO$_3$ solution. Dried the DCM layer over MgSO$_4$, filtered and evaporated down to dryness to give 70 mg of the title product as an off-white solid, which was used as is for next step. LC/MS m/z=617.15 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (254 nm); Retention Time: 1.44 min.

methyl 3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazoline-8-carboxylate (Int JD45) and Int JD44

Int JD44

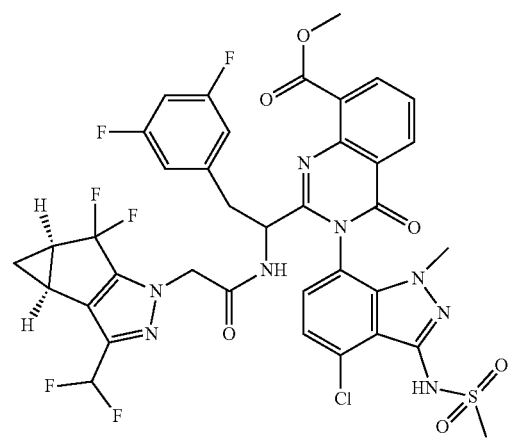

Mix of two stereoisomers

Int JD45

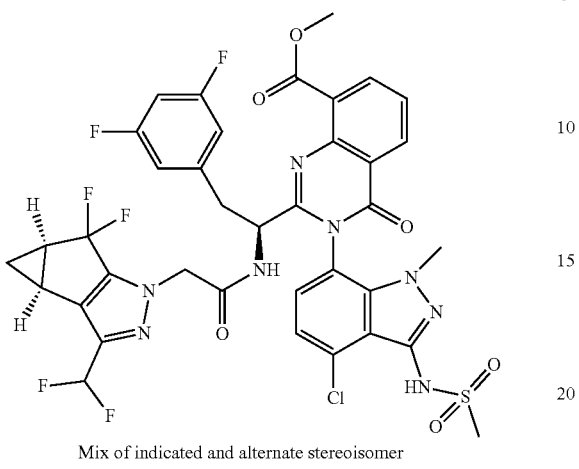

Mix of indicated and alternate stereoisomer

Within a septum cap vial equipped with a magnetic stirrer bar was added methyl (S)-2-(1-amino-2-(3,5-difluorophenyl)ethyl)-3-(4-chloro-1-methyl-3-(methylsulfonamido)-1H-indazol-7-yl)-4-oxo-3,4-dihydroquinazoline-8-carboxylate (70 mg, 0.100 mmol) (Int JD6b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (31.8 mg, 0.120 mmol), and HOAT (4.10 mg, 0.030 mmol) in DMF (1.5 mL). TEA (98 µl, 0.703 mmol) followed by EDC (48.1 mg, 0.251 mmol) was added. The vial was capped and the suspension was stirred at RT overnight. The reaction mixture was filtered and purified by preparative HPLC to give two elutes.

Int JD44 First eluting peak, 4.2 mg. LC/MS m/z=863.06 (M+H)⁺. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 98%; Retention Time: 2.03 min.

Int JD45 Second eluting peak, 6.5 mg. LC/MS m/z=863.07 (M+H)⁺. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 97%; Retention Time: 2.1 min.

tert-butyl (1-(3-(4-chloro-3-(N-(4-methoxybenzyl)methylsulfonamido)-1-methyl-1H-indazol-7-yl)-5-methyl-4-oxo-3,4-dihydroquinazolin-2-yl)-2-(3,5-difluorophenyl)ethyl)carbamate (Int JD7a)

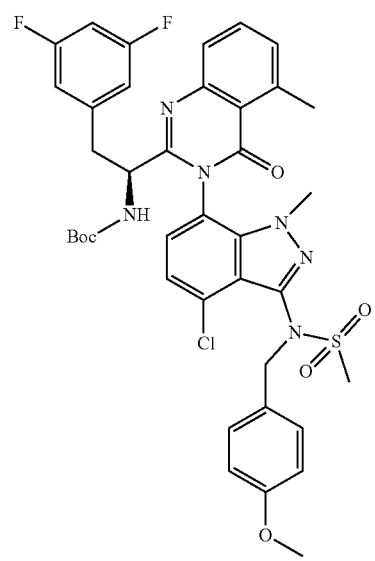 [SMILES: COc1ccc(CN(c2nn(C)c3c(-n4c([C@H](Cc5cc(F)cc(F)c5)NC(=O)OC(C)(C)C)nc5cccc(C)c5c4=O)ccc(Cl)c23)S(C)(=O)=O)cc1]

Within a septum top vial equipped with a magnetic stirrer bar was added (S)-2-((tert-butoxycarbonyl)amino)-3-(3,5-difluorophenyl)propanoic acid (100 mg, 0.332 mmol), 2-amino-6-methylbenzoic acid (50.2 mg, 0.332 mmol), and diphenyl phosphite (0.225 mL, 1.162 mmol) in pyridine (1.5 mL). The vial was capped and the mixture was heated in an aluminum block for 1.5 hours at 70° C. N-(7-amino-4-chloro-1-methyl-1H-indazol-3-yl)-N-(4-methoxybenzyl)methanesulfonamide (144 mg, 0.365 mmol) (Int 17d) was then added to the mixture and the cap placed on the vial, and the reaction was again heated to 70° C. for an additional 2 hours. Dried down the reaction slowly under a stream of nitrogen to give a residue. The residue was dissolved in DCM and was transferred to the top of a 40 g silica gel flash chromatography column. The desired product was eluted with 0-100% ethyl acetate/hexanes over 1.2 L of total solvent. Like fractions (TLC: R$_f$=0.68; 50% ethyl acetate/hexanes) were combined and concentrated down to give 170 mg of title product as a red solid. LC/MS m/z=793.20 (M+H)⁺. Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 0.5 min hold at 100% B; Flow: 0.8 mL/min; Detection: UV (254 nm); Retention Time: 1.71 min.

339

(S)—N-(7-(2-(1-amino-2-(3,5-difluorophenyl)ethyl)-5-methyl-4-oxoquinazolin-3(4H)-yl)-4-chloro-1-methyl-1H-indazol-3-yl)methanesulfonamide (Int JD7b)

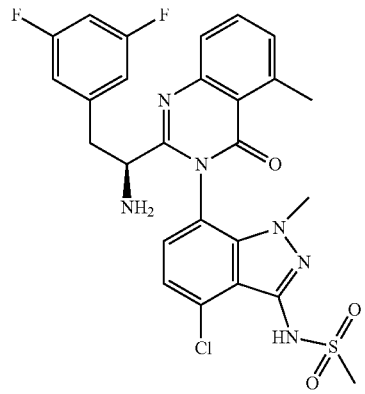 [SMILES: Cc1cccc2nc([C@@H](N)Cc3cc(F)cc(F)c3)n(-c3ccc(Cl)c4c(NS(C)(=O)=O)nn(C)c34)c(=O)c12]

At RT, within a septum top vial equipped with a magnetic stirrer bar was added tert-butyl (S)-(1-(3-(4-chloro-3-(N-(4-methoxybenzyl)methylsulfonamido)-1-methyl-1H-indazol-7-yl)-5-methyl-4-oxo-3,4-dihydroquinazolin-2-yl)-2-(3,5-difluorophenyl)ethyl)carbamate (170 mg, 0.214 mmol) (Int JD7a) in TFA (1.238 mL, 16.07 mmol). Triflic acid (0.114 mL, 1.286 mmol) was added to the reaction and rapidly stirred for 30 minutes. Dried down the reaction slowly under a stream of nitrogen to remove TFA, then diluted the remaining residue in DCM (3 mL). Partitioned the organic layer with 20 mL saturated aqueous NaHCO$_3$ solution. Dried the DCM layer over MgSO$_4$, filtered and evaporated down to dryness to give 160 mg of the title product as a pink solid, which was used as is for next step. LC/MS m/z=573.2 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 0.5 min hold at 100% B; Flow: 0.8 mL/min; Detection: UV (254 nm); Retention Time: 1.48 min.

N—((S)-1-(3-(4-chloro-1-methyl-3-(methylsulfonamido)-1H-indazol-7-yl)-5-methyl-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 126) and Example 125

Example 125

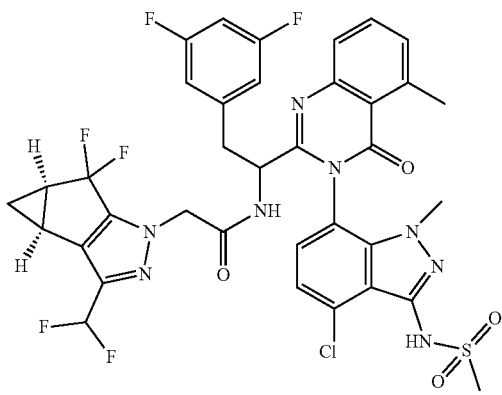

Mix of two stereoisomers

340

-continued

Example 126

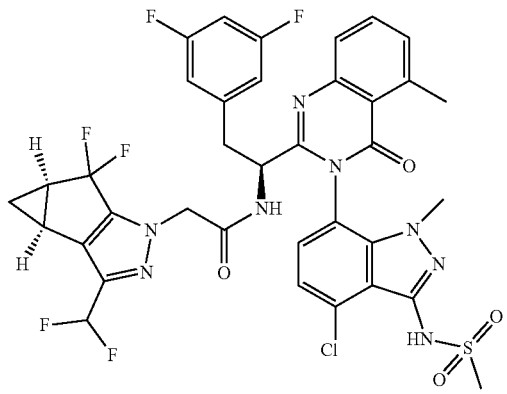

Mix of indicated and alternate stereoisomer

Within a red septum cap vial equipped with a magnetic stirrer bar was added (S)—N-(7-(2-(1-amino-2-(3,5-difluorophenyl)ethyl)-5-methyl-4-oxoquinazolin-3(4H)-yl)-4-chloro-1-methyl-1H-indazol-3-yl)methanesulfonamide (80 mg, 0.098 mmol) (Int JD7b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (29.7 mg, 0.112 mmol), and HOAT (3.99 mg, 0.029 mmol) in DMF (1.5 mL). TEA (95 μl, 0.684 mmol) followed by EDC (46.8 mg, 0.244 mmol) was added. The vial was capped and the suspension was stirred at RT overnight. The reaction mixture was filtered and purified by preparative HPLC to give two elutes.

Example 125 First Eluting Peak, 13.0 mg

LC/MS m/z=819.08 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.12 min.

Example 126 Second Eluting Peak, 16.1 mg

LC/MS m/z=819.09 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 99%; Retention Time: 2.18 min.

341 tert-butyl (S)-(1-(3-(4-chloro-3-(N-(4-methoxyben-zyl)methylsulfonamido)-1-methyl-1H-indazol-7-yl)-4-oxo-5-(trifluoromethyl)-3,4-dihydroquinazolin-2-yl)-2-(3,5-difluorophenyl)ethyl)carbamate (Int JD8a)

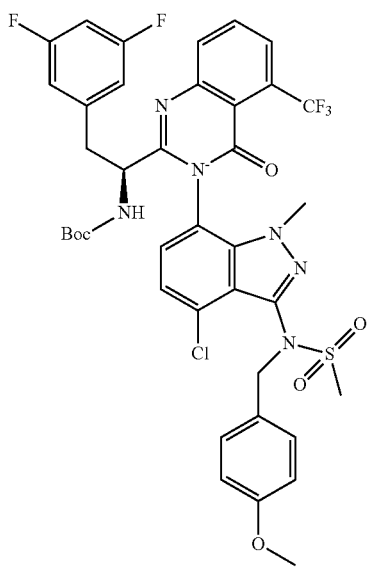

Within a septum top vial equipped with a magnetic stirrer bar was added (S)-2-((tert-butoxycarbonyl)amino)-3-(3,5-difluorophenyl)propanoic acid (100 mg, 0.332 mmol), 2-amino-6-(trifluoromethyl)benzoic acid (68.1 mg, 0.332 mmol), and diphenyl phosphite (0.225 mL, 1.162 mmol) in pyridine (1.5 mL). The vial was capped and the mixture was heated in an aluminum block for 1.5 hours at 70° C. N-(7-amino-4-chloro-1-methyl-1H-indazol-3-yl)-N-(4-methoxybenzyl)methanesulfonamide (144 mg, 0.365 mmol) (Int17d) was then added to the mixture and the cap placed on the vial, and the reaction was again heated to 70° C. for an additional 2 hours. LC/MS after cooling showed the desired product as a major peak. LC/MS showed the desired MW product as a major peak. Dry down reaction slowly under a stream of nitrogen. The residue was dissolved in DCM and was transferred to the top of a 40 g silica gel chromatography column. The desired product was eluted with 0-100% ethyl acetate/hexanes over 1.2 L of total solvent. Like fractions (TLC: $R_f$=0.67; 50% ethyl acetate/hexanes) were concentrated down to give 210 mg off-white solid, which was used as is for next step. LC/MS m/z=791.05 (M−55)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 0.5 min hold at 100% B; Flow: 0.8 mL/min; Detection: UV (254 nm); Retention Time: 1.76 min.

342

(S)—N-(7-(2-(1-amino-2-(3,5-difluorophenyl)ethyl)-4-oxo-5-(trifluoromethyl)quinazolin-3(4H)-yl)-4-chloro-1-methyl-1H-indazol-3-yl)methanesulfonamide (Int JD8b)

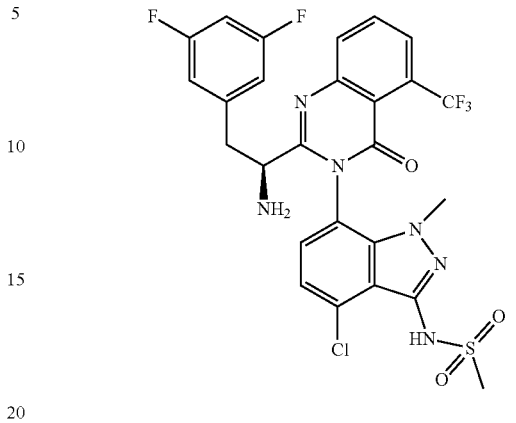

At RT, within a septum top vial equipped with a magnetic stirrer bar was added tert-butyl (S)-(1-(3-(4-chloro-3-(N-(4-methoxybenzyl)methylsulfonamido)-1-methyl-1H-indazol-7-yl)-4-oxo-5-(trifluoromethyl)-3,4-dihydroquinazolin-2-yl)-2-(3,5-difluorophenyl)ethyl)carbamate (210 mg, 0.248 mmol) (Int JD8a) in TFA (1.432 mL, 18.59 mmol). Triflic acid (0.132 mL, 1.487 mmol) was added to the reaction and rapidly stirred for 30 minutes. Dried down the reaction slowly under a stream of nitrogen to remove TFA, then diluted the remaining residue in DCM (3 mL). Partitioned the organic layer with 20 mL saturated aqueous NaHCO$_3$ solution. Dried the DCM layer over MgSO$_4$, filtered and evaporated down to dryness to give 220 mg of the title product as an off-white solid. This material was used as is for next step. LC/MS m/z=627.15 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (254 nm); Retention Time: 1.51 min.

N—((S)-1-(3-(4-chloro-1-methyl-3-(methylsulfonamido)-1H-indazol-7-yl)-4-oxo-5-(trifluoromethyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 128) and Example 127

Example 127

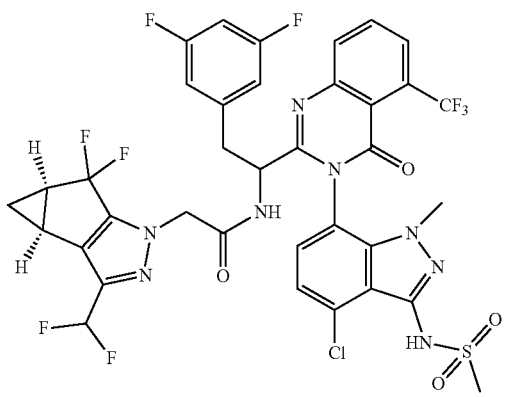

Mix of two stereoisomers

Example 128

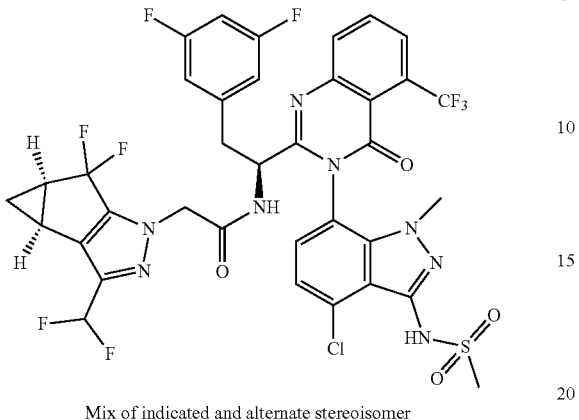

Mix of indicated and alternate stereoisomer

Within a septum cap vial equipped with a magnetic stirrer bar was added (S)—N-(7-(2-(1-amino-2-(3,5-difluorophenyl)ethyl)-4-oxo-5-(trifluoromethyl)quinazolin-3(4H)-yl)-4-chloro-1-methyl-1H-indazol-3-yl)methanesulfonamide (90 mg, 0.100 mmol) (Int JD8b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (30.5 mg, 0.116 mmol), and HOAT (4.10 mg, 0.030 mmol) in DMF (1.5 mL). TEA (98 µl, 0.703 mmol) followed by EDC (48.2 mg, 0.251 mmol) was added. The vial was capped and the suspension was stirred at RT overnight. The reaction mixture was filtered and purified by preparative HPLC to give two elutes.

Example 127 First Eluting Peak, 6.6 mg

LC/MS m/z=873.09 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.14 min.

Example 128 Second Eluting Peak, 21.1 mg

LC/MS m/z=873.09 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 99%; Retention Time: 2.2 min.

tert-butyl (S)-(1-(3-(4-chloro-3-(N-(4-methoxybenzyl)methylsulfonamido)-1-methyl-1H-indazol-7-yl)-5,7-difluoro-4-oxo-3,4-dihydroquinazolin-2-yl)-2-(3,5-difluorophenyl)ethyl)carbamate (Int JD9a)

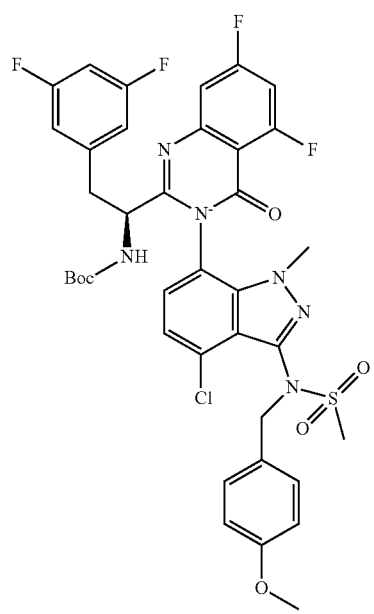

Within a septum top vial equipped with a magnetic stirrer bar was added (S)-2-((tert-butoxycarbonyl)amino)-3-(3,5-difluorophenyl)propanoic acid (200 mg, 0.664 mmol), 2-amino-4,6-difluorobenzoic acid (115 mg, 0.664 mmol), and diphenyl phosphite (0.449 mL, 2.323 mmol) in pyridine (1.5 mL). The vial was capped and the mixture was heated in an aluminum block for 1.5 hours at 70° C. N-(7-amino-4-chloro-1-methyl-1H-indazol-3-yl)-N-(4-methoxybenzyl)methanesulfonamide (288 mg, 0.730 mmol) (Int17d) was then added to the mixture and the cap placed on the vial, and the reaction was again heated to 70° C. for an additional 2 hours. LC/MS after cooling showed the desired product as a major peak. Dried down the reaction slowly under a stream of nitrogen. The residue was dissolved in DCM and was transferred to the top of a 40 g silica gel chromatography column. The desired product was eluted with 0-100% ethyl acetate/hexanes over 1.2 L of total solvent. Like fractions (TLC: R$_f$=0.69; 50% ethyl acetate/hexanes) were concentrated down to give 310 mg of yellow foam. This material will used as is for next step. LC/MS m/z=759.2 (M-55)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (254 nm); Retention Time: 1.88 min.

345

(S)—N-(7-(2-(1-amino-2-(3,5-difluorophenyl)ethyl)-5,7-difluoro-4-oxoquinazolin-3(4H)-yl)-4-chloro-1-methyl-1H-indazol-3-yl)methanesulfonamide (Int JD9b)

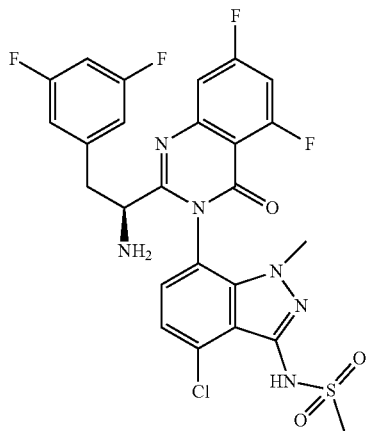

At RT, within a septum top vial equipped with a magnetic stirrer bar was added tert-butyl (S)-(1-(3-(4-chloro-3-(N-(4-methoxybenzyl)methylsulfonamido)-1-methyl-1H-indazol-7-yl)-5,7-difluoro-4-oxo-3,4-dihydroquinazolin-2-yl)-2-(3,5-difluorophenyl)ethyl)carbamate (310 mg, 0.380 mmol) (Int JD9a) in TFA (2.197 mL, 28.5 mmol). Triflic acid (0.203 mL, 2.282 mmol) was added to the reaction and rapidly stirred for 1 hour. Dried down the reaction slowly under a stream of nitrogen to remove TFA, then diluted the remaining residue in DCM (3 mL). Partitioned the organic layer with 20 mL saturated aqueous NaHCO₃ solution. Dried the DCM layer over MgSO₄, filtered and evaporated down to dryness to give 301 mg of title product which was used as is for next step. LC/MS m/z=595.2 (M+H)⁺. Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (254 nm); Retention Time: 1.51 min.

N—((S)-1-(3-(4-chloro-1-methyl-3-(methylsulfonamido)-1H-indazol-7-yl)-5,7-difluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 130) and Example 129

Example 129

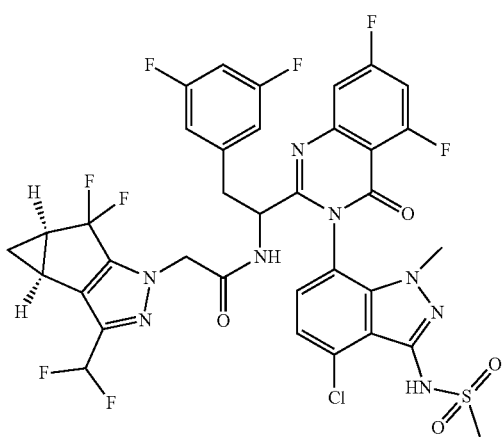

Mix of two stereoisomers

346

-continued

Example 130

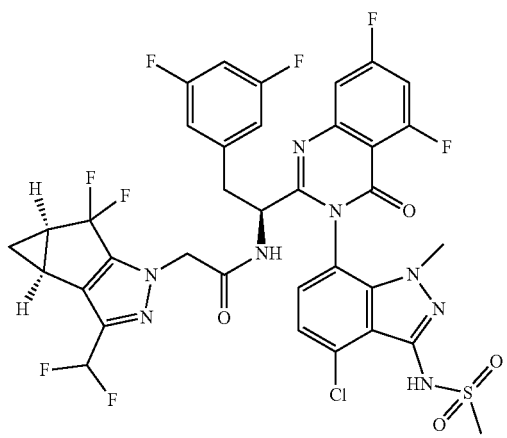

Mix of indicated and alternate stereoisomer

Within a red septum cap vial equipped with a magnetic stirrer bar was added (S)—N-(7-(2-(1-amino-2-(3,5-difluorophenyl)ethyl)-5,7-difluoro-4-oxoquinazolin-3(4H)-yl)-4-chloro-1-methyl-1H-indazol-3-yl)methanesulfonamide (60 mg, 0.101 mmol) (Int JD9b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (30.6 mg, 0.116 mmol), and HOAT (4.12 mg, 0.030 mmol) in DMF (1.5 mL). TEA (98 µl, 0.706 mmol) followed by EDC (48.3 mg, 0.252 mmol) was added. The vial was capped and the suspension was stirred at RT overnight. The reaction mixture was filtered and purified by preparative HPLC to give two elutes.

Example 129 First eluting peak, 5.4 mg. LC/MS m/z=841.03 (M+H)⁺. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.09 min.

Example 130 Second Eluting Peak, 16.5 mg

LC/MS m/z=841.04 (M+H)⁺. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.15 min.

(S)—N-(1-(3-(4-chloro-1-methyl-3-(methylsulfona-mido)-1H-indazol-7-yl)-5,7-difluoro-4-oxo-3,4-dihy-droquinazolin-2-yl)-2-(3,5-difluorophenyl)ethyl)-2-(3-cyclopropyl-1H-pyrazol-1-yl)acetamide
(Example 132 and Example 131)

Example 131

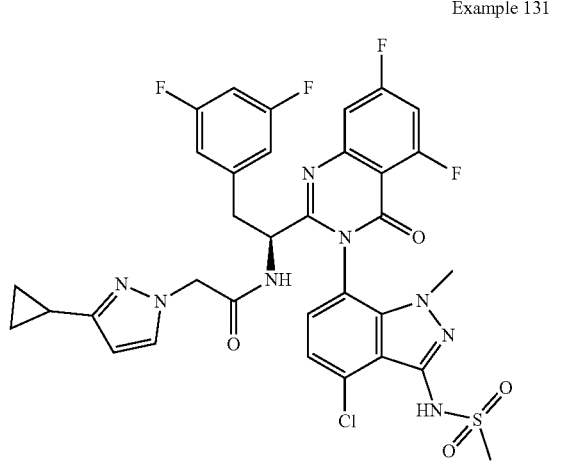

Mix of enantiomers of unknown proportion

Example 132

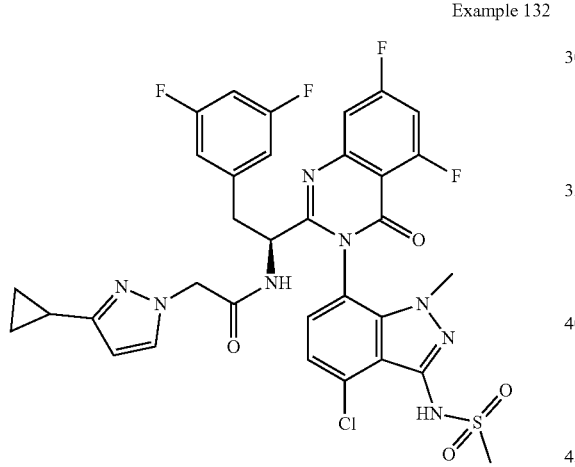

Mix of enantiomers of unknown proportion

Within a septum cap vial equipped with a magnetic stirrer bar was added (S)—N-(7-(2-(1-amino-2-(3,5-difluorophe-nyl)ethyl)-5,7-difluoro-4-oxoquinazolin-3(4H)-yl)-4-chloro-1-methyl-1H-indazol-3-yl)methanesulfonamide (65 mg, 0.101 mmol) (Int JD9b), 2-(3-cyclopropyl-1H-pyrazol-1-yl)acetic acid (19.21 mg, 0.116 mmol), and HOAT (4.10 mg, 0.030 mmol) in DMF (1.0 mL). TEA (98 µl, 0.704 mmol) followed by EDC (48.2 mg, 0.251 mmol) was added. The vial was capped and the suspension was stirred at RT overnight. The reaction mixture was filtered and purified by preparative HPLC to give two elutes.

Example 131 First Eluting Peak, 5.6 mg

LC/MS m/z=743.12 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammo-nium acetate; Temperature: 50° C.; Gradient: 0% B to 100% B over 3 min, then a 0.75 min hold at 100% B; Flow: 1 mL/min; Detection: MS and UV (220 nm); Purity: 96%; Retention Time: 1.94 min.

Example 132 Second Eluting Peak, 15.3 mg

LC/MS m/z=743.07 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammo-nium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.05 min.

(S)-N-(1-(3-(4-chloro-1-methyl-3-(methylsulfona-mido)-1H-indazol-7-yl)-5-methyl-4-oxo-3,4-dihyd-roquinazolin-2-yl)-2-(3,5-difluorophenyl)ethyl)-2-(3-cyclopropyl-1H-pyrazol-1-yl)acetamide
(Example 134 and Example 133)

Example 133

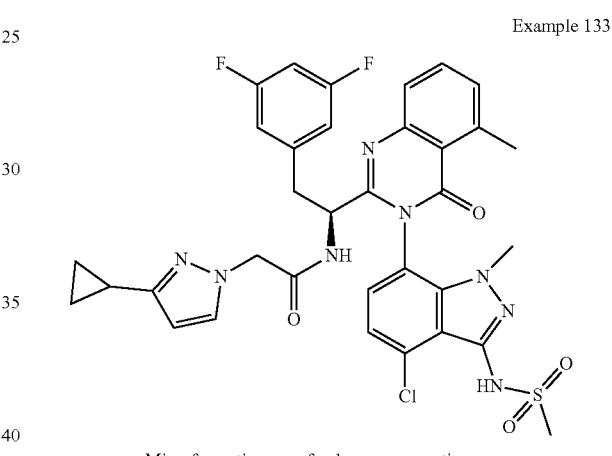

Mix of enantiomers of unknown proportion

Example 134

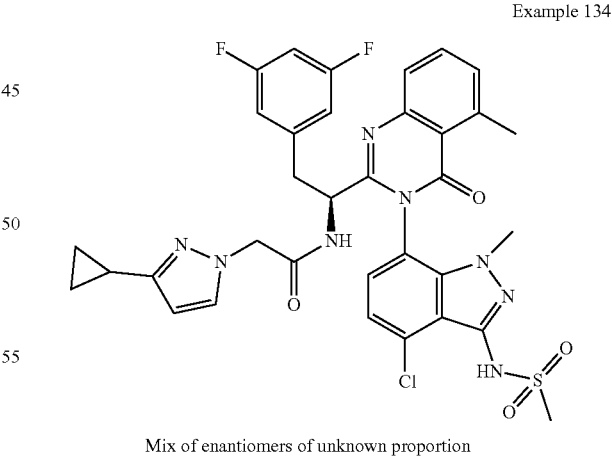

Mix of enantiomers of unknown proportion

Within a septum cap vial equipped with a magnetic stirrer bar was added (S)—N-(7-(2-(1-amino-2-(3,5-difluorophe-nyl)ethyl)-5-methyl-4-oxoquinazolin-3(4H)-yl)-4-chloro-1-methyl-1H-indazol-3-yl)methanesulfonamide (65 mg, 0.101 mmol) (Int JD7b), 2-(3-cyclopropyl-1H-pyrazol-1-yl)acetic acid (19.29 mg, 0.116 mmol), and HOAT (4.12 mg, 0.030 mmol) in DMF (1.25 mL). TEA (99 µl, 0.707 mmol)

followed by EDC (48.4 mg, 0.252 mmol) was added. The vial was capped and the suspension was stirred at RT overnight. The reaction mixture was filtered and purified by preparative HPLC to give two elutes.

Example 133 First eluting peak, 13.9 mg

LC/MS m/z=721.11 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 99%; Retention Time: 2.02 min.

Example 134 Second Eluting Peak, 21.9 mg

LC/MS m/z=721.12 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.15 min. $^1$H NMR (500 MHz, DMSO-d$_6$; WS (water suppression)) δ 9.92 (s, 1H), 8.88 (br d, J=7.9 Hz, 1H), 7.82 (t, J=7.8 Hz, 1H), 7.66 (br d, J=7.9 Hz, 2H), 7.49-7.34 (m, 2H), 7.28-7.21 (m, 1H), 7.08-6.93 (m, 1H), 6.70 (br d, J=6.4 Hz, 2H), 5.83 (s, 1H), 4.62-4.51 (m, 1H), 4.37 (br d, J=15.9 Hz, 1H), 4.25 (br d, J=15.9 Hz, 1H), 3.58 (s), 3.08-2.88 (m), 2.76 (s), 1.74 (br dd, J=8.4, 4.4 Hz, 1H), 1.24 (s, 1H), 0.76 (br d, J=8.2 Hz, 2H), 0.51 (br s, 2H).

(S)—N-(1-(3-(4-chloro-1-methyl-3-(methylsulfonamido)-1H-indazol-7-yl)-4-oxo-5-(trifluoromethyl)-3,4-dihydroquinazolin-2-yl)-2-(3,5-difluorophenyl)ethyl)-2-(3-cyclopropyl-1H-pyrazol-1-yl)acetamide (Example 136 and Example 135)

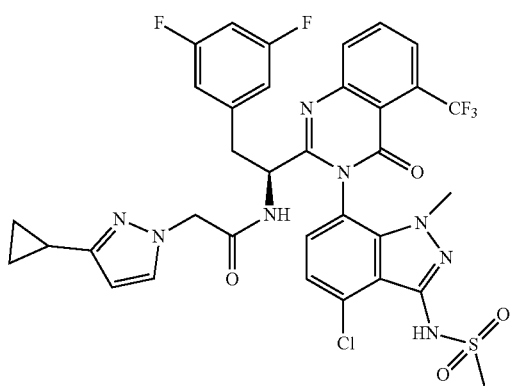

Example 135
Mix of two stereoisomers

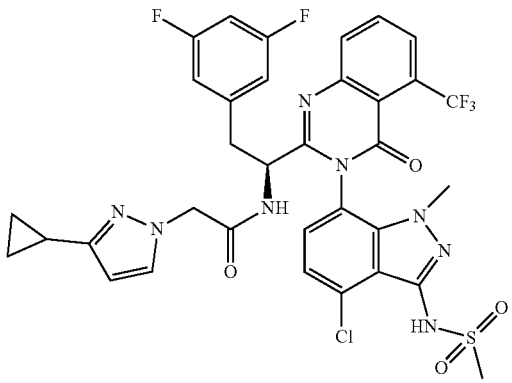

Example 136
A mixture of indicated stereoisomer and a stereoisomer

Within a septum cap vial equipped with a magnetic stirrer bar was added (S)—N-(7-(2-(1-amino-2-(3,5-difluorophenyl)ethyl)-4-oxo-5-(trifluoromethyl)quinazolin-3(4H)-yl)-4-chloro-1-methyl-1H-indazol-3-yl)methanesulfonamide (65 mg, 0.101 mmol) (Int JD8b), 2-(3-cyclopropyl-1H-pyrazol-1-yl)acetic acid (19.22 mg, 0.116 mmol), and HOAT (4.11 mg, 0.030 mmol) in DMF (1.25 mL). TEA (98 μl, 0.704 mmol) followed by EDC (48.2 mg, 0.251 mmol) was added. The vial was capped and the suspension was stirred at RT overnight. The reaction mixture was filtered and purified by preparative HPLC to give two elutes.

Example 135 First eluting peak, 11.1 mg. LC/MS m/z=775.07 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.02 min.

Example 136 Second Eluting Peak, 35.4 mg

LC/MS m/z=775.06 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 99%; Retention Time: 2.13 min.

351 tert-butyl (S)-(1-(3-(4-chloro-3-(N-(4-methoxybenzyl)methylsulfonamido)-1-methyl-1H-indazol-7-yl)-4-oxo-7-(trifluoromethyl)-3,4-dihydroquinazolin-2-yl)-2-(3,5-difluorophenyl)ethyl)carbamate (Int JD10a)

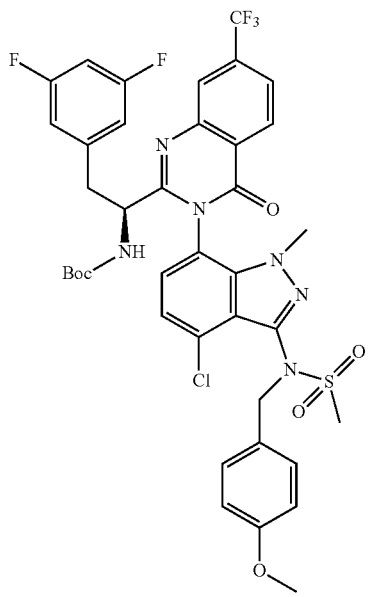 [SMILES: COc1ccc(CN(c2nn(C)c3c(-n4c([C@H](Cc5cc(F)cc(F)c5)NC(=O)OC(C)(C)C)nc5cc(C(F)(F)F)ccc5c4=O)ccc(Cl)c23)S(C)(=O)=O)cc1]

Within a septum top vial equipped with a magnetic stirrer bar was added (S)-2-((tert-butoxycarbonyl)amino)-3-(3,5-difluorophenyl)propanoic acid (100 mg, 0.332 mmol), 2-amino-4-(trifluoromethyl)benzoic acid (68.1 mg, 0.332 mmol), N-(7-amino-4-chloro-1-methyl-1H-indazol-3-yl)-N-(4-methoxybenzyl)methanesulfonamide (131 mg, 0.332 mmol) (Int 17d) and diphenyl phosphite (0.257 mL, 1.328 mmol) in pyridine (1.25 mL) (added last). The vial was capped and the mixture was heated in an aluminum block for about 16 hours at 70° C. LC/MS showed a peak consistent with the desired product. Cool to RT and remove solvents under a stream of nitrogen overnight. The residue was dissolved in DCM and was transferred to the top of a 40 g silica gel chromatography column. The desired product was eluted with 0-100% ethyl acetate/hexanes over 1.2 L of total solvent. Like fractions (TLC: $R_f$=0.79; 50% ethyl acetate/hexanes) were concentrated down to give 190 mg of off-white solid, which was used as is for next step. LC/MS m/z=869.3 (M+Na)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.92 min.

352

(S)—N-(7-(2-(1-amino-2-(3,5-difluorophenyl)ethyl)-4-oxo-7-(trifluoromethyl)quinazolin-3(4H)-yl)-4-chloro-1-methyl-1H-indazol-3-yl)methanesulfonamide (Int JD10b)

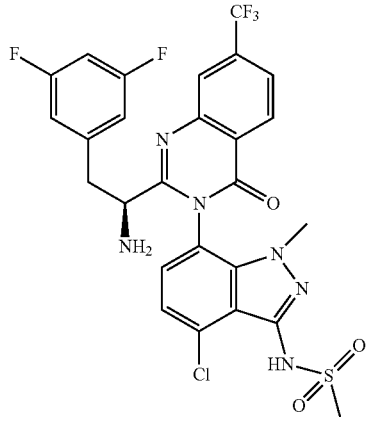 [SMILES: Cn1nc(NS(C)(=O)=O)c2c(Cl)ccc(-n3c([C@@H](N)Cc4cc(F)cc(F)c4)nc4cc(C(F)(F)F)ccc4c3=O)c21]

At RT, within a septum top vial equipped with a magnetic stirrer bar was added tert-butyl (S)-(1-(3-(4-chloro-3-(N-(4-methoxybenzyl)methylsulfonamido)-1-methyl-1H-indazol-7-yl)-4-oxo-7-(trifluoromethyl)-3,4-dihydroquinazolin-2-yl)-2-(3,5-difluorophenyl)ethyl)carbamate (190 mg, 0.224 mmol) (Int JD10a) in TFA (1.296 mL, 16.82 mmol). Triflic acid (0.119 mL, 1.346 mmol) was added to the reaction and rapidly stirred for 1 hour. Dried down the reaction slowly under a stream of nitrogen to remove TFA, then diluted the remaining residue in DCM (3 mL). Partitioned the organic layer with 20 mL saturated aqueous NaHCO$_3$ solution. Dried the DCM layer over MgSO$_4$, filtered and evaporated down to dryness to give 160 mg of off-white solid, which was used as is for next step. LC/MS m/z=627.15 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (254 nm); Retention Time: 1.57 min.

N—((S)-1-(3-(4-chloro-1-methyl-3-(methylsulfonamido)-1H-indazol-7-yl)-4-oxo-7-(trifluoromethyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 138) and Example 137

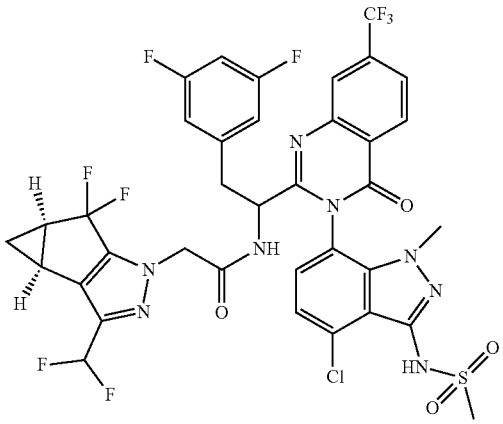

Example 137
Mix of two stereoisomers

-continued

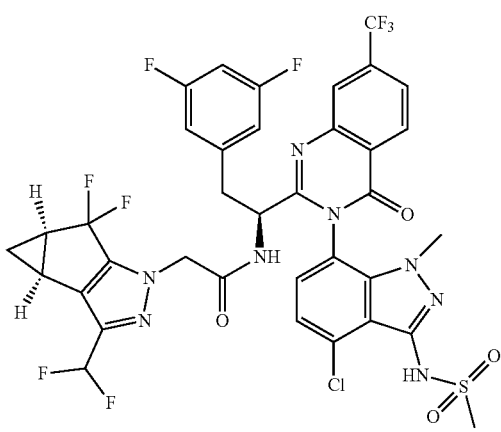

Example 138
Mix of indicated and
alternate stereoisomer

Within a septum cap vial equipped with a magnetic stirrer bar was added (S)—N-(7-(2-(1-amino-2-(3,5-difluorophenyl)ethyl)-4-oxo-7-(trifluoromethyl)quinazolin-3(4H)-yl)-4-chloro-1-methyl-1H-indazol-3-yl)methanesulfonamide (63 mg, 0.100 mmol) (Int JD10b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (30.5 mg, 0.116 mmol), and HOAT (4.10 mg, 0.030 mmol) in DMF (1.5 mL). TEA (98 μl, 0.703 mmol) followed by EDC (48.2 mg, 0.251 mmol) was added. The vial was capped and the suspension was stirred at RT overnight. The reaction mixture was filtered and purified by preparative HPLC to give two elutes.

Example 137 First Eluting Peak, 9.3 mg

LC/MS m/z=873.04 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.25 min.

Example 138 Second Eluting Peak, 18.1 mg

LC/MS m/z=872.99 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.29 min. $^1$H NMR (500 MHz, DMSO-d$_6$, WS (water suppression)) δ 9.89 (s, 1H), 9.17 (br d, J=7.9 Hz, 1H), 8.44 (br d, J=7.9 Hz, 1H), 8.07 (s, 1H), 7.99 (br d, J=8.5 Hz, 1H), 7.74 (br d, J=7.6 Hz, 1H), 7.47 (br d, J=7.9 Hz, 1H), 7.13-6.98 (m, 2H), 6.67 (br d, J=6.7 Hz, 2H), 4.71-4.62 (m, 1H), 4.60 (br s, 1H), 4.58-4.42 (m, 2H), 3.37 (br s), 3.11-2.92 (m), 2.48-2.35 (m, 1H), 1.35 (br d, J=7.0 Hz, 1H), 1.24 (br s, 1H), 0.95-0.74 (m, 1H).

tert-butyl (S)-(1-(3-(4-chloro-3-(N-(4-methoxybenzyl)methylsulfonamido)-1-methyl-1H-indazol-7-yl)-4-oxo-6-(trifluoromethoxy)-3,4-dihydroquinazolin-2-yl)-2-(3,5-difluorophenyl)ethyl)carbamate (Int JD11a)

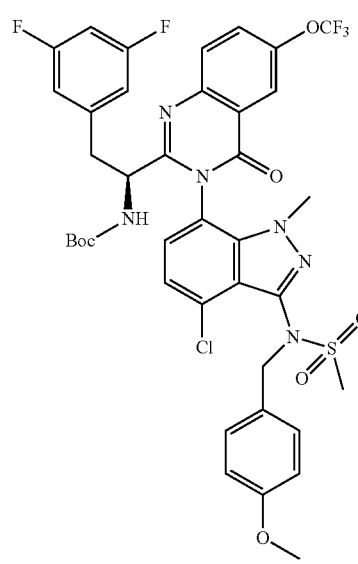

Within a septum top vial equipped with a magnetic stirrer bar was added (S)-2-((tert-butoxycarbonyl)amino)-3-(3,5-difluorophenyl)propanoic acid (100 mg, 0.332 mmol), 2-amino-5-(trifluoromethoxy)benzoic acid (73.4 mg, 0.332 mmol), N-(7-amino-4-chloro-1-methyl-1H-indazol-3-yl)-N-(4-methoxybenzyl)methanesulfonamide (118 mg, 0.299 mmol) (Int17d) and diphenyl phosphite (0.257 mL, 1.328 mmol) in pyridine (1.25 mL; added last). The vial was capped and the mixture was heated in an aluminum block for 48 hours at 70° C. LC/MS showed a peak consistent with the desired product. Cool to RT and remove solvents under a stream of nitrogen overnight. The residue was dissolved in DCM and was transferred to the top of a 40 g silica gel chromatography column. The desired product was eluted with 0-100% ethyl acetate/hexanes over 1.2 L of total solvent. Like fractions (TLC: R$_f$=0.83; 50% ethyl acetate/hexanes) were concentrated down to give 190 mg of off-white solid, which was used as is for next step. LC/MS m/z=807.2 (M-55)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.93 min.

355

(S)—N-(7-(2-(1-amino-2-(3,5-difluorophenyl)ethyl)-4-oxo-6-(trifluoromethoxy)quinazolin-3(4H)-yl)-4-chloro-1-methyl-1H-indazol-3-yl)methanesulfonamide (Int JD11b)

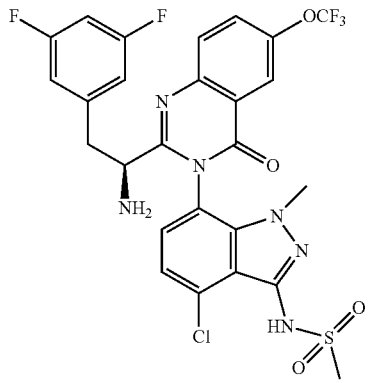 [SMILES: Cn1nc(NS(C)(=O)=O)c2c(Cl)ccc(-n3c([C@@H](N)Cc4cc(F)cc(F)c4)nc4ccc(OC(F)(F)F)cc4c3=O)c21]

At RT, within a septum top vial equipped with a magnetic stirrer bar was added tert-butyl (S)-(1-(3-(4-chloro-3-(N-(4-methoxybenzyl)methylsulfonamido)-1-methyl-1H-indazol-7-yl)-4-oxo-6-(trifluoromethoxy)-3,4-dihydroquinazolin-2-yl)-2-(3,5-difluorophenyl)ethyl)carbamate (190 mg, 0.220 mmol) (Int JD11a) in TFA (1.272 mL, 16.51 mmol). Triflic acid (0.117 mL, 1.321 mmol) was added to the reaction and rapidly stirred for 1 hour. Dried down the reaction slowly under a stream of nitrogen to remove TFA, then diluted the remaining residue in DCM (3 mL). Partitioned the organic layer with 20 mL saturated aqueous NaHCO$_3$ solution. Dried the DCM layer over MgSO$_4$, filtered and evaporated down to dryness to give 150 mg of off-white solid, which was used as is for next step. LC/MS m/z=643.1 (M+H)$^+$. Column: Waters Aquity UPLC BEH C18, 2.1 mm×50 mm, 1.7 µm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (254 nm); Retention Time: 1.35 min.

N—((S)-1-(3-(4-chloro-1-methyl-3-(methylsulfonamido)-1H-indazol-7-yl)-4-oxo-6-(trifluoromethoxy)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 140) and Example 139

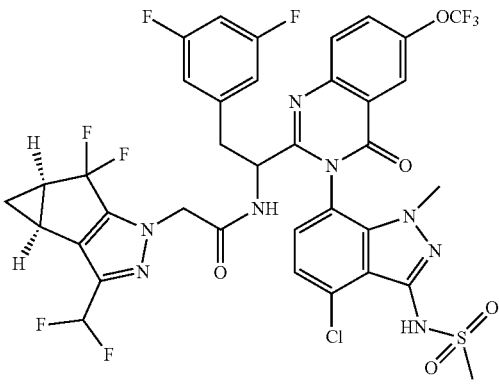

Example 139
Mix of two stereoisomers

356

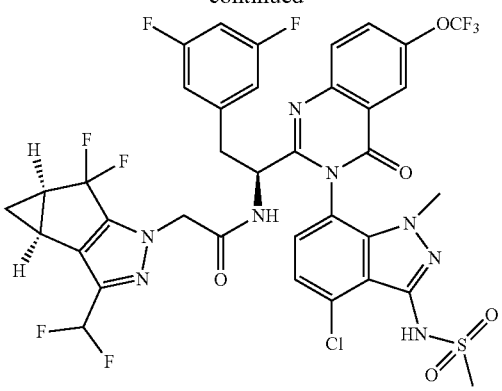

Example 140
Mix of indicated and alternate stereoisomer

Within a septum cap vial equipped with a magnetic stirrer bar was added (S)—N-(7-(2-(1-amino-2-(3,5-difluorophenyl)ethyl)-4-oxo-6-(trifluoromethoxy)quinazolin-3(4H)-yl)-4-chloro-1-methyl-1H-indazol-3-yl)methanesulfonamide (65 mg, 0.101 mmol) (Int JD11b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (30.7 mg, 0.116 mmol), and HOAT (4.13 mg, 0.030 mmol) in DMF (1.5 mL). TEA (99 µl, 0.708 mmol) followed by EDC (48.4 mg, 0.253 mmol) was added. The vial was capped and the suspension was stirred at RT overnight. The vial was capped and the suspension was stirred at RT overnight. The reaction mixture was filtered and purified by preparative HPLC to give two elutes.

Example 139 First Eluting Peak, 7.2 mg

LC/MS m/z=889.13 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 98%; Retention Time: 2.25 min.

Example 140 Second Eluting Peak, 16.6 mg

LC/MS m/z=889.13 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.3 min. $^1$H NMR (500 MHz, DMSO-d$_6$; WS (water suppression)) δ 9.88 (s, 1H), 9.23 (br d, J=7.9 Hz, 1H), 8.07 (br s, 1H), 8.03-7.95 (m, 2H), 7.73 (d, J=7.6 Hz, 1H), 7.47 (d, J=7.6 Hz, 1H), 7.11-6.99 (m, 2H), 6.96-6.89 (m, 1H), 6.82 (s, 1H), 6.65 (br d, J=7.0 Hz, 2H), 4.68-4.62 (m, 1H), 4.59 (br s, 1H), 4.56-4.46 (m, 2H), 3.91 (s), 3.41-3.33 (m), 3.19 (s), 3.06-2.95 (m), 2.48-2.41 (m, 2H), 1.39-1.30 (m, 1H), 1.24 (s, 1H), 0.84 (br s, 1H).

(S)—N-(1-(3-(4-chloro-1-methyl-3-(methylsulfona-mido)-1H-indazol-7-yl)-4-oxo-7-(trifluoromethyl)-3,4-dihydroquinazolin-2-yl)-2-(3,5-difluorophenyl) ethyl)-2-(3-(trifluoromethyl)-1H-pyrazol-1-yl) acetamide (Example 142 and Example 141)

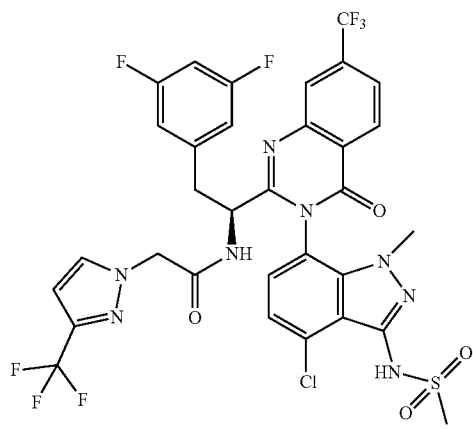

Example 141
Mix of two stereoisomers

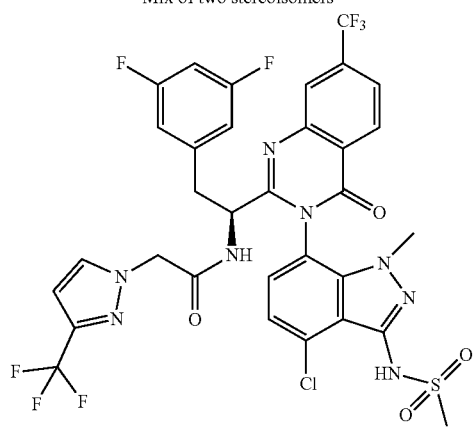

Example 142
Mix of indicated and
alternate stereoisomer

Within a septum cap vial equipped with a magnetic stirrer bar was added (S)—N-(7-(2-(1-amino-2-(3,5-difluorophe-nyl)ethyl)-4-oxo-7-(trifluoromethyl)quinazolin-3(4H)-yl)-4-chloro-1-methyl-1H-indazol-3-yl)methanesulfonamide (63 mg, 0.100 mmol) (Int JD10b), 2-(3-(trifluoromethyl)-1H-pyrazol-1-yl)acetic acid (22.43 mg, 0.116 mmol), and HOAT (4.10 mg, 0.030 mmol) in DMF (1.5 mL). TEA (98 µl, 0.703 mmol) followed by EDC (48.2 mg, 0.251 mmol) was added. The vial was capped and the suspension was stirred at RT overnight. The reaction mixture was filtered and purified by preparative HPLC to give two elutes.

Example 141 First Eluting Peak, 10.4 mg

LC/MS m/z=803.05 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 98%; Retention Time: 2.17 min.

Example 142 Second Eluting Peak, 19.3 mg

LC/MS m/z=803.05 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 97%; Retention Time: 2.25 min.

(S)—N-(1-(3-(4-chloro-1-methyl-3-(methylsulfona-mido)-1H-indazol-7-yl)-4-oxo-6-(trifluoromethoxy)-3,4-dihydroquinazolin-2-yl)-2-(3,5-difluorophenyl) ethyl)-2-(3-(trifluoromethyl)-1H-pyrazol-1-yl) acetamide (Example 144 and Example 143)

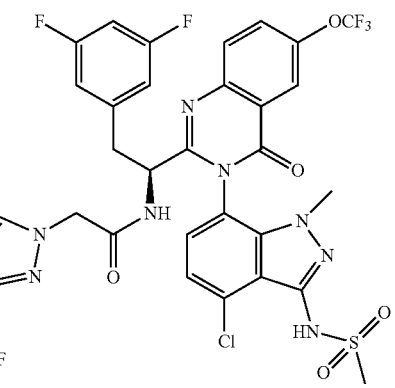

Example 143
Mix of two stereoisomers

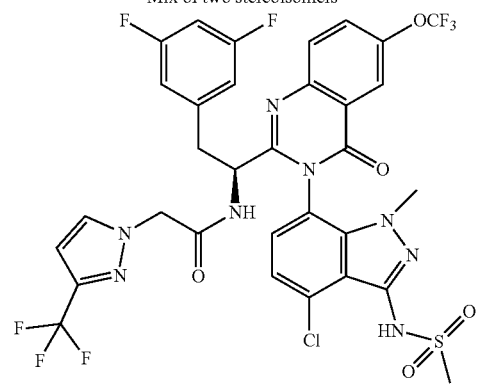

Example 144
Mix of indicated and
alternate stereoisomer

Within a septum cap vial equipped with a magnetic stirrer bar was added (S)—N-(7-(2-(1-amino-2-(3,5-difluorophe-nyl)ethyl)-4-oxo-6-(trifluoromethoxy)quinazolin-3(4H)-yl)-4-chloro-1-methyl-1H-indazol-3-yl)methanesulfonamide (64 mg, 0.100 mmol) (Int JD11b), 2-(3-(trifluoromethyl)-1H-pyrazol-1-yl)acetic acid (22.22 mg, 0.114 mmol), and HOAT (4.06 mg, 0.030 mmol) in DMF (1.5 mL). TEA (97 µl, 0.697 mmol) followed by EDC (47.7 mg, 0.249 mmol) was added. The vial was capped and the suspension was stirred at RT overnight. The reaction mixture was filtered and purified by preparative HPLC to give two elutes.

Example 143 First Eluting Peak, 13.6 mg

LC/MS m/z=819.0 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 99%; Retention Time: 2.2 min.

Example 144 Second Eluting Peak, 30.0 mg

LC/MS m/z=818.99 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.28 min.

tert-butyl (S)-(1-((4-chloro-3-(N-(4-methoxybenzyl) methylsulfonamido)-1-methyl-1H-indazol-7-yl) amino)-3-(3,5-difluorophenyl)-1-oxopropan-2-yl) carbamate (Int JD13a)

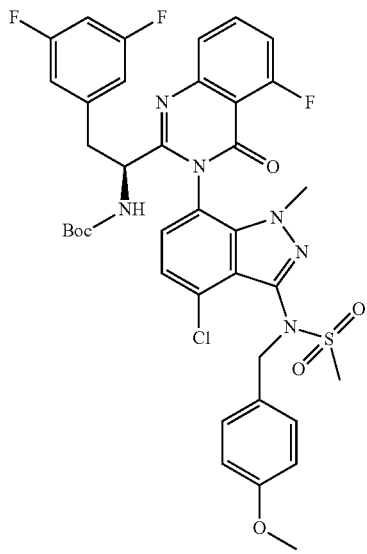 [SMILES: COc1ccc(CN(c2nn(C)c3c(-n4c([C@H](Cc5cc(F)cc(F)c5)NC(=O)OC(C)(C)C)nc5cccc(F)c5c4=O)ccc(Cl)c23)S(C)(=O)=O)cc1]

Within a septum top vial equipped with a magnetic stirrer bar was added (S)-2-((tert-butoxycarbonyl)amino)-3-(3,5-difluorophenyl)propanoic acid (250 mg, 0.830 mmol), 2-amino-6-fluorobenzoic acid (129 mg, 0.830 mmol), N-(7-amino-4-chloro-1-methyl-1H-indazol-3-yl)-N-(4-methoxybenzyl)methanesulfonamide (311 mg, 0.788 mmol) and diphenyl phosphite (0.803 mL, 4.15 mmol) in pyridine (2 mL; added last). The vial was capped and the mixture was heated in an aluminum block for about 16 hours at 70° C. LC/MS showed a peak consistent with the desired product. Cool to RT and remove solvents under a stream of nitrogen overnight. The residue was dissolved in DCM and was transferred to the top of a 40 g silica gel chromatography column. The desired product was eluted with 0-100% ethyl acetate/hexanes over 1.3 L of total solvent. Like fractions (TLC: R$_f$=0.38; 50% ethyl acetate/hexanes) were concentrated down to give 710 mg of material which was used as is for next step. LC/MS m/z=741.15 (M−55)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 0.5 min hold at 100% B; Flow: 0.8 mL/min; Detection: UV (220 nm); Retention Time: 1.64 min.

(S)—N-(7-(2-(1-amino-2-(3,5-difluorophenyl)ethyl)-5-fluoro-4-oxoquinazolin-3(4H)-yl)-4-chloro-1-methyl-1H-indazol-3-yl)methanesulfonamide (Int JD13b)

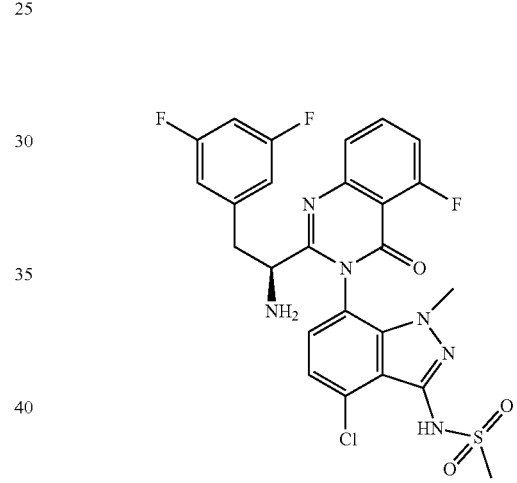

At RT, within a septum top vial equipped with a magnetic stirrer bar was added tert-butyl (S)-(1-(3-(4-chloro-3-(N-(4-methoxybenzyl)methylsulfonamido)-1-methyl-1H-indazol-7-yl)-5-fluoro-4-oxo-3,4-dihydroquinazolin-2-yl)-2-(3,5-difluorophenyl)ethyl)carbamate (710 mg, 0.891 mmol) (Int JD13a) in TFA (1.37 E+04 μl, 178 mmol). Triflic acid (949 μl, 10.69 mmol) was added to the reaction and rapidly stirred for 1 hour. Dried down the reaction slowly under a stream of nitrogen to remove TFA, then diluted the remaining residue in DCM (3 mL). Partitioned the organic layer with 20 mL saturated aqueous NaHCO$_3$ solution. Dried the DCM layer over MgSO$_4$, filtered and evaporated down to dryness to afford 660 mg of product which was used as is for next step. LC/MS m/z=577.15 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (254 nm); Retention Time: 1.49 min.

361 tert-butyl (S)-(1-(3-(4-chloro-3-(N-(4-methoxybenzyl)methylsulfonamido)-1-methyl-1H-indazol-7-yl)-5,8-difluoro-4-oxo-3,4-dihydroquinazolin-2-yl)-2-(3,5-difluorophenyl)ethyl)carbamate (Int JD14a)

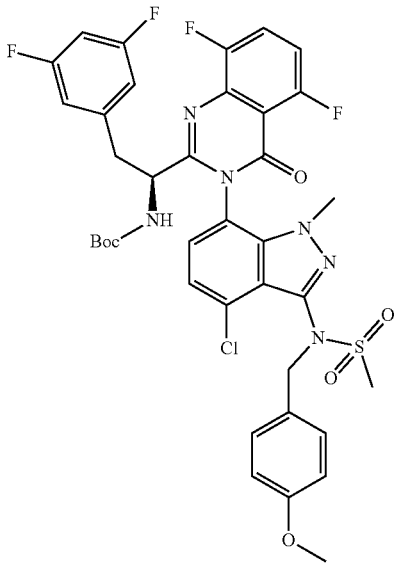 [SMILES: COc1ccc(CN(c2nn(C)c3c(-n4c([C@H](Cc5cc(F)cc(F)c5)NC(=O)OC(C)(C)C)nc5c(F)ccc(F)c5c4=O)ccc(Cl)c23)S(C)(=O)=O)cc1]

Within a septum top vial equipped with a magnetic stirrer bar was added (S)-2-((tert-butoxycarbonyl)amino)-3-(3,5-difluorophenyl)propanoic acid (220 mg, 0.730 mmol), 2-amino-3,6-difluorobenzoic acid (126 mg, 0.730 mmol), N-(7-amino-4-chloro-1-methyl-1H-indazol-3-yl)-N-(4-methoxybenzyl)methanesulfonamide (274 mg, 0.694 mmol) (Int17d) and diphenyl phosphite (0.565 mL, 2.92 mmol) in pyridine (2 mL) (added last). The vial was capped and the mixture was heated in an aluminum block for about 16 hours at 70° C. LC/MS showed a peak consistent with the desired product. Cool to RT and remove solvents under a stream of nitrogen overnight. The residue was dissolved in DCM and was transferred to the top of a 40 g silica gel chromatography column. The desired product was eluted with 0-100% ethyl acetate/hexanes over 1.3 L of total solvent. Like fractions (TLC: $R_f$=0.55; 50% ethyl acetate/hexanes) were concentrated down to give 378 mg of off-white solid, which was used as is in the next step. LC/MS m/z=759.2 (M−55)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.92 min.

362

(S)—N-(7-(2-(1-amino-2-(3,5-difluorophenyl)ethyl)-5,8-difluoro-4-oxoquinazolin-3(4H)-yl)-4-chloro-1-methyl-1H-indazol-3-yl)methanesulfonamide (Int JD14b)

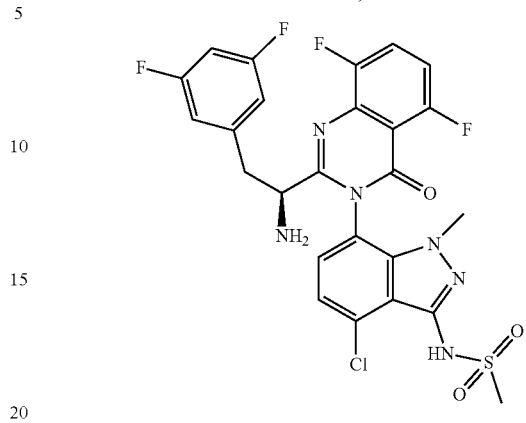

At RT, within a septum top vial equipped with a magnetic stirrer bar was added tert-butyl (S)-(1-(3-(4-chloro-3-(N-(4-methoxybenzyl)methylsulfonamido)-1-methyl-1H-indazol-7-yl)-5,8-difluoro-4-oxo-3,4-dihydroquinazolin-2-yl)-2-(3,5-difluorophenyl)ethyl)carbamate (710 mg, 0.871 mmol) (Int JD14a) in TFA (1.34 E+04 μl, 174 mmol). Triflic acid (928 μl, 10.45 mmol) was added to the reaction and rapidly stirred for 1 hour. Dried down the reaction slowly under a stream of nitrogen to remove TFA, then diluted the remaining residue in DCM (3 mL). Partitioned the organic layer with 20 mL saturated aqueous NaHCO$_3$ solution. Dried the DCM layer over MgSO$_4$, filtered and evaporated down to dryness to give 380 mg of material that was used as is for next step. LC/MS m/z=595.15 (M+H)$^+$. Column: Waters Aquity UPLC BEH C18, 2.1 mm×50 mm, 1.7 μm particles; Mobile Phase A: 100% water with 0.05% TFA; Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.48 min.

(S)—N-(1-(3-(4-chloro-1-methyl-3-(methylsulfonamido)-1H-indazol-7-yl)-5,8-difluoro-4-oxo-3,4-dihydroquinazolin-2-yl)-2-(3,5-difluorophenyl)ethyl)-2-(3-cyclopropyl-1H-pyrazol-1-yl)acetamide (Example 146 and Example 145)

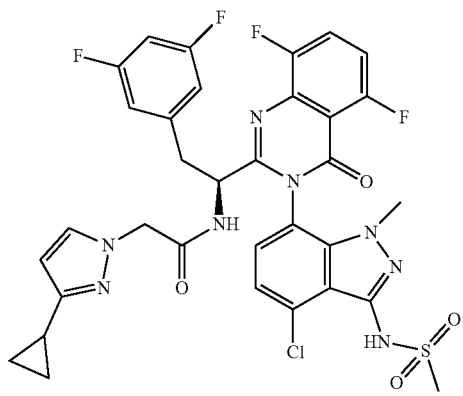

Example 145
Mix of enantiomers of unknown proportion

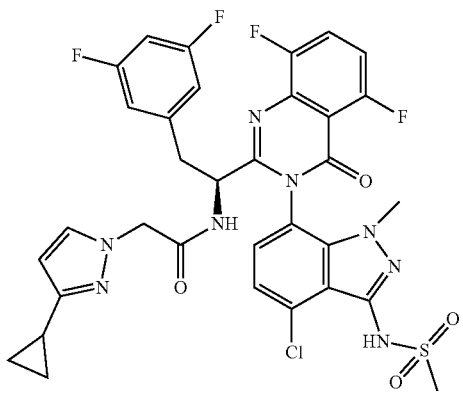

Example 146
Mix of enantiomers of unknown
proportion

Within a septum cap vial equipped with a magnetic stirrer bar was added (S)—N-(7-(2-(1-amino-2-(3,5-difluorophenyl)ethyl)-5,8-difluoro-4-oxoquinazolin-3(4H)-yl)-4-chloro-1-methyl-1H-indazol-3-yl)methanesulfonamide (63 mg, 0.100 mmol) (Int JD14b), 2-(3-cyclopropyl-1H-pyrazol-1-yl)acetic acid (19.02 mg, 0.114 mmol), and HOAT (4.06 mg, 0.030 mmol) in DMF (1.5 mL). TEA (0.097 mL, 0.697 mmol) followed by EDC (47.7 mg, 0.249 mmol) was added. The vial was capped and the suspension was stirred at RT overnight. The reaction mixture was filtered and purified by preparative HPLC to afford two elutes.

Example 145 First Eluting Peak, 8.1 mg

LC/MS m/z=743.05 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.0 min.

Example 146 Second Eluting Peak, 17.8 mg

LC/MS m/z=743.06 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 99%; Retention Time: 2.11 min.

N—((S)-1-(3-(4-chloro-1-methyl-3-(methylsulfonamido)-1H-indazol-7-yl)-5,8-difluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 148) and Example 147

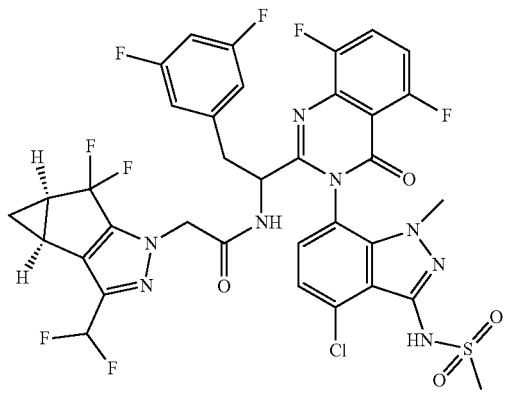

Example 147
Mix of two stereoisomers

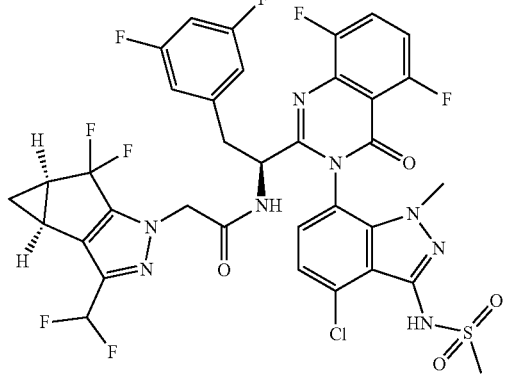

Example 148
A mixture of indicated
stereoisomer and a stereoisomer

Within a septum cap vial equipped with a magnetic stirrer bar was added (S)—N-(7-(2-(1-amino-2-(3,5-difluorophenyl)ethyl)-5,8-difluoro-4-oxoquinazolin-3(4H)-yl)-4-chloro-1-methyl-1H-indazol-3-yl)methanesulfonamide (63 mg, 0.100 mmol) (Int JD14b), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (30.2 mg, 0.114 mmol), and HOAT (4.06 mg, 0.030 mmol) in DMF (1.5 mL). TEA (0.097 mL, 0.697 mmol) followed by EDC (47.7 mg, 0.249 mmol) was added. The vial was capped and the suspension was stirred at RT overnight. The reaction mixture was filtered and purified by preparative HPLC to afford two elutes.

Example 147 First Eluting Peak, 7.8 mg

LC/MS m/z=841.01 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100%

B over 3 min, then a 0.75 min hold at 100% B; Flow: 1 mL/min; Detection: MS and UV (220 nm); Purity: 100%; Retention Time: 2.17 min.

Example 148 Second Eluting Peak, 9.9 mg

LC/MS m/z=841.02 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.22 min. $^1$H NMR (500 MHz, DMSO-d$_6$; WS (water suppression)) δ 9.19 (br d, J=7.3 Hz, 1H), 7.95-7.88 (m, 1H), 7.71 (dd, J=7.9, 2.1 Hz, 1H), 7.50-7.42 (m, 2H), 7.14-6.99 (m, 1H), 6.94-6.89 (m, 1H), 6.81 (s, 1H), 6.68 (br d, J=6.7 Hz, 2H), 4.63-4.45 (m, 3H), 3.91 (s), 3.41 (br), 3.19 (s), 3.05-2.97 (m), 2.56-2.54 (m, 1H), 2.48-2.41 (m, 1H), 1.40-1.30 (m, 1H), 1.24 (s, 1H), 0.90-0.81 (m, 1H).

(S)—N-(1-(3-(4-chloro-1-methyl-3-(methylsulfonamido)-1H-indazol-7-yl)-4-oxo-7-(trifluoromethyl)-3,4-dihydroquinazolin-2-yl)-2-(3,5-difluorophenyl)ethyl)-2-(3-cyclopropyl-1H-pyrazol-1-yl)acetamide (Example 151 and Example 150)

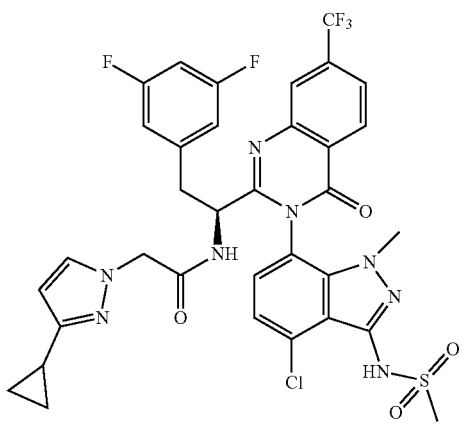

Example 150
Mix of enantiomers of unknown proportion

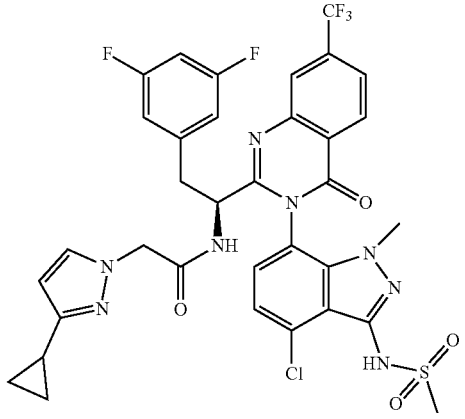

Example 151
Mix of enantiomers of unknown proportion

To a septum cap vial equipped with a magnetic stirrer bar was added (S)—N-(7-(2-(1-amino-2-(3,5-difluorophenyl)ethyl)-4-oxo-7-(trifluoromethyl)quinazolin-3(4H)-yl)-4-chloro-1-methyl-1H-indazol-3-yl)methanesulfonamide (63 mg, 0.100 mmol) (Int JD10b), 2-(3-cyclopropyl-1H-pyrazol-1-yl)acetic acid (20.87 mg, 0.126 mmol), and HOAT (4.10 mg, 0.030 mmol) in DMF (1.5 mL). TEA (0.098 mL, 0.703 mmol) followed by EDC (48.2 mg, 0.251 mmol) was added. The vial was capped and the suspension was stirred at RT overnight. LC/MS suggests formation of the desired MW product after stirring overnight with addition of 7 N ammonia in methanol. The reaction mixture was filtered and purified by preparative HPLC to give (S)—N-(1-(3-(4-chloro-1-methyl-3-(methylsulfonamido)-1H-indazol-7-yl)-4-oxo-7-(trifluoromethyl)-3,4-dihydroquinazolin-2-yl)-2-(3,5-difluorophenyl)ethyl)-2-(3-cyclopropyl-1H-pyrazol-1-yl)acetamide, as two compounds.

Example 150 First Eluting Peak, 16.6 mg

LC/MS m/z=775.02 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.3 min.

Example 151 Second Eluting Peak, 24.2 mg

LC/MS m/z=775.01 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.4 min. $^1$H NMR (500 MHz, DMSO-d$_6$; WS (water suppression)) δ 8.83 (br d, J=7.9 Hz, 1H), 8.49-8.36 (m, J=8.2 Hz, 1H), 8.10 (s, 1H), 8.05-7.89 (m, J=8.2 Hz, 1H), 7.77-7.62 (m, J=7.9 Hz, 1H), 7.49-7.36 (m, J=7.9 Hz, 1H), 7.27 (s, 1H), 7.03 (br t, J=9.3 Hz, 1H), 6.70 (br d, J=6.4 Hz, 2H), 5.85 (s, 1H), 4.67-4.52 (m, 1H), 4.39 (d, J=15.9 Hz, 1H), 4.31 (d, J=15.9 Hz, 1H), 3.49-3.35 (m), 3.02 (br dd, J=14.2, 10.2 Hz), 1.84-1.62 (m, 1H), 1.24 (s, 1H), 0.75 (br d, J=8.2 Hz, 2H), 0.51 (br dd, J=9.8, 4.9 Hz, 2H).

(S)—N-(1-(3-(4-chloro-1-methyl-3-(methylsulfonamido)-1H-indazol-7-yl)-4-oxo-6-(trifluoromethoxy)-3,4-dihydroquinazolin-2-yl)-2-(3,5-difluorophenyl)ethyl)-2-(3-cyclopropyl-1H-pyrazol-1-yl)acetamide (Example 153 and Example 152)

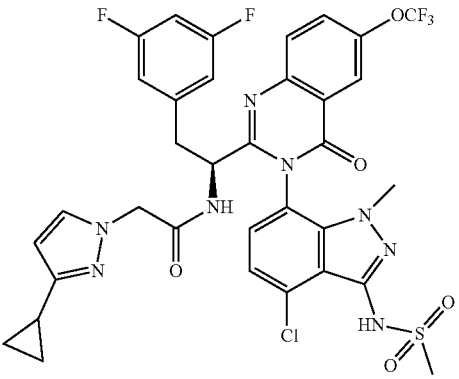

Example 152
Mix of enantiomers of unknown proportion

367

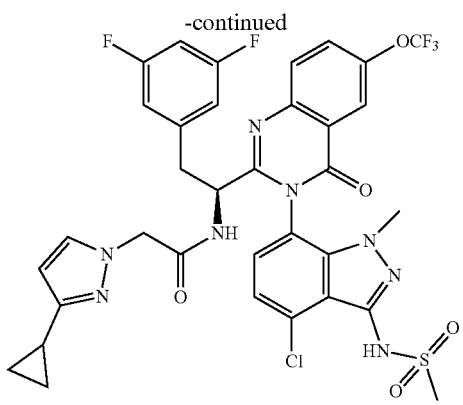

Example 153
Mix of enantiomers of unknown proportion

Within a septum cap vial equipped with a magnetic stirrer bar was added (S)—N-(7-(2-(1-amino-2-(3,5-difluorophenyl)ethyl)-4-oxo-6-(trifluoromethoxy)quinazolin-3(4H)-yl)-4-chloro-1-methyl-1H-indazol-3-yl)methanesulfonamide (42 mg, 0.065 mmol) (Int JD11b), 2-(3-cyclopropyl-1H-pyrazol-1-yl)acetic acid (13.57 mg, 0.082 mmol), and HOAT (2.67 mg, 0.020 mmol) in DMF (1.5 mL). TEA (0.064 mL, 0.457 mmol) followed by EDC (31.3 mg, 0.163 mmol) was added. The vial was capped and the suspension was stirred at RT overnight. LC/MS suggests formation of the desired MW product after stirring overnight with addition of 7 N ammonia in methanol. The reaction mixture was filtered and purified by preparative HPLC to give (S)—N-(1-(3-(4-chloro-1-methyl-3-(methylsulfonamido)-1H-indazol-7-yl)-4-oxo-6-(trifluoromethoxy)-3,4-dihydroquinazolin-2-yl)-2-(3,5-difluorophenyl)ethyl)-2-(3-cyclopropyl-1H-pyrazol-1-yl)acetamide, as two compounds.

Example 152 First Eluting Peak, 8.4 mg

LC/MS m/z=790.99 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 100%; Retention Time: 2.35 min.

Example 153 Second Eluting Peak, 17.8 mg

LC/MS m/z=791.03 (M+H)⁺. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm); Purity: 98%; Retention Time: 2.46 min. ¹H NMR (500 MHz, DMSO-d₆; WS (water suppression)) δ 8.88 (br d, J=8.2 Hz, 1H), 8.07 (s, 1H), 8.04-7.91 (m, 2H), 7.69 (d, J=7.9 Hz, 1H), 7.41 (d, J=7.9 Hz, 1H), 7.26 (s, 1H), 7.02 (br t, J=9.3 Hz, 1H), 6.68 (br d, J=6.4 Hz, 2H), 5.84 (s, 1H), 4.69-4.51 (m, 1H), 4.38 (d, J=15.9 Hz, 1H), 4.30 (d, J=15.9 Hz, 1H), 3.52-3.48 (m), 3.01 (br dd, J=13.9, 10.5 Hz), 1.74 (dq, J=8.9, 4.3 Hz, 1H), 1.36-1.21 (m, 1H), 0.76 (br d, J=8.5 Hz, 2H), 0.58-0.39 (m, 2H).

368

Methyl (S)-2-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-3-(3,5-difluorophenyl)propanoate (Int MS1a)

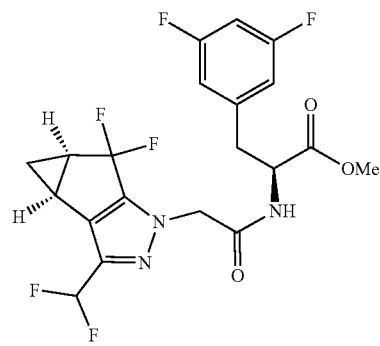 [SMILES: COC(=O)[C@H](Cc1cc(F)cc(F)c1)NC(=O)Cn1nc(C(F)F)c2c1C(F)(F)[C@@H]1C[C@H]21]

To a magnetically stirred solution of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (1.11 g, 4.20 mmol), 1-hydroxy-7-azabenzotriazole (150 mg, 1.102 mmol), and methyl (S)-2-amino-3-(3,5-difluorophenyl)propanoate (0.920 g, 4.28 mmol) in dichloromethane (40 mL), under nitrogen is added N-methylmorpholine (2.00 ml, 18.2 mmol). Then added EDC (940 mg, 4.90 mmol), and stirred at room temp for 3.5 h. Added more EDC (150 mg) and N-methylmorpholine (0.20 mL) and stirred room temp 2 h more. Apply reaction directly onto the head of a 80g Teledyne Isco Silica Flash Column. Elute the column with a linear gradient from 100% dichloromethane to 60% ethyl acetate over 9 column volumes, collecting fractions in 16×150 mm test tubes. The desired product fractions were combined and evaporated, then dried on high vacuum to give 1.70 g of the title compound. LC/MS m/z=462.2 (M+H)⁺; Column: Waters Aquity UPLC BEH C18, 2.1 mm×50 mm, 1.7 μm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.44 min.

(S)-2-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-3-(3,5-difluorophenyl)propanoic acid (Int MS1b)

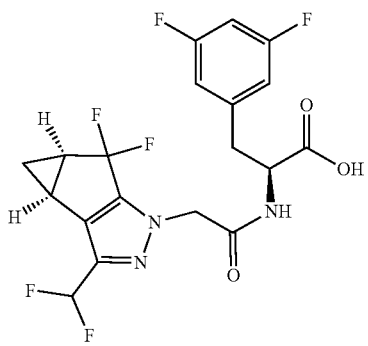 [SMILES: O=C(Cn1nc(C(F)F)c2c1C(F)(F)[C@@H]1C[C@H]21)N[C@@H](Cc1cc(F)cc(F)c1)C(=O)O]

To a solution of methyl (S)-2-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-3-(3,5-difluorophenyl)propanoate (1.7 g, 3.68 mmol) (Int MS1a) in ClCH$_2$CH$_2$Cl (50 mL) was added trimethyltin hydroxide (2.0 g, 11.1 mmol). The reaction was flushed well with nitrogen, capped and placed in an 80° C. oil for 3h, evaporated. The residue was dissolved in ethyl acetate (450 mL) and washed 1.0 M aqueous HCl (4×20 mL), brine (1×20 mL), dried over Na2SO4, filtered, and evaporate to dryness. After drying further on high vacuum, obtained 1.68 g of the title compound. LC/MS m/z=448.2 (M+H)$^+$; Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.39 min.

$^1$H NMR (500 MHz, DMSO-d$_6$) δ 12.96 (br s, 1H), 8.62 (br d, J=7.9 Hz, 1H), 7.11-6.85 (m, 4H), 4.84-4.77 (m, 1H), 4.74-4.67 (m, 1H), 4.51 (td, J=8.5, 5.0 Hz, 1H), 3.11 (dd, J=13.9, 5.0 Hz, 1H), 2.93 (dd, J=13.9, 9.0 Hz, 1H), 2.62-2.54 (m, 2H), 1.46-1.35 (m, 1H), 0.95 (br d, J=3.2 Hz, 1H).

$^{19}$F NMR (470 MHz, DMSO-d$_6$) δ −79.40 (br dd, J=252.0, 12.1 Hz, 1F), −102.63 (br dd, J=253.1, 11.0 Hz, 1F), −110.35--110.90 (m, 1F), −111.30 (br d, J=55.0 Hz, 1F), −112.21 (br d, J=55.0 Hz, 1F), −112.86 (br d, J=55.0 Hz, 1F)

Unless specified differently, the following conditions were used for Example 154-Example 192

QC-ACN-TFA-XB conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

QC-ACN-AA-XB conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

(E)-N-((3-bromoquinoxalin-2-yl)methylene)-2-methylpropane-2-sulfinamide (Int JB1a)

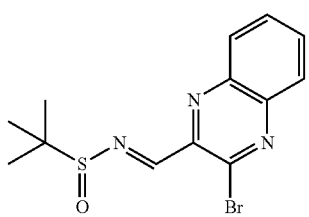 [SMILES: CC(C)(C)S(=O)/N=C/c1nc2ccccc2nc1Br]

Copper(II) sulfate (676 mg, 4.24 mmol) was added solution of 3-bromoquinoxaline-2-carbaldehyde (502 mg, 2.12 mmol) and 2-methylpropane-2-sulfinamide (282 mg, 2.33 mmol) in DCM (20 mL) and the reaction mixture was stirred at rt ON. The reaction mixture was diluted with water (60 mL) and extracted with EtOAc (100 mL). The organic layer was washed with brine (50 mL), dried (MgSO$_4$), filtered and concentrated. The residue was purified using a Biotage Horizon (40 g SiO$_2$, 15-30% EtOAc/hexanes) to afford the title compound (826 mg) as an off-white solid. LC/MS retention time=1.25 min; m/z=340.1, 342.1 (1:1) [M+H]$^+$. Column: Acquity BEH 2.1×50 mm, 1.7 µm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

$^1$H NMR (500 MHz, CDCl$_3$) δ 9.20 (s, 1H), 8.32-8.26 (m, 1H), 8.15-8.10 (m, 1H), 7.95-7.86 (m, 2H), 1.39 (s, 9H).

N-(1-(3-bromoquinoxalin-2-yl)-2-(3,5-difluorophenyl)ethyl)-2-methylpropane-2-sulfinamide (Int JB1b)

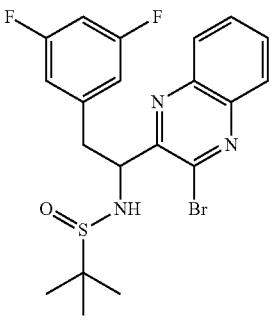 [SMILES: CC(C)(C)S(=O)NC(Cc1cc(F)cc(F)c1)c1nc2ccccc2nc1Br]

1-(Bromomethyl)-3,5-difluorobenzene (0.55 mL, 4.2 mmol) was slowly added to a stirred mixture of magnesium (102 mg, 4.21 mmol) in diethyl ether (6 mL) under nitrogen over 10 min). The reaction solution was stirred for 1.5h at rt and then added dropwise to a stirred solution of Int JB1a (717 mg, 2.11 mmol) in THF (16 mL) at −78° C. The reaction mixture was then allowed warm to rt and was stirred for 3h. The reaction mixture was quenched with sat. NH$_4$Cl and extracted with EtOAc. The organic layer was washed with water and brine and then dried (MgSO$_4$), filtered and concentrated. The crude material was purified using a Biotage Horizon (40 g SiO$_2$, 20-40% EtOAc/hexanes) to afford the title compound (580 mg) as a yellow solid and a ~1:4 of diastereomers. The material was used without additional purification. LC/MS retention time=1.43 min (minor), 1.46 min (major); m/z=468.2, 470.2 (1:1) [M+H]$^+$. Column: Acquity BEH 2.1×50 mm, 1.7 m; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

371 tert-butyl (R)-(1-(3-bromoquinoxalin-2-yl)-2-(3,5-difluorophenyl)ethyl)carbamate (Int JB1c) and tert-butyl (S)-(1-(3-bromoquinoxalin-2-yl)-2-(3,5-difluorophenyl)ethyl)carbamate (Int JB1d)

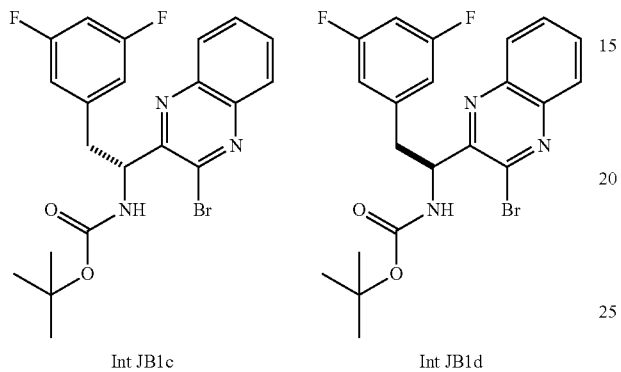

Int JB1c      Int JB1d

4M HCl (3 mL, 12 mmol) in dioxane was added to a solution of Int JB1b (580 mg, 1.24 mmol) in MeOH (4 mL) and the reaction mixture was stirred at rt for 3h (precipitate formed). The reaction mixture was concentrated and the residue was combined with di-tert-butyl dicarbonate (324 mg, 1.49 mmol) and DCM (5 mL). TEA (0.43 mL, 3.1 mmol) in DCM (~2 mL) was then added and the reaction mixture was stirred at rt ON. The reaction mixture was diluted with water and EtOAc. The layers were separated and the organic component was washed with brine, dried (MgSO$_4$), filtered and concentrated to dryness. The residue was purified using a Biotage Horizon (20-40% EtOAc, hexanes, 40g SiO$_2$) to afford a racemic mixture of the desired product (432 mg). This material was then purified by Chiral Preparative SFC (Column: Lux Cellulos-2, 21×250 mm, 5 μm; Mobile Phase: 5% ACN:EtOH (1:1) w/0.5% DEA/95% CO$_2$; Pressure: 200 bar; Temperature: 40° C.; Flow Rate: 60 mL/min; UV: 240 nm; Injection: 0.25 mL (~20 mg/mL in EtOH:ACN:CHCl$_3$ (1:2)) stacked @ 4.00'; Fraction Collection: Slope and Level; Make-up flow=7 mL/min ACN:EtOH (1:1) w/0.5% DEA) to afford: 1$^{st}$ eluting enantiomer: Int JB11e (153 mg off-white solid) and 2$^{nd}$ eluting enantiomer: Int JB11d (170 mg off-white solid). LC/MS retention time=1.60 min; m/z=364.1 [M+H-Boc]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm. $^1$H NMR (500 MHz, CDCl$_3$) δ 8.14-8.01 (m, 2H), 7.89-7.78 (m, 2H), 6.66 (br d, J=7.3 Hz, 2H), 5.91-5.53 (m, 1H), 3.37 (br dd, J=13.3, 4.7 Hz, 1H), 3.13-2.84 (m, 1H), 1.45 (s, 9H).

372 tert-butyl (S)-(1-(3-(4-chloro-1-methyl-3-(methylsulfonamido)-1H-indazol-7-yl)quinoxalin-2-yl)-2-(3,5-difluorophenyl)ethyl)carbamate (Int JB1e)

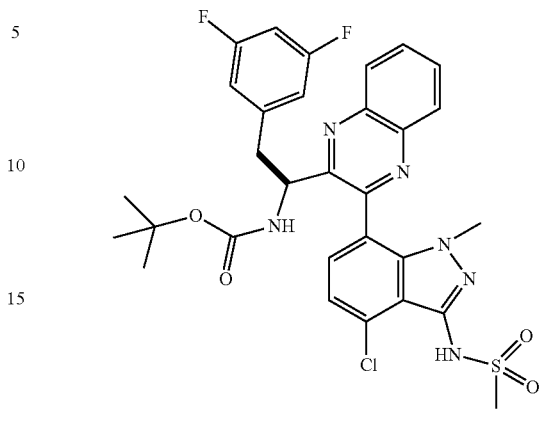

Nitrogen was bubbled through a slurry of Int JB1d (81 mg, 0.17 mmol) and N-(4-chloro-1-methyl-7-(4,4,5,5-tetramethyl-1,3,2-dioxaborolan-2-yl)-1H-indazol-3-yl)methanesulfonamide (81 mg, 0.21 mmol) in dioxane (3 mL) and 1M sodium bicarbonate (1.0 mL, 1.0 mmol) for 1 minute. Then PdCl$_2$(dppf)-CH$_2$Cl$_2$ adduct (14 mg, 0.017 mmol) was added and the reaction mixture was sealed into a microwave vessel and then heated at 140° C. with microwave irradiation for 50 min. The reaction mixture was filtered through Celite (flushing with EtOAc) and then partitioned between EtOAc and water. The aqueous component was further extracted with additional EtOAc and the combined organic components were washed with brine, dried (MgSO$_4$), filtered and concentrated to dryness. The residue was then purified by using a Biotage Horizon (12 g SiO$_2$, 10-50% EtOAc/hexanes, loaded onto column with DCM) to afford the title compound (54 mg) as a yellow solid. LC/MS retention time=1.46 min; m/z=665.3 [M+Na]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

N—((S)-1-(3-(4-chloro-1-methyl-3-(methylsulfonamido)-1H-indazol-7-yl)quinoxalin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide
(Example 154)

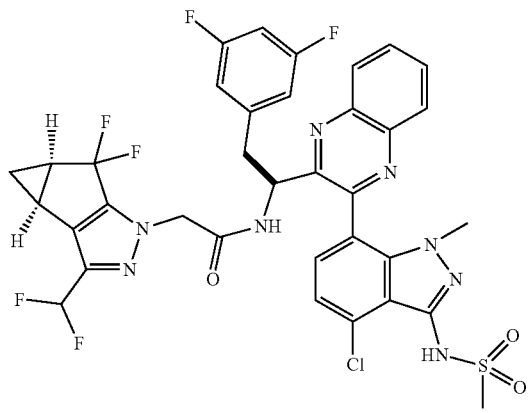 [SMILES: Cn1nc(NS(C)(=O)=O)c2c(Cl)ccc(-c3nc4ccccc4nc3[C@H](Cc3cc(F)cc(F)c3)NC(=O)Cn3nc(C(F)F)c4c3C(F)(F)[C@@H]3C[C@H]43)c21]

A solution of 4M HCl (0.84 mL, 3.4 mmol) in dioxane was added to a solution of Int JB1e (54 mg, 0.084 mmol) in MeOH (1.5 mL) and the reaction mixture was stirred at rt ON. The reaction mixture was concentrated to dryness and then treated with 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (29 mg, 0.11 mmol), DMF (1.0 mL) and DIPEA (0.073 mL, 0.420 mmol) and stirred. The reaction mixture was then treated with HATU (42 mg, 0.11 mmol) and stirred at rt for 3h. The crude reaction mixture was purified by prep-HPLC (Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 40-80% B over 23 minutes, then a 4-minute hold at 100% B; Flow: 20 mL/min) to afford the title compound (47.4 mg). LC/MS retention time=2.15 min; m/z=789.1 [M+H]$^+$, (Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). By $^{19}$F NMR the material appears to be a ~1:1 mixture of diastereomers. $^{19}$F NMR (376 MHz, CD$_3$OD) δ −82.2 (d, J=254.6 Hz, 1F), −82.4 (d, J=254.9 Hz, 1F), −105.2 (d, J=254.6 Hz, 1F), −105.3 (d, J=254.6 Hz, 1F), −111.3 (s, 2F), −111.7 (s, 2F), −113.2 (d, J=313.3 Hz, 2F), −114.5 (d, J=311.9 Hz, 1F), −114.6 (d, J=311.9 Hz, 1F).

tert-butyl (R)-(1-(3-(4-chloro-1-methyl-3-(methylsulfonamido)-1H-indazol-7-yl)quinoxalin-2-yl)-2-(3,5-difluorophenyl)ethyl)carbamate (Int JB2a)

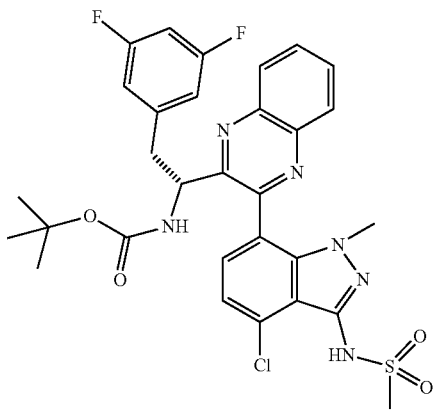 [SMILES: Cn1nc(NS(C)(=O)=O)c2c(Cl)ccc(-c3nc4ccccc4nc3[C@@H](Cc3cc(F)cc(F)c3)NC(=O)OC(C)(C)C)c21]

Nitrogen was bubbled through a slurry of Int JB1c (82 mg, 0.18 mmol) and N-(4-chloro-1-methyl-7-(4,4,5,5-tetramethyl-1,3,2-dioxaborolan-2-yl)-1H-indazol-3-yl)methanesulfonamide (82 mg, 0.21 mmol) in dioxane (3 mL) and 1M sodium bicarbonate (1.0 mL, 1.0 mmol) for 1 minute. Then PdCl$_2$(dppf)-CH$_2$Cl$_2$ adduct (14 mg, 0.017 mmol) was added and the reaction mixture was sealed into a microwave vessel and then heated at 140° C. with microwave irradiation for 50 min. The reaction mixture was filtered through Celite (flushing with EtOAc) and then partitioned between EtOAc and water. The aqueous component was further extracted with additional EtOAc and the combined organic components were washed with brine, dried (MgSO$_4$), filtered and concentrated to dryness. The residue was then purified by using a Biotage Horizon (12 g SiO$_2$, 10-50% EtOAc/hexanes, loaded onto column with DCM) to afford the title compound (30 mg). LC/MS retention time=1.46 min; m/z=665.3 [M+Na]$^+$. Column: Acquity BEH 2.1×50 mm, 1.7 µm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

N—((R)-1-(3-(4-chloro-1-methyl-3-(methylsulfonamido)-1H-indazol-7-yl)quinoxalin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide
(Example 155)

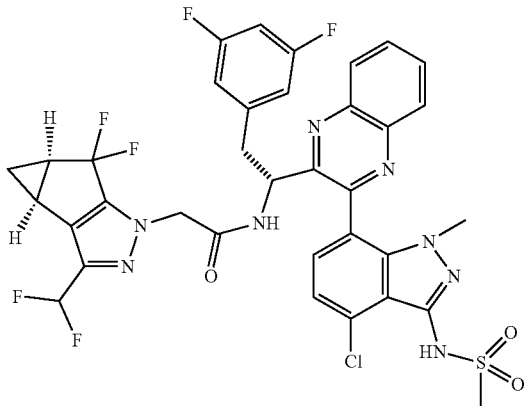 [SMILES: Cn1nc(NS(C)(=O)=O)c2c(Cl)ccc(-c3nc4ccccc4nc3[C@@H](Cc3cc(F)cc(F)c3)NC(=O)Cn3nc(C(F)F)c4c3C(F)(F)[C@@H]3C[C@H]43)c21]

A solution of 4M HCl (0.47 mL, 1.9 mmol) in dioxane was added to a solution of Int JB2a (30 mg, 0.047 mmol) in MeOH (1.5 mL) and the reaction mixture was stirred at rt ON. The reaction mixture was concentrated to dryness and then treated with 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (18.5 mg, 0.070 mmol), DMF (1.0 mL) and DIPEA (0.04 mL, 0.2 mmol) and stirred. The reaction mixture was then treated with HATU (27 mg, 0.07 mmol) and stirred at rt for 3h. The reaction mixture was then treated with MeOH, stirred 30 min. at rt and purified by prep-HPLC (Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 40-80% B over 23 minutes, then a 4-minute hold at 100% B; Flow: 20 mL/min) to afford the title compound (22.4 mg). LC/MS retention time=2.19 min; m/z=789.1 [M+H]$^+$, (Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). By $^{19}$F NMR the material appears to be a ~1:1 mixture of atropisomers. $^{19}$F NMR (376 MHz, CD$_3$OD) δ −82.2 (d, J=256.1 Hz, 1F), −82.2 (d, J=256.1 Hz, 1F), −105.3 (d, J=254.6 Hz, 1F), −105.5 (d, J=254.6 Hz, 1F), −111.3 (s, 2F), −111.8 (s, 2F), −113.3 (d, J=311.9 Hz, 1F), −113.3 (d, J=311.9 Hz, 1F), −114.4 (d, J=311.9 Hz, 1F), −114.5 (d, J=311.9 Hz, 1F).

tert-butyl (S)-(2-(3,5-difluorophenyl)-1-(3-(4-(morpholinosulfonyl)phenyl)quinoxalin-2-yl)ethyl)carbamate (Int JB3a)

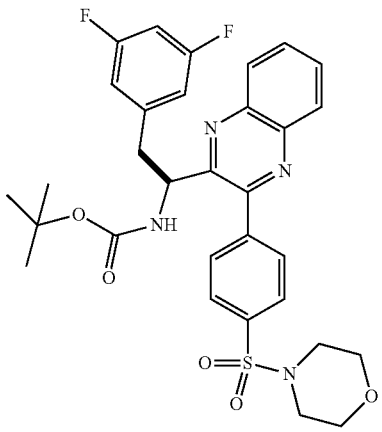 [SMILES: CC(C)(C)OC(=O)N[C@@H](Cc1cc(F)cc(F)c1)c1nc2ccccc2nc1-c1ccc(S(=O)(=O)N2CCOCC2)cc1]

Nitrogen was bubbled through a slurry of Int JB1d (41 mg, 0.09 mmol) and 4-((4-(4,4,5,5-tetramethyl-1,3,2-dioxaborolan-2-yl)phenyl)sulfonyl)morpholine (37 mg, 0.11 mmol) in dioxane (1.5 mL) and 1M sodium bicarbonate (0.53 mL, 0.53 mmol) for 1 minute. Then PdCl$_2$(dppf)-CH$_2$Cl$_2$ adduct (7 mg, 0.009 mmol) was added and the reaction mixture was sealed into a microwave vessel and then heated at 140° C. with microwave irradiation for 50 min. The reaction mixture was filtered through Celite (flushing with EtOAc) and then partitioned between EtOAc and water. The aqueous component was further extracted with additional EtOAc and the combined organic components were washed with brine, dried (MgSO$_4$), filtered and concentrated to dryness. The residue was then purified by using a Biotage Horizon (12 g SiO$_2$, 10-50% EtOAc/hexanes, loaded onto column with DCM) to afford the title compound (50 mg) as a yellow solid. LC/MS retention time=1.53 min; m/z=611.4 [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(4-(morpholinosulfonyl)phenyl)quinoxalin-2-yl)ethyl)acetamide (Example 156)

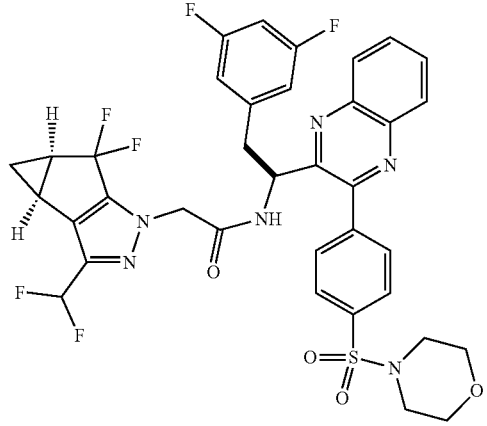 [SMILES: O=C(Cn1nc(C(F)F)c2c1C(F)(F)[C@@H]1C[C@H]21)N[C@@H](Cc1cc(F)cc(F)c1)c1nc2ccccc2nc1-c1ccc(S(=O)(=O)N2CCOCC2)cc1]

A solution of 4M HCl (0.84 mL, 3.3 mmol) in dioxane was added to a solution of Int JB3a (51 mg, 0.084 mmol) in MeOH (1.5 mL) and the reaction mixture was stirred at rt ON. The reaction mixture was concentrated to dryness and then treated with 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (24 mg, 0.092 mmol), DMF (1.0 mL) and DIPEA (0.07 mL, 0.4 mmol) and stirred. The reaction mixture was then treated with HATU (41 mg, 0.11 mmol) and stirred at rt ON. The reaction mixture was filtered and purified by prep-HPLC (Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 43-83% B over 23 minutes, then a 4-minute hold at 100% B; Flow: 20 mL/min) to afford the title compound (22.4 mg). LC/MS retention time=2.24 min; m/z=757.1 [M+H]$^+$, (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, MeOH-d$_4$) δ 8.29-8.23 (m, 1H), 8.14-8.10 (m, 1H), 7.99-7.86 (m, 4H), 7.72 (d, J=8.2 Hz, 2H), 6.85-6.59 (m, 2H), 6.36 (br d, J=6.1 Hz, 2H), 5.68 (t, J=7.5 Hz, 1H), 4.88 (s, 2H), 3.76 (t, J=4.6 Hz, 4H), 3.26-3.14 (m, 2H), 3.07 (br s, 4H), 2.51-2.43 (m, 2H), 1.39 (q, J=6.9 Hz, 1H), 1.09-1.03 (m, 1H). $^{19}$F NMR (471 MHz, MeOH-d$_4$) δ −82.2 (d, J=256.1 Hz, 1F), −105.3 (d, J=256.1 Hz, 1F), −111.5 (s, 2F), −113.3 (d, J=311.9 Hz, 1F), −114.4 (d, J=311.9 Hz, 1F).

tert-butyl (S)-(2-(3,5-difluorophenyl)-1-(3-(3-oxoisoindolin-5-yl)quinoxalin-2-yl)ethyl)carbamate (Int JB4a)

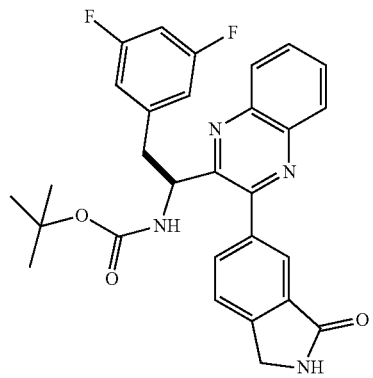 [SMILES: CC(C)(C)OC(=O)N[C@@H](Cc1cc(F)cc(F)c1)c1nc2ccccc2nc1-c1ccc2c(c1)C(=O)NC2]

Nitrogen was bubbled through a slurry of Int JB1d (41 mg, 0.09 mmol) 6-(4,4,5,5-tetramethyl-1,3,2-dioxaborolan-2-yl)isoindolin-1-one (28 mg, 0.11 mmol) in dioxane (3 mL) and 1M sodium bicarbonate (0.53 mL, 0.53 mmol) for 1 minute. Then PdCl$_2$(dppf)-CH$_2$Cl$_2$ adduct (7 mg, 0.009 mmol) was added and the reaction mixture was sealed into a microwave vessel and then heated at 140° C. with microwave irradiation for 50 min. The reaction mixture was diluted with EtOAc, filtered through Celite (flushing with EtOAc) and then partitioned between EtOAc and water. The aqueous component was further extracted with additional EtOAc and the combined organic components were washed 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(3-oxoisoindolin-5-yl)quinoxalin-2-yl)ethyl)acetamide (Example 157)

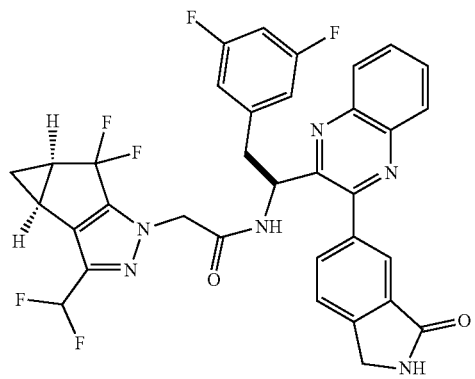 [SMILES: O=C(Cn1nc(C(F)F)c2c1C(F)(F)[C@@H]1C[C@H]21)N[C@@H](Cc1cc(F)cc(F)c1)c1nc2ccccc2nc1-c1ccc2c(c1)C(=O)NC2]

A solution of 4M HCl (0.41 mL, 1.6 mmol) in dioxane was added to a solution of Int JB4a (21 mg, 0.041 mmol) in MeOH (1.0 mL) and the reaction mixture was stirred at rt ON. The reaction mixture was concentrated to dryness and then treated with 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (12 mg, 0.045 mmol), DMF (1.0 mL) and DIPEA (0.04 mL, 0.2 mmol) and stirred. The reaction mixture was then treated with HATU (20 mg, 0.05 mmol) and stirred at rt ON. The reaction mixture was filtered and purified by prep-HPLC (Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 43-83% B over 23 minutes, then a 4-minute hold at 100% B; Flow: 20 mL/min) to afford the title compound (22.4 mg). LC/MS retention time=1.94 min; m/z=663.1 [M+H]$^+$, (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, MeOH-d$_4$) δ 8.24 (d, J=8.2 Hz, 1H), 8.15-8.10 (m, 1H), 7.98-7.88 (m, 2H), 7.86 (dd, J=7.8, 1.4 Hz, 1H), 7.78-7.69 (m, 2H), 6.84-6.57 (m, 2H), 6.36 (br d, J=6.4 Hz, 2H), 5.76 (t, J=7.3 Hz, 1H), 4.84 (s, 2H), 4.67-4.55 (m, 3H), 3.26-3.13 (m, 2H), 2.47 (br d, J=5.5 Hz, 2H), 1.42-1.34 (m, 1H), 1.06 (br d, J=2.4 Hz, 1H). $^{19}$F NMR (471 MHz, MeOH-d$_4$) δ −82.3 (d, J=256.1 Hz, 1F), −105.3 (d, J=254.6 Hz, 1F), −112.1 (s, 2F), −113.2 (d, J=311.9 Hz, 1F), −114.4 (d, J=311.9 Hz, 1F).

(S)—N-(2-(3,5-difluorophenyl)-1-(3-(3-oxoisoindolin-5-yl)quinoxalin-2-yl)ethyl)-2-(5-hydroxy-1H-indol-3-yl)acetamide (Example 158)

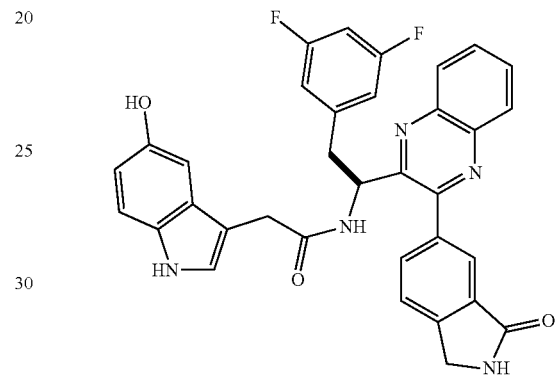

A solution of 4M HCl (0.41 mL, 1.6 mmol) in dioxane was added to a solution of Int JB4a (41 mg, 0.041 mmol) in MeOH (1.0 mL) and the reaction mixture was stirred at rt ON. The reaction mixture was concentrated to dryness and then treated with 2-(5-hydroxy-1H-indol-3-yl)acetic acid (9 mg, 0.05 mmol) DMF (1.0 mL) and DIPEA (0.04 mL, 0.2 mmol) and stirred. The reaction mixture was then treated with HATU (20 mg, 0.05 mmol) and stirred at rt ON. The reaction mixture was filtered and purified by prep-HPLC (Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 21-61% B over 20 minutes, then a 4-minute hold at 100% B; Flow: 20 mL/min) to afford the title compound (22.4 mg). LC/MS retention time=1.53 min; m/z=590.2 [M+H]$^+$, (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, MeOH-d$_4$) δ 8.11-8.04 (m, 1H), 8.03-7.98 (m, 1H), 7.91-7.83 (m, 2H), 7.81 (dd, J=7.8, 1.4 Hz, 1H), 7.77 (s, 1H), 7.65 (d, J=7.9 Hz, 1H), 7.20 (d, J=8.5 Hz, 1H), 7.11 (s, 1H), 6.87 (d, J=2.1 Hz, 1H), 6.72-6.60 (m, 2H), 6.28 (br d, J=6.4 Hz, 2H), 5.73 (t, J=7.3 Hz, 1H), 4.58 (s, 2H), 3.69-3.57 (m, 2H), 3.15-3.01 (m, 2H).

tert-butyl (S)-(1-(5-chloro-3-(4-chloro-3-(N-(4-methoxybenzyl)methylsulfonamido)-1-methyl-1H-indazol-7-yl)-6-fluoro-4-oxo-3,4-dihydroquinazolin-2-yl)-2-(3,5-difluorophenyl)ethyl)carbamate (Int JB6a)

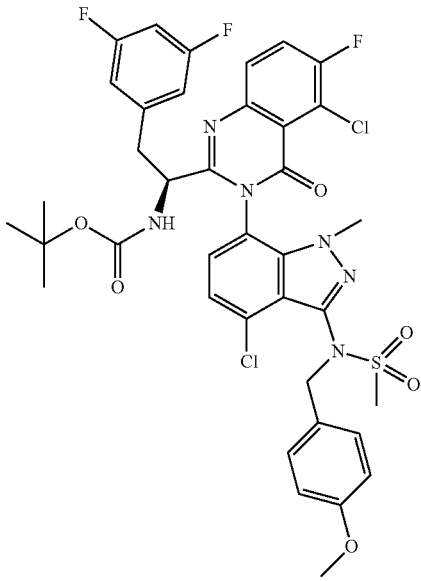 [SMILES: COc1ccc(CN(c2nn(C)c3c(-n4c([C@H](Cc5cc(F)cc(F)c5)NC(=O)OC(C)(C)C)nc5ccc(F)c(Cl)c5c4=O)ccc(Cl)c23)S(C)(=O)=O)cc1]

A mixture of (S)-2-((tert-butoxycarbonyl)amino)-3-(3,5-difluorophenyl)propanoic acid (67.1 mg, 0.223 mmol) and 6-amino-2-chloro-3-fluorobenzoic acid (42.2 mg, 0.223 mmol) in pyridine (2 mL) and diphenyl phosphite (0.13 mL, 0.67 mmol) was flushed with nitrogen and heated at 70° C. for 2h in a sealed tube. The reaction mixture was allowed to cool to rt and then treated with N-(7-amino-4-chloro-1-methyl-1H-indazol-3-yl)-N-(4-methoxybenzyl)methanesulfonamide (80 mg, 0.203 mmol) and reheated at 70° C. for 2h in a sealed tube and then at 90° C. for 3h. The reaction mixture was concentrated to dryness, diluted with EtOAc (~10 mL) and washed with 5% citric acid (~5 mL), 1.5 M $K_3PO_4$ (5 mL) and brine (5 mL). The organic component was concentrated to dryness and purified on an ISCO (24 g $SiO_2$, 0-50% EtOAc/hex) to afford the title compound (101 mg) as a light yellow solid. LC/MS retention time=1.15 min; m/z=775.1 [M−tBu+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

(S)—N-(7-(2-(1-amino-2-(3,5-difluorophenyl)ethyl)-5-chloro-6-fluoro-4-oxoquinazolin-3(4H)-yl)-4-chloro-1-methyl-1H-indazol-3-yl)methanesulfonamide (Int JB6b)

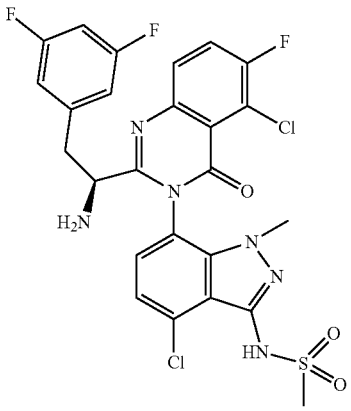 [SMILES: Cn1nc(NS(C)(=O)=O)c2c(Cl)ccc(-n3c([C@@H](N)Cc4cc(F)cc(F)c4)nc4ccc(F)c(Cl)c4c3=O)c21]

Int JB6a (99 mg, 0.12 mmol) was dissolved into DCM (1.0 mL) and stirred. The reaction mixture was then treated with TFA (0.5 mL) followed by triflic acid (0.053 mL, 0.60 mmol) dropwise and stirred at rt for 30 min. The reaction mixture was concentrated and the residue was dissolved into EtOAc (~8 mL), washed with sat NaHCO$_3$(~4 mL), filtered and concentrated to afford the title compound (110 mg) which was used without additional purification. By LCMS there are two peaks (1:4 ratio) which appear to be stereoisomers. The major peak LC/MS retention time=0.77 min; m/z=611.2 [M+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

N—((S)-1-(5-chloro-3-(4-chloro-1-methyl-3-(methylsulfonamido)-1H-indazol-7-yl)-6-fluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 160) and Example 159 and 161

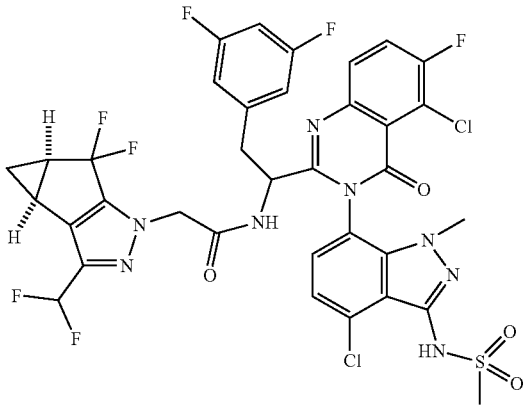

Example 159
Mix of stereoisomers

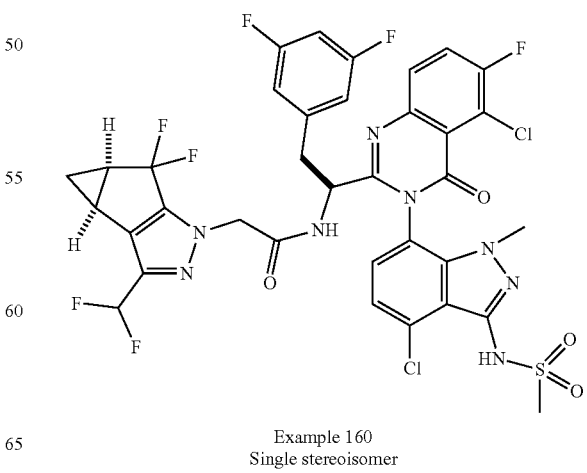

Example 160
Single stereoisomer

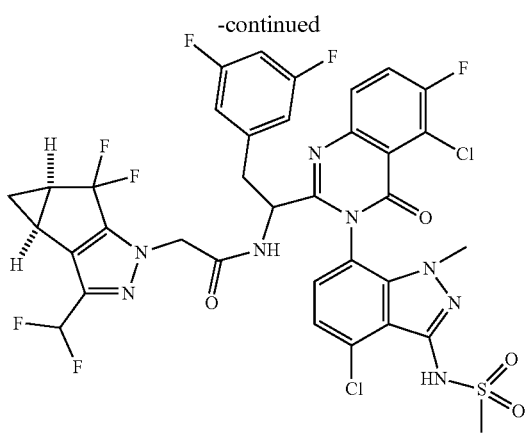

Example 161
Single stereoisomer

EDC (24.6 mg, 0.128 mmol) and then N-methylmorpholine (0.01 mL, 0.5 mmol) were added to a stirred solution of Int JB6b (108 mg, 0.117 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (30.8 mg, 0.117 mmol) in 1 M 3H-[1,2,3]triazolo[4,5-b]pyridin-3-ol (0.039 mL, 0.058 mmol) in DMA and DMF. The reaction mixture was stirred at rt for 2h, filtered and purified by preparative HPLC (Column: XBridge C18, 200 mm×19 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 41% B, 41-81% B over 25 minutes, then a 7-minute hold at 100% B; Flow Rate: 20 mL/min; Column Temperature: 25° C. Fraction collection was triggered by MS and UV signals. Fractions containing the desired product were combined and dried via centrifugal evaporation) to retrieve two isolates, each as a mixture of stereoisomers.

Example 159: First Elute (16.9 mg, Mixture of Stereoisomers)

QC-ACN-TFA-XB: (Purity: 100.0%; RT: 2.22 min; Obs. Adducts: [M+H]; Obs. Masses: 857.12)

The second elute (50.6 mg, mixture of stereoisomers) was further purified by chiral SFC (Instrument: Waters 100 Prep SFC; Column: Chiral OD 30×250 mm. 5 µm; Mobile Phase: 80% $CO_{2/20}$% MeOH w/0.1% DEA; Flow Conditions: 100 mL/min; Detector Wavelength: 220 nm; Injection Details: 1200 µL 50.6 mg dissolved in 3 mL MeOH/ACN). Two elutes of stereoisomeric relation were isolated.

Example 160: First Elute (32.9 mg)

QC-ACN-AA-XB: (Purity: 99.0%; RT: 2.14 min; Obs. Adducts: [M+H]; Obs. Masses: 857.02)

Example 161: Second Elute (9.4 mg)

QC-ACN-AA-XB: (Purity: 99.3%; RT: 2.14; Obs. Adducts: [M+H]; Obs. Masses: 857.04). $^1$H NMR (500 MHz, MeOH-$d_4$) δ 7.91-7.81 (m, 2H), 7.29-7.19 (m, 2H), 6.83-6.55 (m, 4H), 4.53 (s, 2H), 3.62 (s, 3H), 3.43 (br dd, J=13.7, 4.3 Hz, 1H), 3.22 (s, 3H), 3.06 (br dd, J=13.7, 9.5 Hz, 1H), 2.67 (s, 1H), 2.43 (br s, 2H), 1.41-1.23 (m, 1H), 1.00 (br s, 1H). $^{19}$F NMR (471 MHz, MeOH-$d_4$) δ −82.0 (br d, J=256.1 Hz, 1F), −105.4 (br d, J=256.1 Hz, 1F), −111.7 (s, 2F), −113.3 (s, 1F), −113.2 (d, J=311.9 Hz, 1F), −114.6 (d, J=311.9 Hz, 1F).

tert-butyl (S)-(1-(7-bromo-3-(6-isopropylpyridin-3-yl)-4-oxo-3,4-dihydroquinazolin-2-yl)-2-(3,5-difluorophenyl)ethyl)carbamate (Int JB10a)

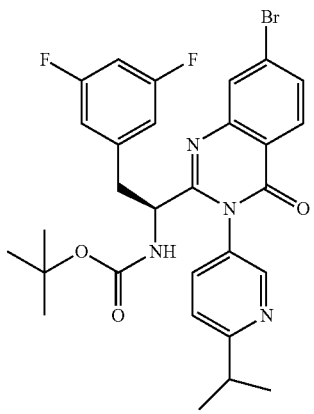 [SMILES: CC(C)c1ccc(-n2c([C@H](Cc3cc(F)cc(F)c3)NC(=O)OC(C)(C)C)nc3cc(Br)ccc3c2=O)cn1]

A mixture of (S)-2-((tert-butoxycarbonyl)amino)-3-(3,5-difluorophenyl)propanoic acid (1.00 g, 3.32 mmol), 2-amino-4-bromobenzoic acid (0.717 g, 3.32 mmol) and diphenyl phosphite (2.1 mL, 11 mmol) in pyridine (15 mL) was sealed and heated with microwave irradiation at 70° C. for 2 h. The reaction was allowed to cool to rt and then 6-isopropylpyridin-3-amine (0.497 g, 3.65 mmol) was added and the reaction solution was heated at 70° C. for 2 h. The reaction mixture was concentrated and the residue was partitioned between water (250 mL) and EtOAc (50 mL). The organic component was washed with 1.5 M $K_3PO_4$ and brine, dried ($MgSO_4$), filtered and concentrated. The residue was purified by FCC (120 g silica gel cartridge, 035% EtOAc-hexanes) to afford the title compound (940 mg) as an off-white foam. LC/MS retention time=1.57 min; m/z=599.3, 601.3 (1:1) [M+H]$^+$. Column: Acquity BEH 2.1×50 mm, 1.7 µm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)-2-(1-amino-2-(3,5-difluorophenyl)ethyl)-7-bromo-3-(6-isopropylpyridin-3-yl)quinazolin-4(3H)-one (Int JB10b)

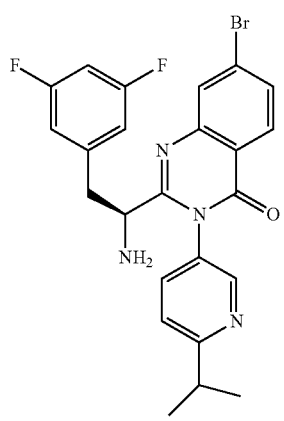 [SMILES: CC(C)c1ccc(-n2c([C@@H](N)Cc3cc(F)cc(F)c3)nc3cc(Br)ccc3c2=O)cn1]

383

To a solution of Int JB10a (50 mg, 0.083 mmol) in DCM (2.5 mL) was added 4 M HCl in 1,4-dioxane (0.42 mL, 1.7 mmol). The resulting light yellow solution was stirred at rt for 2 h. The reaction mixture was concentrated to afford an HCl salt of the title compound (48 mg) as a white solid. This material was used without additional purification. LC/MS retention time=1.11 min; m/z=499.2, 501.2 (1:1) [M+H]+. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

N—((S)-1-(7-bromo-3-(6-isopropylpyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int JB10)

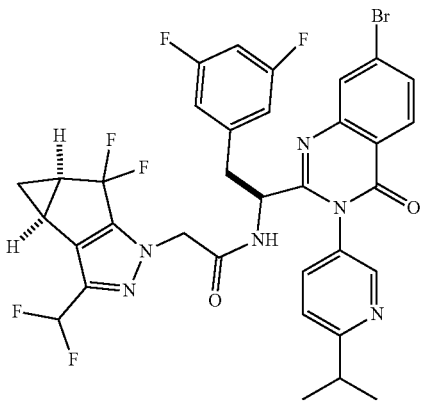 [SMILES: CC(C)c1ccc(-n2c([C@H](Cc3cc(F)cc(F)c3)NC(=O)Cn3nc(C(F)F)c4c3C(F)(F)[C@@H]3C[C@H]43)nc3cc(Br)ccc3c2=O)cn1]

To a solution of an HCl salt of Int JB10b (48 mg, 0.084 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (26.6 mg, 0.101 mmol) and HATU (47.8 mg, 0.126 mmol) in DMF (1.4 mL) was added N,N-diisopropylethylamine (0.088 mL, 0.50 mmol) and the reaction mixture was stirred at rt for 2 h. The crude material was purified via preparative LC/MS (XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 43-83% B over 20 minutes, then a 5-minute hold at 100% B; Flow: 20 mL/min) to afford the title compound (47.5 mg) as a mixture of stereoisomers. QC-ACN-AA-XB (Purity: 100.0%; RT: 2.41 min; Obs. Adducts: [M+H]; Obs. Masses: 745.05).

384 tert-butyl (S)-(2-(3,5-difluorophenyl)-1-(3-(6-isopropylpyridin-3-yl)-7-(methylsulfonamido)-4-oxo-3,4-dihydroquinazolin-2-yl)ethyl)carbamate (Int JB11a)

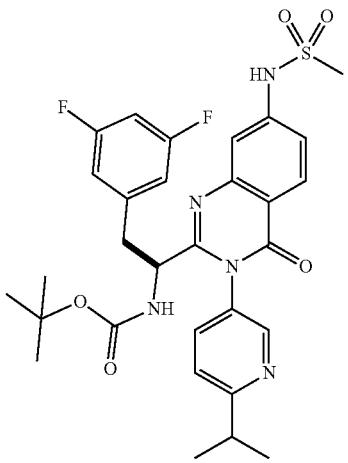 [SMILES: CC(C)c1ccc(-n2c([C@H](Cc3cc(F)cc(F)c3)NC(=O)OC(C)(C)C)nc3cc(NS(C)(=O)=O)ccc3c2=O)cn1]

A reaction mixture of Int JB10a (11.4 mg, 0.120 mmol), potassium carbonate (27.7 mg, 0.200 mmol), allylpalladium (II) chloride dimer (1.8 mg, 5.0 μmol), and 2-di-tert-butylphosphino-2',4',6'-triisopropylbiphenyl (6.38 mg, 0.015 mmol) in dioxane (0.8 mL) was vacuum flushed with N2 (3×), sealed and heated with microwave irradiation at 80° C. for 2 h. The crude reaction mixture was partitioned between water (25 mL) and EtOAc (10 mL). The organic component was washed with brine, dried (MgSO4), filtered and concentrated. The residue was purified by FCC (4 g silica gel cartridge, 0-100% EtOAc-hexanes) to afford the title compound (47 mg) as a light yellow solid. LC/MS retention time=1.34 min; m/z=614.3 [M+H]+. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

$^1$H NMR (500 MHz, CDCl$_3$) δ 8.63-8.17 (m, 2H), 7.76-7.58 (m, 1.4H), 7.48 (br d, J=8.2 Hz, 0.6H), 7.36-7.22 (m, 1H), 7.13-6.85 (m, 1H), 6.76-6.54 (m, 1H), 6.47-6.17 (m, 2H), 5.62-5.38 (m, 1H), 5.33 (s, 1H), 4.82-4.47 (m, 1H), 3.23 (d, J=2.5 Hz, 4H), 3.15-2.97 (m, 1H), 2.90-2.62 (m, 1H), 1.46-1.36 (m, 12H), 1.30-1.10 (m, 3H).

(S)—N-(2-(1-amino-2-(3,5-difluorophenyl)ethyl)-3-(6-isopropylpyridin-3-yl)-4-oxo-3,4-dihydroquinazolin-7-yl)methanesulfonamide (Int JB11b)

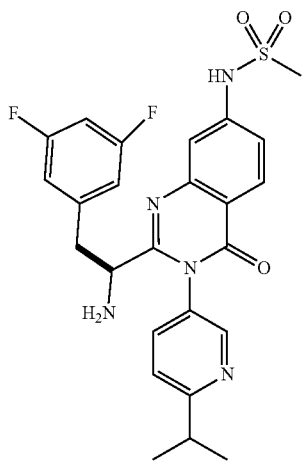 [SMILES: CC(C)c1ccc(-n2c([C@@H](N)Cc3cc(F)cc(F)c3)nc3cc(NS(C)(=O)=O)ccc3c2=O)cn1]

To a solution of Int JB11a (45 mg, 0.073 mmol) in DCM (0.5 mL) was added 4 M HCl in 1,4-dioxane (0.37 mL, 1.5 mmol) and the reaction mixture was stirred at rt for 2 h. The reaction mixture was concentrated to afford an HCl salt of the title compound (43 mg) as a white solid. This material was used without additional purification. LC/MS retention time=1.02 min; m/z=514.3 [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

tert-butyl (S)-(1-(7-cyano-3-(6-isopropylpyridin-3-yl)-4-oxo-3,4-dihydroquinazolin-2-yl)-2-(3,5-difluorophenyl)ethyl)carbamate (Int JB14a)

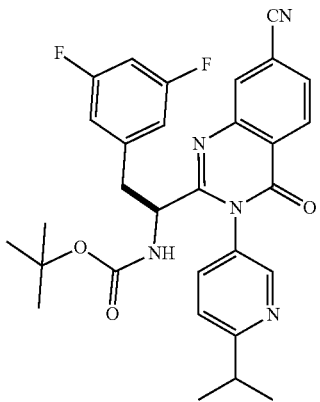 [SMILES: CC(C)c1ccc(-n2c([C@H](Cc3cc(F)cc(F)c3)NC(=O)OC(C)(C)C)nc3cc(C#N)ccc3c2=O)cn1]

A mixture of Int JB10a (300 mg, 0.500 mmol), zinc cyanide (41 mg, 0.35 mmol), t-BuXPhos Pd G3 (20 mg, 0.025 mmol), THF (2 mL) and water (8 mL) was vacuum flushed with nitrogen (3×), sealed and heated with microwave irradiation at 60° C. for 2 h. The reaction mixture was partitioned between water (50 mL) and EtOAc (25 mL). The organic component was washed with brine, (MgSO$_4$), filtered, and concentrated under reduced pressure. The residue was purified by FCC (80 g silica gel cartridge, 0-40% EtOAc-hexanes) to afford the title compound (152 mg) as a white foam and recovered Int JB10a (110 mg). LC/MS retention time=1.47 min; m/z=546.35 [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)-2-(1-amino-2-(3,5-difluorophenyl)ethyl)-3-(6-isopropylpyridin-3-yl)-4-oxo-3,4-dihydroquinazoline-7-carbonitrile (Int JB14b)

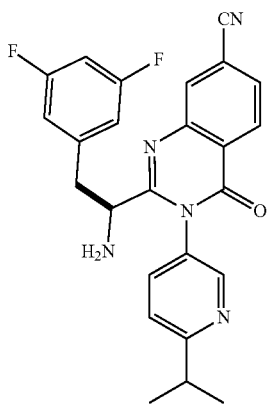 [SMILES: CC(C)c1ccc(-n2c([C@@H](N)Cc3cc(F)cc(F)c3)nc3cc(C#N)ccc3c2=O)cn1]

To a solution of Int JB14a (50 mg, 0.092 mmol) in DCM (1 mL) was added 4 M HCl in 1,4-dioxane (0.46 mL, 1.8 mmol) and the reaction mixture was stirred at rt for 2 h. The solvents were removed in vacuo and the residue was dissolved into DCM (1 mL) and TFA (0.11 mL, 1.4 mmol), and then stirred at rt overnight. The reaction mixture was concentrated and then treated with 2 M HCl in ether and reconcentrated (2×) to afford an HCl salt of the title compound (48 mg) as an off-white solid. This material was used without additional purification. LC/MS retention time=1.08 min; m/z=446.35 [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)—N-(1-(7-cyano-3-(6-isopropylpyridin-3-yl)-4-oxo-3,4-dihydroquinazolin-2-yl)-2-(3,5-difluorophenyl)ethyl)-2-(5-hydroxy-1H-indol-3-yl)acetamide (Example 162)

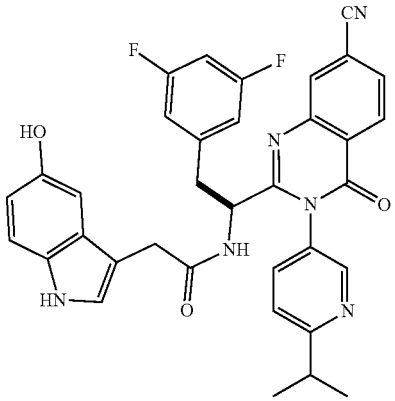 [SMILES: CC(C)c1ccc(-n2c([C@H](Cc3cc(F)cc(F)c3)NC(=O)Cc3c[nH]c4ccc(O)cc34)nc3cc(C#N)ccc3c2=O)cn1]

To a solution of an HCl salt of Int JB14b (23 mg, 0.044 mmol), 2-(5-hydroxy-1H-indol-3-yl)acetic acid (10.2 mg, 0.053 mmol) and HATU (25.3 mg, 0.067 mmol) in DMF (0.8 mL) was added N,N-diisopropylethylamine (0.046 mL, 0.27 mmol), and the reaction mixture was stirred at rt for 2 h. The crude reaction mixture was purified via preparative LC/MS (Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 26-66% B over 20 minutes, then a 5-minute hold at 100% B; Flow: 20 mL/min.) to afford the title compound (12.2 mg) as a tan solid and a mixture of stereoisomers. QC-ACN-TFA-XB (Purity: 100.0%; RT: 1.72 min; Obs. Adducts: [M+H]; Obs. Masses: 619.18). $^1$H NMR (500 MHz, DMSO-d$_6$) δ 10.53 (br s, 1H), 8.80-8.47 (m, 3H), 8.32-8.23 (m, 1H), 8.11 (d, J=15.6 Hz, 1H), 8.01-7.74 (m, 2H), 7.65-7.40 (m, 1H), 7.10 (d, J=8.5 Hz, 1H), 7.05-6.96 (m, 2H), 6.81 (dd, J=6.4, 1.8 Hz, 1H), 6.59 (dd, J=8.5, 2.1 Hz, 1H), 6.49 (br d, J=6.7 Hz, 2H), 4.60-4.31 (m, 1H), 3.50-3.41 (m, 1H), 3.34 (hidden under H$_2$O peak, 1H) 3.22-3.04 (m, 2H), 2.95-2.82 (m, 1H), 1.35-1.26 (m, 6H).

N—((S)-1-(7-cyano-3-(6-isopropylpyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 163)

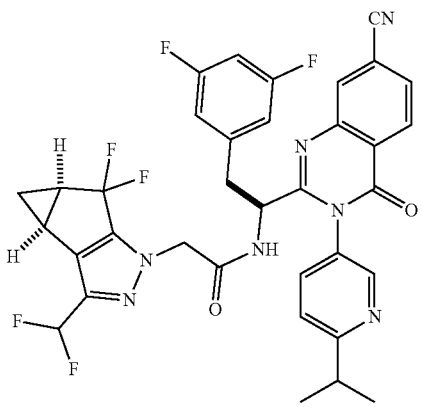 [SMILES: CC(C)c1ccc(-n2c([C@H](Cc3cc(F)cc(F)c3)NC(=O)Cn3nc(C(F)F)c4c3C(F)(F)[C@@H]3C[C@H]43)nc3cc(C#N)ccc3c2=O)cn1]

To a solution of an HCl salt of Int JB14b (23 mg, 0.044 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (14 mg, 0.053 mmol) and HATU (25 mg, 0.067 mmol) in DMF (0.8 mL) was added N,N-diisopropylethylamine (0.046 mL, 0.27 mmol) and the reaction mixture stirred was at rt for 2 h. The crude reaction mixture was purified via preparative LC/MS (Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 38-83% B over 20 minutes, then a 5-minute hold at 100% B; Flow: 20 mL/min) to afford the title compound (17.7 mg) as a mixture of stereoisomers. QC-ACN-TFA-XB (Purity: 97.4%; RT: 2.14 min; Obs. Adducts: [M+H]; Obs. Masses: 692.17).

tert-butyl (S)-(1-(3-(2-chloro-4-methoxyphenyl)-4-oxo-3,4-dihydroquinazolin-2-yl)-2-(3,5-difluorophenyl)ethyl)carbamate (Int JB16a1 and Int JB16a2)

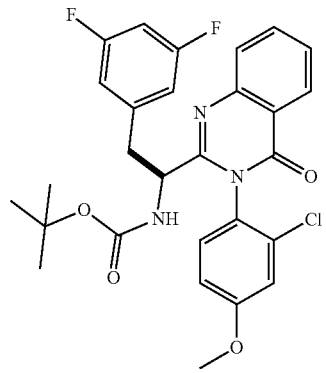 [SMILES: COc1ccc(-n2c([C@H](Cc3cc(F)cc(F)c3)NC(=O)OC(C)(C)C)nc3ccccc3c2=O)c(Cl)c1]

A mixture of (S)-2-((tert-butoxycarbonyl)amino)-3-(3,5-difluorophenyl)propanoic acid (300 mg, 0.996 mmol), 2-aminobenzoic acid (137 mg, 0.996 mmol) and diphenyl phosphite (0.636 mL, 3.29 mmol) in pyridine (4 mL) was sealed and heated with microwave irradiation at 50° C. for 2 h. The reaction mixture was cooled to rt and then treated with 2-chloro-4-methoxyaniline (173 mg, 1.10 mmol) heated with microwave irradiation at 50° C. for 12 h. The reaction mixture was concentrated and then partitioned between water (25 mL) and EtOAc (25 mL). The organic component was washed with 1.5 M $K_3PO_4$ and brine, dried ($MgSO_4$), filtered and concentrated. The residue was purified by FCC (80 g silica gel cartridge, 0-35% EtOAc-hexanes) to afford two isolates each enhanced in a single peak but containing the alternate peak as an impurity.

Int JB16a1: First elute (135 mg, light brown oil). LC/MS retention time=1.56 min; m/z=542.25 [M+H]$^+$. Column: Acquity BEH 2.1×50 mm, 1.7 m; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm. LC/MS also showed a shoulder with RT same as Int JB16a2.

Int JB16a2: Second elute (55 mg, light brown oil). LC/MS retention time=1.60 min; m/z=542.30 [M+H]$^+$. Column: Acquity BEH 2.1×50 mm, 1.7 m; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm. LC/MS also showed a peak with RT same as Int JB16a1.

(S)-2-(1-amino-2-(3,5-difluorophenyl)ethyl)-3-(2-chloro-4-methoxyphenyl)quinazolin-4(3H)-one (Int JB16b2)

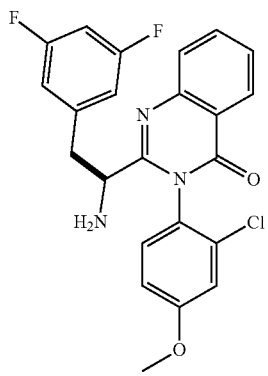 [SMILES: COc1ccc(-n2c([C@@H](N)Cc3cc(F)cc(F)c3)nc3ccccc3c2=O)c(Cl)c1]

To a solution of Int JB16a2 (50 mg, 0.092 mmol) in DCM (1.5 mL) was added 4 M HCl in 1,4-dioxane (0.46 mL, 1.8 mmol), the the reaction mixture was stirred ON. The reaction mixture was concentrated to afford an HCl salt of the title compound (44 mg) as a white solid, which was used without additional purification. LC/MS retention time=1.10 min; m/z=442.20[M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

389 tert-butyl (S)-(2-(3,5-difluorophenyl)-1-(3-(4-(morpholinosulfonyl)phenyl)-4-oxo-3,4-dihydroquinazolin-2-yl)ethyl)carbamate (Int JB18a)

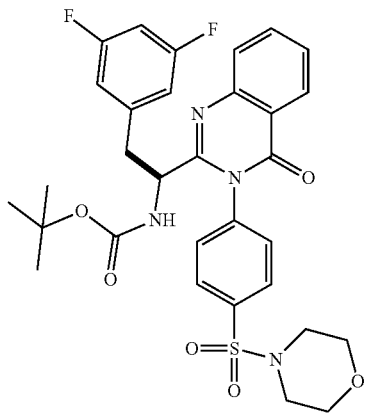 [SMILES: CC(C)(C)OC(=O)N[C@@H](Cc1cc(F)cc(F)c1)c1nc2ccccc2c(=O)n1-c1ccc(S(=O)(=O)N2CCOCC2)cc1]

A mixture of (S)-2-((tert-butoxycarbonyl)amino)-3-(3,5-difluorophenyl)propanoic acid (125 mg, 0.415 mmol), 2-aminobenzoic acid (56.9 mg, 0.415 mmol) and diphenyl phosphite (0.265 mL, 1.369 mmol) in pyridine (2 mL) was heated with microwave irradiation at 50° C. for 2 h. The reaction mixture was cooled to rt and then 4-(morpholinosulfonyl)aniline (111 mg, 0.456 mmol) was added and the reaction mixture solution was reheated with microwave irradiation at 50° C. for 12 h. The reaction was concentrated and the residue was partitioned between water (25 mL) and EtOAc (25 mL). The organic component was washed with 1 M HCl, 5% citric acid and brine, dried (MgSO$_4$), filtered and evaporated in vacuo. The residue was purified by FCC (24 g silica gel cartridge, 0-40% EtOAc-hexanes) to afford the title compound (133 mg) as a white foam. LC/MS retention time=1.49 min; m/z=627.35 [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)-2-(1-amino-2-(3,5-difluorophenyl)ethyl)-3-(4-(morpholinosulfonyl)phenyl)quinazolin-4(3H)-one (Int JB18b)

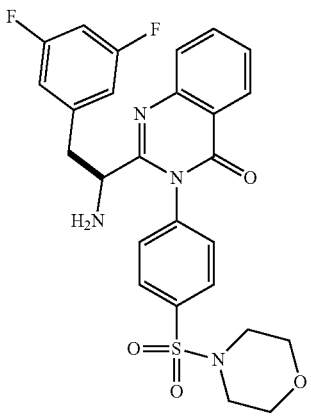 [SMILES: N[C@@H](Cc1cc(F)cc(F)c1)c1nc2ccccc2c(=O)n1-c1ccc(S(=O)(=O)N2CCOCC2)cc1]

390

To a solution of Int JB18a (130 mg, 0.21 mmol) in DCM (1 mL) was added 4 M HCl in 1,4-dioxane (1.04 mL, 4.15 mmol). The reaction mixture was stirred at rt for 2 h, concentrated, triturated with ether, and dried in vacuo to afford an HCl salt of the title compound (103 mg) as a light yellow solid, which was used without additional purification. LC/MS retention time=1.00 min; m/z=527.25 [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)—N-(2-(3,5-difluorophenyl)-1-(3-(4-(morpholinosulfonyl)phenyl)-4-oxo-3,4-dihydroquinazolin-2-yl)ethyl)-2-(5-hydroxy-1H-indol-3-yl)acetamideacetamide (Example 164)

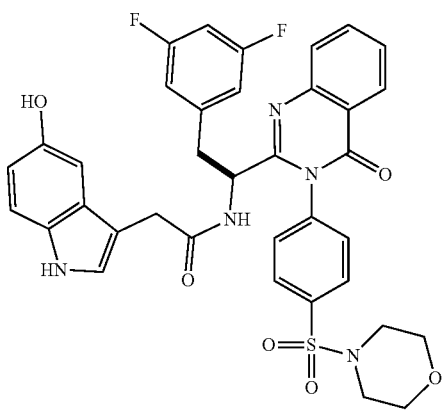 [SMILES: O=C(Cc1c[nH]c2ccc(O)cc12)N[C@@H](Cc1cc(F)cc(F)c1)c1nc2ccccc2c(=O)n1-c1ccc(S(=O)(=O)N2CCOCC2)cc1]

To a solution of an HCl salt of Int JB18b (25 mg, 0.044 mmol), 2-(5-hydroxy-1H-indol-3-yl)acetic acid (10 mg, 0.053 mmol) and HATU (25 mg, 0.067 mmol) in DMF (1 mL) was added N,N-diisopropylethylamine (0.047 mL, 0.27 mmol) and the reaction mixture was stirred at rt for 2 h. The crude material was purified via preparative LC/MS (Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 27-67% B over 15 minutes, then a 5-minute hold at 100% B; Flow: 20 mL/min.) to afford the title compound (14.5 mg). QC-ACN-TFA-XB (Purity: 97.7%; RT: 1.72 min; Obs. Adducts: [M+H]; Obs. Masses: 700.06). $^1$H NMR (500 MHz, MeOH-d$_4$) δ 8.21 (d, J=7.6 Hz, 1H), 7.94-7.86 (m, 2H), 7.79 (d, J=8.2 Hz, 1H), 7.63-7.56 (m, 2H), 7.44 (dd, J=8.2, 1.8 Hz, 1H), 7.27 (dd, J=8.2, 1.8 Hz, 1H), 7.20 (d, J=8.5 Hz, 1H), 7.08 (s, 1H), 6.90 (d, J=2.1 Hz, 1H), 6.74 (br t, J=9.3 Hz, 1H), 6.69 (dd, J=8.5, 2.1 Hz, 1H), 6.61 (br d, J=6.4 Hz, 2H), 4.75 (t, J=7.2 Hz, 1H), 4.57 (s, 2H), 3.71 (t, J=4.6 Hz, 4H), 3.60-3.54 (m, 1H), 3.52-3.46 (m, 1H), 3.39-3.35 (m, 1H), 3.04-2.92 (m, 4H).

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(4-(morpholinosulfonyl)phenyl)-4-oxo-3,4-dihydroquinazolin-2-yl)ethyl)acetamide (Example 165)

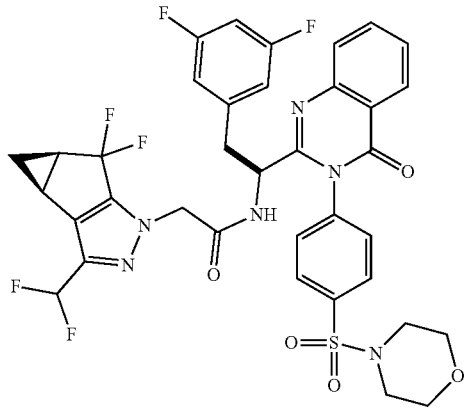 [SMILES: O=C(Cn1nc(C(F)F)c2c1C(F)(F)[C@@H]1C[C@H]21)N[C@@H](Cc1cc(F)cc(F)c1)c1nc2ccccc2c(=O)n1-c1ccc(S(=O)(=O)N2CCOCC2)cc1]

To a solution of an HC salt of Int JB18b (25 mg, 0.044 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (14 mg, 0.053 mmol) and HATU (25 mg, 0.067 mmol) in DMF (1 mL) was added N,N-diisopropylethylamine (0.047 mL, 0.27 mmol) and the reaction mixture was stirred at rt for 2 h. The crude material was purified via preparative LC/MS (Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 40-80% B over 15 minutes, then a 5-minute hold at 100% B; Flow: 20 mL/min) to afford the title compound (24.3 mg). QC-ACN-TFA-XB (Purity: 100.0%; RT: 2.10 min; Obs. Adducts: [M+H]; Obs. Masses: 773.08). $^1$H NMR (500 MHz, MeOH-$d_4$) δ 8.25 (d, J=7.9 Hz, 1H), 7.98-7.86 (m, 4H), 7.69-7.60 (m, 2H), 7.33 (br d, J=7.9 Hz, 1H), 6.79 (br t, J=9.3 Hz, 1H), 6.73 (t, $J_{HF}$=54.6 Hz, 1H), 6.68-6.60 (m, 2H), 4.82-4.78 (m, 2H), 4.76-4.69 (m, 1H), 4.57 (s, 2H), 3.73 (t, J=4.6 Hz, 4H), 3.40 (dt, J=13.7, 6.8 Hz, 1H), 3.10-2.99 (m, 5H), 2.52-2.42 (m, 2H), 1.40 (q, J=7.0 Hz, 1H), 1.04 (br d, J=2.4 Hz, 1H). $^{19}$F NMR (471 MHz, MeOH-$d_4$) δ −82.08 (d, J=256.1 Hz, 1F), −105.24 (d, J=256.1 Hz, 1F), −111.66 (s, 2F), −113.3 (d, J=311.9 Hz, 1F), −114.5 (d, J=311.9 Hz, 1F).

tert-butyl (S)-(1-(7-bromo-3-(4-cyclopropylphenyl)-4-oxo-3,4-dihydroquinazolin-2-yl)-2-(3,5-difluorophenyl)ethyl)carbamate (Int JB23a)

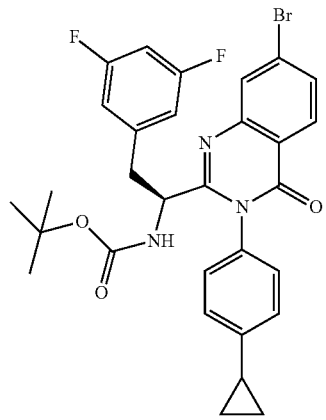 [SMILES: CC(C)(C)OC(=O)N[C@@H](Cc1cc(F)cc(F)c1)c1nc2cc(Br)ccc2c(=O)n1-c1ccc(C2CC2)cc1]

A mixture of (S)-2-((tert-butoxycarbonyl)amino)-3-(3,5-difluorophenyl)propanoic acid (1.00 g, 3.32 mmol), 2-amino-4-bromobenzoic acid (0.717 g, 3.32 mmol) and diphenyl phosphite (2.12 mL, 11.0 mmol) in pyridine (15 mL) was sealed and heated with microwave irradiation at 70° C. for 2 h. The reaction mixture was allowed to cool to rt, treated with 4-cyclopropylaniline (0.486 g, 3.65 mmol) and then resealed and heated at 70° C. for 2 h. The reaction mixture was concentrated and the residue was partitioned between water (250 mL) and EtOAc (50 mL). The organic component was washed with 5% citric acid and brine, dried it over MgSO$_4$, filtered, and concentrated in vacuo. The residue was purified by FCC (120 g silica gel cartridge, 0-20% EtOAc-hexanes) to afford the crude title compound (1.98 g) as a white solid which was used without additional purification. LC/MS retention time=1.74 min; m/z=596.30, 598.25 (1:1) [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)-2-(1-amino-2-(3,5-difluorophenyl)ethyl)-7-bromo-3-(4-cyclopropylphenyl)quinazolin-4(3H)-one (Int JB23b)

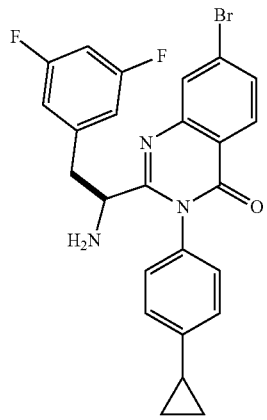 [SMILES: N[C@@H](Cc1cc(F)cc(F)c1)c1nc2cc(Br)ccc2c(=O)n1-c1ccc(C2CC2)cc1]

A solution of crude Int JB23a (1.98 g) and 4 M hydrogen chloride in 1,4-dioxane (16.6 ml, 66.4 mmol) was stirred at rt overnight. The reaction mixture was concentrated in vacuo and azeotroped with DCM to afford an off-white solid. This white solid was triturated it with Et$_2$O, and dried in vacuo to afford an HCl salt of the title compound (687 mg) as a white powder. This material was used without additional purification. LC/MS retention time=1.30 min; m/z=496.20, 498.25 (1:1) [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)—N-(1-(7-bromo-3-(4-cyclopropylphenyl)-4-oxo-3,4-dihydroquinazolin-2-yl)-2-(3,5-difluorophenyl)ethyl)-2-(5-hydroxy-1H-indol-3-yl)acetamide (Int JB23)

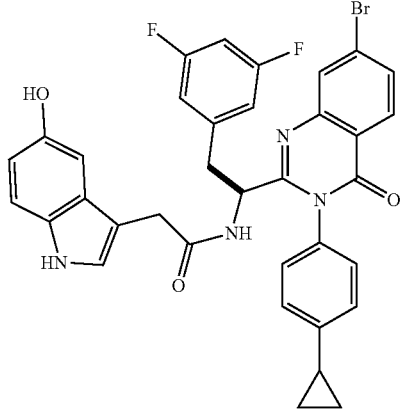 [SMILES: O=C(Cc1c[nH]c2ccc(O)cc12)N[C@@H](Cc1cc(F)cc(F)c1)c1nc2cc(Br)ccc2c(=O)n1-c1ccc(C2CC2)cc1]

To a solution of an HCl salt of Int JB23b (23 mg, 0.040 mmol), 2-(5-hydroxy-1H-indol-3-yl)acetic acid (9.3 mg, 0.048 mmol) and HATU (23 mg, 0.061 mmol) in DMF (0.8 mL) was added N,N-diisopropylethylamine (0.042 mL, 0.242 mmol), and the reaction mixture was stirred at rt for 2 h. The crude material was purified via preparative LC/MS (Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 35-75% B over 25 minutes, then a 4-minute hold at 100% B; Flow: 20 mL/min.) to afford the title compound (17.8 mg) as white solid. QC-ACN-AA-XB (Purity: 96.6%; RT: 2.13 min; Obs. Adducts: [M+H]; Obs. Masses: 669.06). $^{1}$H NMR (500 MHz, MeOH-$d_4$) δ 8.05 (d, J=8.5 Hz, 1H), 7.71-7.64 (m, 2H), 7.29 (br d, J=8.2 Hz, 1H), 7.25-7.17 (m, 3H), 7.09-7.04 (m, 2H), 6.84 (d, J=2.1 Hz, 1H), 6.76-6.66 (m, 2H), 6.32 (br d, J=6.4 Hz, 2H), 3.64-3.56 (m, 1H), 3.54-3.48 (m, 1H), 3.10 (br dd, J=13.9, 4.7 Hz, 1H), 2.81-2.68 (m, 2H), 2.09-2.02 (m, 1H), 1.09 (br dd, J=8.4, 1.7 Hz, 2H), 0.85-0.77 (m, 2H).

N—((S)-1-(7-bromo-3-(4-cyclopropylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int JB24)

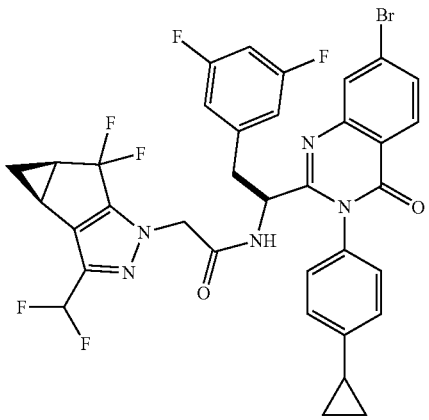 [SMILES: O=C(Cn1nc(C(F)F)c2c1C(F)(F)[C@@H]1C[C@H]21)N[C@@H](Cc1cc(F)cc(F)c1)c1nc2cc(Br)ccc2c(=O)n1-c1ccc(C2CC2)cc1]

To a solution of an HCl salt of Int JB23b (23 mg, 0.040 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (13 mg, 0.048 mmol) and HATU (23 mg, 0.061 mmol) in DMF (0.8 mL) was added N,N-diisopropylethylamine (0.042 mL, 0.242 mmol), and the reaction mixture was stirred at rt for 2 h. The crude material was purified via preparative LC/MS (Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 53-93% B over 20 minutes, then a 4-minute hold at 100% B; Flow: 20 mL/min.) to afford the title compound (23.7 mg) as solid. QC-ACN-AA-XB (Purity: 100.0%; RT: 2.52 min; Obs. Adducts: [M+H]; Obs. Masses: 742.04). $^{1}$H NMR (500 MHz, MeOH-$d_4$) δ 8.11 (d, J=8.5 Hz, 1H), 8.00 (d, J=1.8 Hz, 1H), 7.74 (dd, J=8.4, 1.7 Hz, 1H), 7.35-7.27 (m, 3H), 7.09 (dd, J=7.9, 1.8 Hz, 1H), 6.79-6.73 (m, 1H), 6.70 (t, $J_{HF}$=54.6 Hz, 1H), 6.40 (br d, J=6.1 Hz, 2H), 4.84 (d, J=16.5 Hz, 1H), 4.76 (d, J=16.5 Hz, 1H), 3.21 (dd, J=13.9, 4.7 Hz, 1H), 2.88 (dd, J=14.0, 9.2 Hz, 1H), 2.50-2.41 (m, 2H), 2.12-2.03 (m, 1H), 1.39 (q, J=6.9 Hz, 1H), 1.13-1.01 (m, 3H), 0.82 (td, J=4.9, 2.1 Hz, 2H). Note: One aliphatic proton unaccounted for. $^{19}$F NMR (471 MHz, MeOH-$d_4$) δ −82.3 (d, J=256.1 Hz, 1F), −105.2 (d, J=256.1 Hz, 1F), −111.8 (s, 2F), −113.1 (d, J=313.3 Hz, 1F), −114.5 (d, J=313.3 Hz, 1F).

tert-butyl (S)-(1-(3-(4-cyclopropylphenyl)-7-(methylsulfonamido)-4-oxo-3,4-dihydroquinazolin-2-yl)-2-(3,5-difluorophenyl)ethyl)carbamate (Int JB25a)

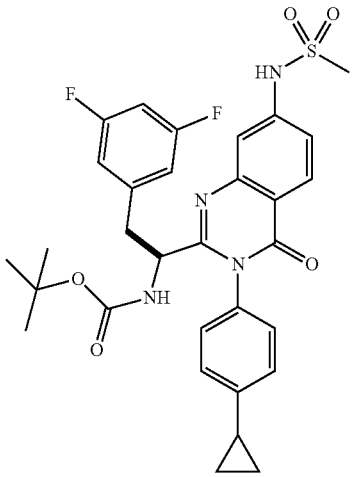 [SMILES: CC(C)(C)OC(=O)N[C@@H](Cc1cc(F)cc(F)c1)c1nc2cc(NS(C)(=O)=O)ccc2c(=O)n1-c1ccc(C2CC2)cc1]

A mixture of Int JB23a (120 mg, 0.201 mmol), methanesulfonamide (23 mg, 0.24 mmol), potassium carbonate (55.6 mg, 0.402 mmol), allylpalladium(II) chloride dimer (3.7 mg, 10 μmol), 2-di-tert-butylphosphino-2',4',6'-triisopropylbiphenyl (12.8 mg, 0.030 mmol) and dioxane (2 mL) was vacuum flushed with nitrogen (3×). The reaction mixture was then heated with microwave irradiation at 80° C. for 2 h. The reaction mixture was added to 5% citric acid (25 mL) and extracted with EtOAc (20 mL). The organic component was washed with brine, dried over MgSO$_4$, filtered and concentrated. The residual tan solid was used without further purification. LC/MS retention time=1.48 min; m/z=611.3 [M+H]$^{+}$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)—N-(2-(1-amino-2-(3,5-difluorophenyl)ethyl)-3-(4-cyclopropylphenyl)-4-oxo-3,4-dihydroquinazolin-7-yl)methanesulfonamide (Int JB25b)

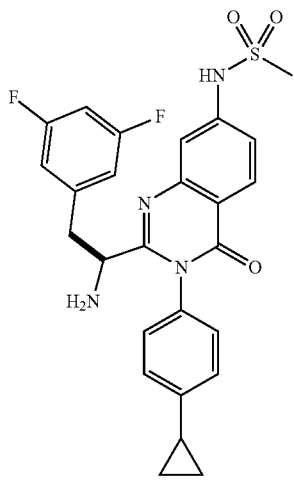 [SMILES: CS(=O)(=O)Nc1ccc2c(=O)n(-c3ccc(C4CC4)cc3)c([C@@H](N)Cc3cc(F)cc(F)c3)nc2c1]

To a slurry of Int JB25a (123 mg, 0.201 mmol) in DCM (2 mL) was added 4 M HCl in 1,4-dioxane (1.007 mL, 4.03 mmol) and the reaction mixture was stirred at rt overnight. The crude reaction mixture was concentrated and the residue was triturated with ET$_2$O to afford an HCl salt of the title compound (105 mg) as an off-white solid, which was used without additional purification. LC/MS retention time=1.07 min; m/z=511.25 [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

tert-butyl (S)-(1-(3-(4-chloro-3-(N-(4-methoxybenzyl)methylsulfonamido)-1-methyl-1H-indazol-7-yl)-7-cyano-4-oxo-3,4-dihydroquinazolin-2-yl)-2-(3,5-difluorophenyl)ethyl)carbamate (Int 27b)

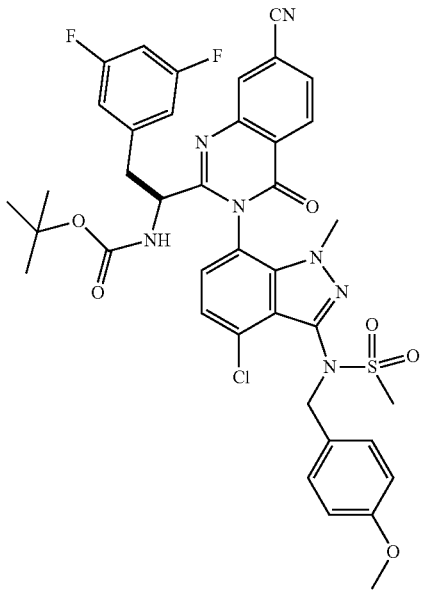 [SMILES: COc1ccc(CN(c2nn(C)c3c(-n4c([C@H](Cc5cc(F)cc(F)c5)NC(=O)OC(C)(C)C)nc5cc(C#N)ccc5c4=O)ccc(Cl)c23)S(C)(=O)=O)cc1]

A mixture of (S)-2-((tert-butoxycarbonyl)amino)-3-(3,5-difluorophenyl)propanoic acid (140 mg, 0.465 mmol), 2-amino-4-cyanobenzoic acid (79 mg, 0.47 mmol) and diphenyl phosphite (0.33 mL, 1.5 mmol) in pyridine (2.5 mL) was sealed into a high pressure vessel and heated in an oil bath at 70° C. for 2 h. The reaction mixture was allowed to cool to rt and then treated with N-(7-amino-4-chloro-1-methyl-1H-indazol-3-yl)-N-(4-methoxybenzyl)methanesulfonamide (202 mg, 0.511 mmol) resealed and heated in an oil bath at 90° C. for 4 h. The reaction mixture was concentrated in vacuo and the residue was partitioned between water (20 mL) and EtOAc (10 mL). The organic component was washed with water, 5% citric acid, 1 M NaOH and brine, dried over MgSO$_4$, filtered and concentrated. The residue was purified by FCC (24 g silica gel cartridge, 0-60% EtOAc-hexanes) to afford the title compound (210 mg) as a light yellow foam. LC/MS retention time=1.12 min; m/z=748.2 [M−tBu+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

(S)—N-(7-(2-(1-amino-2-(3,5-difluorophenyl)ethyl)-7-cyano-4-oxoquinazolin-3(4H)-yl)-4-chloro-1-methyl-1H-indazol-3-yl)methanesulfonamide (Int 27c)

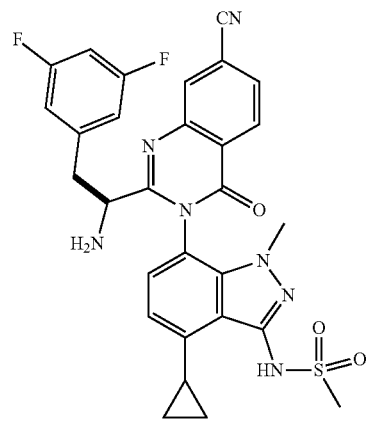 [SMILES: Cn1nc(NS(C)(=O)=O)c2c(C3CC3)ccc(-n3c([C@@H](N)Cc4cc(F)cc(F)c4)nc4cc(C#N)ccc4c3=O)c21]

TFA (0.200 mL) and triflic acid (0.12 mL, 1.3 mmol) were added to an ice bath cooled solution of Int JB42a (210 mg, 0.261 mmol) in DCM (0.2 mL) and the reaction mixture was stirred at rt for 1 h. The reaction mixture was concentrated and the residue was partitioned between EtOAc (5 mL) and sat. NaHCO$_3$ (10 mL). The organic component was washed with brine, dried over MgSO$_4$, filtered, and concentrated to afford the title compound (182 mg) as an off-white foam and a mixture of diastereomers (~2:1). This material was used without further purification. LC/MS retention time=0.67 and 0.72 min (1:2); m/z=584.0 and 584.1 [M+H]*(respectively). Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

N—((S)-1-(3-(4-chloro-1-methyl-3-(methylsulfona-mido)-1H-indazol-7-yl)-7-cyano-4-oxo-3,4-dihydro-quinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 20) and Example 166

Example 20: Second Elute (22 mg, Single Stereoisomer)

tert-butyl (S)-(1-(3-(4-cyclopropylphenyl)-4-oxo-7-((2,2,2-trifluoroethyl)amino)-3,4-dihydroquinazolin-2-yl)-2-(3,5-difluorophenyl)ethyl)carbamate (Int JB48a)

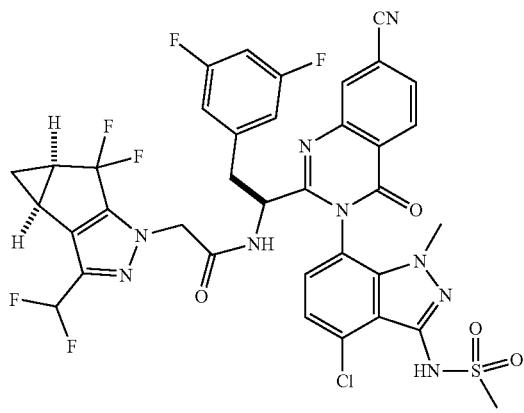 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(C#N)ccc4c3=O)c21]

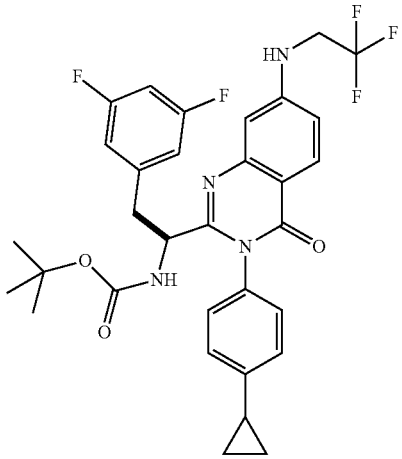 [SMILES: CC(C)(C)OC(=O)N[C@@H](Cc1cc(F)cc(F)c1)c1nc2cc(NCC(F)(F)F)ccc2c(=O)n1-c1ccc(C2CC2)cc1]

To a solution of Int 27c (182 mg, 0.262 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (69.2 mg, 0.262 mmol) and HOAt (1 M in DMA, 0.13 mL, 0.13 mmol) in DMF (3 mL) was added EDC (55.2 mg, 0.288 mmol) and N-methylmorpholine (0.12 mL, 1.1 mmol) and the reaction mixture was stirred at rt overnight. The reaction mixture was poured into 5% citric acid (20 mL) and extracted with EtOAc (10 mL, ×2). The combined organic components were washed with brine, dried over MgSO$_4$, and concentrated. The residue (200 mg) was purified via preparative LC/MS (Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 31% B, 31-71% B over 25 minutes, then a 4-minute hold at 100% B; Flow Rate: 20 mL/min; Column Temperature: 25° C.) to retrieve two isolates, each as a mixture of stereoisomers.

Example 166: First Elute (23 mg, Mixture of Stereoisomers)

QC-ACN-AA-XB (Purity: 100.0%; RT: 2.02 min; Obs. Adducts: [M+H]; Obs. Masses: 830.09).

The second elute (66 mg, mixture of stereoisomers, QC-ACN-AA-XB (Purity: 97.0%; RT: 2.09 min; Obs. Adducts: [M+H]; Obs. Masses: 830.07) was further purified by chiral SFC (Column: ChiralPak IF-H, 21×250 mm, 5 mm; Mobile Phase: 70% CO$_{2/30}$% IPA; Pressure: 150 bar; Temperature: 40° C.; Flow Conditions: 60 mL/min; Detector Wavelength: 320 nm; Injection Details: 0.2 mL (~50 mg/mL in IPA:CHCh (1:1)). Two elutes of stereoisomeric relation were isolated.

A reaction mixture of phenol (10.4 mg, 0.111 mmol), Int JB23a (60 mg, 0.101 mmol), 2,2,2-trifluoroethan-1-amine (0.016 mL, 0.20 mmol), allylpalladium(II) chloride dimer (1.8 mg, 5.0 µmol), 5-(di-tert-butylphosphino)-1',3',5'-triphenyl-1'h-1,4'-bipyrazole (5.1 mg, 10 µmol) and potassium tert-butoxide (12 mg, 0.11 mmol) in 1,4-dioxane (2 mL) was vacuum flushed with nitrogen (3×) and then heated with microwave irradiation at 100° C. for 2 h. The crude reaction mixture was poured into water (10 mL) and extracted with EtOAc (10 mL). The organic component was washed with 1 M NaOH and brine, dried over MgSO$_4$, filtered and concentrated. The residue was purified by FCC (12 g silica gel cartridge, 0-40% EtOAc-hexanes) to afford the title compound (60 mg) as an off-white foam. LC/MS retention time=1.59 min; m/z=615.4 [M+H]$^+$. Column: Acquity BEH 2.1×50 mm, 1.7 µm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)-2-(1-amino-2-(3,5-difluorophenyl)ethyl)-3-(4-cyclopropylphenyl)-7-((2,2,2-trifluoroethyl)amino)quinazolin-4(3H)-one (Int JB48b)

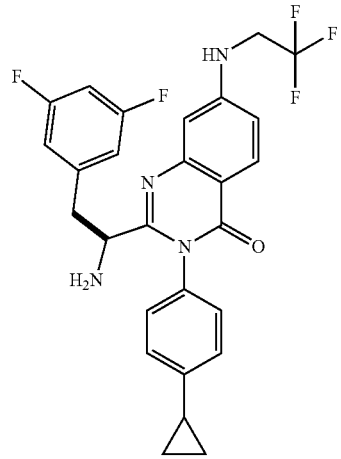 [SMILES: N[C@@H](Cc1cc(F)cc(F)c1)c1nc2cc(NCC(F)(F)F)ccc2c(=O)n1-c1ccc(C2CC2)cc1]

A solution crude Int JB48a (60 mg, 0.098 mmol) and 4 M hydrogen chloride in 1,4-dioxane (0.488 mL, 1.952 mmol) was stirred at rt overnight. The reaction mixture was concentrated and the residue azeotroped with DCM until a off-white solid resulted. The solids were triturated with ether and dried in vacuo to afford an HCl salt of the title compound (68 mg) as a white powder. The material which was used without additional purification. LC/MS retention time=1.16 min; m/z=515.3 [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

tert-butyl (S)-(1-(5-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int JB53a)

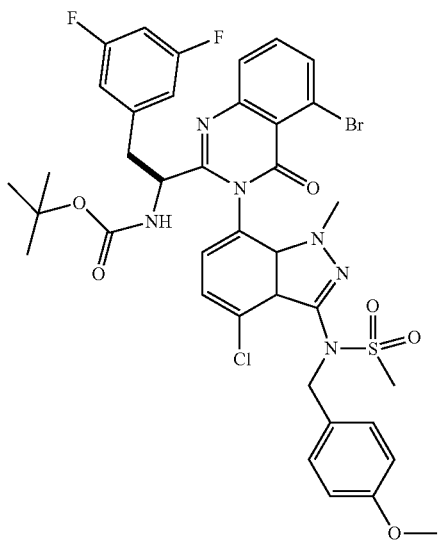 [SMILES: COc1ccc(CN(C2=NN(C)C3C(n4c([C@H](Cc5cc(F)cc(F)c5)NC(=O)OC(C)(C)C)nc5cccc(Br)c5c4=O)=CC=C(Cl)C23)S(C)(=O)=O)cc1]

A mixture of (S)-2-((tert-butoxycarbonyl)amino)-3-(3,5-difluorophenyl)propanoic acid (200 mg, 0.664 mmol), 2-amino-6-bromobenzoic acid (143 mg, 0.664 mmol) and diphenyl phosphite (0.47 mL, 2.2 mmol) in pyridine (3.5 mL) was sealed and heated with microwave irradiation at 70° C. for 2 h. The reaction mixture was allowed to cool to rt, and then treated with N-(7-amino-4-chloro-1-methyl-1H-indazol-3-yl)-N-(4-methoxybenzyl)methanesulfonamide (288 mg, 0.730 mmol), resealed and reheated with microwave irradiation at 70° C. for another 2 h. The reaction mixture was concentrated and the residue partitioned between water (20 mL) and EtOAc (10 mL). The organic component was washed with 5% citric acid, 1 M NaOH and brine, dried (MgSO$_4$), filtered, and concentrated. The residue was purified by FCC (80 g silica gel cartridge, 0-40% EtOAc-hexanes) to afford the title compound (415 mg) as a white foam. LC/MS retention time=1.67 min; m/z=879.3, 881.3 (1:1) [M+Na]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)—N-(7-(2-(1-amino-2-(3,5-difluorophenyl)ethyl)-5-bromo-4-oxoquinazolin-3(4H)-yl)-4-chloro-1-methyl-1H-indazol-3-yl)-N-(4-methoxybenzyl)methanesulfonamide (Int JB53b)

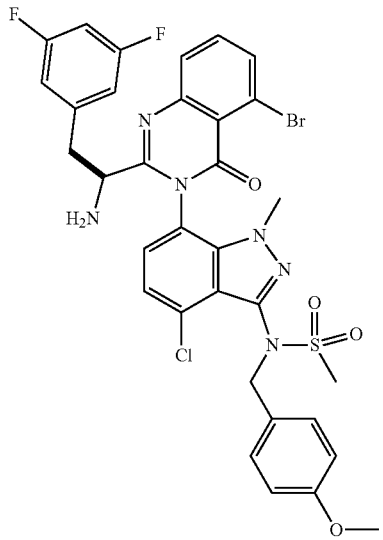 [SMILES: COc1ccc(CN(c2nn(C)c3c(-n4c([C@@H](N)Cc5cc(F)cc(F)c5)nc5cccc(Br)c5c4=O)ccc(Cl)c23)S(C)(=O)=O)cc1]

To a a solution of Int JB53a (78 mg, 0.091 mmol) in DCM (0.8 mL) was added 4 M HCl in 1,4-dioxane (0.80 mL, 3.2 mmol) and the reaction mixture was stirred at rt overnight. The reaction mixture was concentrated and triturated with ether to afford an HCl salt of the title compound as an off-white solid and a mixture of stereoisomers, which was used without additional purification. LC/MS retention time=1.20 and 1.25 min; m/z=757.2, 759.2 (1:1) [M+H]$^+$ and =757.2, 759.2 (1:1) [M+H]$^+$ (1:2.5, respectively). Column: Acquity BEH 2.1×50 mm, 1.7 m; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

N—((S)-1-(5-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int JB53c)

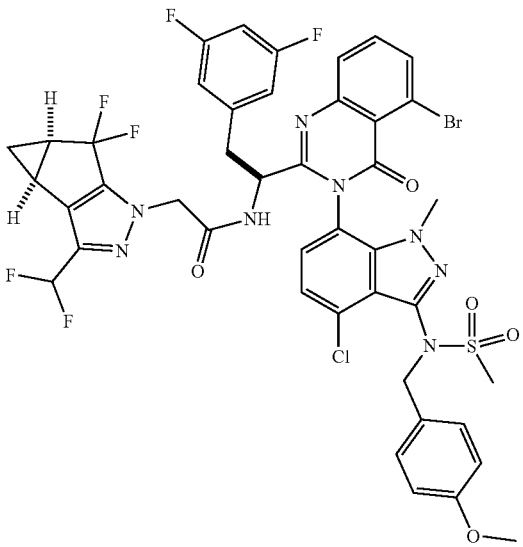 [SMILES: COc1ccc(CN(c2nn(C)c3c(-n4c([C@H](Cc5cc(F)cc(F)c5)NC(=O)Cn5nc(C(F)F)c6c5C(F)(F)[C@@H]5C[C@H]65)nc5cccc(Br)c5c4=O)ccc(Cl)c23)S(C)(=O)=O)cc1]

To a solution of Int JB53b (45 mg, 0.057 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (15.71 mg, 0.059 mmol) and HATU (24 mg, 0.062 mmol) in DMF (1 mL) was added N,N-diisopropylethylamine (0.030 mL, 0.17 mmol) and the reaction mixture was stirred at rt for 2 h. The reaction mixture was poured in to 5% citric acid (10 mL) and extracted with EtOAc (5 mL). The organic component was washed with brine, dried ($MgSO_4$) and concentrated. The residue was purified by FCC (24 g silica gel cartridge, 0%~50% EtOAc-Hexanes) to afford the title compound (52 mg) as a white glass. LC/MS retention time=1.59 min; m/z=1025.4, 1027.3 (1:1) [M+Na]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

N—((S)-1-(5-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int JB53.2) and Int JB53.1

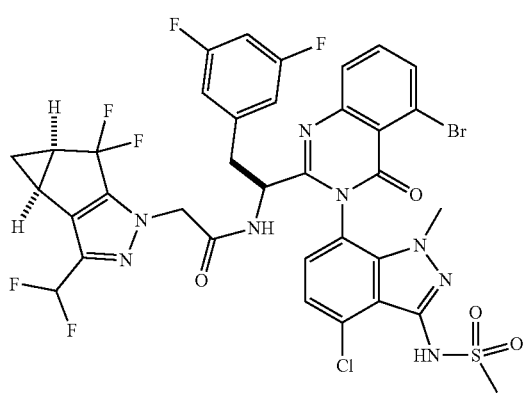

Chemical Formula: $C_{35}H_{26}BrClF_6N_8O_4S$
Exact Mass: 882.06
Molecular Weight: 884.05

To an ice bath cooled solution of Int JB53c (52 mg, 0.052 mmol) in DCM (0.25 mL) was added TFA (0.25 mL) and triflic acid (0.023 mL, 0.26 mmol). The reaction mixture was stirred at rt for 1 h. The crude material was purified via preparative LC/MS (Column: XBridge C18, 200 mm×19 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 40% B, 40-80% B over 20 minutes, then a 5-minute hold at 100% B; Flow Rate: 20 mL/min; Column Temperature: 25° C.) to afford two isolates, each as a mixture of stereoisomers.

Int JB53.1: First elute (12.8 mg). QC-ACN-TFA-XB (Purity: 98.7%; RT: 2.15 min; Obs. Adducts: [M+H]; Obs. Masses: 883.0)

Int JB53.2: Second elute (24.8 mg). QC-ACN-AA-XB (Purity: 100.0%; RT: 2.18 min; Obs. Adducts: [M+H]; Obs. Masses: 882.93). For major stereoisomer: $^{19}$F NMR (471 MHz, MeOH-$d_4$) δ −82.18 (br d, J=256.1 Hz, 1F), −105.03 (d, J=254.6 Hz, 1F), −111.67 (s, 2F), −113.33 (d, J=311.9 Hz, 1F), −114.53 (d, J=311.9 Hz, 1F).

N—((S)-1-(7-chloro-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 168) and Example 167

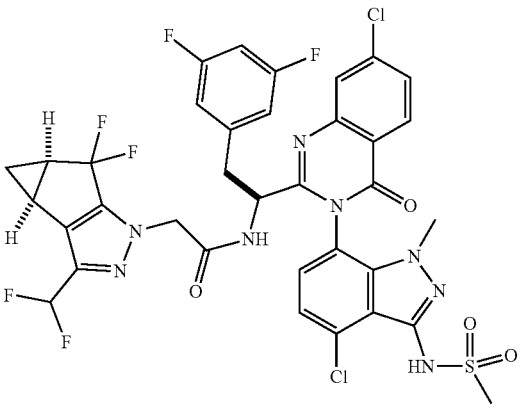 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(Cl)ccc4c3=O)c21]

The crude material was purified via preparative LC/MS (Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 41% B, 41-81% B over 20 minutes, then a 4-minute hold at 100% B; Flow Rate: 20 mL/min; Column Temperature: 25° C.) to afford two elutes, each as a mixture of stereoisomers.

Example 167: First Elute (21.6 mg)

QC-ACN-TFA-XB (Purity: 99.5%; RT: 3.35 min; Obs. Adducts: [M+H]; Obs. Masses: 839.39).

Example 168 (39.2 mg)

QC-ACN-TFA-XB (Purity: 100.0%; RT: 3.47 min; Obs. Adducts: [M+H]; Obs. Masses: 839.02). For major stereoisomer: $^1$H NMR (500 MHz, MeOH-$d_4$) δ 8.27 (br d, J=8.2 Hz, 1H), 7.92 (s, 1H), 7.67 (br d, J=7.9 Hz, 1H), 7.34-7.21 (m, 2H), 6.83-6.57 (m, 4H), 4.85-4.81 (m, 1H), 4.53 (br s, 2H), 3.61 (s, 3H), 3.45 (br dd, J=13.9, 4.7 Hz, 1H), 3.26 (s, 3H), 3.08 (br dd, J=13.4, 10.1 Hz, 1H), 2.44 (br s, 2H), 1.40-1.33 (m, 1H), 1.00 (br s, 1H). $^{19}$F NMR (471 MHz, MeOH-$d_4$) δ −82.16 (d, J=256.1 Hz, 1F), −105.04 (br d, J=254.6 Hz, 1F), −111.64 (s, 2F), −113.33 (d, J=311.9 Hz, 1F), −114.52 (d, J=311.9 Hz, 1F).

403 methyl 3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazoline-7-carboxylate (Int JB59.2) and Int JB59.1

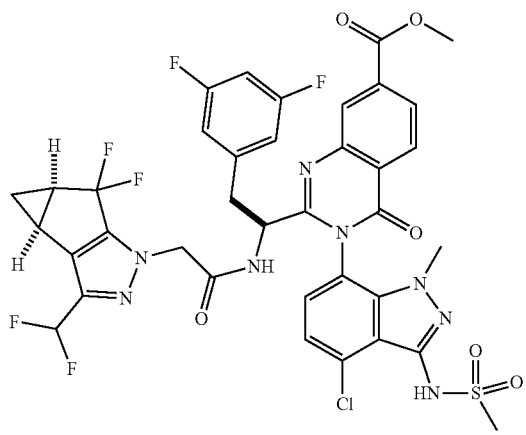 [SMILES: COC(=O)c1ccc2c(=O)n(-c3ccc(Cl)c4c(NS(C)(=O)=O)nn(C)c34)c([C@H](Cc3cc(F)cc(F)c3)NC(=O)Cn3nc(C(F)F)c4c3C(F)(F)[C@@H]3C[C@H]43)nc2c1]

The crude material was purified via preparative LC/MS (Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 3-minute hold at 37% B, 37-77% B over 20 minutes, then a 4-minute hold at 100% B; Flow Rate: 20 mL/min; Column Temperature: 25° C.) to afford two elutes, each as a mixture of stereoisomers.

Int JB59.1: First elute (8.2 mg). (QC-ACN-TFA-XB (Purity: 98.6%; RT: 3.14 min; Obs. Adducts: [M+H]; Obs. Masses: 863.04).

Int JB59.2: Second elute (14 mg). QC-ACN-TFA-XB (Purity: 100.0%; RT: 3.24; Obs. Adducts: [M+H]; Obs. Masses: 863.06). $^1$H NMR (500 MHz, MeOH-d$_4$) δ 8.50 (s, 1H), 8.40-8.36 (m, 1H), 8.21 (br d, J=7.6 Hz, 1H), 7.35-7.23 (m, 2H), 6.82-6.57 (m, 4H), 4.85 (br s, 1H), 4.54 (br s, 2H), 4.05 (s, 3H), 3.61 (s, 3H), 3.47 (br dd, J=14.3, 4.3 Hz, 1H), 3.26 (d, J=2.1 Hz, 3H), 3.10 (br dd, J=13.4, 9.5 Hz, 1H), 2.48-2.40 (m, 2H), 1.35 (br dd, J=14.2, 7.2 Hz, 1H), 1.00 (br s, 1H). $^{19}$F NMR (471 MHz, MeOH-d$_4$) δ −82.16 (br d, J=254.6 Hz, 1F), −105.05 (br d, J=254.6 Hz, 1F), −111.65 (s, 2F), −113.33 (d, J=311.9 Hz, 1F), −114.51 (d, J=311.9 Hz, 1F).

404 tert-butyl (S)-(1-(3-(4-chloro-3-(N-(4-methoxybenzyl)methylsulfonamido)-1-methyl-1H-indazol-7-yl)-5-methoxy-4-oxo-3,4-dihydroquinazolin-2-yl)-2-(3,5-difluorophenyl)ethyl)carbamate (Int JB62a)

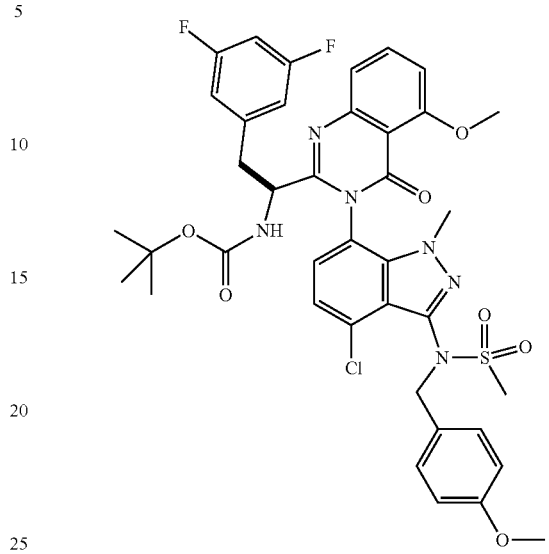

A mixture of (S)-2-((tert-butoxycarbonyl)amino)-3-(3,5-difluorophenyl)propanoic acid (75 mg, 0.25 mmol), 2-amino-6-methoxybenzoic acid (41.6 mg, 0.249 mmol) and diphenyl phosphite (0.18 mL, 0.82 mmol) in pyridine (2 mL) was sealed and heated with oil bath at 70° C. for 2 h. The reaction mixture was allowed to cool to rt, treated with N-(7-amino-4-chloro-1-methyl-1H-indazol-3-yl)-N-(4-methoxybenzyl)methanesulfonamide (108 mg, 0.274 mmol), and then resealed and heated at 70° C. for another 2 h. The reaction mixture was concentrated and the residue partitioned between water (20 mL) and EtOAc (10 mL). The organic component was washed with water, 5% citric acid, dried (MgSO$_4$), filtered and concentrated. The residue was purified by prep-HPLC to afford the title compound (80 mg) as a tan gum. LC/MS retention time=1.11 min; m/z=809.4 [M+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

(S)—N-(7-(2-(1-amino-2-(3,5-difluorophenyl)ethyl)-5-methoxy-4-oxoquinazolin-3(4H)-yl)-4-chloro-1-methyl-1H-indazol-3-yl)methanesulfonamide (Int JB62b)

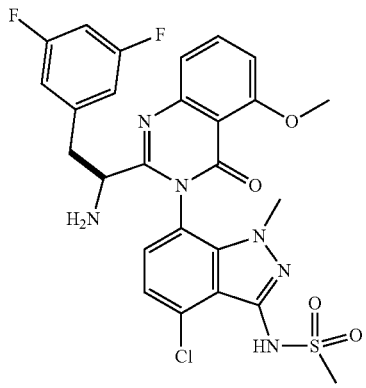 [SMILES: COc1cccc2nc([C@@H](N)Cc3cc(F)cc(F)c3)n(-c3ccc(Cl)c4c(NS(C)(=O)=O)nn(C)c34)c(=O)c12]

To an ice-bath cooled solution of Int JB62a (80 mg, 0.099 mmol) in DCM (0.4 mL) was added TFA (0.40 mL) and triflic acid (0.04 mL, 0.5 mmol) and the reaction mixture was stirred at rt for 1 h. The reaction mixture was concentrated and the residue was partitioned between EtOAc (5 mL) and sat. NaHCO$_3$ (10 mL). The organic component was washed with brine, dried (MgSO$_4$), filtered, and concentrated to afford the title compound (60 mg) as an off-white foam and a mixture of stereoisomers. This material was used without additional purification. LC/MS retention time=0.63 and 0.69 min (1:2.5); m/z=589.2, 589.2 (respectively) [M+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

N—((S)-1-(3-(4-chloro-1-methyl-3-(methylsulfonamido)-1H-indazol-7-yl)-5-methoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 170) and Example 169

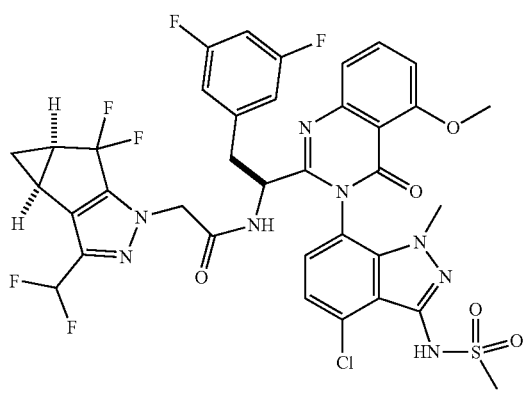 [SMILES: COc1cccc2nc([C@H](Cc3cc(F)cc(F)c3)NC(=O)Cn3nc(C(F)F)c4c3C(F)(F)[C@@H]3C[C@H]43)n(-c3ccc(Cl)c4c(NS(C)(=O)=O)nn(C)c34)c(=O)c12]

To a solution of Int JB62b (60 mg, 0.092 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (24 mg, 0.092 mmol) and HOAt (1 M in DMA, 0.05 mL, 0.05 mmol) in DMF (1 mL) was added EDC (19 mg, 0.10 mmol) and N-methylmorpholine (0.05 mL, 0.4 mmol). The reaction mixture was poured into 5% citric acid (20 mL) and extracted with EtOAc (2×10 mL). The combined organic components were washed with brine, dried (MgSO$_4$), filtered and concentrated. The residue was taken up in DMF (2 mL) and the crude material was purified via preparative LC/MS (Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 34% B, 34-74% B over 30 minutes, then a 4-minute hold at 100% B; Flow Rate: 20 mL/min; Column Temperature: 25° C.) to afford two elutes, each as a mixture of stereoisomers.

Example 169: First Elute (5.8 mg)

QC-ACN-TFA-XB (Purity: 100.0%; RT: 1.99 min; Obs. Adducts: [M+H]; Obs. Masses: 835.43).

Example 170: Second Elute (15.8 mg)

QC-ACN-TFA-XB (Purity: 100.0%; RT: 2.04; Obs. Adducts: [M+H]; Obs. Masses: 835.42). $^1$H NMR (500 MHz, MeOH-d$_4$) δ 7.91-7.84 (m, 1H), 7.46 (br d, J=7.9 Hz, 1H), 7.28 (br d, J=7.6 Hz, 1H), 7.19 (br d, J=8.2 Hz, 1H), 7.13 (br d, J=7.9 Hz, 1H), 6.82-6.54 (m, 4H), 4.82 (br dd, J=7.5, 4.7 Hz, 1H), 4.52 (s, 2H), 3.96 (s, 3H), 3.64 (s, 3H), 3.49-3.40 (m, 1H), 3.24 (s, 3H), 3.12-3.02 (m, 1H), 2.43 (br s, 2H), 1.42-1.33 (m, 1H), 1.01 (br s, 1H). $^{19}$F NMR (471 MHz, MeOH-d$_4$) δ −82.18 (br d, J=256.1 Hz, 1F), −105.06 (br d, J=254.6 Hz, 1F), −111.73 (s, 2F), −113.33 (d, J=311.9 Hz, 1F), −114.49 (d, J=311.9 Hz, 1F).

tert-butyl (S)-(1-(3-(4-chloro-3-(N-(4-methoxybenzyl)methylsulfonamido)-1-methyl-1H-indazol-7-yl)-4-oxo-5-(thiazol-2-yl)-3,4-dihydroquinazolin-2-yl)-2-(3,5-difluorophenyl)ethyl)carbamate (Int JB65a)

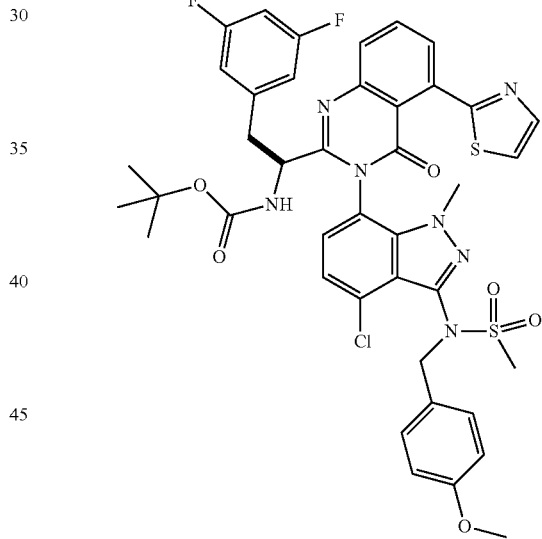

A vessel containing Int JB53a (240 mg, 0.280 mmol), 2-(tributylstannyl)thiazole (126 mg, 0.336 mmol), bis(triphenylphosphine)palladium(II) chloride (9.8 mg, 0.014 mmol) and toluene (5 mL) was vacuum flushed with N$_2$ (3×). The reaction vessel was sealed and heated at 120° C. for 12 h. The reaction mixture was then cooled, filtered through a pad of Celite, and concentrated in vacuo. The residue was taken up in DCM and purified by FCC (24 g silica gel cartridge, 0-70% EtOAc-hexanes) to afford the title compound (170 mg) as a white glass. LC/MS retention time=1.11 min; m/z=862.4 [M+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

407

(S)—N-(7-(2-(1-amino-2-(3,5-difluorophenyl)ethyl)-4-oxo-5-(thiazol-2-yl)quinazolin-3(4H)-yl)-4-chloro-1-methyl-1H-indazol-3-yl)methanesulfonamide (Int JB65b)

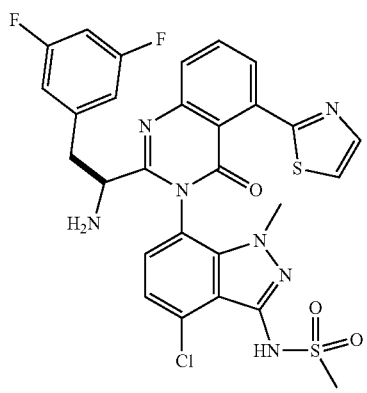 [SMILES: Cn1nc(NS(C)(=O)=O)c2c(Cl)ccc(-n3c([C@@H](N)Cc4cc(F)cc(F)c4)nc4cccc(-c5nccs5)c4c3=O)c21]

To an ice bath cooled solution of Int JB 65a (170 mg, 0.197 mmol) in DCM (0.8 mL) was added TFA (0.80 mL) and triflic acid (0.09 mL, 1.0 mmol) and the reaction mixture was stirred at rt for 1 h. The reaction mixture was concentrated in vacuo and the residue was partitioned between EtOAc (5 mL) and sat. NaHCO$_3$ (10 mL). The organic component was washed with brine, dried (MgSO$_4$), filtered and concentrated to afford the title compound (133 mg) as a light yellow foam. This material was used without further purification. LC/MS retention time=0.72 min; m/z=642.2 [M+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

tert-butyl (S)-(1-(3-(4-chloro-3-(N-(4-methoxybenzyl)methylsulfonamido)-1-methyl-1H-indazol-7-yl)-5-fluoro-7-methyl-4-oxo-3,4-dihydroquinazolin-2-yl)-2-(3,5-difluorophenyl)ethyl)carbamate (Int JB66a)

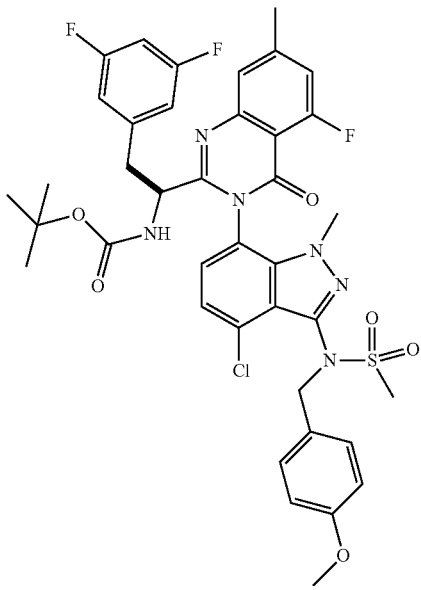 [SMILES: COc1ccc(CN(c2nn(C)c3c(-n4c([C@H](Cc5cc(F)cc(F)c5)NC(=O)OC(C)(C)C)nc5cc(C)cc(F)c5c4=O)ccc(Cl)c23)S(C)(=O)=O)cc1]

408

A mixture of (S)-2-((tert-butoxycarbonyl)amino)-3-(3,5-difluorophenyl)propanoic acid (70 mg, 0.23 mmol), 2-amino-6-fluoro-4-methylbenzoic acid (41.4 mg, 0.232 mmol) and diphenyl phosphite (0.17 mL, 0.77 mmol) in pyridine (2 mL) was sealed and heated with microwave irradiation at 70° C. for 2 h. The reaction mixture was allowed to cool to rt and was then treated with N-(7-amino-4-chloro-1-methyl-1H-indazol-3-yl)-N-(4-methoxybenzyl)methanesulfonamide (101 mg, 0.256 mmol) and heated again with microwave irradiation at 70° C. for another 2 h. The reaction mixture was concentrated and partitioned between water (20 mL) and EtOAc (10 mL). The separated organic component was washed with water, 5% citric acid, 1 M NaOH and brine, dried (MgSO$_4$), filtered and concentrated. The residue was purified by FCC (24 g silica gel cartridge, 0-60% EtOAc-hexanes) to afford the title compound (96 mg) as a white foam. LC/MS retention time=1.15 min; m/z=755.2 [M−tBu+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)—N-(7-(2-(1-amino-2-(3,5-difluorophenyl)ethyl)-5-fluoro-7-methyl-4-oxoquinazolin-3(4H)-yl)-4-chloro-1-methyl-1H-indazol-3-yl)methanesulfonamide (Int JB66b)

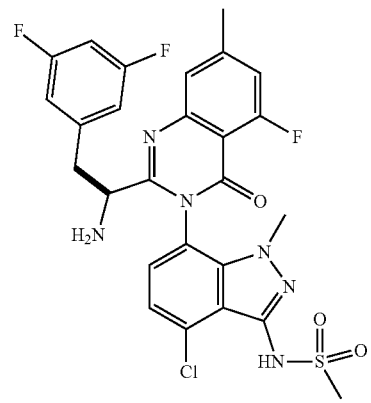 [SMILES: Cc1cc(F)c2c(=O)n(-c3ccc(Cl)c4c(NS(C)(=O)=O)nn(C)c34)c([C@@H](N)Cc3cc(F)cc(F)c3)nc2c1]

To an ice bath cooled solution of Int JB66a (96 mg, 0.118 mmol) in DCM (0.5 mL) was added TFA (0.5 mL) and triflic acid (0.05 mL, 0.6 mmol) and the reaction mixture was stirred at rt for 1 h. The reaction mixture was concentrated and partitioned between EtOAc (5 mL) and sat. NaHCO$_3$ (10 mL). The organic component was washed with brine, dried (MgSO$_4$), filtered, and concentrated to afford the title compound (84 mg) as an off-white foam, and a mixture of stereoisomers. This material was used without additional purification. LC/MS retention time=0.67 and 0.72 min; m/z=642.2 and 642.2 (~2:5, respectively) [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

N—((S)-1-(3-(4-chloro-1-methyl-3-(methylsulfona-
mido)-1H-indazol-7-yl)-5-fluoro-7-methyl-4-oxo-3,
4-dihydroquinazolin-2-yl)-2-(3,5-difluorophenyl)
ethyl)-2-((3bS,4aR)-3-(difluoromethyl)-5,5-difluoro-
3b,4,4a,5-tetrahydro-1H-cyclopropa[3,4]cyclopenta
[1,2-c]pyrazol-1-yl)acetamide (Example 172) and
Example 171

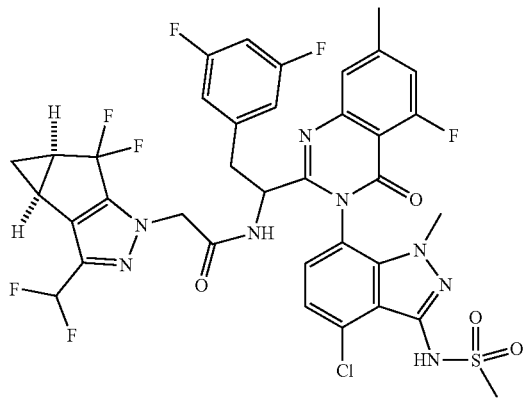 [SMILES: Cc1cc(F)c2c(=O)n(-c3ccc(Cl)c4c(NS(C)(=O)=O)nn(C)c34)c(C(Cc3cc(F)cc(F)c3)NC(=O)Cn3nc(C(F)F)c4c3C(F)(F)[C@@H]3C[C@H]43)nc2c1]

To a solution of Int JB66b (84 mg, 0.12 mmol), 2-((3bS, 4aR)-3-(difluoromethyl)-5,5-difluoro-3b,4,4a,5-tetrahydro-1H-cyclopropa[3,4]cyclopenta[1,2-c]pyrazol-1-yl)acetic acid (31 mg, 0.12 mmol) and HOAt (1 M in DMA, 0.06 mL, 0.06 mmol) in DMF (1 mL) was added EDC (25 mg, 0.13 mmol) and N-methylmorpholine (0.05 mL, 0.5 mmol). The reaction mixture was stirred at rt overnight. The crude material was purified via preparative LC/MS (Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 42% B, 42-88% B over 21 minutes, then a 4-minute hold at 100% B; Flow Rate: 20 mL/min; Column Temperature: 25° C.) to retrieve two isolates, each as a mixture of stereoisomers.

Example 171 First Elute (13.6 mg, Mixture of Stereoisomers)

QC-ACN-TFA-XB-01: (Purity: 99.0%; RT: 2.12; Obs. Adducts: [M+H]; Obs. Masses: 837.49)
The second elute (39.1 mg) was further purified by chiral SFC (Chiralpak IC preparative column, 30×250 mm, 5 mm; Mobile Phase: 25% IPA in CO$_2$, 150 bar; Temp: 35 C; Flow rate: 70.0 mL/min. for 22 min; UV monitored @ 306 nm; Injection: 0.5 mL of ~9 mg/mL solution in 3:1 MeOH: CHCl$_3$ (~37 mg purified by stacked injection)) to afford the Example 172 (20 mg, Single Stereoisomer)

QC-ACN-AA-XB (Purity: 100.0%; RT: 2.20 min; Obs. Adducts: [M+H]; Obs. Masses: 837.05). $^1$H NMR (500 MHz, MeOH-d$_4$) δ 7.54 (s, 1H), 7.30 (d, J=7.9 Hz, 1H), 7.24-7.20 (m, 1H), 7.18 (d, J=7.8 Hz, 1H), 6.82-6.57 (m, 4H), 4.81 (dd, J=9.2, 5.0 Hz, 1H), 4.51 (d, J=1.7 Hz, 2H), 3.65 (s, 3H), 3.44 (dd, J=14.1, 5.1 Hz, 1H), 3.25 (s, 3H), 3.07 (dd, J=14.0, 9.2 Hz, 1H), 2.59 (s, 3H), 2.44 (ddd, J=11.4, 7.7, 4.0 Hz, 2H), 1.41-1.34 (m, 1H), 1.04-0.99 (m, 1H). $^{19}$F NMR (470 MHz, MeOH-d$_4$) δ −82.19 (br d, J=255.3 Hz, 1F), −105.08 (br d, J=257.5 Hz, 1F), −111.72 (s, 2F), −112.36 (s, 1F) −113.35 (d, J=312.5 Hz, 1F), −114.55 (d, J=312.5 Hz, 1F).

tert-butyl (S)-(1-(3-(4-chloro-3-(N-(4-methoxyben-
zyl)methylsulfonamido)-1-methyl-1H-indazol-7-yl)-
6-methoxy-4-oxo-3,4-dihydroquinazolin-2-yl)-2-(3,
5-difluorophenyl)ethyl)carbamate (Int JB70a)

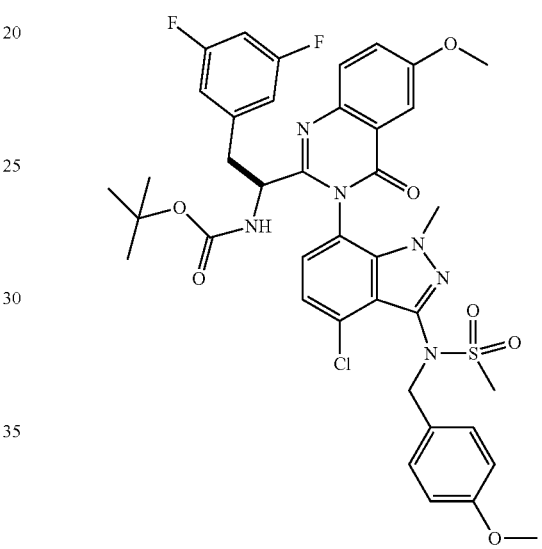

A mixture of (S)-2-((tert-butoxycarbonyl)amino)-3-(3,5-difluorophenyl)propanoic acid (140 mg, 0.465 mmol), 2-amino-5-methoxybenzoic acid (78 mg, 0.47 mmol) and diphenyl phosphite (0.33 mL, 1.5 mmol) in pyridine (2.5 mL) was sealed and heated in an oil bath at 70° C. for 2 h. The reaction mixture was allowed to cool to rt and then treated with N-(7-amino-4-chloro-1-methyl-1H-indazol-3-yl)-N-(4-methoxybenzyl)methanesulfonamide (202 mg, 0.511 mmol) and resealed and reheated in the oil bath at 70° C. for another 2 h and then at 80° C. for an additional 2 h. The reaction mixture was concentrated and the residue was partitioned between water (20 mL) and EtOAc (10 mL). The organic component was washed with water, 5% citric acid, 1.5 M K$_3$PO$_4$ and brine, dried (MgSO$_4$), filtered and concentrated. The residue was purified by FCC (24 g silica gel cartridge, 0-60% EtOAc-hexanes) to afford the title compound (251 mg) as a white foam. LC/MS retention time=1.14 min; m/z=809.3 [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

411

(S)—N-(7-(2-(1-amino-2-(3,5-difluorophenyl)ethyl)-6-methoxy-4-oxoquinazolin-3(4H)-yl)-4-chloro-1-methyl-1H-indazol-3-yl)methanesulfonamide (Int JB70b)

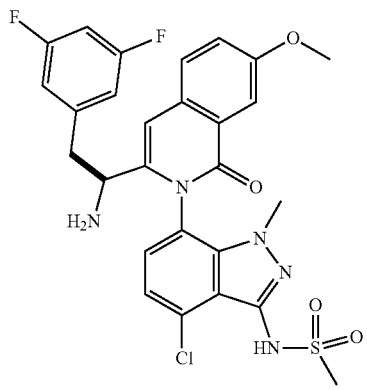 [SMILES: COc1ccc2cc([C@@H](N)Cc3cc(F)cc(F)c3)n(-c3ccc(Cl)c4c(NS(C)(=O)=O)nn(C)c34)c(=O)c2c1]

To an ice bath cooled solution of Int JB70a (251 mg, 0.310 mmol) in DCM (1 mL) was added TFA (1 mL) and triflic acid (0.14 mL, 1.5 mmol) and the reaction mixture was stirred at rt for 1 h. The reaction mixture was concentrated and partitioned between EtOAc (5 mL) and sat. NaHCO3 (10 mL). The organic component was washed with brine, dried (MgSO$_4$), filtered, and concentrated to afford the title compound (211 mg) as an off-white foam, and a mixture of stereoisomers. This material was used without additional purification. LC/MS retention time=0.69 and 0.75 min; m/z=589.2 and 589.2 [M+H]$^+$. Column: Acquity BEH 2.1× 50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

N—((S)-1-(3-(4-chloro-1-methyl-3-(methylsulfonamido)-1H-indazol-7-yl)-6-methoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 174) and Example 173

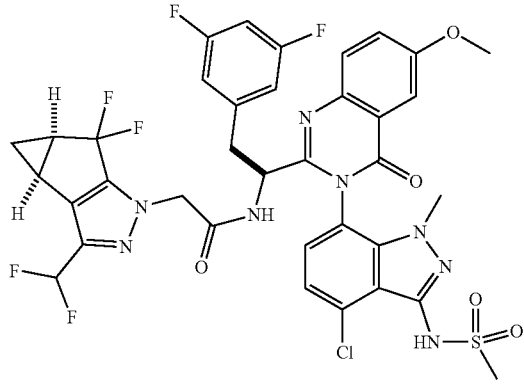 [SMILES: COc1ccc2nc([C@H](Cc3cc(F)cc(F)c3)NC(=O)Cn3nc(C(F)F)c4c3C(F)(F)[C@@H]3C[C@H]43)n(-c3ccc(Cl)c4c(NS(C)(=O)=O)nn(C)c34)c(=O)c2c1]

412

To a solution of Int JB70b (111 mg, 0.164 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetic acid (43.3 mg, 0.164 mmol) and HOAt (1 M in DMA, 0.082 mL, 0.082 mmol) in DMF (1.7 mL) was added EDC (34.6 mg, 0.180 mmol) and N-methylmorpholine (0.073 mL, 0.66 mmol). The reaction mixture was stirred at rt overnight. The crude material was purified via preparative LC/MS (Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 35% B, 35-75% B over 25 minutes, then a 4-minute hold at 100% B; Flow Rate: 20 mL/min; Column Temperature: 25° C.).

Example 173: First Elute (26 mg, Single Stereoisomer)

QC-ACN-TFA-XB (Purity: 100.0%; RT: 2.18 min; Obs. Adducts: [M+H]; Obs. Masses: 835.11).

Example 174: Second Elute (49 mg, Single Stereoisomer)

QC-ACN-TFA-XB (Purity: 99.2%; RT: 2.25 min; Obs. Adducts: [M+H]; Obs. Masses: 835.19). $^1$H NMR (500 MHz, MeOH-d$_4$) δ 7.85 (d, J=8.9 Hz, 1H), 7.69 (d, J=2.7 Hz, 1H), 7.60-7.55 (m, 1H), 7.30 (d, J=7.6 Hz, 1H), 7.15 (br d, J=7.9 Hz, 1H), 6.82-6.57 (m, 4H), 4.85 (br dd, J=9.0, 5.0 Hz, 1H), 4.51 (s, 2H), 3.96 (s, 3H), 3.59 (s, 3H), 3.46 (br dd, J=13.7, 4.9 Hz, 1H), 3.26 (s, 3H), 3.07 (br dd, J=14.2, 9.0 Hz, 1H), 2.47-2.40 (m, 2H), 1.40-1.33 (m, 1H), 1.01 (br s, 1H) $^{19}$F NMR (471 MHz, MeOH-d$_4$) δ −82.16 (br d, J=254.6 Hz, 1F), −105.05 (br d, J=256.1 Hz, 1F), −111.75 (s, 2F), −113.34 (d, J=311.9 Hz, 1F), −114.47 (d, J=311.9 Hz, 1F).

tert-butyl (S)-(1-(6-chloro-3-(4-chloro-3-(N-(4-methoxybenzyl)methylsulfonamido)-1-methyl-1H-indazol-7-yl)-5-fluoro-4-oxo-3,4-dihydroquinazolin-2-yl)-2-(3,5-difluorophenyl)ethyl)carbamate (Int JB72a)

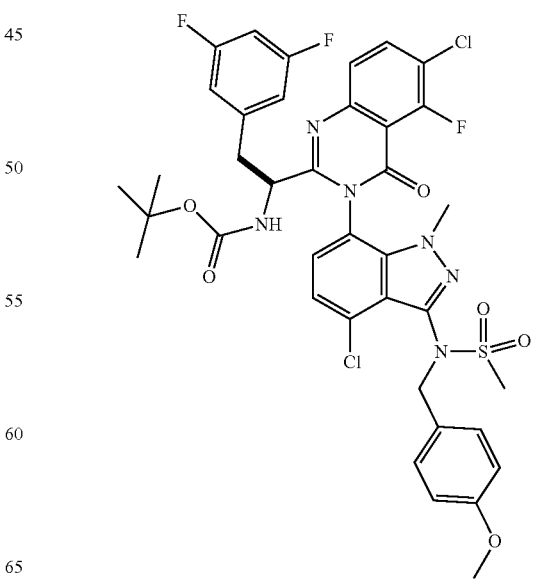

A mixture of (S)-2-((tert-butoxycarbonyl)amino)-3-(3,5-difluorophenyl)propanoic acid (140 mg, 0.465 mmol), 6-amino-3-chloro-2-fluorobenzoic acid (88 mg, 0.47 mmol) and diphenyl phosphite (0.33 mL, 1.5 mmol) in pyridine (2.5 mL) was sealed and heated in an oil bath at 70° C. for 2 h. The reaction mixture was allowed to cool to rt and was then treated with N-(7-amino-4-chloro-1-methyl-1H-indazol-3-yl)-N-(4-methoxybenzyl)methanesulfonamide (202 mg, 0.511 mmol) and heated again in the oil bath at 70° C. for another 2 h. The reaction mixture was concentrated and partitioned between water (20 mL) and EtOAc (10 mL). The separated organic component was washed with water, 5% citric acid, 1.5 M $K_3PO_4$ and brine, dried ($MgSO_4$), filtered and concentrated. The residue was purified by FCC (24 g silica gel cartridge, 0-50% EtOAc-hexanes) to afford the title compound (158 mg) as a white foam. LC/MS retention time=1.14 min; m/z=775.3, 777.3 [M−tBu+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)—N-(7-(2-(1-amino-2-(3,5-difluorophenyl)ethyl)-6-chloro-5-fluoro-4-oxoquinazolin-3(4H)-yl)-4-chloro-1-methyl-1H-indazol-3-yl)methanesulfonamide (Int JB72b)

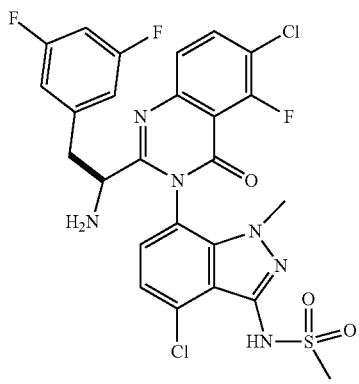 [SMILES: Cn1nc(NS(C)(=O)=O)c2c(Cl)ccc(-n3c([C@@H](N)Cc4cc(F)cc(F)c4)nc4ccc(Cl)c(F)c4c3=O)c21]

To an ice bath cooled solution of Int JB72a (158 mg, 0.203 mmol) in DCM (0.8 mL) was added TFA (0.8 mL) and triflic acid (0.09 mL, 1 mmol) and the reaction mixture was stirred at rt for 1 h. The reaction mixture was concentrated and partitioned between EtOAc (5 mL) and sat. NaHCO$_3$ (10 mL). The organic component was washed with brine, dried (MgSO$_4$), filtered, and concentrated to afford the title compound (140 mg) as an off-white foam, and a mixture of stereoisomers. This material was used without additional purification. LC/MS retention time=0.73 and 0.78 min; m/z=611.1 and 611.1 (~3:5, respectively) [M+H]$^+$. Column: Acquity BEH 2.1×50 mm, 1.7 μm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

N—((S)-1-(6-chloro-3-(4-chloro-1-methyl-3-(methylsulfonamido)-1H-indazol-7-yl)-5-fluoro-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 176) and Example 175 and Example 177

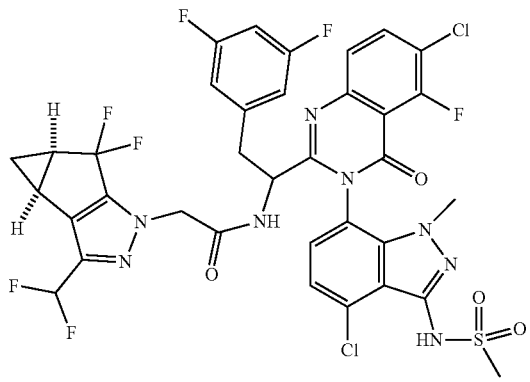

Example 175
mix of two stereoisomers

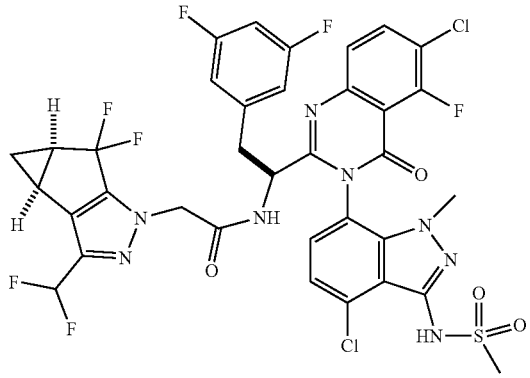

Example 176
single stereoisomer

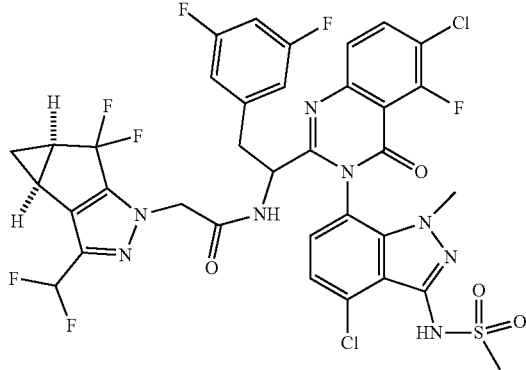

Example 177
single stereoisomer

To a solution of Int JB72b (110 mg, 0.158 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (42 mg, 0.16 mmol) and HOAt (1 M in DMA, 0.079 mL, 0.079 mmol) in DMF (1.7 mL) was added EDC (33.4 mg, 0.174 mmol) and N-methylmorpholine (0.07 mL, 0.6 mmol). The reaction mixture was stirred at rt overnight.

The crude material was purified via preparative LC/MS (Column: XBridge Shield RP18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 29% B, 29-55% B over 45 minutes, then a 10-minute hold at 100% B; Flow Rate: 20 mL/min; Column Temperature: 25° C.) to retrieve two isolates, each as a mixture of stereoisomers.

Example 175: First Elute (14.3 mg, Mixture of Stereoisomers)

QC-ACN-AA-XB (Purity: 98.5%; RT: 2.23 min; Obs. Adducts: [M+H]; Obs. Masses: 857.3). The second elute (39.2 mg, mixture of stereoisomers) was further purified by chiral SFC (Instrument: Waters 100 Prep SFC; Column: Chiral OD 30×250 mm. 5 μm; Mobile Phase: 80% $CO_{2/20}$% MeOH-ACN 50-50; Flow Conditions: 100 mL/min; Detector Wavelength: 220 nm; Injection Details: 750 μL 39.2 mg dissolved in 3 mL MeOH). Two elutes of stereoisomeric relation were isolated.

Example 176: First Elute (14 mg, Single Stereoisomer)

QC-ACN-AA-XB (Purity: 98.5%; RT: 2.23 min; Obs. Adducts: [M+H]; Obs. Masses: 857.3). $^1$H NMR (500 MHz, MeOH-$d_4$) δ 8.04 (br t, J=7.8 Hz, 1H), 7.72 (br d, J=8.5 Hz, 1H), 7.35-7.30 (m, 1H), 7.25 (br d, J=7.9 Hz, 1H), 6.81-6.56 (m, 4H), 4.51 (br s, 2H), 3.66 (s, 3H), 3.44 (dd, J=14.6, 4.6 Hz, 1H), 3.26 (s, 3H), 3.08 (br dd, J=14.2, 9.3 Hz, 1H), 2.43 (br d, J=3.7 Hz, 2H), 1.40-1.34 (m, 1H), 1.00 (br d, J=2.4 Hz, 1H). $^{19}$F NMR (471 MHz, MeOH-$d_4$) δ −82.20 (br d, J=254.6 Hz, 1F), −105.02 (br d, J=254.6 Hz, 1F), −111.66 (s, 2F), −112.65 (s, 1F), −113.32 (d, J=311.9 Hz, 1F), −114.61 (d, J=311.9 Hz, 1F).

Example 177: Second Elute (6.4 mg, Single Stereoisomer)

QC-ACN-AA-XB (Purity: 98.5%; RT: 2.23 min; Obs. Adducts: [M+H]; Obs. Masses: 857.0).

tert-butyl(S)-(1-(5,7-dichloro-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int JB73a)

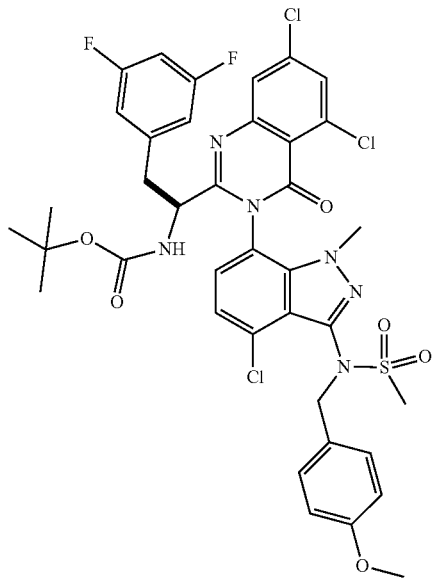 [SMILES: COc1ccc(CN(c2nn(C)c3c(-n4c([C@H](Cc5cc(F)cc(F)c5)NC(=O)OC(C)(C)C)nc5cc(Cl)cc(Cl)c5c4=O)ccc(Cl)c23)S(C)(=O)=O)cc1]

In a pressure vessel, a mixture of (S)-2-((tert-butoxycarbonyl)amino)-3-(3,5-difluorophenyl)propanoic acid (84 mg, 0.28 mmol) and 2-amino-4,6-dichlorobenzoic acid (57.4 mg, 0.279 mmol) were dissolved into pyridine (2 mL) and diphenyl phosphite (0.16 mL, 0.84 mmol) and the reaction mixture was flushed with nitrogen, sealed and then heated at 70° C. for 4h. The reaction mixture was allowed to cool to rt and was then treated with N-(7-amino-4-chloro-1-methyl-1H-indazol-3-yl)-N-(4-methoxybenzyl)methanesulfonamide (100 mg, 0.253 mmol), resealed and heated at 70° C. for 3.5h. The reaction mixture was concentrated to dryness and then diluted with EtOAc (~10 mL) and washed with 5% citric acid (~5 mL), 1.5 M $K_3PO_4$ (5 mL), and brine (5 mL). The organic component was concentrated and the residue was purified by using an ISCO (24 g $SiO_2$, 0-50% EtOAc/hex) to afford the title compound (153 mg) as a white solidified foam. LC/MS retention time=1.21 min; m/z=793.3 [M−tBu+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

(S)—N-(7-(2-(1-amino-2-(3,5-difluorophenyl)ethyl)-5,7-dichloro-4-oxoquinazolin-3(4H)-yl)-4-chloro-1-methyl-1H-indazol-3-yl)methanesulfonamide (Int JB73b)

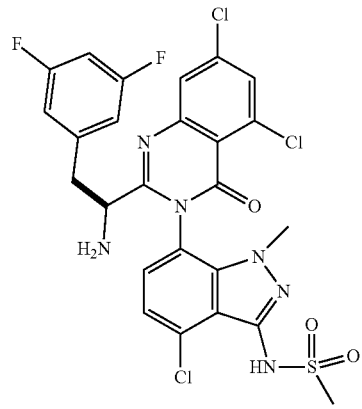 [SMILES: Cn1nc(NS(C)(=O)=O)c2c(Cl)ccc(-n3c([C@@H](N)Cc4cc(F)cc(F)c4)nc4cc(Cl)cc(Cl)c4c3=O)c21]

Triflic acid (0.08 mL, 0.9 mmol) was added dropwise to a solution of Int JB73a (150 mg, 0.177 mmol) in DCM (1.5 mL) and TFA (0.75 mL) and the reaction mixture was stirred at rt for 1.5h. The crude mixture was concentrated and the residue was dissolved into EtOAc (~8 mL) and washed with sat $NaHCO_3$ (~4 mL). The organic component was dried with $MgSO_4$, filtered and concentrated to afford the title compound (166 mg; yellow glass) as a mixture of stereoisomers. This material was used without additional purification. LC/MS retention time=0.75 and 0.80 min (1:3.5); m/z=627.1 [M+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

N—((S)-1-(5,7-dichloro-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 179) and Example 178 and 180

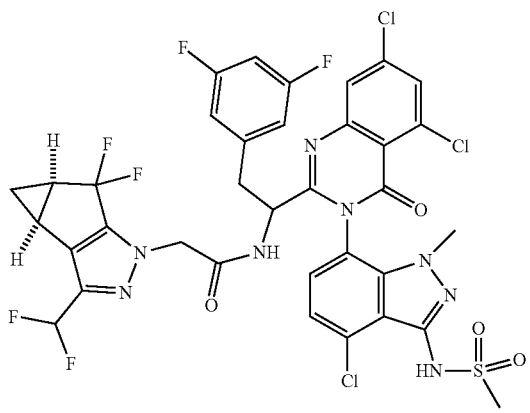

Example 178
mix of stereoisomers

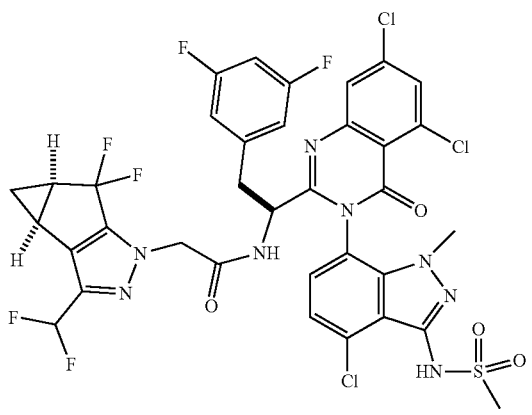

Example 179
single stereoisomer

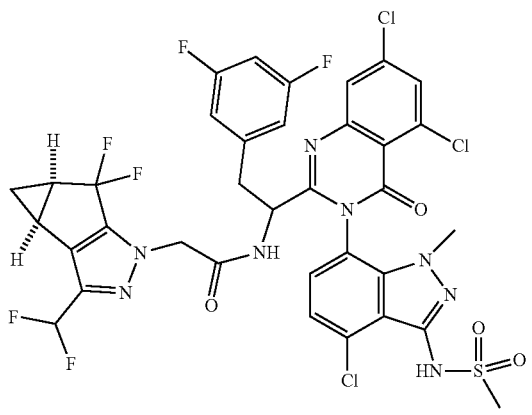

Example 180
single stereoisomer

EDC (36.4 mg, 0.190 mmol) and N-methylmorpholine (0.076 mL, 0.690 mmol) were added to a stirred solution of Int JB73b (164 mg, 0.172 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (45.5 mg, 0.172 mmol) and 1M 3H-[1,2,3]triazolo[4,5-b]pyridin-3-ol in DMA (0.06 mL, 0.06 mmol) and DMF (1.7 mL). The reaction mixture was stirred at rt for 2h. The crude reaction mixture was filtered and was purified via preparative LC/MS (Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 40% B, 40-82% B over 25 minutes, then a 4-minute hold at 100% B; Flow Rate: 20 mL/min; Column Temperature: 25° C.) to retrieve two isolates, each as a mixture of stereoisomers.

Example 178: First Elute (13.5 mg)

QC-ACN-AA-XB (Purity: 100%; RT: 2.32 min; Obs. Adducts: [M+H]; Obs. Masses: 873.07).

The second elute (75.5 mg) was further purified by chiral SFC (Instrument: Waters 100 Prep SFC; Column: Chiral IC 21×250 mm. 5 µm; Mobile Phase: 70% $CO_{2}$/30% IPA w/0.1% DEA; Flow Conditions: 60 mL/min; Detector Wavelength: 220 nm; Injection Details: 500 µL 75.5 mg dissolved in 3 mL MeOH). Two elutes of stereoisomeric relation were isolated.

Example 179: First elute (34.7 mg). QC-ACN-AA-XB (Purity: 100%; RT: 2.37 min; Obs. Adducts: [M+H]; Obs. Masses: 873.2). $^1$H NMR (500 MHz, MeOH-$d_4$) δ 7.84 (d, J=2.1 Hz, 1H), 7.71 (d, J=2.1 Hz, 1H), 7.33-7.28 (m, 1H), 7.24 (br d, J=7.9 Hz, 1H), 6.81-6.56 (m, 4H), 4.79 (br dd, J=9.6, 4.7 Hz, 1H), 4.52 (br d, J=5.8 Hz, 2H), 3.66 (s, 3H), 3.43 (br dd, J=14.0, 4.6 Hz, 1H), 3.26 (s, 3H), 3.12-3.01 (m, 1H), 2.44 (br s, 2H), 1.41-1.33 (m, 1H), 1.00 (br s, 1H). $^{19}$F NMR (471 MHz, MeOH-$d_4$) δ -82.18 (br d, J=254.6 Hz, 1F), -105.02 (br d, J=254.6 Hz, 1F), -111.62 (s, 2F), -113.33 (d, J=311.9 Hz, 1F), -114.58 (d, J=311.9 Hz, 1F)

Example 180: Second Elute (27.2 mg)

QC-ACN-AA-XB (Purity: 100%; RT: 2.38 min; Obs. Adducts: [M+H]; Obs. Masses: 873.23).

421 tert-butyl (S)-(1-(3-(4-chloro-3-(N-(4-methoxybenzyl)methylsulfonamido)-1-methyl-1H-indazol-7-yl)-5,7-dimethoxy-4-oxo-3,4-dihydroquinazolin-2-yl)-2-(3,5-difluorophenyl)ethyl)carbamate (Int JB74a)

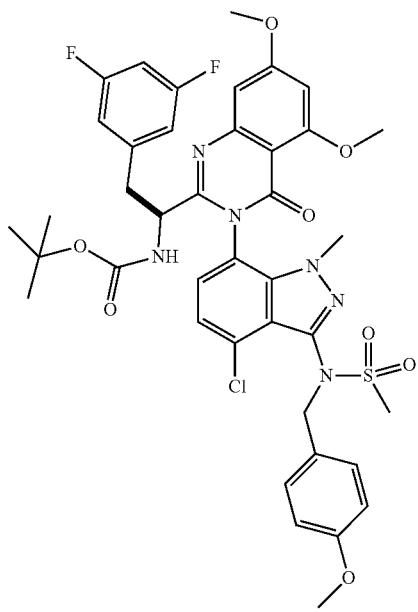 [SMILES: COc1ccc(CN(c2nn(C)c3c(-n4c([C@H](Cc5cc(F)cc(F)c5)NC(=O)OC(C)(C)C)nc5cc(OC)cc(OC)c5c4=O)ccc(Cl)c23)S(C)(=O)=O)cc1]

A mixture of (S)-2-((tert-butoxycarbonyl)amino)-3-(3,5-difluorophenyl)propanoic acid (153 mg, 0.506 mmol), 2-amino-4,6-dimethoxybenzoic acid (100 mg, 0.506 mmol) and N-(7-amino-4-chloro-1-methyl-1H-indazol-3-yl)-N-(4-methoxybenzyl)methanesulfonamide (100 mg, 0.253 mmol) in pyridine (2 mL) was treated with diphenyl phosphite (0.30 mL, 1.5 mmol) and flushed with nitrogen. The reaction mixture was sealed in a pressure vessel and stirred and heated at 70° C. for 3h. The reaction mixture was partially concentrated under a stream of nitrogen, diluted with EtOAc (~25 mL) and washed with 5% citric acid (~20 mL), sat. K$_3$PO$_4$ (~20 mL) and brine. The organic component were dried (MgSO$_4$), filtered and concentrated. The residue was purified by prep HPLC in 8 injections (Column: Phenomenex Luna C18 5 μm 21.2×100 mm; Solvent A: 90:10 MeOH/H$_2$O with 0.1% TFA; Solvent B: 10:90 MeOH/H$_2$O with 0.1% TFA; Gradient: 50-100% B over 12 min; Flow rate: 20 mL/min; Wavelength: 220 nm) to afford the title compound (108 mg). LC/MS retention time=1.12 min; m/z=839.1 [M+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

422

(S)—N-(7-(2-(1-amino-2-(3,5-difluorophenyl)ethyl)-5,7-dimethoxy-4-oxoquinazolin-3(4H)-yl)-4-chloro-1-methyl-1H-indazol-3-yl)methanesulfonamide (Int JB74b)

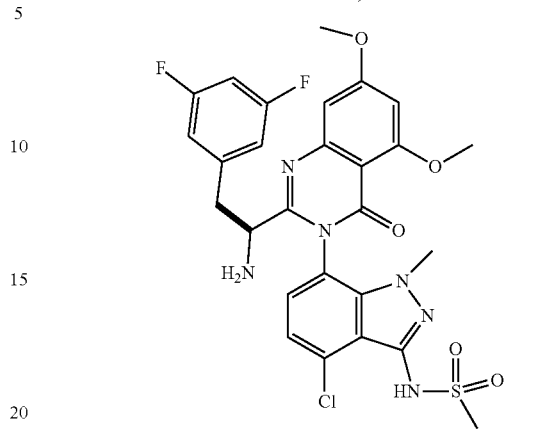

Triflic acid (0.053 mL, 0.60 mmol) was added dropwise to a stirred solution of Int JB74a (108 mg, 0.129 mmol) in DCM (1.0 mL) and TFA (0.5 mL) and the reaction mixture was stirred at rt for 30 min. The reaction mixture was concentrated under a stream of nitrogen and the residue was dissolved into EtOAc (~8 mL) and washed with sat NaHCO$_3$(~4 mL). The organic component was then dried with MgSO$_4$, filtered and concentrated, to afford the title compound (80 mg) as a ~1:1 mixture diastereomers. This material was used without additional purification. LC/MS retention time=0.86 and 0.99 min; m/z=618.9 [M+H]$^+$. Column: BEH C18 2.1×50 mm 1.7 um; Mobile Phase A: 0.05% TFA in water; Mobile Phase B: 0.05% TFA in acetonitrile; Gradient: 2-98% B over 1.0 min, then a 0.5 min hold at 98% B; Detection: UV at 220 nm.

N—((S)-1-(3-(4-chloro-1-methyl-3-(methylsulfonamido)-1H-indazol-7-yl)-5,7-dimethoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 182) and Example 181

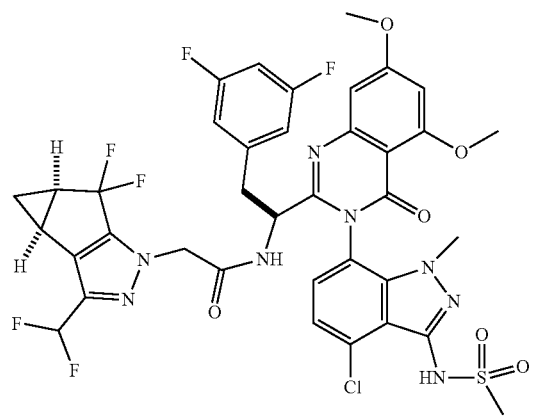 [SMILES: COc1cc(OC)c2c(=O)n(-c3ccc(Cl)c4c(NS(C)(=O)=O)nn(C)c34)c([C@H](Cc3cc(F)cc(F)c3)NC(=O)Cn3nc(C(F)F)c4c3C(F)(F)[C@@H]3C[C@H]43)nc2c1]

EDC (27.2 mg, 0.142 mmol) and N-methylmorpholine (0.06 mL, 0.5 mmol) were added to a stirred solution of Int JB74b (80 mg, 0.129 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (34.1 mg, 0.129 mmol) in 3H-[1,2,3]triazolo[4,5-b]pyridin-3-ol (1M in DMA, 0.04 mL, 0.04 mmol) and DMF (1 mL), and the reaction mixture was then stirred at rt ON. The crude reaction mixture was filtered and purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 45% B, 45-90% B over 22 minutes, then a 5-minute hold at 100% B; Flow Rate: 20 mL/min; Column Temperature: 25° C. Two isolates, each as a single stereoisomer, were isolated.

Example 181: First Elute (8.7 mg)

QC-ACN-AA-XB (Purity: 95%; RT: 2.07 min; Obs. Adducts: [M+H]; Obs. Masses: 865.3).

Example 182: Second Elute (6.4 mg)

QC-ACN-AA-XB (Purity: 100.0%; RT 2.17 min; Obs. Adducts: [M+H]; Obs. Masses: 865.1). $^1$H NMR (500 MHz, MeOH-d$_4$) δ 7.26 (d, J=7.9 Hz, 1H), 7.07 (d, J=7.6 Hz, 1H), 6.93 (s, 1H), 6.83-6.56 (m, 5H), 4.80-4.76 (m, 1H), 4.53 (s, 2H), 4.01 (s, 3H), 3.93 (s, 3H), 3.65 (s, 3H), 3.44 (br dd, J=13.6, 5.0 Hz, 1H), 3.24 (s, 3H), 3.06 (br dd, J=13.7, 9.2 Hz, 1H), 2.48-2.41 (m, 2H), 1.41-1.35 (m, 1H), 1.01 (br s, 1H). $^{19}$F NMR (471 MHz, MeOH-d$_4$) δ −82.14 (br d, J=254.6 Hz, 1F), −105.03 (br d, J=256.1 Hz, 1F), −111.71 (s, 2F), −113.33 (d, J=311.9 Hz, 1F), −114.51 (d, J=311.9 Hz, 1F).

(S)—N-(1-(3-(4-chloro-1-methyl-3-(methylsulfonamido)-1H-indazol-7-yl)-5-fluoro-4-oxo-3,4-dihydroquinazolin-2-yl)-2-(3,5-difluorophenyl)ethyl)-2-(3-cyclopropyl-1H-pyrazol-1-yl)acetamide (Example 184) and Example 183

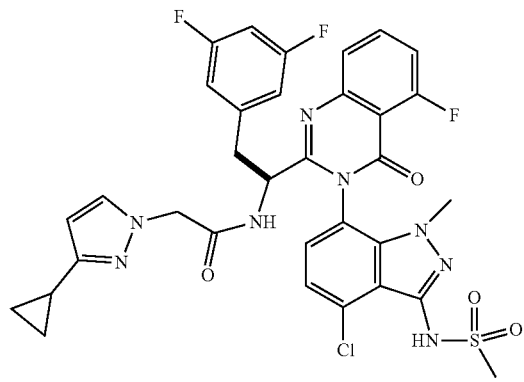 [SMILES: Cn1nc(NS(C)(=O)=O)c2c(Cl)ccc(-n3c([C@H](Cc4cc(F)cc(F)c4)NC(=O)Cn4ccc(C5CC5)n4)nc4cccc(F)c4c3=O)c21]

EDC (32.5 mg, 0.169 mmol) and N-methylmorpholine (0.068 mL, 0.616 mmol) were added to a stirred solution of Int 26b (120 mg, 0.154 mmol) and 2-(3-cyclopropyl-1H-pyrazol-1-yl)acetic acid (25.6 mg, 0.154 mmol) and 3H-[1,2,3]triazolo[4,5-b]pyridin-3-ol in DMA (1M, 0.05 mL, 0.05 mmol) in DMF (1.2 mL), and the reaction mixture was stirred at rt for 2h. The crude reaction mixture was filtered and purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 40% B, 40-90% B over 25 minutes, then a 5-minute hold at 100% B; Flow Rate: 20 mL/min; Column Temperature: 25° C. Two isolates, each as a single stereoisomer, were retrieved.

Example 183: First Elute (25.1 mg)

QC-ACN-AA-XB (Purity: 100.0%; RT: 1.94 min; Obs. Adducts: [M+H]; Obs. Masses: 725.0). $^1$H NMR (500 MHz, MeOH-d$_4$) δ 8.01-7.94 (m, 1H), 7.80 (br d, J=7.9 Hz, 1H), 7.49 (d, J=2.1 Hz, 1H), 7.40-7.29 (m, 2H), 7.22-7.18 (m, 1H), 6.80-6.73 (m, 1H), 6.54 (br d, J=5.8 Hz, 2H), 6.05-6.00 (m, 1H), 4.80-4.66 (m, 3H), 3.41-3.35 (m, 1H), 3.28 (s, 3H), 3.19 (s, 3H), 2.93 (br dd, J=13.7, 6.1 Hz, 1H), 1.94-1.91 (m, 1H), 0.97-0.89 (m, 2H), 0.75-0.68 (m, 2H)

Example 184: Second Elute (48.3 mg)

QC-ACN-AA-XB (Purity: 100.0%; RT: 2.06 min; Obs. Adducts: [M+H]; Obs. Masses: 725.1). $^1$H NMR (500 MHz, MeOH-d$_4$) δ 7.99-7.91 (m, 1H), 7.73 (br d, J=8.2 Hz, 1H), 7.39-7.29 (m, 3H), 7.25-7.21 (m, 1H), 6.79-6.72 (m, 1H), 6.65 (br d, J=7.0 Hz, 2H), 5.93 (br s, 1H), 4.97-4.89 (m, 1H), 4.43-4.36 (m, 1H), 4.33-4.26 (m, 1H), 3.67-3.62 (m, 3H), 3.46 (br dd, J=14.0, 5.2 Hz, 1H), 3.30-3.26 (m, 3H), 3.05 (br dd, J=14.2, 8.7 Hz, 1H), 1.91-1.81 (m, 1H), 0.91-0.84 (m, 2H), 0.65 (br d, J=3.1 Hz, 2H). $^{19}$F NMR (471 MHz, MeOH-d$_4$) δ −111.22 (s, 1F), −111.73 (s, 2F).

tert-butyl 2,6-difluoro-4-methoxybenzoate (Int JB76a)

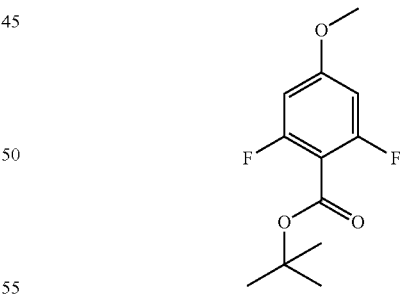

To an ice bath cooled solution of 2-bromo-1,3-difluoro-5-methoxybenzene (4.42 g, 19.8 mmol) in THF (50 mL) was added 1.3 M isopropylmagnesium chloride/lithium chloride complex in THF (15.2 mL, 19.8 mmol) dropwise via an addition funnel. The resultant solution was stirred at this temp for 30 min. A solution of di-tert-butyl dicarbonate (5.06 mL, 21.8 mmol) in THF (10 mL) was added dropwise via an addition funnel and the resulted solution was stirred at this temp for 1 h. The reaction was quenched with 5% citric acid and extracted with EtOAc (50 mL). The organic component was washed with brine, dried over MgSO₄, filtered and evaporated in vacuo. The residual slurry was taken up into DCM (10 mL), filtered, and purified using FCC (a silica gel cartridge (80 g), 0-30% EtOAc-hexanes) to afford the title compound (4.40 g) as a colorless oil. $^1$H NMR (499 MHz, CDCl₃) δ 6.50-6.46 (m, 1H), 6.46-6.43 (m, 1H), 3.83 (s, 3H), 1.60 (s, 9H). $^{19}$F NMR (470 MHz, CDCl₃) δ −109.35 (s, 2F).

tert-butyl 2-amino-6-fluoro-4-methoxybenzoate (Int JB76b)

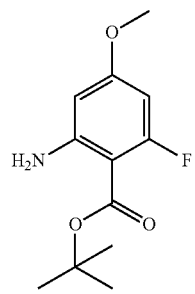

A pressure vessel containing Int JB76a (2.44 g, 9.99 mmol) and DMSO (20 mL) was cooled with an ice bath while ammonia gas was bubbled through the solution. The vessel was sealed and heated in an oil bath at 90° C. for 20 h. The reaction mixture was poured into water (200 mL) and extracted with EtOAc (40 mL, ×2). The combined organic layers were washed with brine, dried over MgSO₄, filtered and evaporated in vacuo. The residual oil was purified by FCC (120 g silica gel cartridge, 0~20% EtOAc-hexanes) to afford Int JB76b (0.581 g) as a colorless oil. $^1$H NMR (499 MHz, CDCl₃) δ 5.97 (dd, J=13.2, 2.4 Hz, 1H), 5.94-5.89 (m, 1H), 3.78 (s, 3H), 1.59 (s, 9H). $^{19}$F NMR (470 MHz, chloroform-d) δ -103.52 (s, 1F).

2-amino-6-fluoro-4-methoxybenzoic acid (Int JB76c)

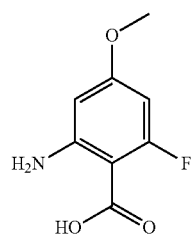

To a solution of Int JB76b (203 mg, 0.841 mmol) in DCM (1 mL) was added TFA (0.65 mL, 8.4 mmol) and the formed solution was stirred at rt for 2 h. The volatiles were removed by a steady stream of nitrogen. The residual solid was triturated with hexanes and dried in vacuo to afford a TFA salt of Int JB76c (230 mg) as an off-white solid. $^1$H NMR (499 MHz, DMSO-d₆) 6.10 (dd, J=2.4, 0.9 Hz, 1H), 5.94 (dd, J=13.7, 2.5 Hz, 1H), 3.72 (s, 3H). 19F NMR (470 MHz, DMSO-d₆) δ −75.02 (s, 1F), −104.55 (s, 1F).

tert-butyl (S)-(1-(3-(4-chloro-3-(N-(4-methoxybenzyl)methylsulfonamido)-1-methyl-1H-indazol-7-yl)-5-fluoro-7-methoxy-4-oxo-3,4-dihydroquinazolin-2-yl)-2-(3,5-difluorophenyl)ethyl)carbamate (Int JB76d)

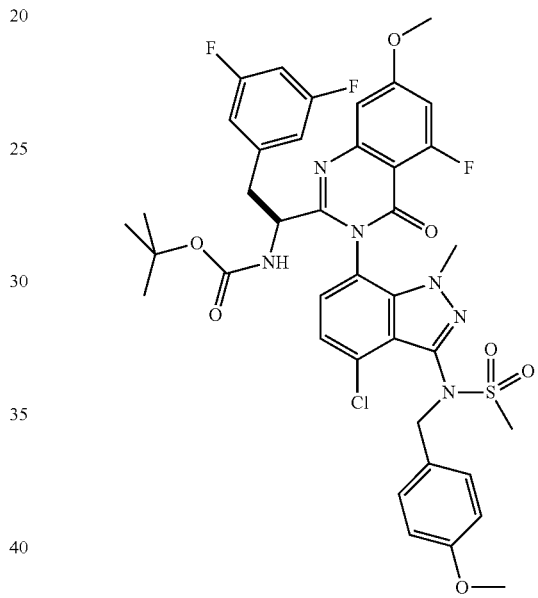

A mixture of TFA salt of Int JB76c (181 mg, 0.604 mmol), (S)-2-((tert-butoxycarbonyl)amino)-3-(3,5-difluorophenyl)propanoic acid (182 mg, 0.604 mmol), and diphenyl phosphite (0.78 mL, 3.6 mmol) in pyridine (3 mL) was sealed in a reaction vessel and heated in an oil bath at 70° C. for 2 h. N-(7-amino-4-chloro-1-methyl-1H-indazol-3-yl)-N-(4-methoxybenzyl)methanesulfonamide (262 mg, 0.664 mmol) was added to the reaction mixture, and it was again sealed and heated at 85° C. for another 2 h. The solvent was removed by a steady stream of nitrogen. The residue was poured into water (20 mL) and extracted with EtOAc (10 mL, ×2). The combined organic layers were washed with 5% citric acid, 1.5 M K₃PO₄ and brine, dried over MgSO₄, filtered and evaporated in vacuo. The residue was purified by FCC (24 g silica gel cartridge, 0~50% EtOAc-hexanes) to afford Int JB76d (390 mg) as a mixture of stereoisomers. LC/MS retention time=1.12 min; m/z=727.5 [M-Boc]⁺, 827.08 [M+H] (Column: Acquity UPLC BEH, 2.1×50 mm, 1.7 µm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

427

(S)—N-(7-(2-(1-amino-2-(3,5-difluorophenyl)ethyl)-5-fluoro-7-methoxy-4-oxoquinazolin-3(4H)-yl)-4-chloro-1-methyl-1H-indazol-3-yl)methanesulfonamide (Int JB76e)

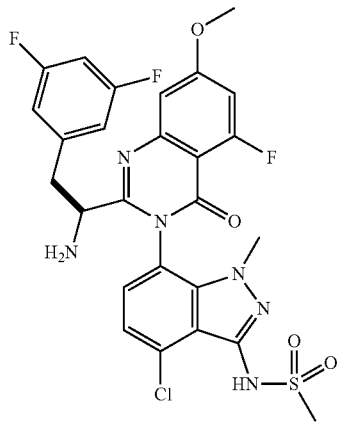 [SMILES: COc1cc(F)c2c(=O)n(-c3ccc(Cl)c4c(NS(C)(=O)=O)nn(C)c34)c([C@@H](N)Cc3cc(F)cc(F)c3)nc2c1]

To an ice bath cooled solution of Int JB76d (390 mg, 0.471 mmol) in DCM (2 mL) was added TFA (2.0 mL) and triflic acid (0.21 mL, 2.4 mmol). The reaction mixture was stirred at rt for 1 h. The volatiles were removed with a steady stream of nitrogen and the residue was partitioned between EtOAc (10 mL) and sat. $NaHCO_3$ (10 mL). The organic component was washed with brine, dried over $MgSO_4$, filtered and evaporated in vacuo to afford Int JB76e (342 mg) as a mixture of stereoisomers. This material was used without further purification. LC/MS retention time=0.66, 0.71 min; m/z=607.08 [M+H](Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

N—((S)-1-(3-(4-chloro-1-methyl-3-(methylsulfonamido)-1H-indazol-7-yl)-5-fluoro-7-methoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 186) and Example 185 & Example 187

Example 185

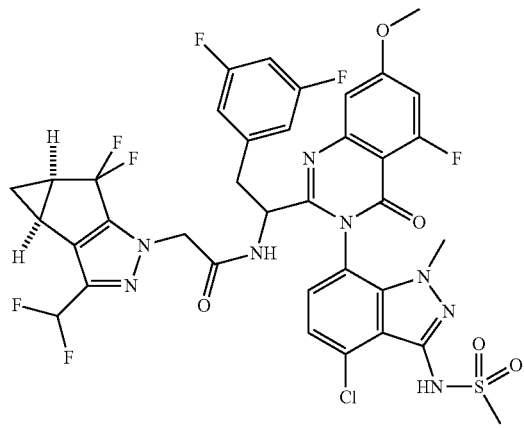

mix of stereoisomers

428

-continued

Example 186

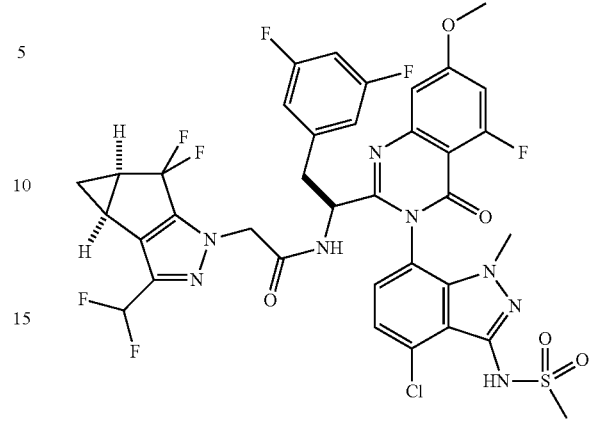

single stereoisomer

Example 187

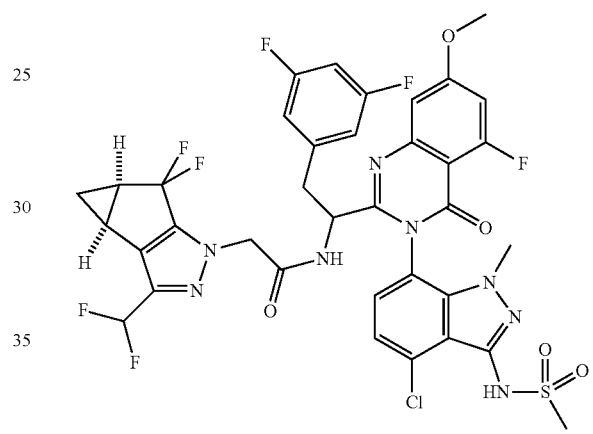

single stereoisomer

To a solution of Int JB76e (130 mg, 0.180 mmol), 2-((3bS,4aR)-3-(difluoromethyl)-5,5-difluoro-3b,4,4a,5-tetrahydro-1H-cycopropa[3,4]cyclopenta[1,2-c]pyrazol-1-yl) acetic acid (47.5 mg, 0.180 mmol) and HOAt (1 M in DMA, 0.090 mL, 0.090 mmol) in DMF (1.7 mL) was added EDC (38 mg, 0.20 mmol) and N-methylmorpholine (0.079 mL, 0.72 mmol). The reaction mixture was stirred at rt overnight. The crude material was purified via preparative LC/MS (Column: XBridge Shield RP18, 200 mm×19 mm, 5 μm particles; Mobile Phase A: 5:95 acetonitrile:water with 10 mM ammonium acetate; Mobile Phase B: 95:5 acetonitrile: water with 10 mM ammonium acetate; Gradient: a 0-minute hold at 29% B, 29-55% B over 45 minutes, then a 10-minute hold at 100% B; Flow Rate: 20 mL/min; Column Temperature: 25° C.) to retrieve two isolates, each as a mixture of stereoisomers.

Example 185: First Elute (26.5 mg, Mixture of Stereoisomers)

QC-ACN-AA-XB (Purity: 99.0%; RT: 2.07 min; Obs. Adducts: [M+H]; Obs. Masses: 852.9). The second elute (57.3 mg, mixture of stereoisomers) was further purified by chiral SFC (Instrument: Waters 100 Prep SFC; Column: Chiral OD 30×250 mm. 5 μm; Mobile Phase: 85% $CO_2$/

15%/0.1% MeOH-DEA; Flow Conditions: 100 mL/min; Detector Wavelength: 220 nm; Injection Details: 57.3 mg dissolved in 4 mL MeOH). Two elutes of stereoisomeric relation were isolated.

Example 186

The first elute from the chiral column purification (34.9 mg, 87% chiral purity) was purified again by another chiral SFC (Instrument: Waters 100 Prep SFC; Column: Chiralpak IC preparative column OD 30×250 mm. 5 μm; Mobile Phase: 70% $CO_{2/30}$% IPA; Flow Conditions: 70 mL/min for 13 min; Detector Wavelength: 242 nm; Injection Details: 0.5 ml of ~17 mg/mL solution in 1:1 IPA:CHCl3, ~33 mg purified by stacked injection) to afford Example 186 (25 mg, single stereoisomer, but found to contain an unidentified impurity). This material was further purified by preparative LC/MS (Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 37% B, 37-77% B over 20 minutes, then a 4-minute hold at 100% B; Flow Rate: 20 mL/min; Column Temperature: 25° C.) to afford Example 186 (18.4 mg, single stereoisomer). QC-ACN-TFA-XB (Purity: 100%; RT: 211 min; Obs. Adducts: [M+H]; Obs. Masses: 853.06). $^1$H NMR (500 MHz, DMSO-$d_6$) δ 9.09 (br d, J=7.9 Hz, 1H), 7.66 (d, J=7.9 Hz, 1H), 7.41 (d, J=7.9 Hz, 1H), 7.12 (br d, J=12.5 Hz, 1H), 7.07-6.81 (m, 3H), 6.64 (br d, J=6.4 Hz, 2H), 4.67-4.60 (m, 1H), 4.55-4.43 (m, 2H), 3.98 (s, 3H), 3.55 (s, 3H), 3.44-3.30 (m, 1H), 3.18 (s, 3H), 3.03-2.95 (m, 1H), 2.50-2.42 (m, 2H), 1.41-1.33 (m, 1H), 0.86 (br s, 1H). $^{19}$F NMR (471 MHz, DMSO-$d_6$) δ −79.51 (br d, J=253.2 Hz, 1F), −102.89 (br d, J=253.2 Hz, 1F), −108.07 (s, 1F), −110.10 (s, 2F), −110.94 (d, J=309.0 Hz, 1F), −112.74 (d, J=309.0 Hz, 1F).

Example 187

Second elute from the chiral column purification (6.6 mg, single stereoisomer). QC-ACN-AA-XB (Purity: 100%; RT: 2.13 min; Obs. Adducts: [M+H]; Obs. Masses: 852.9).

(S)—N-(1-(3-(4-chloro-1-methyl-3-(methylsulfonamido)-1H-indazol-7-yl)-5-fluoro-7-methoxy-4-oxo-3,4-dihydroquinazolin-2-yl)-2-(3,5-difluorophenyl)ethyl)-2-(3-cyclopropyl-1H-pyrazol-1-yl)acetamide (Example 189) and Example 188 and Example 190

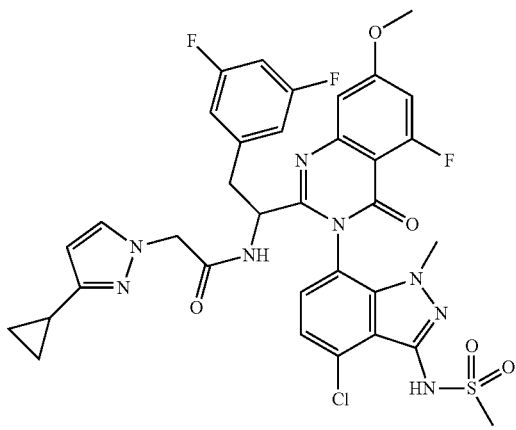

Example 188 mix of stereoisomers

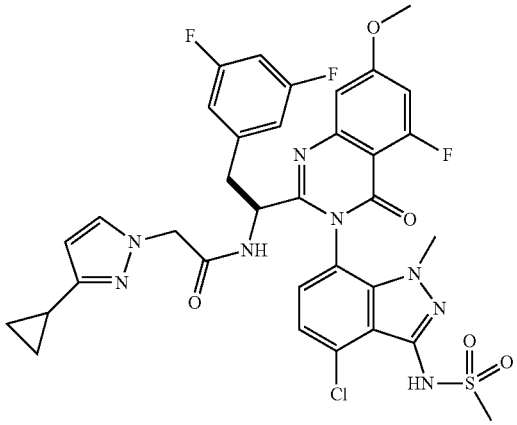

Example 189 single stereoisomer

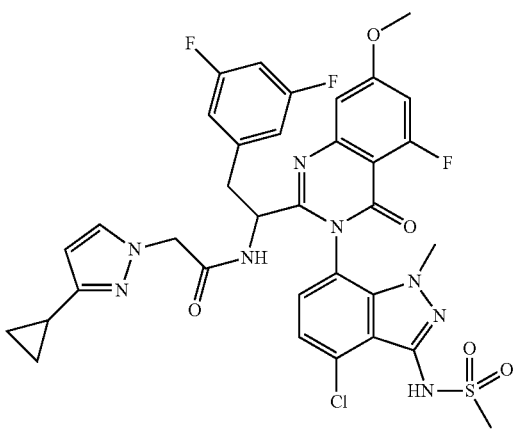

Example 190 single stereoisomer

To a solution of Int JB76e (130 mg, 0.180 mmol), 2-(3-cyclopropyl-1H-pyrazol-1-yl)acetic acid (31.5 mg, 0.180 mmol) and HOAt (1 M in DMA, 0.090 mL, 0.090 mmol) in DMF (1.7 mL) was added EDC (37.9 mg, 0.198 mmol) and N-methylmorpholine (0.08 mL, 0.7 mmol). The reaction mixture was stirred at rt overnight. The crude material was purified via preparative LC/MS (Column: XBridge Shield RP18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 29% B, 29-55% B over 45 minutes, then a 10-minute hold at 100% B; Flow Rate: 20 mL/min; Column Temperature: 25° C.) to retrieve two isolates, each as a mixture of stereoisomers.

Example 188: First Elute (23.1 mg, Mixture of Stereoisomers)

QC-ACN-AA-XB (Purity: 100%; RT: 1.93 min; Obs. Adducts: [M+H]; Obs. Masses: 755.3).

The second elute (61.1 mg, mixture of stereoisomers) was further purified by chiral SFC (Instrument: Waters 100 Prep SFC; Column: Chiral OD 30×250 mm. 5 μm; Mobile Phase: 80% $CO_{2/20}$%/0.1% MeOH-DEA; Flow Conditions: 100 mL/min; Detector Wavelength: 220 nm; Injection Details: 61.1 mg dissolved in 9 mL MeOH). Two elutes of stereoisomeric relation were isolated.

Example 189: First Elute (34.0 mg, Single Stereoisomer)

QC-ACN-AA-XB (Purity: 100%; RT: 2.15 min; Obs. Adducts: [M+H]; Obs. Masses: 755.3). $^1$H NMR (500 MHz, DMSO-$d_6$) δ 8.79 (d, J=8.2 Hz, 1H), 7.64 (d, J=7.9 Hz, 1H), 7.38 (d, J=7.9 Hz, 1H), 7.26 (d, J=2.1 Hz, 1H), 7.11 (br d, J=12.2 Hz, 1H), 7.07 (d, J=1.8 Hz, 1H), 7.02 (br t, J=9.3 Hz, 1H), 6.68 (br d, J=6.1 Hz, 2H), 5.85 (d, J=2.1 Hz, 1H), 4.59-4.51 (m, 1H), 4.42-4.34 (m, 1H), 4.31-4.24 (m, 1H), 3.99 (s, 3H), 3.59 (s, 3H), 3.43-3.35 (m, 1H), 3.19 (s, 3H), 3.02-2.94 (m, 1H), 1.80-1.70 (m, 1H), 0.80-0.73 (m, 2H), 0.53 (br t, J=5.6 Hz, 2H). $^{19}$F NMR (471 MHz, DMSO-$d_6$) δ −108.12 (s, 1F), −110.08 (s, 2F).

Example 190: Second Elute (7.7 mg, Single Stereoisomer)

QC-ACN-AA-XB (Purity: 90%; RT: 2.15 min; Obs. Adducts: [M+H]; Obs. Masses: 755.3).

tert-butyl (S)-(1-(3-(4-chloro-1-(2,2-difluoroethyl)-3-(N-(4-methoxybenzyl)methylsulfonamido)-1H-indazol-7-yl)-7-methoxy-4-oxo-3,4-dihydroquinazolin-2-yl)-2-(3,5-difluorophenyl)ethyl)carbamate (Int JB79a)

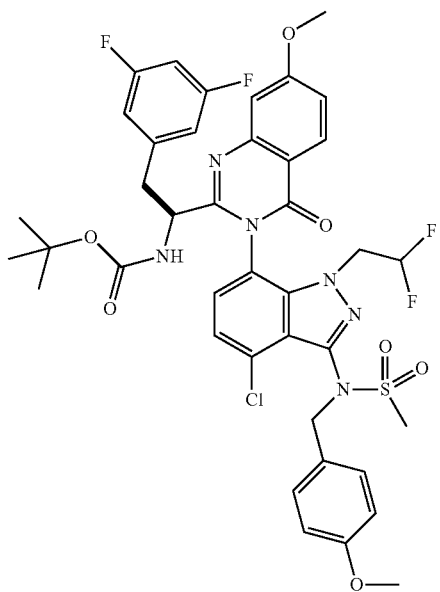 [SMILES: COc1ccc(CN(c2nn(CC(F)F)c3c(-n4c([C@H](Cc5cc(F)cc(F)c5)NC(=O)OC(C)(C)C)nc5cc(OC)ccc5c4=O)ccc(Cl)c23)S(C)(=O)=O)cc1]

A mixture (S)-2-((tert-butoxycarbonyl)amino)-3-(3,5-difluorophenyl)propanoic acid (102 mg, 0.337 mmol), 2-amino-4-methoxybenzoic acid (56.4 mg, 0.337 mmol) and N-(7-amino-4-chloro-1-(2,2-difluoroethyl)-1H-indazol-3-yl)-N-(4-methoxybenzyl)methanesulfonamide (Int CI12d, 100 mg, 0.225 mmol) in pyridine (2 mL) and diphenyl phosphite (0.22 mL, 1.1 mmol) was flushed with nitrogen, sealed in a reaction vessel and heated with an oil bath at 70° C. for 3.5 h. The reaction mixture was partially concentrated, diluted with EtOAc (25 mL) and washed with 5% citric acid (~20 mL), 1.5 M $K_3PO_4$ (~20 mL) and brine. The organic component dried over $MgSO_4$, filtered and evaporated in vacuo. The residue was purified by FCC (24 g silica gel cartridge, 10-50% EtOAc/hexanes) to afford Int JB79a (81 mg). LC/MS retention time=1.13 min; m/z=859.3 [M+H]$^+$ (Column: BEH, 2.1×50 mm, 1.7 µm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

(S)—N-(7-(2-(1-amino-2-(3,5-difluorophenyl)ethyl)-7-methoxy-4-oxoquinazolin-3(4H)-yl)-4-chloro-1-(2,2-difluoroethyl)-1H-indazol-3-yl)methanesulfonamide (Int JB79b)

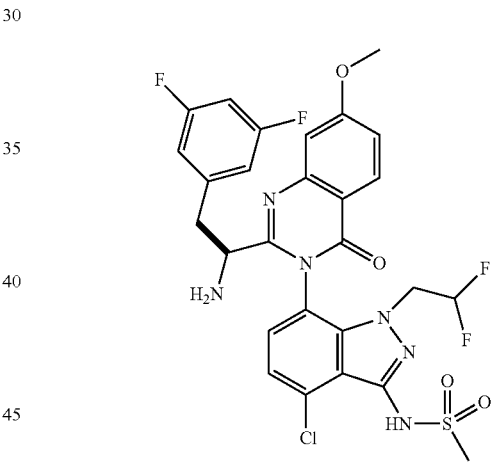

To an ice bath cooled solution of Int JB79a (81 mg, 0.094 mmol) in DCM (1 mL) was added TFA (0.5 mL) and triflic acid (0.04 mL, 0.5 mmol). The reaction mixture was stirred at rt for 0.5 h. The volatiles were removed with a steady stream of nitrogen and the residue was partitioned between EtOAc (8 mL) and sat. $NaHCO_3$ (4 mL). The organic component was washed with brine, dried over $MgSO_4$, filtered and evaporated in vacuo to afford Int JB79b (60 mg). This material was used without further purification. LC/MS retention time=0.75 min; m/z=639.0 [M+H]$^+$ (Column: BEH, 2.1×50 mm, 1.7 µm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

N—((S)-1-(3-(4-chloro-1-(2,2-difluoroethyl)-3-(methylsulfonamido)-1H-indazol-7-yl)-7-methoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 191) and Example 191.2 and Example 191.3

Example 191

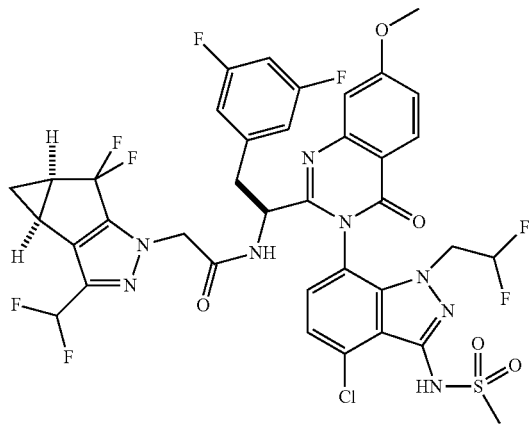

single stereoisomer

Example 191.2

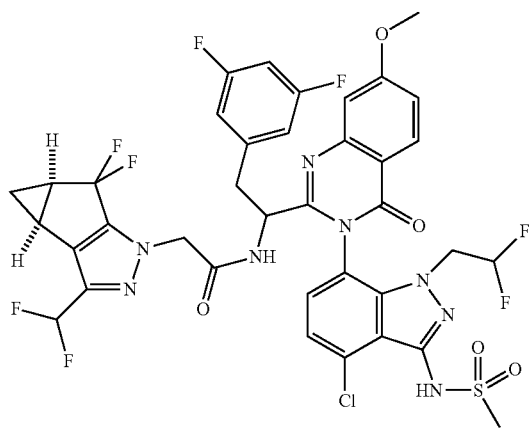

single stereoisomer

Example 191.3

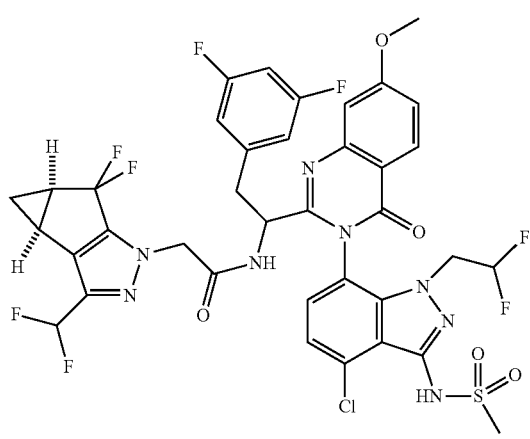

single stereoisomer

To a solution of (S)—N-(7-(2-(1-amino-2-(3,5-difluorophenyl)ethyl)-7-methoxy-4-oxoquinazolin-3(4H)-yl)-4-chloro-1-(2,2-difluoroethyl)-1H-indazol-3-yl)methanesulfonamide (Int JB79b, 0.060 g, 0.094 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (25 mg, 0.094 mmol) and HOAt (1 M in DMA, 0.05 mL, 0.05 mmol) in DMF (1.0 mL) was added EDC (0.020 g, 0.10 mmol) and then N-methylmorpholine (0.04 mL, 0.4 mmol) and the reaction mixture was stirred at rt overnight. The crude material was purified via preparative LC/MS (Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 39% B, 39-79% B over 20 minutes, then a 4-minute hold at 100% B; Flow Rate: 20 mL/min; Column Temperature: 25° C.) to afford a single major isolate (32.9 mg) which was further purified by chiral SFC (Instrument: Waters 100 Prep SFC; Column: Chiral OD 30×250 mm. 5 μm; Mobile Phase: 80% $CO_{2/20}$%/0.1% MeOH-DEA; Flow Conditions: 100 mL/min; Detector Wavelength: 220 nm; Injection Details: 32.9 mg dissolved in 3 mL MeOH/ACN). Three elutes where isolated.

Example 191: First Elute (22.9 mg, Single Stereoisomer)

QC-ACN-AA-XB (Purity: 100%; RT: 2.17 min; Obs. Adducts: [M+H]; Obs. Masses: 885.4). $^1$H NMR (500 MHz, MeOH-d$_4$) δ 8.18 (d, J=8.9 Hz, 1H), 7.30 (d, J=2.1 Hz, 1H), 7.26-7.19 (m, 2H), 7.15-7.08 (m, 1H), 6.82-6.48 (m, 4H), 6.16-5.87 (m, 1H), 4.74 (br dd, J=9.0, 4.7 Hz, 1H), 4.71-4.59 (m, 2H), 4.29-4.16 (m, 1H), 4.03 (s, 3H), 3.91-3.75 (m, 1H), 3.41-3.34 (m, 1H), 3.16-3.12 (m, 3H), 3.05-2.97 (m, 1H), 2.50-2.40 (m, 2H), 1.43-1.33 (m, 1H), 1.02 (br s, 1H) $^{19}$F NMR (471 MHz, MeOH-d$_4$) δ −82.23 (br d, J=256.1 Hz, 1F), −105.05 (br d, J=256.1 Hz, 1F), −111.71 (s, 2F), −113.33 (d, J=311.9 Hz, 1F), −114.43 (d, J=311.9 Hz, 1F), −122.60 (br d, J=5.7 Hz, 2F)

Example 191.2: Second Elute (1.2 mg)

QC-ACN-AA-XB (Purity: 95%; RT: 2.21 min; Obs. Adducts: [M+H]; Obs. Masses: 885.2).

Example 191.3: Third Elute (3.6 mg, Single Stereoisomer)

QC-ACN-AA-XB (Purity: 97%; RT: 2.14 min; Obs. Adducts: [M+H]; Obs. Masses: 885.3).

435 tert-butyl (S)-(1-(3-(4-chloro-1-(2,2-difluoroethyl)-3-(N-(4-methoxybenzyl)cyclopropanesulfonamido)-1H-indazol-7-yl)-7-methoxy-4-oxo-3,4-dihydroquinazolin-2-yl)-2-(3,5-difluorophenyl)ethyl)carbamate (Int JB80a)

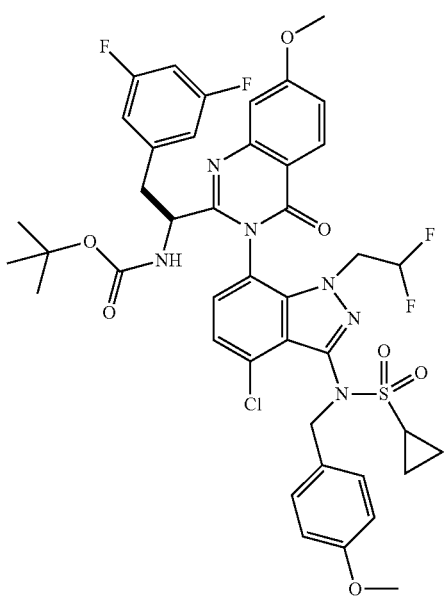 [SMILES: COc1ccc(CN(c2nn(CC(F)F)c3c(-n4c([C@H](Cc5cc(F)cc(F)c5)NC(=O)OC(C)(C)C)nc5cc(OC)ccc5c4=O)ccc(Cl)c23)S(=O)(=O)C2CC2)cc1]

A mixture (S)-2-((tert-butoxycarbonyl)amino)-3-(3,5-difluorophenyl)propanoic acid (96 mg, 0.32 mmol), 2-amino-4-methoxybenzoic acid (53 mg, 0.32 mmol) and N-(7-amino-4-chloro-1-(2,2-difluoroethyl)-1H-indazol-3-yl)-N-(4-methoxybenzyl)cyclopropanesulfonamide (Int CI13d, 100 mg, 0.212 mmol) in pyridine (2 mL) and diphenyl phosphite (0.21 mL, 1.1 mmol) was flushed with nitrogen, sealed in a reaction vessel and heated with an oil bath at 70° C. for 3.5 h. The reaction mixture was partially concentrated, diluted with EtOAc (25 mL) and washed with 5% citric acid (~20 mL), 1.5 M K$_3$PO$_4$ (~20 mL) and brine. The organic component dried over MgSO$_4$, filtered and evaporated in vacuo. The residue was purified by FCC (24 g silica gel cartridge, 10-50% EtOAc/hexanes) to afford Int JB80a (141 mg). LC/MS retention time=1.15 min; m/z=829.0 [M−tBu+H]$^+$ (Column: BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

436

(S)—N-(7-(2-(1-amino-2-(3,5-difluorophenyl)ethyl)-7-methoxy-4-oxoquinazolin-3(4H)-yl)-4-chloro-1-(2,2-difluoroethyl)-1H-indazol-3-yl)cyclopropanesulfonamide (Int JB80b)

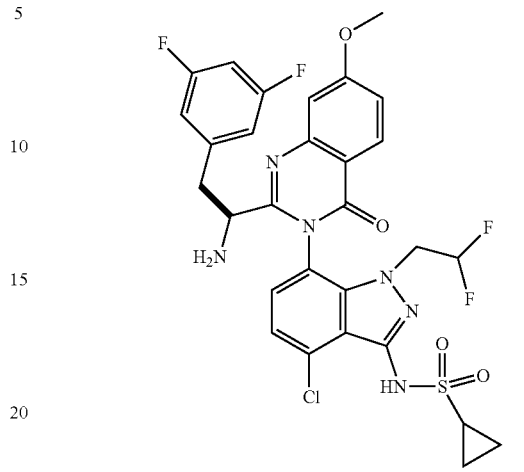

To an ice bath cooled solution of Int JB80a (140 mg, 0.158 mmol) in DCM (1 mL) was added TFA (0.5 mL) and triflic acid (0.07 mL, 0.8 mmol). The reaction mixture was stirred at rt for 0.5 h. The volatiles were removed with a steady stream of nitrogen and the residue was partitioned between EtOAc (8 mL) and sat. NaHCO$_3$ (4 mL). The organic component was washed with brine, dried over MgSO$_4$, filtered and evaporated in vacuo to afford Int JB80b (60 mg). This material was used without further purification. LC/MS retention time=0.77 min; m/z=664.9 [M+H]$^+$ (Column: BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Wavelength=220 nm).

N—((S)-1-(3-(4-chloro-3-(cyclopropanesulfonamido)-1-(2,2-difluoroethyl)-1H-indazol-7-yl)-7-methoxy-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 192) and Example 192.2 and Example 192.3

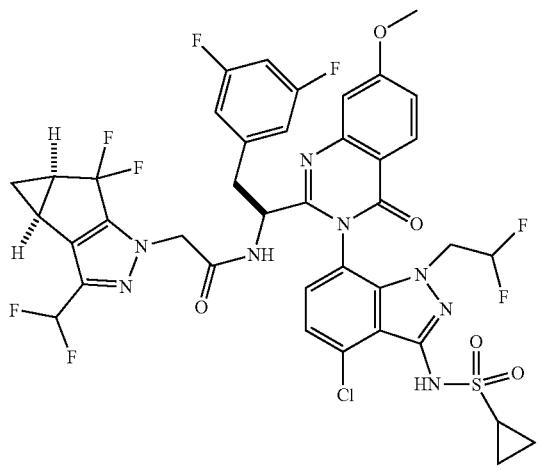 [SMILES: COc1ccc2c(=O)n(-c3ccc(Cl)c4c(NS(=O)(=O)C5CC5)nn(CC(F)F)c34)c([C@H](Cc3cc(F)cc(F)c3)NC(=O)Cn3nc(C(F)F)c4c3C(F)(F)[C@@H]3C[C@H]43)nc2c1]

To a solution of (S)—N-(7-(2-(1-amino-2-(3,5-difluorophenyl)ethyl)-7-methoxy-4-oxoquinazolin-3(4H)-yl)-4- chloro-1-(2,2-difluoroethyl)-1H-indazol-3-yl)cyclopropanesulfonamide (Int JB80b, 0.105 g, 0.158 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.042 g, 0.16 mmol) and HOAt (1 M in DMA, 0.08 mL, 0.08 mmol) in DMF (1.6 mL) was added EDC (0.033 g, 0.17 mmol) and then N-methylmorpholine (0.07 mL, 0.6 mmol) and the reaction mixture was stirred at rt overnight. The crude material was purified via preparative LC/MS (Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 41% B, 41-81% B over 20 minutes, then a 4-minute hold at 100% B; Flow Rate: 20 mL/min; Column Temperature: 25° C.) to afford a single major isolate (39.5 mg) which was further purified by chiral SFC (Instrument: Waters 100 Prep SFC; Column: Chiral OD 30×250 mm. 5 µm; Mobile Phase: 85% $CO_2$/15%/0.1% MeOH-DEA; Flow Conditions: 100 mL/min; Detector Wavelength: 220 nm; Injection Details: 39.5 mg dissolved in 3 mL MeOH/ACN). Three elutes where isolated.

Example 192: First Elute (20.5 mg, Single Stereoisomer)

QC-ACN-AA-XB (Purity: 100%; RT: 2.25 min; Obs. Adducts: [M+H]; Obs. Masses: 911.3). $^1$H NMR (500 MHz, MeOH-$d_4$) δ 8.18 (d, J=8.8 Hz, 1H), 7.33-7.28 (m, 2H), 7.24 (dd, J=8.7, 2.3 Hz, 1H), 7.16 (d, J=7.9 Hz, 1H), 6.82-6.51 (m, 4H), 6.15-5.88 (m, 1H), 4.73 (dd, J=9.0, 5.0 Hz, 1H), 4.70-4.64 (m, 1H), 4.63-4.58 (m, 1H), 4.36-4.25 (m, 1H), 4.04 (s, 3H), 3.94-3.82 (m, 1H), 3.41-3.35 (m, 1H), 3.03 (dd, J=13.9, 9.0 Hz, 1H), 2.92-2.87 (m, 1H), 2.49-2.39 (m, 2H), 1.12-1.07 (m, 2H), 1.01 (br s, 1H), 0.93 (br d, J=4.9 Hz, 2H) $^{19}$F NMR (471 MHz, MeOH-$d_4$) δ −82.28 (br d, J=256.1 Hz, 1F), −105.05 (br d, J=254.6 Hz, 1F), −111.66 (s, 2F), −113.49 (d, J=311.9 Hz, 1F), −114.49 (d, J=311.9 Hz, 1F), −122.49 (s, 2F).

Example 192.2: Second Elute (1.3 mg)

QC-ACN-AA-XB (Purity: 98%; RT: 2.29 min; Obs. Adducts: [M+H]; Obs. Masses: 911.2).

Example 192.3: Third Elute (1.9 mg, Single Stereoisomer)

QC-ACN-AA-XB (Purity: 100%; RT: 2.23 min; Obs. Adducts: [M+H]; Obs. Masses: 911.4).

Methyl 6-bromo-2-(methylthio)thiazolo[4,5-b]pyridine-5-carboxylate (Int MP1a)

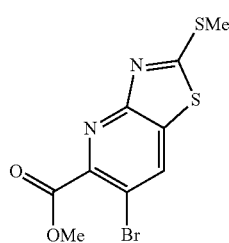 [SMILES: COC(=O)c1nc2nc(SC)sc2cc1Br]

To a suspension of methyl 6-amino-3-bromo-5-mercaptopicolinate, HCl (4.0 g, 13.35 mmol) in DCE (200 mL) was added DIEA (7.0 mL, 40.1 mmol) and the mixture was stirred at room temp for 5 min. Mixture was then cooled to 0° C. and thiophosgene (1.12 mL, 14.69 mmol) was added dropwise. Mixture was then allowed to warm to room temp and stirred for an additional 2 h. LC/MS at this point indicates starting material was consumed and peak consistent with dimer M.W (dimethyl 5,5'-(thiocarbonylbis(sulfanediyl))bis(6-amino-3-bromopicolinate, LC/MS (M+H)$^+$ =566.8) was formed. Mixture was then diluted with dichloromethane and washed with 0.1N HCl, dried (Na$_2$SO$_4$), filtered and concentrated. The residue was then diluted with ethanol (30 mL) and heated at 90° C. for 2.5 h. LC/MS at this point indicates completion of reaction and desired cyclized product as major (LC/MS (M+H)$^+$=304.8). Mixture was then cooled and concentrated. The residue was then diluted with ethyl acetate, washed with water, dried (Na$_2$SO$_4$), filtered and concentrated in vacuo. To a solution of above residue in DMF (100 mL) at 0° C. was added K$_2$CO$_3$ (1.84 g, 13.35 mmol) followed by MeI (0.84 mL, 13.35 mmol). After stirring for 1 h at 0° C., mixture was allowed to warm to room temp. Water was then added and the mixture was extracted with ethyl acetate, washed with brine, dried (Na$_2$SO4), filtered and concentrated. The residue was then purified by Biotage (5-50% EtOAc/hexane) to afford the title compound (1.3 g) as off-white solid. $^1$H NMR (400 MHz, CDCl$_3$) δ 8.36 (s, 1H), 4.03 (s, 3H), 2.88 (s, 3H). LC/MS: m/z=318.8 [M+H]$^+$.

6-Bromo-2-(methylthio)thiazolo[4,5-b]pyridine-5-carbaldehyde (Int MP1b)

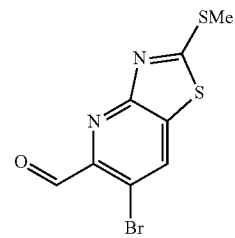 [SMILES: CSc1nc2nc(C=O)c(Br)cc2s1]

To a solution of methyl 6-bromo-2-(methylthio)thiazolo[4,5-b]pyridine-5-carboxylate (Int MP1a, 3.20 g, 10.03 mmol) in THF (100 mL) at −78° C. was added 1M DIBAL-H (30.1 mL, 30.1 mmol) over 20 min and stirred for an additional 2.5 h at −78° C. Mixture was then quenched with methanol, diluted with ethyl acetate and washed with sat. NH4Cl solution. The organic layer was then dried (Na$_2$SO$_4$), filtered and concentrated. The residue was then treated with Dess-Martin periodinane (2.12 g, 5.01 mmol) in CH$_2$Cl$_2$ (100 mL) at room temp for 2 h. Sat. NaHCO$_3$ solution was then added and the mixture was extracted with dichloromethane, dried (Na$_2$SO$_4$), filtered and concentrated. The residue was then purified by Biotage (5-100% EtOAc/hexane) to afford the title compound (2.4 g) as off-white solid. $^1$H NMR (400 MHz, CDCl$_3$) δ 10.24 (s, 1H), 8.41 (s, 1H), 2.92 (s, 3H). LC/MS: m/z=288.8 [M+H]$^+$.

(S,E)-N-((6-bromo-2-(methylthio)thiazolo[4,5-b]pyridin-5-yl)methylene)-2-methylpropane-2-sulfinamide (Int MP1c)

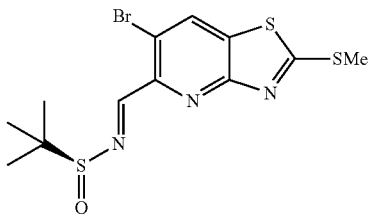 [SMILES: CSc1nc2nc(/C=N/[S@@](=O)C(C)(C)C)c(Br)cc2s1]

To a solution of 6-bromo-2-(methylthio)thiazolo[4,5-b]pyridine-5-carbaldehyde (Int MP1b, 2.40 g, 8.30 mmol) in $CH_2Cl_2$ (150 mL) was added (S)-2-methylpropane-2-sulfinamide (1.11 g, 9.13 mmol) followed by cupric sulfate (2.65 g, 16.60 mmol) and the resulting mixture was stirred at room temp for 24 h. Mixture was then filtered through a pad of Celite and the pad was washed with dichloromethane. The filtrate was then concentrated and purified by Biotage (5-50% EtOAc/hexane) to afford the title compound (2.8 g) as white solid. $^1$H NMR (400 MHz, $CDCl_3$) δ 9.08 (s, 1H), 8.38 (s, 1H), 2.90 (s, 3H), 1.34 (s, 9H). LC/MS: m/z=391.9 $[M+H]^+$.

(S)—N-(1-(6-bromo-2-(methylthio)thiazolo[4,5-b]pyridin-5-yl)-2-(3,5-difluorophenyl)ethyl)-2-methylpropane-2-sulfinamide (Int MP1d)

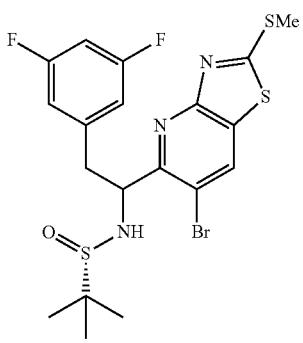 [SMILES: CSc1nc2nc(C(Cc3cc(F)cc(F)c3)N[S@@](=O)C(C)(C)C)c(Br)cc2s1]

To a stirred solution of magnesium turning (Int MP1c, 0.35 g, 14.27 mmol) in ethyl ether (20 mL) was added drop wise 1-(bromomethyl)-3,5-difluorobenzene (1.85 mL, 14.27 mmol) and the mixture was stirred at rt for 1 hr. This Grignard reagent was then added slowly to a previously stirred solution of (S,E)-N-((6-bromo-2-(methylthio)thiazolo[4,5-b]pyridin-5-yl)methylene)-2-methylpropane-2-sulfinamide (2.80 g, 7.14 mmol) in THF (100 mL) at −78° C. and the mixture was stirred for additional 2 h. at −78° C. The reaction mixture was then quenched with saturated ammonium chloride solution and extracted with ethyl acetate. Organic layer was then washed with water, brine, dried ($Na_2SO_4$), filtered and concentrated. The residue was then purified by Biotage (5-70% EtOAc/hexane) to afford the title compound (2.7 g) as approx. (3:1) inseparable mixture of diastereomers. $^1$H NMR (500 MHz, $CDCl_3$) δ 8.25 (s, 0.7H), 8.18 (s, 0.3H), 6.81-6.73 (m, 1.4H), 6.72-6.58 (m, 1.6H), 5.35-5.27 (m, 0.3H), 5.24-5.19 (m, 0.7H), 4.92 (d, J=9.8 Hz, 0.7H), 4.53 (d, J=10.1 Hz, 0.3H), 3.47-3.34 (m, 0.6H), 3.17 (dd, J=13.8, 5.0 Hz, 0.7H), 3.01 (dd, J=13.9, 9.6 Hz, 0.7H), 2.91 (s, 0.8H), 2.90 (m, 1.2H), 1.15 (s, 1H), 1.13 (s, 8H). LC/MS: m/z=519.9 $[M+H]^+$.

1-(6-bromo-2-(methylthio)thiazolo[4,5-b]pyridin-5-yl)-2-(3,5-difluorophenyl)ethan-1-amine (Int MP1e)

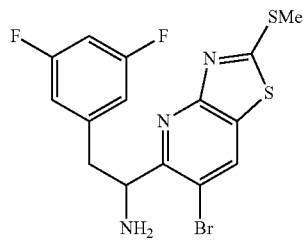 [SMILES: CSc1nc2nc(C(N)Cc3cc(F)cc(F)c3)c(Br)cc2s1]

To a suspension of (S)—N-(1-(6-bromo-2-(methylthio)thiazolo[4,5-b]pyridin-5-yl)-2-(3,5-difluorophenyl)ethyl)-2-methylpropane-2-sulfinamide (Int MP1d, 2.7 g, 5.2 mmol) in dioxane (30 mL) was added 4M HCl (13.0 mL, 51.9 mmol) in dioxane and the resulting mixture was stirred at room temp for 2 h. The reaction mixture was then concentrated and dried under high vacuum to afford the title compound (2.1 g) as light pink solid. $^1$H NMR (400 MHz, DMSO-$d_6$) δ 8.86 (s, 1H), 8.76 (br s, 3H), 7.14 (tt, J=9.5, 2.3 Hz, 1H), 6.91-6.72 (m, 2H), 5.08-4.92 (m, 1H), 3.37-3.10 (m, 2H), 2.85 (s, 3H). LC/MS: m/z=415.9 $[M+H]^+$.

tert-Butyl (1-(6-bromo-2-(methylthio)thiazolo[4,5-b]pyridin-5-yl)-2-(3,5-difluorophenyl)ethyl)carbamate (Int MP1f)

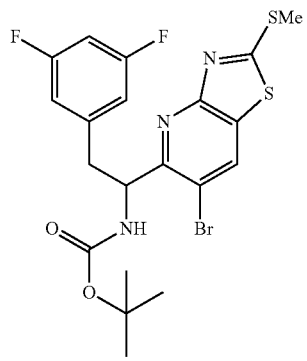 [SMILES: CSc1nc2nc(C(Cc3cc(F)cc(F)c3)NC(=O)OC(C)(C)C)c(Br)cc2s1]

To a stirred solution of 1-(6-bromo-2-(methylthio)thiazolo[4,5-b]pyridin-5-yl)-2-(3,5-difluorophenyl)ethan-1-amine (Int MP1e, 2.10 g, 5.04 mmol) in DCM (50 mL) at 0° C. was added TEA (1.41 mL, 10.09 mmol) followed by $Boc_2O$ (1.32 g, 6.05 mmol) and the resulting mixture was allowed to warm to room temperature and stirred for an additional 2 h. The mixture was then diluted with DCM (100 mL) and washed with water (50 mL), brine (50 mL), dried (Na2SO4), filtered and concentrated. The residue was then purified by Biotage (5-40% EtOAc/hexanes) to afford mixture of enantiomers (2.3 g) which was submitted for chiral SFC separation (Chiralpak AS-H preparative column, 30×250 mm, 5 μm, Mobile Phase: 15% IPA in CO$_2$, 150 bar) to afford two enantiomers. Int MP1f-E1 (First eluting enantiomer, 530 mg): $^1$H NMR (400 MHz, CDCl$_3$) δ 8.23 (s, 1H), 6.82-6.55 (m, 3H), 5.97 (br d, J=9.0 Hz, 1H), 5.70-5.55 (m, 1H), 3.21-3.11 (m, 1H), 2.98 (br dd, J=13.3, 8.0 Hz, 1H), 2.90 (s, 3H), 1.38 (s, 9H). LC/MS: m/z=516.0 [M+H]$^+$.

Int MP1f-E2 (second eluting enantiomer, 1.5 g): was processed to the next step.

tert-Butyl (1-(6-(4-chloro-1-methyl-3-(methylsulfonamido)-1H-indazol-7-yl)-2-(methylthio)thiazolo[4,5-b]pyridin-5-yl)-2-(3,5-difluorophenyl)ethyl)carbamate (Int MP1g)

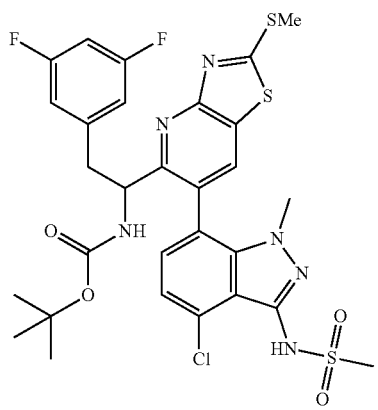 [SMILES: CSc1nc2nc(C(Cc3cc(F)cc(F)c3)NC(=O)OC(C)(C)C)c(-c3ccc(Cl)c4c(NS(C)(=O)=O)nn(C)c34)cc2s1]

To a microwave vial was added tert-Butyl (1-(6-bromo-2-(methylthio)thiazolo[4,5-b]pyridin-5-yl)-2-(3,5-difluorophenyl)ethyl)carbamate (Int MP1f-E2, 0.25 g, 0.48 mmol), N-(4-chloro-1-methyl-7-(4,4,5,5-tetramethyl-1,3,2-dioxaborolan-2-yl)-1H-indazol-3-yl)methanesulfonamide (0.22 g, 0.58 mmol) followed by dioxane (10 mL) and 1N sodium bicarbonate (2.90 mL, 2.90 mmol) and the mixture was degassed for 10 min. PdCl$_2$(dppf)-CH$_2$Cl$_2$ adduct (39.5 mg, 0.048 mmol) was then added and the mixture was heated in microwave at 140° C. for 1 h. The reaction mixture was then filtered through a plug of Celite and washed with ethyl acetate. Water was then added to the mixture and extracted with ethyl acetate (2×25 mL). The organic layer was dried (Na$_2$SO$_4$), filtered and concentrated. The residue was then purified by Biotage (5-100% EtOAc/hexanes) to afford the title compound (125 mg) as a mixture of stereoisomers (~1:3 by LC/MS). $^1$H NMR (400 MHz, CDCl$_3$) δ 7.92 (s, 1H), 7.40-7.29 (m, 1H), 7.26-7.18 (m, 1H), 7.12 (d, J=7.5 Hz, 0.3H), 6.95 (d, J=7.5 Hz, 0.7H), 6.63 (tt, J=9.0, 2.3 Hz, 1H), 6.34-6.25 (m, 2.3H), 6.15 (d, J=7.5 Hz, 0.7H), 5.86-5.80 (m, 0.7H), 5.65-5.61 (m, 0.3H), 4.81-4.67 (m, 1H), 3.41 (s, 1H), 3.40 (s, 1H), 3.38 (s, 2H), 3.33 (s, 2H), 3.18-3.01 (m, 2H), 2.97 (s, 2H), 1.39 (s, 2H), 1.34 (s, 7H). LC/MS: m/z=695.1 [M+H]$^+$, 717.0 [M+Na]$^+$.

N-(7-(5-(1-amino-2-(3,5-difluorophenyl)ethyl)-2-(methylthio)thiazolo[4,5-b]pyridin-6-yl)-4-chloro-1-methyl-1H-indazol-3-yl)methanesulfonamide, HCl (Int MP1h)

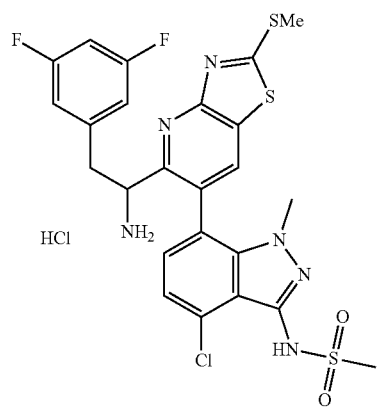 [SMILES: CSc1nc2nc(C(N)Cc3cc(F)cc(F)c3)c(-c3ccc(Cl)c4c(NS(C)(=O)=O)nn(C)c34)cc2s1 ; Cl]

To a suspension of tert-Butyl (1-(6-(4-chloro-1-methyl-3-(methylsulfonamido)-1H-indazol-7-yl)-2-(methylthio)thiazolo[4,5-b]pyridin-5-yl)-2-(3,5-difluorophenyl)ethyl)carbamate (Int MP1g, 0.25 g, 0.36 mmol) indioxane (3 mL) was added 4M HCl in dioxane (0.90 mL, 3.60 mmol) and the resulting mixture was stirred at room temp for 2.5 h. The reaction mixture was then concentrated and dried under high vacuum to afford the title compound (185 mg) as brown solid, which was used in the next step without further purification. LC/MS: m/z=595.0 [M+H]$^+$.

N-(1-(6-(4-chloro-1-methyl-3-(methylsulfonamido)-1H-indazol-7-yl)-2-(methylthio)thiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 193)

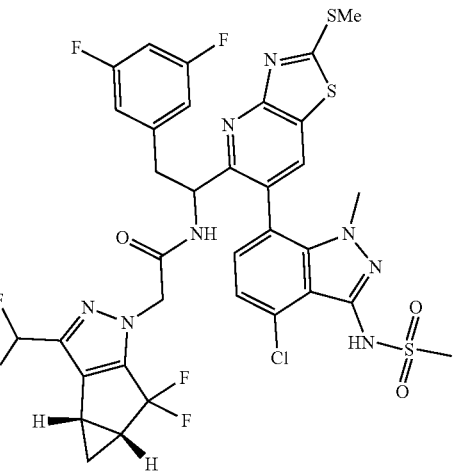

To a mixture of N-(7-(5-(1-amino-2-(3,5-difluorophenyl)ethyl)-2-(methylthio)thiazolo[4,5-b]pyridin-6-yl)-4-chloro-1-methyl-1H-indazol-3-yl)methanesulfonamide (Int MP1h, 0.18 g, 0.30 mmol) and 2-((3bS,4aR)-3-(difluoromethyl)-5, 5-difluoro-3b,4,4a,5-tetrahydro-1H-cyclopropa[3,4]cyclopenta[1,2-c]pyrazol-1-yl)acetic acid (80 mg, 0.30 mmol) in DMF (5 mL) was added DIEA (0.16 mL, 0.91 mmol) followed by HATU (127 mg, 0.333 mmol) and the resulting mixture was stirred at room temp for 16 h. Water was then added and the mixture was extracted with ethyl acetate, washed with brine, dried ($Na_2SO_4$), filtered and concentrated. The residue was then purified by Biotage (5-70% EtOAc/hexane) to afford Example 193 (160 mg; stereoisomers ratio, ~25:75). LC-MS retention time=2.11 and 2.24 min; m/z=841.0 [M+H]$^+$. Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-d$_6$) δ 9.21 (d, J=8.2 Hz, 0.7H), 9.0.5 (d, J=8.2 Hz, 0.3H), 8.55 (s, 0.3H), 8.51 (s, 0.7H), 7.28-6.74 (m, 4H), 6.57 (br. d, J=6.4 Hz, 0.7H), 6.43 (br d, J=6.4 Hz, 0.3H), 5.14-5.09 (m, 0.3H), 4.88-4.82 (m, 0.7H), 4.81-4.60 (m, 2H), 3.26-3.16 (m, 3H), 3.15-2.96 (m, 2H), 2.90 (s, 3H), 2.60-2.39 (m, 5H), 1.45-1.33 (m, 1H), 0.95 (br d, J=3.4 Hz, 0.3H), 0.84 (br s, 0.7H).

N-(1-(2-amino-6-(4-chloro-1-methyl-3-(methylsulfonamido)-1H-indazol-7-yl)thiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide (Example 194)

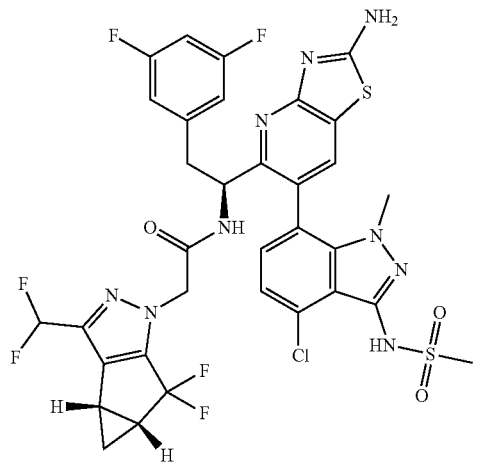 [SMILES: Cn1nc(NS(C)(=O)=O)c2c(Cl)ccc(-c3cc4sc(N)nc4nc3[C@H](Cc3cc(F)cc(F)c3)NC(=O)Cn3nc(C(F)F)c4c3C(F)(F)[C@@H]3C[C@H]43)c21]

A mixture of N-(1-(6-(4-chloro-1-methyl-3-(methylsulfonamido)-1H-indazol-7-yl)-2-(methylthio)thiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 193, 20 mg, 0.02 mmol) and 7M ammonia in methanol (0.34 mL, 2.38 mmol) was heated in a sealed tube at 70° C. for 4 days. The mixture was then concentrated and purified by prep-HPLC with the following conditions: Prep-HPLC: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: a 0-minute hold at 27% B, 27-67% B over 25 minutes, then a 4-minute hold at 100% B; Flow Rate: 20 mL/min. Fractions containing the desired product were combined and dried. Although the stereoisomers (~25:75 ratio) were separable, they were recombined to afford Example 194 (4 mg; stereoisomers ratio, 25:75). LC-MS retention time=1.75 and 1.85 min; m/z=810.0 [M+H]$^+$, (Column: Acquity UPLC BEH, 2.1×50 mm, 1.7 μm particles; Solvent A=0.05% TFA in 100% Water. Solvent B=0.05% TFA in 100% Acetonitrile. Flow Rate=1 mL/min. Start % B=0. Final % B=100. Gradient Time=2.2 min, then a 1 min hold at 100% B. Detection: MS and UV (220 nm). $^1$H NMR (500 MHz, DMSO-d$_6$) δ 9.01 (br d, J=8.5 Hz, 0.7H), 8.90 (br d, J=8.3 Hz, 0.3H), 8.18 (s, 0.6H), 8.15 (s, 1.4H), 8.07 (s, 0.3H), 8.02 (s, 0.7H), 7.21-6.76 (m, 4H), 6.55 (br d, J=6.7 Hz, 1.4H), 6.43 (br d, J=6.7 Hz, 0.6H), 4.94-4.87 (m, 0.3H), 4.84-4.58 (m, 2.7H), 3.29-2.90 (m, 5H), 2.62-2.41 (m, 5H), 1.45-1.41 (m, 0.3H), 1.39-1.31 (m, 0.7H), 0.99-0.93 (m, 0.3H), 0.86 (br s, 0.7H).

Tert-Butyl (S)-(I-(7-acetyl-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int MP3a)

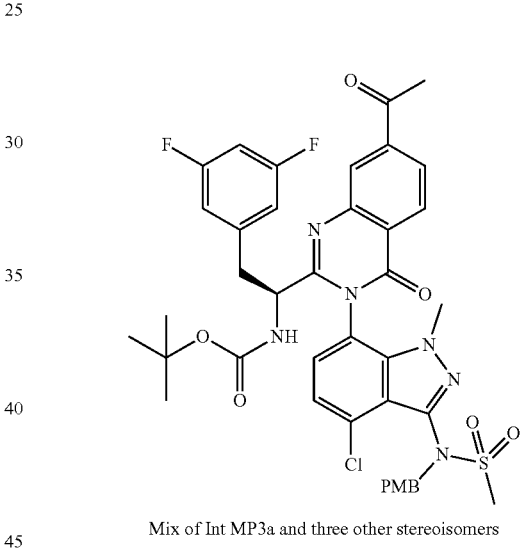

Mix of Int MP3a and three other stereoisomers

A solution of tert-Butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int 27a, 0.50 g, 0.58 mmol), tributyl(1-ethoxyvinyl)stannane (0.25 g, 0.67 mmol) and bis(triphenylphosphine)palladium(II) chloride (40.9 mg, 0.06 mmol) in toluene (10 mL) was heated at 110° C. for 3 h. Mixture was then cooled and filtered through a pad of Celite. The filtrate was then concentrated and the crude material was redissolved in THF (10 mL) and 1N HCl (0.25 mL) was added to the mixture. The resulting mixture was then stirred at room temp for 1 h. Water was then added and the mixture was extracted with ethyl acetate, dried (Na2SO4), filtered and concentrated. The residue was then purified by Biotage (5-50% EtOAc/hexane) to afford the title compound (290 mg) which was a mix of stereoisomers due to racemization in a reaction sequence and presence of stable atropisomers. LC/MS: m/z=843.2[M+Na].

tert-Butyl (S)-(1-(3-(4-chloro-3-(N-(4-methoxybenzyl)methylsulfonamido)-1-methyl-1H-indazol-7-yl)-7-(1,1-difluoroethyl)-4-oxo-3,4-dihydroquinazolin-2-yl)-2-(3,5-difluorophenyl)ethyl)carbamate (Int MP3b)

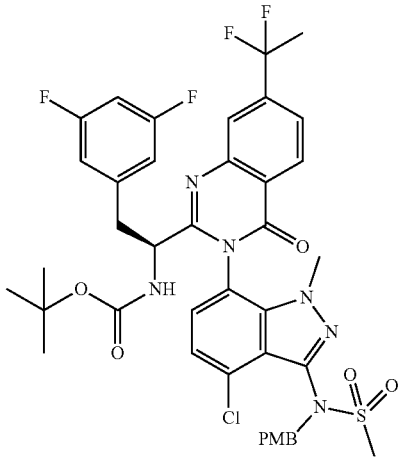

Mix of Int MP3b and three other stereoisomers

To a solution of tert-Butyl (S)-(1-(7-acetyl-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int MP3a, 0.29 g, 0.35 mmol) in CH$_2$Cl$_2$ (2 mL) in a sealed tube was added DAST (1.2 mL, 8.8 mmol) and one drop of EtOH. The tube was then sealed and the mixture was stirred at 60° C. for 16 h. After cooling to room temp, the reaction mixture was poured into a sat. NaHCO$_3$ solution and extracted with DCM, dried (Na$_2$SO$_4$), filtered and concentrated. The residue was then purified by Biotage (5-40% EtOAc/hexane) to afford the title compound (120 mg) as a mix of stereoisomers. LC/MS: m/z=865.2 [M+Na].

(S)—N-(7-(2-(1-amino-2-(3,5-difluorophenyl)ethyl)-7-(1,1-difluoroethyl)-4-oxoquinazolin-3(4H)-yl)-4-chloro-1-methyl-1H-indazol-3-yl)methanesulfonamide (Int MP3c)

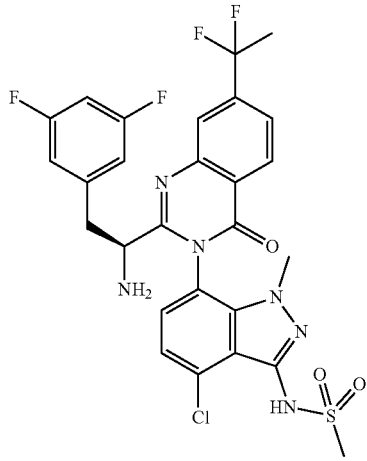

Mix of Int MP3c and three other stereoisomers

To a solution of tert-Butyl (S)-(1-(3-(4-chloro-3-(N-(4-methoxybenzyl)methylsulfonamido)-1-methyl-1H-indazol-7-yl)-7-(1,1-difluoroethyl)-4-oxo-3,4-dihydroquinazolin-2-yl)-2-(3,5-difluorophenyl)ethyl)carbamate (Int MP3b, 0.12 g, 0.14 mmol) in CH$_2$Cl$_2$ (1 mL) was added TFA (2 mL) followed by triflic acid (0.04 mL, 0.43 mmol) and the mixture was stirred at room temp for 1 h. Mixture was then concentrated under reduced pressure and the residue was diluted with ethyl acetate, washed with 1N NaOH solution (3 mL), water, dried (Na2SO4), filtered and concentrated to afford the title compound (80 mg) which as a mixture of stereoisomers. LC/MS: m/z=623.2 [M+H]$^+$.

N—((S)-1-(3-(4-chloro-1-methyl-3-(methylsulfonamido)-1H-indazol-7-yl)-7-(1,1-difluoroethyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 196), Example 195 and Example 195.2

Example 195

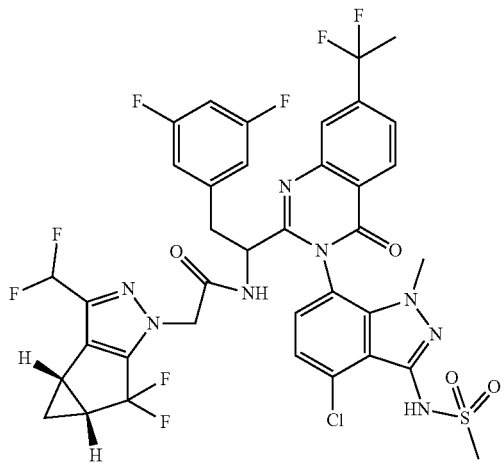

Mix of two stereoisomers

Example 195.2

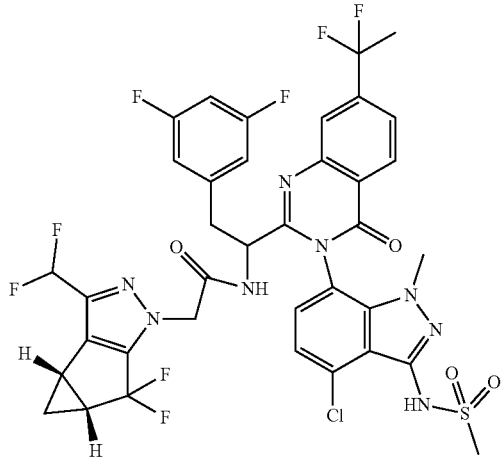

homochiral

Example 196

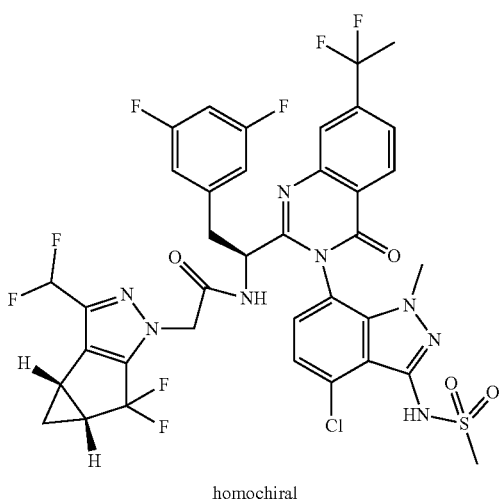

homochiral

To a stirred solution of (S)—N-(7-(2-(1-amino-2-(3,5-difluorophenyl)ethyl)-7-(1,1-difluoroethyl)-4-oxoquinazolin-3(4H)-yl)-4-chloro-1-methyl-1H-indazol-3-yl)methanesulfonamide (Int MP3c, 60 mg, 0.10 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (25 mg, 0.10 mmol) in DMF (3 mL) was added DIEA (0.05 mL, 0.29 mmol) followed by HATU (40 mg, 0.11 mmol) and the resulting mixture was stirred at room temp for 16 h. Water was then added and the mixture was extracted with ethyl acetate, washed with brine, dried (Na$_2$SO$_4$), filtered and concentrated. The residue was then treated with 2M ammonia in methanol (2 mL) and the mixture was stirred for 10 min. Mixture was then concentrated and purified by prep-HPLC with the following conditions to retrieve two isolates, each as a mixture of stereoisomer. Prep-HPLC: XBridge C18, 19×200 mm mm, 5 μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 36% B, 36-76% B over 25 minutes, then a 4-minute hold at 100% B; Flow Rate: 20 mL/min. Fractions containing the desired product were combined and dried. Detection: MS and UV (220 nm).

Example 195

First elute (10 mg, a mixture of stereoisomers), LC/MS: m/z=869.1 [M+H]$^+$.

Second elute (70 mg, a mixture of stereoisomers) was further purified by Chiralpak IF-H preparative column, 21×250 mm, 5 μm; Mobile Phase: 30% IPA in CO$_2$, 150 bar, Temp: 40° C., Flow rate: 60.0 mL/min. in 10 min. UV monitored @ 220 nm Injection: 0.25 mL of ~25 mg/mL in 1:1 IPA:DMF. Two elutes of stereoisomeric relation were isolated.

Example 195.2: First Elute (12 mg, Single Stereoisomer)

Example 196: Second Elute (37 mg, Single Stereoisomer)

$^1$H NMR (500 MHz, DMSO-d$_6$) δ 9.12 (br d, J=8.5 Hz, 1H), 8.31 (br d, J=8.2 Hz, 1H), 7.95 (s, 1H), 7.81 (br d, J=8.5 Hz, 1H), 7.59 (br d, J=7.9 Hz, 1H), 7.38 (br d, J=7.6 Hz, 1H), 7.02-6.74 (m, 3H), 6.59 (br d, J=6.7 Hz, 2H), 4.62-4.42 (m, 3H), 3.98 (br d, J=4.9 Hz, 3H), 3.35 (br d, J=12.8 Hz, 1H), 3.15 (s, 3H), 3.04-2.92 (m, 1H), 2.41 (br d, J=3.4 Hz, 1H), 2.05 (br t, J=19.1 Hz, 3H), 1.39-1.28 (m, 1H), 1.19 (s, 1H), 0.81 (br s, 1H). LC/MS: m/z=869.1 [M+H]$^+$.

(S)—N-(7-(2-(1-amino-2-(3,5-difluorophenyl)ethyl)-7-bromo-4-oxoquinazolin-3(4H)-yl)-4-chloro-1-methyl-1H-indazol-3-yl)methanesulfonamide (Int MP4a)

Mix of Int MP4a and three other stereoisomers

To a solution of tert-Butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int 27a, 0.59 g, 0.69 mmol) in CH$_2$Cl$_2$ (2 mL) was added TFA (4 mL) followed by triflic acid (0.18 mL, 2.06 mmol) and the mixture was stirred at room temp for 1 h. Mixture was then concentrated under reduced pressure and the residue was diluted with ethyl acetate, washed with 1 N NaOH solution (5 mL), water, dried (Na$_2$SO$_4$), filtered and concentrated to afford the title compound (420 mg) as a mixture of stereoisomers. LC/MS: m/z=637.8 [M+H]$^+$.

N—((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int MP4b)

Mix of Int MP4b and three other stereoisomers

To a mixture of (S)—N-(7-(2-(1-amino-2-(3,5-difluorophenyl)ethyl)-7-bromo-4-oxoquinazolin-3(4H)-yl)-4-chloro-1-methyl-1H-indazol-3-yl)methanesulfonamide (Int MP4a, 0.40 g, 0.63 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.17 g, 0.63 mmol) in DMF (6 mL) was added DIEA (0.33 mL, 1.88 mmol) followed by HATU (0.26 g, 0.69 mmol) and the resulting mixture was stirred at room temp for 16 h. Water was then added and the mixture was extracted with ethyl acetate, washed with brine, dried (Na$_2$SO$_4$), filtered and concentrated. The residue was then treated with 2M ammonia in methanol (2 mL) and the mixture was stirred for 10 min. Mixture was then concentrated and purified by Biotage (5-70% EtOAc/hexane) to afford the title compound (400 mg) which was a mix of stereoisomers. LC/MS: m/z=883.0 [M+H]$^+$.

N—((S)-1-(7-acetyl-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int MP4c)

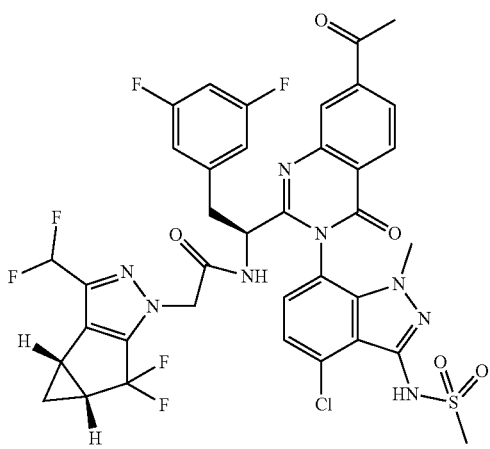

Mix of Int MP4c and three other stereoisomers

A solution of N—((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int MP4b, 0.20 g, 0.23 mmol), tributyl(1-ethoxyvinyl)stannane (98 mg, 0.27 mmol) and bis(triphenylphosphine)palladium(II) chloride (15.9 mg, 0.02 mmol) in toluene (5 mL) was heated at 110° C. for 16 h. Mixture was then cooled and filtered through a pad of Celite. The filtrate was then concentrated and the crude material was redissolved in THF (10 mL) and 1N HCl (0.25 mL) was added to the mixture. The resulting mixture was then stirred at room temp for 1 h. Water was then added and the mixture was extracted with ethyl acetate, dried (Na$_2$SO$_4$), filtered and concentrated. The residue was then purified by Biotage (5-50% EtOAc/hexane) to afford the title compound (90 mg) which was a mixture of stereoisomers. LC/MS: m/z=847.2 [M+H]$^+$.

N—((S)-1-(3-(4-chloro-1-methyl-3-(methylsulfonamido)-1H-indazol-7-yl)-7-cyclopropyl-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 198) and Example MP 197

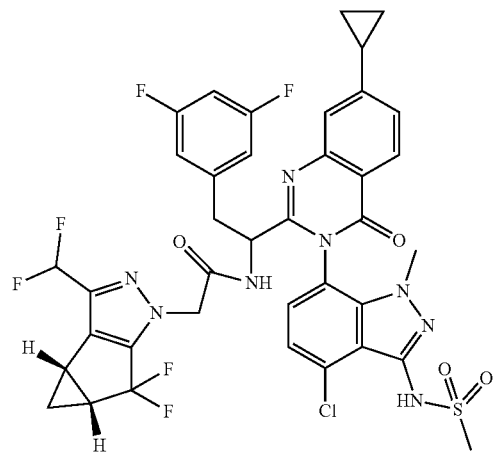

Example MP12.1

Mix of two stereoisomers

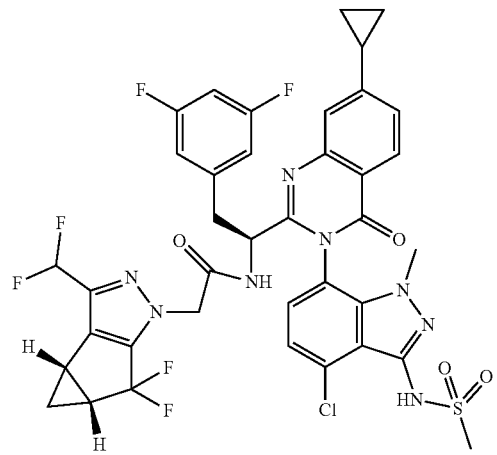

Example MP12.2

Mix of indicated stereosiomer and another stereoisomer

To a Stirred solution of N—((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int MP4b, 0.1 g, 0.11 mmol), cyclopropylboronic acid (15 mg, 0.17 mmol) in toluene (4 mL) and water (0.4 mL) was added potassium phosphate tribasic (72 mg, 0.34 mmol) and the mixture was purged with nitrogen for 30 min. Palladium(ii) acetate (3 mg, 0.01 mmol) and tricyclohexylphosphine (6 mg, 0.02 mmol) were then added under inert atmosphere and the mixture was heated at 100° C. for 16 h. The reaction mixture was then cooled and quenched with water (5 ml), diluted with ethyl acetate (25 ml), washed with water (10 ml), brine solution (10 ml), dried ($Na_2SO_4$), filtered and concentrated. The crude material was purified by prep-HPLC with the following conditions to retrieve two isolates, each as a mixture of stereoisomer. Prep-HPLC: XBridge C18, 19×200 mm mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 34% B, 34-74% B over 25 minutes, then a 4-minute hold at 100% B; Flow Rate: 20 mL/min. Fractions containing the desired product were combined and dried. Detection: MS and UV (220 nm).

Example 197: First Elute (3 mg, a Mixture of Stereoisomers)

LC-MS retention time=2.21 min; m/z=845.1 [M+H]$^+$. (Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-$d_6$) δ 9.09 (br d, J=7.3 Hz, 1H), 8.25-7.80 (m, 2H), 7.62 (s, 1H), 7.43-7.36 (m, 2H), 7.25-7.18 (m, 1H), 7.15-6.84 (m, 2H), 6.54 (br d, J=5.8 Hz, 2H), 4.87-4.64 (m, 2H), 4.56-4.41 (m, 1H), 3.31-3.22 (m, 1H), 3.20 (s, 3H), 3.12-3.09 (m, 3H), 2.95-2.84 (m, 1H), 2.65-2.56 (m, 1H), 2.26-2.16 (m, 1H), 1.41 (br s, 1H), 1.23 (s, 1H), 1.18 (br d, J=8.2 Hz, 1H), 1.01-0.87 (m, 3H).

Example 198: Second Elute (7 mg, a Mixture of Indicated Isomer and a Stereoisomer)

LC-MS retention time=2.26 min; m/z=845.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-$d_6$) δ 9.05 (br d, J=4.0 Hz, 1H), 8.08 (d, J=8.2 Hz, 1H), 7.66 (d, J=7.6 Hz, 1H), 7.46 (s, 1H), 7.39 (br dd, J=19.7, 7.8 Hz, 2H), 7.08-6.77 (m, 2H), 6.65 (br d, J=6.7 Hz, 2H), 4.67-4.41 (m, 3H), 3.18 (s, 3H), 3.05-2.93 (m, 1H), 2.51 (s, 3H), 2.45 (br s, 1H), 2.26-2.14 (m, 1H), 1.36 (br d, J=6.4 Hz, 1H), 1.23 (s, 1H), 1.17 (br d, J=7.9 Hz, 2H), 0.95-0.76 (m, 3H).

N—((S)-1-(3-(4-chloro-1-methyl-3-(methylsulfonamido)-1H-indazol-7-yl)-7-(methylsulfonyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 200) and Example 199

Example MP14.1

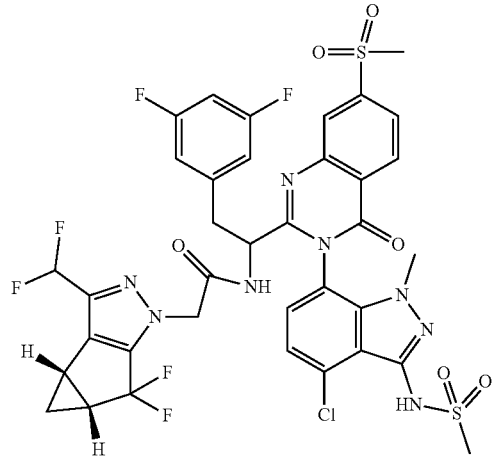

Mix of two stereoisomers

Example MP14.2

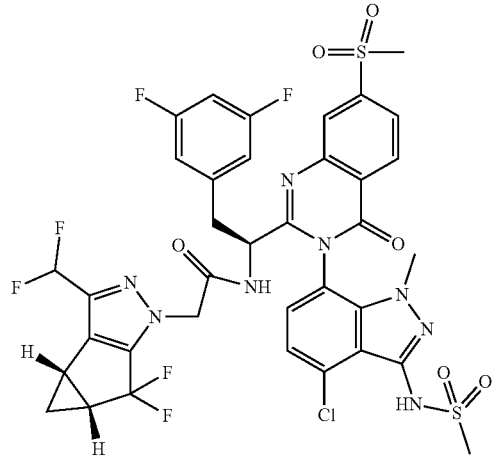

Mix of Indicated stereoisomer and another stereoisomer

To a degassed solution of N—((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Int MP4b, 99 mg, 0.11 mmol), sodium methanesulfinate (14 mg, 0.13 mmol) and L-proline sodium salt (3 mg, 0.02 mmol) in DMSO (3 mL) was added copper(I) iodide (2.133 mg, 0.011 mmol) and the mixture was degassed again for 2 min. Vial was then sealed and the mixture was heated in a microwave at 95° C. for 36 h. Reaction mixture was then passed through a micro-filter and the filtrate was purified by prep-HPLC with the following conditions to retrieve two isolates, each as a mixture of stereoisomer. Prep-HPLC: XBridge C18, 19×200 mm mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 26% B, 26-66% B over 25 minutes, then a 4-minute hold at 100% B; Flow Rate: 20 mL/min. Fractions containing the desired product were combined and dried. Detection: MS and UV (220 nm).

Example 199: First Elute (12 mg, a Mixture of Stereoisomers)

LC-MS retention time=1.9 min; m/z=883.0 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-d$_6$) δ 9.08 (br d, J=6.1 Hz, 1H), 8.49-8.39 (m, 2H), 8.16 (br d, J=8.2 Hz, 1H), 7.48-7.39 (m, 1H), 7.26-7.19 (m, 1H), 7.15-6.80 (m, 2H), 6.53 (br d, J=4.3 Hz, 2H), 4.86-4.66 (m, 2H), 4.61 (q, J=7.2 Hz, 1H), 3.23-3.17 (m, 1H), 3.18-3.11 (m, 6H), 2.98-2.88 (m, 1H), 2.63-2.54 (m, 1H), 2.51 (br s, 3H), 1.41 (br d, J=6.1 Hz, 1H), 1.23 (s, 1H), 0.94 (br s, 1H).

Example 200: Second Elute (35 mg, a Mixture of Indicated Isomer and a Stereoisomer)

LC-MS retention time=1.96 min; m/z=883.0 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-d$_6$) δ 9.16 (br d, J=7.9 Hz, 1H), 8.46 (br d, J=8.2 Hz, 1H), 8.28 (s, 1H), 8.15 (br d, J=8.2 Hz, 1H), 7.71 (br d, J=7.6 Hz, 1H), 7.44 (br d, J=7.6 Hz, 1H), 7.13-6.79 (m, 2H), 6.66 (br d, J=6.1 Hz, 2H), 4.72-4.47 (m, 3H), 3.17 (s, 3H), 3.08-2.92 (m, 1H), 2.51 (br s, 6H), 2.47-2.42 (m, 1H), 1.91 (s, 1H), 1.35 (br d, J=6.7 Hz, 1H), 1.23 (br s, 1H), 0.84 (br s, 1H).

Methyl 2-((tert-butoxycarbonyl)amino)-4-methylbenzoate (Int MP5a)

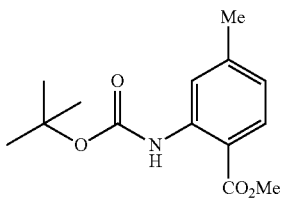 [SMILES: COC(=O)c1ccc(C)cc1NC(=O)OC(C)(C)C]

To a solution of methyl 2-amino-4-methylbenzoate (2.0 g, 12.11 mmol) in THF (100 mL) was added BOC-anhydride (7.0 mL, 30.3 mmol), TEA (4.2 mL, 30.3 mmol) followed by DMAP (1.48 g, 12.11 mmol) and the resulting mixture was stirred at room temp for 16 h. Water was then added and the mixture was extracted with ethyl acetate, dried (Na$_2$SO$_4$), filtered and concentrated. The residue was then purified by Biotage (0-30% EtOAc/hexane) to afford the title compound (2.2 g). $^1$H NMR (400 MHz, DMSO-d$_6$) δ 10.18 (s, 1H), 8.08 (s, 1H), 7.83 (d, J=8.0 Hz, 1H), 6.92 (d, J=8.0 Hz, 1H), 3.83 (s, 3H), 2.34 (s, 3H), 1.47 (s, 9H).

Methyl 4-(bromomethyl)-2-((tert-butoxycarbonyl)amino)benzoate (Int MP5b)

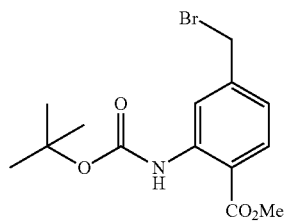 [SMILES: COC(=O)c1ccc(CBr)cc1NC(=O)OC(C)(C)C]

A solution of methyl 2-((tert-butoxycarbonyl)amino)-4-methylbenzoate (Int MP5a, 1.5 g, 5.65 mmol), NBS (1.00 g, 5.65 mmol) and benzoyl peroxide (0.14 g, 0.57 mmol) in CCl$_4$ (30 mL) was heated at 70° C. for 16 h. Mixture was then cooled to room temp and succinimide was filtered and washed with CCl$_4$, and the solvent was evaporated under reduced pressure. The residue was then purified by Biotage (0-10% EtOAc/hexane) to afford the title compound (1.6 g). $^1$H NMR (400 MHz, CDCl$_3$) δ 10.44 (s, 1H), 8.52 (d, J=1.5 Hz, 1H), 7.99 (d, J=8.3 Hz, 1H), 7.05 (dd, J=8.3, 1.5 Hz, 1H), 4.46 (s, 2H), 3.93 (s, 3H), 1.54 (s, 9H). LC/MS: m/z=243.8 [M-Boc].

Methyl 2-((tert-butoxycarbonyl)amino)-4-((methylsulfonyl)methyl)benzoate (Int MP5c)

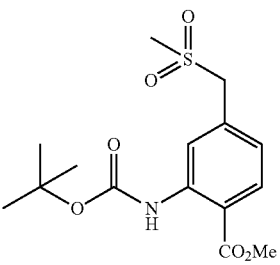 [SMILES: COC(=O)c1ccc(CS(C)(=O)=O)cc1NC(=O)OC(C)(C)C]

To a solution of methyl 4-(bromomethyl)-2-((tert-butoxycarbonyl)amino)benzoate (Int MP5b, 1.60 g, 4.65 mmol) in DMF (30 mL) was added sodium methanesulfinate (0.71 g, 6.97 mmol) and the resulting mixture was heated at 60° C. for 2 h. Mixture was then cooled to room temp, water was added and the mixture was extracted with ethyl acetate, washed with brine, dried (Na$_2$SO$_4$), filtered and concentrated. The residue was then purified by Biotage (5-80% EtOAc/hexane) to afford the title compound (1.0 g). $^1$H NMR (400 MHz, DMSO-d$_6$) δ 10.16 (s, 1H), 8.25 (d, J=1.3 Hz, 1H), 7.94 (d, J=8.0 Hz, 1H), 7.14 (dd, J=8.3, 1.5 Hz, 1H), 4.58 (s, 2H), 3.86 (s, 3H), 2.97 (s, 3H), 1.48 (s, 9H).

Methyl 2-amino-4-((methylsulfonyl)methyl)benzoate (Int MP5d)

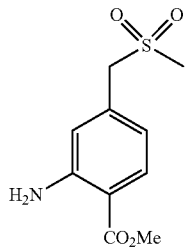

To a solution of methyl 2-((tert-butoxycarbonyl)amino)-4-((methylsulfonyl)methyl)benzoate (Int MP5c, 700 mg, 2.04 mmol) in $CH_2Cl_2$ (4 mL) was added TFA (1.57 mL, 20.38 mmol) and the resulting mixture was stirred at room temp for 2 h. Mixture was then concentrated under reduced pressure and triturated with hexanes to afford the title compound (440 mg) as off-white solid. $^1$H NMR (400 MHz, DMSO-$d_6$) δ 7.69 (d, J=8.3 Hz, 1H), 6.79 (d, J=1.3 Hz, 1H), 6.75 (s, 2H), 6.56 (dd, J=8.3, 1.5 Hz, 1H), 4.38 (s, 2H), 3.78 (s, 3H), 2.92 (s, 3H). LC/MS: m/z=243.9 [M+H]$^+$.

2-amino-4-((methylsulfonyl)methyl)benzoic acid (Int MP5e)

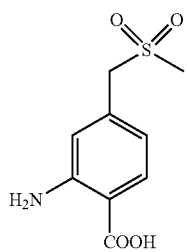

To a solution of methyl 2-amino-4-((methylsulfonyl)methyl)benzoate (Int MP5d, 0.43 g, 1.77 mmol) in THF (8 mL) and water (8 mL) was added LiOH (0.13 g, 5.30 mmol) and the resulting mixture was stirred at room temp for 5 h. Mixture was then concentrated and the residue was dissolved in water and acidified to pH 3 with 1M HCl. Precipitate formed were then filtered off and washed with water and dried under high vac to afford the title compound (350 mg) as white solid. $^1$H NMR (400 MHz, DMSO-$d_6$) δ 10.21-7.90 (m, 1H), 7.68 (d, J=8.3 Hz, 1H), 6.76 (d, J=1.3 Hz, 1H), 6.53 (dd, J=8.3, 1.5 Hz, 1H), 4.36 (s, 2H), 2.92 (s, 3H). LC/MS: m/z=229.9 [M+H]$^+$.

tert-Butyl (S)-(1-(3-(4-chloro-3-(N-(4-methoxybenzyl)methylsulfonamido)-1-methyl-1H-indazol-7-yl)-7-((methylsulfonyl)methyl)-4-oxo-3,4-dihydroquinazolin-2-yl)-2-(3,5-difluorophenyl)ethyl)carbamate (Int MP5f)

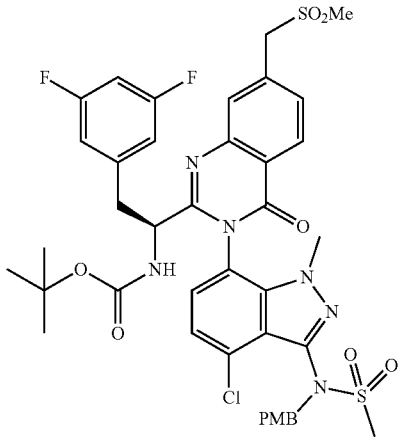

Mix of Int MP5f and three other stereoisomers

A mixture of (S)-2-((tert-butoxycarbonyl)amino)-3-(3,5-difluorophenyl)propanoic acid (0.34 g, 1.13 mmol), 2-amino-4-((methylsulfonyl)methyl)benzoic acid (Int MP5e, 0.26 g, 1.13 mmol) and diphenyl phosphite (0.72 mL, 3.72 mmol) in pyridine (8 mL) was heated at 70° C. for 2 h. N-(7-amino-4-chloro-1-methyl-1H-indazol-3-yl)-N-(4-methoxybenzyl)methanesulfonamide (0.49 g, 1.24 mmol) was then added and the mixture was heated at 70° C. for 16 h. Mixture was then concentrated under reduced pressure and the residue was partitioned between water (25 mL) and EtOAc (100 mL). The separated organic layer was washed with water and brine, dried ($Na_2SO_4$), filtered and concentrated. The residue was purified by Biotage (5-50% EtOAc/hexane) to afford the title compound (300 mg) which was a mix of stereoisomers. LC/MS: m/z=815.1 [M−tBu]$^+$.

(S)—N-(7-(2-(1-amino-2-(3,5-difluorophenyl)ethyl)-7-((methylsulfonyl)methyl)-4-oxoquinazolin-3(4H)-yl)-4-chloro-1-methyl-1H-indazol-3-yl)methanesulfonamide (Int MP5g)

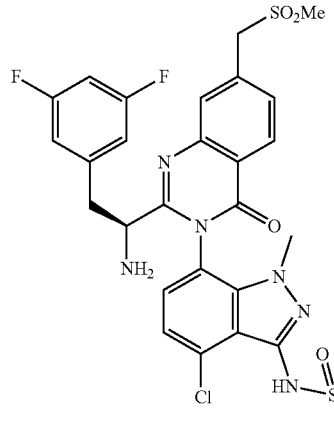

Mix of Int MP5g and three other stereoisomers

To a solution of tert-Butyl (S)-(1-(3-(4-chloro-3-(N-(4-methoxybenzyl)methylsulfonamido)-1-methyl-1H-indazol-7-yl)-7-((methylsulfonyl)methyl)-4-oxo-3,4-dihydroquinazolin-2-yl)-2-(3,5-difluorophenyl)ethyl)carbamate (Int MP5f, 300 mg, 0.344 mmol) in CH$_2$Cl$_2$ (2 mL) was added TFA (4 mL) followed by triflic acid (0.09 mL, 1.03 mmol) and the mixture was stirred at room temp for 1 h. Mixture was then concentrated under reduced pressure and the residue was diluted with ethyl acetate, washed with 1N NaOH solution (5 mL), water, dried (Na$_2$SO$_4$), filtered and concentrated to afford the title compound (200 mg) which was a mix of stereoisomers. LC/MS: m/z=651.1 [M+H]$^+$.

N—((S)-1-(3-(4-chloro-1-methyl-3-(methylsulfonamido)-1H-indazol-7-yl)-7-((methylsulfonyl)methyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 202) and Example 201

Example of MP16.1

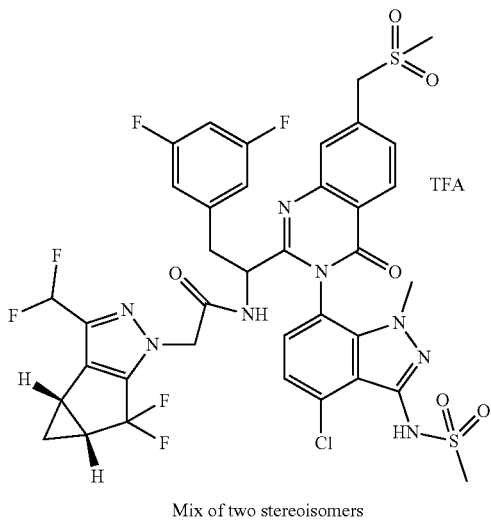

Mix of two stereoisomers

Example of MP16.2

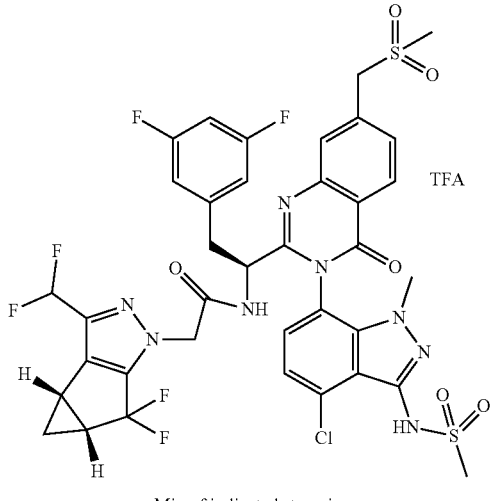

Mix of indicated stereoisomer and another stereoisomer

To a mixture of (S)—N-(7-(2-(1-amino-2-(3,5-difluorophenyl)ethyl)-7-((methylsulfonyl)methyl)-4-oxoquinazolin-3(4H)-yl)-4-chloro-1-methyl-1H-indazol-3-yl)methanesulfonamide (Int MP5g, 70 mg, 0.11 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (28 mg, 0.11 mmol) in DMF (2 mL) was added DIEA (0.06 mL, 0.32 mmol) followed by HATU (45 mg, 0.12 mmol) and the resulting mixture was stirred at room temp for 16 h. The crude material was then purified by prep-HPLC with the following conditions to retrieve two isolates, each as a mixture of stereoisomer. Prep-HPLC: XBridge C18, 19×200 mm mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 23% B, 23-63% B over 25 minutes, then a 4-minute hold at 100% B; Flow Rate: 20 mL/min. Fractions containing the desired product were combined and dried. Detection: MS and UV (220 nm).

Example 201: First Elute (10 mg, a Mixture of Stereoisomers)

LC-MS retention time=1.87 min; m/z=897.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-d$_6$) δ 9.99 (s, 1H), 9.10 (br d, J=7.9 Hz, 1H), 8.24 (br d, J=7.9 Hz, 1H), 8.02 (s, 1H), 7.71 (br d, J=8.2 Hz, 1H), 7.41 (br d, J=7.9 Hz, 1H), 7.23 (br d, J=7.9 Hz, 1H), 7.16-6.88 (m, 2H), 6.53 (br d, J=6.1 Hz, 2H), 4.84 (s, 2H), 4.80 (br d, J=16.8 Hz, 1H), 4.70-4.65 (m, 1H), 4.58-4.52 (m, 1H), 3.27-3.22 (m, 1H), 3.20 (br d, J=10.4 Hz, 3H), 3.04 (s, 3H), 2.95 (br dd, J=13.1, 7.0 Hz, 1H), 2.58 (br d, J=4.9 Hz, 1H), 1.42 (br d, J=6.7 Hz, 1H), 1.24 (s, 1H), 0.95 (br s, 1H). Note: sulfone peak (3H) appear to be under DMSO peak.

Example 202: Second Elute (26 mg, a Mixture of Indicated Isomer and a Stereoisomer)

LC-MS retention time=1.92 min; m/z=897.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-d$_6$) δ 9.99 (s, 1H), 9.10 (br d, J=7.9 Hz, 1H), 8.24 (br d, J=7.9 Hz, 1H), 8.02 (s, 1H), 7.71 (br d, J=8.2 Hz, 1H), 7.41 (br d, J=7.9 Hz, 1H), 7.23 (br d, J=7.9 Hz, 1H), 7.16-6.88 (m, 2H), 6.53 (br d, J=6.1 Hz, 2H), 4.84 (s, 2H), 4.80 (br d, J=16.8 Hz, 1H), 4.70-4.65 (m, 1H), 4.58-4.52 (m, 1H), 3.27-3.22 (m, 1H), 3.20 (s, 2H), 3.04 (s, 3H), 2.58 (br d, J=4.9 Hz, 1H), 2.51 (br s, 6H), 1.42 (br d, J=6.7 Hz, 1H), 1.24 (s, 1H), 0.95 (br s, 1H).

(S)—N-(1-(3-(4-chloro-1-methyl-3-(methylsulfonamido)-1H-indazol-7-yl)-7-((methylsulfonyl)methyl)-4-oxo-3,4-dihydroquinazolin-2-yl)-2-(3,5-difluorophenyl)ethyl)-2-(5-hydroxy-1H-indol-3-yl)acetamide (Example 203 and Example 204)

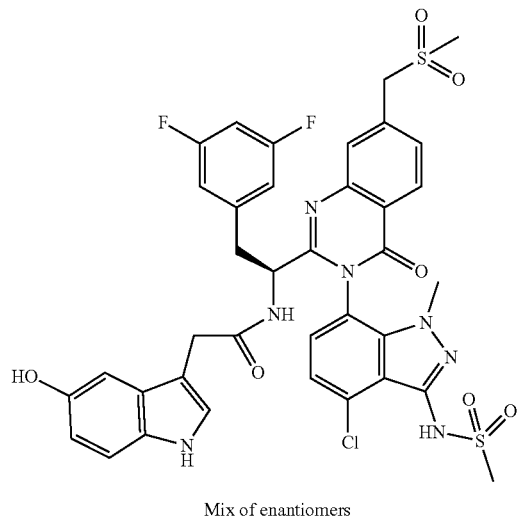

Example 203

Mix of enantiomers

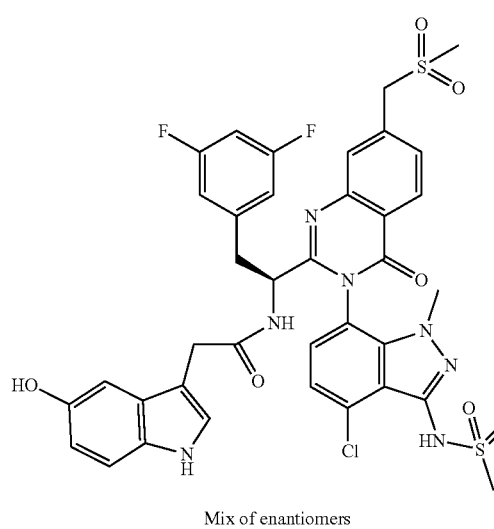

Example 204

Mix of enantiomers

Synthesized from Int MP5g and appropriate acid using the procedure described for the preparation of Example 201/202.

Example 203: First Elute (12 mg, a Mixture of Enantiomers of Unknown Proportion)

LC-MS retention time=1.47 min; m/z=824.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-d$_6$) 10.59 (br s, 1H), 8.70 (br d, J=7.3 Hz, 1H), 8.21 (d, J=8.2 Hz, 1H), 8.01 (s, 1H), 7.69 (br d, J=8.2 Hz, 1H), 7.16 (d, J=8.5 Hz, 1H), 7.09 (d, J=7.9 Hz, 1H), 7.06-6.98 (m, 2H), 6.87 (s, 1H), 6.69 (d, J=7.9 Hz, 1H), 6.63 (br d, J=8.5 Hz, 1H), 6.55 (br d, J=7.0 Hz, 2H), 4.82 (s, 2H), 4.46 (q, J=7.3 Hz, 1H), 3.40-3.22 (m, 1H), 3.19 (s, 2H), 3.05 (s, 3H), 2.96-2.86 (m, 1H). The sulfone fragment peaks appear to be under DMSO peak.

Example 204: Second Elute (33 mg, a Mixture of Enantiomers of Unknown Proportion)

LC-MS retention time=1.58 min; m/z=824.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-d$_6$) δ 10.42 (br s, 1H), 8.76 (br d, J=8.2 Hz, 1H), 8.24 (d, J=7.9 Hz, 1H), 7.89 (s, 1H), 7.72 (br d, J=7.9 Hz, 1H), 7.67 (br d, J=8.2 Hz, 1H), 7.44 (br d, J=7.3 Hz, 1H), 7.05 (d, J=8.5 Hz, 1H), 6.97 (br t, J=9.2 Hz, 1H), 6.78 (s, 1H), 6.70-6.61 (m, 4H), 6.54 (br d, J=8.5 Hz, 1H), 4.81 (br s, 2H), 4.60-4.45 (m, 1H), 3.60 (s, 2H), 3.20 (s, 3H), 3.18-3.09 (m, 2H), 3.02 (s, 3H). The sulfone fragment peak appear to be under DMSO peak.

(S)—N-(1-(3-(4-chloro-1-methyl-3-(methylsulfonamido)-1H-indazol-7-yl)-7-((methylsulfonyl)methyl)-4-oxo-3,4-dihydroquinazolin-2-yl)-2-(3,5-difluorophenyl)ethyl)-2-(3-cyclopropyl-1H-pyrazol-1-yl)acetamide (Example 205 and Example 206)

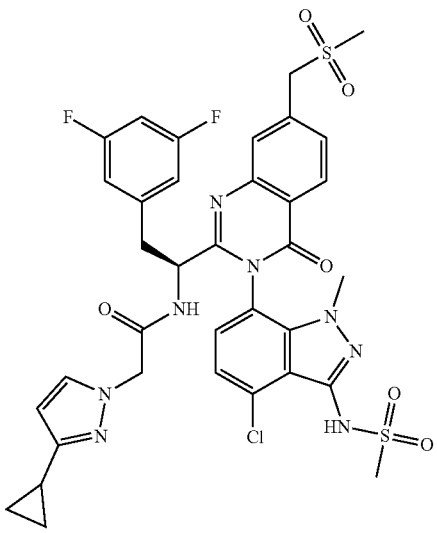

Example 205

Mix of enantiomers

Example 206

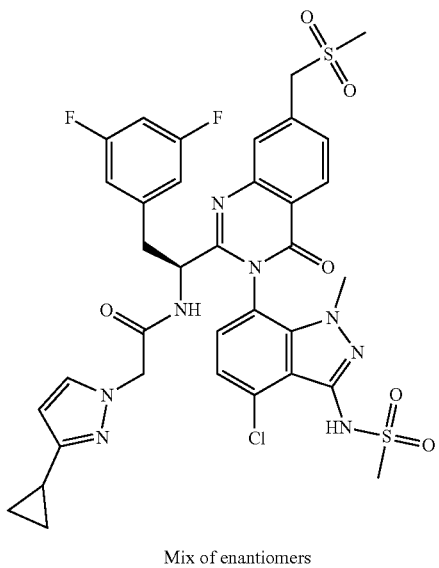

Mix of enantiomers

Synthesized from Int MP5g and appropriate acid using the procedure described for the preparation of Example 201/202.

Example 205: First Elute (14 mg, a Mixture of Enantiomers of Unknown Proportion)

LC-MS retention time=1.66 min; m/z=799.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Example 206: Second Elute (24 mg, a Mixture of Enantiomers of Unknown Proportion)

LC-MS retention time=1.76 min; m/z=799.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Methyl 4-methyl-2-nitrobenzoate (Int MP6a)

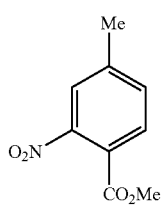

To a solution of 4-methyl-2-nitrobenzoic acid (3.0 g, 16.6 mmol) in DMF (50 mL) was added K$_2$CO$_3$ (4.6 g, 33.1 mmol) followed by MeI (3.1 mL, 49.7 mmol) and the resulting mixture was stirred at room temp for 2 h. Water was then added and the mixture was extracted with ethyl acetate, washed with brine, dried (Na$_2$SO$_4$), filtered and concentrated to afford the title compound (2.9 g). $^1$H NMR (400 MHz, CDCl$_3$) δ 7.70-7.65 (m, 2H), 7.49-7.44 (m, 1H), 3.91 (s, 3H), 2.49 (s, 3H). LC/MS: m/z=195.9 [M+H]$^+$.

Methyl 4-(bromomethyl)-2-nitrobenzoate (Int MP6b)

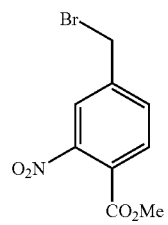 [SMILES: COC(=O)c1ccc(CBr)cc1[N+](=O)[O-]]

A solution of methyl 4-methyl-2-nitrobenzoate (Int MP6a, 2.9 g, 14.9 mmol), NBS (2.6 g, 14.9 mmol) and benzoyl peroxide (0.36 g, 1.49 mmol) in CCl$_4$ (60 mL) was heated at 70° C. for 16 h. Mixture was then cooled to room temp and succinimide was filtered off and washed with CCl$_4$, and the solvent was evaporated under reduced pressure. The residue was then purified by Biotage (0-10% EtOAc/hexane) to afford the title compound (1.7g). $^1$H NMR (400 MHz, CDCl$_3$) δ 7.94 (d, J=1.5 Hz, 1H), 7.79-7.63 (m, 2H), 4.52 (s, 2H), 3.94 (s, 3H). LC/MS: m/z=273.8 [M+H]$^+$.

Methyl 4-((methylsulfonyl)methyl)-2-nitrobenzoate (Int MP6c)

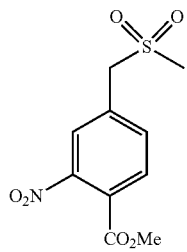 [SMILES: COC(=O)c1ccc(CS(C)(=O)=O)cc1[N+](=O)[O-]]

To a solution of methyl 4-(bromomethyl)-2-nitrobenzoate (Int MP6b, 1.7 g, 6.2 mmol) in DMF (30 mL) was added sodium methanesulfinate (0.95 g, 9.30 mmol) and the resulting mixture was heated at 60° C. for 2 h. Mixture was then cooled to room temp, water was added and the mixture was extracted with ethyl acetate, washed with brine, dried (Na$_2$SO$_4$), filtered and concentrated to afford the title compound (1.4 g). $^1$H NMR (400 MHz, CDCl$_3$) δ 7.99 (d, J=1.3 Hz, 1H), 7.84-7.75 (m, 2H), 4.37 (s, 2H), 3.95 (s, 3H), 2.91 (s, 3H). LC/MS: m/z=274.0 [M+H]$^+$.

463

Methyl 4-(2-(methylsulfonyl)propan-2-yl)-2-nitrobenzoate (Int MP6d)

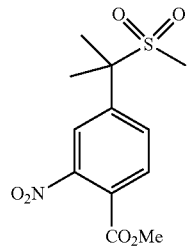

To a solution of methyl 4-((methylsulfonyl)methyl)-2-nitrobenzoate (Int MP6c, 1.0 g, 3.7 mmol) in THF (25 mL) at 0° C. was added 1M solution of potassium tert-butoxide (8.05 mL, 8.05 mmol) and the resulting mixture was stirred for 20 min. Methyl iodide (0.50 mL, 8.05 mmol) was then added dropwise and the mixture was stirred for 1 h. Water was then added and the mixture was extracted with ethyl acetate, washed with brine, dried (Na$_2$SO$_4$), filtered and concentrated. The residue was then purified by Biotage (5-70% EtOAc/hexane) to afford the title compound (800 mg) as off-white solid. $^1$H NMR (400 MHz, CDCl$_3$) δ 8.16 (d, J=2.0 Hz, 1H), 8.01 (dd, J=8.2, 1.9 Hz, 1H), 7.80 (d, J=8.3 Hz, 1H), 3.95 (s, 3H), 2.66 (s, 3H), 1.92 (s, 6H).

Methyl 2-amino-4-(2-(methylsulfonyl)propan-2-yl)benzoate (Int MP6e)

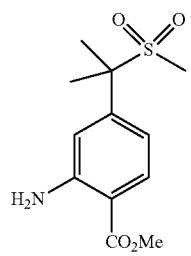 [SMILES: COC(=O)c1ccc(C(C)(C)S(C)(=O)=O)cc1[N+](=O)[O-]]

To a solution of methyl 4-(2-(methylsulfonyl)propan-2-yl)-2-nitrobenzoate (Int MP6d, 0.4 g, 1.3 mmol) in EtOH (20 mL) was added 10% Pd-C (0.14 g, 0.13 mmol) and the mixture was stirred under balloon hydrogen atmosphere for 16 h. Mixture was then filtered through a pad of Celite, washing the pad with EtOH. The filtrate was then concentrated and dried under high vac to afford the title compound (350 mg). $^1$H NMR (400 MHz, CDCl$_3$) δ 7.86 (d, J=8.8 Hz, 1H), 6.96 (d, J=2.0 Hz, 1H), 6.89 (dd, J=8.5, 2.0 Hz, 1H), 5.75 (br.s, 2H), 3.89 (s, 3H), 2.57 (s, 3H), 1.81 (s, 6H). LC/MS: m/z=272.0 [M+H]$^+$.

464

2-amino-4-(2-(methylsulfonyl)propan-2-yl)benzoic acid (Int MP6f)

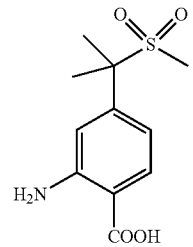

To a solution of methyl 2-amino-4-(2-(methylsulfonyl)propan-2-yl)benzoate (Int MP6e, 0.36 g, 1.33 mmol) in THF (6 mL) and water (6 mL) was added LiOH (0.13 g, 5.31 mmol) and the resulting mixture was stirred at room temp for 48 h. Mixture was then concentrated and the residue was dissolved in water and acidified to pH 3 with 1M HCl. Precipitate formed was then filtered off and washed with water and dried under high vac to afford the title compound (220 mg) as off-white solid. $^1$H NMR (400 MHz, DMSO-d$_6$) δ 8.72 (br.s, 2H), 7.67 (d, J=8.5 Hz, 1H), 6.99 (d, J=1.8 Hz, 1H), 6.75 (dd, J=8.5, 1.8 Hz, 1H), 2.71 (s, 3H), 1.68 (s, 6H). LC/MS: m/z=258.0 [M+H]$^+$.

tert-Butyl (S)-(1-(3-(4-chloro-3-(N-(4-methoxybenzyl)methylsulfonamido)-1-methyl-1H-indazol-7-yl)-7-(2-(methylsulfonyl)propan-2-yl)-4-oxo-3,4-dihydroquinazolin-2-yl)-2-(3,5-difluorophenyl)ethyl)carbamate (Int MP6g)

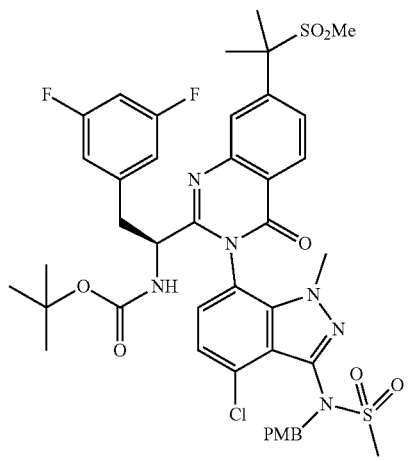

Mix of Int MP6g and three other stereoisomers

A mixture of (S)-2-((tert-butoxycarbonyl)amino)-3-(3,5-difluorophenyl)propanoic acid (0.17 g, 0.56 mmol), 2-amino-4-(2-(methylsulfonyl)propan-2-yl)benzoic acid (Int MP6f, 0.15 g, 0.56 mmol) and diphenyl phosphite (0.36 mL, 1.86 mmol) in pyridine (4 mL) was heated at 70° C. for 2 h. N-(7-amino-4-chloro-1-methyl-1H-indazol-3-yl)-N-(4-methoxybenzyl)methane sulfonamide (0.25 g, 0.62 mmol) was added and the final solution was heated at 70° C. for 16 h. Mixture was then concentrated under reduced pressure and the residue was partitioned between water (25 mL) and EtOAc (100 mL). The separated organic layer was washed with water and brine, dried (Na$_2$SO$_4$), filtered and concentrated. The residue was purified by Biotage (5-50% EtOAc/hexane) to afford the title compound (200 mg) which was a mix of stereoisomers. LC/MS: m/z=843.2 [M−tBu]⁺.

(S)—N-(7-(2-(1-amino-2-(3,5-difluorophenyl)ethyl)-7-(2-(methylsulfonyl)propan-2-yl)-4-oxoquinazolin-3(4H)-yl)-4-chloro-1-methyl-1H-indazol-3-yl)methanesulfonamide (Int MP6h)

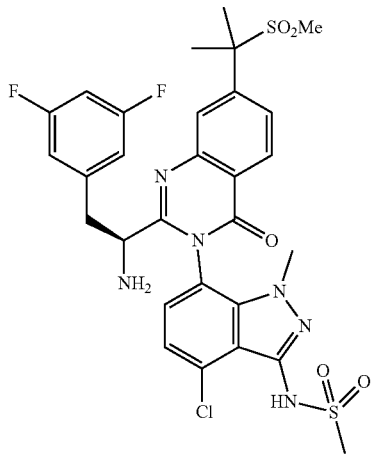

Mix of Int MP6h and three
other stereoisomers

To a solution of tert-Butyl (S)-(1-(3-(4-chloro-3-(N-(4-methoxybenzyl)methylsulfonamido)-1-methyl-1H-indazol-7-yl)-7-(2-(methylsulfonyl)propan-2-yl)-4-oxo-3,4-dihydroquinazolin-2-yl)-2-(3,5-difluorophenyl)ethyl)carbamate (Int MP6g, 0.17 g, 0.19 mmol) in CH₂Cl₂ (1.5 mL) was added TFA (3 mL) followed by triflic acid (0.05 mL, 0.57 mmol) and the mixture was stirred at room temp for 1 h. Mixture was then concentrated under reduced pressure and the residue was diluted with ethyl acetate, washed with 1N NaOH solution (5 mL), water, dried (Na₂SO₄), filtered and concentrated to afford the title compound (120 mg) which was a mix of stereoisomers. LC/MS: m/z=679.1 [M+H]⁺.

N—((S)-1-(3-(4-chloro-1-methyl-3-(methylsulfonamido)-1H-indazol-7-yl)-7-(2-(methylsulfonyl)propan-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 208) and Example 207

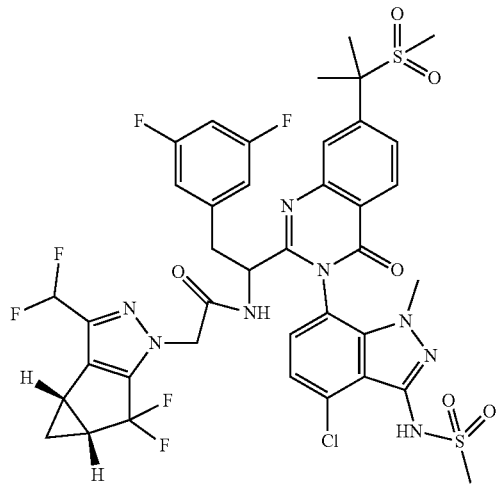

Eaxample 207
Mix of two stereoisomers

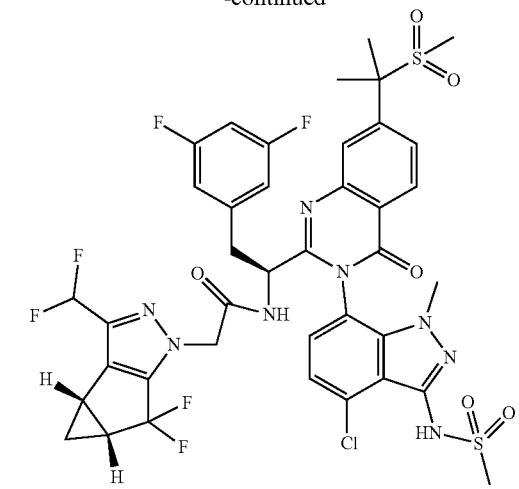

Example 208
Mix of indicated stereoisomer
and another stereoisomer

To a mixture of (S)—N-(7-(2-(1-amino-2-(3,5-difluorophenyl)ethyl)-7-(2-(methylsulfonyl)propan-2-yl)-4-oxoquinazolin-3(4H)-yl)-4-chloro-1-methyl-1H-indazol-3-yl)methanesulfonamide (Int MP6h, 40 mg, 0.06 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (16 mg, 0.06 mmol) in DMF (1.5 mL) was added DIEA (0.03 mL, 0.18 mmol) followed by HATU (25 mg, 0.06 mmol) and the resulting mixture was stirred at room temp for 16 h. 2M ammonia in methanol (0.5 mL) was then added and the mixture was stirred for 30 min. The crude material was then purified by prep-HPLC with the following conditions to retrieve two isolates, each as a mixture of stereoisomer. Prep-HPLC: XBridge C18, 19×200 mm mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 28% B, 28-68% B over 25 minutes, then a 4-minute hold at 100% B; Flow Rate: 20 mL/min. Fractions containing the desired product were combined and dried. Detection: MS and UV (220 nm).

Example 207: First Elute (4 mg, a Mixture of Stereoisomers)

LC-MS retention time=1.97 min; m/z=925.1 [M+H]f (Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). ¹H NMR (500 MHz, DMSO-d₆) δ 9.07 (br d, J=7.9 Hz, 1H), 8.24 (d, J=8.2 Hz, 1H), 8.14 (s, 1H), 7.93 (br d, J=8.2 Hz, 1H), 7.39 (br d, J=7.9 Hz, 1H), 7.22 (br d, J=7.6 Hz, 1H), 7.18-6.75 (m, 2H), 6.54 (br d, J=6.7 Hz, 2H), 4.84-4.77 (m, 1H), 4.71-4.64 (m, 1H), 4.58 (q, J=7.2 Hz, 1H), 3.40-3.06 (m, 3H), 2.96 (br dd, J=12.7, 6.9 Hz, 1H), 2.87 (s, 3H), 2.62-2.56 (m, 1H), 1.92 (br s, 6H), 1.46-1.36 (m, 1H), 1.33-1.17 (m, 2H), 0.95 (br s, 1H).

Example 208: Second Elute (26 mg, a Mixture of Indicated Isomer and a Stereoisomer)

LC-MS retention time=2.03 min; m/z=925.1 [M+H]⁺. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-$d_6$) δ 9.14 (br d, J=7.9 Hz, 1H), 8.25 (d, J=8.2 Hz, 1H), 8.03 (s, 1H), 7.91 (br d, J=8.5 Hz, 1H), 7.71 (d, J=7.9 Hz, 1H), 7.45 (br d, J=7.6 Hz, 1H), 7.12-6.76 (m, 2H), 6.64 (br d, J=6.7 Hz, 2H), 4.71-4.64 (m, 1H), 4.57-4.46 (m, 2H), 3.52 (s, 1.5H), 3.19 (s, 1.5H), 3.07-2.99 (m, 1H), 2.86 (s, 3H), 2.48-2.42 (m, 2H), 1.91 (s, 6H), 1.42-1.31 (m, 1H), 1.24 (s, 1H), 0.85 (br s, 1H).

(S)—N-(1-(3-(4-chloro-1-methyl-3-(methylsulfonamido)-1H-indazol-7-yl)-7-(2-(methylsulfonyl)propan-2-yl)-4-oxo-3,4-dihydroquinazolin-2-yl)-2-(3,5-difluorophenyl)ethyl)-2-(5-hydroxy-1H-indol-3-yl) acetamide (Example 209 and Example 210)

Synthesized from Int MP6h and appropriate acid using the procedure described for the preparation of Example 207/208.

Example 209: First Elute (13 mg, a Mixture of Enantiomers of Unknown Proportion)

LC-MS retention time=1.6 min; m/z=852.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Example 210: Second Elute (20 mg, a Mixture of Enantiomers of Unknown Proportion)

LC-MS retention time=1.7 min; m/z=852.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

(S)—N-(1-(3-(4-chloro-1-methyl-3-(methylsulfonamido)-1H-indazol-7-yl)-7-(2-(methylsulfonyl)propan-2-yl)-4-oxo-3,4-dihydroquinazolin-2-yl)-2-(3,5-difluorophenyl)ethyl)-2-(3-cyclopropyl-1H-pyrazol-1-yl)acetamide (Example 211 and Example 212)

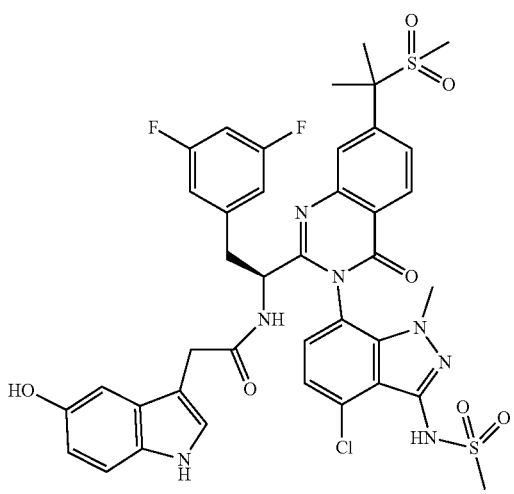

Eaxample 209
Mix of enantiomers

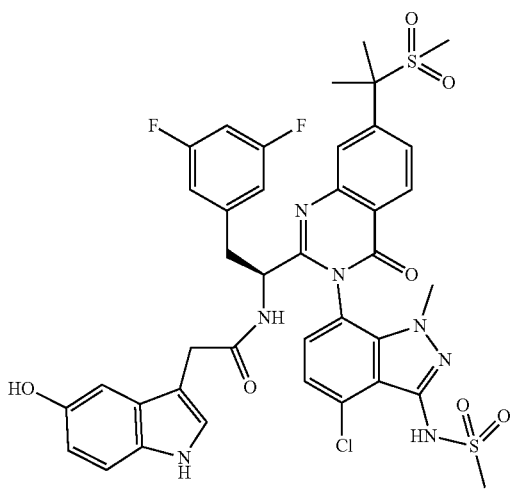

Example 210
Mix of enantiomers

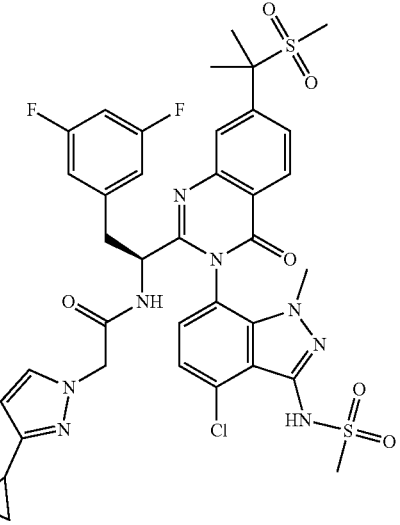

Example 211
Mix of enantiomers

-continued

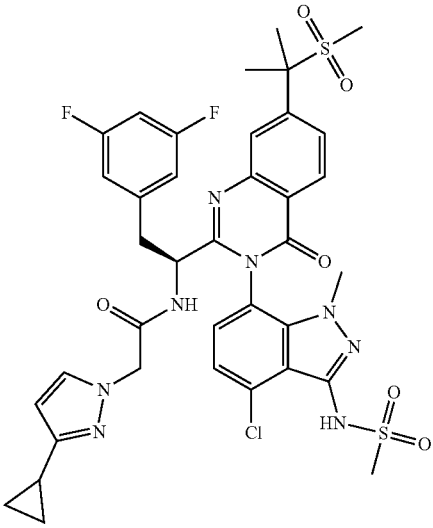

Example 212
Mix of enantiomers

Synthesized from Int MP6h and appropriate acid using the procedure described for the preparation of Example 207/208.

Example 211: First Elute (12 mg, a Mixture of Enantiomers)

LC-MS retention time=1.8 min; m/z=827.1 [M+H]⁺. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Example 212: Second Elute (16 mg, a Mixture of Enantiomers)

LC-MS retention time=1.9 min; m/z=827.1 [M+H]⁺. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

tert-Butyl (S)-(1-(3-(4-chloro-1-(2,2-difluoroethyl)-3-(N-(4-methoxybenzyl)methylsulfonamido)-1H-indazol-7-yl)-7-(2-(methylsulfonyl)propan-2-yl)-4-oxo-3,4-dihydroquinazolin-2-yl)-2-(3,5-difluorophenyl)ethyl)carbamate (Int MP6i)

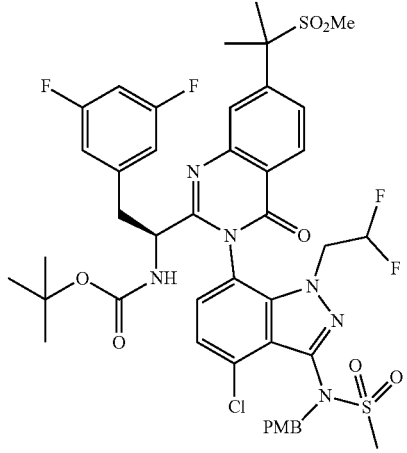

Mix of Int MP6i and three other stereoisomers

A mixture of (S)-2-((tert-butoxycarbonyl)amino)-3-(3,5-difluorophenyl)propanoic acid (55 mg, 0.18 mmol), (2-amino-4-(2-(methylsulfonyl)propan-2-yl)benzoic acid (Int MP6f, 47 mg, 0.18 mmol) and diphenyl phosphite (0.12 mL, 0.60 mmol) in pyridine (1.5 mL) was heated at 70° C. for 2 h. N-(7-amino-4-chloro-1-(2,2-difluoroethyl)-1H-indazol-3-yl)-N-(4-methoxybenzyl)methanesulfonamide (Int 21d, 89 mg, 0.20 mmol) was then added and the mixture was heated at 70° C. for 16 h. Mixture was then concentrated under reduced pressure and the residue was partitioned between water (25 mL) and EtOAc (100 mL). The separated organic layer was washed with water and brine, dried (Na₂SO₄), filtered and concentrated. The residue was purified by Biotage (5-50% EtOAc/hexane) to afford the title compound (50 mg) which was a mix of stereoisomers. LC/MS: m/z=949.1 [M+H]⁺.

(S)—N-(7-(2-(1-amino-2-(3,5-difluorophenyl)ethyl)-7-(2-(methylsulfonyl)propan-2-yl)-4-oxoquinazolin-3(4H)-yl)-4-chloro-1-(2,2-difluoroethyl)-1H-indazol-3-yl)-N-(4-methoxybenzyl)methanesulfonamide, HCl (Int MP6j)

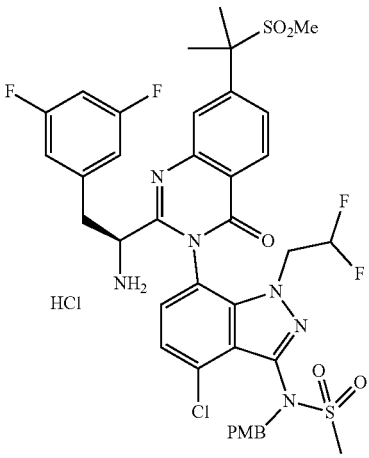

Mix of Int MP6j and three other stereoisomers

HCl (0.66 mL, 2.65 mmol, 4M in dioxane) and tert-Butyl (S)-(1-(3-(4-chloro-1-(2,2-difluoroethyl)-3-(N-(4-methoxybenzyl)methylsulfonamido)-1H-indazol-7-yl)-7-(2-(methylsulfonyl)propan-2-yl)-4-oxo-3,4-dihydroquinazolin-2-yl)-2-(3,5-difluorophenyl)ethyl)carbamate (Int MP6i, 50 mg, 0.053 mmol) in dioxane (1 mL) was stirred at room temp for 2 h and concentrated to afford the title compound (46 mg) which was a mix of stereoisomers. LC/MS: m/z=849.2 [M+H]⁺.

N—((S)-1-(3-(4-chloro-1-(2,2-difluoroethyl)-3-(methylsulfonamido)-1H-indazol-7-yl)-7-(2-(methylsulfonyl)propan-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 213)

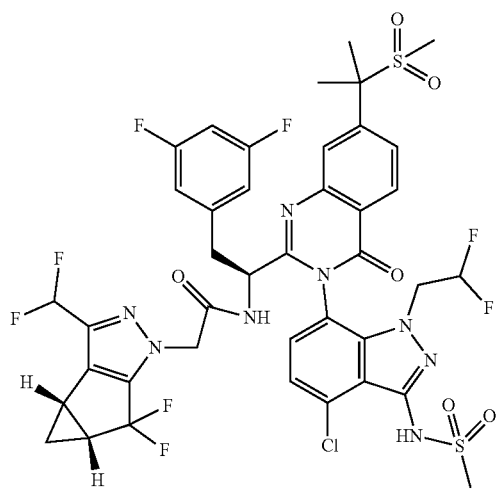

Mixture of Example 213 and three other stereoisomers

To a mixture of (S)—N-(7-(2-(1-amino-2-(3,5-difluorophenyl)ethyl)-7-(2-(methylsulfonyl)propan-2-yl)-4-oxoquinazolin-3(4H)-yl)-4-chloro-1-(2,2-difluoroethyl)-1H-indazol-3-yl)-N-(4-methoxybenzyl)methanesulfonamide, HCl (Int MP6j, 46 mg, 0.05 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (15 mg, 0.06 mmol) in THF (1.5 mL) was added DIEA (0.03 mL, 0.16 mmol) followed by HATU (22 mg, 0.06 mmol) and the resulting mixture was stirred at room temp for 2 h and then concentrated. The residue was taken up in DCM (0.5 mL) and triflic acid (0.05 mL) and TFA (1 mL) were added. The mixture was stirred at rt for 1 h, concentrated and then purified by prep-HPLC with the following conditions to afford the title compound (Example 213, 27 mg) as a mixture of four stereoisomers, where one is dominant. Prep-HPLC: XBridge C18, 19×200 mm mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 29% B, 28-69% B over 25 minutes, then a 4-minute hold at 100% B; Flow Rate: 20 mL/min. Fractions containing the desired product were combined and dried. Detection: MS and UV (220 nm). LC-MS retention time=2.05 min; m/z=975.1 [M+H]⁺. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

tert-Butyl (S)-(1-(3-(4-chloro-1-(2,2-difluoroethyl)-3-(N-(4-methoxybenzyl)cyclopropanesulfonamido)-1H-indazol-7-yl)-7-(2-(methylsulfonyl)propan-2-yl)-4-oxo-3,4-dihydroquinazolin-2-yl)-2-(3,5-difluorophenyl)ethyl)carbamate (Int MP6k)

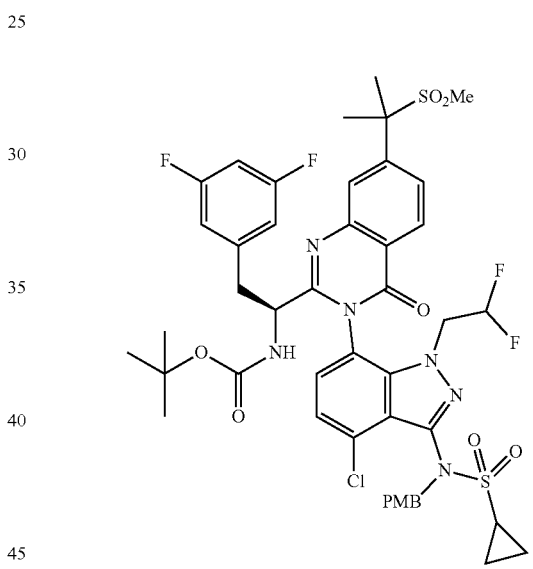

Mix of Int MP6k and three other stereoisomers

A mixture of (S)-2-((tert-butoxycarbonyl)amino)-3-(3,5-difluorophenyl)propanoic acid (55 mg, 0.18 mmol), 2-amino-4-(2-(methylsulfonyl)propan-2-yl)benzoic acid (Int MP6f, 47 mg, 0.18 mmol) and diphenyl phosphite (0.12 mL, 0.60 mmol) in pyridine (1.5 mL) was heated at 70° C. for 2 h. N-(7-amino-4-chloro-1-(2,2-difluoroethyl)-1H-indazol-3-yl)-N-(4-methoxybenzyl)cyclopropanesulfonamide (95 mg, 0.20 mmol) was then added and the mixture was heated at 70° C. for 16 h. Mixture was then concentrated under reduced pressure and the residue was partitioned between water (10 mL) and EtOAc (50 mL). The separated organic layer was washed with water and brine, dried (Na₂SO₄), filtered and concentrated. The residue was purified by Biotage (5-50% EtOAc/hexane) to afford the title compound (50 mg) which was a mix of stereoisomers. LC/MS: m/z=975.1 [M+H]⁺.

(S)—N-(7-(2-(1-amino-2-(3,5-difluorophenyl)ethyl)-7-(2-(methylsulfonyl)propan-2-yl)-4-oxoquinazolin-3(4H)-yl)-4-chloro-1-(2,2-difluoroethyl)-1H-indazol-3-yl)-N-(4-methoxybenzyl)cyclopropanesulfonamide, HCl (Int MP6I)

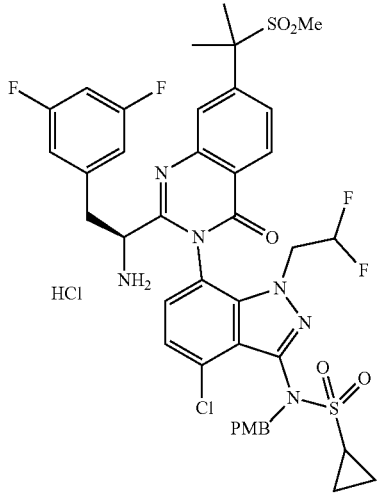

Mix of Int MP6I and three other stereoisomers

HCl (1.3 mL, 5.1 mmol, 4M in dioxane) and tert-Butyl (S)-(1-(3-(4-chloro-1-(2,2-difluoroethyl)-3-(N-(4-methoxybenzyl)cyclopropanesulfonamido)-1H-indazol-7-yl)-7-(2-(methylsulfonyl)propan-2-yl)-4-oxo-3,4-dihydroquinazolin-2-yl)-2-(3,5-difluorophenyl)ethyl)carbamate (Int MP6k, 50 mg, 0.05 mmol) in dioxane (1 mL) was stirred at room temp for 2 h and concentrated to afford the title compound (46 mg) which was a mix of stereoisomers. LC/MS: m/z=875.2 [M+H]+.

N—((S)-1-(3-(4-chloro-3-(cyclopropanesulfonamido)-1-(2,2-difluoroethyl)-1H-indazol-7-yl)-7-(2-(methylsulfonyl)propan-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide, TFA (Example 214)

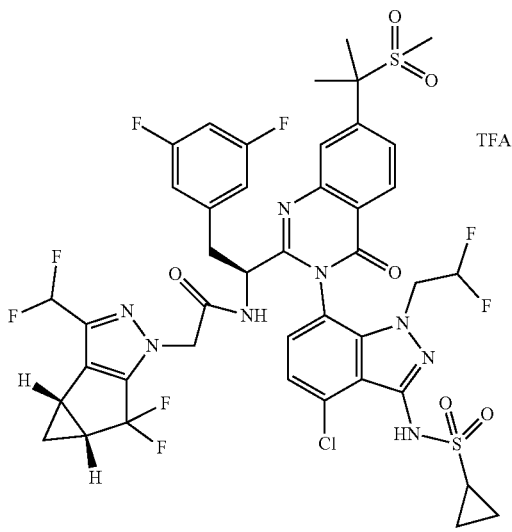

Mixture of Example 214 and three other stereoisomers

To a mixture of (S)—N-(7-(2-(1-amino-2-(3,5-difluorophenyl)ethyl)-7-(2-(methylsulfonyl)propan-2-yl)-4-oxoquinazolin-3(4H)-yl)-4-chloro-1-(2,2-difluoroethyl)-1H-indazol-3-yl)-N-(4-methoxybenzyl)cyclopropanesulfonamide, HCl (Int MP61, 46 mg, 0.05 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (15 mg, 0.06 mmol) in THF (1.5 mL) was added DIEA (0.03 mL, 0.15 mmol) followed by HATU (21 mg, 0.06 mmol) and the resulting mixture was stirred at room temp for 2 h and then concentrated. The residue was taken up in DCM (0.5 mL) and triflic acid (0.05 mL) and TFA (1 mL) were added. The mixture was stirred at rt for 1 h, concentrated and purified by prep-HPLC with the following conditions to afford the title compound (Example 214, 25 mg) as a mixture of four stereoisomers, where one is dominant. Prep-HPLC: XBridge C18, 19×200 mm mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 31% B, 31-71% B over 25 minutes, then a 4-minute hold at 100% B; Flow Rate: 20 mL/min. Fractions containing the desired product were combined and dried. Detection: MS and UV (220 nm). LC-MS retention time=2.12 min; m/z=1001.1 [M+H]+. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

2-amino-4-(tert-Butyl)benzoic acid (Int MP7a)

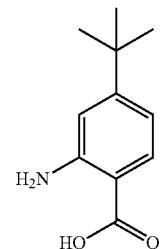

To a solution of 4-(tert-Butyl)-2-nitrobenzoic acid (0.43 g, 1.93 mmol) in Ethanol (20 mL) was added 10% Pd-C (102 mg, 0.096 mmol) and the mixture was stirred under balloon hydrogen atmosphere for 4 h. Mixture was then filtered through a pad of Celite, washing the pad with EtOH. The filtrate was then concentrated and dried under high vac to afford the title compound (350 mg). $^1$H NMR (400 MHz, DMSO-$d_6$) δ 8.54 (br. s, 2H), 7.59 (d, J=8.3 Hz, 1H), 6.73 (d, J=2.0 Hz, 1H), 6.56 (dd, J=8.5, 1.8 Hz, 1H), 1.22 (s, 9H). LC/MS: m/z=194.0 [M+H]+.

tert-Butyl (S)-(1-(7-(tert-Butyl)-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (Int MP7b)

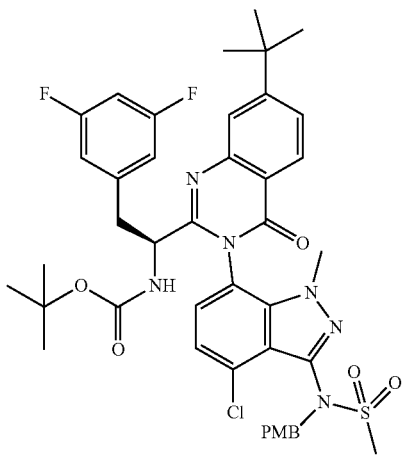

Mix of Int MP7b and three
other stereoisomers

A mixture of (S)-2-((tert-butoxycarbonyl)amino)-3-(3,5-difluorophenyl)propanoic acid (65 mg, 0.22 mmol), 2-amino-4-(tert-Butyl)benzoic acid (Int MP7a, 42 mg, 0.22 mmol) and diphenyl phosphite (0.14 mL, 0.71 mmol) in pyridine (1.5 mL) was heated at 70° C. for 2 h. N-(7-amino-4-chloro-1-methyl-1H-indazol-3-yl)-N-(4-methoxybenzyl) methanesulfonamide (94 mg, 0.24 mmol) was added and the final solution was heated at 70° C. for 16 h. Mixture was then concentrated under reduced pressure and the residue was partitioned between water (10 mL) and EtOAc (50 mL). The separated organic layer was washed with water and brine, dried (Na$_2$SO$_4$), filtered and concentrated. The residue was purified by Biotage (5-50% EtOAc/hexane) to afford the title compound (70 mg) which was a mix of stereoisomers. LC/MS: m/z=835.2 [M+H]$^+$.

(S)—N-(7-(2-(1-amino-2-(3,5-difluorophenyl)ethyl)-7-(tert-Butyl)-4-oxoquinazolin-3(4H)-yl)-4-chloro-1-methyl-1H-indazol-3-yl)-N-(4-methoxybenzyl)methanesulfonamide, HCl (Int MP7c)

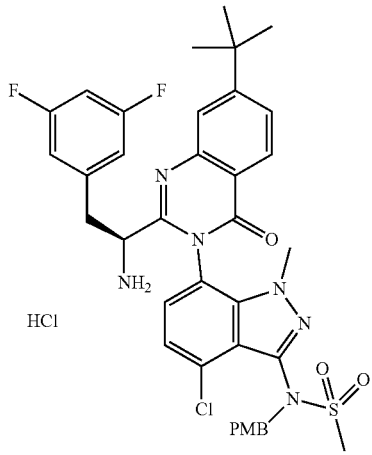

Mix of Int MP7c and three
other stereoisomers

HCl (2 mL, 8.0 mmol, 4M in dioxane) and tert-Butyl (S)-(1-(7-(tert-Butyl)-3-(4-chloro-3-(N-(4-methoxybenzyl) methylsulfonamido)-1-methyl-1H-indazol-7-yl)-4-oxo-3,4-dihydroquinazolin-2-yl)-2-(3,5-difluorophenyl)ethyl)carbamate (Int MP7b, 68 mg, 0.08 mmol) was stirred at room temp for 1 h and then concentrated to give the title compound (62 mg) which was a mixture of stereoisomers. LC/MS: m/z=735.2 [M+H]$^+$.

N—((S)-1-(7-(tert-Butyl)-3-(4-chloro-1-methyl-3-(methylsulfonamido)-1H-indazol-7-yl)-4-oxo-3,4-dihydroquinazolin-2-yl)-2-(3,5-difluorophenyl) ethyl)-2-((3bS,4aR)-3-(difluoromethyl)-5,5-difluoro-3b,4,4a,5-tetrahydro-1H-cyclopropa[3,4]cyclopenta [1,2-c]pyrazol-1-yl)acetamide (Example 216) and Example 215

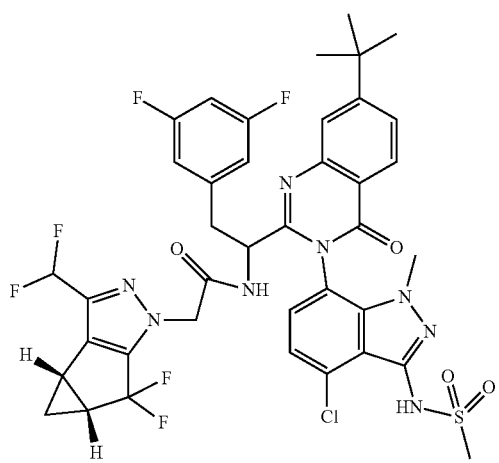

Eaxample 215
Mix of two stereoisomers

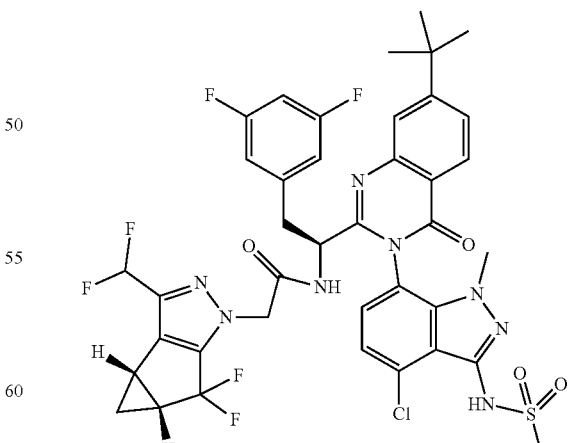

Example 216
Mix of indicated stereoisomer
and another stereoisomer

To a mixture of (S)—N-(7-(2-(1-amino-2-(3,5-difluorophenyl)ethyl)-7-(tert-Butyl)-4-oxoquinazolin-3(4H)-yl)-4-chloro-1-methyl-1H-indazol-3-yl)-N-(4-methoxybenzyl)methanesulfonamide, HCl (Int MP7c, 60 mg, 0.08 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (23 mg, 0.09 mmol) in THF (2 mL) was added DIEA (0.04 mL, 0.23 mmol) followed by HATU (33 mg, 0.09 mmol) and the resulting mixture was stirred at room temp for 2 h and then concentrated. The residue was taken up in DCM (0.5 mL) and triflic acid (0.05 mL) and TFA (1 mL) were added. The mixture was stirred at rt for 1 h, concentrated and then purified by prep-HPLC with the following conditions to retrieve two isolates, each as a mixture of stereoisomer. Prep-HPLC: XBridge C18, 19×200 mm mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 40% B, 40-80% B over 27 minutes, then a 4-minute hold at 100% B; Flow Rate: 20 mL/min. Fractions containing the desired product were combined and dried. Detection: MS and UV (220 nm).

Example 215: First Elute (26 mg, a Mixture of Stereoisomers)

LC-MS retention time=2.37 min; m/z=861.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-d$_6$) δ 9.08-8.94 (m, 1H), 8.14 (d, J=8.5 Hz, 1H), 7.88 (s, 1H), 7.78 (br d, J=8.5 Hz, 1H), 7.43-7.34 (m, 1H), 7.23 (br d, J=7.6 Hz, 1H), 7.15-6.85 (m, 2H), 6.59-6.39 (m, 2H), 4.87-4.65 (m, 2H), 4.55 (q, J=7.2 Hz, 1H), 3.20 (br d, J=8.9 Hz, 3H), 2.98-2.88 (m, 1H), 2.62-2.52 (m, 2H), 1.43 (br.s, 10H), 1.24 (s, 1H), 0.95 (br s, 1H). Methyl sulfone peak appears to be under DMSO peak.

Example 216: Second Elute (30 mg, a Mixture of Indicated Isomer and a Stereoisomer)

LC-MS retention time=2.42 min; m/z=861.1 [M+H]$^+$. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). $^1$H NMR (500 MHz, DMSO-d$_6$) δ 9.15-9.04 (m, 1H), 8.15 (br d, J=7.3 Hz, 1H), 7.76 (br s, 2H), 7.67 (br d, J=6.7 Hz, 1H), 7.43 (br d, J=7.0 Hz, 1H), 7.09-6.78 (m, 2H), 6.65 (br d, J=6.4 Hz, 2H), 4.73-4.44 (m, 3H), 3.50 (s, 1.5H), 3.19 (s, 1.5H), 3.09-2.92 (m, 1H), 2.48-2.39 (m, 2H), 1.42 (br s, 9H), 1.35 (br d, J=5.2 Hz, 1H), 1.24 (br s, 1H), 0.85 (br s, 1H). Methyl sulfone peak appears to be under DMSO peak. LC/MS: m/z=861.1 [M+H]$^+$.

tert-Butyl (S)-(1-(7-(tert-Butyl)-3-(4-chloro-1-(2,2-difluoroethyl)-3-(N-(4-methoxybenzyl)methylsulfonamido)-1H-indazol-7-yl)-4-oxo-3,4-dihydroquinazolin-2-yl)-2-(3,5-difluorophenyl)ethyl)carbamate (Int MP7d)

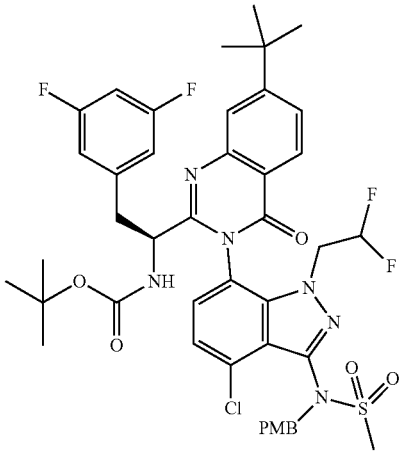

Mix of Int MP7d and three other stereoisomers

A mixture of (S)-2-((tert-butoxycarbonyl)amino)-3-(3,5-difluorophenyl)propanoic acid (65 mg, 0.22 mmol), 2-amino-4-(tert-Butyl)benzoic acid (Int MP7a, 42 mg, 0.22 mmol) and diphenyl phosphite (0.14 mL, 0.71 mmol) in pyridine (1.5 mL) was heated at 70° C. for 2 h. N-(7-amino-4-chloro-1-(2,2-difluoroethyl)-1H-indazol-3-yl)-N-(4-methoxybenzyl)methanesulfonamide (0.11 g, 0.24 mmol) was added and the final solution was heated at 70° C. for 16 h. Mixture was then concentrated under reduced pressure and the residue was partitioned between water (10 mL) and EtOAc (50 mL). The separated organic layer was washed with water and brine, dried (Na$_2$SO$_4$), filtered and concentrated. The residue was purified by Biotage (5-50% EtOAc/hexane) to afford the title compound (75 mg) which was a mix of stereoisomers. LC/MS: m/z=885.3 [M+H]$^+$.

(S)—N-(7-(2-(1-amino-2-(3,5-difluorophenyl)ethyl)-7-(tert-Butyl)-4-oxoquinazolin-3(4H)-yl)-4-chloro-1-(2,2-difluoroethyl)-1H-indazol-3-yl)-N-(4-methoxybenzyl)methanesulfonamide, HCl (Int MP7e)

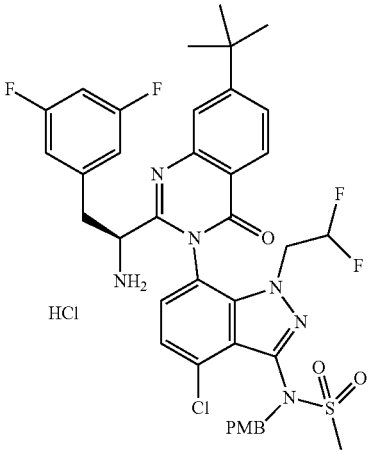

Mix of Int MP7e and three other stereoisomers

HCl (2 mL, 8.0 mmol, 4M in dioxane) and tert-Butyl (S)-(1-(7-(tert-Butyl)-3-(4-chloro-1-(2,2-difluoroethyl)-3-(N-(4-methoxybenzyl)methylsulfonamido)-1H-indazol-7-yl)-4-oxo-3,4-dihydroquinazolin-2-yl)-2-(3,5-difluorophenyl)ethyl)carbamate (Int MP7d, 74 mg, 0.08 mmol) was stirred at room temp for 1 h and then concentrated to give the title compound (68 mg) which was a mixture of stereoisomers. LC/MS: m/z=785.2 [M+H]+.

N—((S)-1-(7-(tert-Butyl)-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2c]pyrazol-1-yl)acetamide (Example 217)

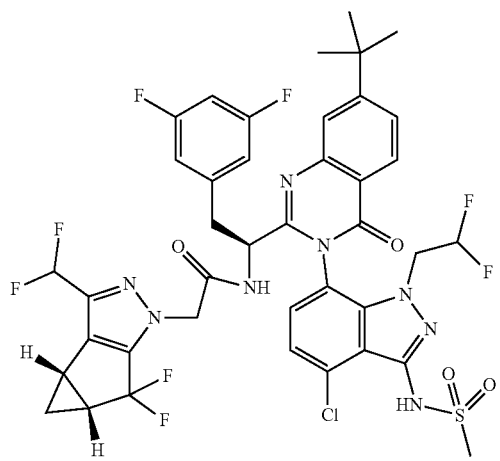

Mixture of Example 217 and three other stereoisomers

To a mixture of (S)—N-(7-(2-(1-amino-2-(3,5-difluorophenyl)ethyl)-7-(tert-Butyl)-4-oxoquinazolin-3(4H)-yl)-4-chloro-1-(2,2-difluoroethyl)-1H-indazol-3-yl)-N-(4-methoxybenzyl)methanesulfonamide, HCl (Int MP7e, 68 mg, 0.08 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (24 mg, 0.1 mmol) in THF (2 mL) was added DIEA (0.04 mL, 0.25 mmol) followed by HATU (35 mg, 0.1 mmol) and the resulting mixture was stirred at room temp for 2 h and then concentrated. The residue was taken up in DCM (0.5 mL) and triflic acid (0.05 mL) and TFA (1 mL) were added. The mixture was stirred at rt for 1 h, concentrated and purified by prep-HPLC with the following conditions to afford the title compound (Example 217, 49 mg) as a mixture of four stereoisomers, where one is dominant. Prep-HPLC: XBridge C18, 19×200 mm mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 41% B, 41-81% B over 25 minutes, then a 4-minute hold at 100% B; Flow Rate: 20 mL/min. Fractions containing the desired product were combined and dried. Detection: MS and UV (220 nm). LC-MS retention time=2.53 min; m/z=911.1 [M+H]+. (Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

tert-Butyl (S)-(1-(7-(tert-Butyl)-3-(4-chloro-1-(2,2-difluoroethyl)-3-(N-(4-methoxybenzyl)cyclopropanesulfonamido)-1H-indazol-7-yl)-4-oxo-3,4-dihydroquinazolin-2-yl)-2-(3,5-difluorophenyl)ethyl)carbamate (Int MP7f)

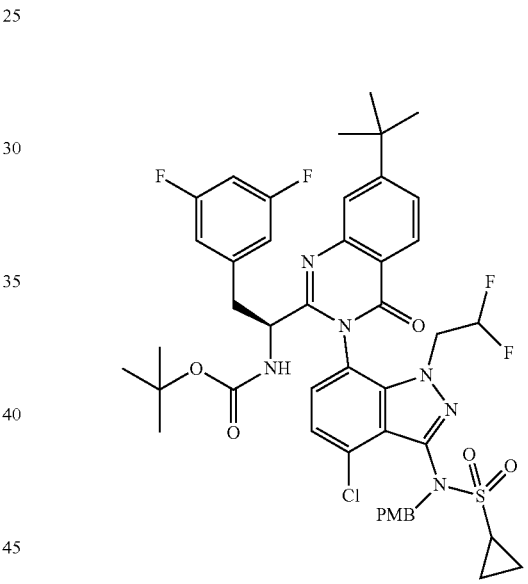

Mix of Int MP7f and three other stereoisomers

A mixture of (S)-2-((tert-butoxycarbonyl)amino)-3-(3,5-difluorophenyl)propanoic acid (65 mg, 0.22 mmol), 2-amino-4-(tert-Butyl)benzoic acid (Int MP7a, 42 mg, 0.22 mmol) and diphenyl phosphite (0.14 mL, 0.71 mmol) in pyridine (1.5 mL) was heated at 70° C. for 2 h. N-(7-amino-4-chloro-1-(2,2-difluoroethyl)-1H-indazol-3-yl)-N-(4-methoxybenzyl)cyclopropane sulfonamide (0.11 g, 0.24 mmol) was added and the final solution was heated at 70° C. for 16 h. Mixture was then concentrated under reduced pressure and the residue was partitioned between water (10 mL) and EtOAc (50 mL). The separated organic layer was washed with water and brine, dried (Na2SO4), filtered and concentrated. The residue was purified by Biotage (5-50% EtOAc/hexane) to afford the title compound (83 mg) which was a mix of stereoisomers. LC/MS: m/z=911.2 [M+H]+.

(S)—N-(7-(2-(1-amino-2-(3,5-difluorophenyl)ethyl)-7-(tert-Butyl)-4-oxoquinazolin-3(4H)-yl)-4-chloro-1-(2,2-difluoroethyl)-1H-indazol-3-yl)-N-(4-methoxybenzyl)cyclopropanesulfonamide, HCl (Int MP7g)

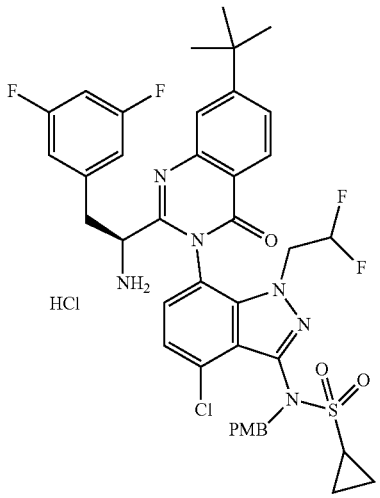

Mix of Int MP7g and three
other stereoisomers

HCl (2 mL, 8.00 mmol, 4M in dioxane) and tert-butyl (S)-(1-(7-(tert-butyl)-3-(4-chloro-1-(2,2-difluoroethyl)-3-(N-(4-methoxybenzyl)cyclopropanesulfonamido)-1H-indazol-7-yl)-4-oxo-3,4-dihydroquinazolin-2-yl)-2-(3,5-difluorophenyl)ethyl)carbamate (Int MP7f, 80 mg, 0.1 mmol) was stirred at room temp for 1 h and then concentrated to give the title compound (74 mg) which was a mixture of stereoisomers. LC/MS: m/z=811.2 [M+H]$^+$.

N—((S)-1-(7-(tert-Butyl)-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide
(Example 218)

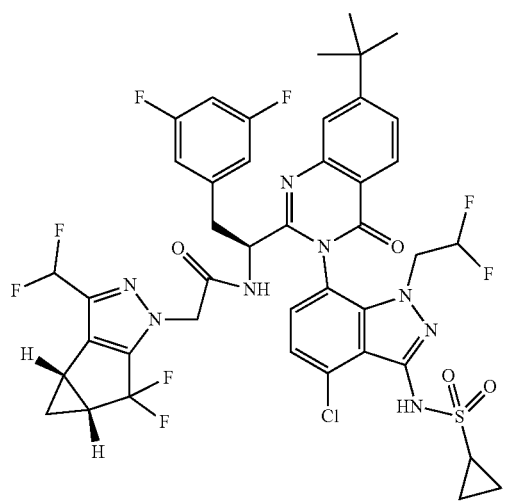

Mixture of Example 218 and
three other stereoisomers

To a mixture of (S)—N-(7-(2-(1-amino-2-(3,5-difluorophenyl)ethyl)-7-(tert-Butyl)-4-oxoquinazolin-3(4H)-yl)-4-chloro-1-(2,2-difluoroethyl)-1H-indazol-3-yl)-N-(4-methoxybenzyl)cyclopropanesulfonamide, HCl (Int MP7g, 74 mg, 0.1 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (25 mg, 0.1 mmol) in THF (2 mL) was added DIEA (0.046 mL, 0.262 mmol), followed by HATU (37 mg, 0.1 mmol) and the resulting mixture was stirred at room temp for 2 h and then concentrated. The residue was taken up in DCM (0.5 mL) and triflic acid (0.05 mL) and TFA (1 mL) were added. The mixture was stirred at rt for 1 h, concentrated and purified by prep-HPLC with the following conditions to afford the title compound (Example 218, 55 mg) as a mixture of four stereoisomers, where one is dominant. Prep-HPLC: XBridge C18, 19×200 mm mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 44% B, 44-84% B over 25 minutes, then a 4-minute hold at 100% B; Flow Rate: 20 mL/min. Fractions containing the desired product were combined and dried. Detection: MS and UV (220 nm). LC-MS retention time=2.49 min; m/z=937.1 [M+H]$^+$. (Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm)

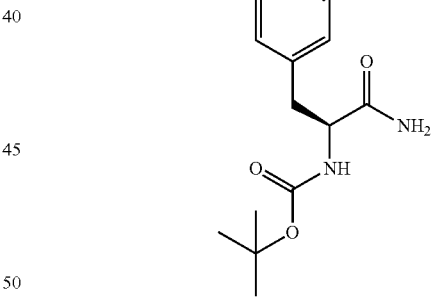

To a solution of (S)-2-((tert-butoxycarbonyl)amino)-3-(3,5-difluorophenyl)propanoic acid (5.0 g, 16.6 mmol) in CH$_2$Cl$_2$ (75 mL) were added HOBT (2.80 g, 18.25 mmol) and 1-(3-dimethylaminopropy)-3-ethylcarbodiimide hydrochloride (3.50 g, 18.25 mmol). Mixture was then cooled to 0° C. and added dropwise 30% ammonium hydroxide (4.31 mL, 33.2 mmol) and the mixture was stirred at room temp for 2 h. Water was then added and the precipitate formed were collected by filtration and washed with water to afford the title compound (3.1 g) as a white solid. $^1$H NMR (400 MHz, DMSO-d$_6$) δ 7.39 (br s, 2H), 7.14-6.95 (m, 3H), 6.91 (br d, J=9.0 Hz, 1H), 4.14-4.05 (m, 1H), 2.98 (br dd, J=13.6, 3.8 Hz, 1H), 2.77-2.66 (m, 1H), 1.29 (s, 9H). LC/MS: m/z=323.0 [M+Na].

Ethyl (S)-2-((tert-butoxycarbonyl)amino)-3-(3,5-difluorophenyl)propanimidate (Int MP10b)

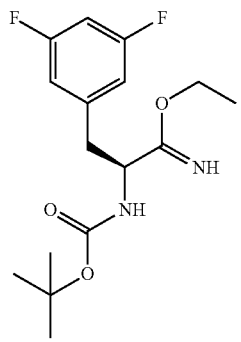 [SMILES: CCOC(=N)[C@H](Cc1cc(F)cc(F)c1)NC(=O)OC(C)(C)C]

To a suspension of tert-butyl (S)-(1-amino-3-(3,5-difluorophenyl)-1-oxopropan-2-yl)carbamate (Int MP10a, 3.4 g, 11.3 mmol) in $CH_2Cl_2$ (100 mL) was added triethyloxonium tetrafluoroborate (2.6 g, 13.6 mmol) and the resulting mixture was stirred at room temp for 24 h (Suspension became clear overnight). Sat. $K_2CO_3$ solution was then added and the mixture was extracted with dichloromethane. The organic layer was dried ($Na_2SO_4$), filtered and concentrated to afford the title compound (3.4 g) as white solid (used as is). $^1$H NMR (400 MHz, DMSO-$d_6$) δ 7.74 (s, 1H), 7.33 (br d, J=9.0 Hz, 1H), 7.12-7.03 (m, 1H), 6.95 (br d, J=7.3 Hz, 2H), 4.24-4.15 (m, 1H), 4.04 (q, J=6.9 Hz, 2H), 2.98 (br dd, J=13.7, 4.6 Hz, 1H), 2.72 (br dd, J=13.4, 10.7 Hz, 1H), 1.30 (s, 9H), 1.17 (t, J=7.0 Hz, 3H).

tert-Butyl (S)-(1-(1-(4-cyclopropylphenyl)-4-methyl-6-oxo-1,6-dihydropyrimidin-2-yl)-2-(3,5-difluorophenyl)ethyl)carbamate (Int MP10c)

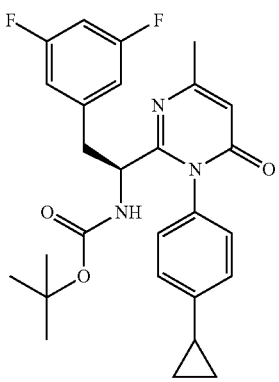 [SMILES: Cc1cc(=O)n(-c2ccc(C3CC3)cc2)c([C@H](Cc2cc(F)cc(F)c2)NC(=O)OC(C)(C)C)n1]

To a solution of ethyl (S)-2-((tert-butoxycarbonyl)amino)-3-(3,5-difluorophenyl)propanimidate (Int MP10b, 500 mg, 1.52 mmol) in toluene (8 mL) was added 4-cyclopropylaniline (203 mg, 1.52 mmol) and the resulting mixture was heated at 100° C. for 16 h. Mixture was then cooled to room temp, 2,2,6-trimethyl-4H-1,3-dioxin-4-one (649 mg, 4.57 mmol) was added and the mixture was heated at 100° C. for another 16 h. Mixture was then cooled, concentrated and purified by Biotage (5-70% EtOAc/hexane) to afford the title compound (30 mg). $^1$H NMR (400 MHz, $CDCl_3$) δ 7.35-7.30 (m, 1H), 7.25-7.18 (m, 1H), 7.15-7.04 (m, 1H), 6.81 (br d, J=7.8 Hz, 1H), 6.74-6.62 (m, 2H), 6.27 (br d, J=6.3 Hz, 2H), 5.93-5.74 (m, 1H), 4.76-4.66 (m, 1H), 2.95 (dd, J=13.6, 5.0 Hz, 1H), 2.76 (br dd, J=13.3, 8.8 Hz, 1H), 2.40 (s, 3H), 2.05-1.97 (m, 1H), 1.38 (s, 9H), 1.12-1.06 (m, 2H), 0.85-0.75 (m, 2H). LC/MS: m/z=482.2 $[M+H]^+$.

(S)-2-(1-amino-2-(3,5-difluorophenyl)ethyl)-3-(4-cyclopropylphenyl)-6-methylpyrimidin-4(3H)-one, HCl (Int MP10d)

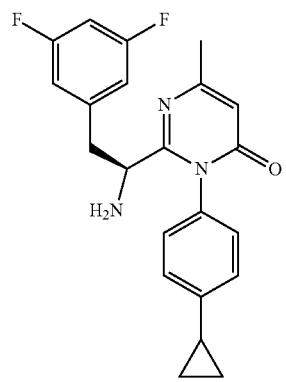 [SMILES: Cc1cc(=O)n(-c2ccc(C3CC3)cc2)c([C@@H](N)Cc2cc(F)cc(F)c2)n1]

HCl (1.15 mL, 4.6 mmol, 4M indioxane) and tert-butyl (S)-(1-(1-(4-cyclopropylphenyl)-4-methyl-6-oxo-1,6-dihydropyrimidin-2-yl)-2-(3,5-difluorophenyl)ethyl)carbamate (Int MP10c, 22 mg, 0.05 mmol) was stirred at room temp for 2 h and concentrated to afford the title compound (20 mg). LC/MS: m/z=381.9 $[M+H]^+$.

Biological Methods

HIV cell culture assay—MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 μg/ml penicillin G and up to 100 units/mL streptomycin. The 293T cells were propagated in DMEM media supplemented with 10% heat inactivated FBS, 100 μg/mL penicillin G and 100 μg/mL streptomycin. A recombinant $NL_{4-3}$ proviral clone, in which a section of the nef gene was replaced with the Renilla luciferase gene, was used to make the reference virus used in these studies. The recombinant virus was prepared through transfection of the recombinant $NL_{4-3}$ proviral clone into 293T cells using Transit-293 Transfection Reagent from Mirus Bio LLC (Madison, Wis.). Supernatent was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, Wis.). Antiviral activities of compounds toward the recombinant virus were quantified by measuring luciferase activity in MT-2 cells infected for 4-5 days with the recombinant virus in the presence of serial dilutions of the compound.

The 50% effective concentration (ECs) was calculated by using the exponential form of the median effect equation where (Fa)=1/[1+(ED$_{50}$/drug conc.)$^m$] (Johnson Va., Byington RT. Infectivity Assay. In Techniques in HIV Research. ed. Aldovini A, Walker BD. 71-76. New York: Stockton Press. 1990).

Compound cytotoxicity and the corresponding CC$_{50}$ values were determined using the same protocol as described in the antiviral assay except that uninfected cells were used. Cytotoxicity was assessed on day 4 in uninfected MT2 cells by using a XTT (2,3-bis[2-Methoxy-4-nitro-5-sulfophenyl]-2H-tetrazolium-5-carboxyanilide inner salt)-based colorimetric assay (Sigma-Aldrich, St Louis, Mo.). Biological data for select compounds of the invention are contained in Table 1 and Table 1a

TABLE 1

| Example | Structure | EC$_{50}$ μM | CC$_{50}$ μM |
| --- | --- | --- | --- |
| Example 1.1 | 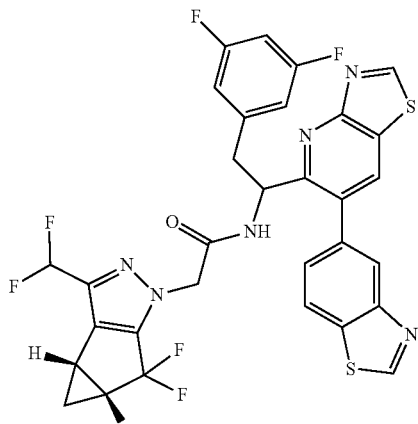 1st eluting diastereomer homochiral | 0.0031 | >100.0 |
| Example 1.2 | 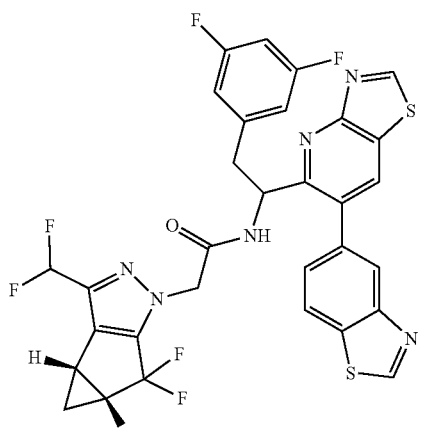 2nd eluting diastereomer homochiral | 2.85 | >33.3 |

TABLE 1-continued
| Example | Structure | EC$_{50}$ μM | CC$_{50}$ μM |
|---|---|---|---|
| Example 1.3 | 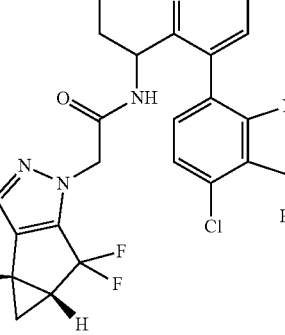<br>1st eluting atropisomer<br>diastereomer 1<br>homochiral | 0.0003 | >10.0 |
| Example 1.4 | 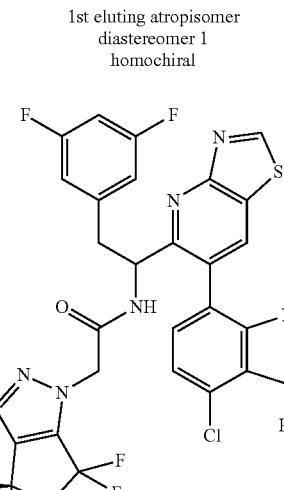<br>2nd eluting atropisomer<br>diastereomer 1<br>homochiral | 0.0001 | >10.0 |
| Example 1.5 | 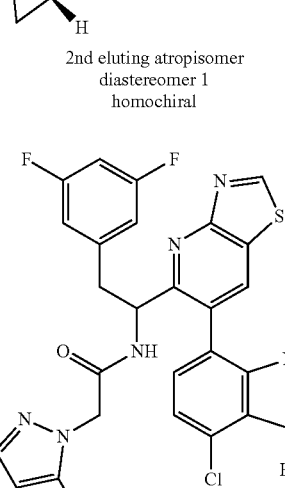<br>1st eluting atropisomer<br>diastereomer 2<br>homochiral | 1.15 | >10.0 |

TABLE 1-continued
| Example | Structure | EC$_{50}$ μM | CC$_{50}$ μM |
| --- | --- | --- | --- |
| Example 1.6 | 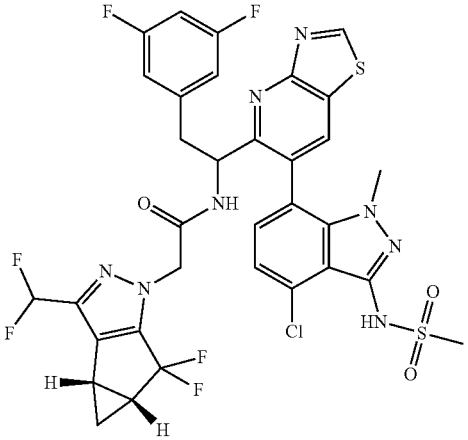<br>2nd eluting atropisomer<br>diastereomer 2<br>homochiral | 1.78 | >10.0 |
| Example 1.7 | 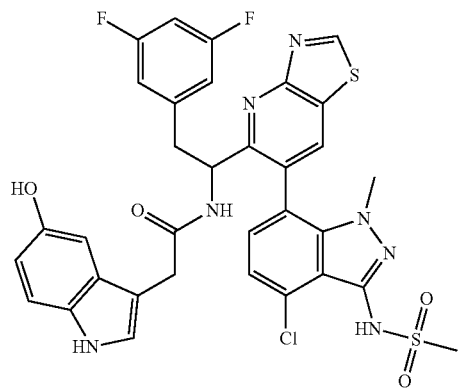<br>homochiral | 0.011 | >100.0 |
| Example 2.1 | 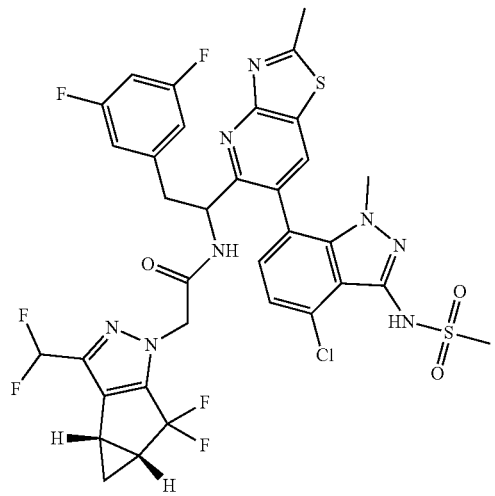<br>diastereomer 1<br>mix of atropisomers | 0.0001 | >10.0 |

TABLE 1-continued
| Example | Structure | EC$_{50}$ μM | CC$_{50}$ μM |
|---|---|---|---|
| Example 2.2 | 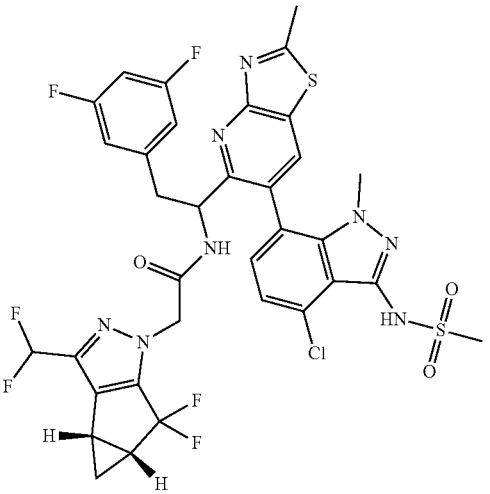<br>diastereomer 2<br>mix of atropisomers | 1.15 | >10.0 |
| Example 2.3 | 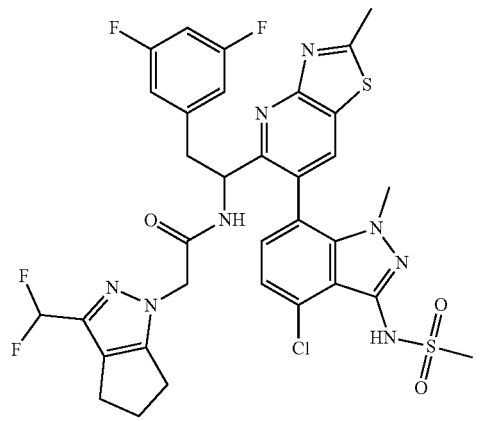<br>enantiomer 1<br>mix of atropisomers | 0.0001 | >10.0 |
| Example 2.4 | 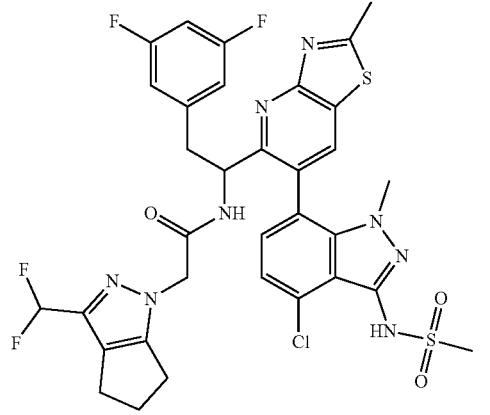<br>enantiomer 2<br>mix of atropisomers | 0.69 | >10.0 |

TABLE 1-continued
| Example | Structure | EC$_{50}$ μM | CC$_{50}$ μM |
| --- | --- | --- | --- |
| Example 3.1 | 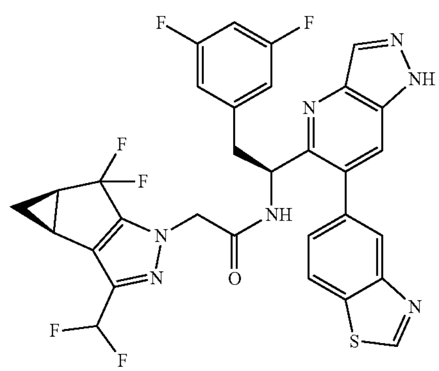 | 0.022 | 42.1 |
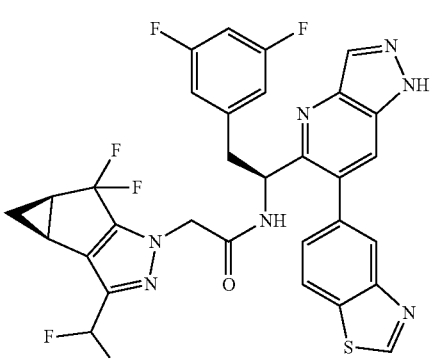
1st eluting diastereomer
homochiral
| Example 3.2 | | 0.96 | 12.7 |
| --- | --- | --- | --- |
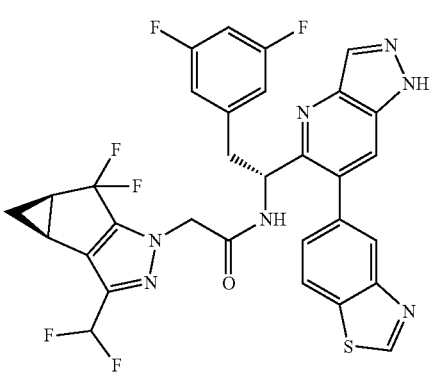
2nd eluting diastereomer
homochiral
| Example 3.3 | | 0.0057 | 42.4 |
| --- | --- | --- | --- |
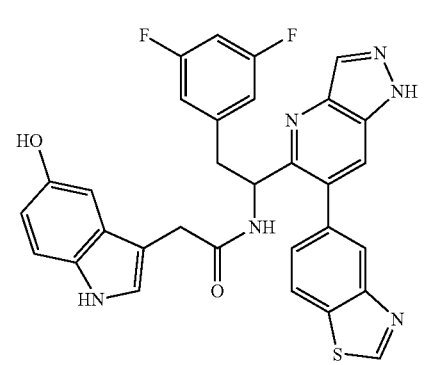
1st eluting enatiomer
homochiral TABLE 1-continued

| Example | Structure | EC$_{50}$ µM | CC$_{50}$ µM |
| --- | --- | --- | --- |
| Example 3.4 | 2nd eluting enatiomer homochiral | 0.47 | 83.9 |
| Example 3.5 | 1st eluting enatiomer homochiral | 0.020 | 32.1 |
| Example 3.6 | 2nd eluting enatiomer homochiral | 0.23 | 32.6 |

TABLE 1-continued
| Example | Structure | EC$_{50}$ μM | CC$_{50}$ μM |
|---|---|---|---|
| Example 3.7 | 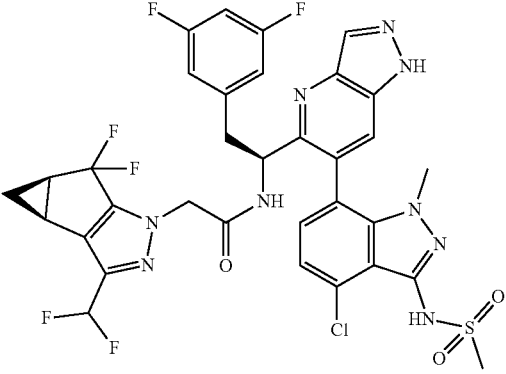<br>1st diastereomer<br>mix of atropisomers | 0.0012 | 33.9 |
| Example 3.8 | 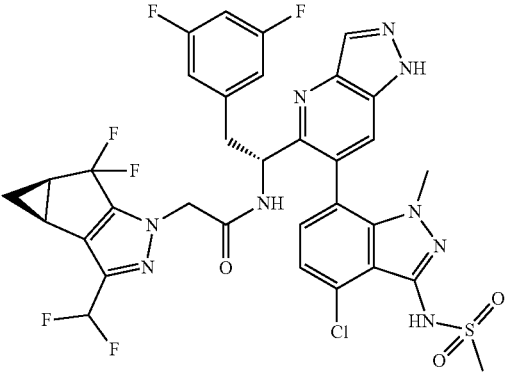<br>2nd diastereomer<br>mix of atropisomers | 0.021 | 10.2 |
| Example 3.9 | 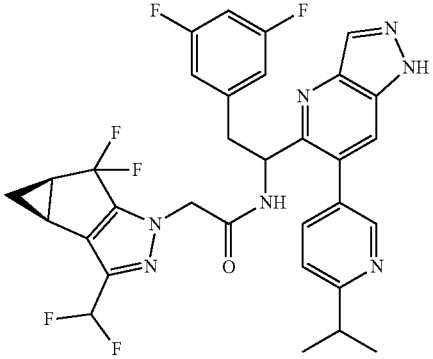<br>single enantiomer<br>homochiral | 0.0099 | 9.6 |

TABLE 1-continued
| Example | Structure | EC$_{50}$ µM | CC$_{50}$ µM |
| --- | --- | --- | --- |
| Example 3.10 | 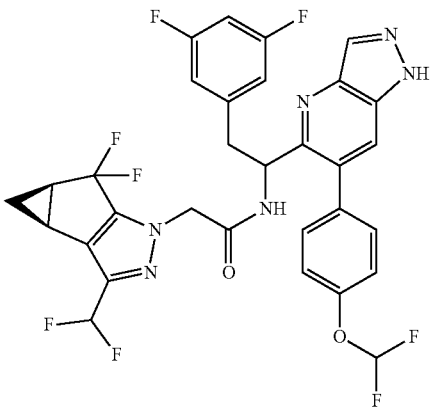<br>single enantiomer<br>homochiral | 0.32 | 6.8 |
| Example 3.11 | 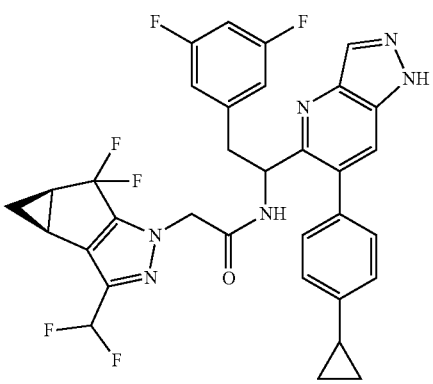<br>single enantiomer<br>homochiral | 0.67 | 4.2 |
| Example 4.1 | 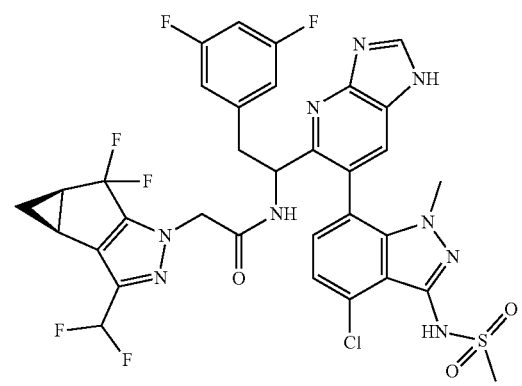<br>Diastereomer 1<br>mix of atropisomers | 0.23 | >10.0 |

TABLE 1-continued
| Example | Structure | EC$_{50}$ µM | CC$_{50}$ µM |
|---|---|---|---|
| Example 4.2 | 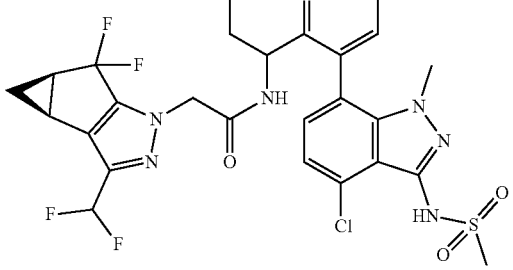<br>Diastereomer 2<br>Mix of atropisomers | 0.0010 | >10.0 |
| Example 5.1 | 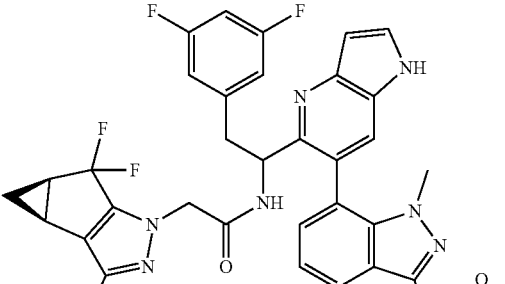<br>Diastereomer 1<br>Atropisomer 1<br>homochiral | 0.22 | >10.0 |
| Example 5.2 | 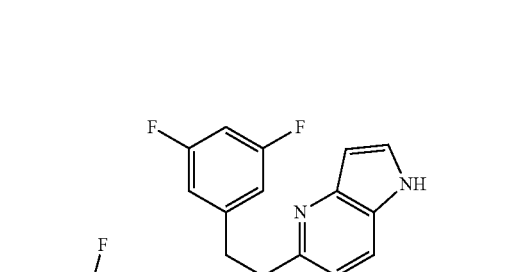<br>Diastereomer 1<br>Atropisomer2<br>homochiral | 0.40 | >10.0 |

TABLE 1-continued

| Example | Structure | EC$_{50}$ µM | CC$_{50}$ µM |
|---|---|---|---|
| Example 5.3 | Diastereomer 2<br>Atropisomer 1<br>homochiral | 0.0002 | >10.0 |
| Example 5.4 | Diastereomer 2<br>Atropisomer2<br>homochiral | 0.0002 | >10.0 |
| Example 6.1 | Diastereomer 1<br>Mix of atropisomers | 1.02 | >10.0 |

TABLE 1-continued

| Example | Structure | EC$_{50}$ μM | CC$_{50}$ μM |
| --- | --- | --- | --- |
| Example 6.2 | Diastereomer 2<br>Mix of atropisomers | 0.0043 | >10.0 |
| Example 7.1 | Homochiral | 0.14 | 16.2 |
| Example 7.2 | homochiral | 0.0090 | 17.5 |

TABLE 1-continued
| Example | Structure | EC$_{50}$ μM | CC$_{50}$ μM |
| --- | --- | --- | --- |
| Example 7.3 | 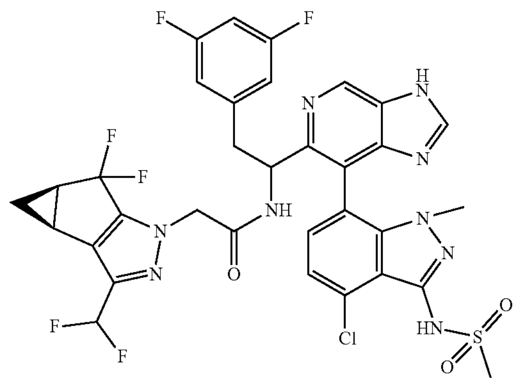 | 10.00 | >10.0 |
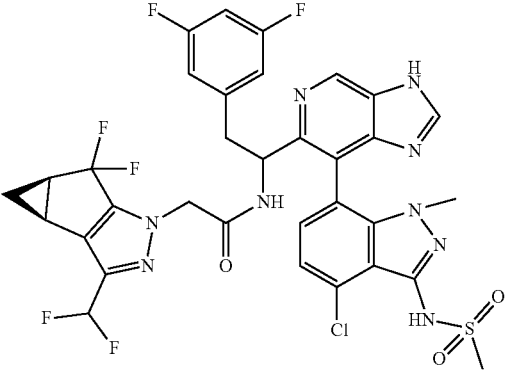
homochiral isomer 1
| Example 7.4 | | 0.30 | >10.0 |
| --- | --- | --- | --- |
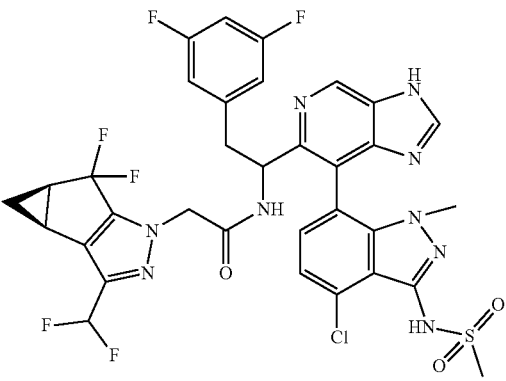
homochiral isomer 2
| Example 7.5 | | 1.32 | >10.0 |
| --- | --- | --- | --- |
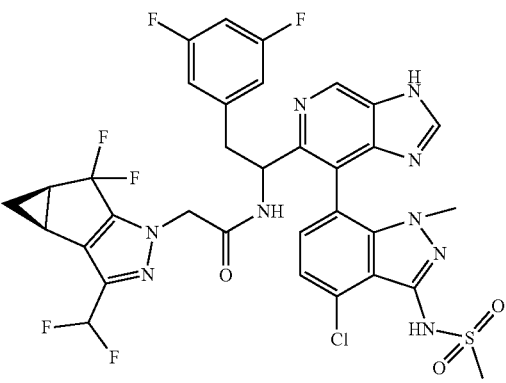
homochiral isomer 3

TABLE 1-continued
| Example | Structure | EC$_{50}$ μM | CC$_{50}$ μM |
|---|---|---|---|
| Example 7.6 | 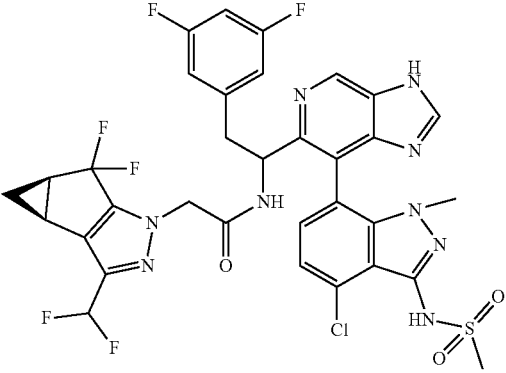<br>homochiral isomer 4 | 0.0081 | >10.0 |
| Example 8.1 | 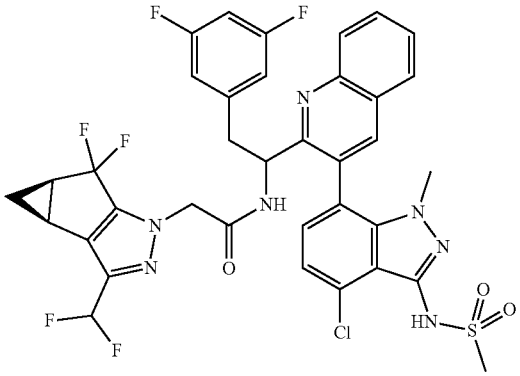<br>diasteremer 1<br>mix of atropisomers | 0.0002 | >10.0 |
| Example 8.2 | 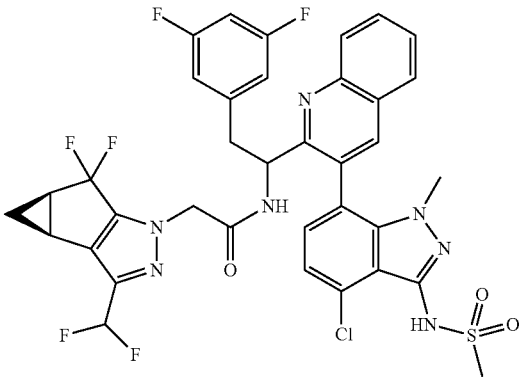<br>diastereomer 2<br>mix of atropisomers | 0.18 | >10.0 |

TABLE 1-continued

| Example | Structure | EC$_{50}$ µM | CC$_{50}$ µM |
| --- | --- | --- | --- |
| Example 9.1 | homochiral | 0.0061 | 8.1 |
| Example 9.2 | homochiral | 0.0047 | >10.0 |
| Int 6a | racemic | 0.11 | 29.2 |
| Example 10.1 | Racemic | 0.14 | >10.0 |

TABLE 1-continued
| Example | Structure | EC$_{50}$ μM | CC$_{50}$ μM |
| --- | --- | --- | --- |
| Example 10.2 | 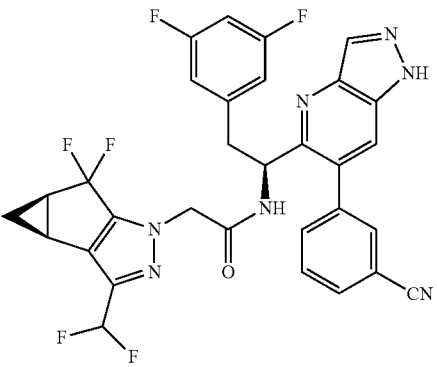
homochiral | 0.46 | 9.7 |
| Example 10.3 | 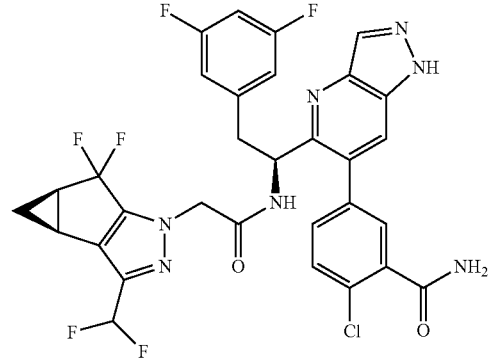
homochiral | 0.084 | >10.0 |
| Example 10.4 | 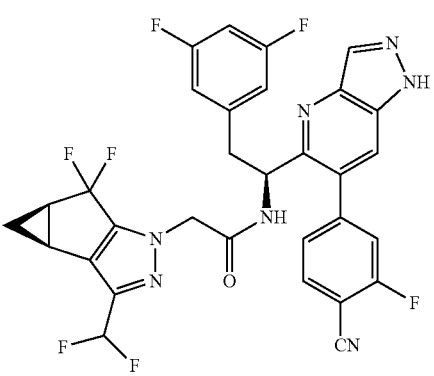
homochiral | 1.15 | 8.24 |

TABLE 1-continued
| Example | Structure | EC$_{50}$ μM | CC$_{50}$ μM |
| --- | --- | --- | --- |
| Example 10.5 | 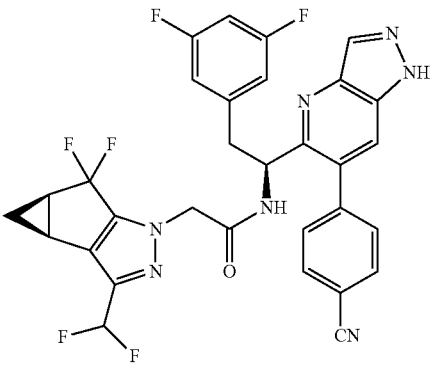<br>homochiral | 0.30 | 9.3456 |
| Example 10.6 | 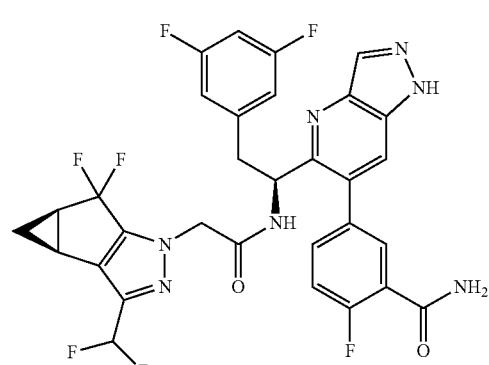<br>homochiral | 0.016 | >10.0 |
| Example 10.7 | 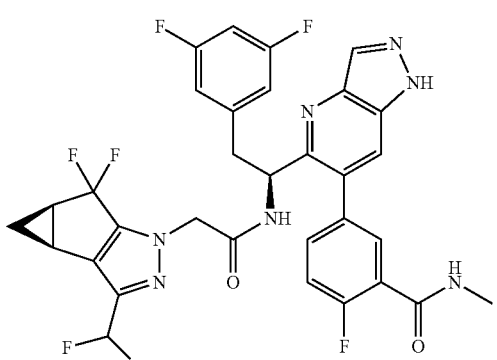<br>homochiral | 0.051 | >10.0 |

TABLE 1-continued
| Example | Structure | EC$_{50}$ µM | CC$_{50}$ µM |
|---|---|---|---|
| Example 10.8 | 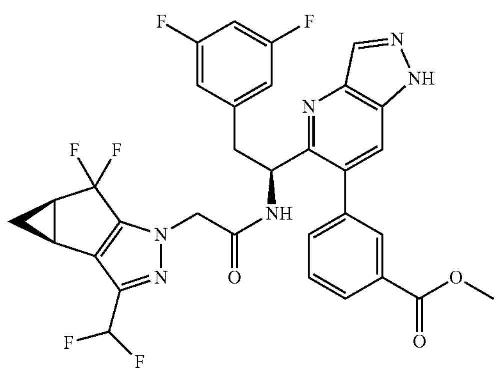 | 1.20 | >10.0 |
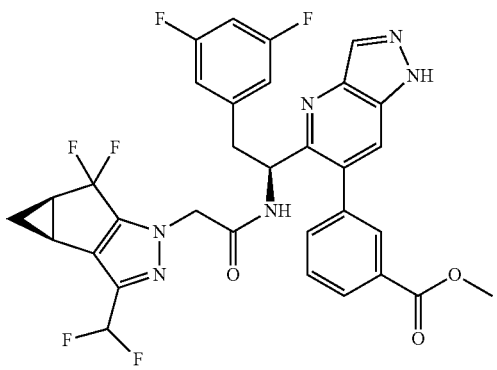
homochiral
| | | | |
|---|---|---|---|
| Example 10.9 | | 1.08 | 8.95 |
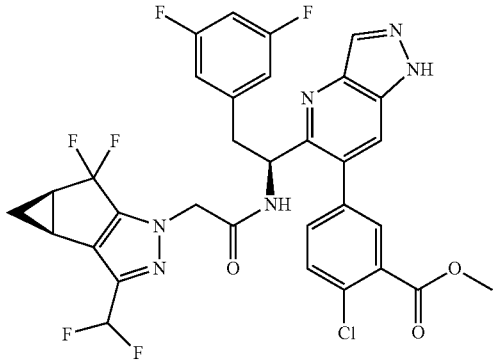
homochiral
| | | | |
|---|---|---|---|
| Example 10.10 | | 0.14 | >10.0 |
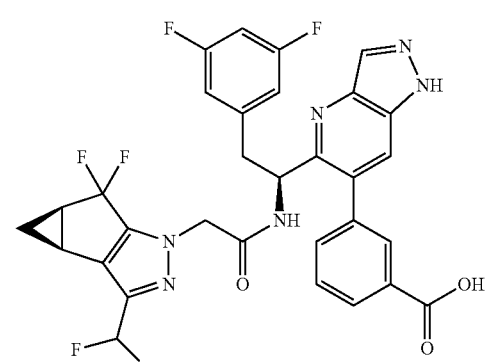
homochiral TABLE 1-continued

| Example | Structure | EC$_{50}$ μM | CC$_{50}$ μM |
| --- | --- | --- | --- |
| Example 10.11 | homochiral | 0.81 | >10.0 |
| Example 10.12 | homochiral | 0.095 | >10.0 |
| Example 10.13 | homochiral | 0.012 | >10.0 |
| Example 10.14 | homochiral | 0.0025 | >10.0 |

TABLE 1-continued
| Example | Structure | EC$_{50}$ μM | CC$_{50}$ μM |
| --- | --- | --- | --- |
| Example 10.15 | 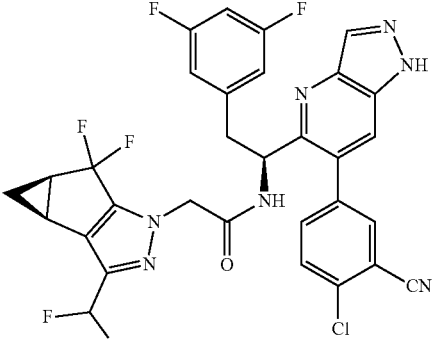<br>homochiral | 1.17 | 5.5 |
| Example 10.16 | 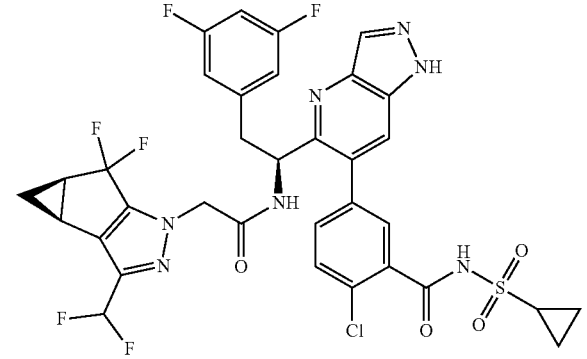<br>homochiral | 0.34 | >10.0 |
| Example 10.17 | 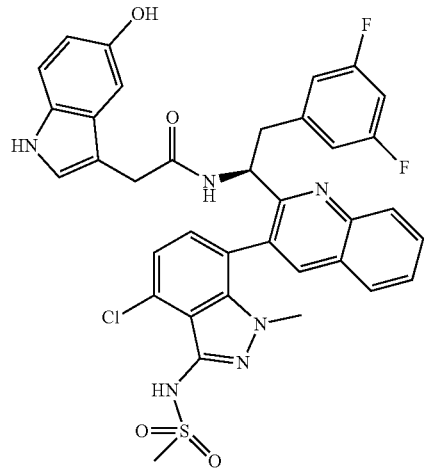<br>homochiral | 0.0024 | >10.0 |

TABLE 1-continued

| Example | Structure | EC$_{50}$ μM | CC$_{50}$ μM |
|---|---|---|---|
| Example 10.18 | homochiral | 0.67 | >10.0 |
| Example 10.19 | homochiral | 0.22 | >10.0 |
| Example 10.20 | homochiral | 0.29 | >10.0 |
| Example 10.21 | homochiral | 0.24 | >10.0 |

TABLE 1-continued
| Example | Structure | EC$_{50}$ μM | CC$_{50}$ μM |
| --- | --- | --- | --- |
| Example 10.22 | 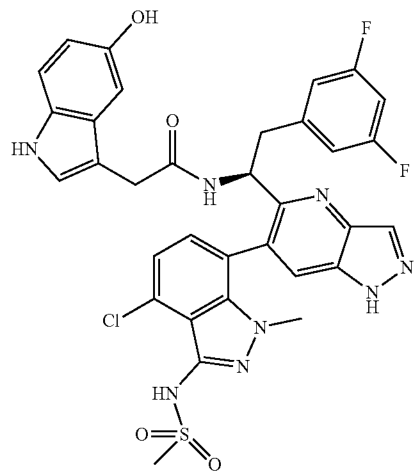 | 0.022 | >10.0 |
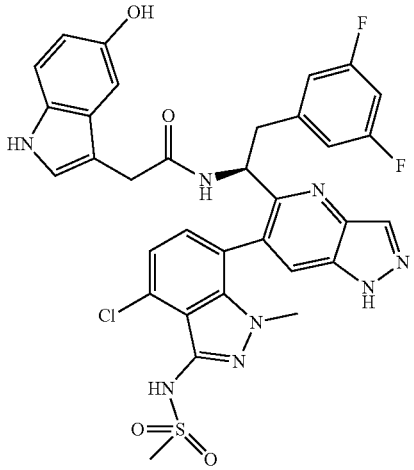
homochiral
| | | | |
| --- | --- | --- | --- |
| Example 10.23 | | 0.0027 | >10.0 |
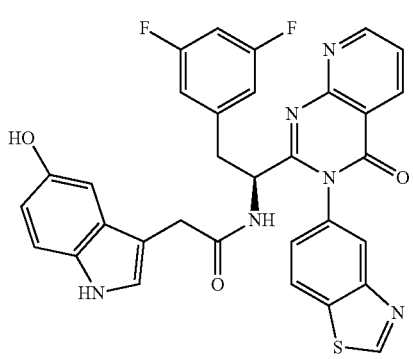
homochiral
| | | | |
| --- | --- | --- | --- |
| Example 10.24 | | 0.0017 | >10.0 |
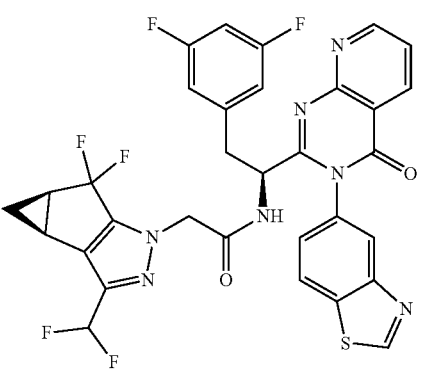
homochiral TABLE 1-continued

| Example | Structure | EC$_{50}$ μM | CC$_{50}$ μM |
| --- | --- | --- | --- |
| Example 10.25 | homochiral | 0.58 | >10.0 |
| Example 10.26 | homochiral | 0.93 | >10.0 |
| Example 10.27 | homochiral | 0.82 | >10.0 |
| Example 10.28 | homochiral | 0.51 | >10.0 |

TABLE 1-continued

| Example | Structure | EC$_{50}$ µM | CC$_{50}$ µM |
|---|---|---|---|
| Example 10.29 | homochiral | 0.61 | >10.0 |
| Example 10.30 | homochiral | 0.008 | >10.0 |
| Example 10.31 | homochiral | 0.018 | >10.0 |

TABLE 1-continued
| Example | Structure | EC$_{50}$ µM | CC$_{50}$ µM |
|---|---|---|---|
| Example 10.32 | 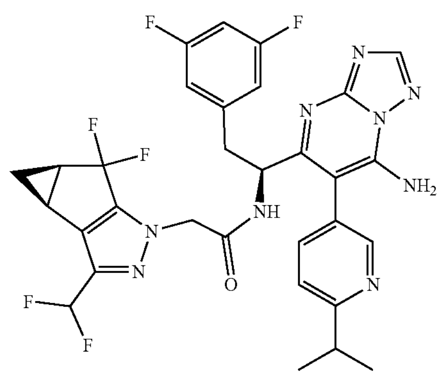 | 0.054 | >10.0 |
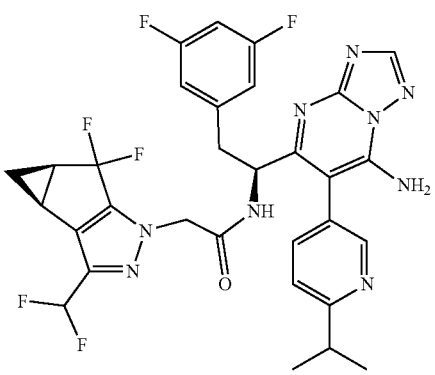
homochiral
| | | | |
|---|---|---|---|
| Example 10.33 | | 0.049 | >10.0 |
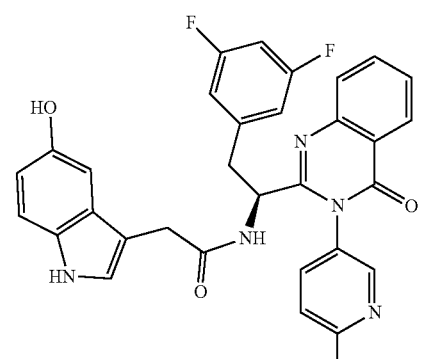
homochiral
| | | | |
|---|---|---|---|
| Example 10.34 | | 0.015 | 7.9 |
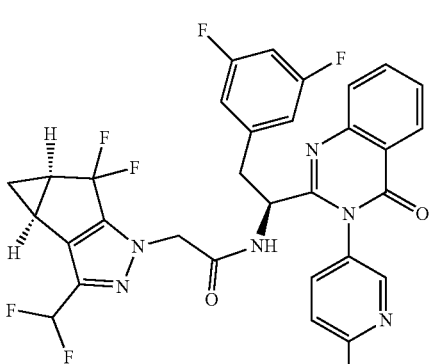
homochiral TABLE 1-continued
| Example | Structure | EC$_{50}$ µM | CC$_{50}$ µM |
| --- | --- | --- | --- |
| Example 10.35 | 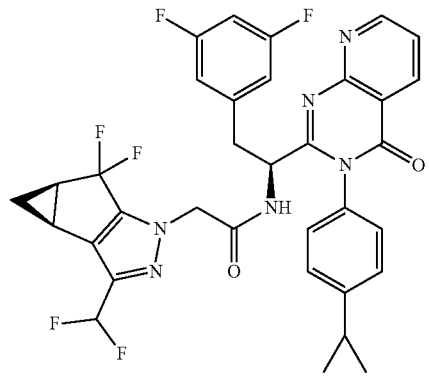 homochiral | 0.0017 | 1.9 |
| Example 10.36 | 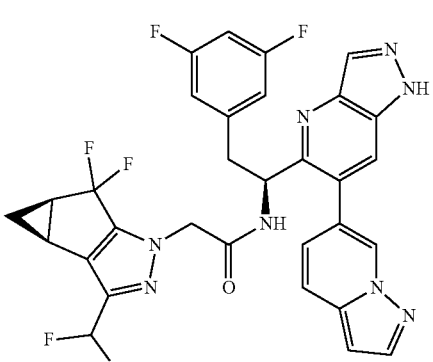 homochiral | 0.080 | >10.0 |
| Example 10.37 | 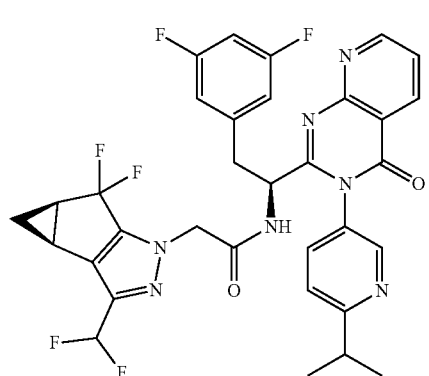 homochiral | 0.0048 | 6.9 |

TABLE 1-continued
| Example | Structure | EC$_{50}$ μM | CC$_{50}$ μM |
| --- | --- | --- | --- |
| Example 10.38 | 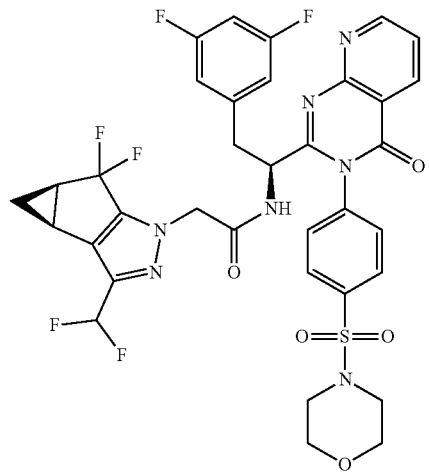    homochiral | 0.000204 | >10.0 |
| Example 10.39 | 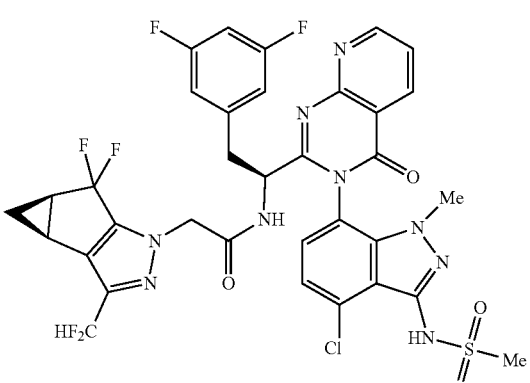    Homochiral atropoisomer 1 | 0.00698 | >10 |
| Example 10.40 | 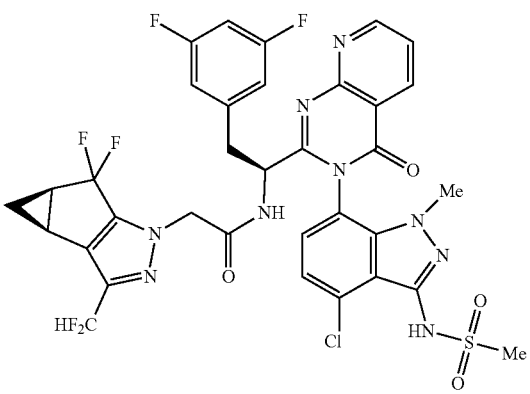    Homochiral atropoisomer 2 | 0.0000189 | >10 |

TABLE 1-continued
| Example | Structure | EC$_{50}$ μM | CC$_{50}$ μM |
| --- | --- | --- | --- |
| Example 11.1 | 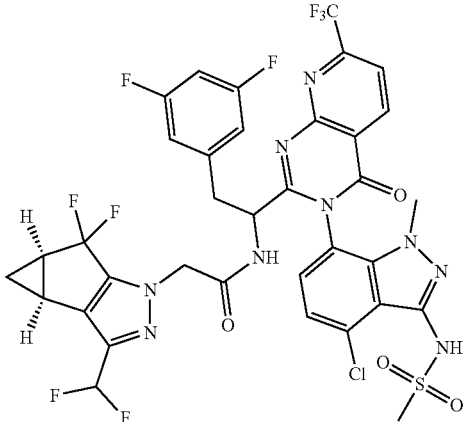<br>Mix of two stereoisomers | 0.52 | >10.0 |
| Example 11.2 | 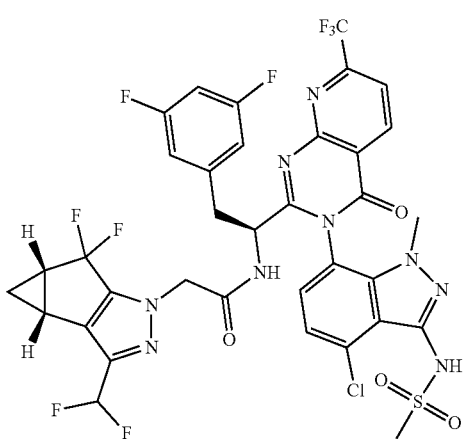<br>Single stereoisomer | 0.051 | >10.0 |
| Example 12.1 | 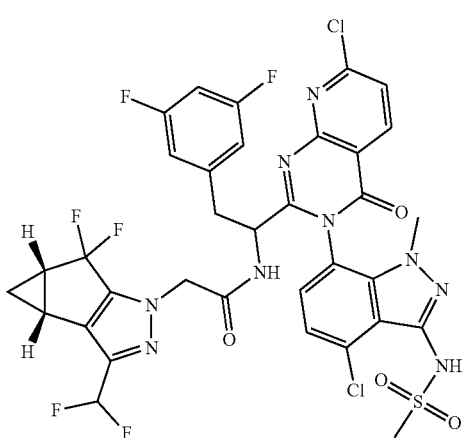<br>mixture of two steroisomers | 4.31 | >10.0 |

TABLE 1-continued
| Example | Structure | EC$_{50}$ µM | CC$_{50}$ µM |
|---|---|---|---|
| Example 12.2 | 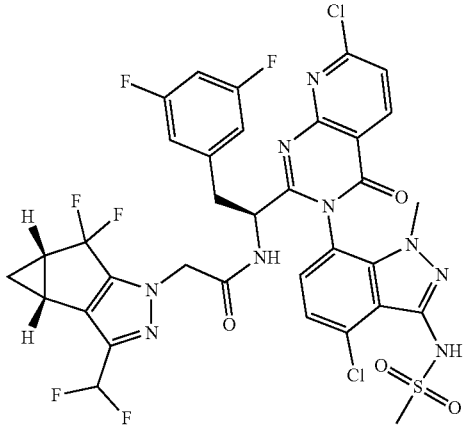<br>single stereoisomer | 0.042 | >3.3 |
| Example 13.1 | 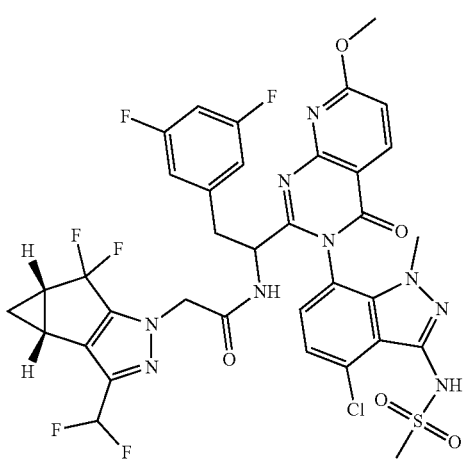<br>Mixture of two stereoisomers | 14.3 | >10.0 |
| Example 13.2 | 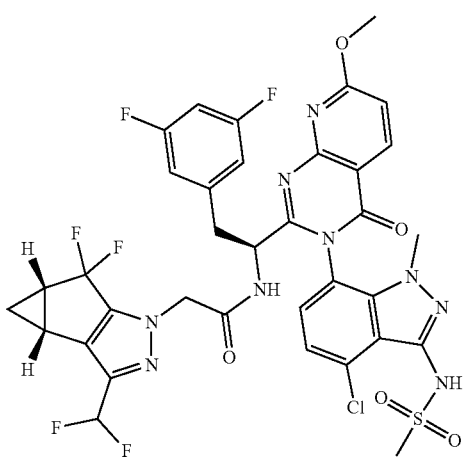<br>Single stereoisomer | 0.018 | >10.0 |

TABLE 1-continued
| Example | Structure | EC$_{50}$ μM | CC$_{50}$ μM |
| --- | --- | --- | --- |
| Example 14.1 | 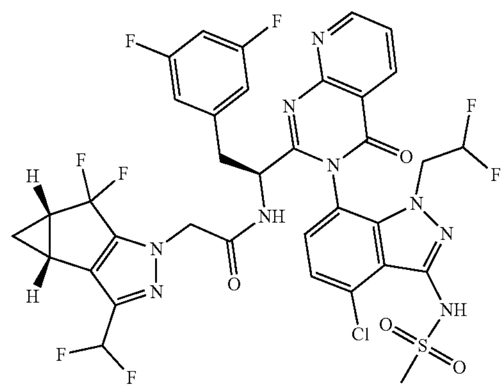 | 0.049 | >10.0 |
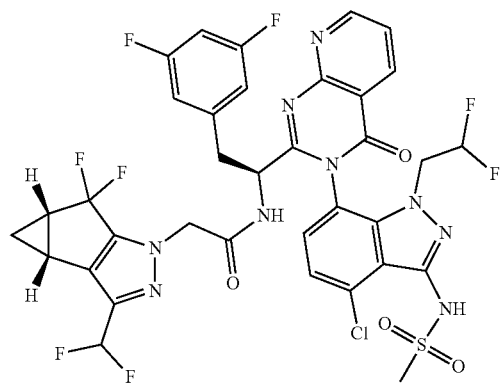
First eluting stereoisomer
| | | | |
| --- | --- | --- | --- |
| Example 15 | | 0.32 | >1.0 |
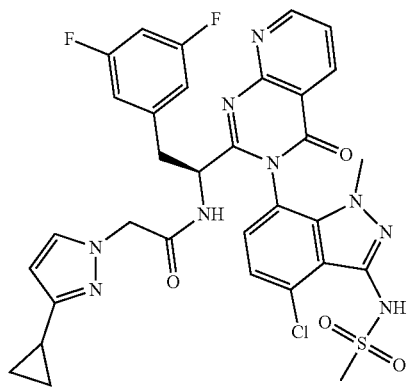 [SMILES: Cn1nc(NS(C)(=O)=O)c2c(Cl)ccc(-n3c([C@H](Cc4cc(F)cc(F)c4)NC(=O)Cn4ccc(C5CC5)n4)nc4ncccc4c3=O)c21]
| | | | |
| --- | --- | --- | --- |
| Example 16 | | 0.049 | >10.0 |
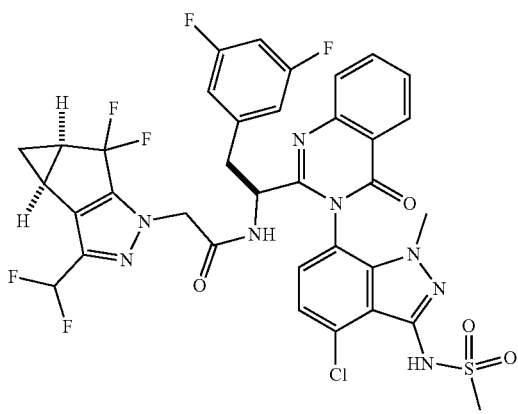 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4ccccc4c3=O)c21]

TABLE 1-continued
| Example | Structure | EC$_{50}$ μM | CC$_{50}$ μM |
| --- | --- | --- | --- |
| Example 17 | 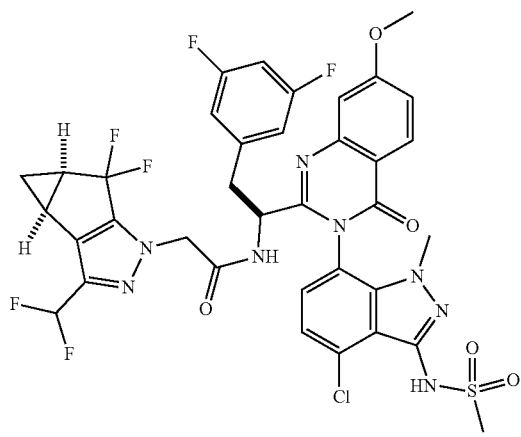 [SMILES: COc1ccc2c(=O)n(-c3ccc(Cl)c4c(NS(C)(=O)=O)nn(C)c34)c([C@H](Cc3cc(F)cc(F)c3)NC(=O)Cn3nc(C(F)F)c4c3C(F)(F)[C@@H]3C[C@H]43)nc2c1] | 0.061 | >10.0 |
| Example 18 | 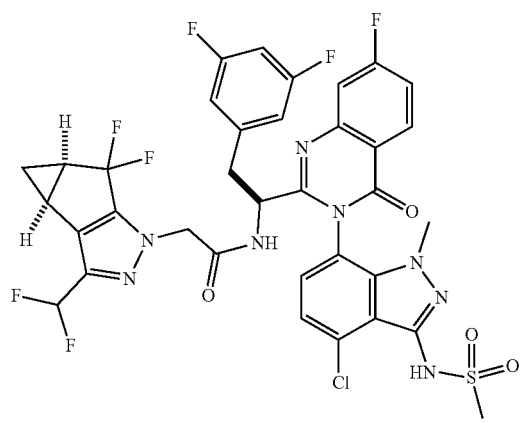 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(F)ccc4c3=O)c21] | 0.036 | >10.0 |
| Example 19 | 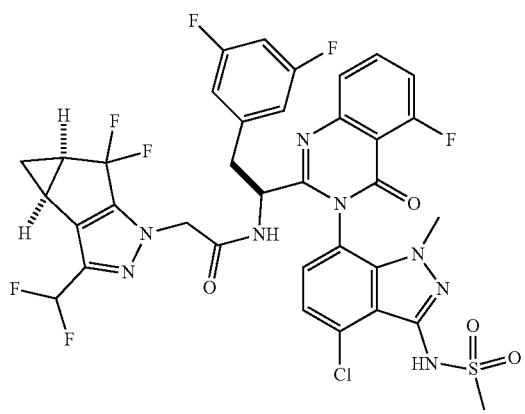 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cccc(F)c4c3=O)c21] | 0.13 | >8.0 |

TABLE 1-continued
| Example | Structure | EC$_{50}$ µM | CC$_{50}$ µM |
| --- | --- | --- | --- |
| Example 20 | 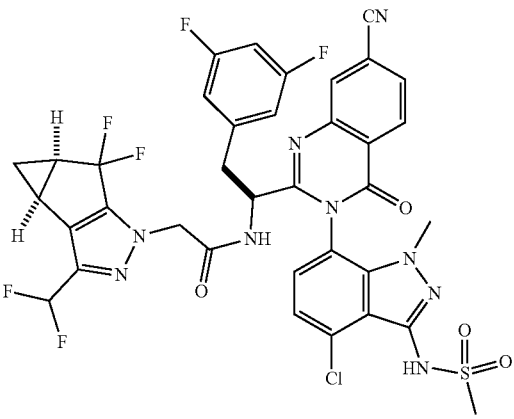 | 0.024 | >10.0 |
| Example 21 | 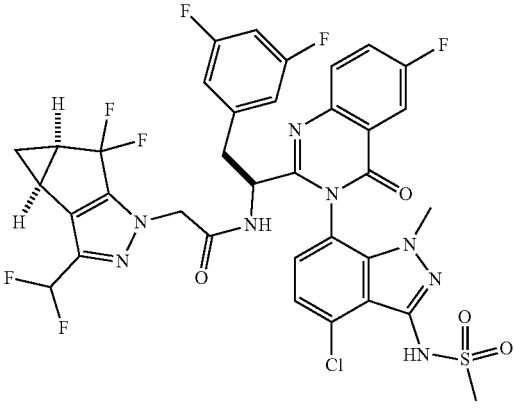 | 0.045 | >2.7 |
| Example 22.1 | 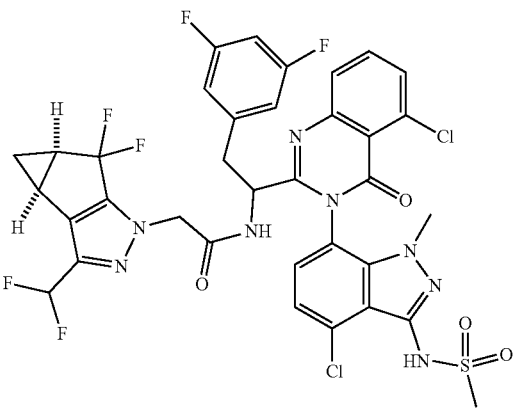<br>First eluting | 31.6 | >1 |

TABLE 1-continued

| Example | Structure | EC$_{50}$ μM | CC$_{50}$ μM |
|---|---|---|---|
| Example 22.2 | 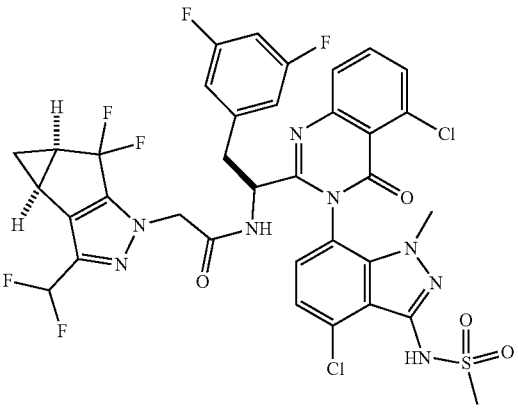 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4ccc(F)cc4c3=O)c21]<br>2nd eluting homochiral | 0.13 | >1 |

TABLE 1a

| Example | EC$_{50}$ nM | CC$_{50}$ μM |
|---|---|---|
| Example 23 | 21.8 | 10 |
| Example 24 | 1374.7 | >10 |
| Example 25 | 5.78 | 7.94 |
| Example 26 | 18.7 | 5.01 |
| Example 27 | 4.94 | 5.01 |
| Example 28 | 19.9 | >10 |
| Example 29 | 26.0 | >10 |
| Example 30 | 5.03 | 3.16 |
| Example 31 | 0.99 | >10 |
| Example 32 | 1.10 | >10 |
| Example 33 | 3.92 | >10 |
| Example 34 | 6.93 | >10 |
| Example 35 | 16.30 | 1.58 |
| Example 36 | 10.4 | >1 |
| Example 37.2 | 0.54 | >10 |
| Example 38 | | |
| Example 39 | 3.76 | 2.0 |
| Example 40.1 | 0.58 | >1 |
| Example 41.1 | 21.2 | >10 |
| Example 41.2 | 0.022 | >10 |
| Example 42.1 | 12.0 | >10 |
| Example 42.2 | 0.016 | >10 |
| Example 43.1 | 30.0 | >10 |
| Example 43.2 | 0.132 | >10 |
| Example 44.1 | 0.049 | >10 |
| Example 45.2 | 0.024 | >1 |
| Example 46.1 | 10.3 | >1 |
| Example 46.2 | 0.044 | >0.1 |
| Example 47.1 | 226.8 | >1 |
| Example 47.2 | 1.70 | >1 |
| Example 48.2 | 0.16 | >1 |
| Example 49.1 | 93.0 | >1 |
| Example 50.2 | 32.1 | >1 |
| Example 51 | 1.04 | >1 |
| Example 52 | 0.039 | >1 |
| Example 53 | 5.71 | >1 |
| Example 54.1 | 43.4 | >1 |
| Example 54.2 | 0.026 | >1 |
| Example 55.1 | 28.5 | >1 |
| Example 55.2 | 0.330 | >1 |
| Example 56.2 | 0.022 | >1 |
| Example 57.2 | 0.33 | >1 |
| Example 58.1 | 2.26 | >1 |
| Example 58.2 | 0.168 | >1 |
| Example 59.1 | 47.0 | >1 |
| Example 59.2 | 0.227 | >1 |
| Example 60.1 | 0.39743 | >1 |
| Example 60.2 | 0.01735 | >1 |
| Example 61 | 4.51 | >10 |
| Example 62 | 86.3 | >10 |
| Example 63 | 12.9 | >10 |
| Example 64 | 4.00 | >10 |
| Example 65 | 2.03 | 2.0 |
| Example 66 | 1540.6 | 10 |
| Example 67 | 183.2 | >1 |
| Example 68 | 4.69 | >1 |
| Example 69 | 78.3 | >1 |
| Example 70 | 0.130 | >1 |
| Example 71 | 9.58 | >1 |
| Example 72 | 0.068 | >1 |
| Example 73 | 1.53362 | >1 |
| Example 74 | 0.05129 | >1 |
| Example 75 | 108.547 | >1 |
| Example 76 | 0.118 | >1 |
| Example 78 | 0.478 | >1 |
| Example 80 | 0.389 | >1 |
| Example 81 | 13.6 | 10 |
| Example 82 | 3.81 | 6.31 |
| Example 83 | 1.02 | >10 |
| Example 84 | 0.94 | >10 |
| Example 85 | 298.6 | >3.16 |
| Example 86 | 1097.1 | >10 |
| Example 87 | 72.4 | >10 |
| Example 88 | 0.61 | >10 |
| Example 89 | 0.66 | >10 |
| Example 90 | 1.48 | >10 |
| Example 91 | | |
| Example 92 | 0.161 | >10 |
| Example 93 | 0.099 | >10 |
| Example 94 | 0.146 | >1 |
| Example 95 | 0.094 | >1 |
| Example 96 | 0.26 | >1 |
| Example 97 | 30.6 | >1 |
| Example 98 | 0.747 | >1 |
| Example 99 | 17.8 | >1 |
| Example 100 | 0.033 | >1 |
| Example 101 | 335.278 | >1 |
| Example 102 | 1.04 | >1 |
| Example 103 | | >1 |
| Example 104 | 0.064 | >1 |
| Example 105 | | |
| Example 106 | 23.8 | >1 |
| Example 107 | 27.3 | >1 |
| Example 108 | 0.85 | >1 |
| Example 109 | 118.0 | >1 |
| Example 110 | 0.072 | >1 |
| Example 111 | 92.6 | >1 |
| Example 112 | 0.51 | >1 |

TABLE 1a-continued

| Example | EC$_{50}$ nM | CC$_{50}$ μM |
|---|---|---|
| Example 113 | 8.43 | >1 |
| Example 114 | 0.071 | >1 |
| Example 115 | 68.432 | >1 |
| Example 116 | 0.231 | >1 |
| Example 117 | 0.243 | >10 |
| Example 118 | 0.162 | >10 |
| Example 119 | 0.0924 | >10 |
| Example 120 | 0.0753 | >10 |
| Example 121 | 170.6 | >10 |
| Example 122 | 172.1 | >10 |
| Example 123 | 408.1 | >1 |
| Example 124 | 208.2 | >1 |
| Example 125 | 63.9 | >1 |
| Example 126 | 0.054 | >1 |
| Example 127 | 379.1 | >1 |
| Example 128 | 0.62 | >1 |
| Example 129 | | |
| Example 130 | 0.15 | >1 |
| Example 131 | 111.1 | >1 |
| Example 132 | | |
| Example 133 | 126.8 | >1 |
| Example 134 | 2.21 | >1 |
| Example 135 | | |
| Example 136 | 38.9 | >1 |
| Example 137 | 9.89 | >1 |
| Example 138 | 0.042 | >1 |
| Example 139 | | |
| Example 140 | 0.32 | >1 |
| Example 141 | 217.0 | >1 |
| Example 142 | 4.98 | >1 |
| Example 143 | 84.0 | >1 |
| Example 144 | 8.08 | >1 |
| Example 145 | 30.2 | >1 |
| Example 146 | 0.62 | >1 |
| Example 147 | 27.9 | >1 |
| Example 148 | 0.13 | >1 |
| Example 150 | | >1 |
| Example 151 | 0.74 | >1 |
| Example 152 | 172.7 | >1 |
| Example 153 | 0.97 | >1 |
| Example 154 | 0.43 | >10 |
| Example 155 | 35.8 | >10 |
| Example 156 | 16.4 | >10 |
| Example 157 | 10.4 | >10 |
| Example 158 | 102.1 | >10 |
| Example 159 | 9.49 | >1 |
| Example 160 | 0.18 | >1 |
| Example 161 | 28.9 | >1 |
| Example 162 | 6.56 | >10 |
| Example 163 | 11.9 | 3.98 |
| Example 164 | 1.17 | >10 |
| Example 165 | 0.23 | >10 |
| Example 166 | 26.0 | >1 |
| Example 167 | 80.5 | >1 |
| Example 168 | 0.058 | >1 |
| Example 169 | 119.0 | >1 |
| Example 170 | 0.052 | >1 |
| Example 171 | 3.96 | >1 |
| Example 172 | | |
| Example 173 | 32.0 | >1 |
| Example 174 | 0.096 | >1 |
| Example 175 | 10.9 | >1 |
| Example 176 | 0.19 | >1 |
| Example 177 | 45.0 | >1 |
| Example 178 | 18.1 | >1 |
| Example 179 | 0.077 | >1 |
| Example 180 | 87.4 | >1 |
| Example 181 | 23.1 | >1 |
| Example 182 | 0.061 | >1 |
| Example 183 | 21.5 | >1 |
| Example 184 | 0.35 | >1 |
| Example 185 | 87.3 | >1 |
| Example 186 | 0.072 | >1 |
| Example 187 | 177.9 | >1 |
| Example 188 | | >1 |
| Example 189 | 6.46 | >1 |
| Example 190 | 42.2 | >1 |
| Example 191 | 0.060 | >1 |

TABLE 1a-continued

| Example | EC$_{50}$ nM | CC$_{50}$ μM |
|---|---|---|
| Example 192 | 0.04 | >1 |
| Example 193 | 0.18 | >10 |
| Example 194 | 1.90 | >10 |
| Example 195 | 74.4 | >1 |
| Example 196 | 0.081 | >1 |
| Example 197 | 42.6 | >1 |
| Example 198 | 0.15 | >1 |
| Example 199 | 32.8 | >1 |
| Example 200 | 0.20 | >1 |
| Example 201 | 71.8 | >1 |
| Example 202 | 0.30 | >1 |
| Example 203 | 166.1 | >1 |
| Example 204 | 31.9 | >1 |
| Example 205 | | >1 |
| Example 206 | 0.64 | >1 |
| Example 207 | 4.49 | >1 |
| Example 208 | 0.083 | >1 |
| Example 209 | | |
| Example 210 | 23.2 | >1 |
| Example 211 | | |
| Example 212 | 0.63 | >1 |
| Example 213 | 0.28 | >1 |
| Example 214 | 0.071 | >1 |
| Example 215 | 354.1 | >1 |
| Example 216 | 0.059 | >1 |
| Example 217 | 0.25 | >1 |
| Example 218 | 0.73 | >1 |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed is:

1. A compound of Formula I, or a pharmaceutically acceptable salt thereof:

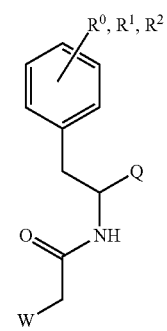

wherein:

$R^0$, $R^1$, and $R^2$ are each independently hydrogen, Cl, F, -OMe, —CN, —C$_1$-C$_3$alkyl, or —C$_3$-C$_5$cycloalkyl, wherein —C$_1$-C$_3$alkyl may be optionally substituted with from 1-3 fluorines;

Q is selected from:
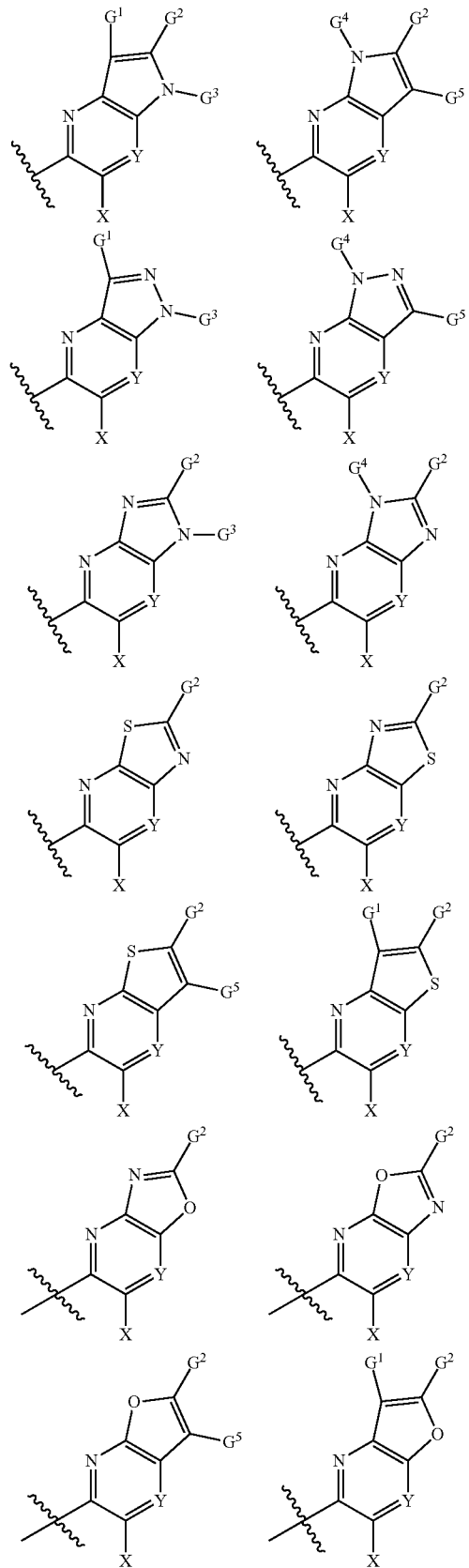
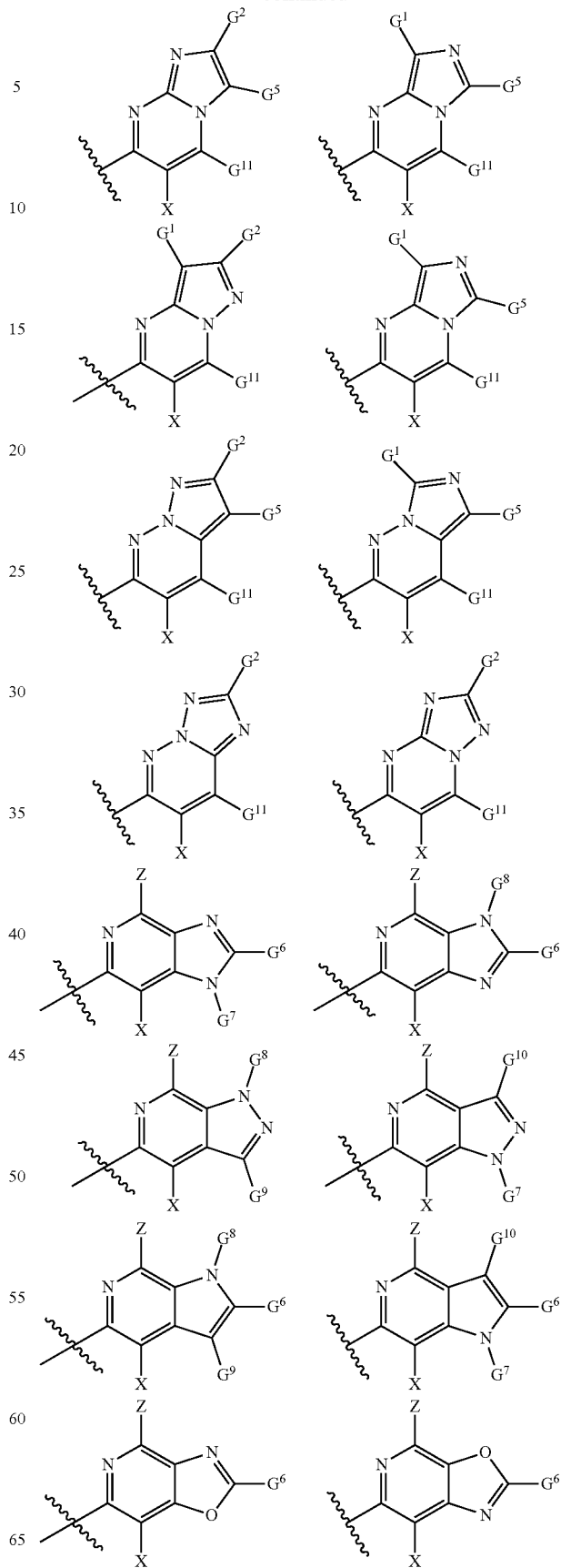

-continued

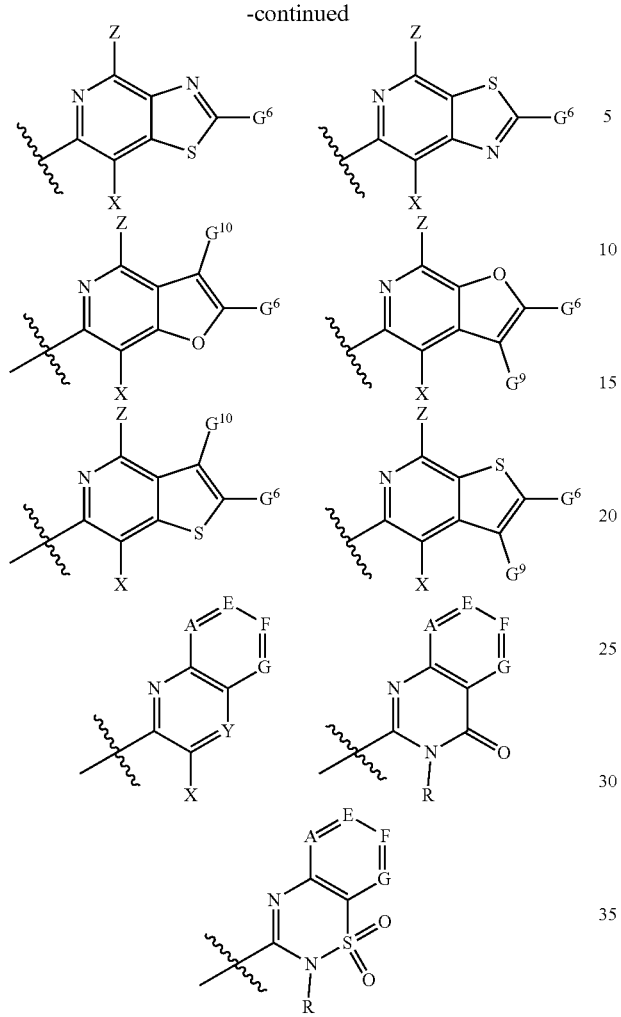

G$^1$ is hydrogen, C$_1$-C$_5$alkyl, —SO$_2$CH$_3$, —CO$_2$H, —C(O)NG$^{12}$G$^{13}$-(C$_1$-C$_3$alkyl)SO$_2$CH$_3$, —(C$_1$-C$_3$alkyl)C(O)NG$^{12}$G$^{13}$, —(C$_1$-C$_3$alkyl)NG$^{12}$G$^{13}$, —(C$_1$-C$_3$alkyl)CO$_2$H, —CCC(CH$_3$)$_2$SO$_2$CH$_3$, —(C$_1$-C$_3$alkyl)CO$_2$H, Cl, or F wherein C$_1$-C$_3$alkyl or C$_1$-C$_5$alkyl is optionally substituted with 1-3 fluorines;

G$^2$ is hydrogen, C$_1$-C$_5$alkyl, —SO$_2$CH$_3$, —CO$_2$H, —C(O)NG$^{12}$G$^{13}$, —NG$^{12}$G$^{13}$, —(C$_1$-C$_3$ alkyl)SO$_2$CH$_3$, —(C$_1$-C$_3$alkyl)C(O)NG$^{12}$G$^{13}$, —(C$_1$-C$_3$alkyl)NG$^{12}$G$^{13}$, —(C$_1$-C$_3$alkyl)CO$_2$H, —CCC(CH$_3$)$_2$SO$_2$CH$_3$, —(C$_1$-C$_3$alkyl)CO$_2$H, Cl, or F, wherein C$_1$-C$_5$alkyl or C$_1$-C$_5$alkyl is optionally substituted with 1-3 fluorines or 1-2 CH$_3$ groups;

G$^3$ is hydrogen, —SO$_2$CH$_3$, benzyl, or C$_1$-C$_3$alkyl, wherein C$_1$-C$_3$alkyl is optionally substituted with 1-3 fluorines;

G$^4$ is hydrogen, C$_1$-C$_3$alkyl, -benzyl, —SO$_2$(C$_1$-C$_3$alkyl), —(C$_2$-C$_3$alkyl)SO$_2$CH$_3$, —C(O)NG$^{12}$G$^{13}$, —(C$_1$-C$_3$alkyl)C(O)NG$^{12}$G$^{13}$, —(C$_2$-C$_3$alkyl)C(O)NG$^{12}$G$^{13}$, —(C$_1$-C$_3$ alkyl)CO$_2$H, —(C$_1$-C$_3$alkyl)CO$_2$H, wherein C$_1$-C$_3$alkyl is optionally substituted with 1-3 fluorines;

G$^5$ is hydrogen, C$_1$-C$_3$alkyl, —SO$_2$(C$_1$-C$_3$alkyl), —C(O)NG$^{12}$G$^{13}$, CO$_2$H, —NG$^{12}$G$^{13}$, or CN wherein C$_1$-C$_3$alkyl is optionally substituted with 1-3 fluorines or chlorines;

G$^6$ is hydrogen or methyl wherein methyl is optionally substituted with 1-3 fluorines;

G$^7$ is hydrogen, or C$_1$-C$_3$alkyl wherein C$_1$-C$_3$alkyl is optionally substituted with 1-3 fluorines;

G$^8$ is hydrogen, C$_1$-C$_3$alkyl, -benzyl, —SO$_2$(C$_1$-C$_3$alkyl), —(C$_2$-C$_3$alkyl)SO$_2$CH$_3$, —C(O)NG$^{12}$G$^{13}$-(C$_1$-C$_3$alkyl)C(O)NG$^{12}$G$^{13}$, —(C$_2$-C$_3$ alkyl)C(O)NG$^{12}$G$^{13}$, —(C$_1$-C$_3$ alkyl)CO$_2$H, —(C$_1$-C$_3$alkyl)CO$_2$H, wherein C$_1$-C$_3$alkyl is optionally substituted with 1-3 fluorines;

G$^9$ is hydrogen or methyl wherein methyl is optionally substituted with 1-3 fluorines;

G$^{10}$ is hydrogen or methyl wherein methyl is optionally substituted with 1-3 fluorines;

Y is N or C-G$^{11}$;

G$^{11}$ is hydrogen, C$_1$-C$_3$alkyl, —O(C$_1$-C$_3$alkyl), —SO$_2$CH$_3$, —CO$_2$H, —NG$^{12}$G$^{13}$, CN, or —C(O)NG$^{12}$G$^{13}$ wherein C$_1$-C$_3$alkyl is optionally substituted with 1-3 fluorines;

Z is hydrogen, —C$_1$-C$_3$alkyl, —NH$_2$, —SO$_2$(C$_1$-C$_3$alkyl), —O(C$_1$-C$_3$alkyl), —(C$_1$-C$_3$alkyl)SO$_2$CH$_3$, —C(O)NG$^{12}$G$^{13}$, —(C$_1$-C$_3$alkyl)C(O)NG$^{12}$G$^{13}$, —(C$_1$-C$_3$alkyl)NG$^{12}$G$^{13}$, —CCC(CH$_3$)$_2$SO$_2$CH$_3$, —CCC(CH$_3$)$_2$OH, —(C$_1$-C$_3$alkyl)COOH, —CCC(CH$_3$)$_2$C(O)NG$^{12}$G$^{13}$, —CCC(CH$_3$)$_2$COOH, —CCC(CH$_3$)$_3$, —CCC(CH$_3$)$_2$OC$_1$-C$_3$alkyl, wherein —C$_1$-C$_3$alkyl is optionally substituted with 1-3 fluorines;

G$^{12}$ and G$^{13}$ are each independently hydrogen or C$_1$-C$_3$alkyl;

A is N or C-G$^{14}$;

E is N or C-G$^{14}$;

F is N or C-G$^{15}$;

G is N, C-G$^{16}$;

with the proviso that no more than two of A, E, F, or G may be N;

G$^{14}$ is hydrogen, —C$_1$-C$_5$alkyl, —C$_3$-C$_6$cycloalkyl, —SO$_2$CH$_3$, —CO$_2$H, —CO$_2$Me, —C(O)NG$^{12}$G$^{13}$, —NG$^{12}$G$^{13}$, —(C$_1$-C$_3$alkyl)SO$_2$CH$_3$, —(C$_1$-C$_3$alkyl)C(O)NG$^{12}$G$^{13}$, —(C$_1$-C$_3$alkyl)NG$^{12}$G$^{13}$, —(C$_1$-C$_3$alkyl)CO$_2$H, —CCC(CH$_3$)$_2$SO$_2$CH$_3$, —(C$_1$-C$_3$alkyl)C$_2$H, Cl, F, Br, —CN, or —O—C$_1$-C$_5$alkyl, wherein C$_1$-C$_5$alkyl, —O—C$_1$-C$_5$alkyl, or —C$_3$-C$_6$cycloalkyl is optionally substituted with 1-3 fluorines;

G$^{15}$ is hydrogen, C$_1$-C$_5$alkyl, —C$_3$-C$_5$cycloalkyl, —SO$_2$CH$_3$, —CO$_2$H, —CO$_2$Me, —C(O)NG$^{12}$G$^{13}$, —NG$^{12}$G$^{13}$, CN, Cl, F, Br, —O—C$_1$-C$_5$alkyl, wherein C$_1$-C$_5$alkyl, C$_1$-C$_5$cycloalkyl or —O—C$_1$-C$_5$alkyl is optionally substituted with 1-3 fluorines;

G$^{16}$ is hydrogen, —C$_1$-C$_5$alkyl, —NH$_2$, Cl, F, Br, —CN, or —O—C$_1$-C$_5$alkyl, wherein C$_1$-C$_5$alkyl or —O—C$_1$-C$_5$alkyl, is optionally substituted with 1-3 fluorines;

X is

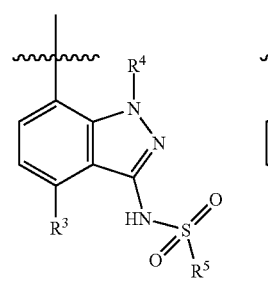 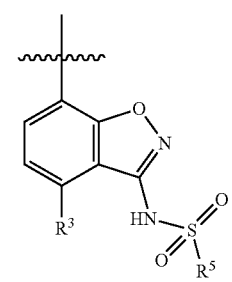

-continued

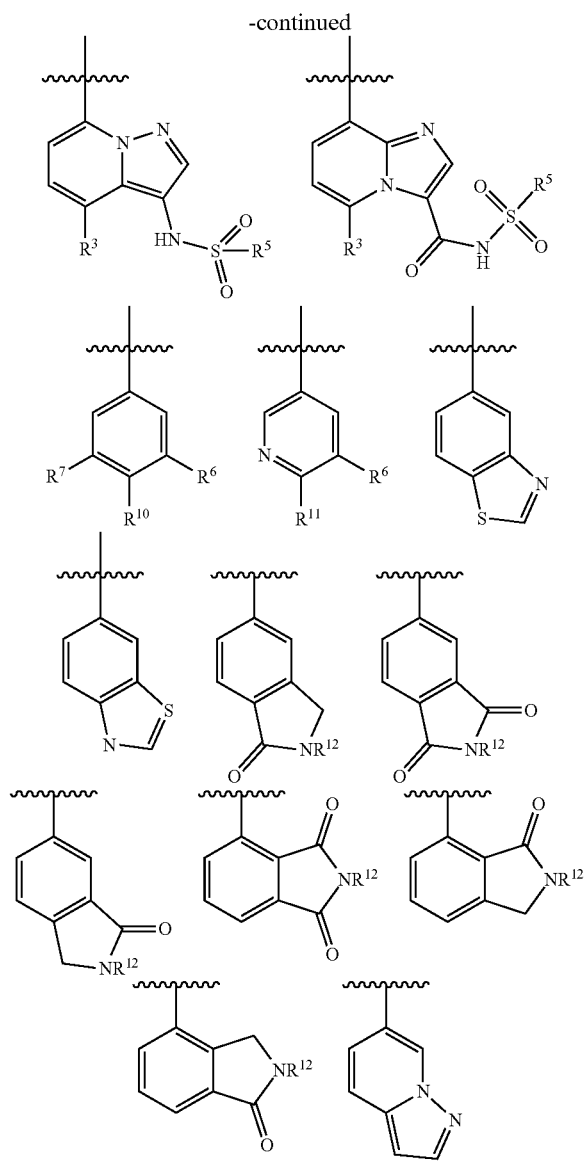

R=X;

$R^3$ is hydrogen, Cl, F, -OMe, —CN, —$C_1$-$C_3$alkyl, or —$C_3$-$C_5$cycloalkyl, wherein —$C_1$-$C_3$alkyl may be optionally substituted with from 1-3 fluorines;

$R^4$ is hydrogen, $C_1$-$C_3$alkyl, or —$SO_2CH_3$ wherein $C_1$-$C_3$alkyl is optionally substituted with 1-3 fluorines;

$R^5$ is $C_1$-$C_6$alkyl, $C_3$-$C_6$cycloalkyl, or $NG^{12}$, $G^{13}$;

$R^6$ and $R^7$ are each independently hydrogen, chlorine, fluorine, —$OC_1$-$C_3$alkyl, —CN, —$CO_2H$, —$CONG^{12}G^{13}$, —$NG^{12}G^{13}$, —$NHCOR^8$, or —$CONHSO_2R^9$ or —$NHSO_2R^9$ wherein —$C_1$-$C_3$alkyl, —$OC_1$-$C_3$alkyl, or —$C_3$-$C_5$cycloalkyl is optionally substituted with 1-3 fluorines;

$R^8$ is —$C_1$-$C_3$alkyl;

$R^9$ is —$C_1$-$C_6$alkyl, —$C_3$-$C_5$cycloalkyl or $NG^{12}$, $G^{13}$ wherein —$C_3$-$C_5$cycloalkyl is optionally substituted with a methyl group;

$R^{10}$ is hydrogen, chlorine, fluorine, —$C_1$-$C_3$alkyl, —$OC_1$-$C_3$alkyl, —$C_3$-$C_5$cycloalkyl, —CN, —$CO_2H$, —$SO_2C_1$-$C_3$alkyl, —$SO_2NR^aR^b$, —$CONG^{12}G^{13}$, —$NG^{12}G^{13}$, —$NHCOR^8$, or —$CONHSO_2R^9$ or —$NHSO_2R^9$ wherein —$C_1$-$C_3$alkyl, —$OC_1$-$C_3$alkyl, or —$C_3$-$C_5$cycloalkyl is optionally substituted with 1-3 fluorines;

$R^a$ and $R^b$ are independently H, —$C_1$-$C_3$alkyl, or together with the N to which they are attached form a morpholine, azetidine, pyrrolidine, piperidine, piperazine, or N-Me piperazine;

$R^{11}$ is hydrogen, —$C_1$-$C_3$alkyl, $C_3$-$C_5$cycloalkyl —$OC_1$-$C_3$alkyl, —$CONG^{12}G^{13}$, —$NG^{12}G^{13}$, —$NHCOR^8$, —$CONHSO_2R^9$ or —$NHSO_2R^9$ wherein —$C_1$-$C_3$alkyl, —$OC_1$-$C_3$alkyl, or —$C_3$-$C_5$ cycloalkyl is optionally substituted with 1-3 Fluorines;

$R^{12}$ is -hydrogen or methyl;

$R^{13}$ is —$C_1$-$C_3$alkyl or —$C_3$-$C_6$cycloalkyl wherein —$C_1$-$C_3$alkyl is optionally substituted with 1-3 fluorines; and W is selected from:

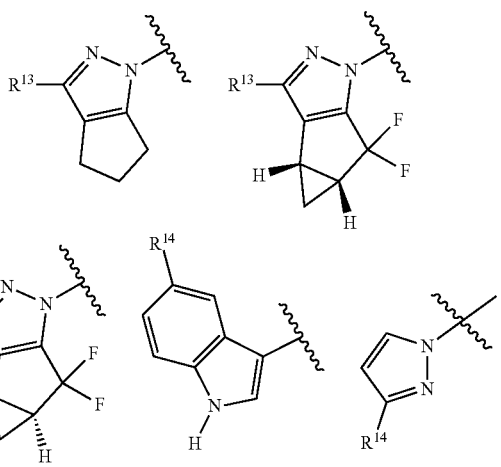

wherein $R^{14}$ is —$NHSO_2CH_3$, —$C_1$-$C_3$alkyl, —$C_3$-$C_6$cycloalkyl, —OH, —F, Cl, Br, or methyl, wherein methyl is optionally substituted with 1-3 fluorines.

2. A compound or salt according to claim 1 wherein said compound or salt is a compound of Formula II, or a pharmaceutically acceptable salt thereof:

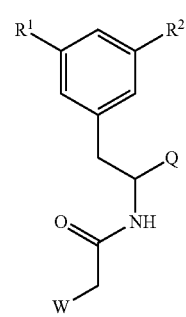

II wherein Q and W are as defined in claim 1; and $R^1$ and $R^2$ are each independently hydrogen or F.

3. A compound or salt according to claim 2, wherein the stereochemistry of the carbon to which Q is bonded is as depicted below in Formula III:

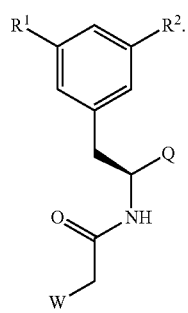
4. A compound or salt according to claim 3 wherein R¹ and R² are each F.
5. A compound or salt of claim 1, selected from the group consisting of:
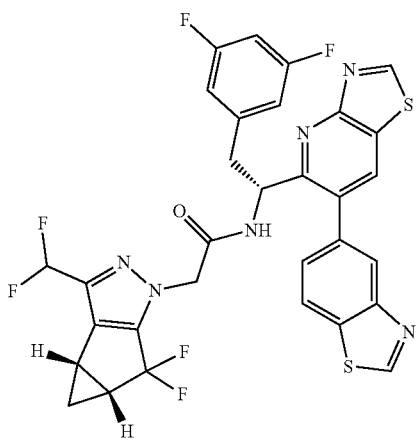
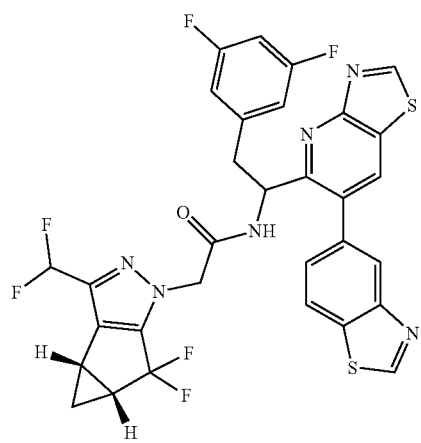
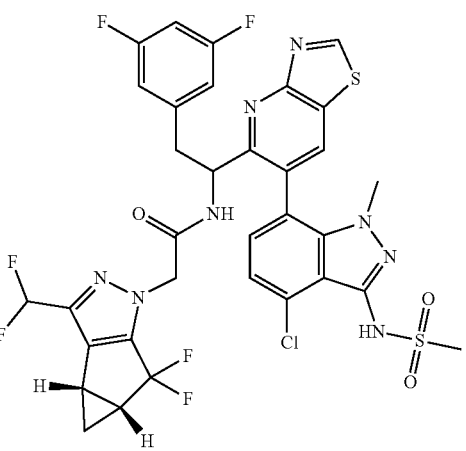
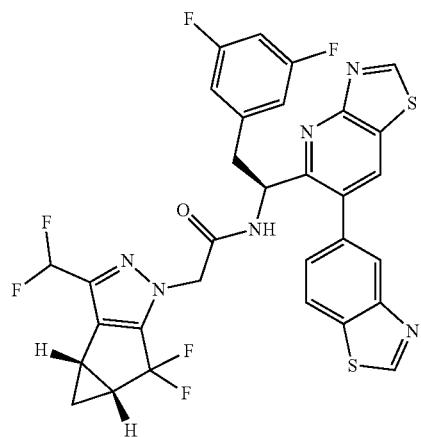
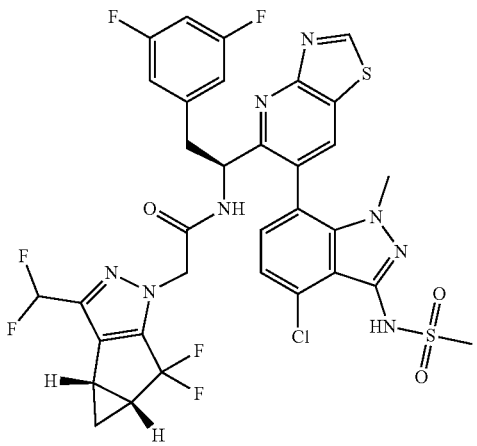

559
-continued
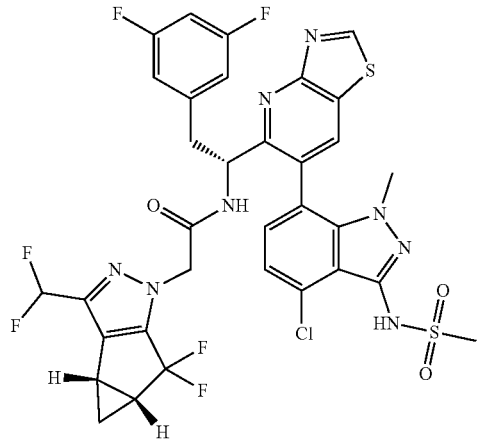
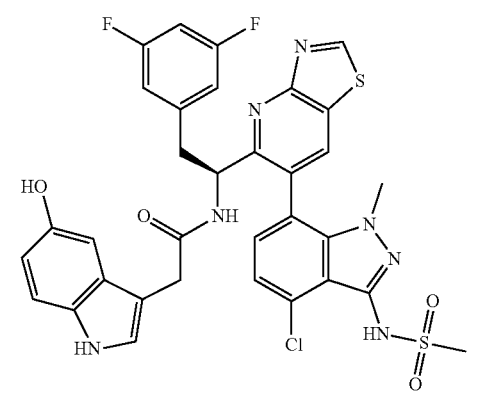
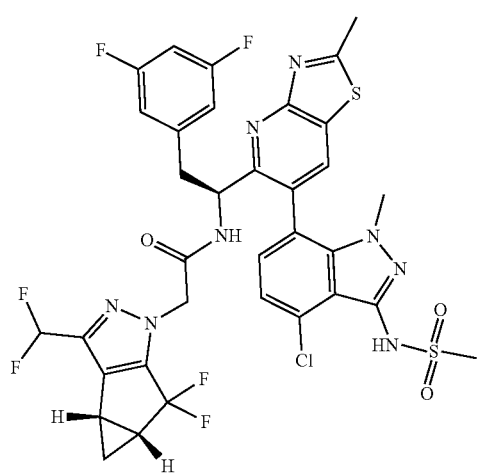
560
-continued
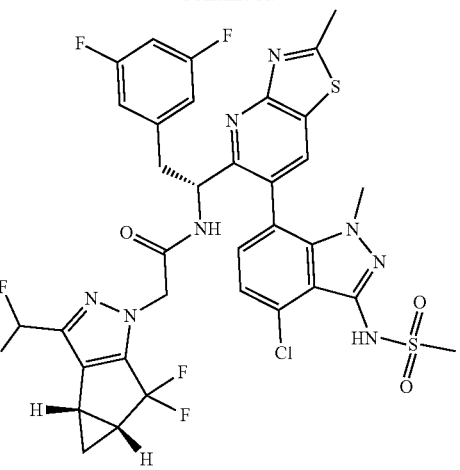
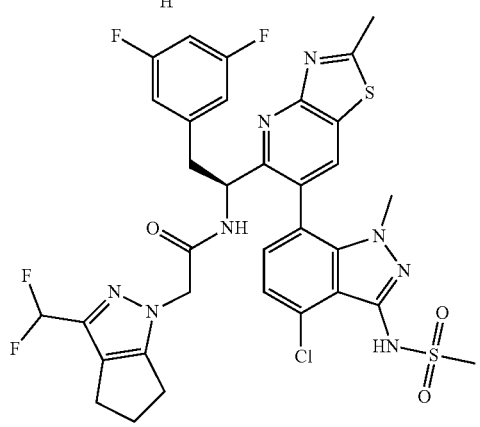
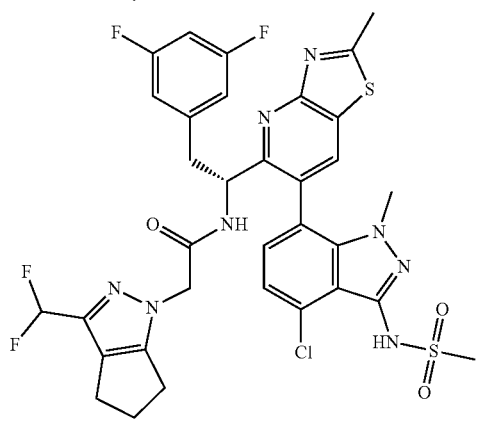
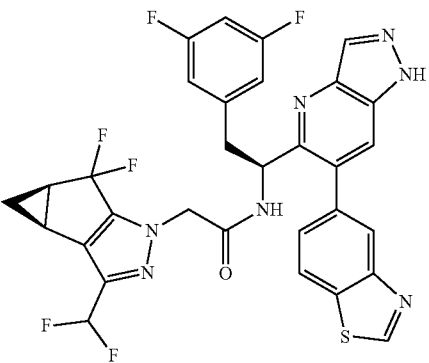

561
-continued
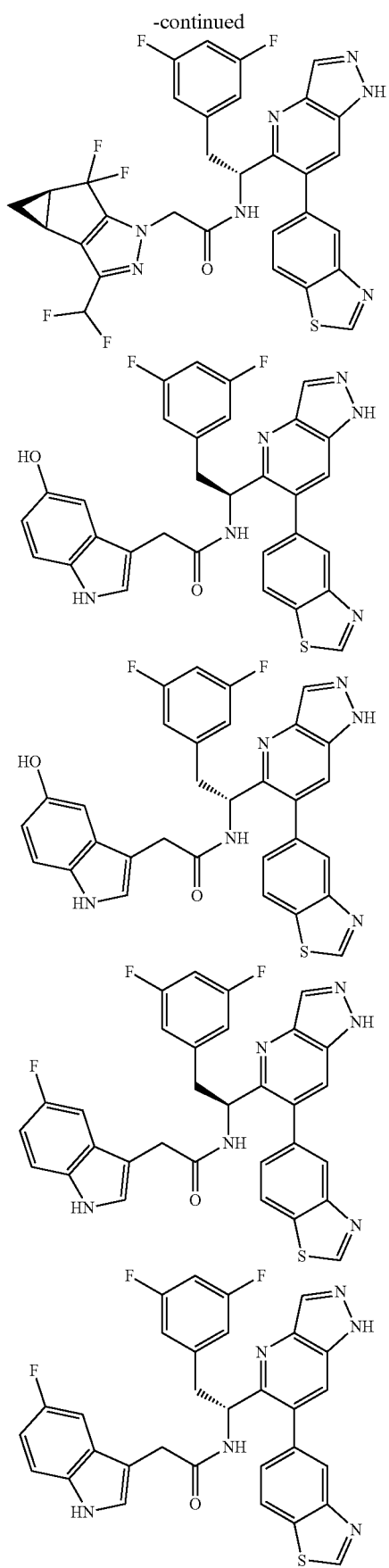
562
-continued
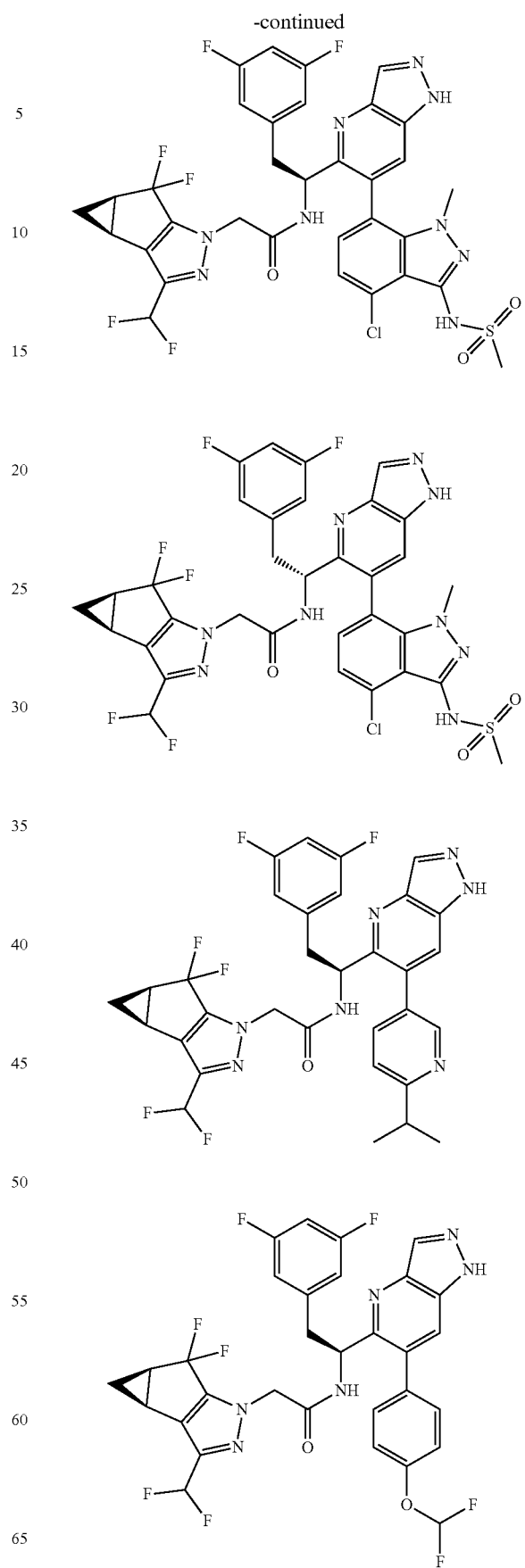

563
-continued
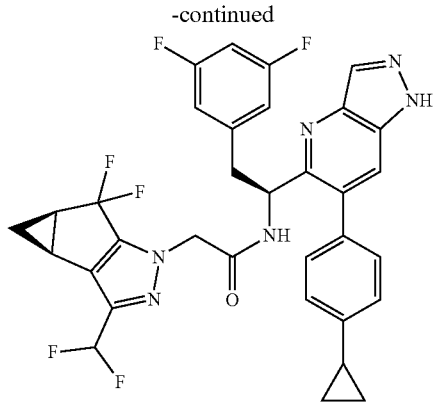
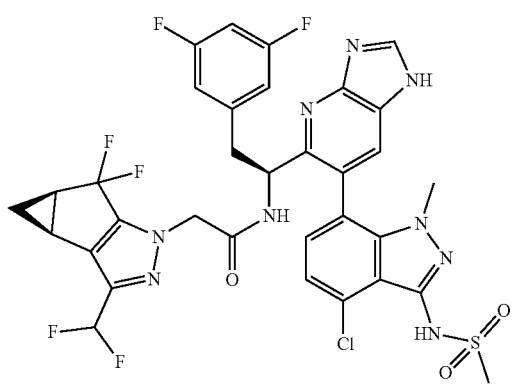
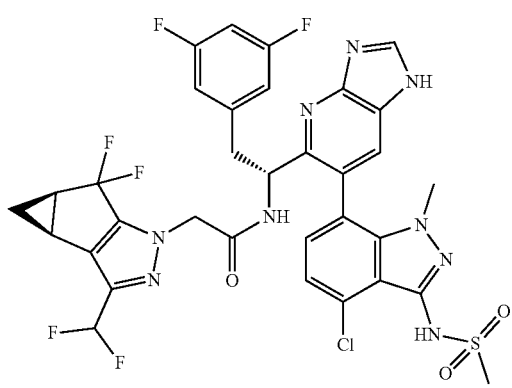
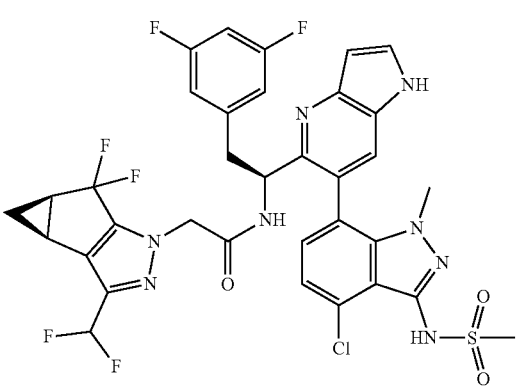
564
-continued
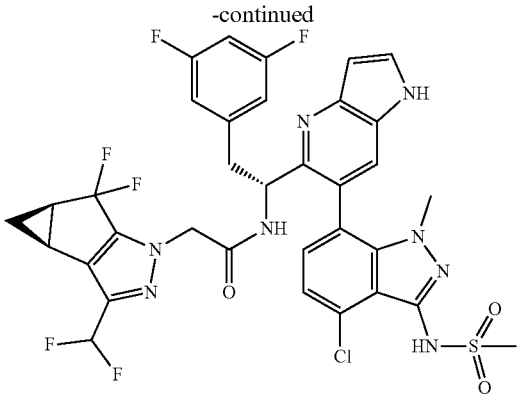
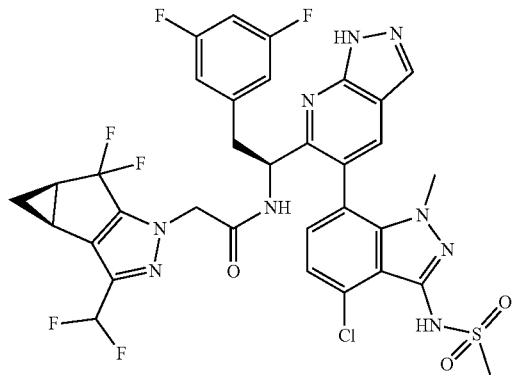
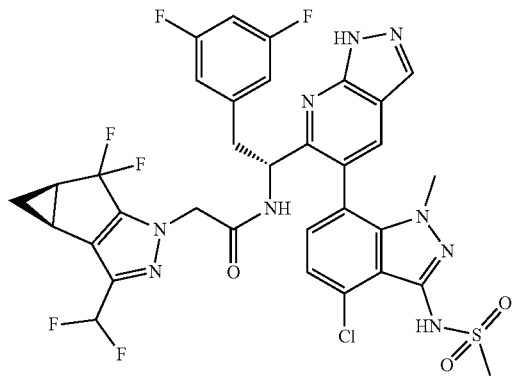
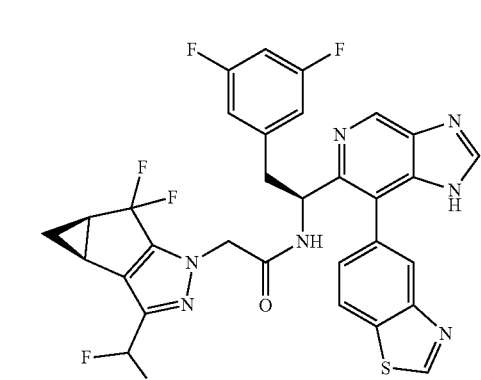

565
-continued
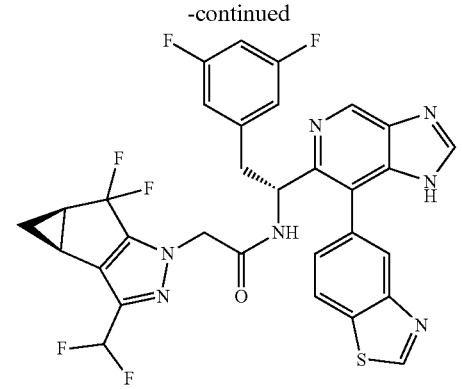
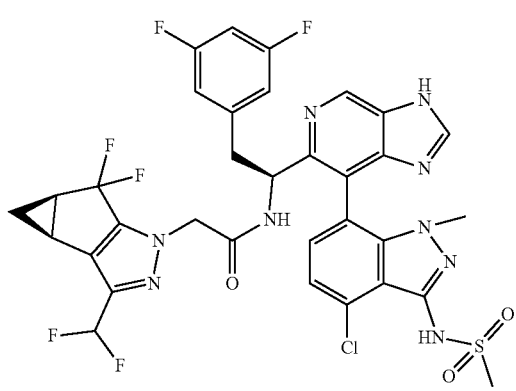
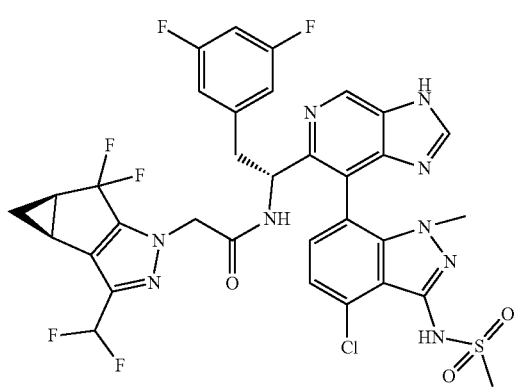
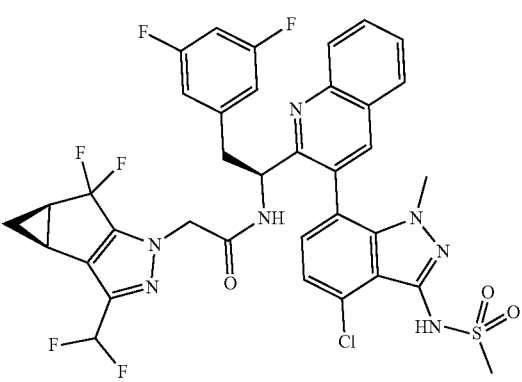
566
-continued
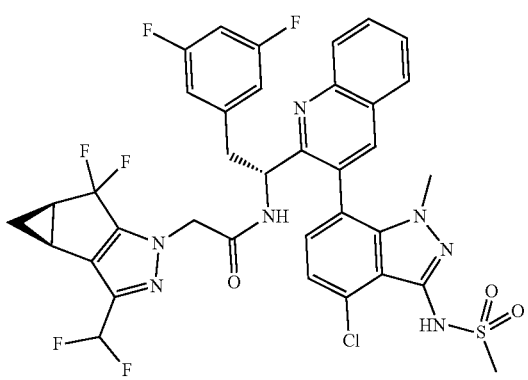
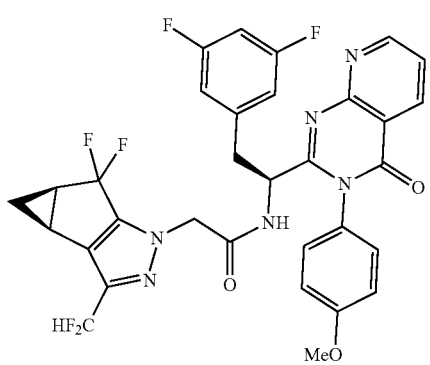
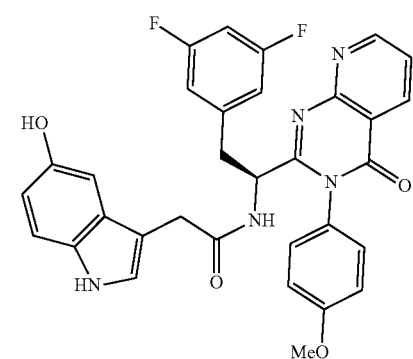
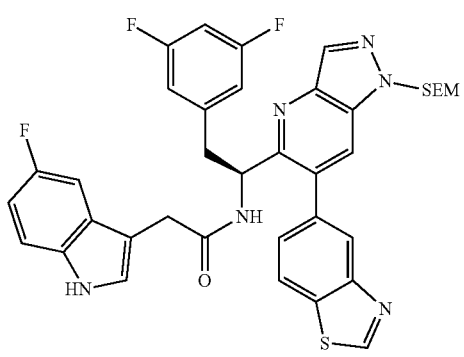

567
-continued
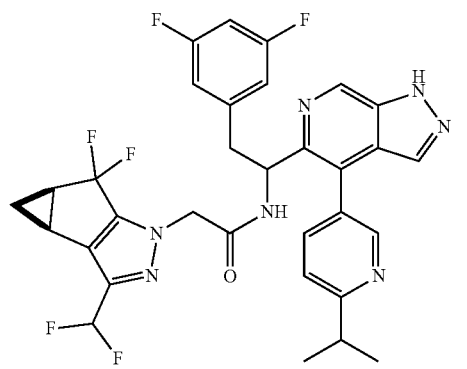
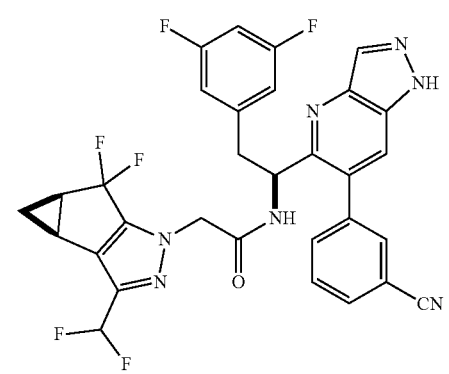
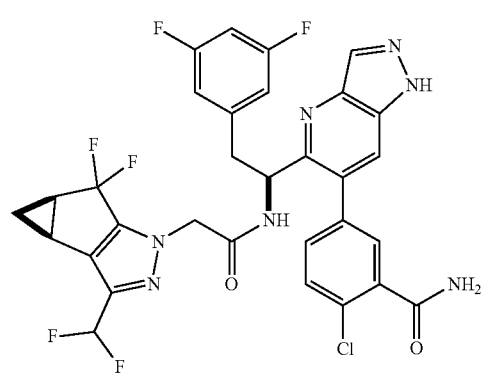
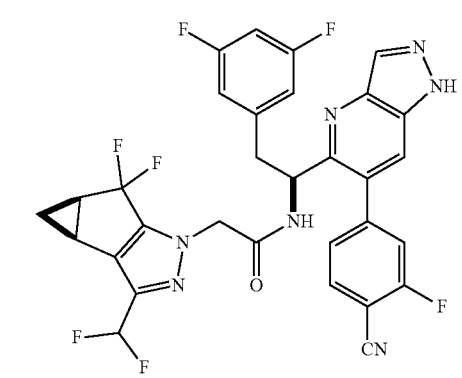
568
-continued
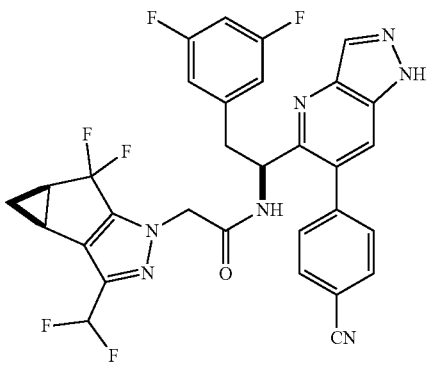
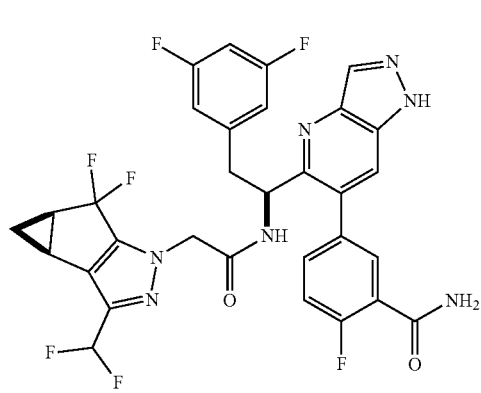
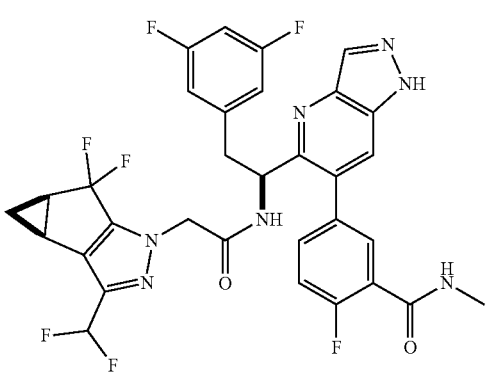
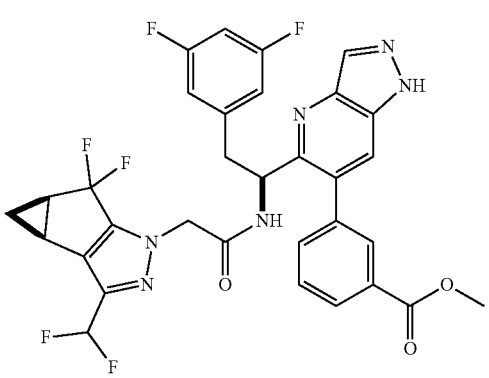

| 569 -continued | 570 -continued |
|---|---|
| 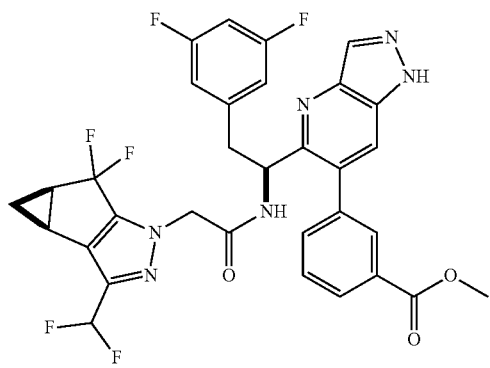 | 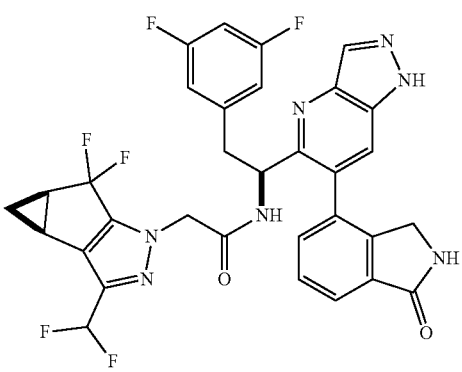 |
| 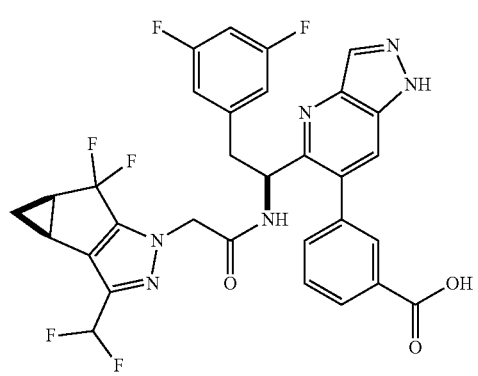 | 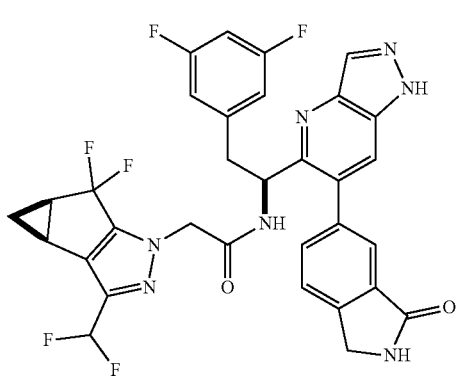 |
| 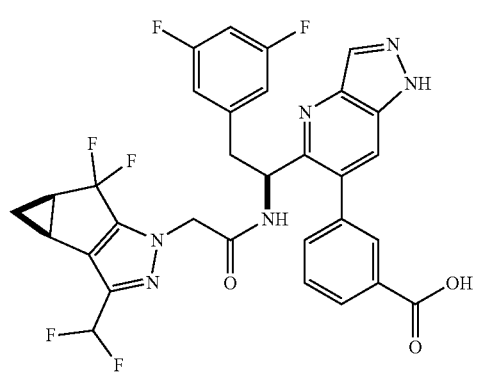 | 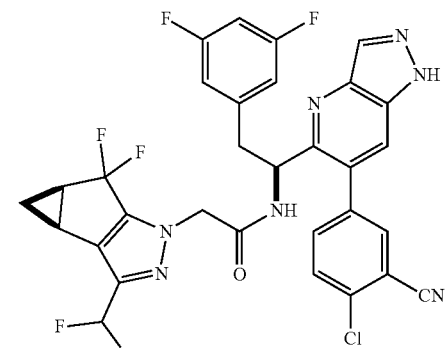 |
| 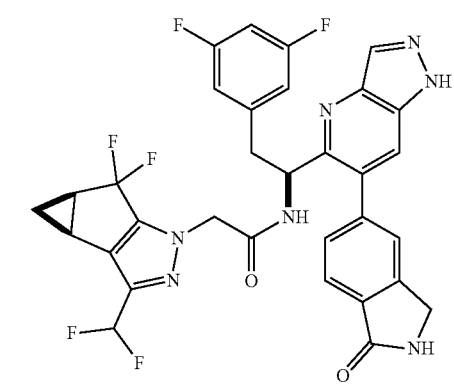 | 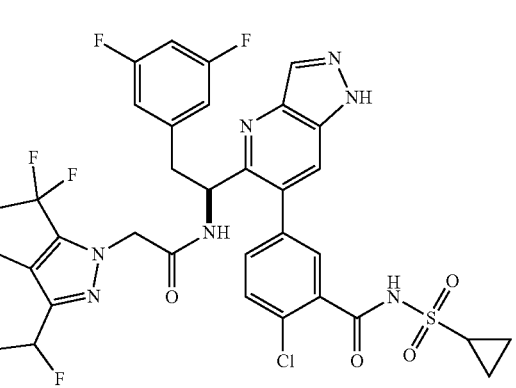 |

571
-continued
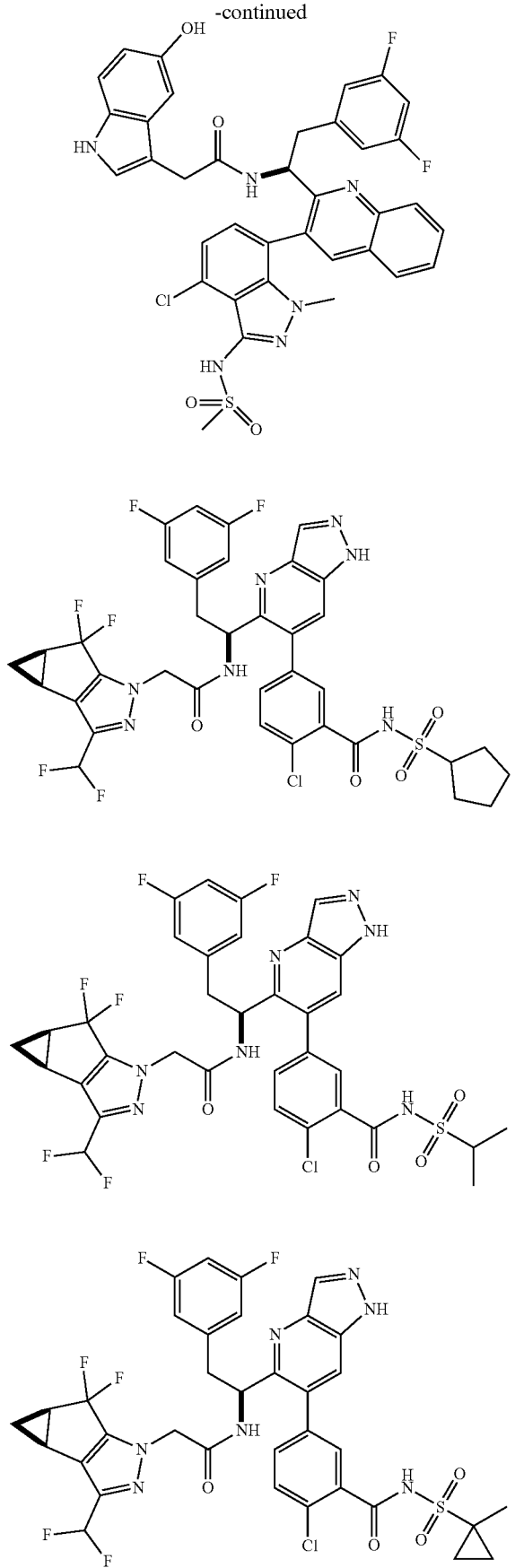
572
-continued
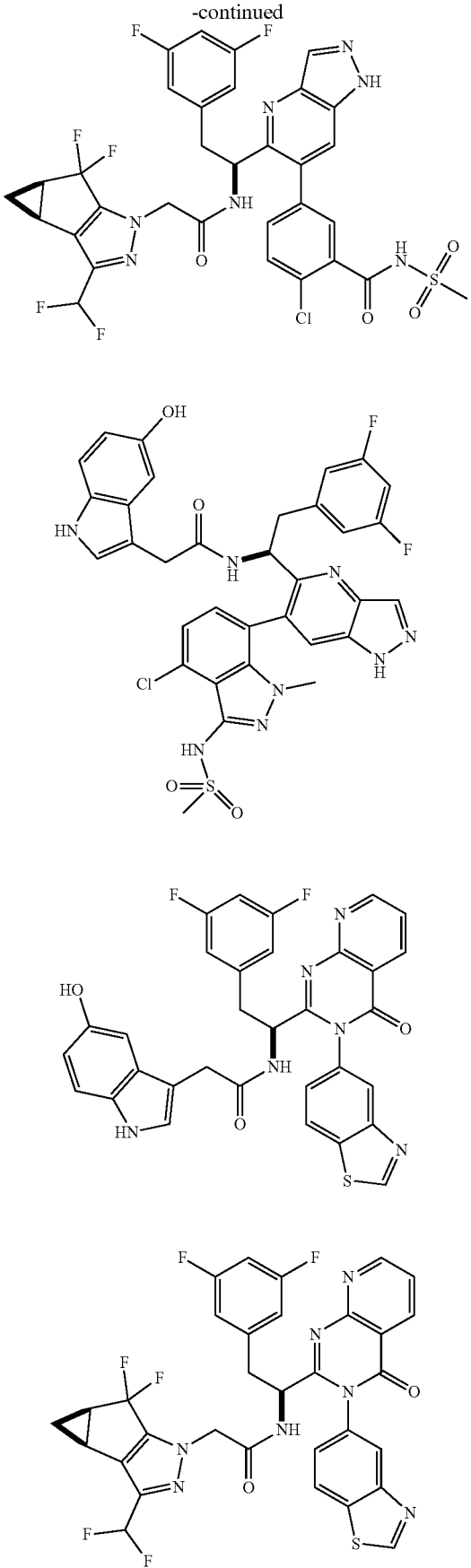

573
-continued
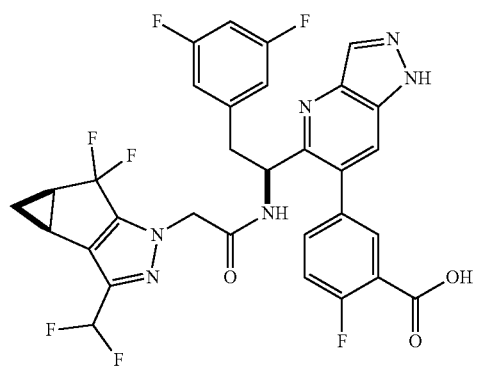
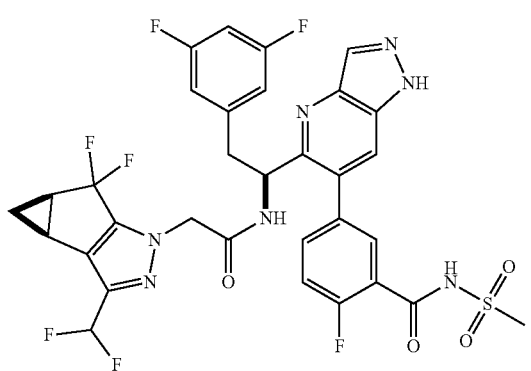
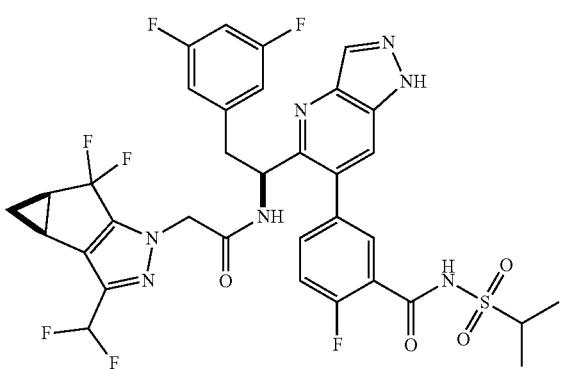
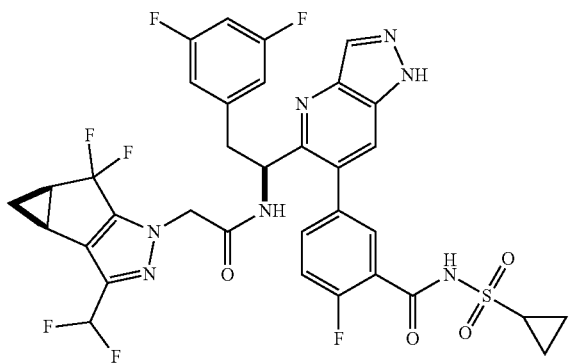
574
-continued
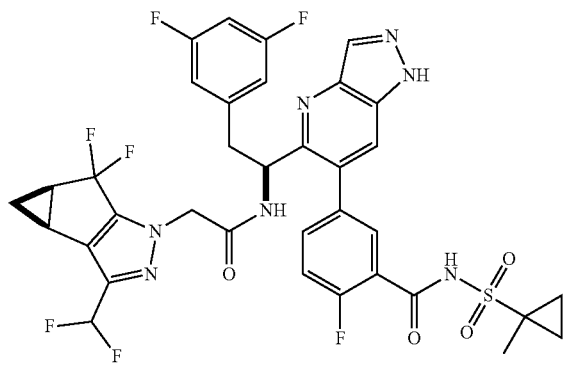
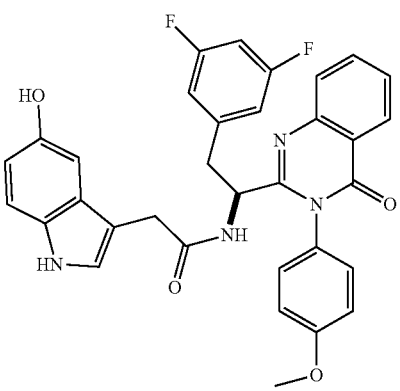
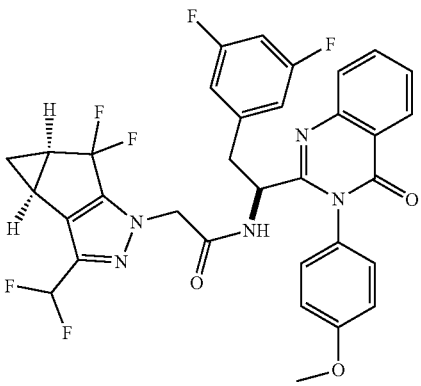
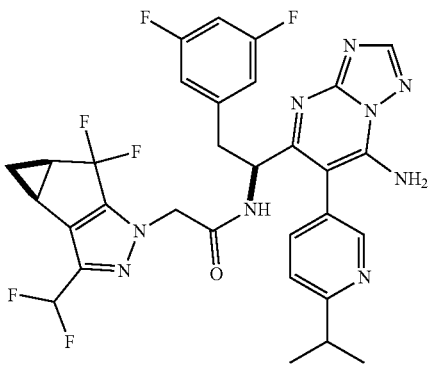

575
-continued
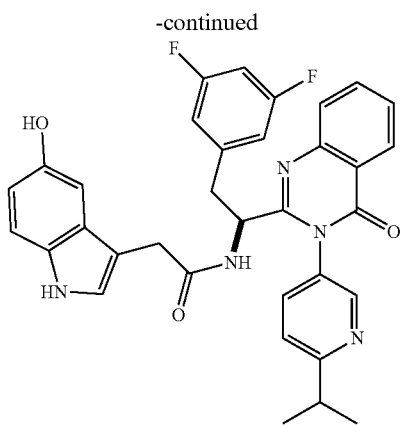
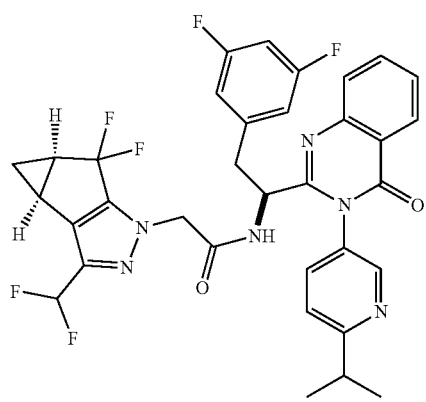
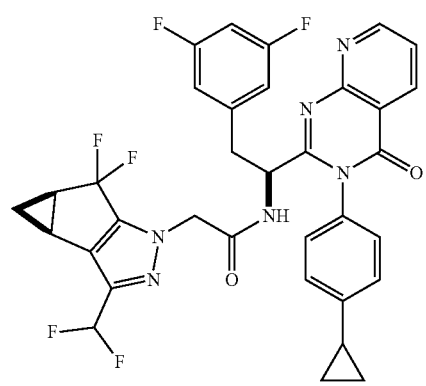
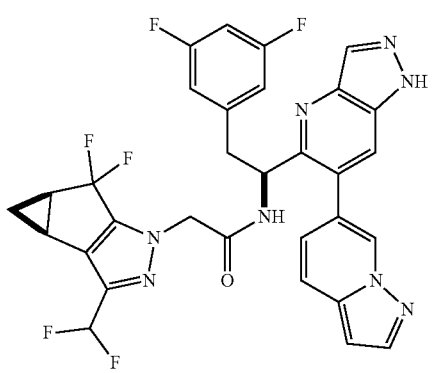
576
-continued
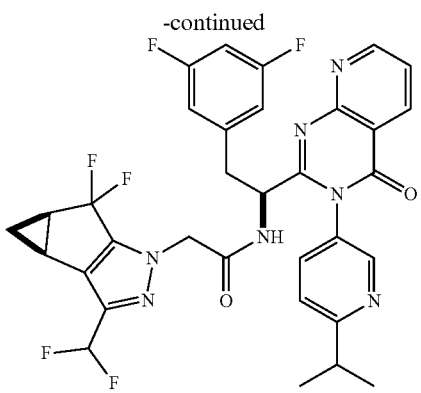
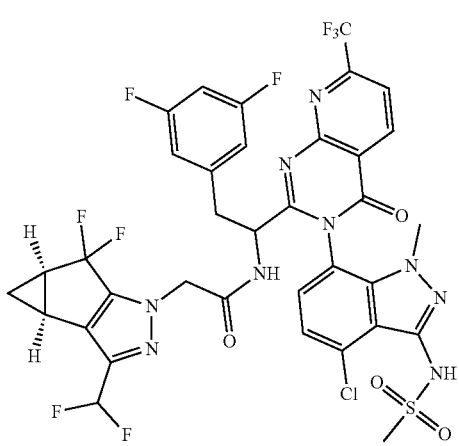
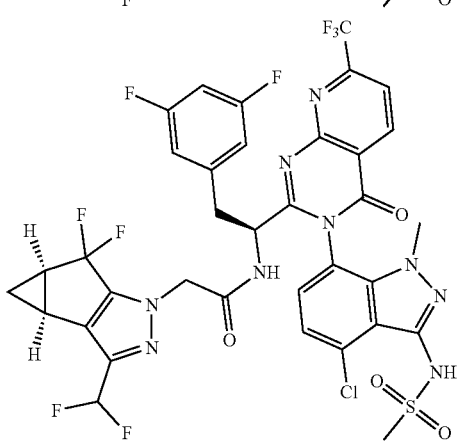
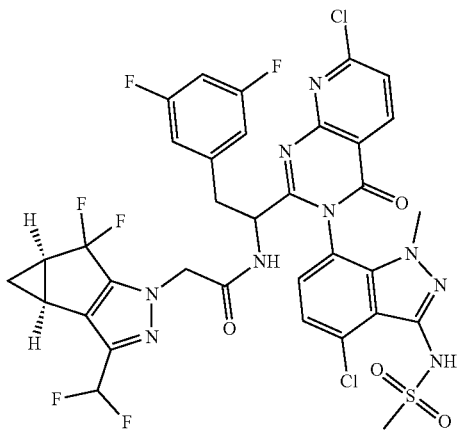

577
-continued
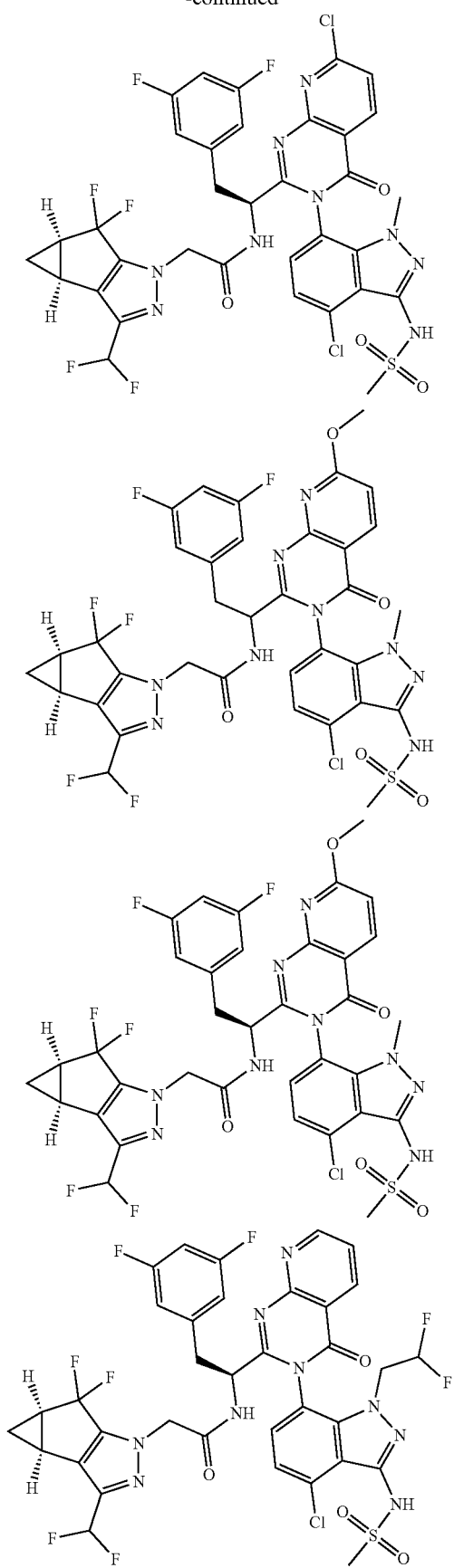
578
-continued
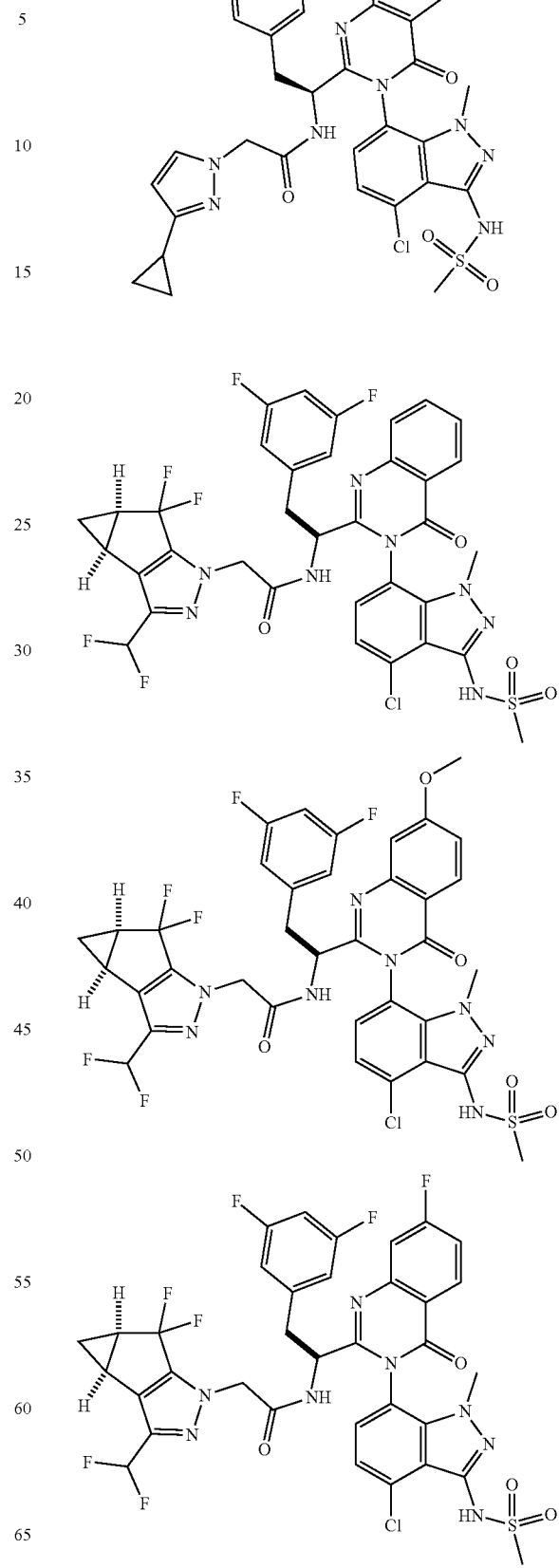

579
-continued
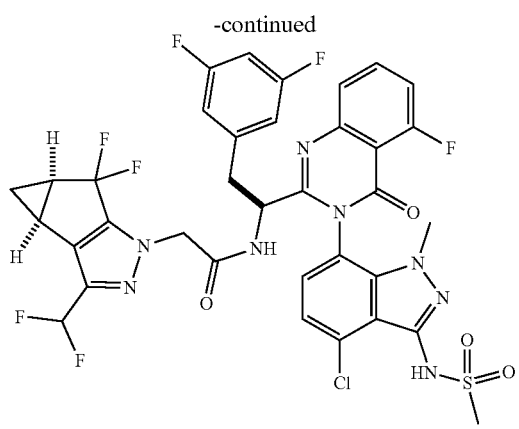
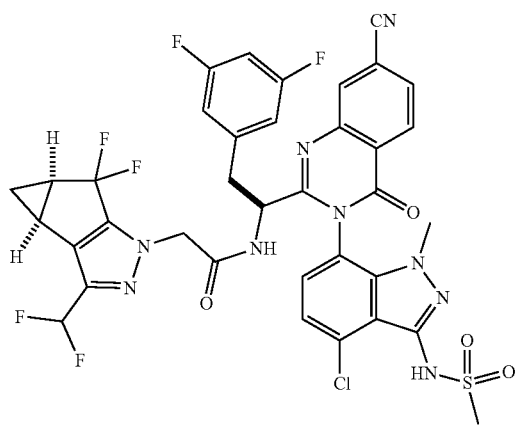
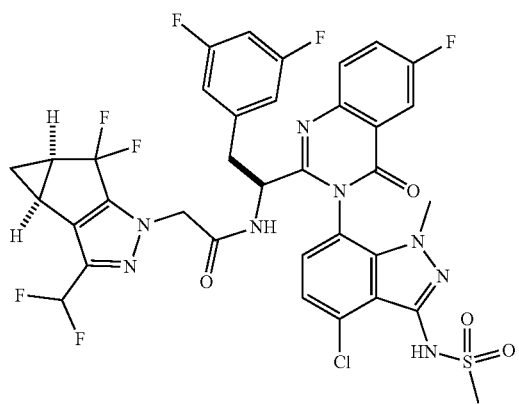
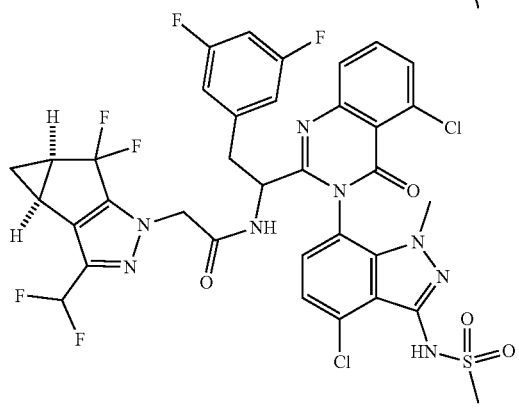
580
-continued
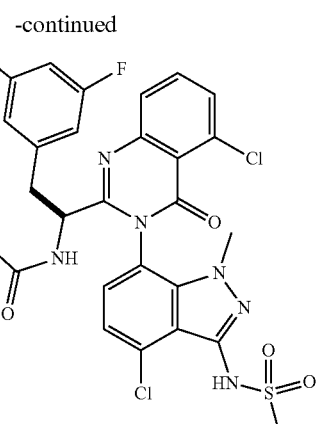
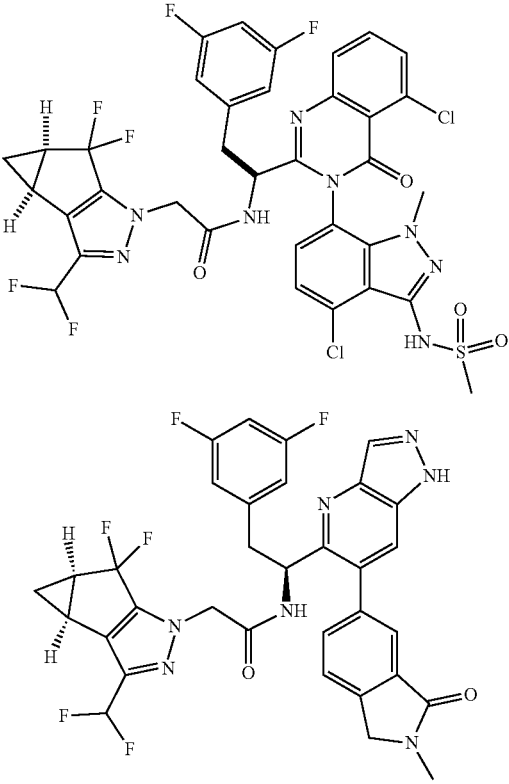
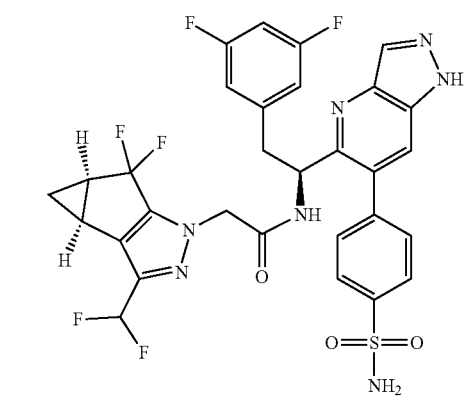
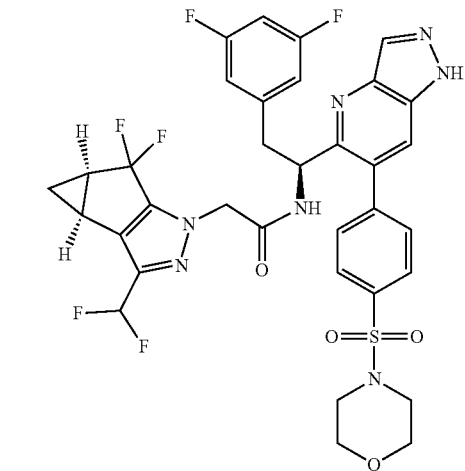

581
-continued
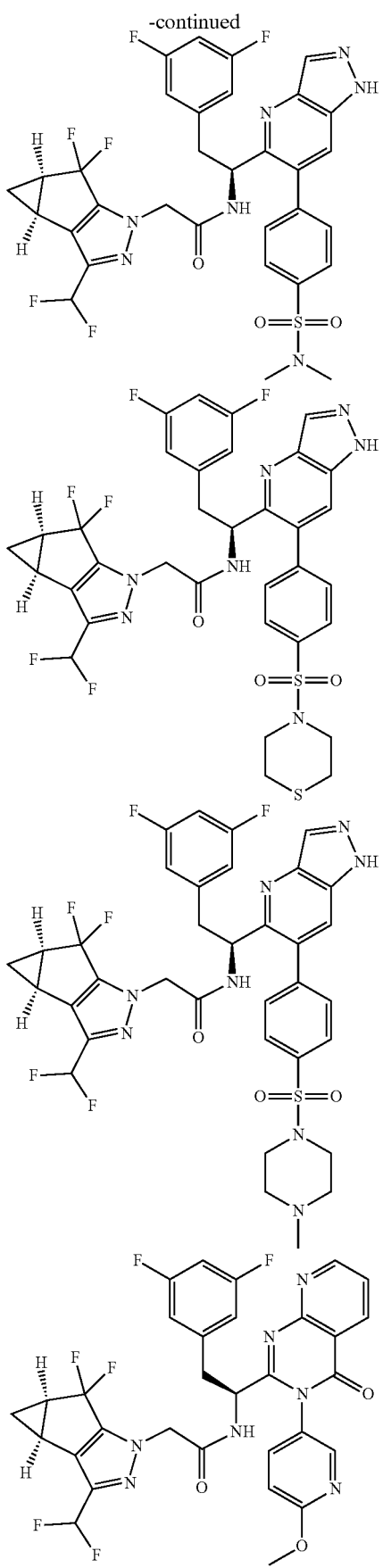
582
-continued
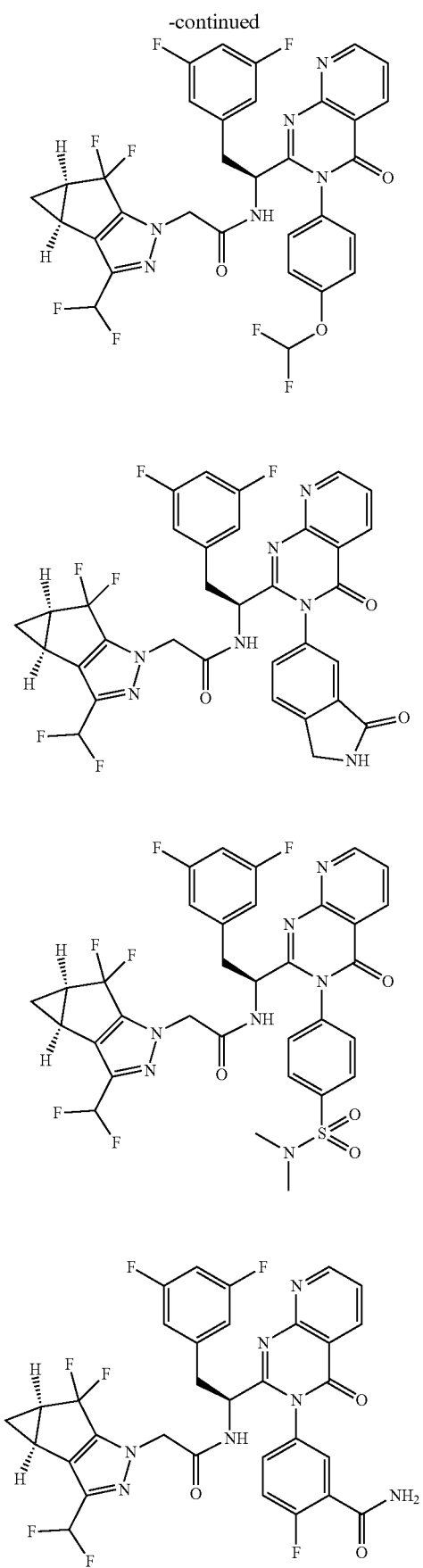

583
-continued
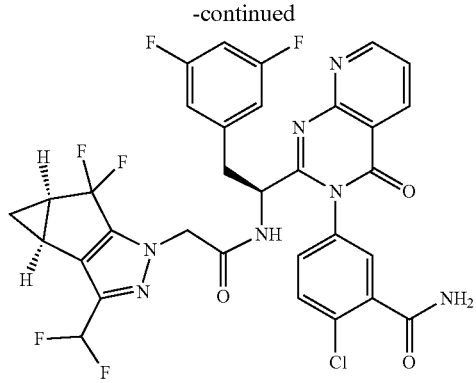
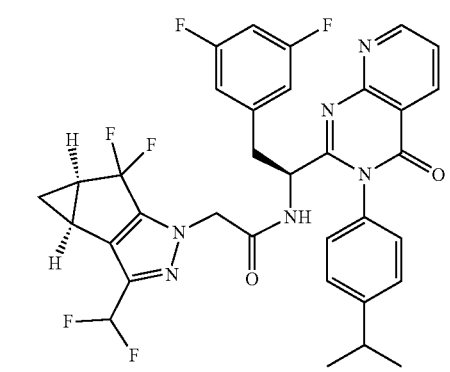
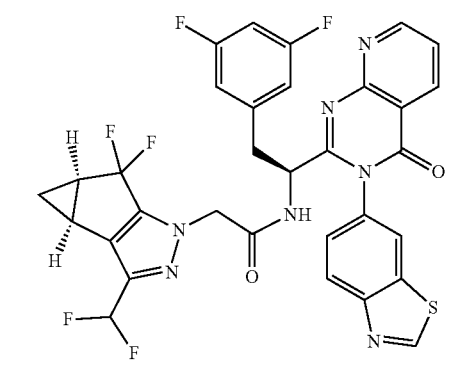
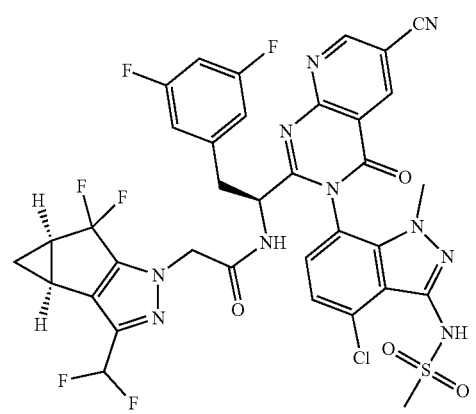
584
-continued
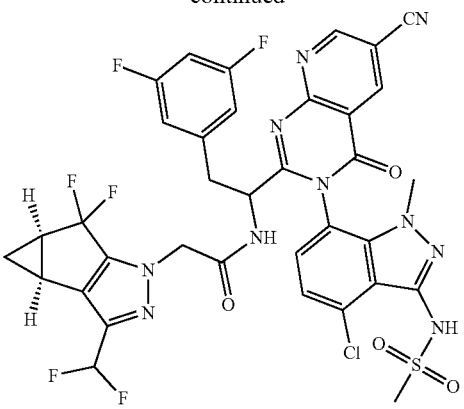
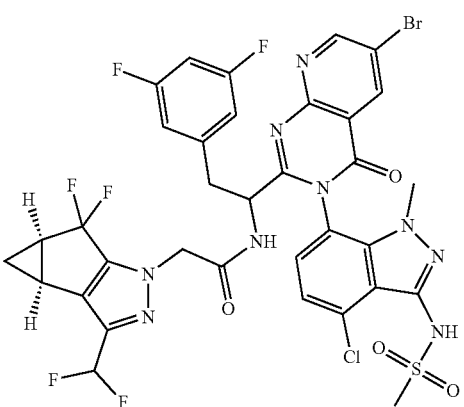
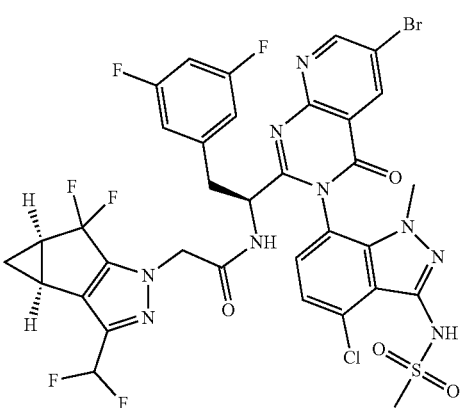
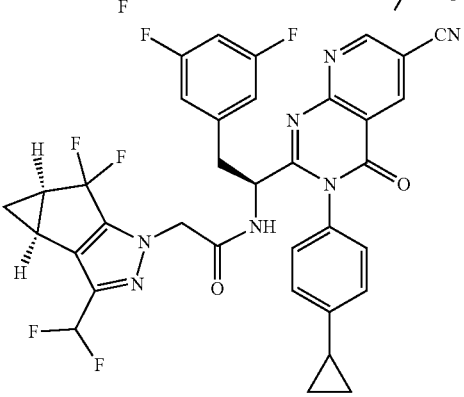

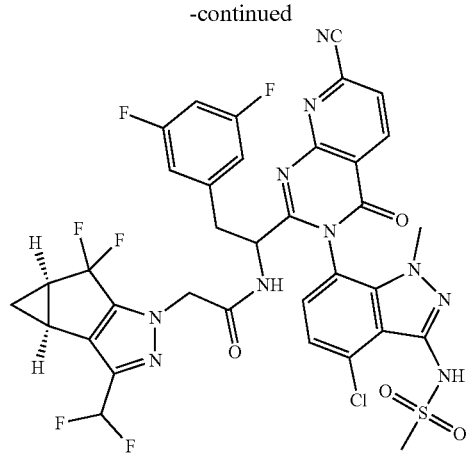
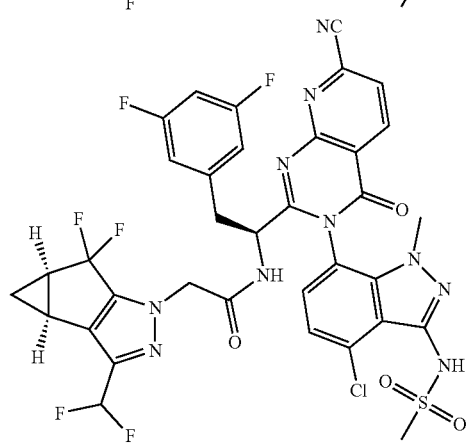
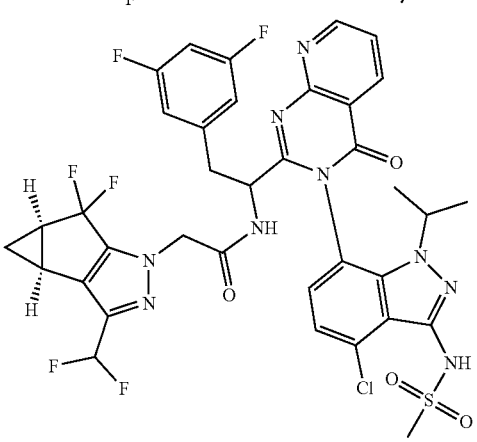
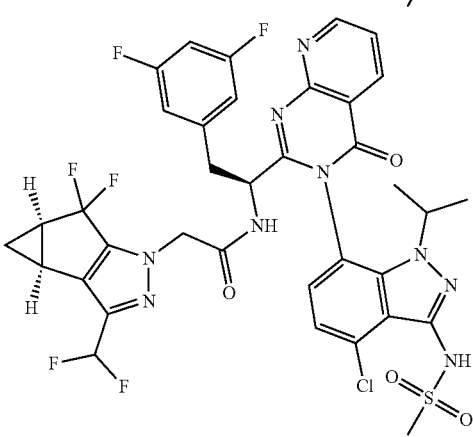
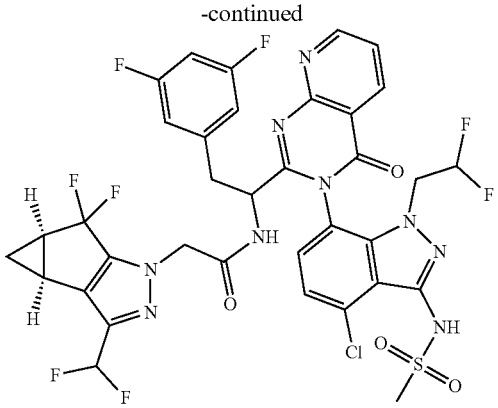
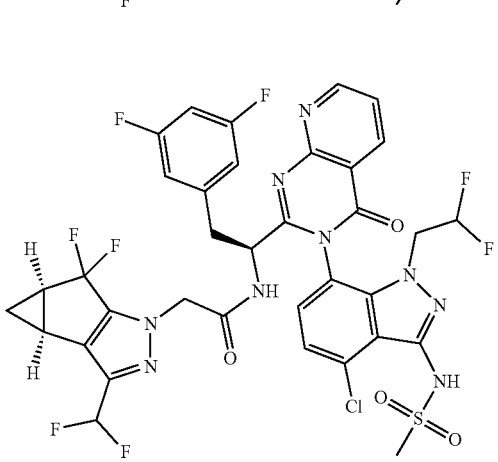
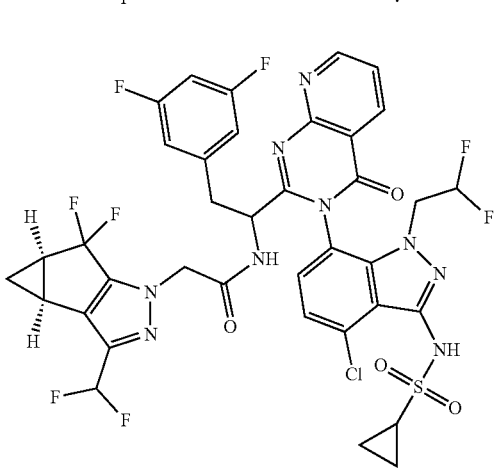

587
-continued
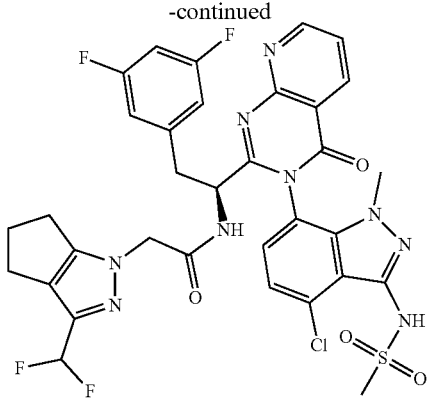
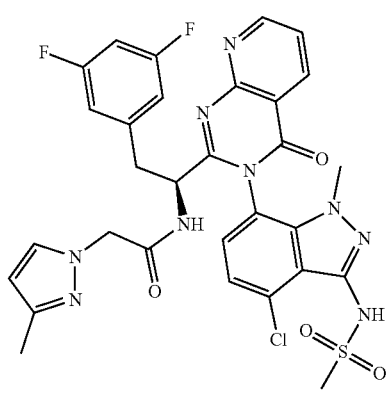
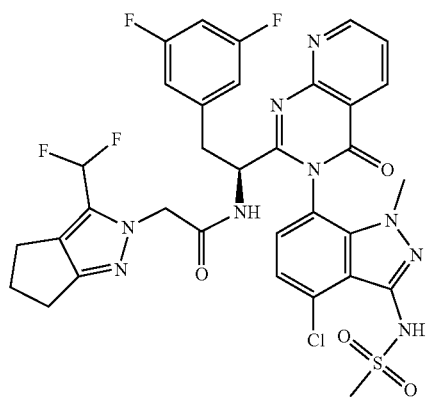
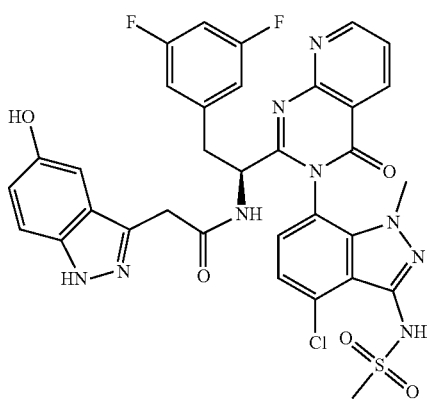
588
-continued
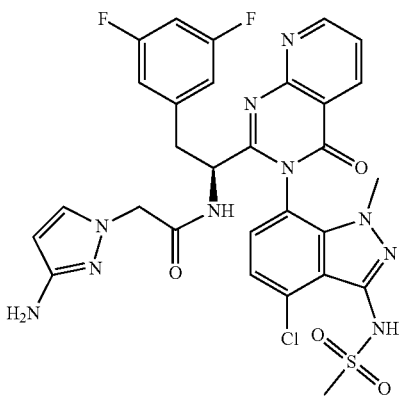
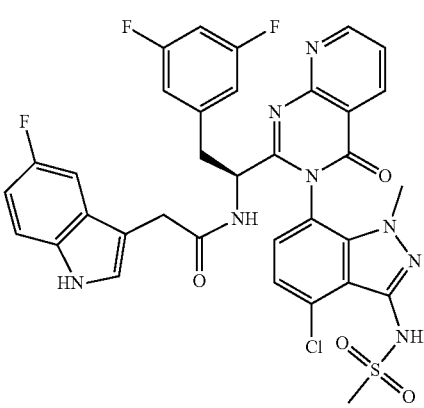
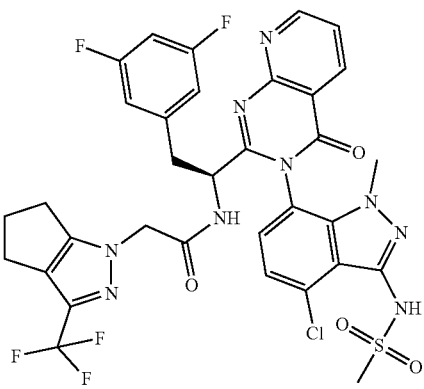
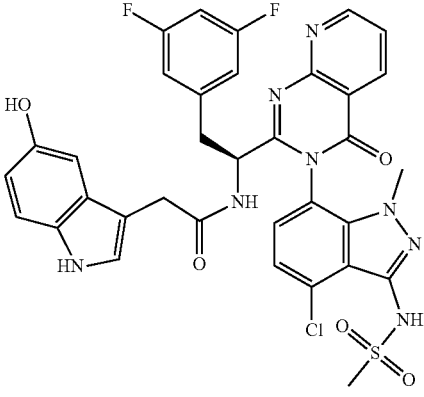

589
-continued
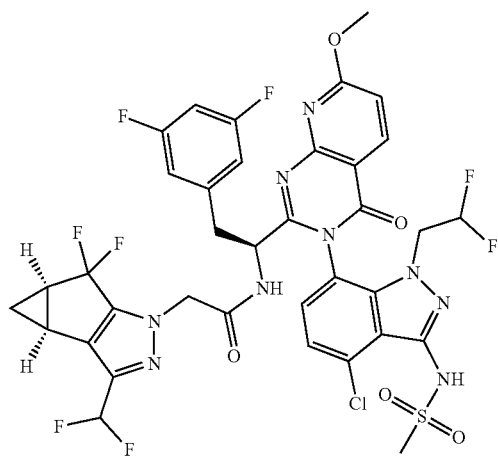
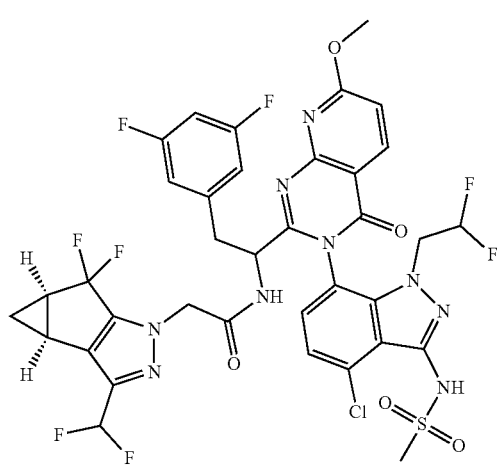
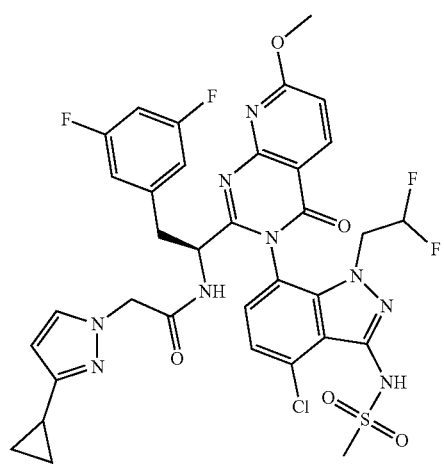 [SMILES: COc1ccc2c(=O)n(-c3ccc(Cl)c4c(NS(C)(=O)=O)nn(CC(F)F)c34)c([C@H](Cc3cc(F)cc(F)c3)NC(=O)Cn3ccc(C4CC4)n3)nc2n1]
590
-continued
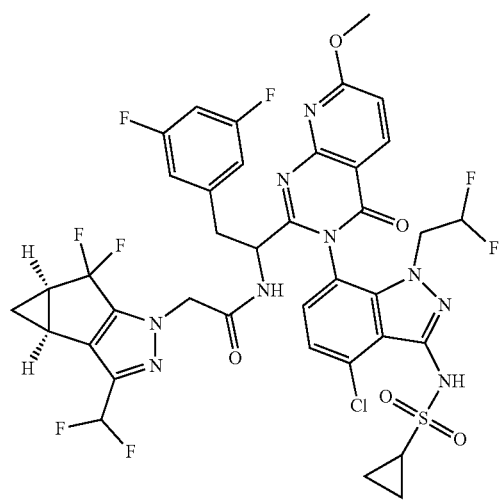
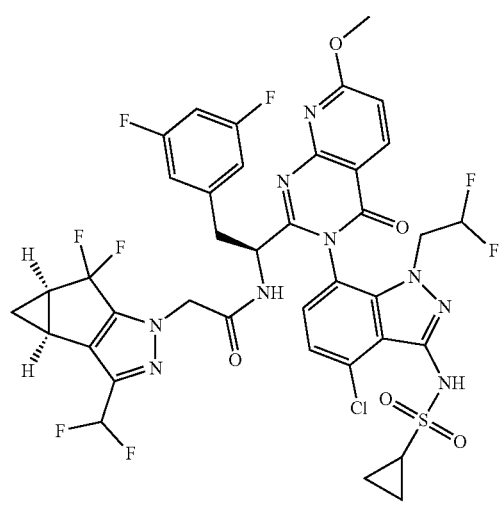

591
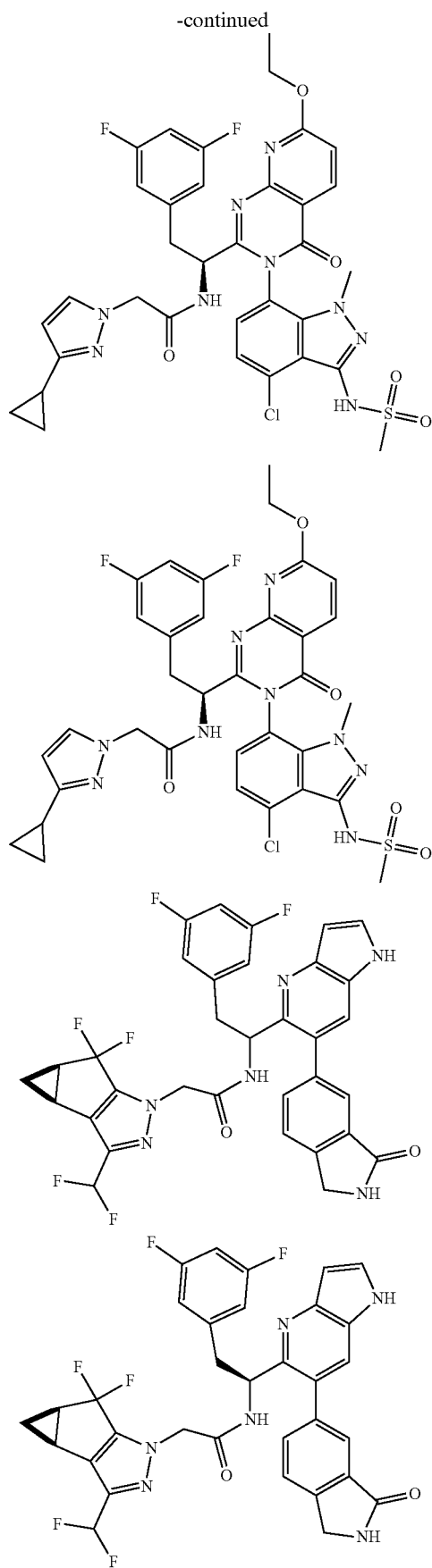
592
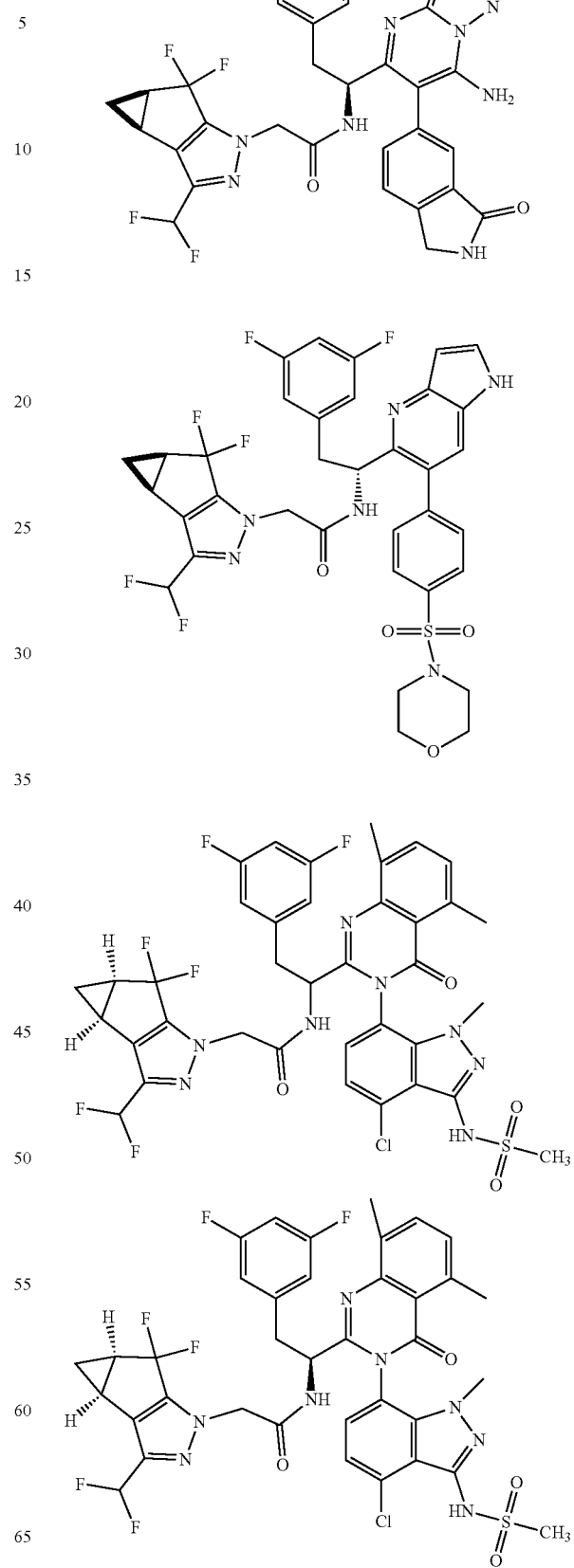

593                                             594
-continued                                      -continued
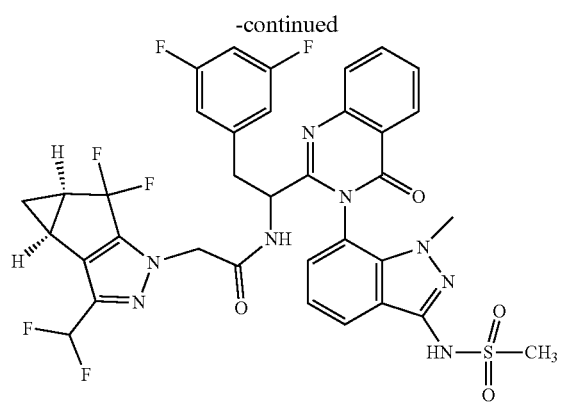
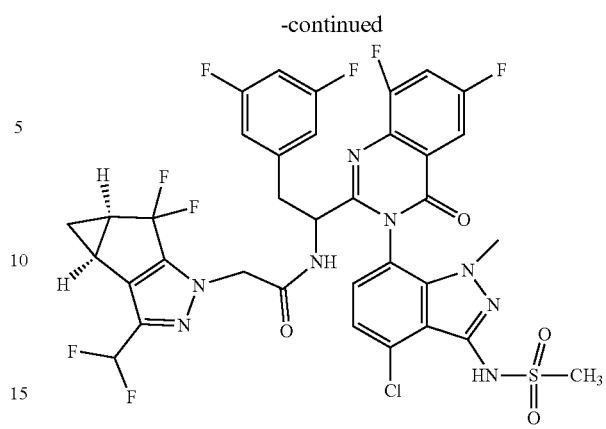
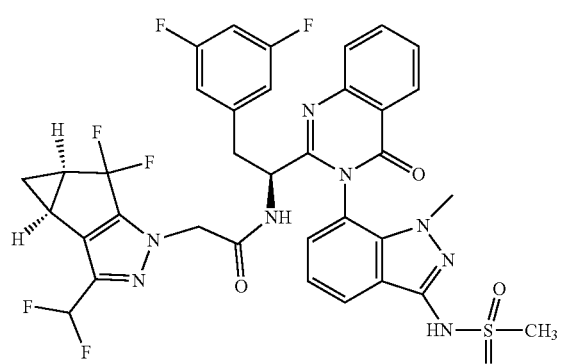
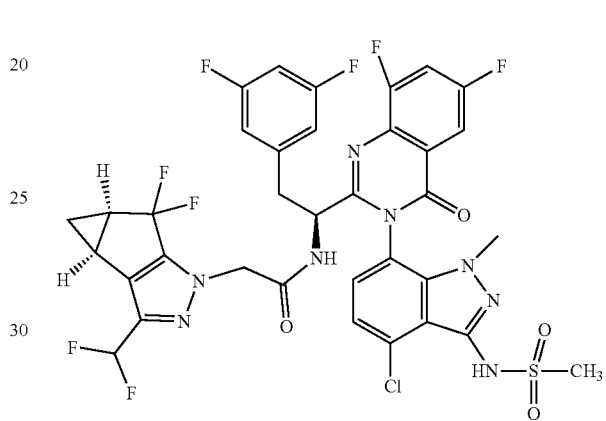
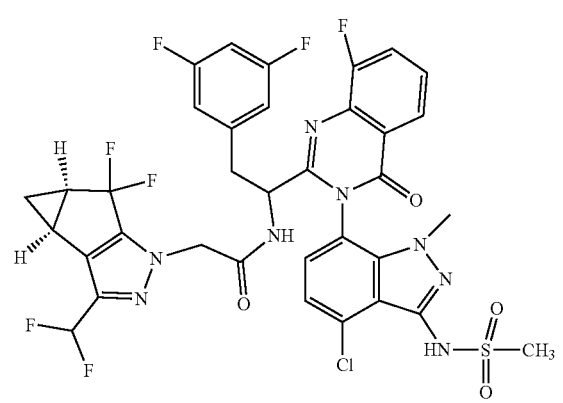
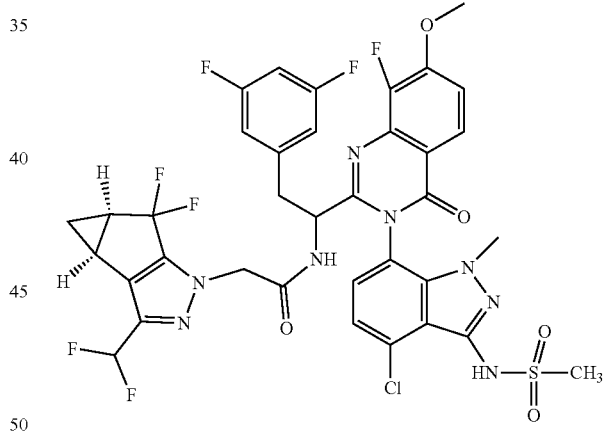
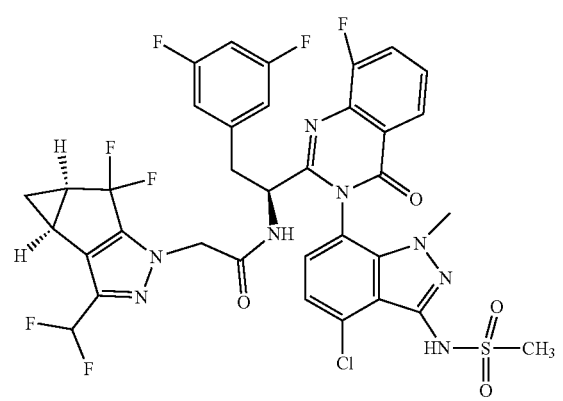
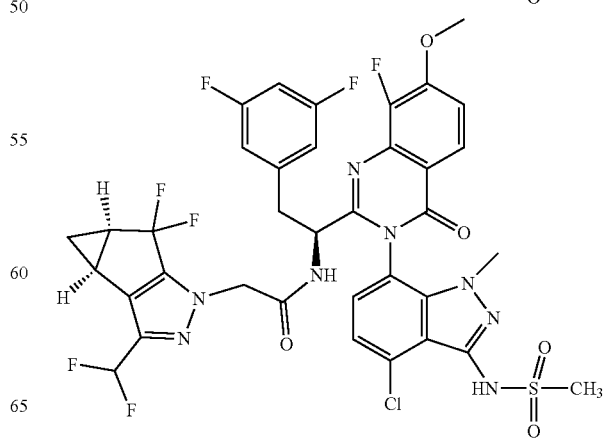

-continued
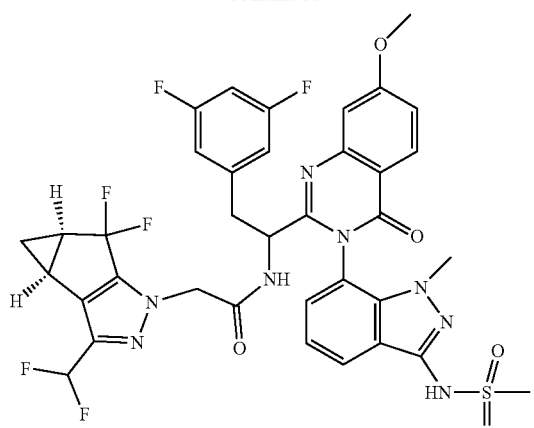
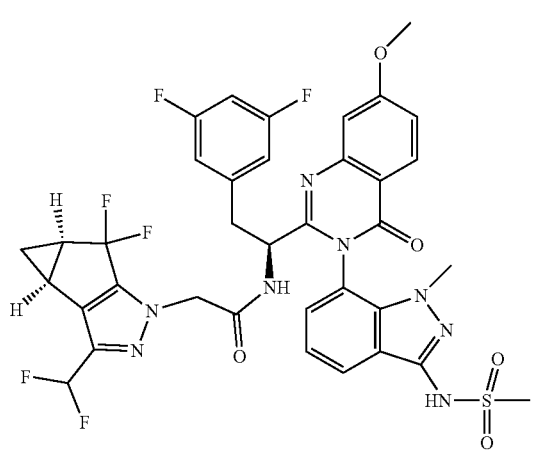
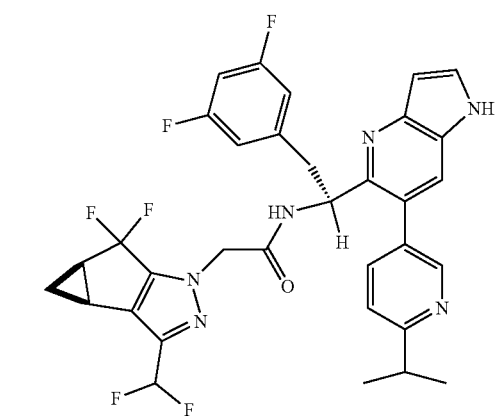
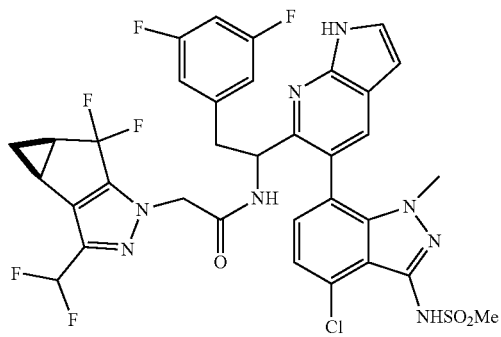
-continued
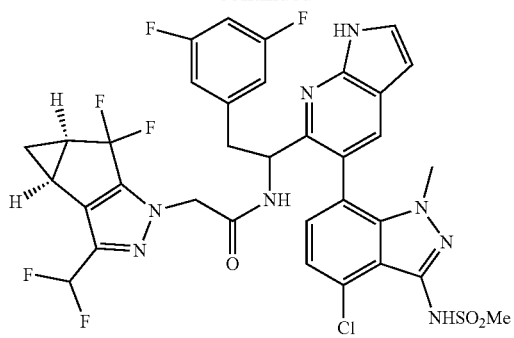
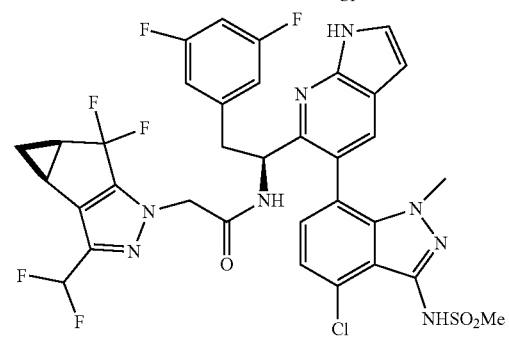
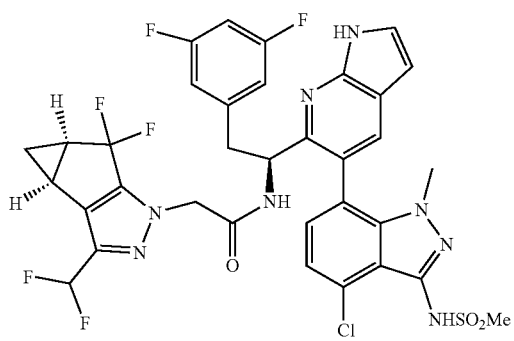
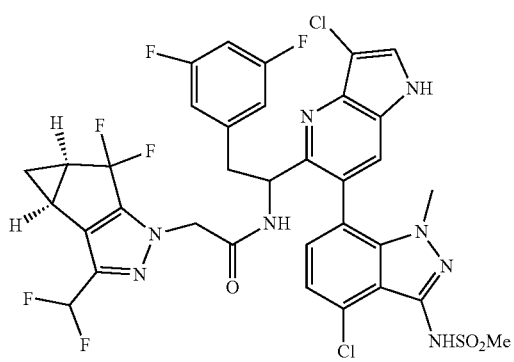
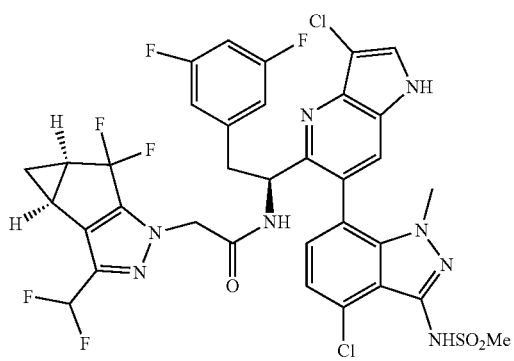

597
-continued
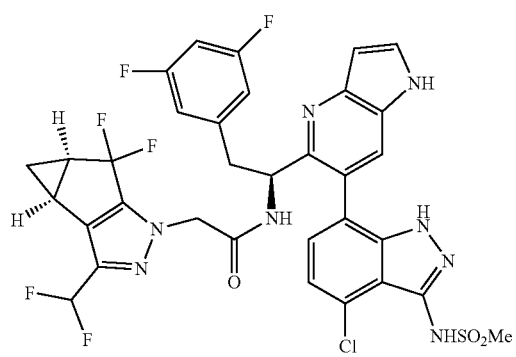
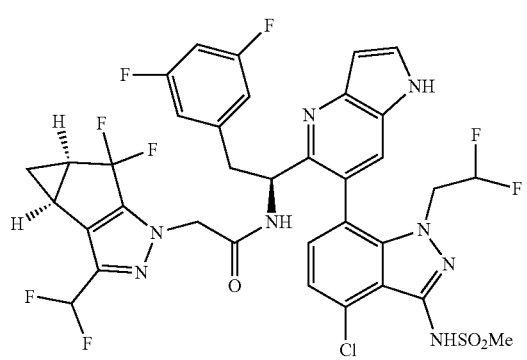
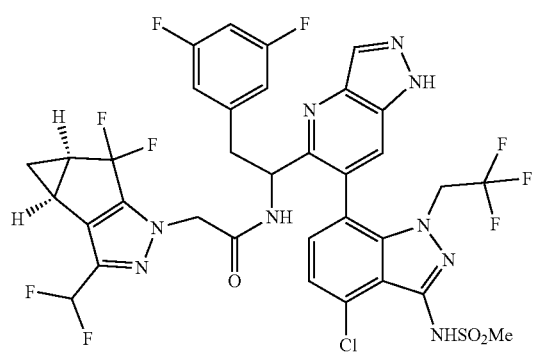
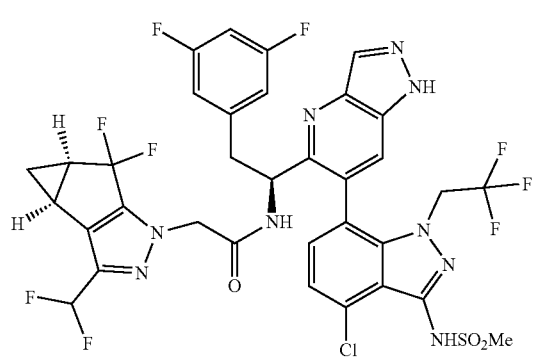
598
-continued
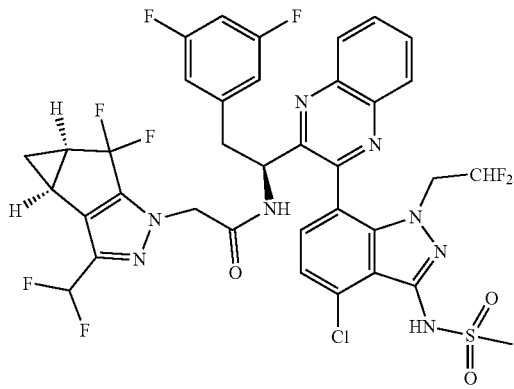
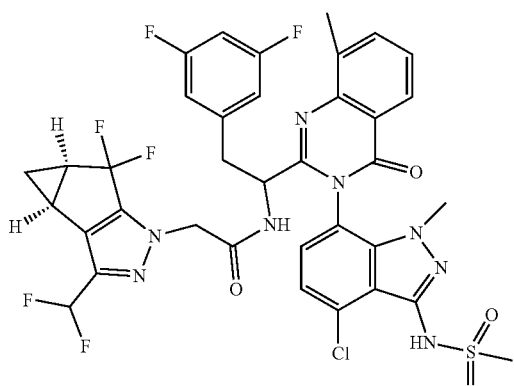
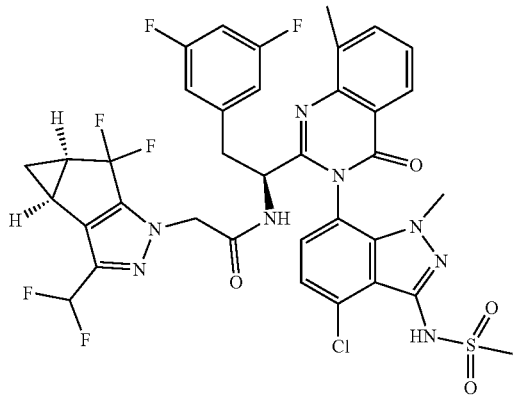
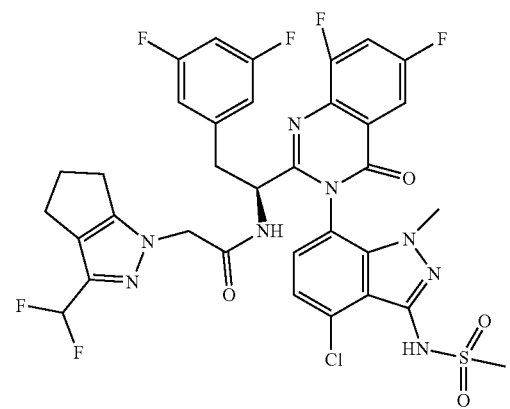

599
-continued
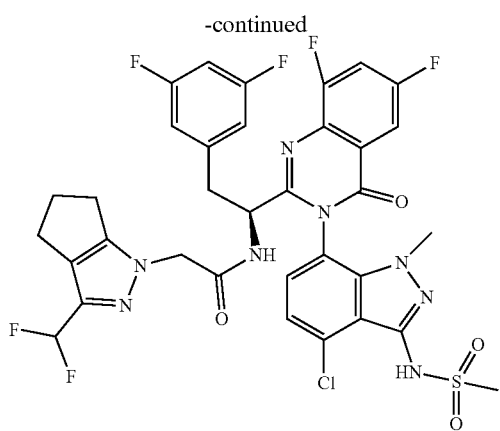
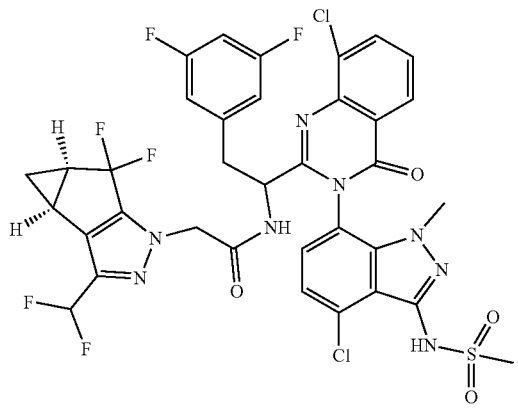
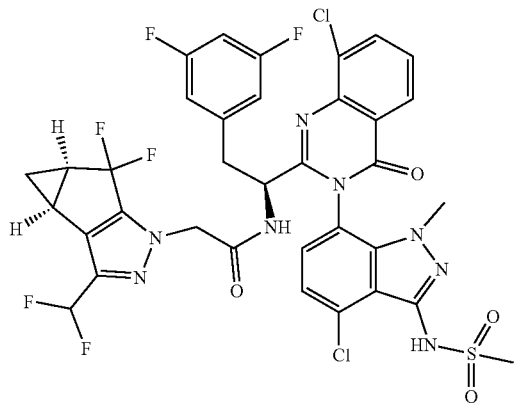
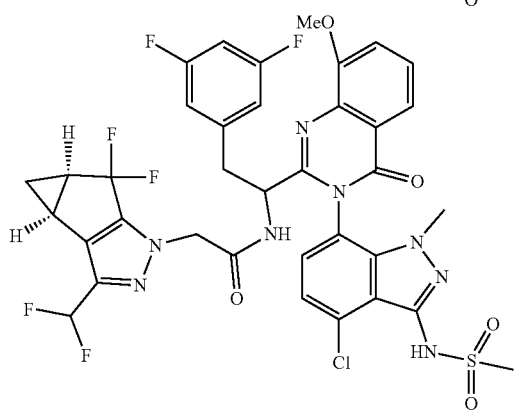
600
-continued
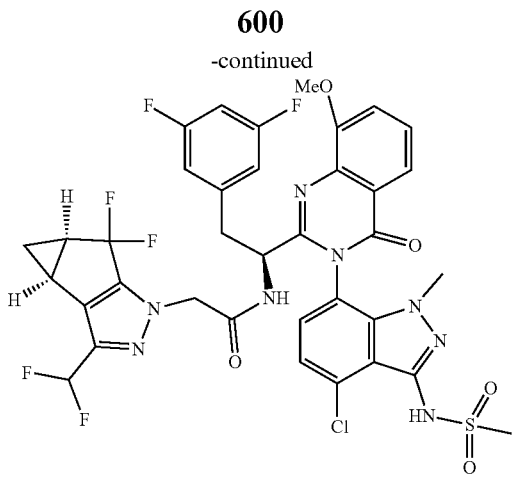
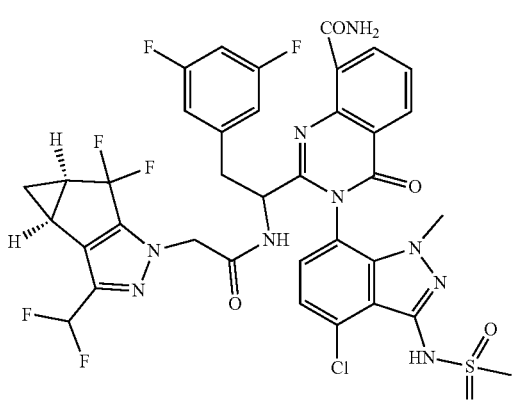
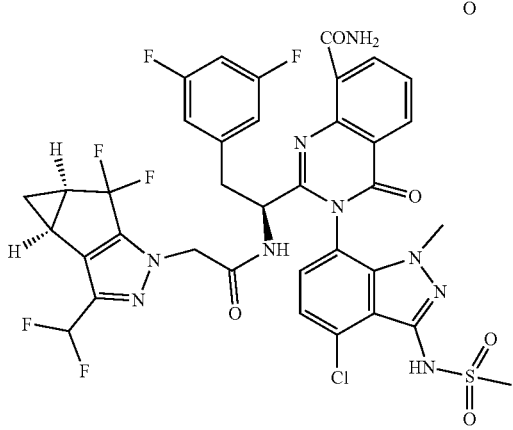
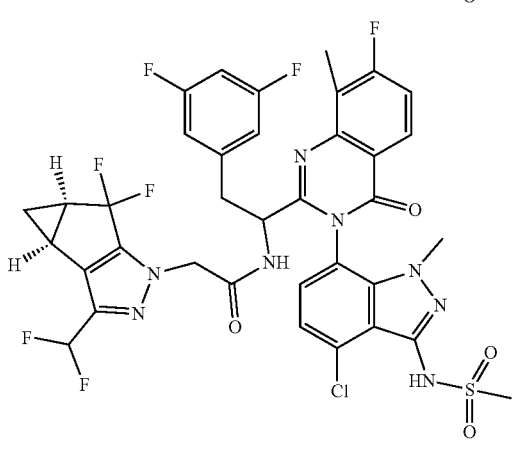

601
-continued
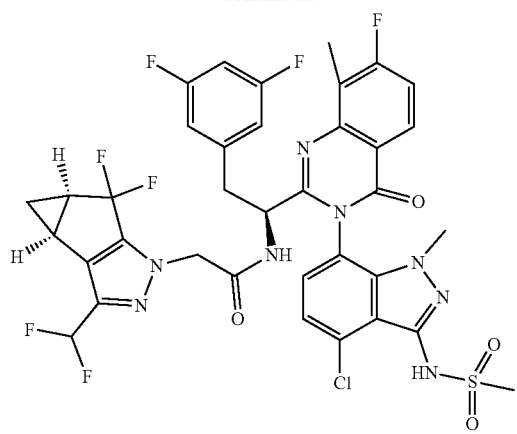
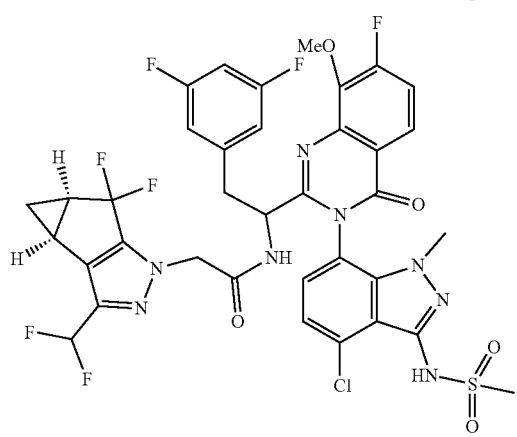
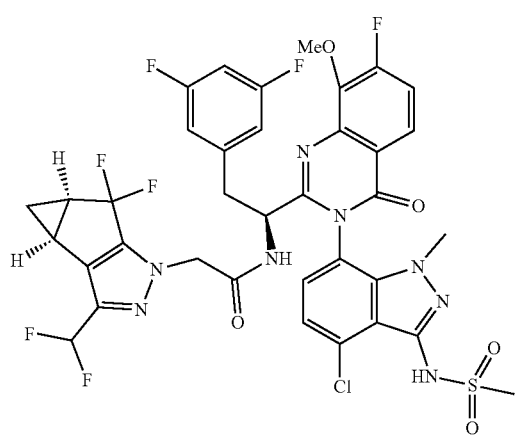
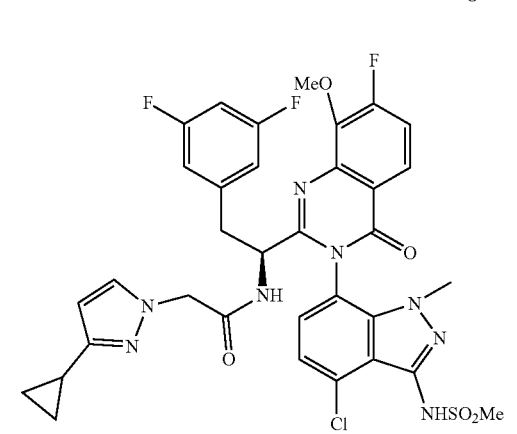
602
-continued
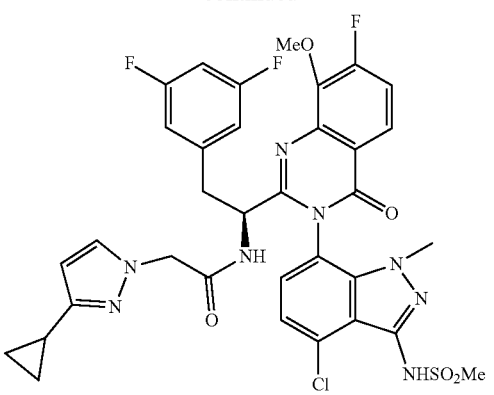
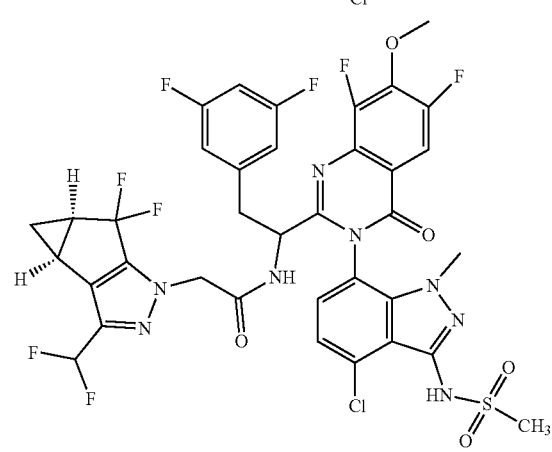
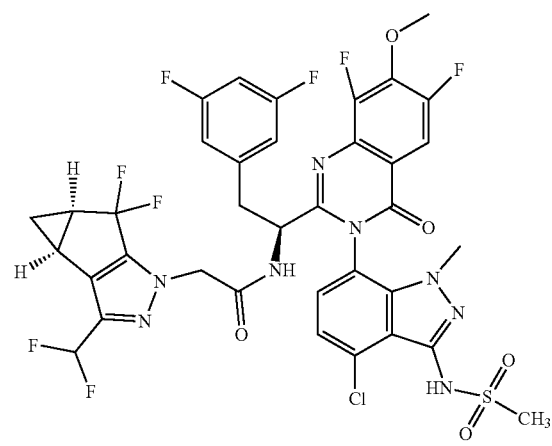
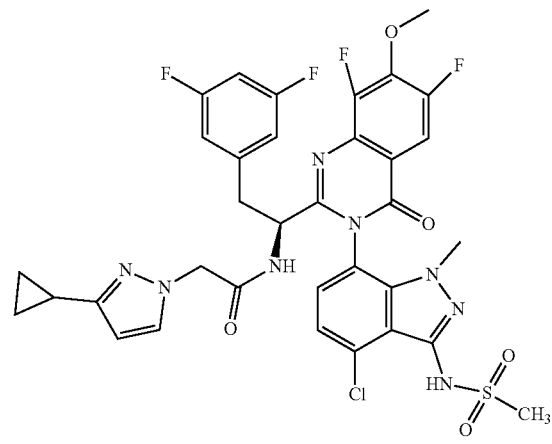

603
-continued
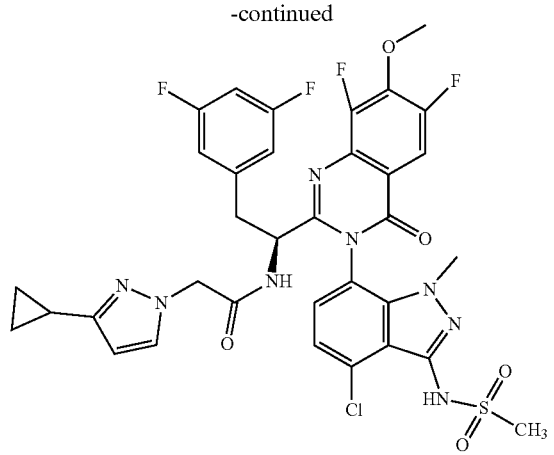
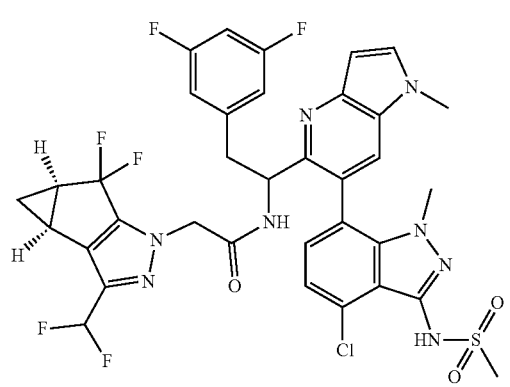
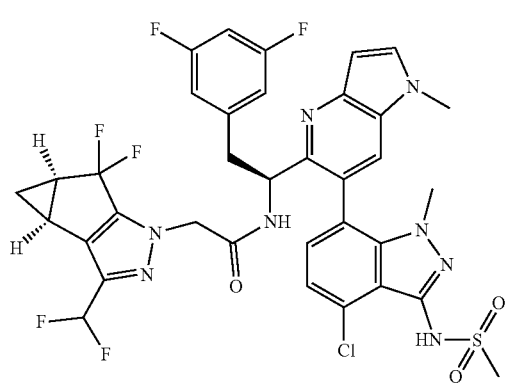
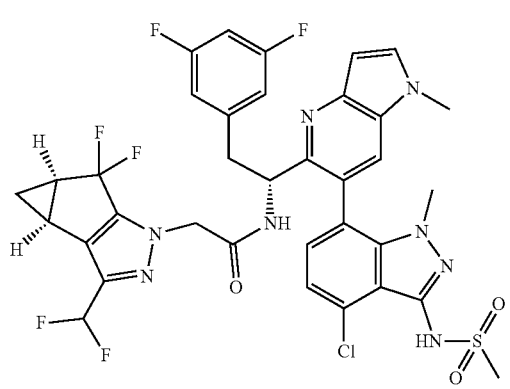
604
-continued
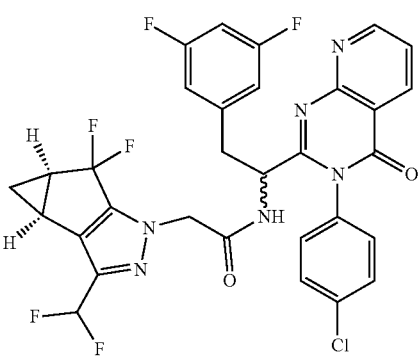
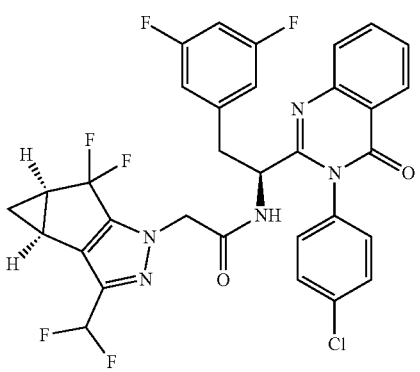
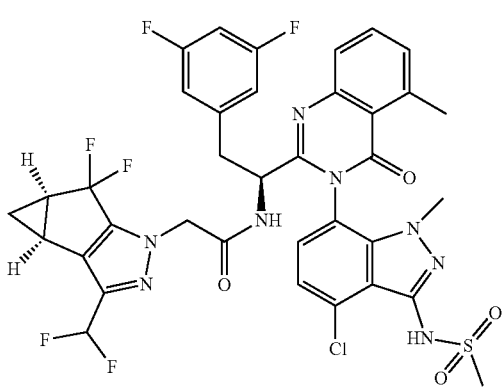
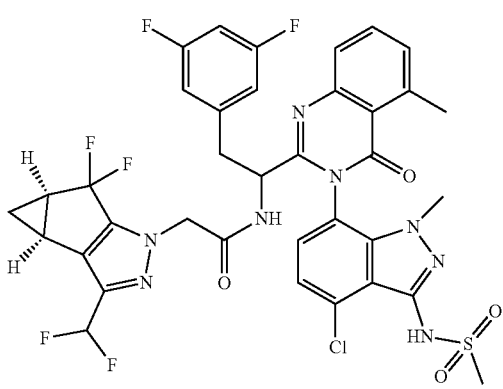

605
-continued
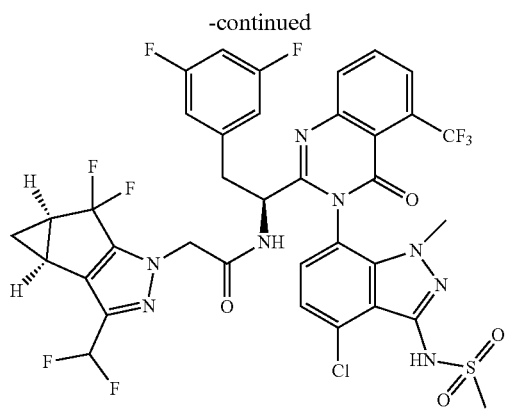
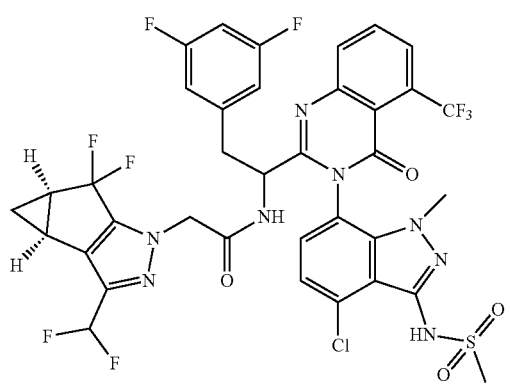
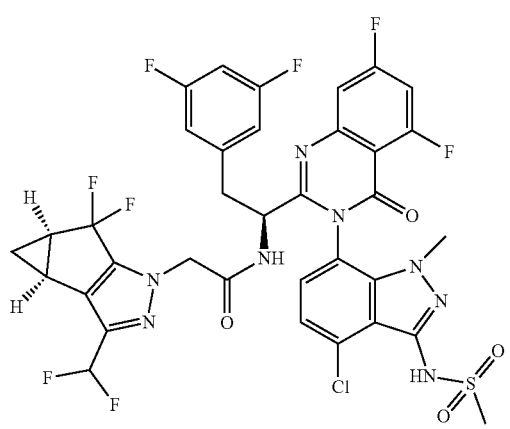
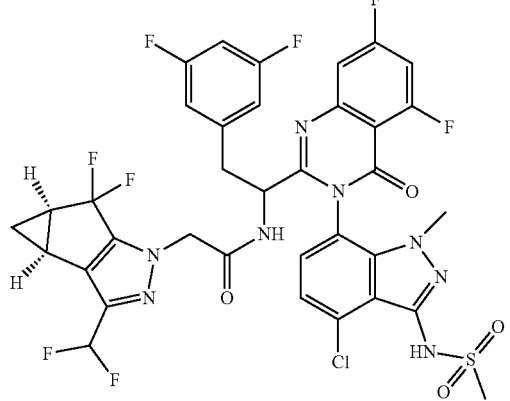
606
-continued
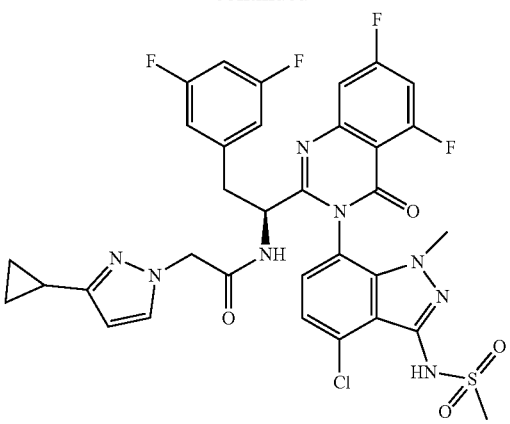
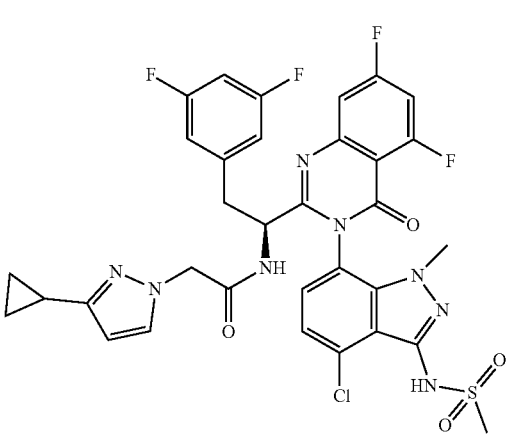
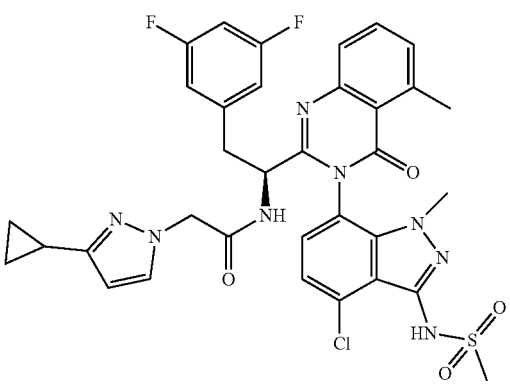
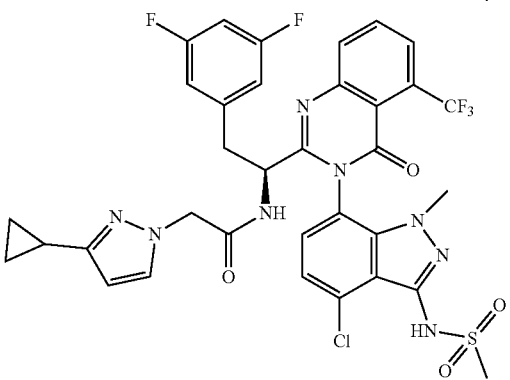

607
-continued
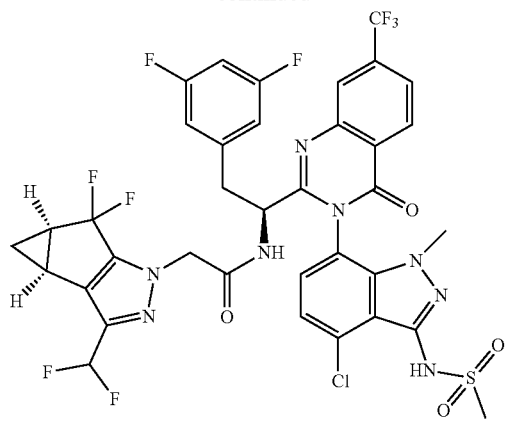
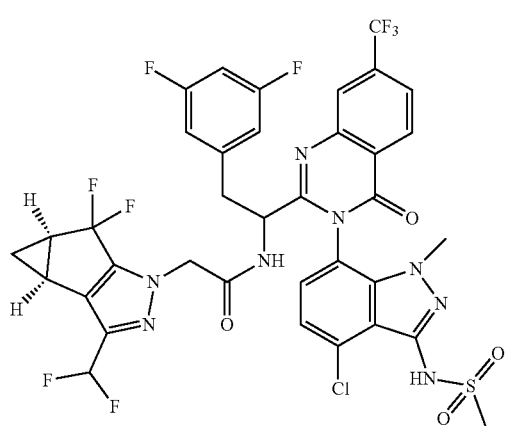
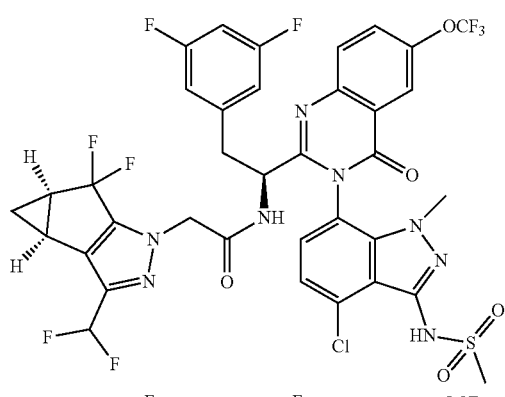
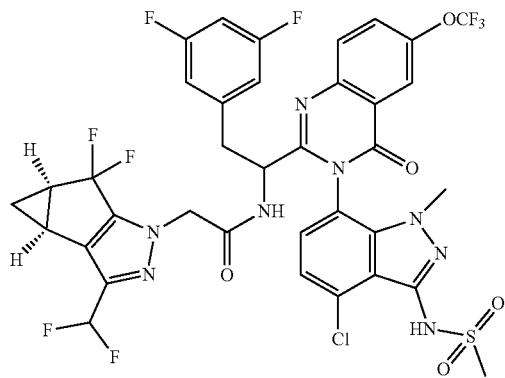
608
-continued
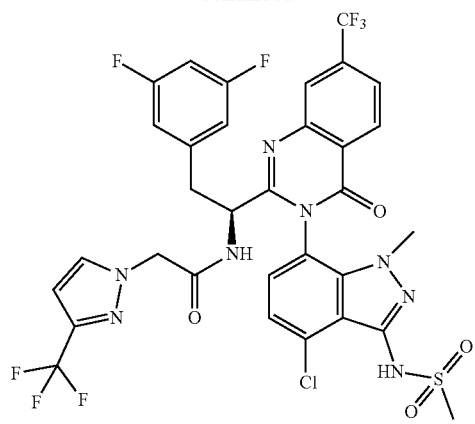
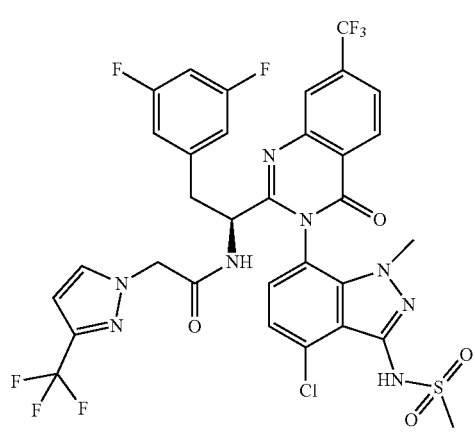
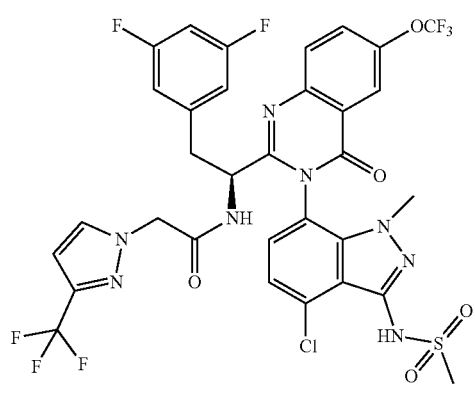
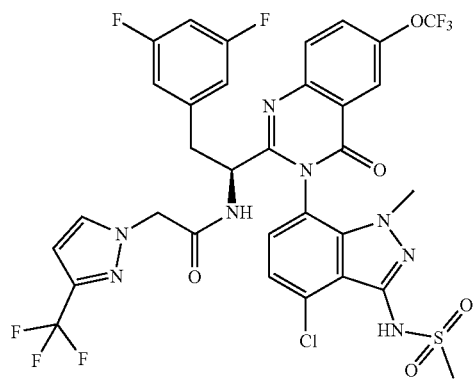

609
-continued
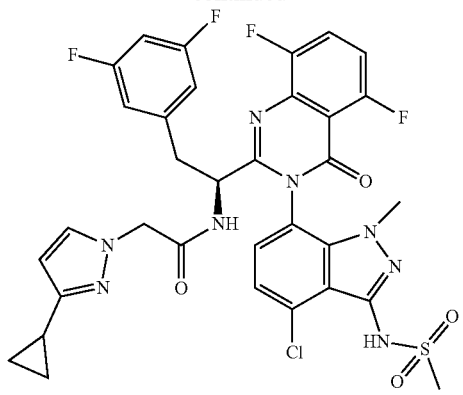
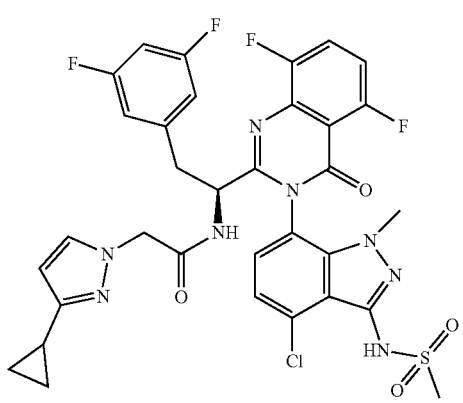
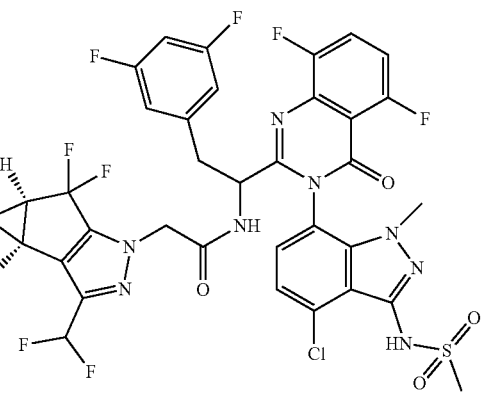
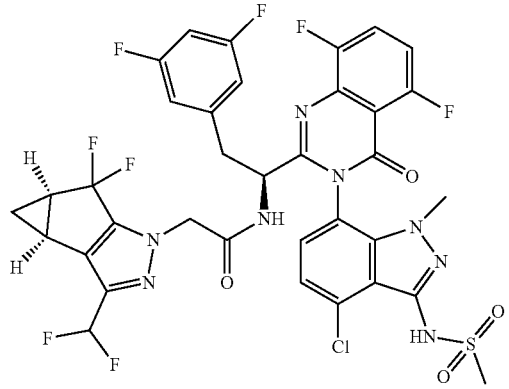
610
-continued
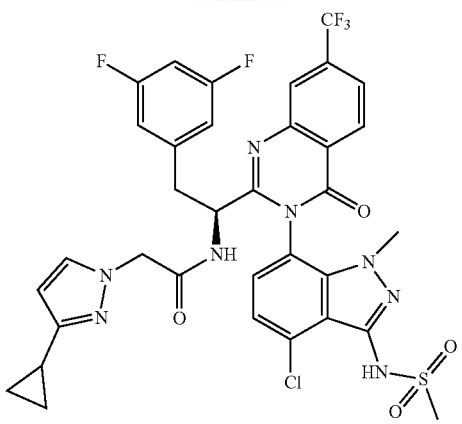
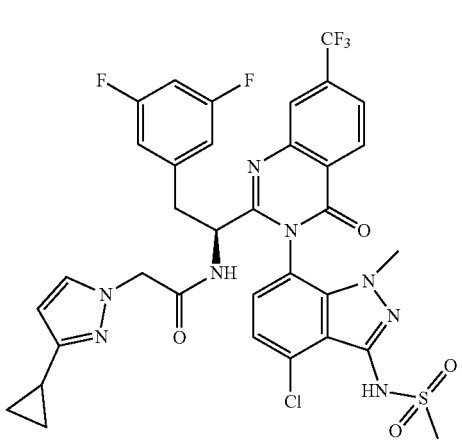
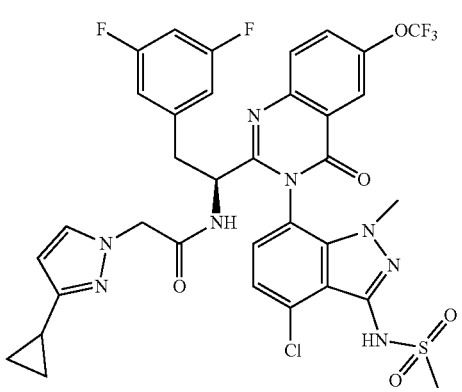
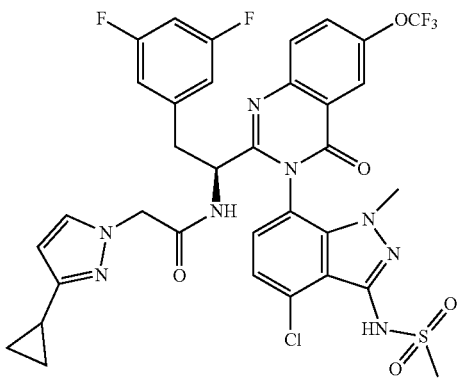

| 611 -continued | 612 -continued |
|---|---|
| 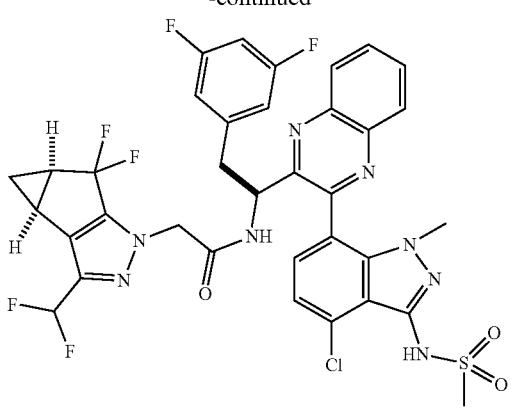 | 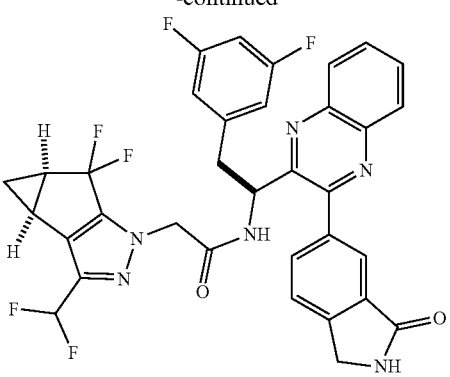 |
| 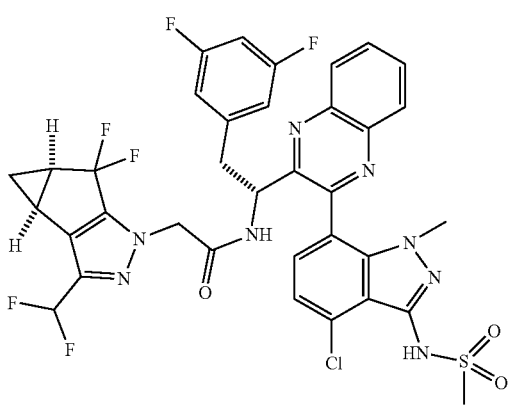 | 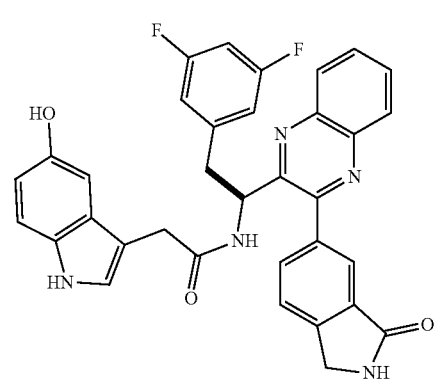 |
| 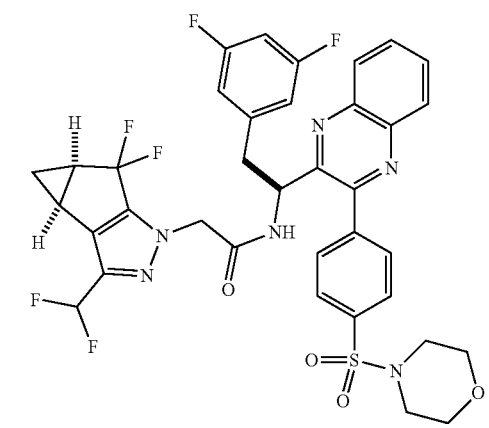 | 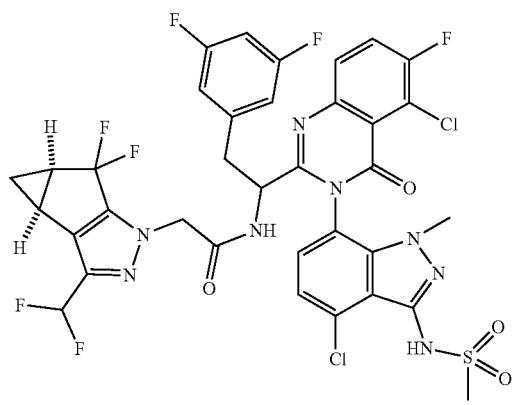 |
| 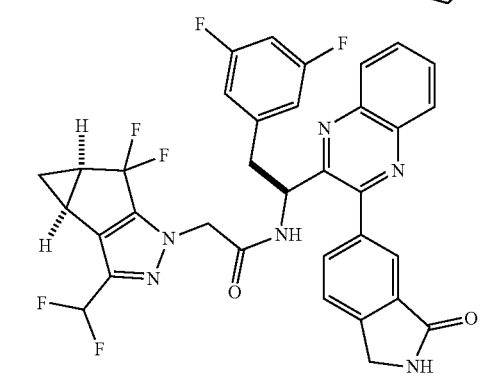 | 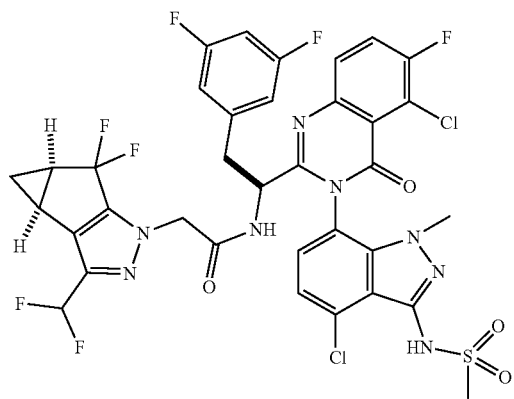 |

613
-continued
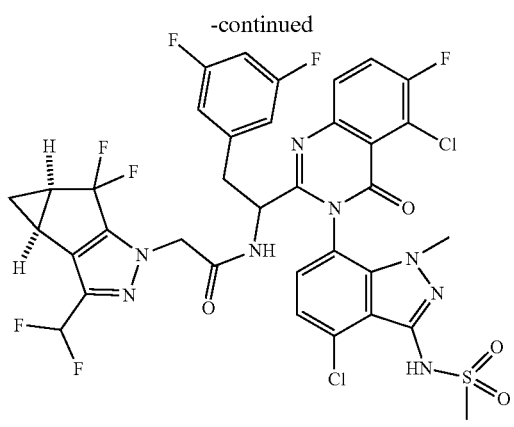
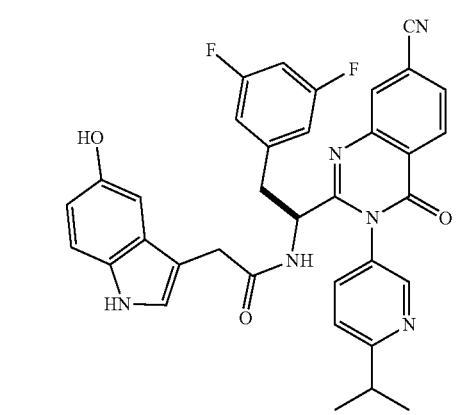
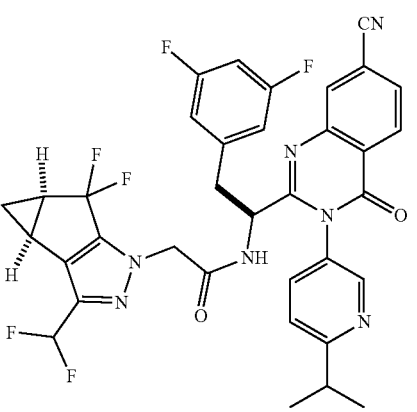
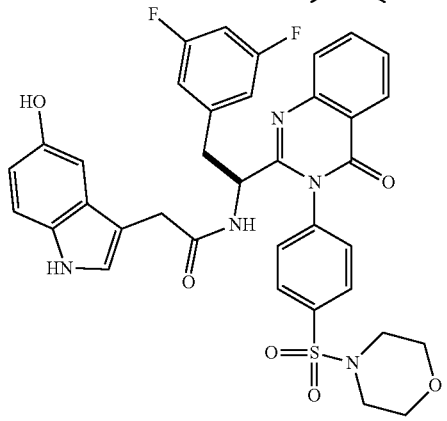
614
-continued
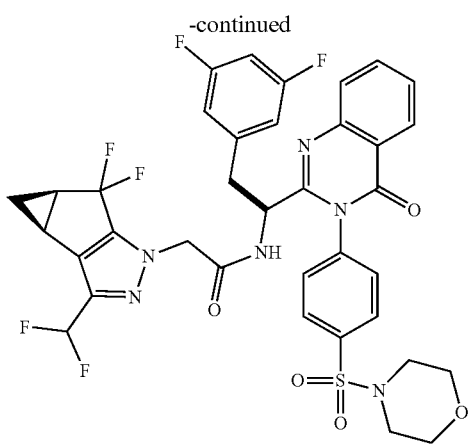
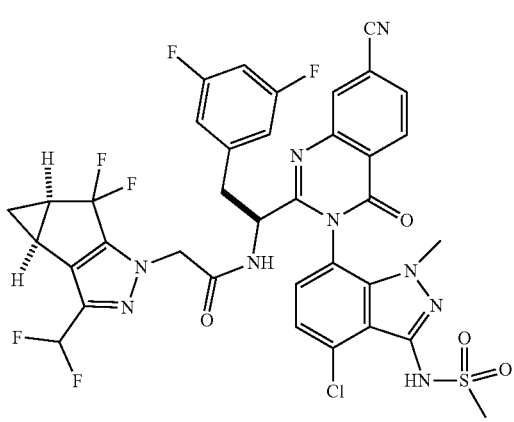
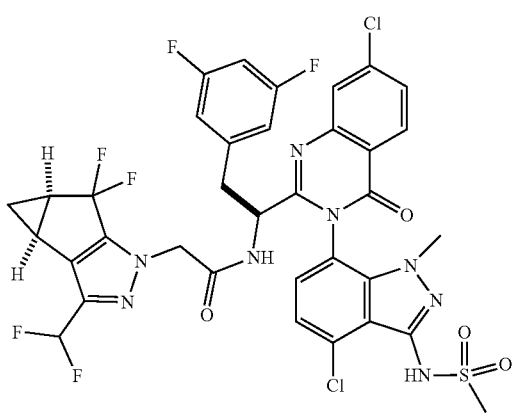
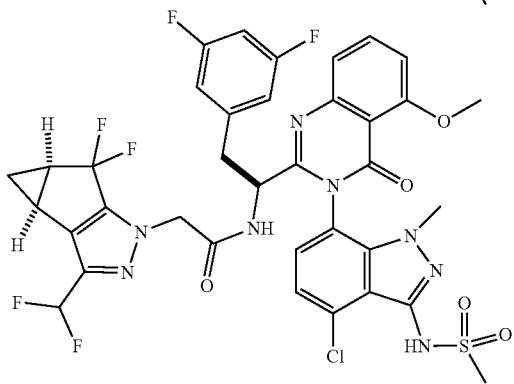

615
-continued
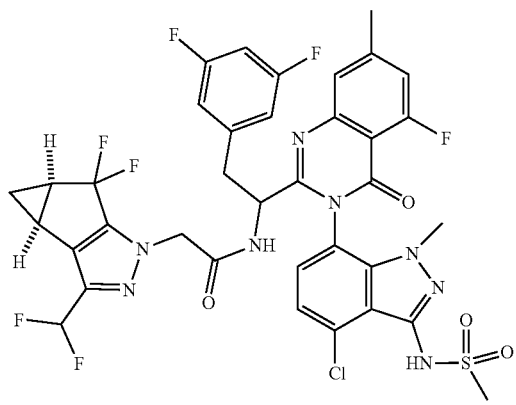
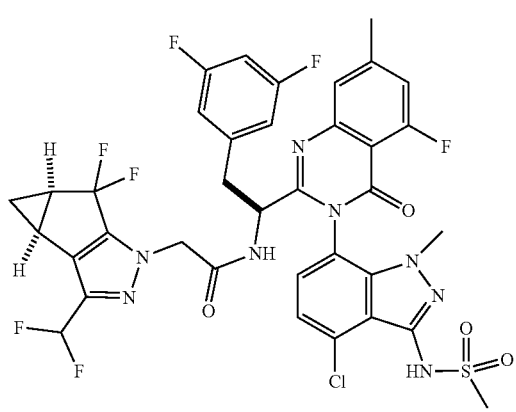
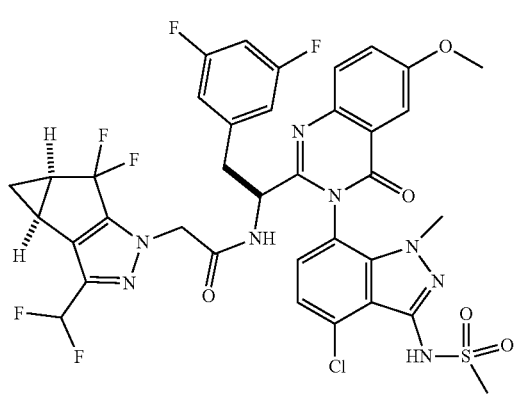
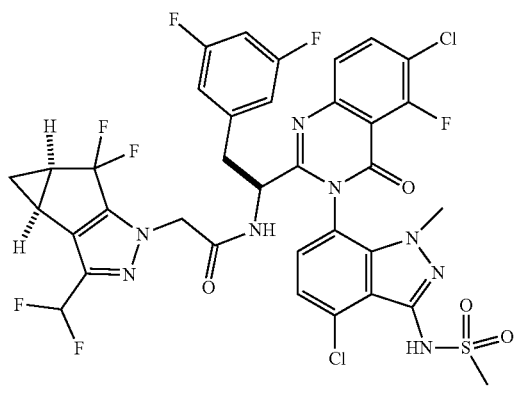
616
-continued
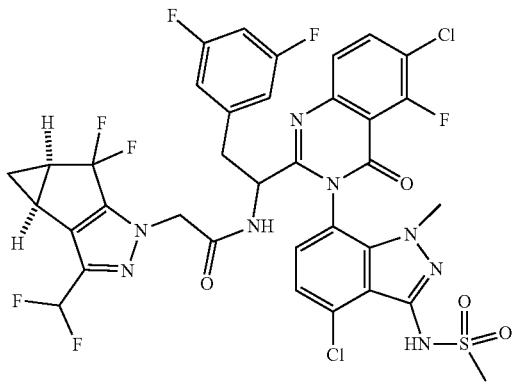
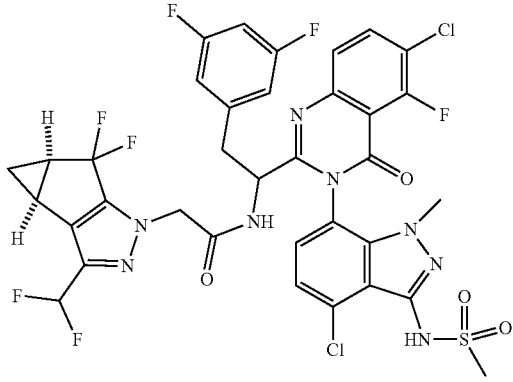
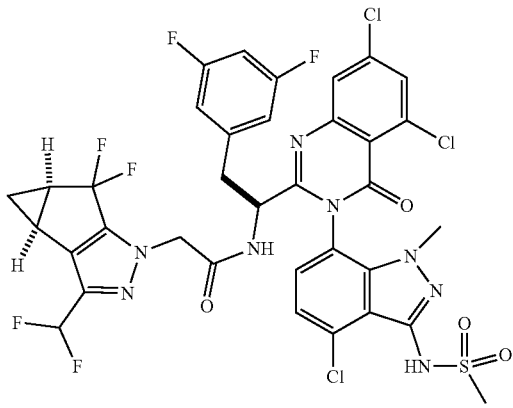
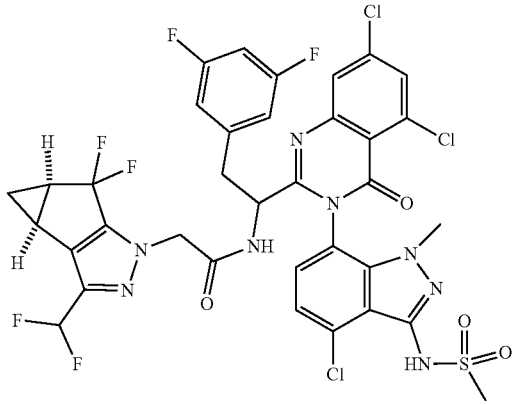

617
-continued
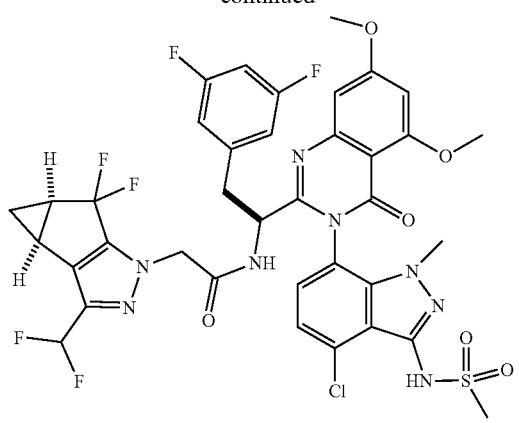
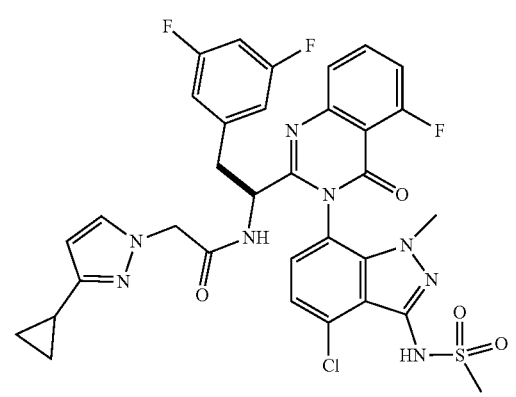
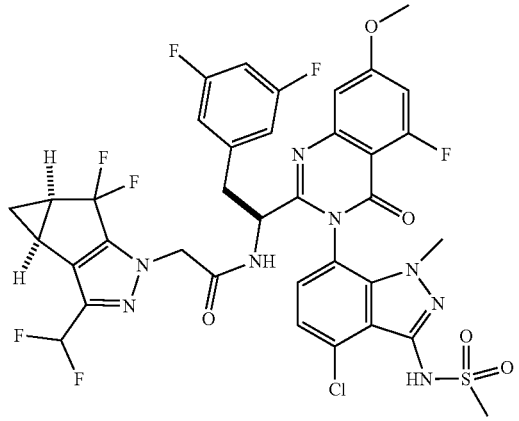
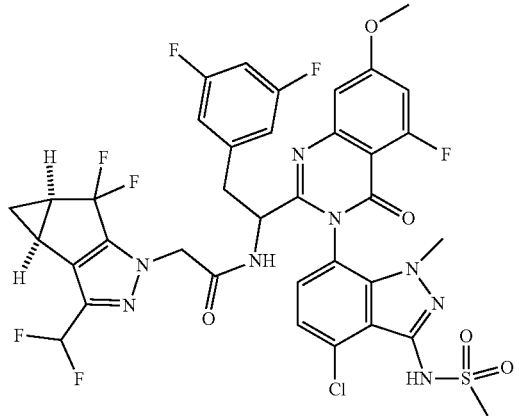
618
-continued
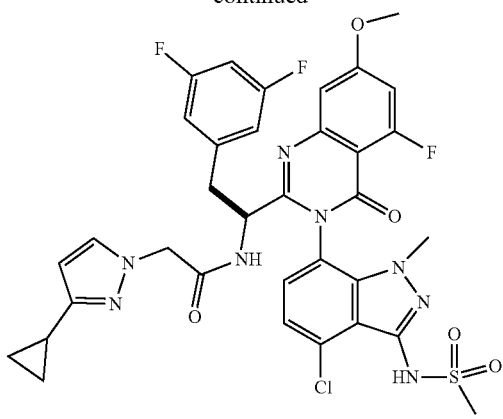
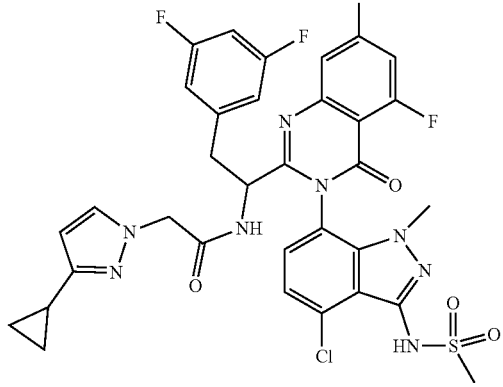
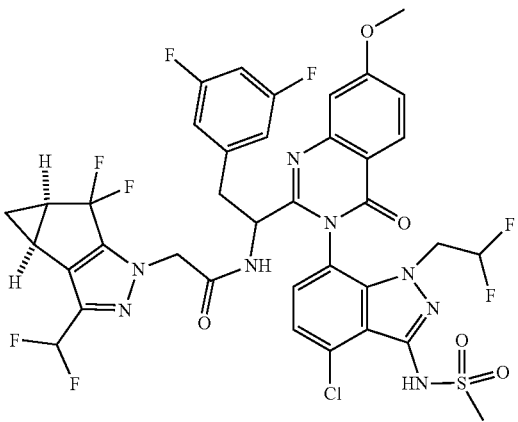
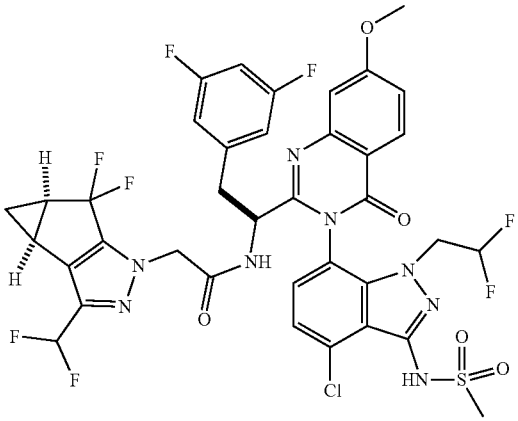

619
-continued
620
-continued
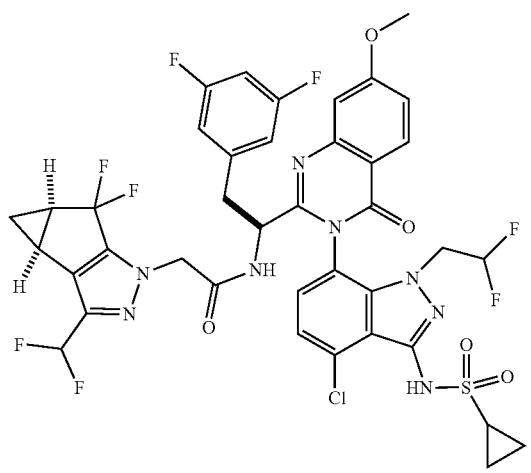
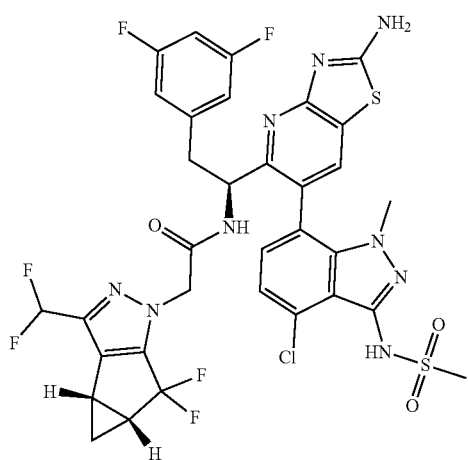
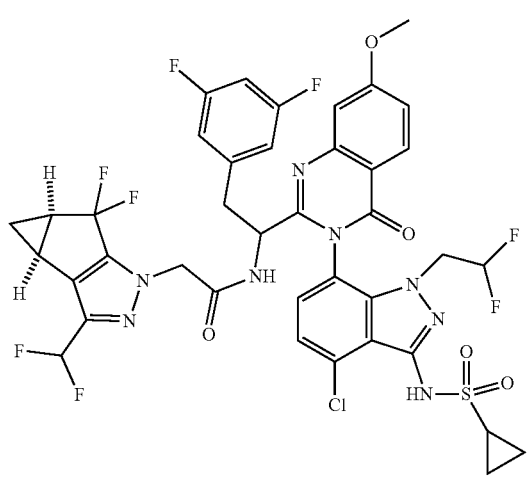
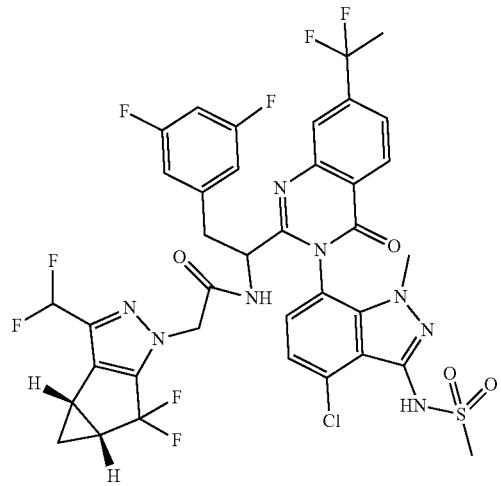
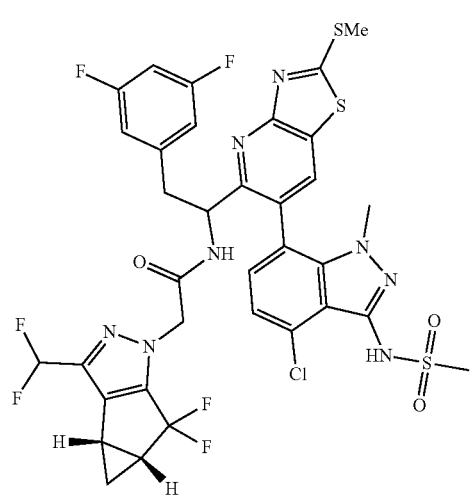
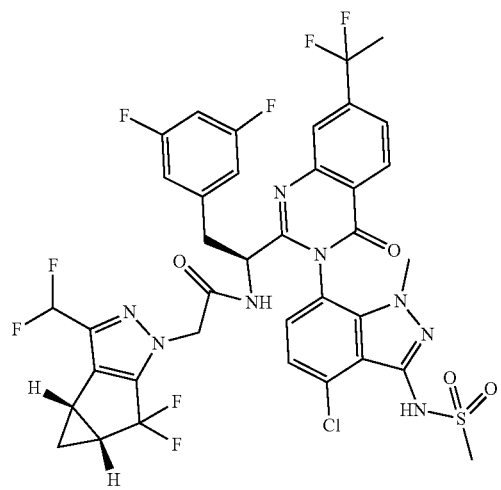

621
-continued
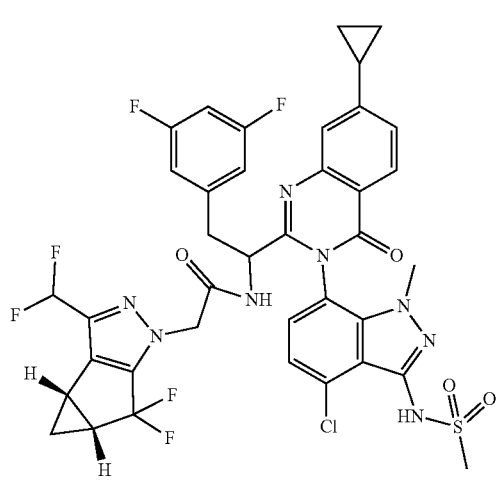
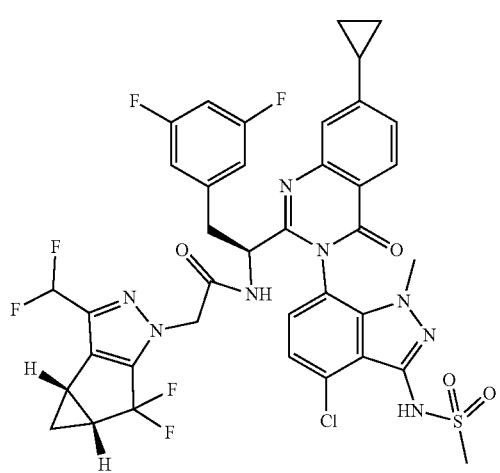
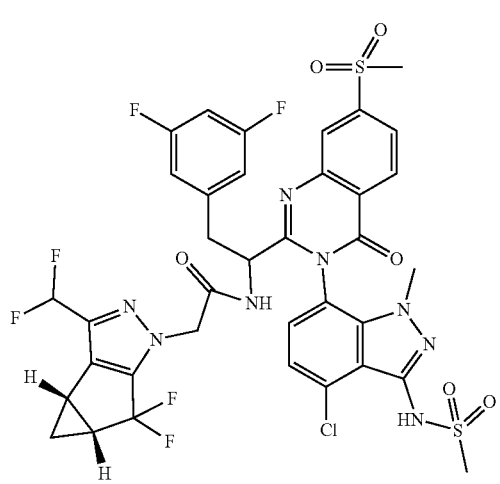
622
-continued
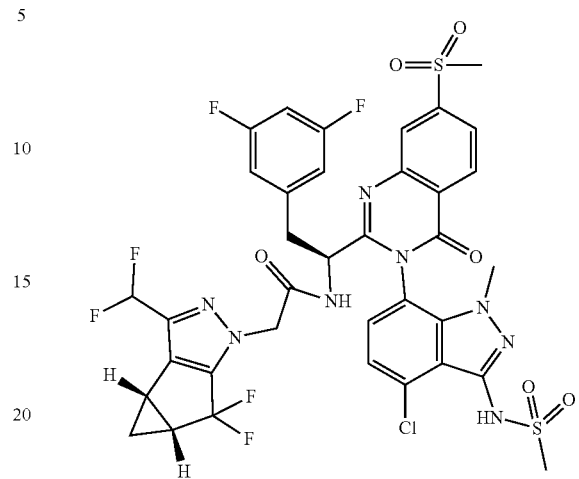
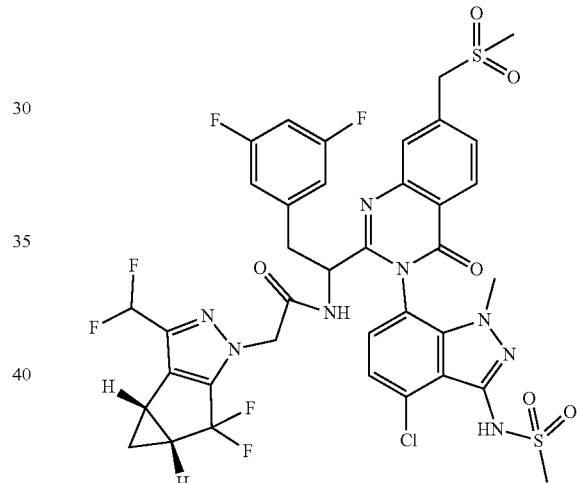
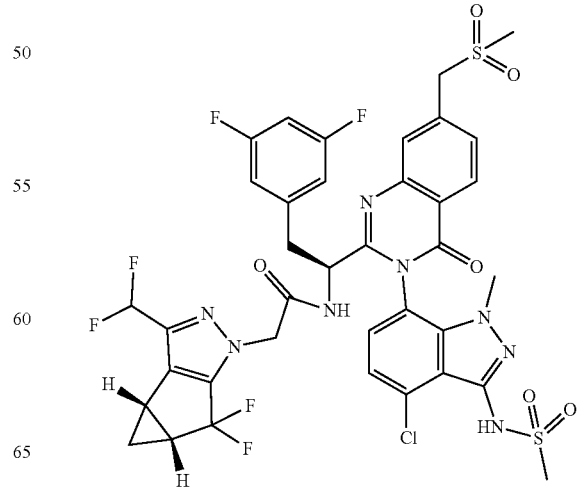

623
-continued
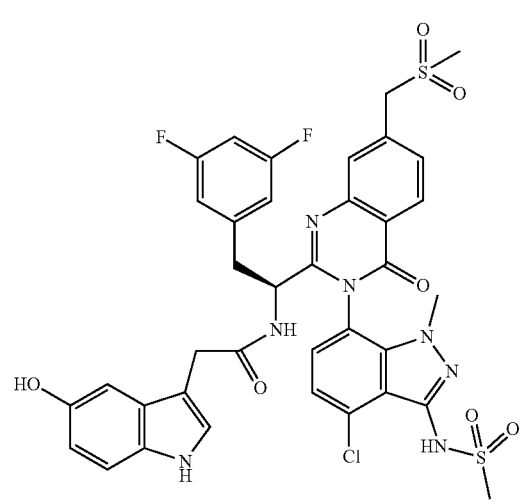
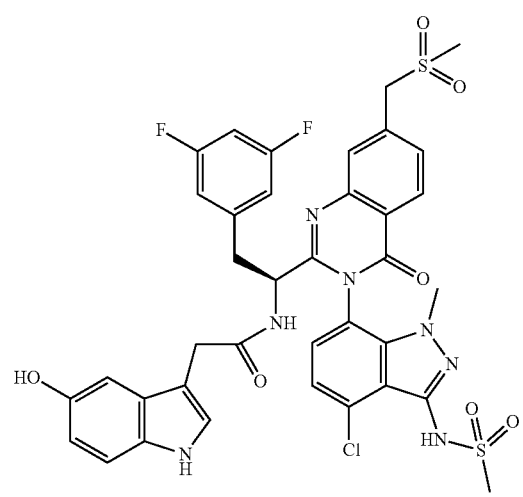
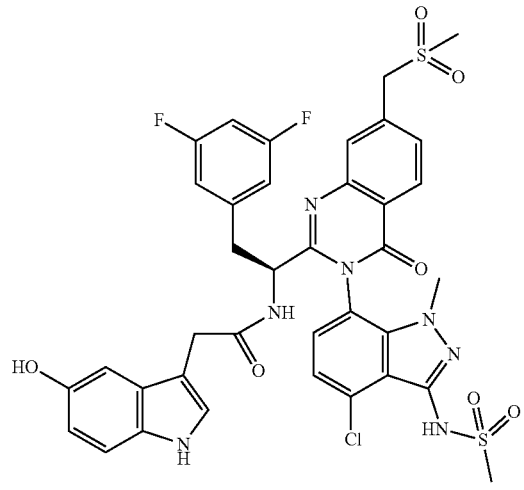
624
-continued
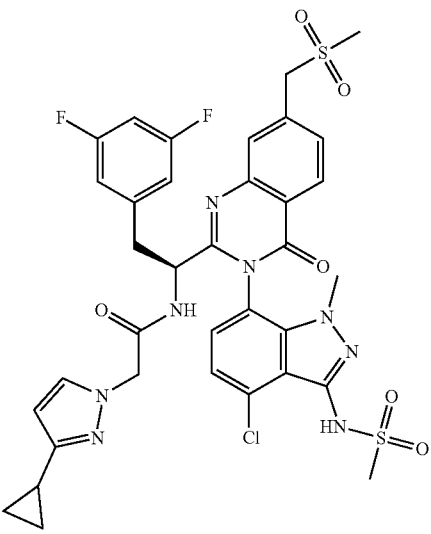
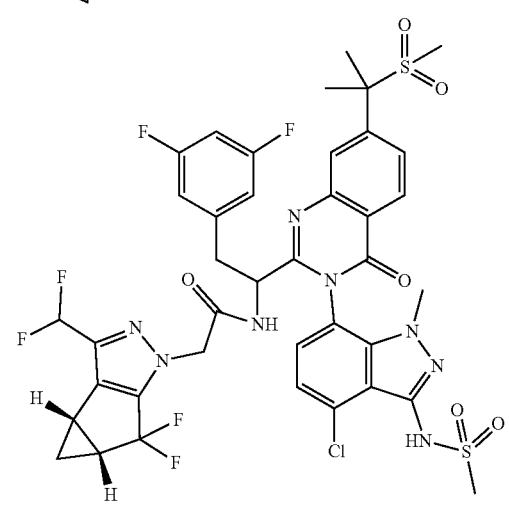
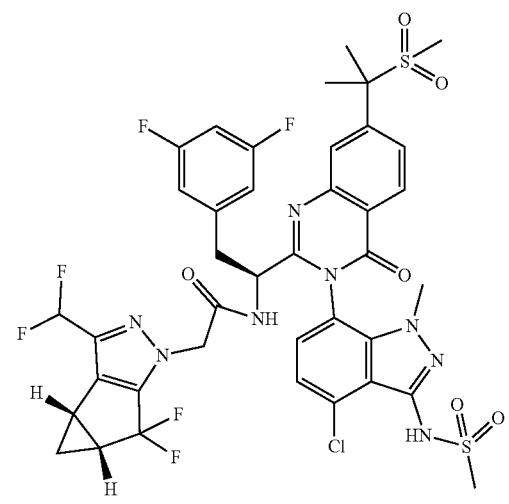

625
-continued
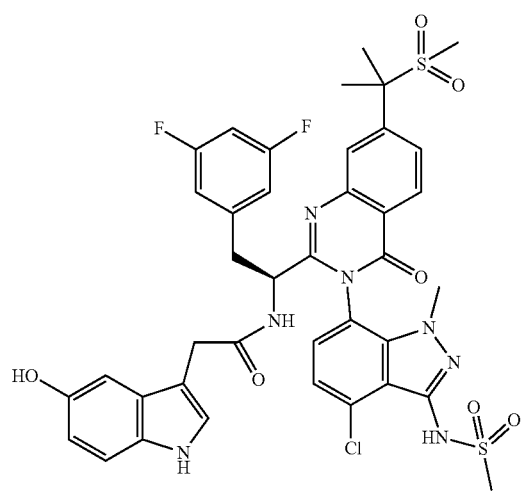
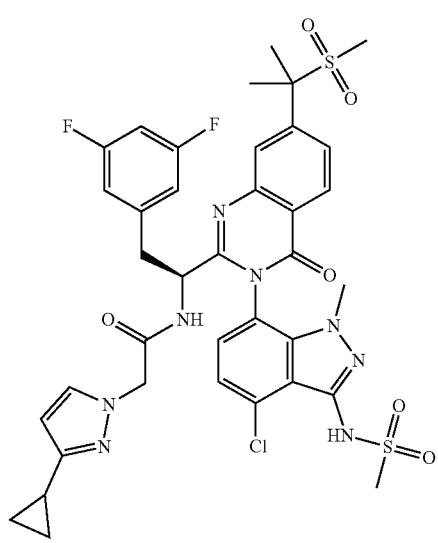
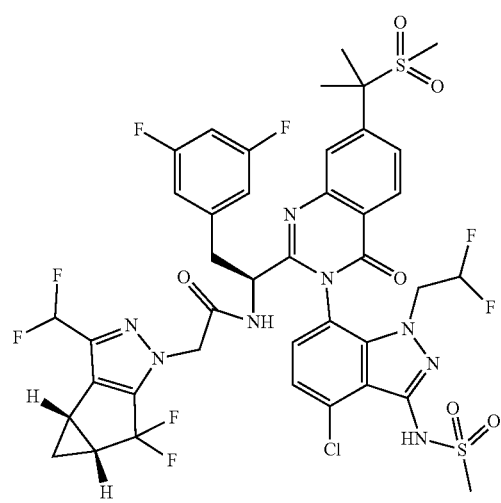
626
-continued
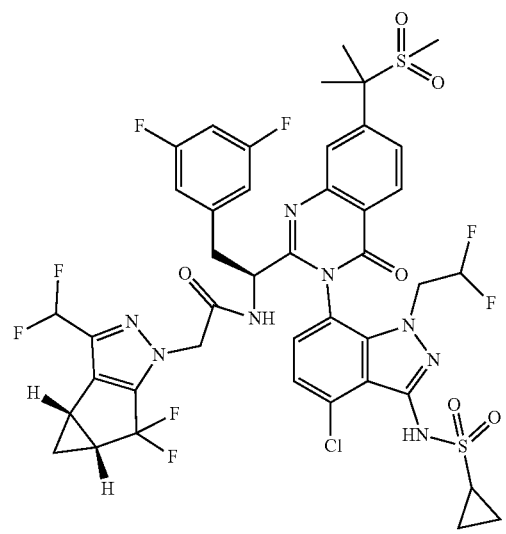
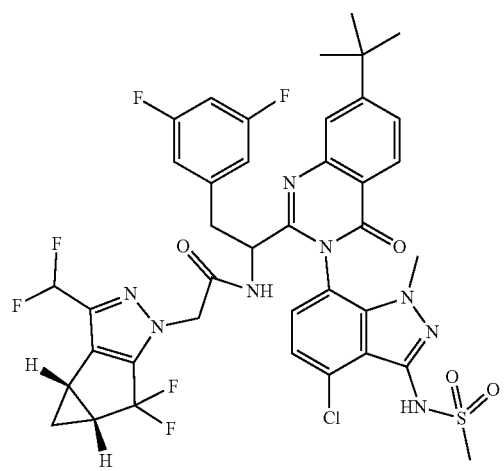
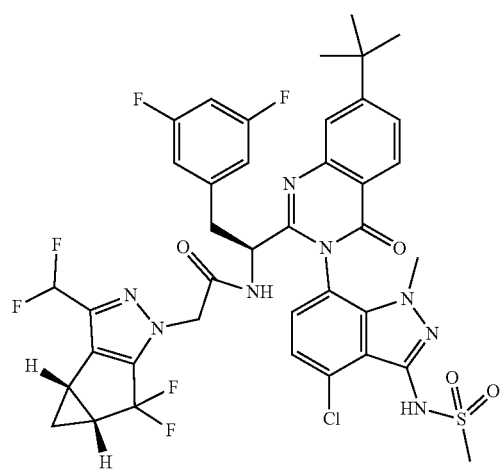

627
-continued

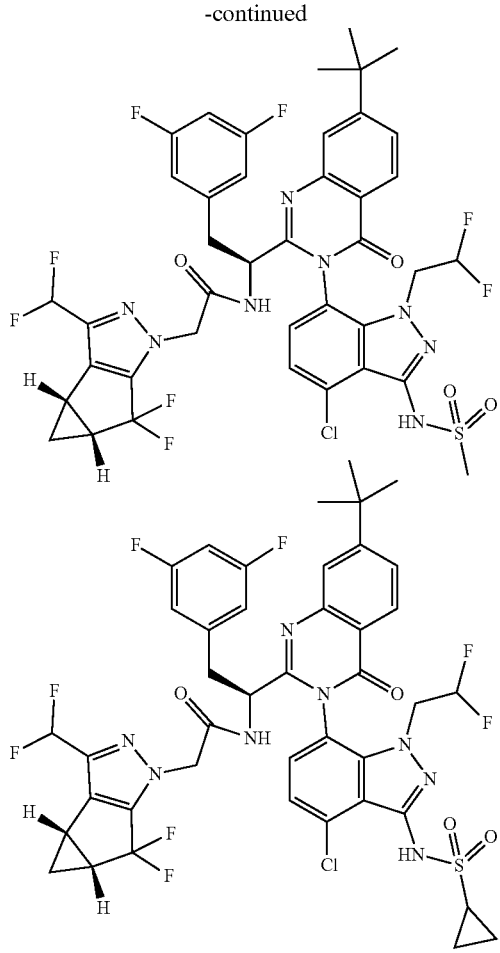

and pharmaceutically acceptable salts thereof.

628

6. A pharmaceutical composition comprising a compound or salt according to claim 1 and further comprising a pharmaceutically acceptable carrier, excipient, and/or diluent.

7. A method of treating HIV infection comprising administering a composition according to claim 6 to a patient.

8. The method of claim 7 wherein said administration is oral.

9. The method of claim 8 wherein said administration comprises administering by injection or subcutaneously to a patient to achieve a long acting effect which would require an infrequent dosing interval.

10. The method of claim 7 wherein said method further comprises administration of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

11. The method of claim 10 wherein said at least one other agent is selected from the group consisting of FTC, ibalizumab, PRO-140, dolutegravir, abacavir lamivudine, fosamprenavir, rilpivirine, atazanavir, darunavir, MK-8718, MK-8591, tenofovir alfenamide, and bictegravir.

* * * * *